US012570632B2

(12) United States Patent
Bancet et al.

(10) Patent No.: US 12,570,632 B2
(45) Date of Patent: Mar. 10, 2026

(54) INDOLE DERIVATIVES AND USES THEREOF FOR TREATING A CANCER

(71) Applicants: Universite Claude Bernard Lyon 1, Villeurbanne (FR); Institut National de la Sante et de la Recherche Medicale, Paris (FR); Centre National de la Recherche Scientifique, Paris (FR); Ecole Normale Superieure de Lyon, Lyons (FR); Commissariat à l'Energie Atomique et aux Energies Alternatives, Paris (FR); Centre Leon Berard, Lyons (FR)

(72) Inventors: Alexandre Bancet, Villeurbanne (FR); Claude Cochet, Claix (FR); Odile Filhol-Cochet, Claix (FR); Isabelle Krimm, Neuville Sur Saone (FR); Thierry Lomberget, Villeurbanne (FR); Marc Le Borgne, Poleymieux-Au-Mont-D'orr (FR)

(73) Assignees: Universite Claude Bernard Lyon 1, Villeurbanne (FR); Institute National de la Santa et de la Recherche Madicale, Paris (FR); Centre National de la Recherche Scientifique, Paris (FR); Ecole Normale Superieure de Lyon, Lyons (FR); Commissariat à l'Energie Atomique et aux Energies Alternatives, Paris (FR); Centre Leon Berard, Lyons (FR)

( * ) Notice: Subject to any disclaimer, the term of this patent is extended or adjusted under 35 U.S.C. 154(b) by 521 days.

(21) Appl. No.: 18/004,380

(22) PCT Filed: Jul. 6, 2021

(86) PCT No.: PCT/EP2021/068575

§ 371 (c)(1),
(2) Date: Jan. 5, 2023

(87) PCT Pub. No.: WO2022/008475

PCT Pub. Date: Jan. 13, 2022

(65) Prior Publication Data

US 2023/0278983 A1 Sep. 7, 2023

(30) Foreign Application Priority Data

Jul. 6, 2020 (EP) .................................... 20305767

(51) Int. Cl.

| | |
|---|---|
| ***C07D 401/14*** | (2006.01) |
| ***A61K 45/06*** | (2006.01) |
| ***A61P 35/00*** | (2006.01) |
| ***C07D 405/14*** | (2006.01) |
| ***C07D 413/14*** | (2006.01) |

(52) U.S. Cl.

CPC ............ *C07D 401/14* (2013.01); *A61K 45/06* (2013.01); *A61P 35/00* (2018.01); *C07D 405/14* (2013.01); *C07D 413/14* (2013.01)

(58) Field of Classification Search

CPC .. C07D 401/14; C07D 405/14; C07D 413/14; A61K 45/06; A61P 35/00

See application file for complete search history.

(56) References Cited

PUBLICATIONS

Qiao, et al.; European Journal of Medicinal Chemistry, v181, Article 111581, pp. 1-24; 2019 (Year: 2019).*
Cozza, G. et al., "Protein kinase CK2 inhibitors: a patent review," Expert Opinion on Therapeutic Patents (2012); 22(9): pp. 1081-1097.

* cited by examiner

*Primary Examiner* — Jeffrey S Lundgren
*Assistant Examiner* — W. Justin Youngblood
(74) *Attorney, Agent, or Firm* — Fox Rothschild LLP

(57) ABSTRACT

The present invention relates to indole derivatives of formula (I') as CK2 inhibitor and pharmaceutical compositions comprising the same. The present invention further relates to the use of such compounds of formula (I) for use for preventing and/or treating a cancer.

(I')

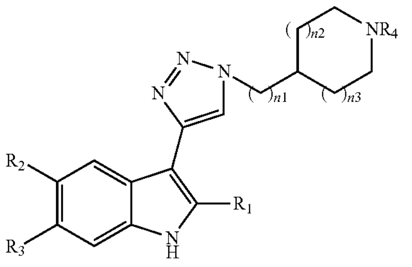

21 Claims, 10 Drawing Sheets

Figure 1:
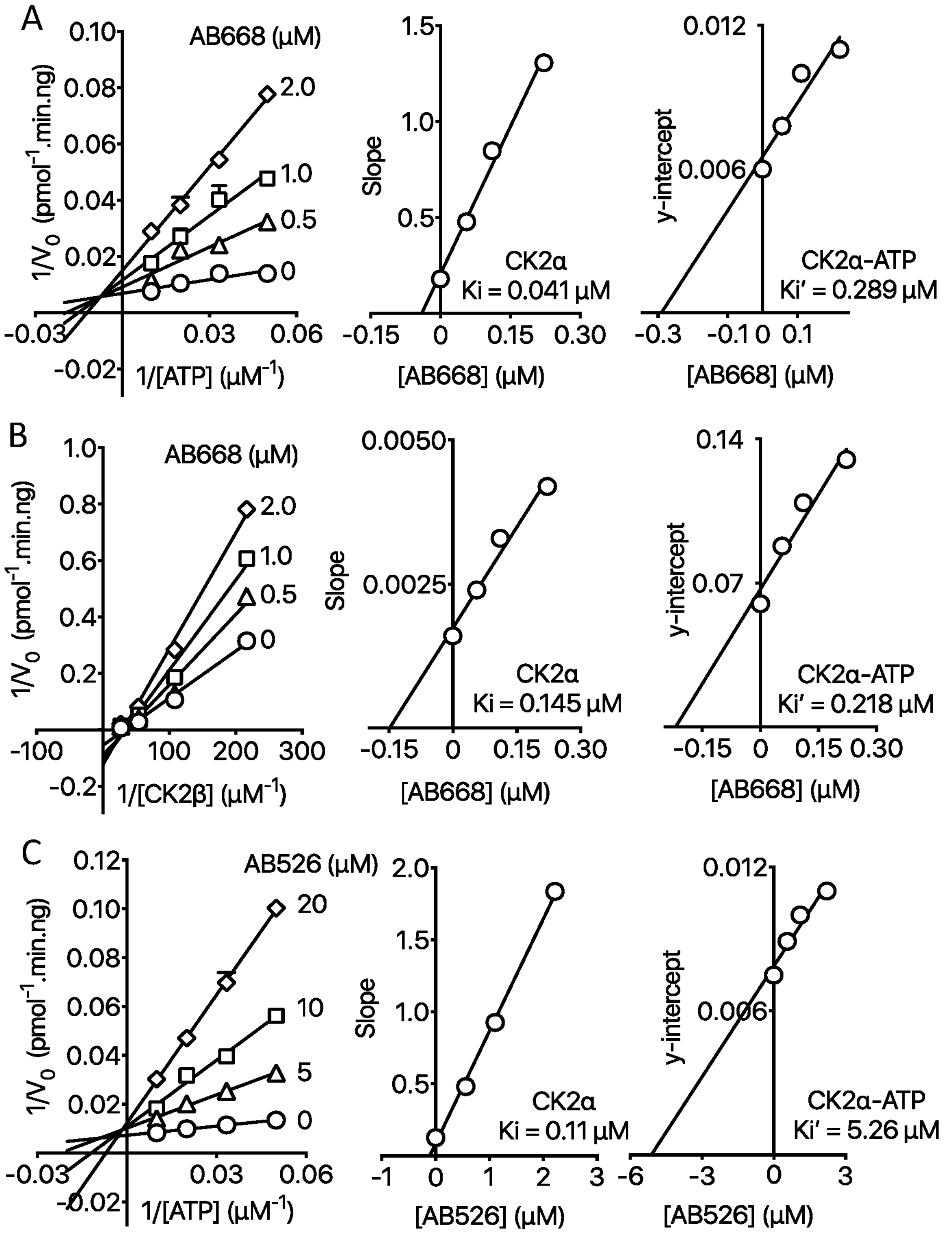
Figure 1:
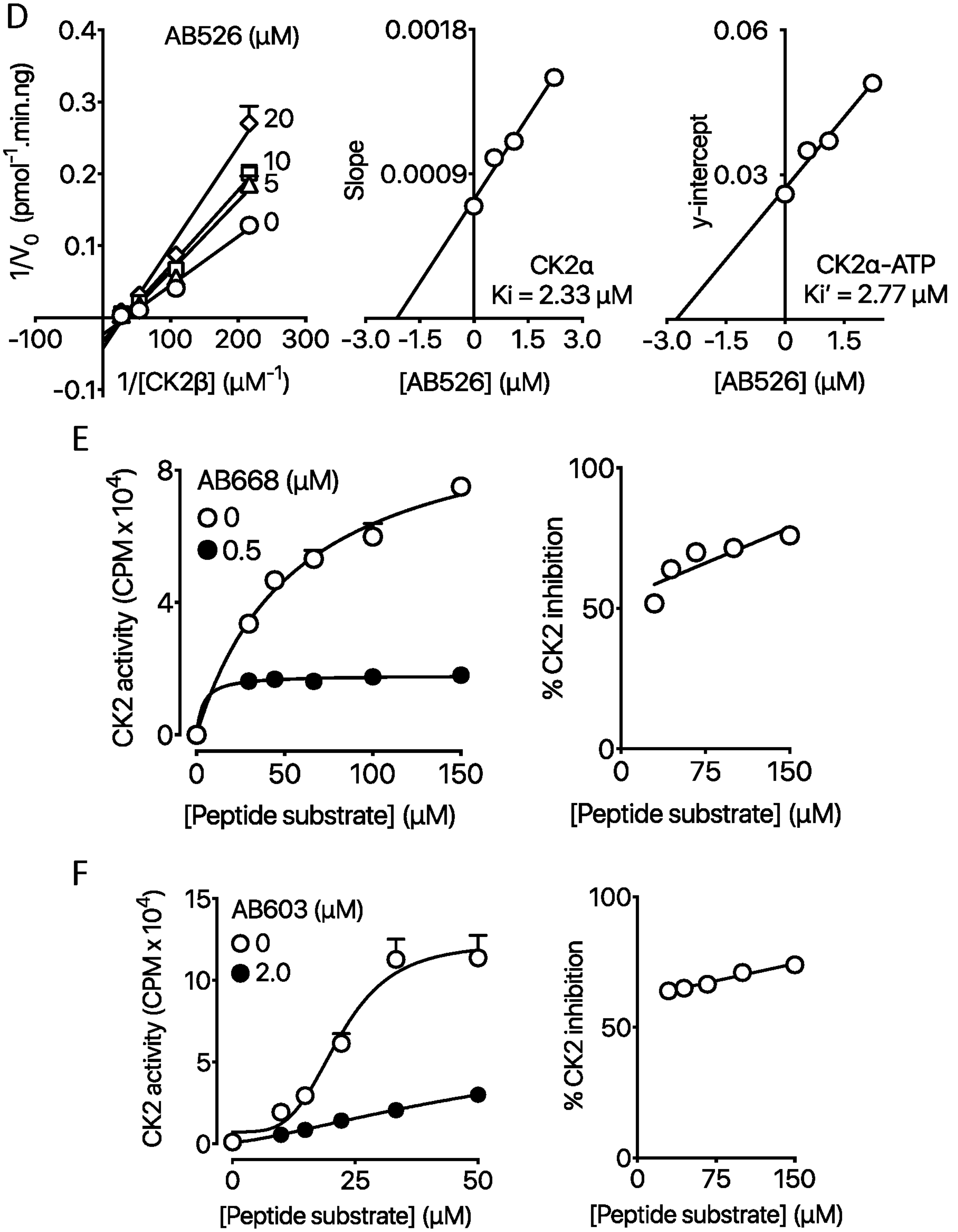
Figure 1:
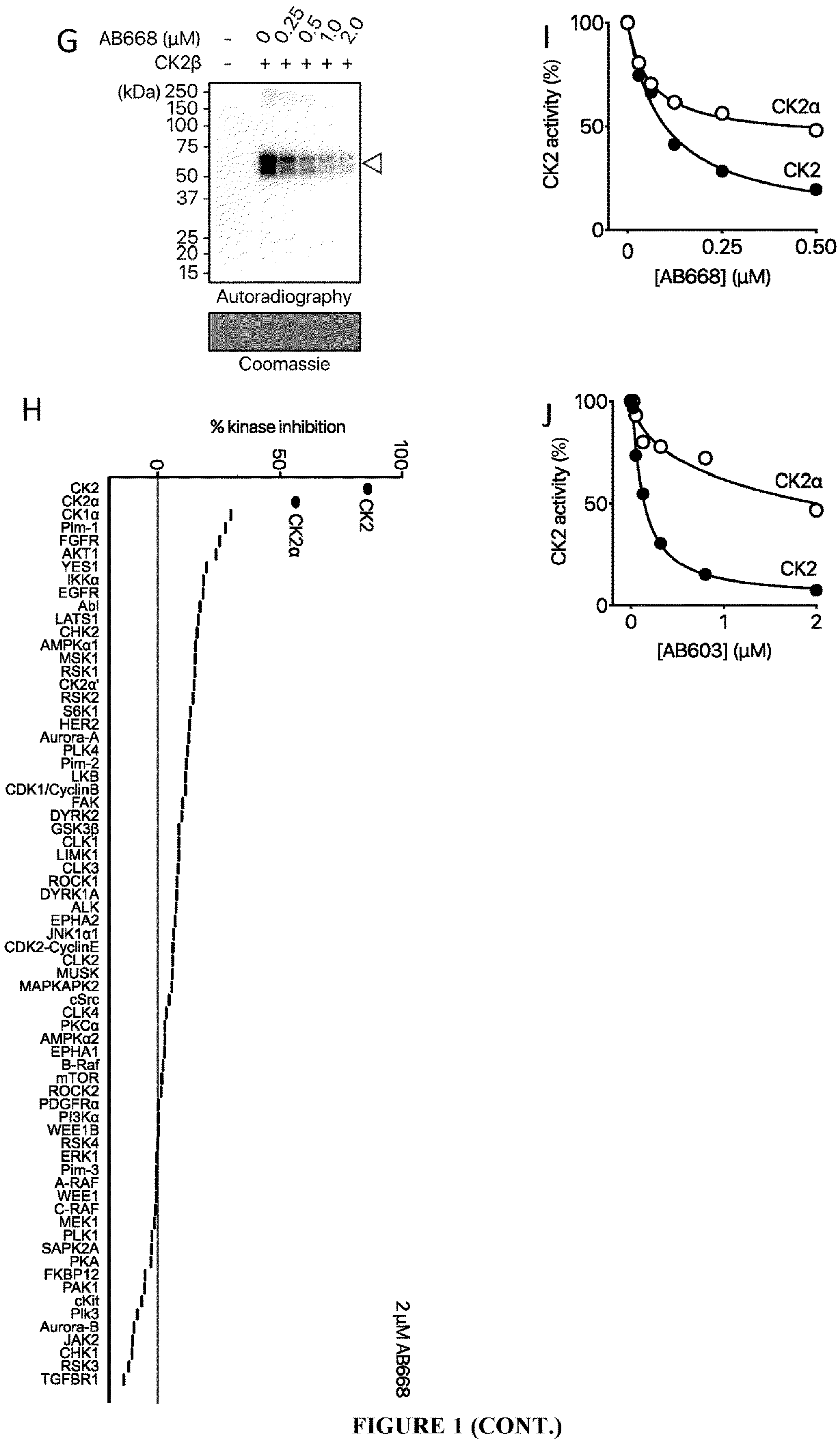

Specification includes a Sequence Listing.

f

INDOLE DERIVATIVES AND USES THEREOF FOR TREATING A CANCER

CROSS-REFERENCE TO RELATED APPLICATIONS

This application is the U.S. national phase of International Patent Application No. PCT/EP2021/068575, filed on Jul. 6, 2021, which claims priority to European Patent Application No. 20305767.4, filed on Jul. 6, 2020, the contents of which are incorporated herein by reference in their entirety.

FIELD OF THE INVENTION

The present invention relates to the field of medicine, in particular indole derivatives as kinase inhibitors and their uses for treating a cancer.

BACKGROUND OF THE INVENTION

Cancer is the second leading cause of death worldwide. Indeed, nearly 1 in 6 deaths is due to cancer. The prevalence of cancer is also extremely high as more than 15 million new cases are diagnosed each year, and the number of new cases is expected to rise by about 70% over the next 2 decades. Among the most common cancers, lung cancers account for 1.69 million deaths per year, colorectal cancer for 774 000 deaths per year, and breast cancer for 571 000 deaths per year. Many treatment options exist nowadays for cancer, including for example surgery, chemotherapy, radiation therapy, hormonal therapy, targeted therapy, immunotherapy and palliative care. The choice of the best treatments depends on the type, location and grade of the cancer as well as the patient's health and preferences.

Kinases proteins represent one of the main targets for treating cancers and are the second target of anticancer or antitumor drugs after G protein-coupled receptors. So far, 61 kinase inhibitors have been approved by Food and Drugs Administration (FDA), and among these 61 kinase inhibitors, more 46 mainly act as adenosine triphosphate (ATP) mimetics. However, despite a therapeutic efficacy widely demonstrated, kinase inhibitors may generate side effects for the patient and resistance may occur after several weeks or months of treatment. Such kinase inhibitor limitations can be mainly explained by i) a weak intracellular concentration of the kinase inhibitor due to the efflux pumps; ii) the occurrence of pharmacology resistance due to mutations in the ATP site; iii) activation of alternative signaling pathways by the cancer cells; iv) DNA damage repair mechanisms, and v) a lack of selectivity of the kinase inhibitor for its target protein due to the high conservation of ATP site, which is called "off-target effect".

To avoid side effects and resistance, the protein kinase CK2 has been investigated as a therapeutic target. The CK2 holoenzyme is a tetrameric association of two catalytic subunits (CK2α and CK2α') and two regulatory subunits (CK2β) and the regulation of CK2 is based on the reversible interaction of its α/β subunits. Studies' have highlighted the anti-apoptotic properties of CK2 and its role for promoting neo-vascularization and stabilization of the oncokinome. Also, overexpression of CK2 has been correlated with a large panel of cancers, such as multiple myeloma, brain cancer, breast cancer, colon cancer, kidney cancer, leukemia, liver cancer, lung cancer, ovarian cancer, and pancreas cancer (Trembley et al.: Cell. Mol. Life Sci., 2009, 66, 1858-1867). In addition, it has been reported that CK2 plays also a role in chemoresistance phenomena, such as regulation of Multidrug resistance (MDR) efflux pumps, control of signaling pathways to avoid a pharmacological response (PI3K/AKT/PTEN, NF-KB, p53), and maintenance of cancer stem cells (Borgo et al.: Journal of Experimental & Clinical Cancer Research).

Consequently, the discovery of CK2 inhibitors is a relevant approach for cancer therapy. In this context, the ATP-binding pocket of CK2α has been considered as the orthosteric site to design ATP-competitive inhibitors and the potent compound CX-4945 (also called silmitasertib) has entered phase II clinical trials. However, although CX-4945 exhibits a nanomolar efficacy (IC50=1.5 nM against CK2α), it still suffers from low selectivity by inhibiting more than about ten different kinases (off-target effect) and generates resistance due to the mutation of the ATP site of CK2.

Therefore, there remains a need to identify further drugs, and more particularly, to develop new anticancer molecules as non-ATP competitive selective CK2 inhibitors that can avoid resistance phenomena.

SUMMARY OF THE INVENTION

In this context, the inventors have provided new indole derivatives exhibiting a selective inhibition of the protein kinase CK2, demonstrating thereby the therapeutic interest of such compounds in medicine, more particularly in cancer therapies.

The present invention thus provides a compound having the following formula (I'):

(I')

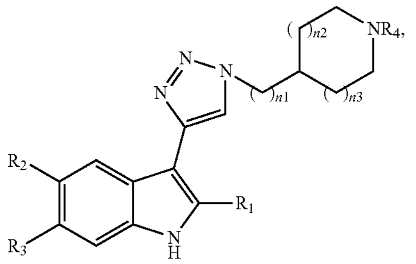

wherein:

$R_1$ is a radical selected in the group consisting of:
- a hydrogen,
- a $(C_1\text{-}C_6)$alkyl optionally substituted by a hydroxy, a $(C_1\text{-}C_6)$alkyloxy, an amino group, a —$N(CH_3)_2$ group, or a heterocycloalkyl group,
- a $(C_1\text{-}C_6)$alkyloxy,
- a —$CO_2R_5$, a-$CONHR_5$, a —$COR_5$, or a —$CH_2$—O—$R_5$ group with $R_5$ being a radical selected in the group consisting of:
  - a hydrogen,
  - a $(C_1\text{-}C_6)$alkyl optionally substituted by a hydroxy, an amino group, a cycloalkyl, or a heterocycloalkyl,
  - a $(C_2\text{-}C_6)$alkenyl,
  - a 3-10 membered ring selected in the group consisting of a heterocycloalkyl, a cycloalkyl, an aryl, and a heteroaryl, said 3-10 membered ring being optionally substituted by a $(C_1\text{-}C_6)$alkyl, and
- a heteroaryl optionally substituted a $(C_1\text{-}C_6)$alkyl optionally substituted by a cycloalkyl;

$R_2$ is a hydrogen, a halogen, or a $(C_1\text{-}C_6)$alkyl optionally substituted by at least one fluorine;

$R_3$ is a hydrogen or a halogen; and $R_4$ is a radical selected in the group consisting of:

a —$CH_2$—$CH_2$—NH—$SO_2$—$R_6$ or a —$CH_2$—$CH_2$—NH—$SO_2$—$CH_2$—$R_6$ group with $R_6$ being a 3-10 membered ring optionally substituted by at least one radical selected in the group consisting of:

a halogen, a hydroxy, a ($C_1$-$C_6$)alkyl optionally substituted by at least one fluorine, a cycloalkyl or an aryl, a ($C_1$-$C_6$)alkyloxy optionally substituted by at least one fluorine, a 3-10 membered ring optionally substituted by at least one radical selected in the group consisting of:

a halogen, a heterocycloalkyl, a —$CH_2$-heterocycloalkyl, a cyano, a ($C_1$-$C_6$)alkyl optionally substituted by at least one ($C_1$-$C_6$)alkyloxy or one halogen, a ($C_1$-$C_6$)alkyloxy optionally substituted by at least one halogen, a —$N(CH_3)_2$ group, and a hydroxy, and a —O-3-10 membered ring, a X—$R_7$ group in which:

X represents —$CH_2$—, —CO—, —NH—CO—NH—, or —$SO_2$—, and $R_7$ represents a 3-10 membered ring optionally substituted by at least one radical selected in the group consisting of:

a halogen, a ($C_1$-$C_6$)alkyl optionally substituted by at least one fluorine, a ($C_1$-$C_6$)alkyloxy, and a 3-10 membered ring, a —O-3-10 membered ring, a —$CH_2$-3-10 membered ring, or a —O—$CH_2$-3-10 membered ring, said rings are optionally substituted by at least one radical selected in the group consisting of:

a ($C_1$-$C_6$)alkyl optionally substituted by at least one ($C_1$-$C_6$)alkyloxy or one halogen, a ($C_1$-$C_6$)alkyloxy, a halogen, a —$COR_8$ with $R_8$ being a hydrogen or a ($C_1$-$C_6$)alkyl, and an aryl;

n1 is 0 or 1; and n2 and n3 are independently 0, 1, or 2;

and the stereoisomers, the tautomers, the hydrates, and the pharmaceutical salts thereof.

The present invention also provides a compound having the following formula (I):

(I)

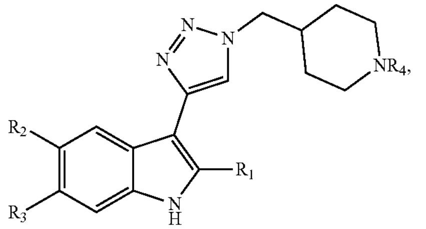

wherein:

$R_1$ is a radical selected in the group consisting of:

a hydrogen, a —$CO_2R_5$, a-$CONHR_5$, a —$COR_5$, or a —$CH_2$—O—$R_5$ group with $R_5$ being a radical selected in the group consisting of:

hydrogen, a ($C_1$-$C_6$)alkyl optionally substituted by a hydroxy, an amino group, or a cycloalkyl, and a heterocycloalkyl optionally substituted by a ($C_1$-$C_6$)alkyl, and a heteroaryl optionally substituted a ($C_1$-$C_6$)alkyl optionally substituted by a cycloalkyl;

$R_2$ is a hydrogen, a halogen, or a ($C_1$-$C_6$)alkyl optionally substituted by at least one fluorine;

$R_3$ is a hydrogen or a halogen; and $R_4$ is a radical selected in the group consisting of:

a —$CH_2$—$CH_2$—NH—$SO_2$—$R_6$ group with $R_6$ being a 3-10 membered ring optionally substituted by a radical selected in the group consisting of:

a halogen, a ($C_1$-$C_6$)alkyl optionally substituted by at least one fluorine, a cycloalkyl or an aryl, a ($C_1$-$C_6$)alkyloxy optionally substituted by at least one fluorine, a 3-10 membered ring, and a —O-3-10 membered ring, a X—$R_7$ group in which:

X represents —$CH_2$—, —CO—, —NH—CO—NH—, or —$SO_2$—, and $R_7$ represents a 3-10 membered ring optionally substituted by at least one radical selected in the group consisting of:

a halogen, a ($C_1$-$C_6$)alkyl optionally substituted by at least one fluorine, a ($C_1$-$C_6$)alkyloxy, and a 3-10 membered ring, a —O-3-10 membered ring, a —$CH_2$-3-10 membered ring, or a —O—$CH_2$-3-10 membered ring, said rings are optionally substituted by at least one radical selected in the group consisting of:

a ($C_1$-$C_6$)alkyl optionally substituted by at least one ($C_1$-$C_6$)alkyloxy or one halogen, a ($C_1$-$C_6$)alkyloxy, a halogen, a —$COR_8$ with $R_5$ being a hydrogen or a ($C_1$-$C_6$)alkyl, and an aryl;

and the stereoisomers, the tautomers, the hydrates, and the pharmaceutical salts thereof.

In a particular embodiment, $R_1$ is a radical selected in the group consisting of:

a hydrogen, a ($C_1$-$C_6$)alkyl optionally substituted by a hydroxy, and a —$CO_2R_5$, a —$COR_5$, or a-$CONHR_5$ group with $R_5$ being a radical selected in the group consisting of:

hydrogen, a ($C_1$-$C_6$)alkyl optionally substituted by a hydroxy or an amino group, and a cycloalkyl, a heterocycloalkyl, or a heteroaryl.

In a preferred embodiment, $R_1$ is a —$CO_2R_5$—$COR_5$ with $R_5$ being a ($C_1$-$C_6$)alkyl. More preferably $R_1$ is or —$COCH_3$.

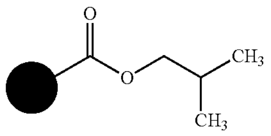

In a particular embodiment, $R_2$ is a halogen. Preferably, $R_2$ is a fluorine.

In a particular embodiment, $R_3$ is a hydrogen.

In a particular embodiment, $R_4$ is a —$CH_2$—$CH_2$—NH—$SO_2$—$R_6$ group with $R_6$ being a phenyl or a naphtalenyl optionally substituted by a radical selected in the group consisting of:

a halogen, preferably a chlorine;

a ($C_1$-$C_6$)alkyl optionally substituted by at least one fluorine, preferably a methyl, a trifluoromethyl, an ethyl, or an isopropyl.

In a preferred embodiment, $R_4$ is a radical selected in the group consisting of a —$CH_2$—$CH_2$—NH—$SO_2$—$R_6$ group with $R_6$ being a phenyl substituted by a ($C_1$-$C_6$)alkyl. More preferably, $R_6$ is

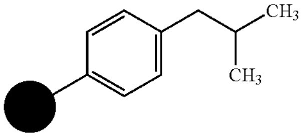

or

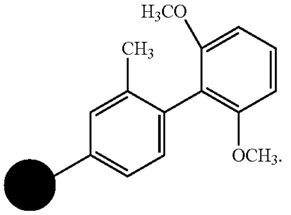

In a further particular embodiment, wherein $R_4$ is a X—$R_7$ group in which:

X represents —$CH_2$—, —CO—, or —$SO_2$—, and $R_7$ represents a phenyl, a dihydrobenzofuran, or a piperazinyl optionally substituted by at least one radical selected in the group consisting of:

- a halogen, preferably a chlorine,
- a ($C_1$-$C_6$)alkyl optionally substituted by at least one fluorine, preferably an isopropyl, a tert-butyl, or a trifluoromethyl,
- a ($C_1$-$C_6$)alkyloxy, preferably an isobutoxy or an isopentyloxy, and
- a radical selected in the group consisting of a phenyl, an indolyl, a dihydrobenzofuranyl, a dihydrobenzofuranoxy, a phenoxy, and a benzyl, said radicals are optionally substituted by at least one radical selected in the group consisting of:
  - a ($C_1$-$C_6$)alkyl optionally substituted by at least one ($C_1$-$C_6$)alkyloxy or one halogen, preferably a methyl, an isopropyl, a methoxymethyl, or a trifluoromethyl,
  - a ($C_1$-$C_6$)alkyloxy, preferably a methoxy or an isopentyloxy, and
  - a —$COR_8$ with $R_8$ being ($C_1$-$C_6$)alkyl, preferably a methyl.

In a further preferred embodiment, $R_4$ is a X—$R_7$ group in which:

X represents —$CH_2$— or —CO—, and $R_7$ represents a phenyl disubstituted:

- in meta position by a radical selected in the group consisting of:
  - a halogen, preferably a chlorine,
  - a ($C_1$-$C_6$)alkyl optionally substituted by at least one fluorine, preferably an isopropyl or a trifluoromethyl, and,
  - a phenyl optionally substituted by ($C_1$-$C_6$)alkyl optionally substituted by at least one fluorine, preferably a trifluoromethyl, and
- in para position by a radical selected in the group consisting of:
  - a ($C_1$-$C_6$)alkyloxy, preferably an isobutoxy or an isopentyloxy, and
  - a phenyl, an indolyl, a dihydrobenzofuranyl, a dihydrobenzofuranoxy, a phenoxy, and a benzyl, said radicals are optionally substituted by at least one radical selected in the group consisting of:
    - a ($C_1$-$C_6$)alkyl optionally substituted by at least one ($C_1$-$C_6$)alkyloxy, preferably a methyl, an isopropyl, or a methoxymethyl,
    - a ($C_1$-$C_6$)alkyloxy, preferably a methoxy or an isopentyloxy, and
    - a —$COR_8$ with $R_8$ being ($C_1$-$C_6$)alkyl, preferably a methyl.

In a further particular embodiment, $R_4$ is a radical selected in the group consisting of:

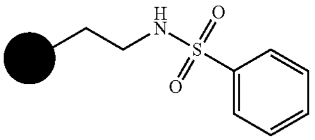

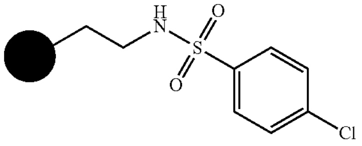

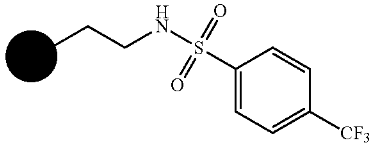

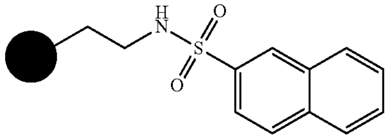

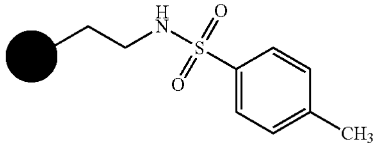

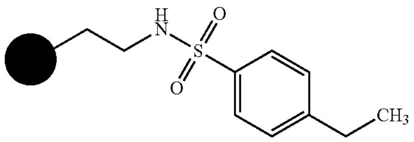

-continued
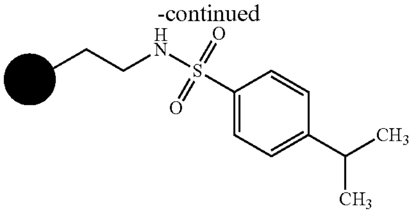
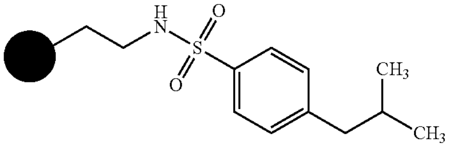
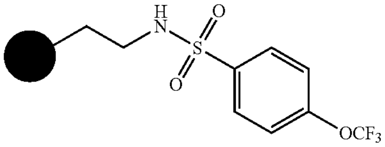
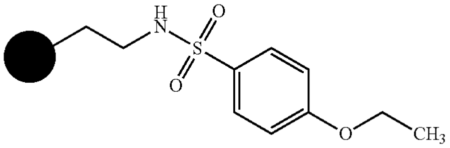
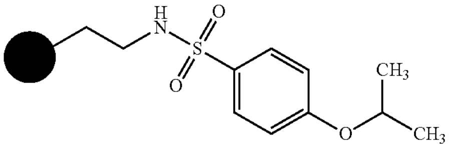
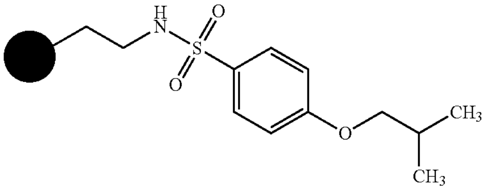
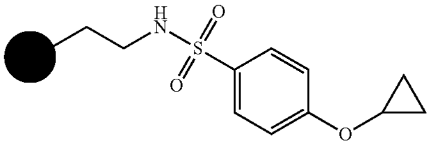
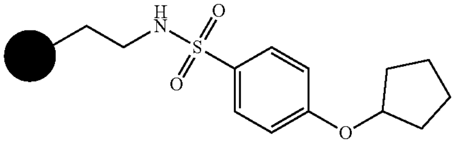
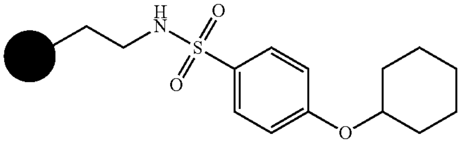
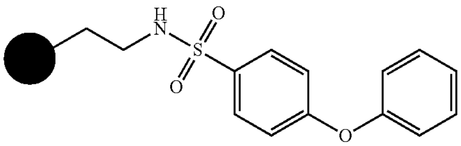
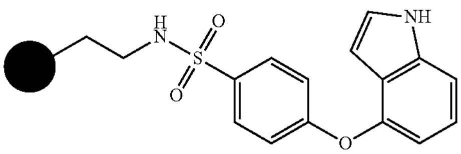
-continued
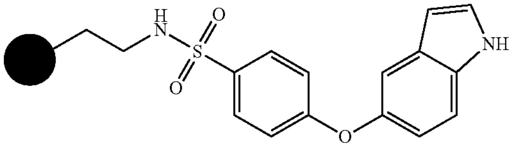
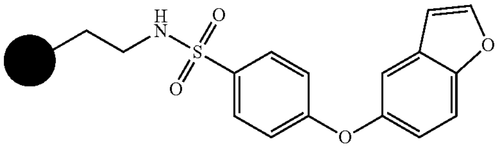
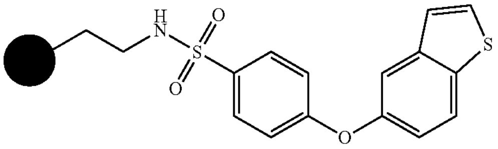
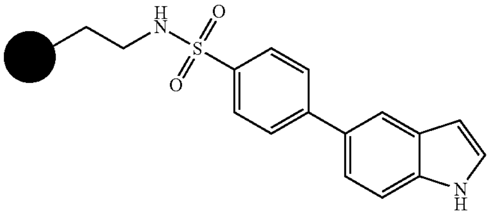
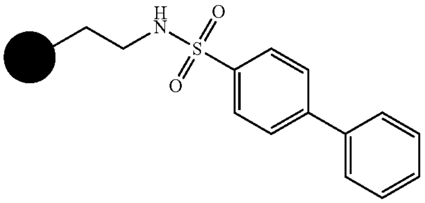
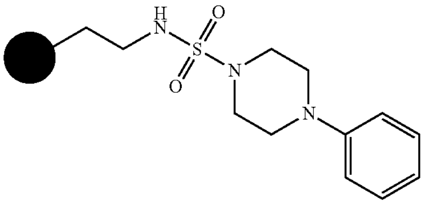
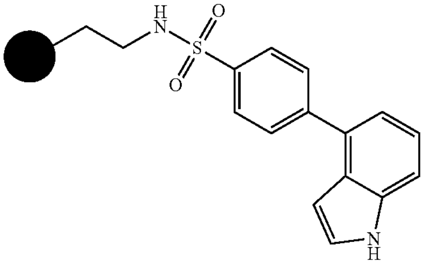
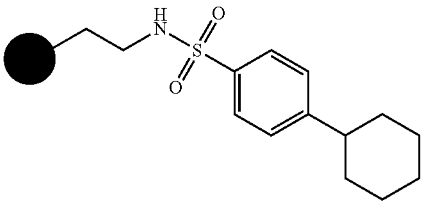
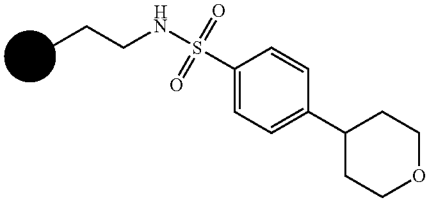

-continued
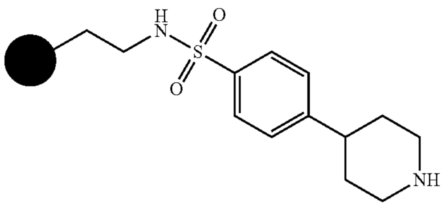
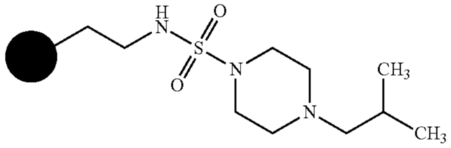
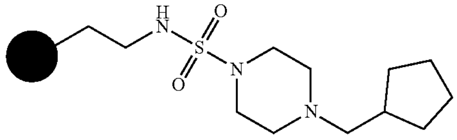
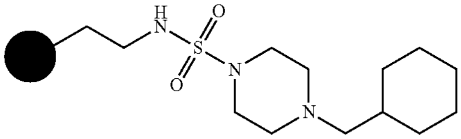
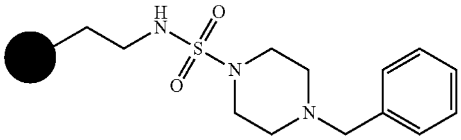
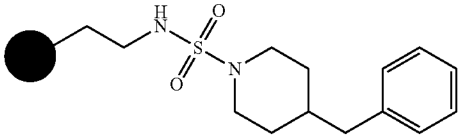
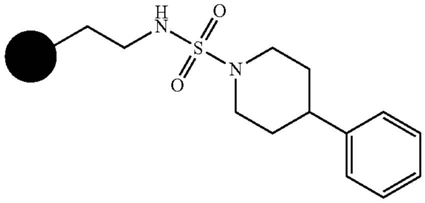
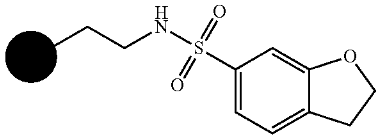
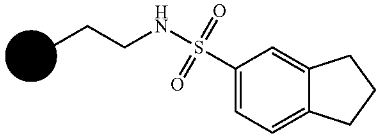
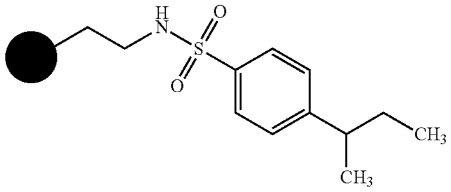
-continued
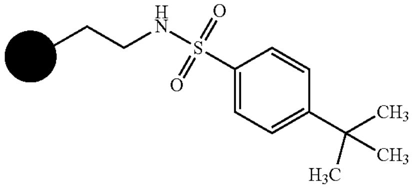
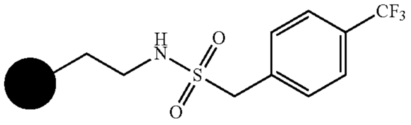
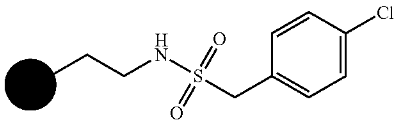
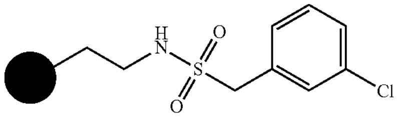
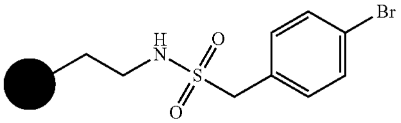
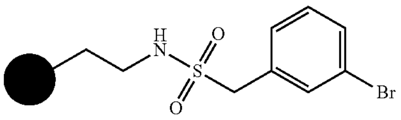
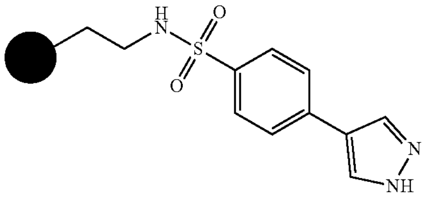
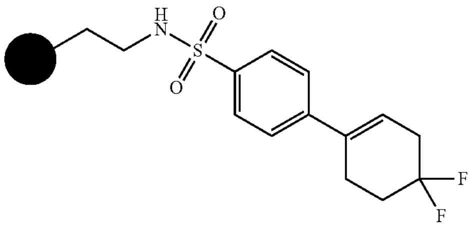
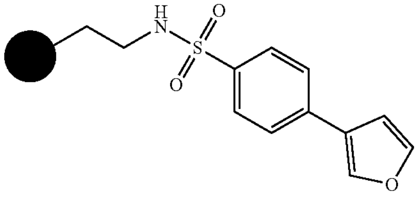
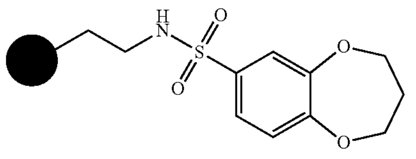

-continued
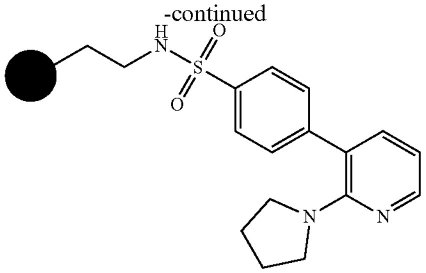
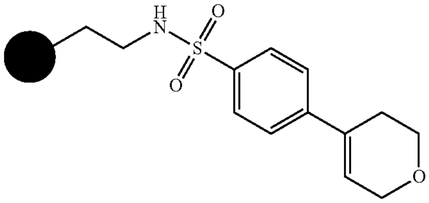
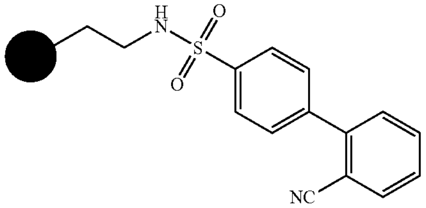
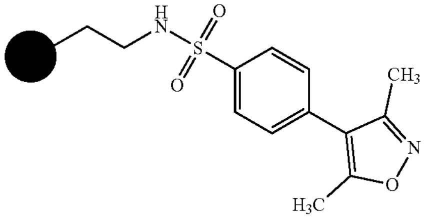
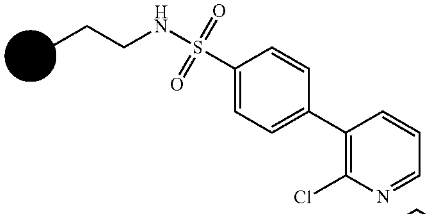
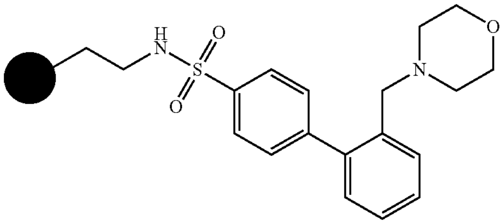
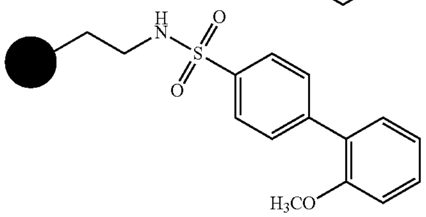
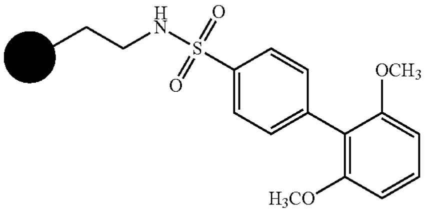
-continued
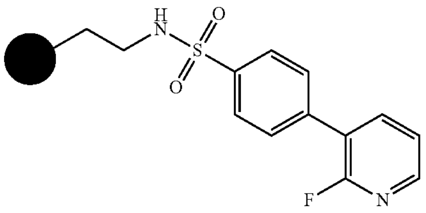
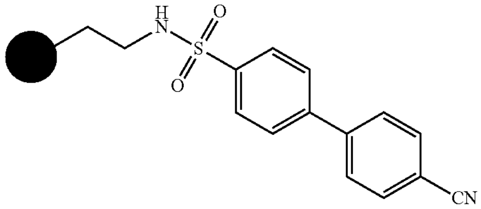
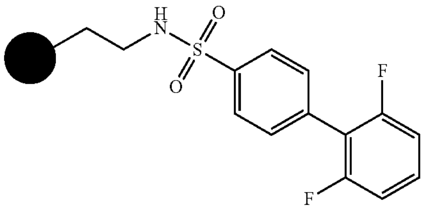
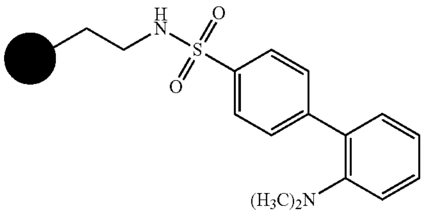
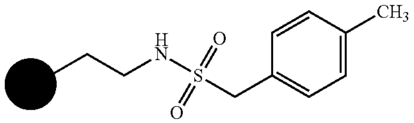
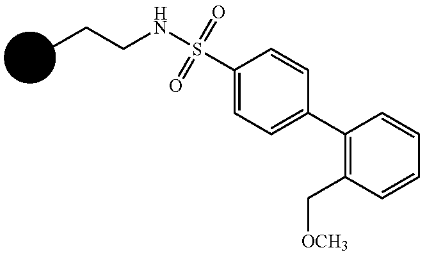
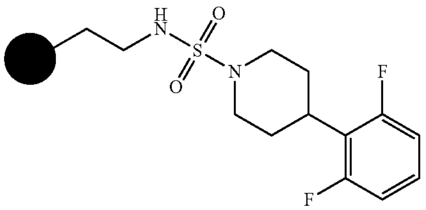
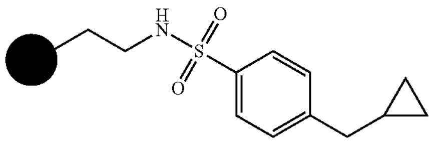

-continued
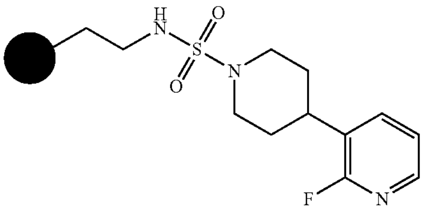
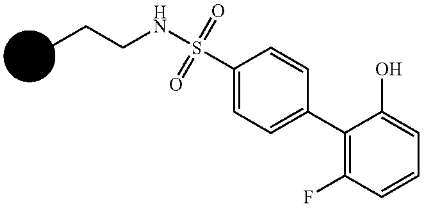
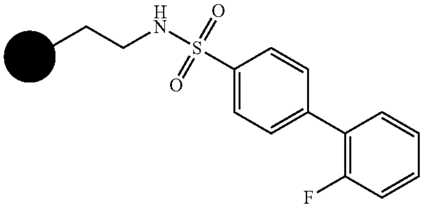
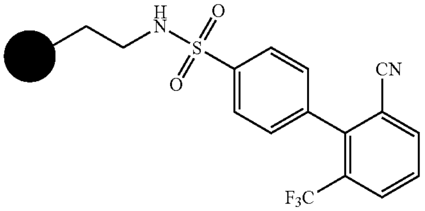
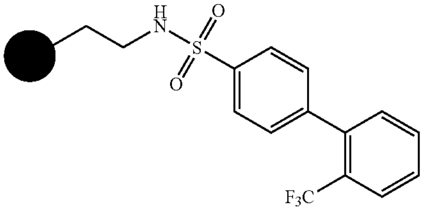
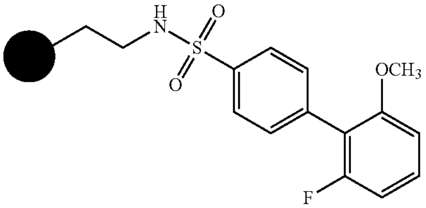
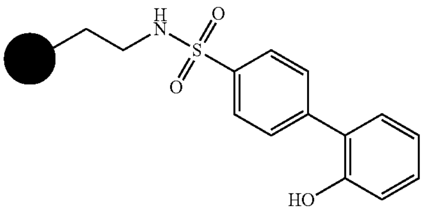
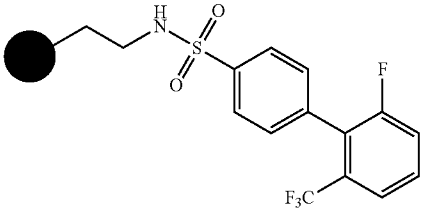
-continued
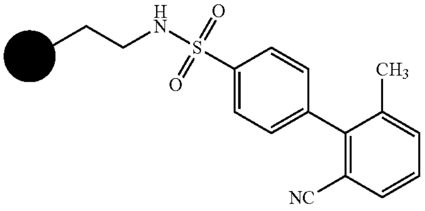
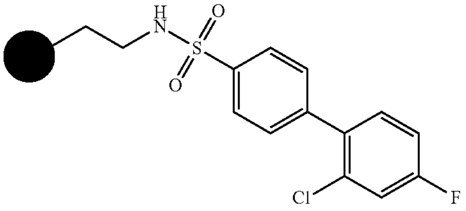
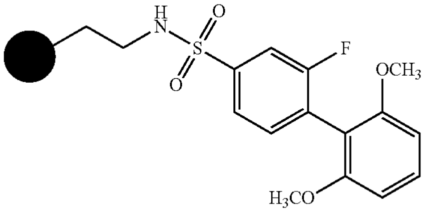
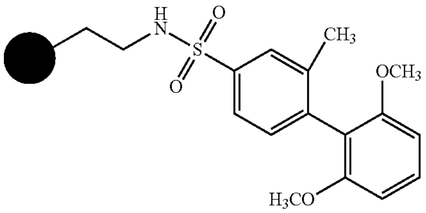
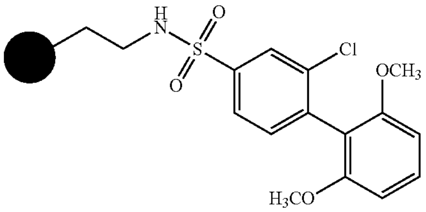
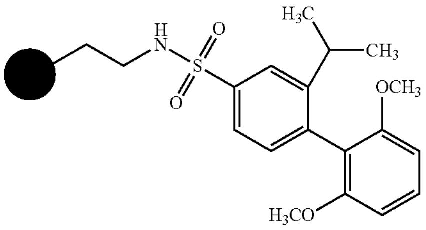
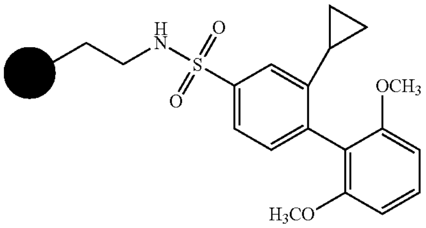
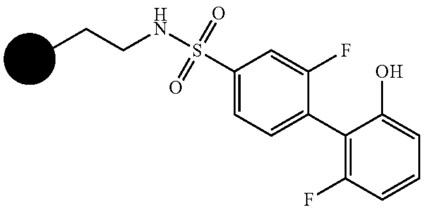

-continued
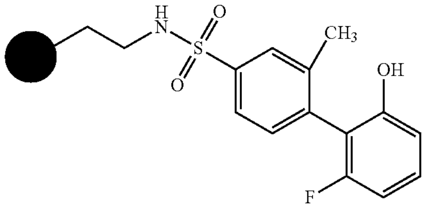
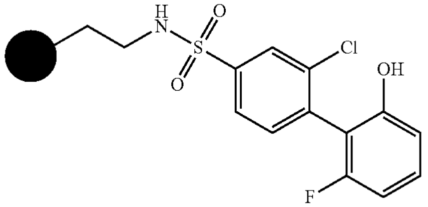
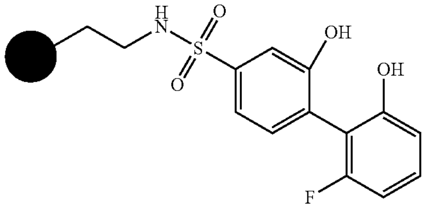
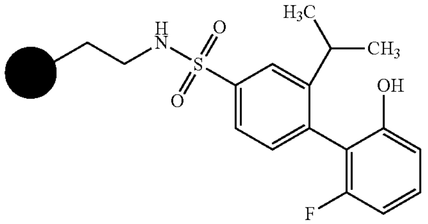
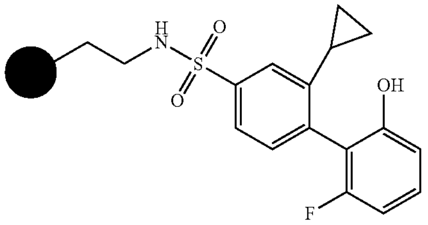
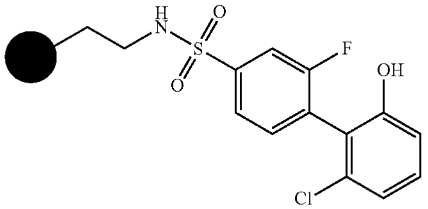
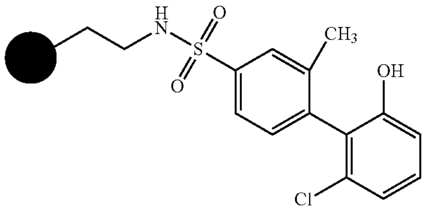
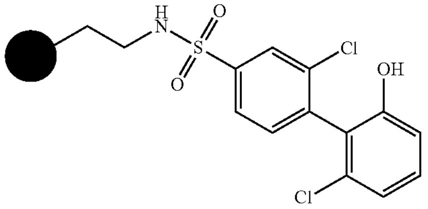
-continued
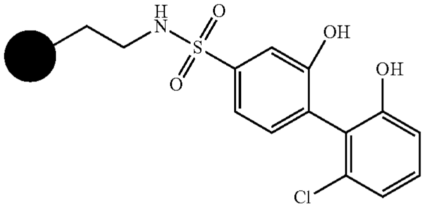
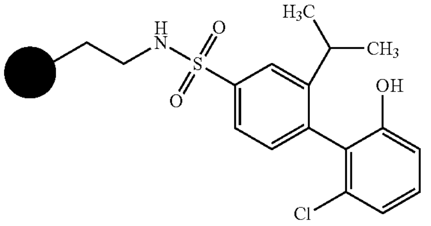
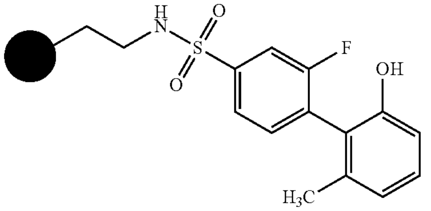
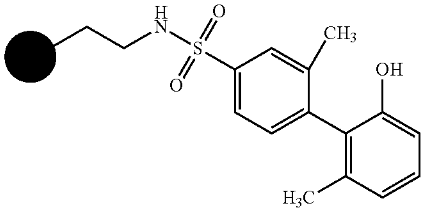
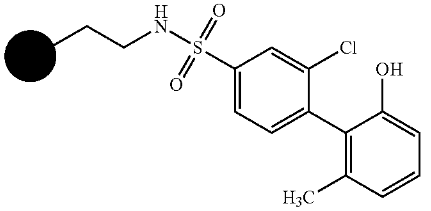
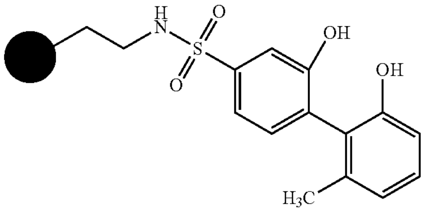
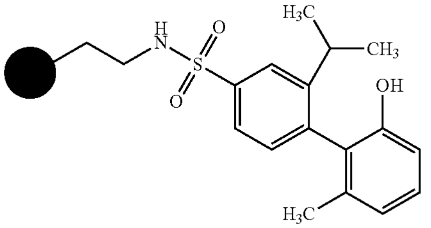
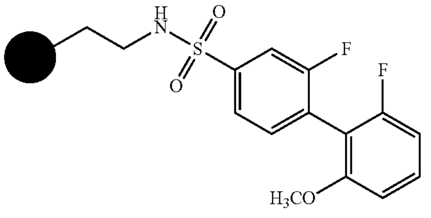

-continued
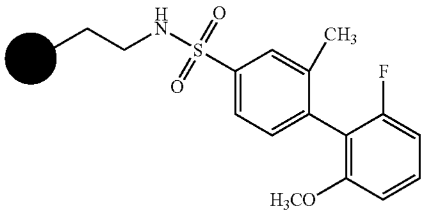
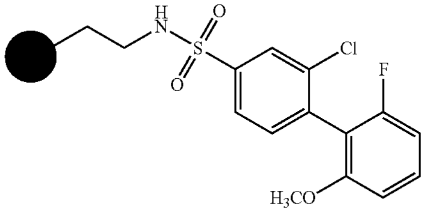
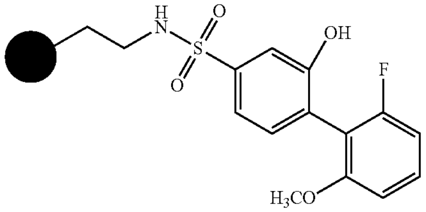
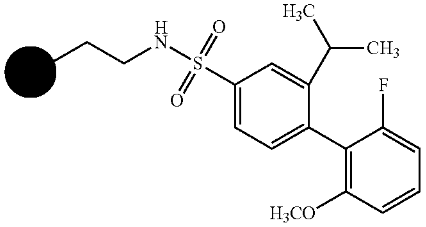
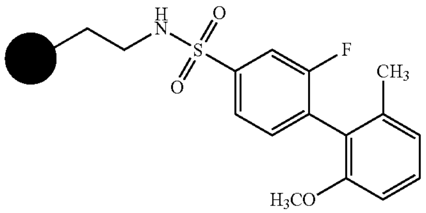
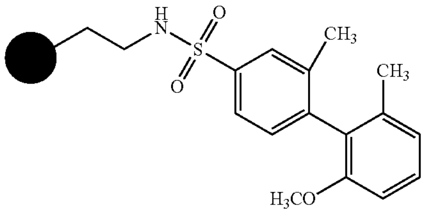
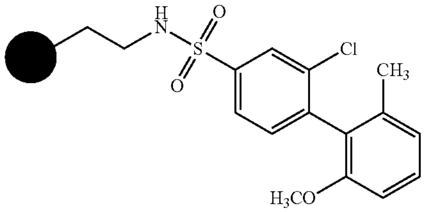
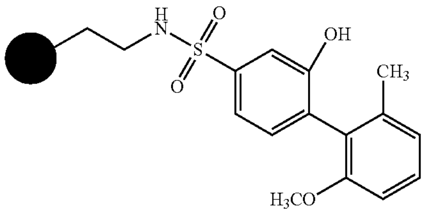
-continued
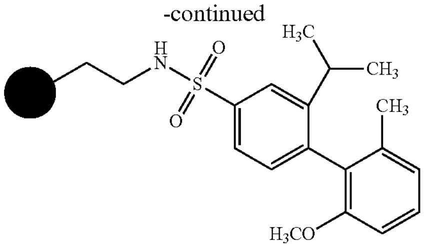
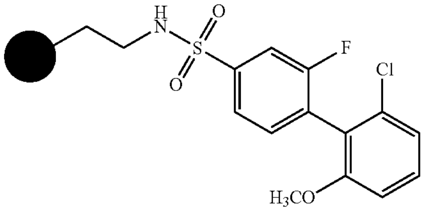
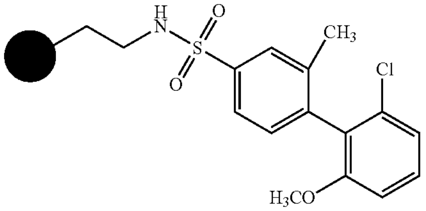
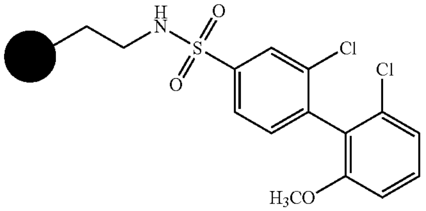
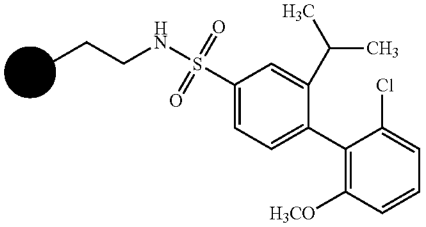
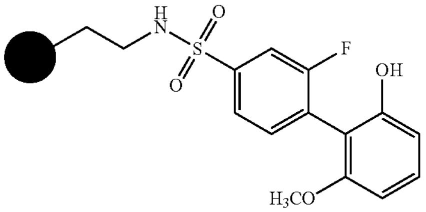
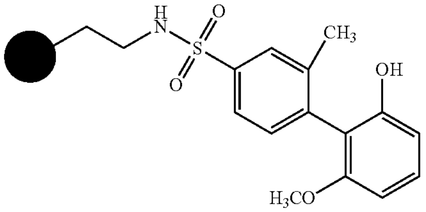
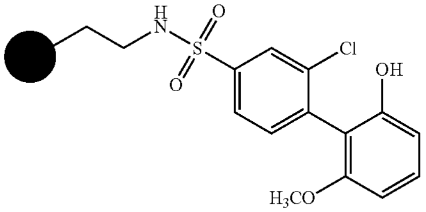

-continued
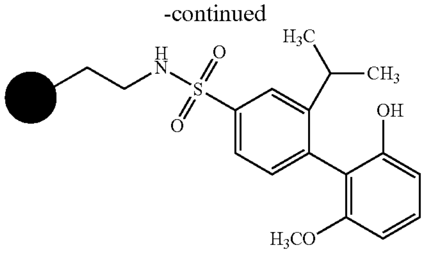
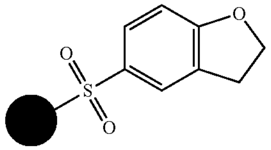
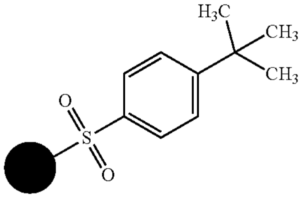
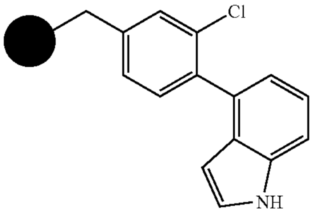
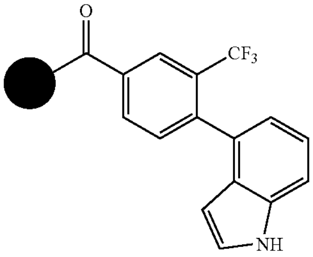
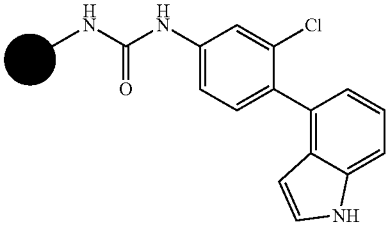
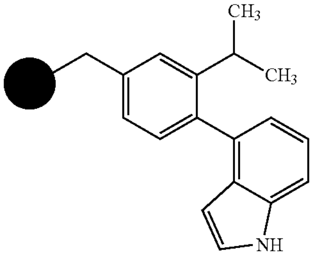
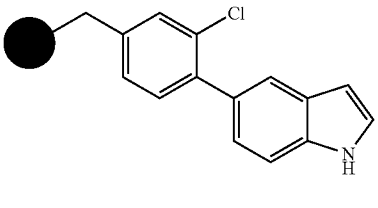
-continued
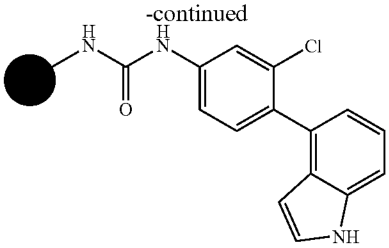
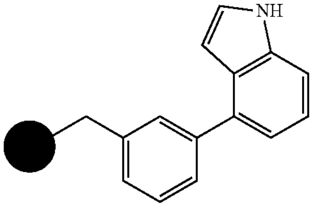
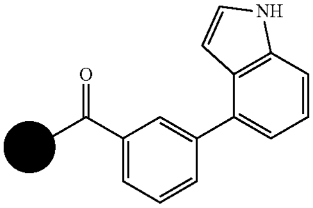
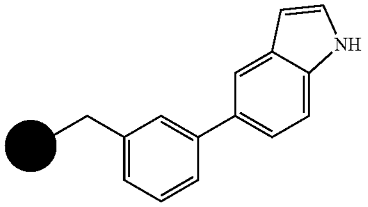
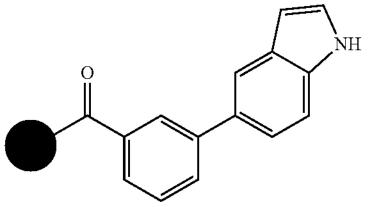
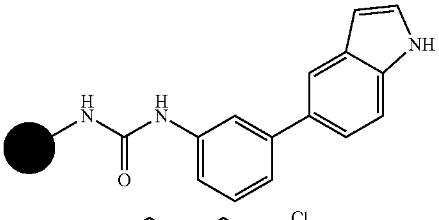
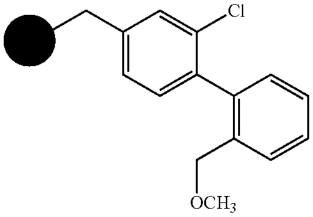
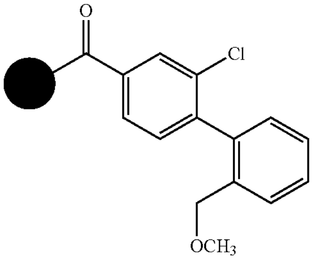

-continued
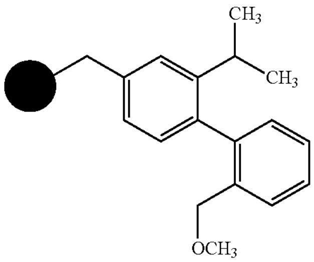
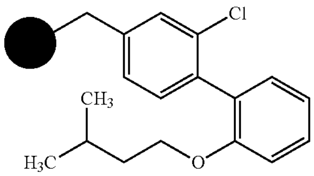
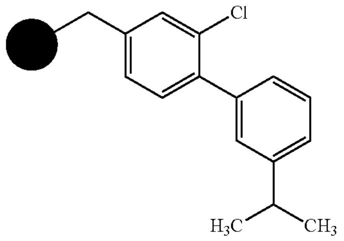
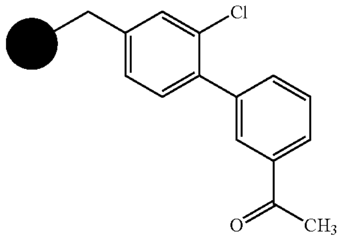
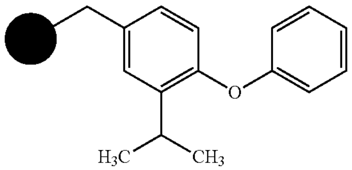
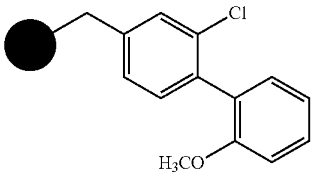
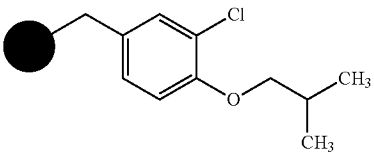
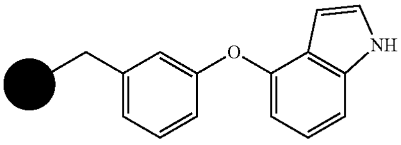
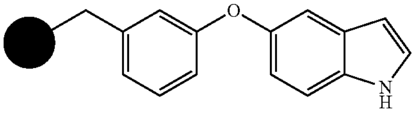
-continued
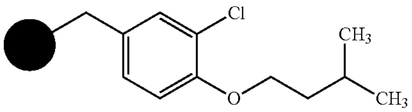
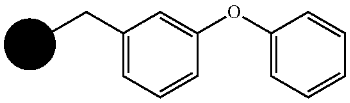
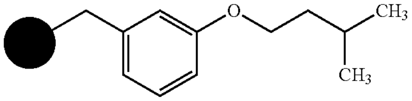
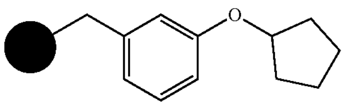
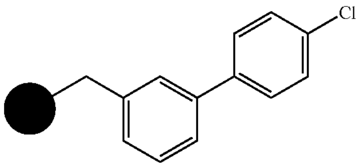
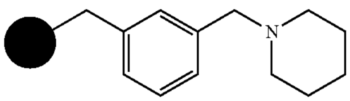
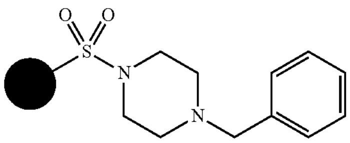
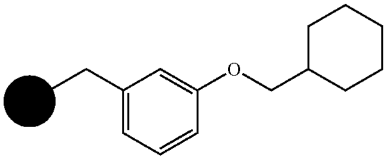
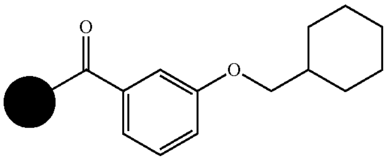
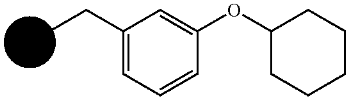
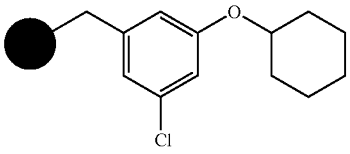
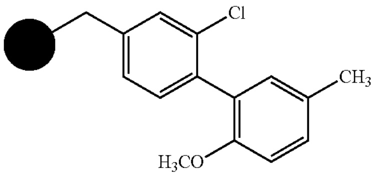
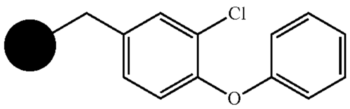

-continued

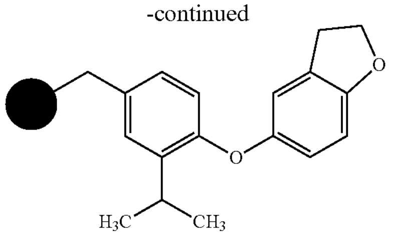

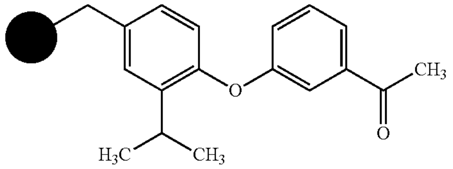

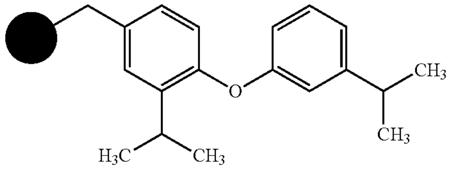

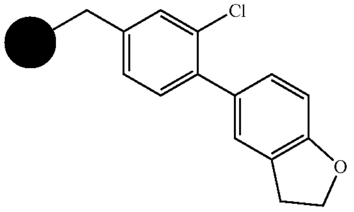

In a more preferred embodiment, a compound of formula (I') or (I) is selected in the group consisting of:

AB150: N-(2-(4-((4-(1H-indol-3-yl)-1H-1,2,3-triazol-1-yl)methyl)piperidin-1-yl)ethyl)benzenesulfonamide;

AB152: N-(2-(4-((4-(1H-indol-3-yl)-1H-1,2,3-triazol-1-yl)methyl)piperidin-1-yl)ethyl)-4-chlorobenzenesulfonamide;

AB153: 4-chloro-N-(2-(4-((4-(5-fluoro-1H-indol-3-yl)-1H-1,2,3-triazol-1-yl)methyl)piperidin-1-yl)ethyl)benzenesulfonamide;

AB201: 5-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB202: 6-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB401: ethyl 3-(1-((1-(2-((4-chlorophenyl)sulfonamido)ethyl)piperidin-4-yl)methyl)-1H-1,2,3-triazol-4-yl)-5-fluoro-1H-indole-2-carboxylate;

AB460: ethyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB433: ethyl 6-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB504: ethyl 5-fluoro-3-(1-((1-(2-((4-methylphenyl)sulfonamido)ethyl)piperidin-4-yl)methyl)-1H-1,2,3-triazol-4-yl)-1H-indole-2-carboxylate;

AB505: ethyl 5-chloro-3-(1-((1-(2-((4-methylphenyl)sulfonamido)ethyl)piperidin-4-yl)methyl)-1H-1,2,3-triazol-4-yl)-1H-indole-2-carboxylate;

AB503: ethyl 6-chloro-3-(1-((1-(2-((4-methylphenyl)sulfonamido)ethyl)piperidin-4-yl)methyl)-1H-1,2,3-triazol-4-yl)-1H-indole-2-carboxylate;

AB529: ethyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB550: ethyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB526: ethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB543: ethyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB536: ethyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB551: ethyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB579: ethyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB582 ethyl 5-chloro-3-(1-((1-(2-((4-isopropylphenyl)sulfonamido)ethyl)piperidin-4-yl)methyl)-1H-1,2,3-triazol-4-yl)-1H-indole-2-carboxylate;

AB577: isopropyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB578: isopropyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB498: isobutyl 3-(1-((1-(2-((4-chlorophenyl)sulfonamido)ethyl)piperidin-4-yl)methyl)-1H-1,2,3-triazol-4-yl)-5-fluoro-1H-indole-2-carboxylate;

AB499: isobutyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB600: isobutyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB601: isobutyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB556: isobutyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB557: isobutyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB598: isobutyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB599: isobutyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB603: isobutyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB668: isobutyl 5-fluoro-3-(1-((1-(2-((4-isobutylphenyl)sulfonamido)ethyl)piperidin-4-yl)methyl)-1H-1,2,3-triazol-4-yl)-1H-indole-2-carboxylate;

AB651: 3-(1-((1-(2-((4-ethylphenyl)sulfonamido)ethyl)piperidin-4-yl)methyl)-1H-1,2,3-triazol-4-yl)-5-fluoro-N-isobutyl-1H-indole-2-carboxamide;

AB652: 5-fluoro-N-isobutyl-3-(1-((1-(2-((4-isopropylphenyl)sulfonamido)ethyl)piperidin-4-yl)methyl)-1H-1,2,3-triazol-4-yl)-1H-indole-2-carboxamide;

AB663: isopentyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB664: isopentyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB669: isopentyl 5-fluoro-3-(1-((1-(2-((4-isobutylphenyl)sulfonamido)ethyl)piperidin-4-yl)methyl)-1H-1,2,3-triazol-4-yl)-1H-indole-2-carboxylate;

AB670: 3-(1-((1-(2-((4-ethylphenyl)sulfonamido)ethyl)piperidin-4-yl)methyl)-1H-1,2,3-triazol-4-yl)-5-fluoro-N-isopentyl-1H-indole-2-carboxamide;

AB671: 5-fluoro-N-isopentyl-3-(1-((1-(2-((4-isopropylphenyl)sulfonamido)ethyl)piperidin-4-yl)methyl)-1H-1,2,3-triazol-4-yl)-1H-indole-2-carboxamide;

AB597: 2-hydroxyethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB614: 2-aminoethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB680: isobutyl 3-(1-((1-((2-chloro-2'-(methoxymethyl)-[1,1'-biphenyl]-4-yl)methyl)piperidin-4-yl)methyl)-1H-1,2,3-triazol-4-yl)-5-fluoro-1H-indole-2-carboxylate;

AB681: isobutyl 3-(1-((1-(2-chloro-2'-(methoxymethyl)-[1,1'-biphenyl]-4-carbonyl)piperidin-4-yl)methyl)-1H-1,2,3-triazol-4-yl)-5-fluoro-1H-indole-2-carboxylate;

AB689: isobutyl 3-(1-((1-((2-chloro-2'-methoxy-[1,1'-biphenyl]-4-yl)methyl)piperidin-4-yl)methyl)-1H-1,2,3-triazol-4-yl)-5-fluoro-1H-indole-2-carboxylate;

AB690: isobutyl 3-(1-((1-(3-chloro-4-(1H-indol-4-yl)benzyl)piperidin-4-yl)methyl)-1H-1,2,3-triazol-4-yl)-5-fluoro-1H-indole-2-carboxylate;

AB691: isobutyl 3-(1-((1-(3-chloro-4-phenoxybenzyl)piperidin-4-yl)methyl)-1H-1,2,3-triazol-4-yl)-5-fluoro-1H-indole-2-carboxylate;

AB692: isobutyl 3-(1-((1-((2-chloro-2'-methoxy-5'-methyl-[1,1'-biphenyl]-4-yl)methyl)piperidin-4-yl)methyl)-1H-1,2,3-triazol-4-yl)-5-fluoro-1H-indole-2-carboxylate;

AB697: isobutyl 5-fluoro-3-(1-((1-(3-isopropyl-4-phenoxybenzyl)piperidin-4-yl)methyl)-1H-1,2,3-triazol-4-yl)-1H-indole-2-carboxylate;

AB703: isobutyl 3-(1-((1-(4-(1H-indol-4-yl)-3-isopropylbenzyl)piperidin-4-yl)methyl)-1H-1,2,3-triazol-4-yl)-5-fluoro-1H-indole-2-carboxylate;

AB704: isobutyl 5-fluoro-3-(1-((1-((2-isopropyl-2'-(methoxymethyl)-[1,1'-biphenyl]-4-yl)methyl)piperidin-4-yl)methyl)-1H-1,2,3-triazol-4-yl)-1H-indole-2-carboxylate;

AB717: isobutyl 3-(1-((1-(4-((2,3-dihydrobenzofuran-5-yl)oxy)-3-isopropylbenzyl)piperidin-4-yl)methyl)-1H-1,2,3-triazol-4-yl)-5-fluoro-1H-indole-2-carboxylate;

AB718: isobutyl 3-(1-((1-(4-(3-acetylphenoxy)-3-isopropylbenzyl)piperidin-4-yl)methyl)-1H-1,2,3-triazol-4-yl)-5-fluoro-1H-indole-2-carboxylate;

AB713: isobutyl 5-fluoro-3-(1-((1-(3-isopropyl-4-(3-isopropylphenoxy)benzyl)piperidin-4-yl)methyl)-1H-1,2,3-triazol-4-yl)-1H-indole-2-carboxylate;

AB753: isobutyl 3-(1-((1-(3-chloro-4-(1H-indol-5-yl)benzyl)piperidin-4-yl)methyl)-1H-1,2,3-triazol-4-yl)-5-fluoro-1H-indole-2-carboxylate;

AB731: isobutyl 3-(1-((1-(3-chloro-4-(2,3-dihydrobenzofuran-5-yl)benzyl)piperidin-4-yl)methyl)-1H-1,2,3-triazol-4-yl)-5-fluoro-1H-indole-2-carboxylate;

AB739: isobutyl 3-(1-((1-((3'-acetyl-2-chloro-[1,1'-biphenyl]-4-yl)methyl)piperidin-4-yl)methyl)-1H-1,2,3-triazol-4-yl)-5-fluoro-1H-indole-2-carboxylate;

AB758: isobutyl 3-(1-((1-((2-chloro-3'-isopropyl-[1,1'-biphenyl]-4-yl)methyl)piperidin-4-yl)methyl)-1H-1,2,3-triazol-4-yl)-5-fluoro-1H-indole-2-carboxylate;

AB760: isobutyl 3-(1-((1-(3-chloro-4-isobutoxybenzyl)piperidin-4-yl)methyl)-1H-1,2,3-triazol-4-yl)-5-fluoro-1H-indole-2-carboxylate;

AB746: isobutyl 3-(1-((1-(3-chloro-4-(isopentyloxy)benzyl)piperidin-4-yl)methyl)-1H-1,2,3-triazol-4-yl)-5-fluoro-1H-indole-2-carboxylate;

AB743: isobutyl 3-(1-((1-(2-chloro-2'-(isopentyloxy)-[1,1'-biphenyl]-4-carbonyl)piperidin-4-yl)methyl)-1H-1,2,3-triazol-4-yl)-5-fluoro-1H-indole-2-carboxylate;

AB756: isobutyl 3-(1-((1-(4-(1H-indol-4-yl)-3-(trifluoromethyl)benzoyl)piperidin-4-yl)methyl)-1H-1,2,3-triazol-4-yl)-5-fluoro-1H-indole-2-carboxylate; and AB755: isobutyl 3-(1-((1-((4-benzylpiperazin-1-yl)sulfonyl)piperidin-4-yl)methyl)-1H-1,2,3-triazol-4-yl)-5-fluoro-1H-indole-2-carboxylate AB912: isobutyl 5-fluoro-3-(1-((1-(2-((4-(trifluoromethoxy)phenyl)sulfonamido)ethyl) piperidin-4-yl)methyl)-1H-1,2,3-triazol-4-yl)-1H-indole-2-carboxylate;

AB913: isobutyl 3-(1-((1-(2-([1,1'-biphenyl]-4-sulfonamido)ethyl)piperidin-4-yl)methyl)-1H-1,2,3-triazol-4-yl)-5-fluoro-1H-indole-2-carboxylate;

AB914: isobutyl 3-(1-((1-(2-((4-cyclohexylphenyl)sulfonamido)ethyl)piperidin-4-yl)methyl)-1H-1,2,3-triazol-4-yl)-5-fluoro-1H-indole-2-carboxylate;

AB917: isobutyl 5-fluoro-3-(1-((1-(2-((4-isopropoxyphenyl)sulfonamido)ethyl)piperidin-4-yl)methyl)-1H-1,2,3-triazol-4-yl)-1H-indole-2-carboxylate;

AB918: isobutyl 3-(1-((1-(2-((4-benzylpiperidine)-1-sulfonamido)ethyl)piperidin-4-yl)methyl)-1H-1,2,3-triazol-4-yl)-5-fluoro-1H-indole-2-carboxylate;

AB929: isobutyl 5-fluoro-3-(1-((1-(2-((4-phenylpiperidine)-1-sulfonamido) ethyl)piperidin-4-yl)methyl)-1H-1,2,3-triazol-4-yl)-1H-indole-2-carboxylate;

AB930: isobutyl 3-(1-((1-(2-((2,3-dihydrobenzofuran)-5-sulfonamido)ethyl)piperidin-4-yl)methyl)-1H-1,2,3-triazol-4-yl)-5-fluoro-1H-indole-2-carboxylate;

AB931: isobutyl 3-(1-((1-(2-((4-(sec-butyl)phenyl)sulfonamido)ethyl)piperidin-4-yl)methyl)-1H-1,2,3-triazol-4-yl)-5-fluoro-1H-indole-2-carboxylate;

AB932: isobutyl 3-(1-((1-(2-((2,3-dihydro-1H-indene)-5-sulfonamido)ethyl)piperidin-4-yl)methyl)-1H-1,2,3-triazol-4-yl)-5-fluoro-1H-indole-2-carboxylate;

AB933: isobutyl 5-fluoro-3-(1-((1-(2-((4-phenoxyphenyl)sulfonamido)ethyl)piperidin-4-yl)methyl)-1H-1,2,3-triazol-4-yl)-1H-indole-2-carboxylate AB934: isobutyl 3-(1-((1-(2-((4-(tert-butyl)phenyl)sulfonamido)ethyl)piperidin-4-yl)methyl)-1H-1,2,3-triazol-4-yl)-5-fluoro-1H-indole-2-carboxylate;

AB935: isobutyl 5-fluoro-3-(1-((1-(2-(((4-(trifluoromethyl)phenyl)methyl) sulfonamido)ethyl) piperidin-4-yl)methyl)-1H-1,2,3-triazol-4-yl)-1H-indole-2-carboxylate;

AB936: isobutyl 3-(1-((1-(2-(((4-chlorophenyl)methyl)sulfonamido)ethyl)piperidin-4-yl)methyl)-1H-1,2,3-triazol-4-yl)-5-fluoro-1H-indole-2-carboxylate;

AB937: isobutyl 3-(1-((1-(2-(((3-chlorophenyl)methyl)sulfonamido)ethyl)piperidin-4-yl)methyl)-1H-1,2,3-triazol-4-yl)-5-fluoro-1H-indole-2-carboxylate;

AB938: isobutyl 3-(1-((1-((4-(tert-butyl)phenyl)sulfonyl)piperidin-4-yl)methyl)-1H-1,2,3-triazol-4-yl)-5-fluoro-1H-indole-2-carboxylate;

AB939: isobutyl 3-(1-((1-((2,3-dihydrobenzofuran-6-yl)sulfonyl)piperidin-4-yl)methyl)-1H-1,2,3-triazol-4-yl)-5-fluoro-1H-indole-2-carboxylate;

AB1030: isobutyl 3-(1-((1-(2-(((4-bromophenyl)methyl) sulfonamido)ethyl)piperidin-4-yl)methyl)-1H-1,2,3-triazol-4-yl)-5-fluoro-1H-indole-2-carboxylate;

AB1031: isobutyl 3-(1-((1-(2-(((3-bromophenyl)methyl) sulfonamido)ethyl)piperidin-4-yl)methyl)-1H-1,2,3-triazol-4-yl)-5-fluoro-1H-indole-2-carboxylate;

AB1032: isobutyl 3-(1-((1-(2-((4-(1H-pyrazol-4-yl)phenyl) sulfonamido)ethyl)piperidin-4-yl)methyl)-1H-1,2,3-triazol-4-yl)-5-fluoro-1H-indole-2-carboxylate;

AB1070: isobutyl 3-(1-((1-(2-((4',4'-difluoro-2',3',4',5'-tetrahydro-[1,1'-biphenyl])-4-sulfonamido)ethyl)piperidin-4-yl)methyl)-1H-1,2,3-triazol-4-yl)-5-fluoro-1H-indole-2-carboxylate;

AB1071: isobutyl 5-fluoro-3-(1-((1-(2-((4-(furan-3-yl)phenyl)sulfonamido)ethyl)piperidin-4-yl)methyl)-1H-1,2,3-triazol-4-yl)-1H-indole-2-carboxylate;

AB1072: isobutyl 3-(1-((1-(2-((3,4-dihydro-2H-benzo[b][1,4]dioxepine)-7-sulfonamido)ethyl)piperidin-4-yl) methyl)-1H-1,2,3-triazol-4-yl)-5-fluoro-1H-indole-2-carboxylate;

AB1073: isobutyl 5-fluoro-3-(1-((1-(2-((4-(2-(pyrrolidin-1-yl)pyridin-3-yl)phenyl) sulfonamido)ethyl)piperidin-4-yl)methyl)-1H-1,2,3-triazol-4-yl)-1H-indole-2-carboxylate;

AB1074: isobutyl 3-(1-((1-(2-((4-(3,6-dihydro-2H-pyran-4-yl)phenyl) sulfonamido)ethyl)piperidin-4-yl)methyl)-1H-1,2,3-triazol-4-yl)-5-fluoro-1H-indole-2-carboxylate;

AB1075: isobutyl 5-fluoro-3-(1-((1-(2-((2'-(morpholinomethyl)-[1,1'-biphenyl])-4-sulfonamido)ethyl)piperidin-4-yl)methyl)-1H-1,2,3-triazol-4-yl)-1H-indole-2-carboxylate;

AB1076: isobutyl 3-(1-((1-(2-((2'-cyano-[1,1'-biphenyl])-4-sulfonamido)ethyl)piperidin-4-yl)methyl)-1H-1,2,3-triazol-4-yl)-5-fluoro-1H-indole-2-carboxylate;

AB1130: isobutyl 3-(1-((1-(2-((4-(3,5-dimethylisoxazol-4-yl)phenyl)sulfonamido) ethyl)piperidin-4-yl)methyl)-1H-1,2,3-triazol-4-yl)-5-fluoro-1H-indole-2-carboxylate;

AB1133: isobutyl 3-(1-((1-(2-((4-(2-chloropyridin-3-yl) phenyl)sulfonamido)ethyl)piperidin-4-yl)methyl)-1H-1,2,3-triazol-4-yl)-5-fluoro-1H-indole-2-carboxylate;

AB1134: isobutyl 3-(1-((1-(2-((4'-cyano-[1,1'-biphenyl])-4-sulfonamido)ethyl)piperidin-4-yl)methyl)-1H-1,2,3-triazol-4-yl)-5-fluoro-1H-indole-2-carboxylate;

AB1205: isobutyl 5-fluoro-3-(1-((1-(2-((2'-methoxy-[1,1'-biphenyl])-4-sulfonamido)ethyl) piperidin-4-yl)methyl)-1H-1,2,3-triazol-4-yl)-1H-indole-2-carboxylate;

AB1206: isobutyl 3-(1-((1-(2-((2',6'-dimethoxy-[1,1'-biphenyl])-4-sulfonamido)ethyl) piperidin-4-yl)methyl)-1H-1,2,3-triazol-4-yl)-5-fluoro-1H-indole-2-carboxylate;

AB1207: isobutyl 5-fluoro-3-(1-((1-(2-((4-(2-fluoropyridin-3-yl)phenyl)sulfonamido) ethyl)piperidin-4-yl)methyl)-1H-1,2,3-triazol-4-yl)-1H-indole-2-carboxylate;

AB1208: isobutyl 3-(1-((1-(2-((2',6'-difluoro-[1,1'-biphenyl])-4-sulfonamido)ethyl)piperidin-4-yl)methyl)-1H-1,2,3-triazol-4-yl)-5-fluoro-1H-indole-2-carboxylate;

AB1209: isobutyl 3-(1-((1-(2-((2'-(dimethylamino)-[1,1'-biphenyl])-4-sulfonamido) ethyl)piperidin-4-yl)methyl)-1H-1,2,3-triazol-4-yl)-5-fluoro-1H-indole-2-carboxylate;

AB1210: isobutyl 5-fluoro-3-(1-((1-(2-((p-tolylmethyl) sulfonamido)ethyl)piperidin-4-yl)methyl)-1H-1,2,3-triazol-4-yl)-1H-indole-2-carboxylate;

AB1303: isobutyl 5-fluoro-3-(1-((1-(2-((2'-(methoxymethyl)-[1,1'-biphenyl])-4-sulfonamido)ethyl)piperidin-4-yl)methyl)-1H-1,2,3-triazol-4-yl)-1H-indole-2-carboxylate;

AB1131: N-(2-(4-((4-(5-fluoro-2-(pyrrolidine-1-carbonyl)-1H-indol-3-yl)-1H-1,2,3-triazol-1-yl)methyl)piperidin-1-yl)ethyl)-4-isobutylbenzenesulfonamide;

AB1132: N-(2-(4-((4-(5-fluoro-2-(morpholine-4-carbonyl)-1H-indol-3-yl)-1H-1,2,3-triazol-1-yl)methyl)piperidin-1-yl)ethyl)-4-isobutylbenzenesulfonamide;

AB1135: N-(2-(4-((4-(2-acetyl-5-fluoro-1H-indol-3-yl)-1H-1,2,3-triazol-1-yl)methyl) piperidin-1-yl)ethyl)-4-isobutylbenzenesulfonamide;

AB1145: N-(2-(4-((4-(5-fluoro-2-pentanoyl-1H-indol-3-yl)-1H-1,2,3-triazol-1-yl)methyl) piperidin-1-yl)ethyl)-4-isobutylbenzenesulfonamide;

AB1231: N-(2-(4-((4-(2-(cyclopropanecarbonyl)-5-fluoro-1H-indol-3-yl)-1H-1,2,3-triazol-1-yl)methyl)piperidin-1-yl)ethyl)-4-isobutylbenzenesulfonamide;

AB1232: 4-(2-chloropyridin-3-yl)-N-(2-(4-((4-(2-(cyclopropanecarbonyl)-5-fluoro-1H-indol-3-yl)-1H-1,2,3-triazol-1-yl)methyl)piperidin-1-yl)ethyl)benzenesulfonamide;

AB1233: N-(2-(4-((4-(2-butyryl-5-fluoro-1H-indol-3-yl)-1H-1,2,3-triazol-1-yl)methyl) piperidin-1-yl)ethyl)-4-(2-chloropyridin-3-yl)benzenesulfonamide;

AB1235: N-(2-(4-((4-(5-fluoro-2-fornyl-1H-indol-3-yl)-1H-1,2,3-triazol-1-yl)methyl) piperidin-1-yl)ethyl)-4-isobutylbenzenesulfonamide;

AB1281: N-(2-(4-((4-(5-fluoro-2-isobutyryl-1H-indol-3-yl)-1H-1,2,3-triazol-1-yl)methyl) piperidin-1-yl)ethyl)-4-isobutylbenzenesulfonamide;

AB1282: 4-(2-chloropyridin-3-yl)-N-(2-(4-((4-(5-fluoro-2-isobutyryl-1H-indol-3-yl)-1H-1,2,3-triazol-1-yl)methyl) piperidin-1-yl)ethyl)benzenesulfonamide;

AB1283: N-(2-(4-((4-(5-fluoro-2-(3-methylbutanoyl)-1H-indol-3-yl)-1H-1,2,3-triazol-1-yl)methyl)piperidin-1-yl) ethyl)-4-isobutylbenzenesulfonamide;

AB1284: 4-(2-chloropyridin-3-yl)-N-(2-(4-((4-(5-fluoro-2-(3-methylbutanoyl)-1H-indol-3-yl)-1H-1,2,3-triazol-1-yl)methyl)piperidin-1-yl)ethyl)benzenesulfonamide;

AB1285: N-(2-(4-((4-(2-(cyclopropanecarbonyl)-5-fluoro-1H-indol-3-yl)-1H-1,2,3-triazol-1-yl)methyl)piperidin-1-yl)ethyl)-4-(3,5-dimethylisoxazol-4-yl)benzenesulfonamide;

AB1286: N-(2-(4-((4-(2-acetyl-5-fluoro-1H-indol-3-yl)-1H-1,2,3-triazol-1-yl)methyl) piperidin-1-yl)ethyl)-4-(3,5-dimethylisoxazol-4-yl)benzenesulfonamide;

AB1287: N-(2-(4-((4-(2-acetyl-5-fluoro-1H-indol-3-yl)-1H-1,2,3-triazol-1-yl)methyl) piperidin-1-yl)ethyl)-2',6'-dimethoxy-[1,1'-biphenyl]-4-sulfonamide;

AB1288: N-(2-(4-((4-(2-acetyl-5-fluoro-1H-indol-3-yl)-1H-1,2,3-triazol-1-yl)methyl)piperidin-1-yl)ethyl)-2',6'-difluoro-[1,1'-biphenyl]-4-sulfonamide;

AB1289: N-(2-(4-((4-(2-acetyl-5-fluoro-1H-indol-3-yl)-1H-1,2,3-triazol-1-yl)methyl) piperidin-1-yl)ethyl)-4-(2-fluoropyridin-3-yl)benzenesulfonamide;

AB1301: N-(2-(4-((4-(5-fluoro-2-nicotinoyl-1H-indol-3-yl)-1H-1,2,3-triazol-1-yl)methyl) piperidin-1-yl)ethyl)-4-isobutylbenzenesulfonamide;

AB1302: N-(2-(4-((4-(5-fluoro-2-(2-methylbutanoyl)-1H-indol-3-yl)-1H-1,2,3-triazol-1-yl)methyl)piperidin-1-yl) ethyl)-4-isobutylbenzenesulfonamide;

AB1304: N-(2-(4-((4-(2-(cyclopropanecarbonyl)-5-fluoro-1H-indol-3-yl)-1H-1,2,3-triazol-1-yl)methyl)piperidin-1-yl)ethyl)-4-(2,6-difluorophenyl)piperidine-1-sulfonamide;

AB1305: N-(2-(4-((4-(2-(cyclopropanecarbonyl)-5-fluoro-1H-indol-3-yl)-1H-1,2,3-triazol-1-yl)methyl)piperidin-1-yl)ethyl)-1-(4-(trifluoromethyl)phenyl)methanesulfonamide;

AB1306: N-(2-(4-((4-(5-fluoro-2-(3-methylbutanoyl)-1H-indol-3-yl)-1H-1,2,3-triazol-1-yl)methyl)piperidin-1-yl)ethyl)-1-(4-(trifluoromethyl)phenyl)methanesulfonamide;

AB1307: N-(2-(4-((4-(2-butyryl-5-fluoro-1H-indol-3-yl)-1H-1,2,3-triazol-1-yl)methyl) piperidin-1-yl)ethyl)-1-(4-(trifluoromethyl)phenyl)methanesulfonamide;

AB1315: N-(2-(4-((4-(2-acetyl-5-fluoro-1H-indol-3-yl)-1H-1,2,3-triazol-1-yl)methyl) piperidin-1-yl)ethyl)-1-(4-(trifluoromethyl)phenyl)methanesulfonamide;

AB1316: N-(2-(4-((4-(2-acetyl-5-fluoro-1H-indol-3-yl)-1H-1,2,3-triazol-1-yl)methyl) piperidin-1-yl)ethyl)-4-(2,6-difluorophenyl)piperidine-1-sulfonamide AB1317: N-(2-(4-((4-(2-acetyl-5-fluoro-1H-indol-3-yl)-1H-1,2,3-triazol-1-yl)methyl) piperidin-1-yl)ethyl)-4-(cyclopropylmethyl)benzenesulfonamide;

AB1318: (S)—N-(2-(3-((4-(2-acetyl-5-fluoro-1H-indol-3-yl)-1H-1,2,3-triazol-1-yl)methyl) pyrrolidin-1-yl)ethyl)-4-isobutylbenzenesulfonamide;

AB1319: (R)—N-(2-(3-((4-(2-acetyl-5-fluoro-1H-indol-3-yl)-1H-1,2,3-triazol-1-yl)methyl) pyrrolidin-1-yl)ethyl)-4-isobutylbenzenesulfonamide;

AB1321: N-(2-(4-(4-(2-acetyl-5-fluoro-1H-indol-3-yl)-1H-1,2,3-triazol-1-yl)piperidin-1-yl)ethyl)-4-isobutylbenzenesulfonamide;

AB1322: N-(2-(4-((4-(2-acetyl-5-fluoro-1H-indol-3-yl)-1H-1,2,3-triazol-1-yl)methyl) piperidin-1-yl)ethyl)-4-(2-fluoropyridin-3-yl)piperidine-1-sulfonamide;

AB1381: N-(2-(4-((4-(2-acetyl-5-fluoro-1H-indol-3-yl)-1H-1,2,3-triazol-1-yl)methyl) piperidin-1-yl)ethyl)-2'-fluoro-6'-hydroxy-[1,1'-biphenyl]-4-sulfonamide;

AB1390: N-(2-(4-((4-(2-acetyl-5-fluoro-1H-indol-3-yl)-1H-1,2,3-triazol-1-yl)methyl) piperidin-1-yl)ethyl)-2'-fluoro-[1,1'-biphenyl]-4-sulfonamide;

AB1393: N-(2-(4-((4-(2-acetyl-5-fluoro-1H-indol-3-yl)-1H-1,2,3-triazol-1-yl)methyl) piperidin-1-yl)ethyl)-2'-cyano-6'-(trifluoromethyl)-[1,1'-biphenyl]-4-sulfonamide;

AB1394: N-(2-(4-((4-(2-acetyl-5-fluoro-1H-indol-3-yl)-1H-1,2,3-triazol-1-yl)methyl) piperidin-1-yl)ethyl)-2'-(trifluoromethyl)-[1,1'-biphenyl]-4-sulfonamide;

AB1401: N-(2-(4-((4-(2-acetyl-5-fluoro-1H-indol-3-yl)-1H-1,2,3-triazol-1-yl)methyl) piperidin-1-yl)ethyl)-2'-fluoro-6'-methoxy-[1,1'-biphenyl]-4-sulfonamide;

AB1402: isobutyl 5-fluoro-3-(1-((1-(2-((2'-fluoro-6'-hydroxy-[1,1'-biphenyl])-4-sulfonamido)ethyl)piperidin-4-yl)methyl)-1H-1,2,3-triazol-4-yl)-1H-indole-2-carboxylate;

AB1403: (S)—N-(2-(3-((4-(2-acetyl-5-fluoro-1H-indol-3-yl)-1H-1,2,3-triazol-1-yl)methyl) piperidin-1-yl)ethyl)-4-isobutylbenzenesulfonamide;

AB1404: N-(2-(3-((4-(2-acetyl-5-fluoro-1H-indol-3-yl)-1H-1,2,3-triazol-1-yl)methyl) azetidin-1-yl)ethyl)-4-isobutylbenzenesulfonamide;

AB1405: N-(2-(4-((4-(5-fluoro-2-(hydroxymethyl)-1H-indol-3-yl)-1H-1,2,3-triazol-1-yl)methyl)piperidin-1-yl)ethyl)-4-isobutylbenzenesulfonamide;

AB1406: 2'-fluoro-N-(2-(4-((4-(5-fluoro-2-(hydroxymethyl)-1H-indol-3-yl)-1H-1,2,3-triazol-1-yl)methyl)piperidin-1-yl)ethyl)-6'-hydroxy-[1,1'-biphenyl]-4-sulfonamide;

AB1415: 2'-fluoro-N-(2-(4-((4-(5-fluoro-2-propionyl-1H-indol-3-yl)-1H-1,2,3-triazol-1-yl)methyl)piperidin-1-yl)ethyl)-6'-hydroxy-[1,1'-biphenyl]-4-sulfonamide;

AB1416: N-(2-(4-((4-(5-fluoro-2-propionyl-1H-indol-3-yl)-1H-1,2,3-triazol-1-yl)methyl) piperidin-1-yl)ethyl)-2',6'-dimethoxy-[1,1'-biphenyl]-4-sulfonamide;

AB1417: N-(2-(4-((4-(5-fluoro-2-propionyl-1H-indol-3-yl)-1H-1,2,3-triazol-1-yl)methyl) piperidin-1-yl)ethyl)-1-(4-(trifluoromethyl)phenyl)methanesulfonamide;

AB1450: N-(2-(4-((4-(2-acetyl-5-fluoro-1H-indol-3-yl)-1H-1,2,3-triazol-1-yl)methyl) piperidin-1-yl)ethyl)-2'-hydroxy-[1,1'-biphenyl]-4-sulfonamide;

AB1451: N-(2-(4-((4-(2-acetyl-5-fluoro-1H-indol-3-yl)-1H-1,2,3-triazol-1-yl)methyl) piperidin-1-yl)ethyl)-2'-fluoro-6'-(trifluoromethyl)-[1,1'-biphenyl]-4-sulfonamide;

AB1452: N-(2-(4-((4-(2-acetyl-5-fluoro-1H-indol-3-yl)-1H-1,2,3-triazol-1-yl)methyl) piperidin-1-yl)ethyl)-2'-cyano-6'-methyl-[1,1'-biphenyl]-4-sulfonamide;

AB1453: N-(2-(4-((4-(2-acetyl-5-fluoro-1H-indol-3-yl)-1H-1,2,3-triazol-1-yl)methyl) piperidin-1-yl)ethyl)-2'-chloro-4'-fluoro-[1,1'-biphenyl]-4-sulfonamide;

AB1454: N-(2-(4-((4-(2-acetyl-5-fluoro-1H-indol-3-yl)-1H-1,2,3-triazol-1-yl)methyl) piperidin-1-yl)ethyl)-2-fluoro-2',6'-dimethoxy-[1,1'-biphenyl]-4-sulfonamide;

AB1455: N-(2-(4-((4-(2-acetyl-5-fluoro-1H-indol-3-yl)-1H-1,2,3-triazol-1-yl)methyl) piperidin-1-yl)ethyl)-2',6'-dimethoxy-2-methyl-[1,1'-biphenyl]-4-sulfonamide;

AB1456: N-(2-(4-((4-(2-acetyl-5-fluoro-1H-indol-3-yl)-1H-1,2,3-triazol-1-yl)methyl) piperidin-1-yl)ethyl)-2-chloro-2',6'-dimethoxy-[1,1'-biphenyl]-4-sulfonamide; and AB1457: N-(2-(4-((4-(2-acetyl-5-fluoro-1H-indol-3-yl)-1H-1,2,3-triazol-1-yl)methyl) piperidin-1-yl)ethyl)-2,2'-difluoro-6'-hydroxy-[1,1'-biphenyl]-4-sulfonamide.

Another object of the invention is a compound of formula (I') or (I) as defined above for use as a drug. A further object of the invention is a pharmaceutical composition comprising a compound of formula (I') or (I) as defined above, and an acceptable pharmaceutical excipient.

In another particular embodiment, the present invention relates to a compound of formula (I') or (I), or a pharmaceutical composition comprising the same for use for preventing and/or treating a cancer. In a more particular embodiment, the present invention relates to a compound of formula (I') or (I), or a pharmaceutical composition comprising the same for use for preventing and/or treating a cancer in a chemoresistant subject. In a preferred embodiment, the cancer is chosen among multiple myeloma, lymphoma, cholangiocarcinoma, a brain cancer, a breast cancer, a colon cancer, a kidney cancer, a leukemia, a liver cancer, a lung cancer, an ovarian cancer, glioblastoma multiforme, melanoma, a skin cancer, and a pancreas cancer.

In a further particular embodiment, the pharmaceutical composition as defined herein further comprises an antitumor drug.

LEGENDS OF THE FIGURES

FIG. 1: Compounds of the invention potently and selectively inhibit CK2 activity in vitro.

FIGS. 1A to 1D: Interaction of AB668 and AB526 on CK2. The Lineweaver-Burk analysis (n=2) confirmed a non-ATP competitive mechanism of CK2 inhibition and a mixed competitive inhibition towards CK2β. $K_i$ values have been calculated from linear regression analysis of the slopes (a/Vmax) of the Lineweaver-Burk double reciprocal plots and Ki' values from linear regression analysis of the y-intercept (α'/Vmax).

FIGS. 1E to 1F: CK2 inhibition by AB668 or AB603 is non-competitive with respect to peptide substrate. In the presence of 0.5 μM (●) of AB668 (E) or 2 μM (●) of AB603 (F), adding increasing concentrations of CK2β-dependent peptide substrate at a saturating concentration of ATP (100 μM) had no effect on the extent of inhibition showing that the inhibition is also not competitive with the peptide substrate (n=2).

FIG. 1G: AB668 inhibits phosphorylation of a CK2β-dependent protein substrate SIX-1, a protein exclusively phosphorylated by the CK2 holoenzyme. Incubation of SIX-1 with CK2α and increasing concentration of CK2β in the presence of AB668 led to ~90% decrease in SIX-1 phosphorylation (▷) as compared to the same experiment in the absence of inhibitor.

FIG. 1H: A panel of 69 kinases was screened with 2 μM AB668 (n=2), a concentration ~50 times above its $IC_{50}$.

FIGS. 1I and 1J: Effect of AB668 and AB603 on CK2 activity. CK2α (●) and CK2 holoenzyme (●) were not inhibited to the same extent by AB668 (I) or by AB603 (J), indicating that the inhibition pattern was also dependent on the presence of CK2p subunit.

Figure 2:
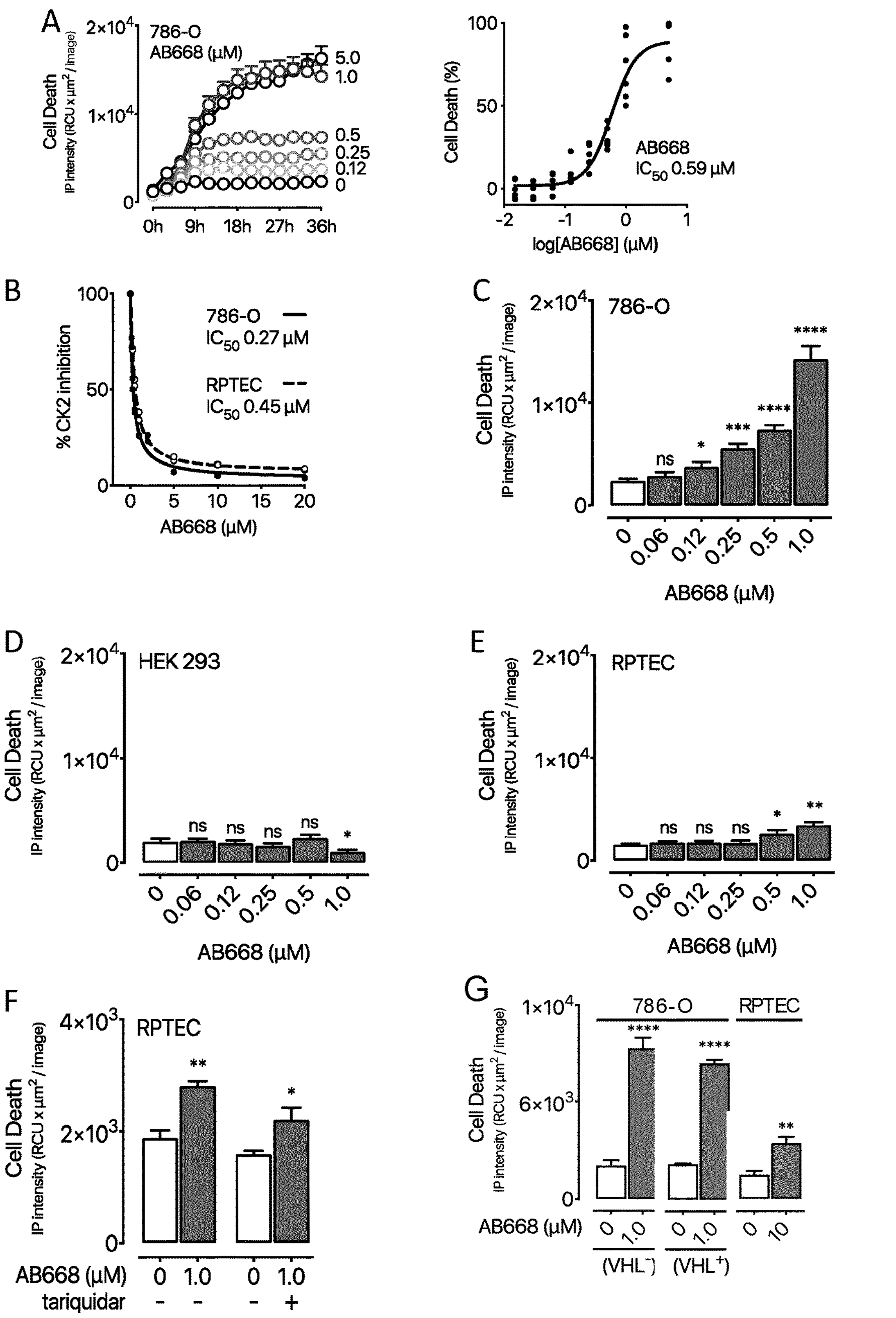
Figure 2:
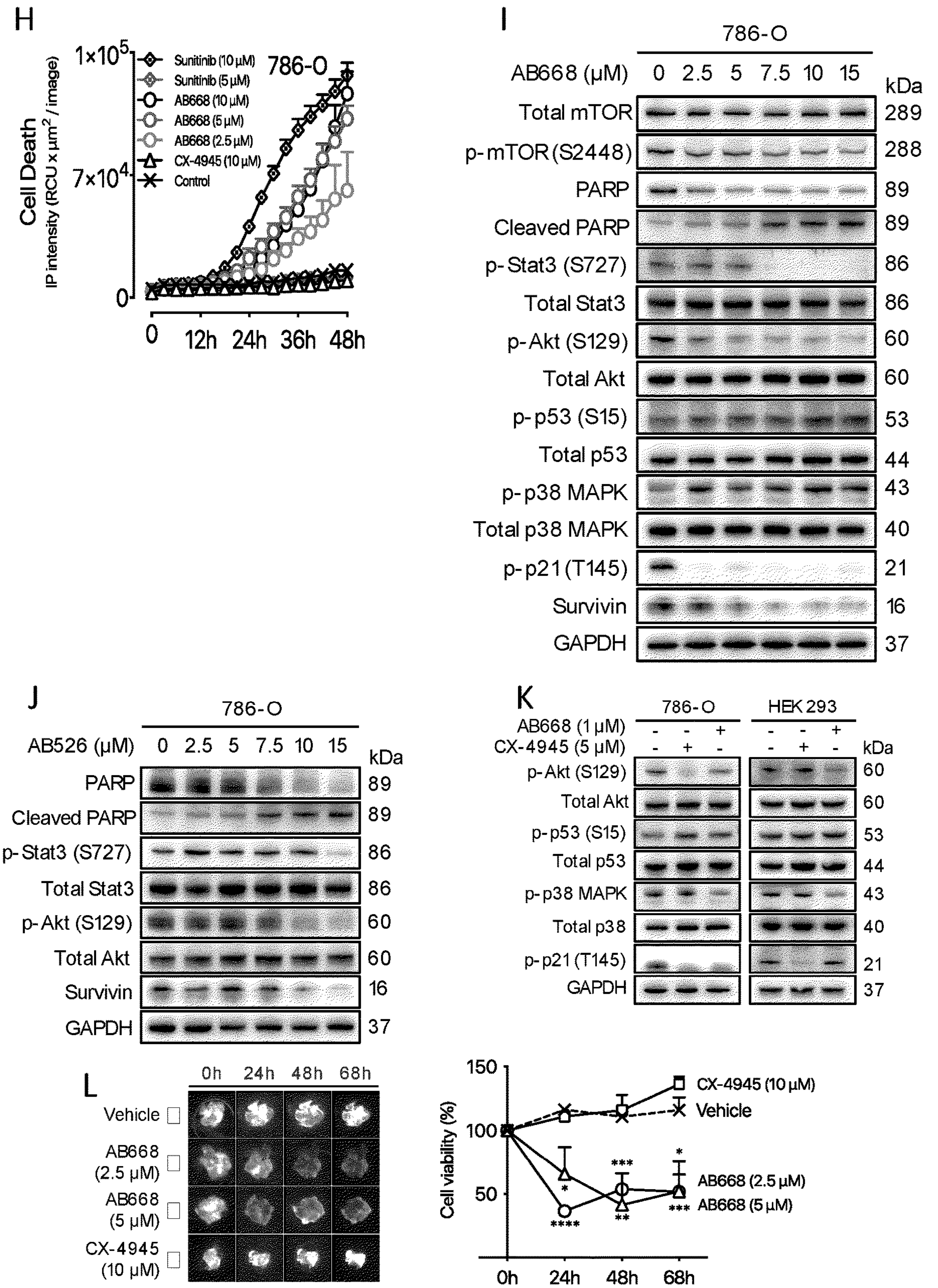

FIG. 2: Compounds of the invention rapidly induce death of human kidney cancer cell lines.

FIG. 2A: Effect of AB668 at various concentrations on human 786-O cell line. $IC_{50}$ value is plotted on the right and determined by linear interpolation after transformation to log[c] scale (n=6).

FIG. 2B: 786-O and RPTEC cells were incubated for 24 hours in the presence of various concentrations of AB668 then CK2 activity in the cell extracts was measured by radiometric kinase assays (n=2).

FIGS. 2C to 2E: Normal or carcinoma renal cell lines were treated for 36 hours with increasing concentrations of AB668. 786-O cells (C) were much more sensitive to AB668-mediated cell death than RPTEC (D) or HEK 293 (E) cells (n=4 to 6).

FIG. 2F: RPTEC cells were treated for 48 hours with 1 μM of AB668 (n=5) or with 1 μM of AB668 combined with 5 μM of tariquidar (Sigma-Aldrich) (n=5). Under the same experimental conditions, the presence of P-glycoprotein inhibitor has not changed the effect of AB668 on normal renal cells.

FIG. 2G: 786-O (VHL+/−) and RPTEC cells were treated for 24 hours with 1 and 10 μM of AB668 respectively (n=5). Compared to normal cells, AB668 was much more efficient in inducing cell death in RCC lines.

FIG. 2H: Effect of AB668, CX-4945 and sunitinib (from Selleck Chemicals), at various concentrations on 786-O cells. Compared to CX-4945 and sunitinib, AB668 was much more efficient in inducing cell death at 5 and 2.5 μM. Cell death was automatically quantified from images captured every 3 hours for the duration of the experiments using an Essen IncuCyte Zoom live cell microscopy incubator.

FIGS. 2I to 2K: AB668 and AB526 inhibit CK2-dependent substrate phosphorylation in cells and induce apoptosis. 786-O and RPTEC cells were incubated for 48 hours (I and J) or for 24 hours (K) with either DMSO or with increasing concentrations of AB668, AB526 or CX-4945. Cells were then lysed and analyzed by western blot with the indicated antibodies. Changes in the expression of two known apoptosis markers, (appearance of cleaved-PARP and decrease of surviving) were observed simultaneously after treatment by increasing concentrations of AB668 and AB526. These inhibitors also affected the phosphorylation levels of several signaling molecules such as Akt and Stat3, used as reporters of CK2 cellular activity, and the cell cycle inhibitor p21, p38-MAPK stress kinase and tumor suppressor protein p53.

FIG. 2L: Effect of AB668 and CX-4945 on tissue slice cultures from 786-O-luc tumor xenografts (n=2). Left panel: luminescence measurement in the tumor slices. Right panel: Cell viability values (mean pixel intensity) was divided by the corresponding slice area and multiplied by 100. This percentage was divided by the one at TO, for all the others time points and was expressed as mean±SEM. The statistical analysis of cell viability was performed with 2-way ANOVA test for each time point compared to vehicle treatment (DMSO).

Figure 3:
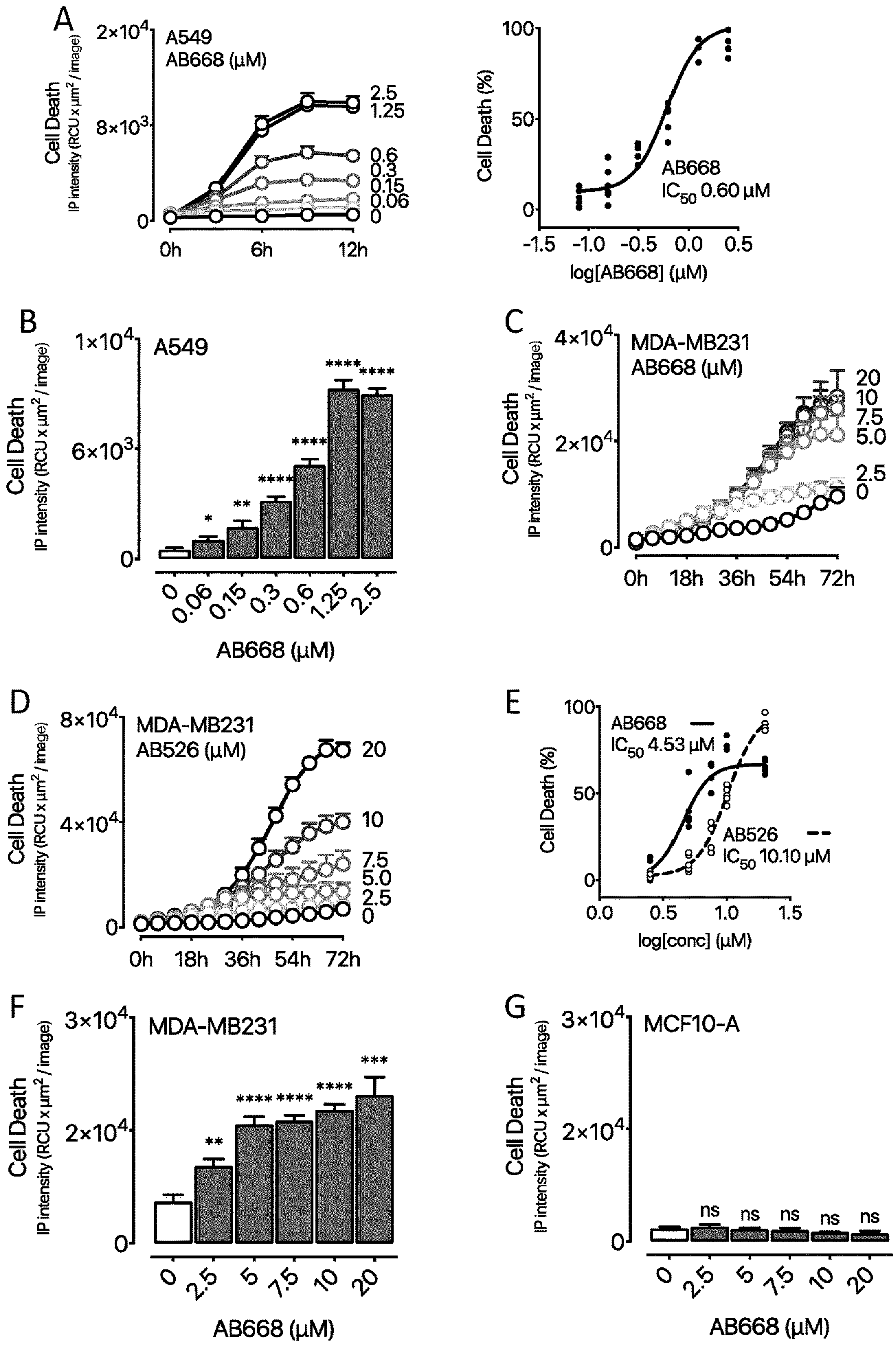
Figure 3:
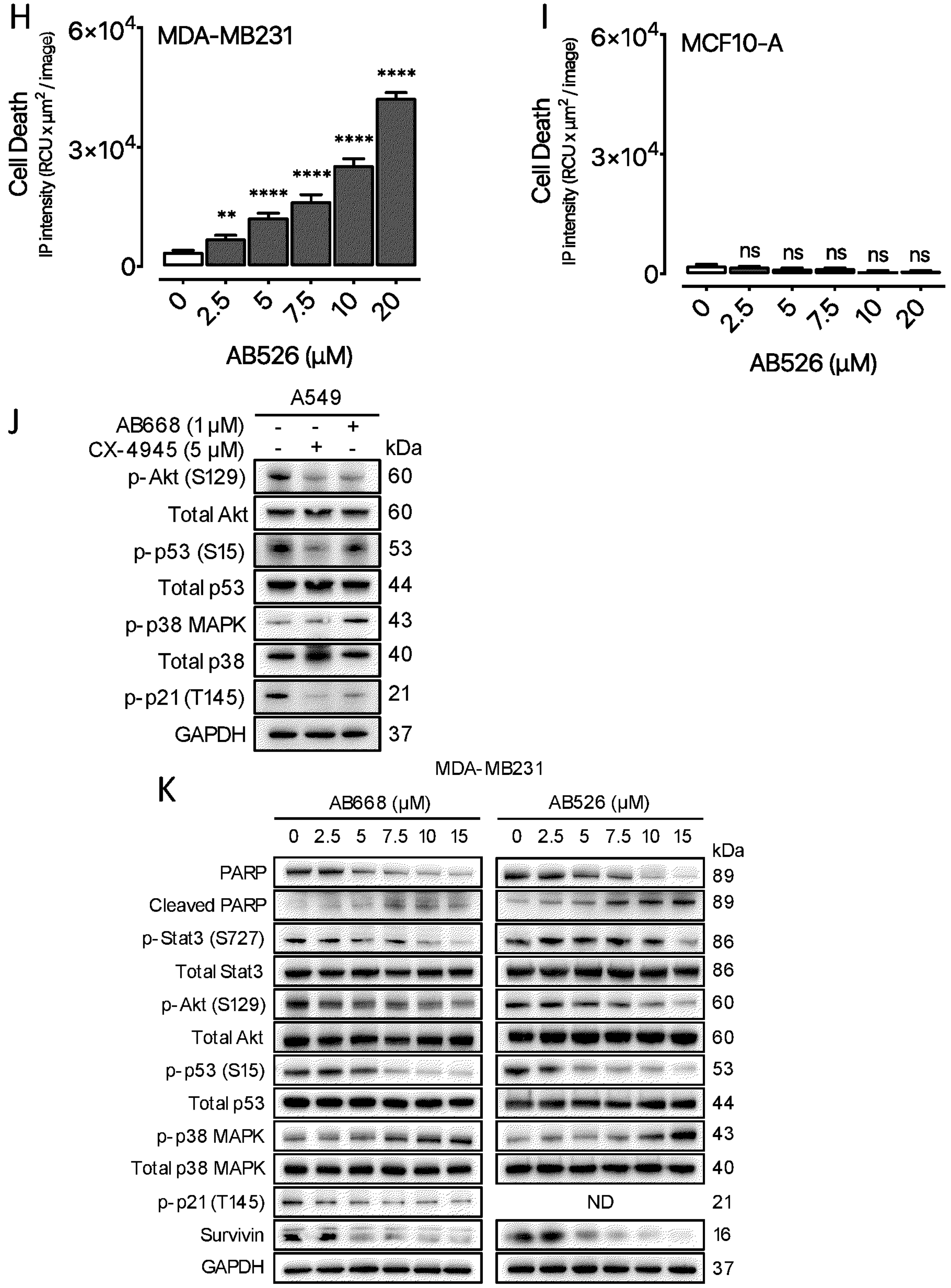

FIG. 3. Compounds according to the invention rapidly induce death of different human breast and lung cancer cell lines.

FIG. 3A: Effect of AB668 at various concentrations on human lung cancer A549 cell line. $IC_{50}$ value is plotted on the right and determined by linear interpolation after transformation to log[c] scale (n=6).

FIG. 3B: A549 cells were incubated for 24 hours in the presence of various concentrations of AB668 (n=6).

FIGS. 3C to 3E: Effect of AB668 or AB526 at various concentrations on human breast cancer MDA-MB231 cell line. $IC_{50}$ values are plotted on the right (E) and determined by linear interpolation after transformation to log[c] scale (n=6).

FIGS. 3F to 3I: MDA-MB231 or MCF10A cells were incubated for 48 hours with increasing concentrations of AB668 (F and G) or AB526 (H and I). Triple-Negative MDA-MB231 cells were much more sensitive to AB668 or AB526-mediated cell death than normal MCF10A cells. Cell death was automatically quantified from images captured every 3 hours for the duration of the experiments using an Essen IncuCyte Zoom live cell microscopy incubator.

FIGS. 3J and 3K:

AB668 and AB526 inhibit CK2-dependent substrate phosphorylation and induce apoptosis in different cancer cell lines. A549 cells were incubated for 24 hours (J) and MDA-MB231 cells for 48 hours (K) with either DMSO or with increasing concentrations of AB668, AB526 or CX-4945. Cells were then lysed and analyzed by western blot with the indicated antibodies. (J) Effects of AB668 and CX-4945 in A549 cell lines. (K) Changes in the expression of two apoptosis markers (appearance of cleaved PARP and decrease of survivin levels) were observed simultaneously after treatment by AB668 and AB526. These inhibitors also affected the phosphorylation levels of Akt and Stat3, used as reporters of CK2 cellular activity, as well as the cell cycle inhibitor p21, p38-MAPK stress kinase and tumor protein p53. ND, not determined.

Figure 4:
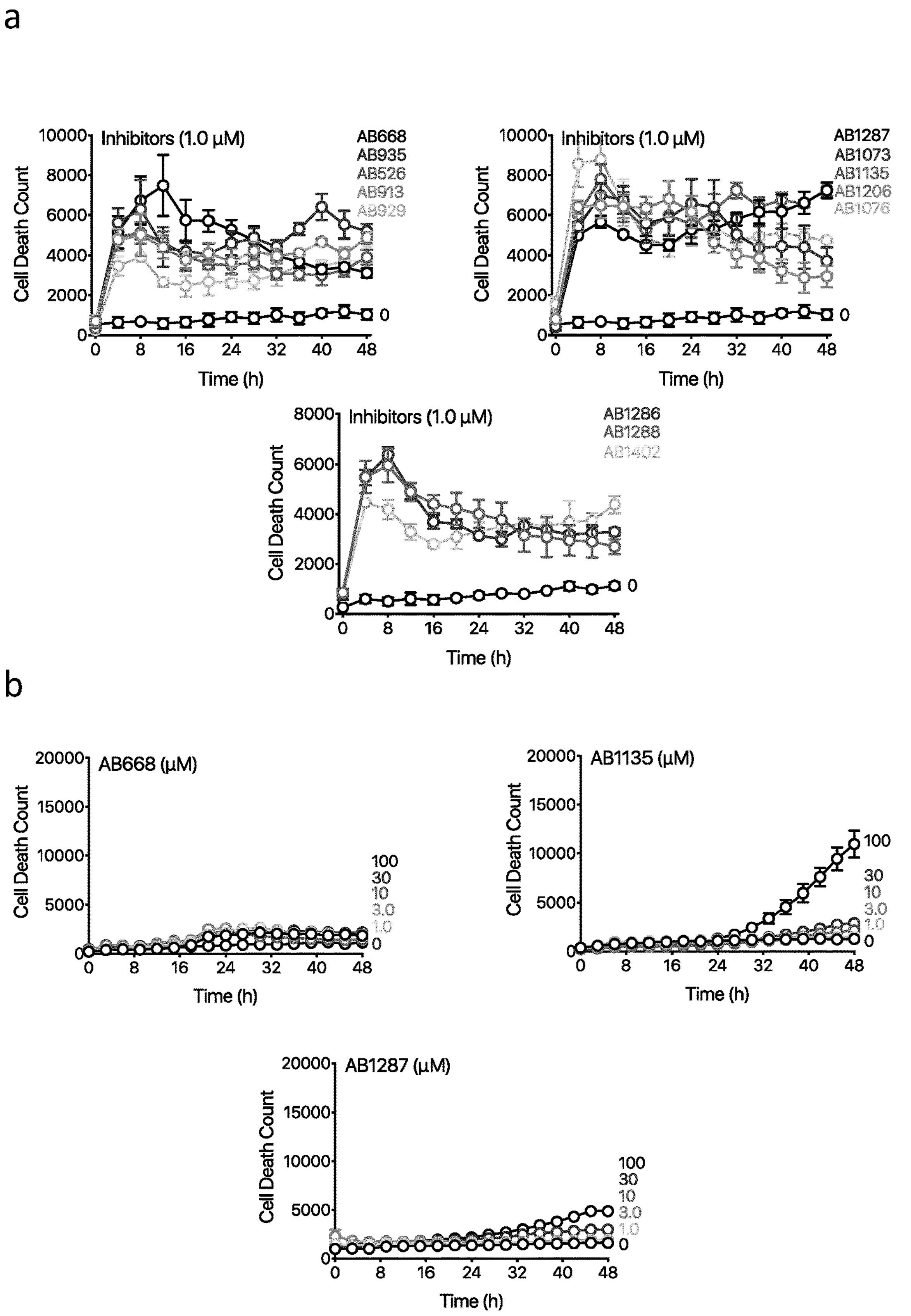
Figure 4:
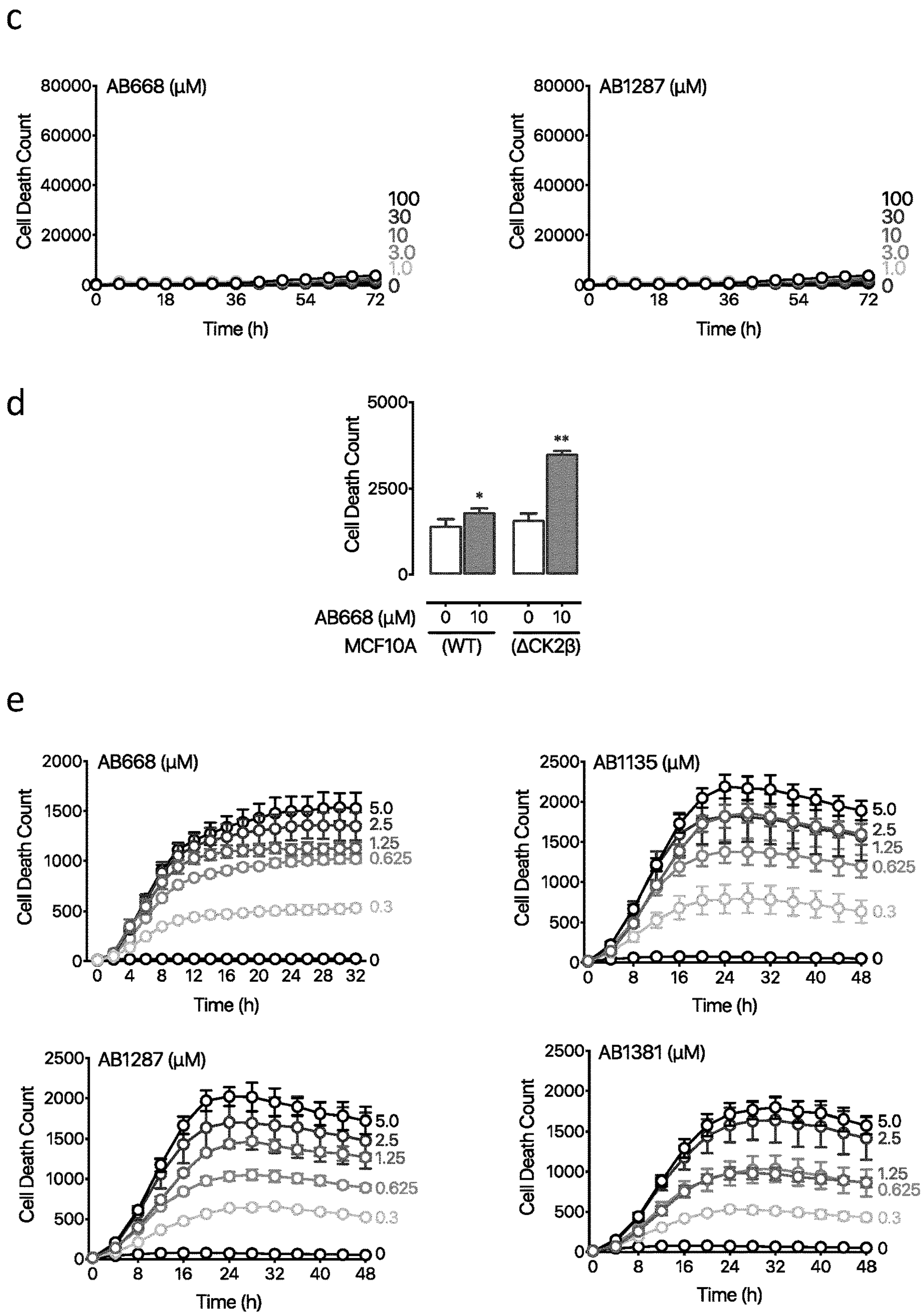
Figure 4:
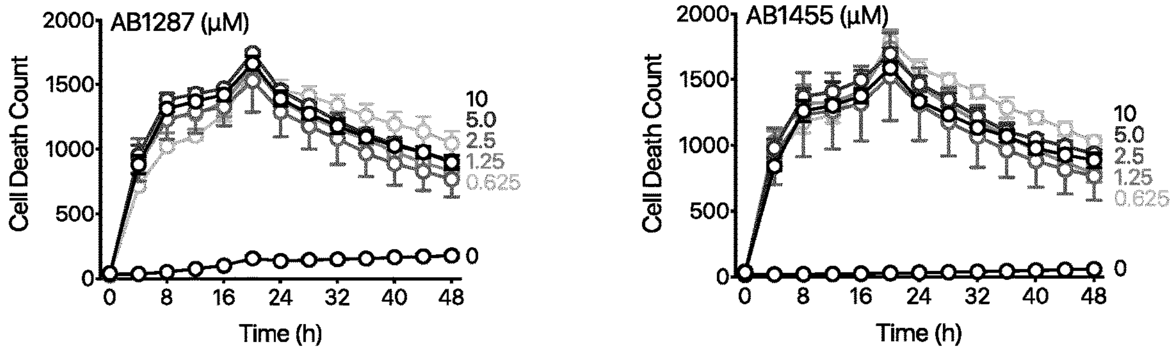

FIG. 4: Compounds according to the invention rapidly induce death of cancer cell lines. FIG. 4*a*: Effect of AB526, AB668, AB913, AB929, AB935, AB1073, AB1076, AB1135, AB1206, AB1286, AB1287, AB1288 and AB1402 at 1.0 μM on human ACHN cell line (n=5).

FIG. 4*b*: Effect of AB668, AB1135 and AB1287 at various concentrations on RPTEC cell line. Compared to normal cells, compounds of the invention were much more efficient in inducing cell death in cancer cell lines (n=5).

FIG. 4*c*: Effect of AB668 and AB1287 at various concentrations on MCF10-A cells. Compared to normal cells, compounds of the invention were much more efficient in inducing cell death in cancer cell lines (n=5).

FIG. 4*d*: Cell death in MCF10-A, induces by AB668 was more pronounced in CK2β-depleted cells than in WT cells, corroborating that this chemical inhibitor behaves as a CK2β antagonist in living cells (n=5).

FIG. 4*e*: Effect of AB668, AB1135, AB1287 and AB1381 at various concentrations on skin cancer A375 cell line (n=5).

FIG. 4*f*: Effect of AB1287 and AB1455 at various concentrations on skin cancer SKMEL-2 cell line (n=5).

DETAILED DESCRIPTION OF THE INVENTION

Definitions

According to the present invention, the terms below have the following meanings:

The terms mentioned herein with prefixes such as for example $C_1$-$C_6$, can also be used with lower numbers of carbon atoms such as $C_1$-$C_2$. If, for example, the term $C_1$-$C_6$ is used, it means that the corresponding hydrocarbon chain may comprise from 1 to 6 carbon atoms, especially 1, 2, 3, 4, 5, or 6 carbon atoms. If, for example, the term $C_1$-$C_3$ is used, it means that the corresponding hydrocarbon chain may comprise from 1 to 3 carbon atoms, especially 1, 2, or 3 carbon atoms.

The term "alkyl" refers to a saturated, linear or branched aliphatic group. The term "($C_1$-$C_6$)alkyl" more specifically means methyl, ethyl, propyl, isopropyl, butyl, isobutyl, pentyl, isopentyl, or hexyl.

The term "alkoxy" or "alkyloxy" corresponds to the alkyl group as above defined bonded to the molecule by an —O— (ether) bond. ($C_1$-$C_6$)alkoxy includes methoxy or methyloxy, ethoxy or ethyloxy, propoxy or propyloxy, isopropoxy or isopropyloxy, butoxy or butyloxy, isobutoxy or isobutyloxy, pentoxy or pentyloxy, isopentoxy or isopentyloxy, and hexoxy hexyloxy.

The term "3-20 membered ring" corresponds to a ring having between 3 and 20 atoms. Such a term includes the term "3-10 membered ring" having between 3 and 10 atoms. The term "ring" corresponds to a mono-, bi, or tricycle, which can be saturated or unsaturated, and optionally comprises at least one heteroatom. Particularly, the term "ring" includes a cycloalkyl, a heterocycloalkyl, an aryl, and a heteroaryl.

The term "cycloalkyl" corresponds to a saturated or unsaturated mono-, bi- or tri-cyclic alkyl group comprising between 3 and 20, preferably between 3 and 10 atoms of carbons. It also includes fused, bridged, or spiro-connected cycloalkyl groups. The term "cycloalkyl" includes for instance cyclopropyl, cyclobutyl, cyclopentyl, and cyclohexyl, preferably cyclopropyl, cyclopentyl, and cyclohexyl.

The term "heterocycloalkyl" corresponds to a saturated or unsaturated cycloalkyl group as above defined further comprising at least one heteroatom such as nitrogen, oxygen, or sulphur atom. It also includes fused, bridged, or spiro-connected heterocycloalkyl groups. Representative heterocycloalkyl groups include, but are not limited to dioxolanyl, benzo [1,3]dioxolyl, azetidinyl, oxetanyl, pyrazolinyl, pyranyl, thiomorpholinyl, pyrazolidinyl, piperidyl, piperazinyl, 1,4-dioxanyl, imidazolinyl, pyrrolinyl, pyrrolidinyl, piperidinyl, imidazolidinyl, morpholinyl, 1,4-dithianyl, pyrrolidinyl, oxozolinyl, oxazolidinyl, isoxazolinyl, isoxazolidinyl, thiazolinyl, thiazolidinyl, isothiazolinyl, isothiazolidinyl, dihydropyranyl, tetrahydropyranyl, tetrahydrofuranyl, and tetrahydrothiophenyl. In a preferred embodiment, the heterocycloalkyl group is pyrrolidinyl, piperidinyl, piperazinyl, and morpholinyl.

"Cycloalkyl" and "heterocycloalkyl" also include cycloalkenyl and heterocycloalkenyl which correspond respectively to unsaturated cycloalkyl and unsaturated heterocycloalkyl such as cyclohexenyl, and dihydropyranyl.

The term "aryl" corresponds to a mono- or bi-cyclic aromatic hydrocarbons having from 6 to 12 carbon atoms. For instance, the term "aryl" includes phenyl, naphtalenyl, or anthracenyl. In a preferred embodiment, the aryl is a phenyl or a naphtalenyl, more preferably a phenyl.

The term "heteroaryl" as used herein corresponds to an aromatic, mono- or poly-cyclic group comprising between 5 and 14 atoms and comprising at least one heteroatom such as nitrogen, oxygen or sulphur atom. As used herein, the term "heteroaryl" further includes the "fused arylheterocycloalkyl" and "fused heteroarylcycloalkyl". The terms "fused arylheterocycloalkyl" and "fused heteroarylcycloalkyl" correspond to a bicyclic group in which an aryl as above defined or a heteroaryl is respectively bounded to the heterocycloalkyl or the cycloalkyl as above defined by at least two-carbons. In other tenns, the aryl or the heteroaryl shares a carbon bond with the heterocycloalkyl or the cycloalkyl. Examples of such mono- and poly-cyclic heteroaryl group, fused arylheterocycloalkyl and fused arylcycloalkyl may be: pyridinyl, thiophenyl, furanyl, pyrrolyl, pyrazolyl, imidazolyl, oxazolyl, isoxazolyl, thiazolyl, isothiazolyl, triazolyl, tetrazolyl, oxadiazolyl, furazanyl, thiadiazolyl, tetrazolyl, benzofuranyl, thianaphthalenyl, indolyl, indolinyl, indanyl, quinolinyl, isoquinolinyl, benzimidazolyl, tetrahydroquinolinyl, tetrahydroisoquinolinyl, triazinyl, thianthrenyl, benzofuranyl, dihydrobenzofuranyl, isobenzofuranyl, benzothiophenyl, isobenzothiophenyl, chromenyl, xanthenyl, phenoxanthinyl, pyrazinyl, pyridazinyl, indolizinyl, isoindolyl, indazolyl, purinyl, quinolizinyl, phtalazinyl, naphthyridinyl, quinoxalinyl, quinazolinyl, cinnolinyl, pteridinyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, indolinyl, isoindolinyl, oxazolidinyl, benzotriazolyl, benzoisoxazolyl, oxindolyl, benzoxazolyl, benzoxazolinyl, benzoxazinyl, benzothienyl, benzothiazolyl, benzodiazepinyl, benzazepinyl, benzoxazepinyl, isatinyl, dihydrobenzodioxepinyl, dihydropyridyl, pyrimidinyl, s-triazinyl, oxazolyl, or thiofuranyl. A fused arylheterocycloalkyl is for instance an indolinyl (phenyl fused to a pyrrolidinyl) and a dihydrobenzofuranyl (phenyl fused to a dihydrofuranyl).

The term "halogen" corresponds to a fluorine, chlorine, bromine, or iodine atom, preferably a fluorine or a chlorine.

The expressions "a radical substituted by a" and "a radical substituted by at least" means that the radical is substituted by one or several groups of the list. For instance, the expression "a ($C_1$-$C_6$)alkyl substituted by at least one halogen, preferably a fluorine, may include a fluoromethyl (—$CH_2F$), a difluoromethyl (—$CHF_2$), or a trifluormethyl (—$CF_3$).

The expression "optionally substituted" means that the radical is not substituted or substituted by one or several groups of the list.

The "stereoisomers" are isomeric compounds that have the same molecular formula and sequence of bonded atoms, but differ in the 3D-dimensional orientations of their atoms in space.

The stereoisomers include enantiomers, diastereoisomers, cis-trans and E-Z isomers, conformers, and anomers. In a preferred embodiment of the invention, the stereoisomers include diastereoisomers and enantiomers.

The "tautomers" are isomeric compounds that differ only in the position of the protons and the electrons.

The "hydrates" are compounds further comprising at least one molecule of water. For instance, if the compound comprises one molecule of water, it corresponds to a monohydrate form. If the compound comprises two molecules of water, it corresponds to a dihydrate form.

The "pharmaceutically salts" include inorganic as well as organic acids salts. Representative examples of suitable inorganic acids include hydrochloric, hydrobromic, hydroiodic, phosphoric, and the like. Representative examples of suitable organic acids include formic, acetic, trichloroacetic, trifluoroacetic, propionic, benzoic, cinnamic, citric, fumaric, maleic, methanesulfonic and the like. Further examples of pharmaceutically inorganic or organic acid addition salts include the pharmaceutically salts listed in J. Pharm. Sci. 1977, 66, 2, and in Handbook of Pharmaceutical Salts: Properties, Selection, and Use edited by P. Heinrich Stahl and Camille G. Wermuth 2002. In a preferred embodiment, the salt is selected from the group consisting of maleate, chlorhydrate, bromhydrate, and methanesulfonate. The "pharmaceutically salts" also include inorganic as well as organic base salts. Representative examples of suitable inorganic bases include sodium or potassium salt, an alkaline earth metal salt, such as a calcium or magnesium salt, or an ammonium salt. Representative examples of suitable salts with an organic base includes for instance a salt with methylamine, dimethylamine, trimethylamine, piperidine, morpholine or tris-(2-hydroxyethyl)amine.

—COR refers to —C(O)—R, —CONHR refers to —C(O)—NH—R, and —$CO_2R$ refers to —C(O)—O—R.

As used herein, the terms "treatment", "treat" or "treating" refer to any act intended to ameliorate the health status of patients such as therapy, prevention, prophylaxis and retardation of a disease, in particular a cancer. In certain embodiments, such terms refer to the amelioration or eradication of the disease, or symptoms associated with it. In other embodiments, this term refers to minimizing the spread or worsening of the disease, resulting from the administration of one or more therapeutic agents to a subject with such a disease.

As used herein, the terms "subject", "individual" or "patient" are interchangeable and refer to a mammal, even more preferably to a human, including adult, child, newborn and human at the prenatal stage. However, the term "subject" can also refer to non-human animals, in particular mammals such as dogs, cats, horses, cows, pigs, sheep and non-human primates, among others. In a particular embodiment, the subject is resistant to any other anticancer treatments. In a preferred embodiment, the subject is a chemoresistant subject.

The terms "quantity," "amount," and "dose" are used interchangeably herein and may refer to an absolute quantification of a molecule.

As used herein, the terms "active principle", "active ingredient", "active pharmaceutical ingredient", and "drug" are equivalent and refers to a component of a pharmaceutical composition having a therapeutic effect.

As used herein, the term "therapeutic effect" refers to an effect induced by an active ingredient, or a pharmaceutical composition according to the invention, capable to prevent or to delay the appearance or development of a disease or disorder, or to cure or to attenuate the effects of a disease or disorder.

As used herein, the term "effective amount" refers to a quantity of an active ingredient or of a pharmaceutical composition which prevents, removes or reduces the deleterious effects of the disease, particularly a cancer. It is obvious that the quantity to be administered can be adapted by the man skilled in the art according to the subject to be treated, to the nature of the disease, etc. In particular, doses and regimen of administration may be function of the nature, of the stage and of the severity of the disease to be treated, as well as of the weight, the age and the global health of the subject to be treated, as well as of the judgment of the doctor.

As used herein, the term "pharmaceutically acceptable excipient" refers to any ingredient except active ingredients which are present in a pharmaceutical composition. Its addition may be aimed to confer a particular consistency or other physical or gustative properties to the final product. A pharmaceutically acceptable excipient must be devoid of any interaction, in particular chemical, with the active ingredients.

Compounds

The present invention provides new compounds of therapeutic interest.

According to the invention, a compound has the following formula (I'):

(I')

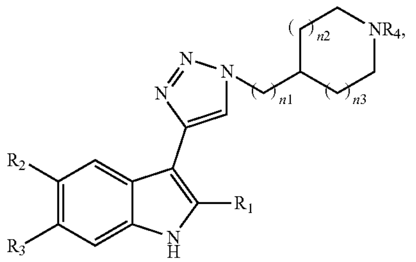

wherein:

$R_1$ is a radical selected in the group consisting of:
- a hydrogen,
- a ($C_1$-$C_6$)alkyl optionally substituted by a hydroxy, a ($C_1$-$C_6$)alkyloxy, an amino group, a —$N(CH_3)_2$ group, or a heterocycloalkyl group,
- a ($C_1$-$C_6$)alkyloxy,
- a —$CO_2R_5$, a-$CONHR_5$, a —$COR_5$, or a —$CH_2$—O—$R_5$ group with $R_5$ being a radical selected in the group consisting of:
  - a hydrogen,
  - a ($C_1$-$C_6$)alkyl optionally substituted by a hydroxy, an amino group, a cycloalkyl, or a heterocycloalkyl,
  - a ($C_2$-$C_6$)alkenyl,
  - a 3-10 membered ring selected in the group consisting of a heterocycloalkyl, a cycloalkyl, an aryl, and a heteroaryl, said 3-10 membered ring being optionally substituted by a ($C_1$-$C_6$)alkyl, and
- a heteroaryl optionally substituted a ($C_1$-$C_6$)alkyl optionally substituted by a cycloalkyl;

$R_2$ is a hydrogen, a halogen, or a ($C_1$-$C_6$)alkyl optionally substituted by at least one fluorine;

$R_3$ is a hydrogen or a halogen; and $R_4$ is a radical selected in the group consisting of:
- a —$CH_2$—$CH_2$—NH—$SO_2$—$R_6$ or a —$CH_2$—$CH_2$—NH—$SO_2$—$CH_2$—$R_6$ group with $R_6$ being a 3-10 membered ring optionally substituted by at least one radical selected in the group consisting of:
  - a halogen,
  - a hydroxy,
  - a ($C_1$-$C_6$)alkyl optionally substituted by at least one fluorine, a cycloalkyl or an aryl,
  - a ($C_1$-$C_6$)alkyloxy optionally substituted by at least one fluorine,
  - a 3-10 membered ring optionally substituted by at least one radical selected in the group consisting of:
    - a halogen,
    - a heterocycloalkyl, a —$CH_2$-heterocycloalkyl, a cyano,
a $(C_1-C_6)$alkyl optionally substituted by at least one $(C_1-C_6)$alkyloxy or one halogen,
a $(C_1-C_6)$alkyloxy optionally substituted by at least one halogen,
a —$N(CH_3)_2$ group, and
a hydroxy, and
a —O-3-10 membered ring,
a X—$R_7$ group in which:
X represents —$CH_2$—, —CO—, —NH—CO—NH—, or —$SO_2$—, and
$R_7$ represents a 3-10 membered ring optionally substituted by at least one radical selected in the group consisting of:
a halogen,
a $(C_1-C_6)$alkyl optionally substituted by at least one fluorine,
a $(C_1-C_6)$alkyloxy, and
a 3-10 membered ring, a —O-3-10 membered ring, a —$CH_2$-3-10 membered ring, or a —O—$CH_2$-3-10 membered ring, said rings are optionally substituted by at least one radical selected in the group consisting of:
a $(C_1-C_6)$alkyl optionally substituted by at least one $(C_1-C_6)$alkyloxy or one halogen,
a $(C_1-C_6)$alkyloxy,
a halogen,
a —$COR_8$ with $R_8$ being a hydrogen or a $(C_1-C_6)$alkyl, and
an aryl;
n1 is 0 or 1; and
n2 and n3 are independently 0, 1, or 2;
and the stereoisomers, the tautomers, the hydrates, and the pharmaceutical salts thereof.

According to the invention, n1 is 0 or 1. In a particular embodiment n1 is 1.

According to the invention n2 and n3 are independently 0, 1, or 2. In a particular embodiment, n2 and n3 are 1. In a further particular embodiment n2 is 0 and n3 is 1 or n2 is 1 and n3 is 0. In a further particular embodiment n2 is 0 and n3 is 1 or n2 is 1 and n3 is 0. In a further particular embodiment n2 is 0 and n3 is 2 or n2 is 2 and n3 is 0. In a further particular embodiment n2 is 0 and n3 is 0. In a preferred embodiment, n2 and n3 are 1.

According to a particular embodiment of the invention, a compound has the following formula (I):

(I)

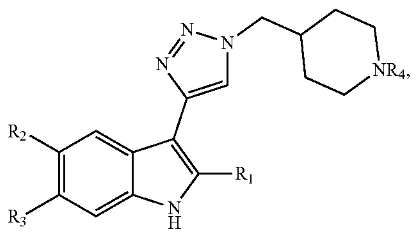

wherein:
$R_1$ is a radical selected in the group consisting of:
a hydrogen,
a —$CO_2R_5$, a-$CONHR_5$, a —$COR_5$, or a —$CH_2$—O—$R_5$ group with $R_5$ being a radical selected in the group consisting of:
hydrogen,
a $(C_1-C_6)$alkyl optionally substituted by a hydroxy, an amino group, or a cycloalkyl, and
a heterocycloalkyl optionally substituted by a $(C_1-C_6)$alkyl, and
a heteroaryl optionally substituted a $(C_1-C_6)$alkyl optionally substituted by a cycloalkyl;
$R_2$ is a hydrogen, a halogen, or a $(C_1-C_6)$alkyl optionally substituted by at least one fluorine;
$R_3$ is a hydrogen or a halogen; and
$R_4$ is a radical selected in the group consisting of:
a —$CH_2$—$CH_2$—NH—$SO_2$—$R_6$ group with $R_6$ being a 3-10 membered ring optionally substituted by a radical selected in the group consisting of:
a halogen,
a $(C_1-C_6)$alkyl optionally substituted by at least one fluorine, a cycloalkyl or an aryl,
a $(C_1-C_6)$alkyloxy optionally substituted by at least one fluorine,
a 3-10 membered ring, and
a —O-3-10 membered ring,
a X—$R_7$ group in which:
X represents —$CH_2$—, —CO—, —NH—CO—NH—, or —$SO_2$—, and
$R_7$ represents a 3-10 membered ring optionally substituted by at least one radical selected in the group consisting of:
a halogen,
a $(C_1-C_6)$alkyl optionally substituted by at least one fluorine,
a $(C_1-C_6)$alkyloxy, and
a 3-10 membered ring, a —O-3-10 membered ring, a —$CH_2$-3-10 membered ring, or a —O—$CH_2$-3-10 membered ring, said rings are optionally substituted by at least one radical selected in the group consisting of:
a $(C_1-C_6)$alkyl optionally substituted by at least one $(C_1-C_6)$alkyloxy,
a $(C_1-C_6)$alkyloxy,
a halogen,
a —$COR_8$ with $R_8$ being a hydrogen or a $(C_1-C_6)$alkyl, and
an aryl;
and the stereoisomers, the tautomers, the hydrates, and the pharmaceutical salts thereof.

In a particular embodiment, $R_1$ is a hydrogen.

In a further particular embodiment, $R_1$ is a $(C_1-C_6)$alkyl optionally substituted by a hydroxy a $(C_1-C_6)$alkyloxy, an amino group, a —$N(CH_3)_2$ group, or a heterocycloalkyl group.

In a further particular embodiment, $R_1$ is a $(C_1-C_6)$ alkyloxy.

In a further particular embodiment, $R_1$ is a $CO_2R_5$, a-$CONHR_5$, a —$COR_5$, or a —$CH_2$—O—$R_5$ group with $R_5$ being a radical selected in the group consisting of:
a hydrogen,
a $(C_1-C_6)$alkyl optionally substituted by a hydroxy, an amino group, a cycloalkyl, or a heterocycloalkyl,
a $(C_2-C_6)$alkenyl,
a 3-10 membered ring selected in the group consisting of a heterocycloalkyl, a cycloalkyl, an aryl, and a heteroaryl, said 3-10 membered ring being optionally substituted by a $(C_1-C_6)$alkyl, and
a heteroaryl optionally substituted a $(C_1-C_6)$alkyl optionally substituted by a cycloalkyl;

In a further particular embodiment, $R_1$ is a radical selected in the group consisting of a —$CO_2R_5$, a-$CONHR_5$, a —$COR_8$, and a —$CH_2$—O—$R_5$ group with $R_5$ being a radical selected in the group consisting of:

hydrogen, a ($C_1$-$C_6$)alkyl optionally substituted by a hydroxy, an amino group, or a cycloalkyl, and a heterocycloalkyl optionally substituted by a ($C_1$-$C_6$) alkyl.

In one aspect, $R_1$ is a —$CO_2R_5$ group with $R_5$ being a radical selected in the group consisting of:

hydrogen, a ($C_1$-$C_6$)alkyl, preferably an ethyl, an isopropyl, an isobutyl, or an isopentyl, and a ($C_1$-$C_6$)alkyl, preferably a methyl or an ethyl, substituted by a hydroxy, an amino group, or a cycloalkyl, preferably a cyclopropyl, a cyclopentyl, or a cyclohexyl.

In a preferred embodiment, $R_1$ is a —$CO_2R_5$ group with $R_5$ being a radical selected in the group consisting of a hydrogen, and a ($C_1$-$C_6$)alkyl optionally substituted by a hydroxy or an amino group. Preferably $R_5$ is an ethyl, an isopropyl, an isobutyl, an isopentyl, or an ethyl substituted by a hydroxy or an amino group.

In a further aspect, $R_1$ is a —$CONHR_5$ group with $R_5$ being a radical selected in the group consisting of:

a ($C_1$-$C_6$)alkyl, preferably an isobutyl or an isopentyl, and a ($C_1$-$C_6$)alkyl, preferably a methyl, substituted by a cycloalkyl, preferably a cyclopentyl or a cyclohexyl.

In a preferred embodiment, $R_1$ is a —$CONHR_5$ group with $R_5$ being a ($C_1$-$C_6$)alkyl. Preferably, $R_5$ is an isobutyl or an isopentyl.

In a further aspect, $R_1$ is a —$COR_5$ group with $R_5$ being a ($C_1$-$C_6$)alkyl or a heterocycloalkyl optionally substituted by a ($C_1$-$C_6$)alkyl. Preferably, $R_5$ is a pyrrolidinyl, a piperidinyl, or a piperazinyl substituted an ethyl, an isopropyl, or an isobutyl.

In a further aspect, $R_1$ is a —$CH_2$—O—$R_5$ group with $R_5$ being a hydrogen or a ($C_1$-$C_6$)alkyl optionally substituted by a cycloalkyl. Preferably $R_5$ is an ethyl, an isobutyl, a methyl substituted by a cyclopropyl, a cyclopentyl, or a cyclohexyl.

In a further particular embodiment, $R_1$ is a heteroaryl optionally substituted a ($C_1$-$C_6$)alkyl optionally substituted by a cycloalkyl. Preferably, $R_1$ is an oxadiazolyl, more preferably a 1,3,4-oxadiazolyl substituted by an isopropyl, an isobutyl, or a methyl substituted by a cyclopropyl, a cyclopentyl, or a cyclohexyl.

In one embodiment, $R_1$ is a radical selected in the group consisting of:

a hydrogen, a ($C_1$-$C_6$)alkyl optionally substituted by a hydroxy, and a —$CO_2R_5$, a —$COR_5$, or a-$CONHR_5$ group with $R_5$ being a radical selected in the group consisting of:

hydrogen, a ($C_1$-$C_6$)alkyl optionally substituted by a hydroxy or an amino group, and a cycloalkyl, a heterocycloalkyl, or a heteroaryl.

More specifically, $R_1$ is a radical selected in the group consisting of:

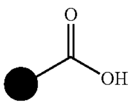
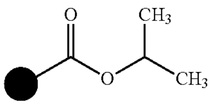
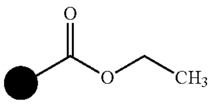
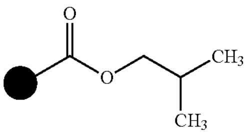

-continued

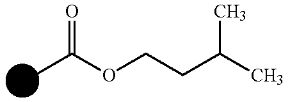
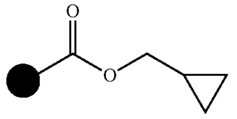
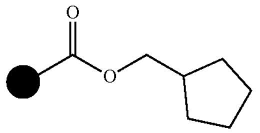
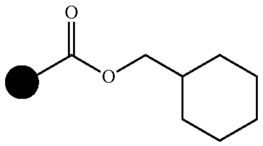
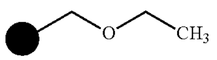
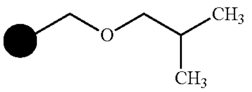
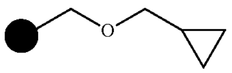
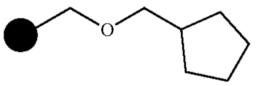
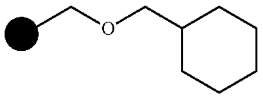
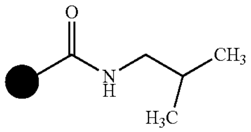
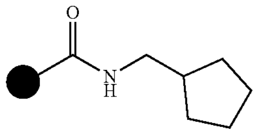
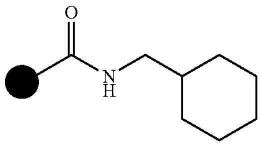
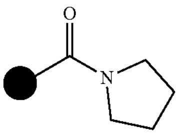
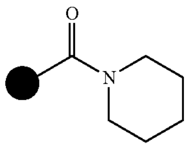
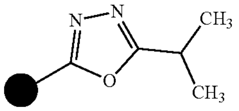
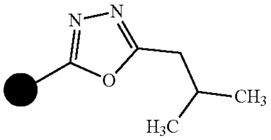
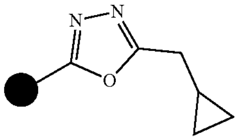
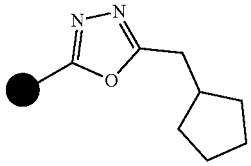
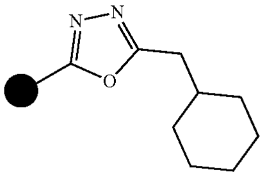
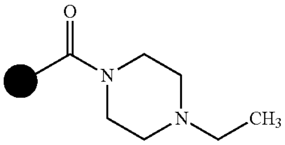
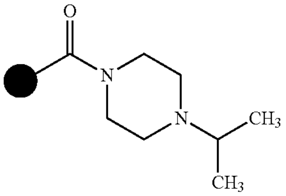
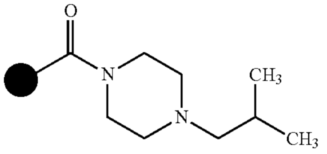
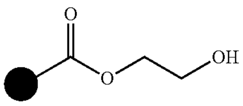

-continued

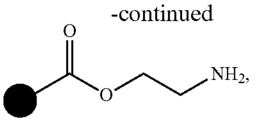

and

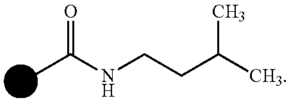

In a further specific embodiment, $R_1$ is a radical selected in the group consisting of:

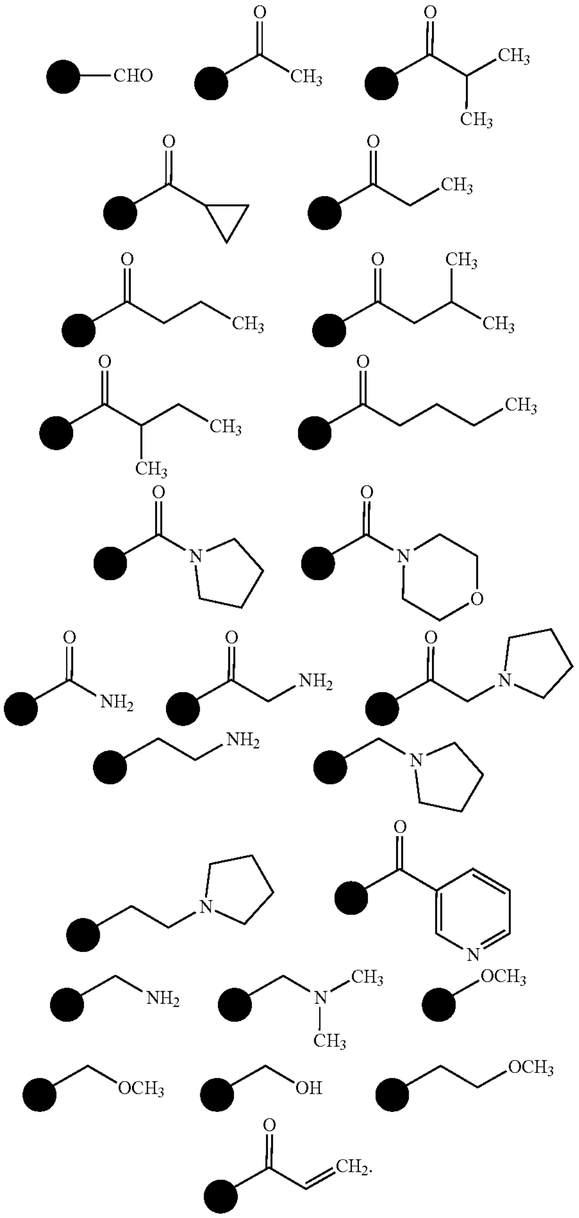

In a preferred embodiment, $R_1$ is a radical selected in the group consisting of:

a hydrogen, and a —$CO_2R_5$ or a-CONHIR$_5$ group with $R_5$ being a radical selected in the group consisting of:

a hydrogen, and a $(C_1-C_6)$alkyl optionally substituted by a hydroxy or an amino group.

In a more preferred embodiment, $R_1$ is a radical selected in the group consisting of:

a hydrogen, a —$CO_2R_5$ with $R_5$ being a radical selected in the group consisting of a hydrogen, and a $(C_1-C_6)$alkyl optionally substituted by a hydroxy or an amino group, preferably an ethyl, an isopropyl, an isobutyl, an isopentyl, or an ethyl substituted by a hydroxy or an amino group, and a —$CONHR_5$ group with $R_5$ being a $(C_1-C_6)$alkyl, preferably an isobutyl or an isopentyl.

In a further preferred embodiment, $R_1$ is a —$COR_5$ with $R_5$ being an imidazolyl, a morpholinyl, a pyridinyl, a hydrogen, a $(C_1-C_6)$alkyl, preferably a methyl, an ethyl, a propyl, an isopropyl, a butyl, an isobutyl, a cyclopropyl. More preferably, $R_1$ is a —$COR_5$ with $R_5$ being a methyl.

In an even more preferred embodiment, $R_1$ is a —$CO_2R_5$ with $R_5$ being a $(C_1-C_6)$alkyl, preferably an ethyl, an isopropyl, or an isobutyl.

In a particular advantageous embodiment, $R_1$ is

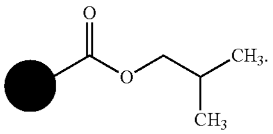

In a further particular advantageous embodiment, $R_1$ is $COCH_3$.

According to the invention, $R_2$ is a hydrogen, a halogen, or a $(C_1-C_6)$alkyl optionally substituted by at least one fluorine.

In a particular embodiment, $R_2$ is a hydrogen, a halogen, or a trifluromethyl. In a more particular embodiment, $R_2$ is a hydrogen or a halogen, preferably a fluorine or a chlorine.

In a preferred embodiment, $R_2$ is a halogen, preferably a fluorine.

According to the invention, $R_3$ is a hydrogen or a halogen.

In a particular embodiment, $R_3$ is a hydrogen or a chlorine.

In a preferred embodiment, $R_3$ is a hydrogen.

In a particular embodiment, $R_4$ is a —$CH_2$—$CH_2$—NH—$SO_2$—$R_6$ or a —$CH_2$—$CH_2$—NH—$SO_2$—$CH_2$—$R_6$ group with $R_6$ being a 3-10 membered ring optionally substituted by at least one radical selected in the group consisting of:

a halogen, a hydroxy, a $(C_1-C_6)$alkyl optionally substituted by at least one fluorine, a cycloalkyl or an aryl, a $(C_1-C_6)$alkyloxy optionally substituted by at least one fluorine, a 3-10 membered ring optionally substituted by at least one radical selected in the group consisting of:

a halogen, a heterocycloalkyl, a —$CH_2$-heterocycloalkyl, a cyano, a $(C_1-C_6)$alkyl optionally substituted by at least one $(C_1-C_6)$alkyloxy or one halogen, a $(C_1-C_6)$alkyloxy optionally substituted by at least one halogen, a —$N(CH_3)_2$ group, and a hydroxy, and a —O-3-10 membered ring, In a particular embodiment, $R_4$ is a —$CH_2$—$CH_2$—NH—$SO_2$—$R_6$ group with $R_6$ being a 3-10 membered ring optionally substituted by a radical selected in the group consisting of:

- a halogen,
- a ($C_1$-$C_6$)alkyl optionally substituted by at least one fluorine, a cycloalkyl or an aryl,
- a ($C_1$-$C_6$)alkyloxy optionally substituted by at least one fluorine,
- a 3-10 membered ring, and
- a —O-3-10 membered ring.

More particularly, $R_6$ is a 3-10 membered ring selected in the group consisting of a phenyl, a naphtalenyl, a piperidinyl, a dihydrobenzofuranyl, an indanyl, a dihydrobenzodioxepinyl, and a piperazinyl, said 3-10 membered ring being optionally substituted by a radical as above defined.

In one aspect, $R_6$ is a phenyl optionally substituted by a radical selected in the group consisting of:

- a halogen, preferably a chlorine,
- a ($C_1$-$C_6$)alkyl optionally substituted by at least one fluorine, preferably a methyl, a trifluoromethyl, an ethyl, an isopropyl, or an isobutyl,
- a ($C_1$-$C_6$)alkyloxy optionally substituted by at least one fluorine, preferably a trifluoromethoxy, an ethoxy, an isopropoxy, or an isobutoxy,
- a 3-10 membered ring selected in the group consisting of a cycloalkyl, preferably a hexyl, a heterocycloalkyl, preferably a tetrahydropyranyl or a piperidinyl, an aryl, preferably a phenyl, and a heteroaryl, preferably an indolyl, and
- a —O-3-10 membered ring selected in the group consisting of a —O-cycloalkyl, preferably a —O-cyclopropyl, a —O-cyclopentyl, or a —O— cyclohexyl, a —O-aryl, preferably a phenoxy (—O-phenyl), and a —O-heteroaryl, preferably a —O-indolyl, a —O-benzofuranyl, or a —O— benzothiophenyl.

Preferably, $R_6$ is a phenyl optionally substituted by a radical selected in the group consisting of:

- a halogen, preferably a chlorine, and
- a ($C_1$-$C_6$)alkyl optionally substituted by at least one fluorine, preferably a methyl, a trifluoromethyl, an ethyl, an isopropyl, or an isobutyl.

In another aspect, $R_6$ is a phenyl optionally substituted by a radical selected in the group consisting of:

- a halogen, preferably a chlorine or a bromine,
- a ($C_1$-$C_6$)alkyl optionally substituted by at least one fluorine, preferably a methyl, a trifluoromethyl, an ethyl, an isopropyl, a butyl, a tert-butyl or an isobutyl, or by a cyclopropyl,
- a ($C_1$-$C_6$)alkyloxy optionally substituted by at least one fluorine, preferably a trifluoromethoxy, an ethoxy, an isopropoxy, or an isobutoxy,
- a 3-10 membered ring selected in the group consisting of a cycloalkyl, preferably a hexyl, a heterocycloalkyl, preferably a tetrahydropyranyl, a cyclohexenyl, a dihydropyranyl, or a piperidinyl, an aryl, preferably a phenyl, and a heteroaryl, preferably an indolyl, an imidazolyl, a furanyl, an isoxazolinyl, a pyridinyl, said 3-10 membered ring being optionally substituted by at least one radical selected in the group consisting of:
  - a halogen, preferably a fluorine or a chlorine,
  - a heterocycloalkyl, preferably a pyrrolidinyl,
  - a —$CH_2$-heterocycloalkyl, preferably a —$CH_2$-morpholinyl,
  - a cyano,
  - a ($C_1$-$C_6$)alkyl optionally substituted by a ($C_1$-$C_6$) alkyloxy, preferably a methyl or a —$CH_2$—O—$CH_3$,
  - a ($C_1$-$C_6$)alkyloxy, preferably a methoxy,
  - a —$N(CH_3)_2$, and
  - a hydroxy,
- a —O-3-10 membered ring selected in the group consisting of a —O-cycloalkyl, preferably a —O-cyclopropyl, a —O-cyclopentyl, or a —O— cyclohexyl, a —O-aryl, preferably a phenoxy (—O-phenyl), and a —O-heteroaryl, preferably a —O-indolyl, a —O-benzofuranyl, or a —O— benzothiophenyl.

More preferably, $R_6$ is a phenyl substituted by a ($C_1$-$C_6$) alkyl, preferably an isobutyl.

In a further aspect, $R_6$ is a naphtalenyl.

In further aspect, $R_6$ is a piperidinyl optionally substituted by a radical selected in a group consisting of:

- a phenyl optionally substituted by a halogen, preferably a fluorine,
- a benzyl (—$CH_2$-phenyl), and
- a pyridinyl optionally substituted by a halogen, preferably a fluorine.

In further aspect $R_6$ is a dihydrobenzofuranyl.

In further aspect $R_6$ is an indanyl.

In further aspect $R_6$ is a dihydrobenzodioxepinyl

In a further aspect, $R_6$ is a piperazinyl optionally substituted by a radical selected in the group consisting of:

- a ($C_1$-$C_6$)alkyl optionally substituted by at least one cycloalkyl or an aryl, preferably an isobutyl, a —$CH_2$-cyclopentyl, a —$CH_2$-cyclohexyl, or a —$CH_2$-phenyl (benzyl), and
- a 3-10 membered ring, preferably a heteroaryl, more preferably a phenyl.

More specifically, $R_4$ is a radical selected in the group consisting of:

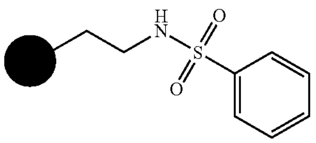

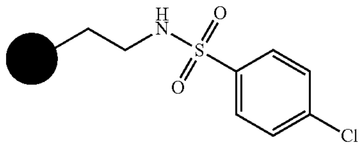

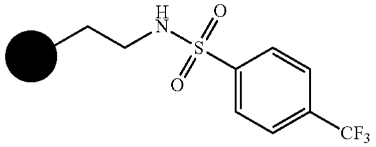

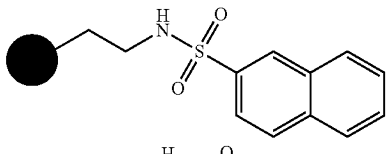

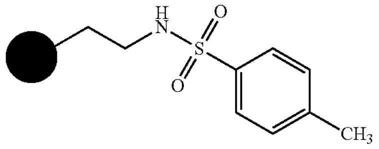

-continued
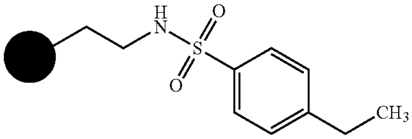
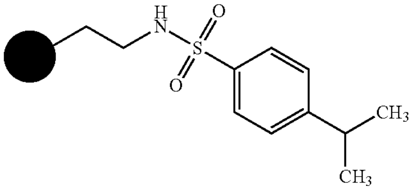
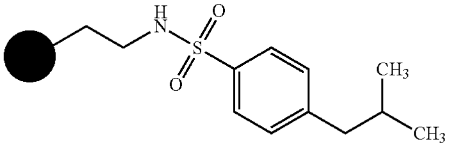
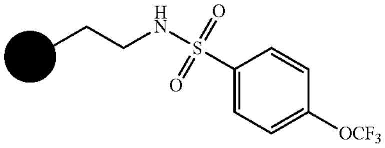
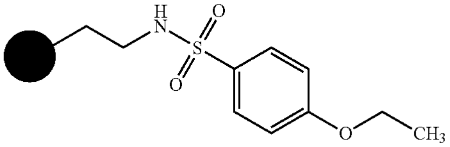
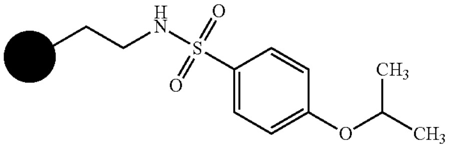
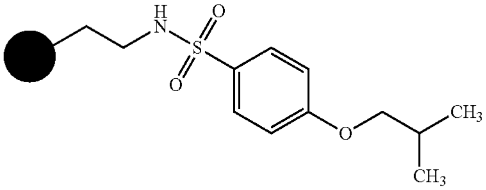
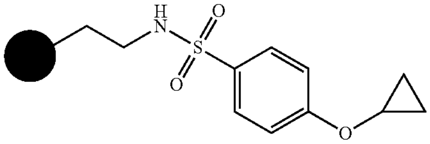
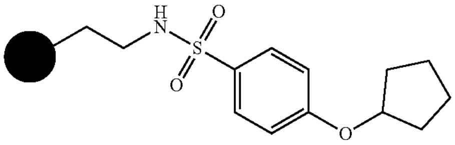
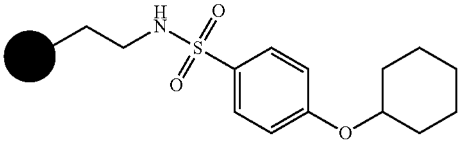
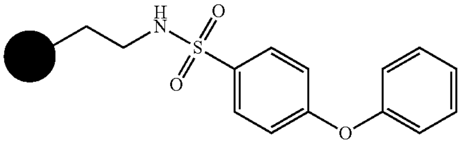
-continued
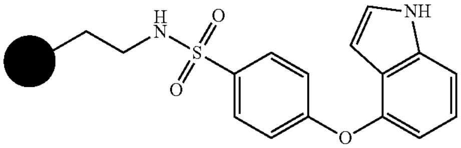
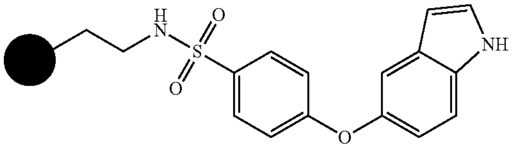
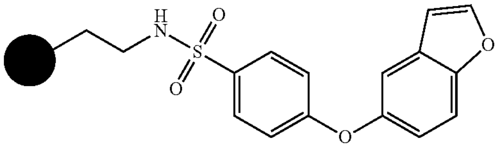
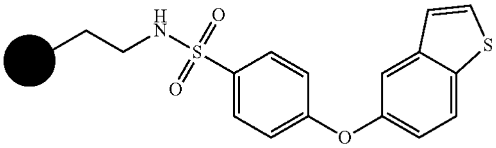
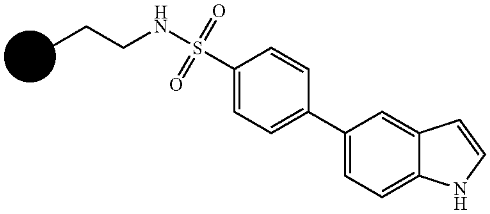
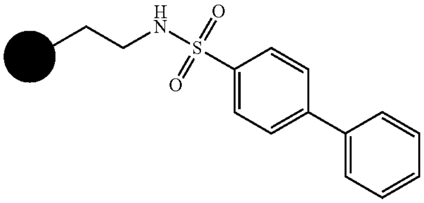
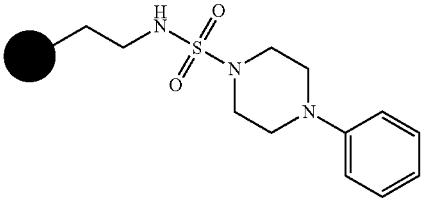
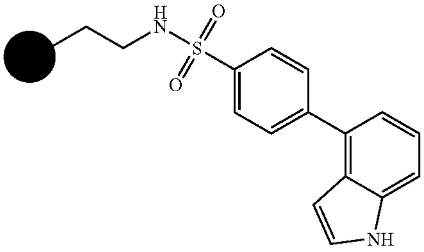
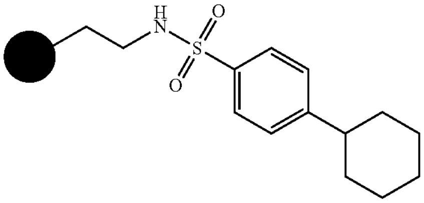

-continued
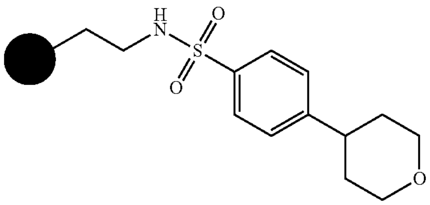
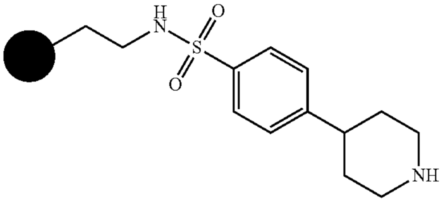
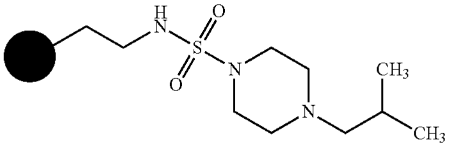
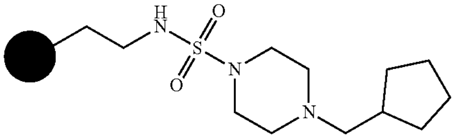
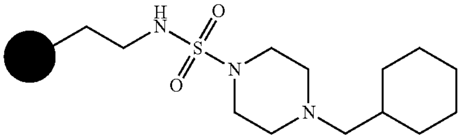
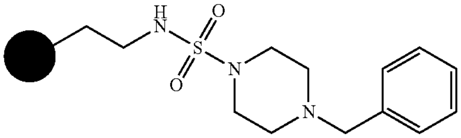
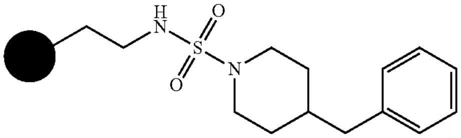
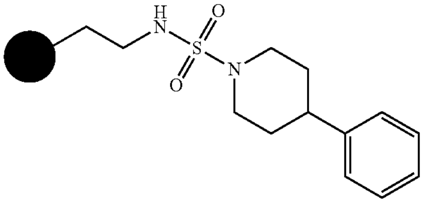
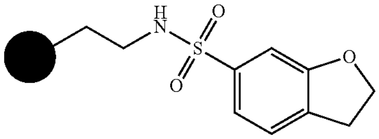
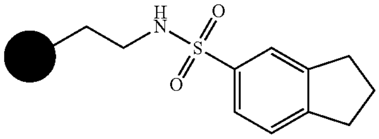
-continued
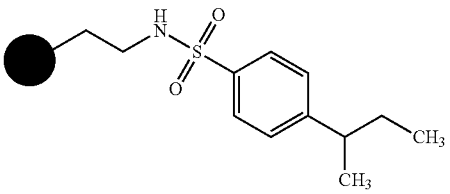
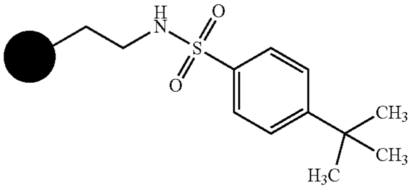
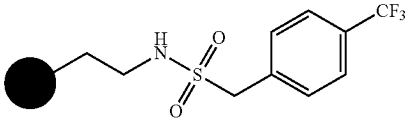
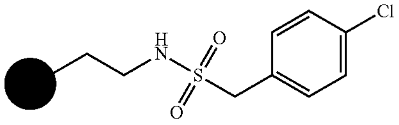
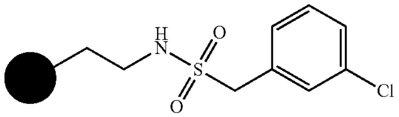
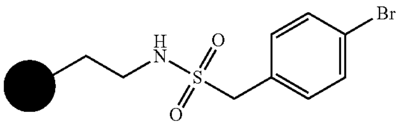
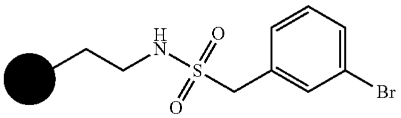
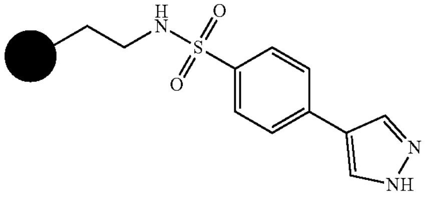
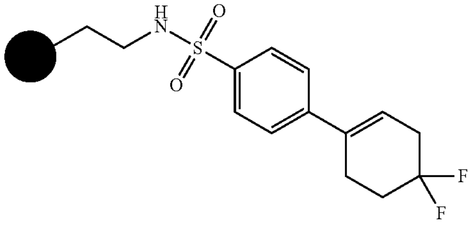
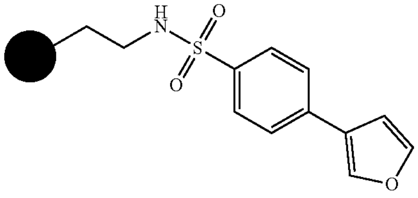

-continued
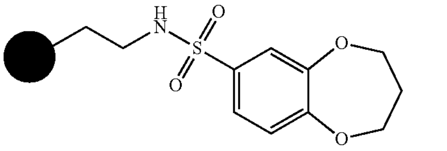
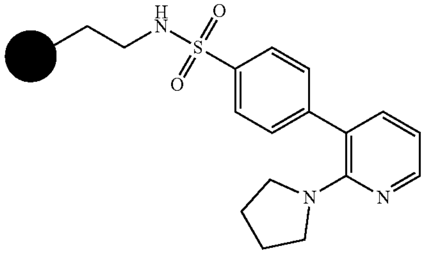
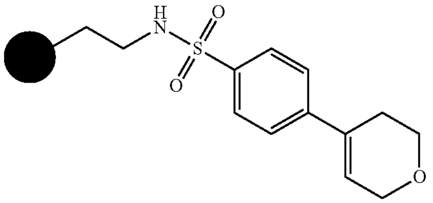
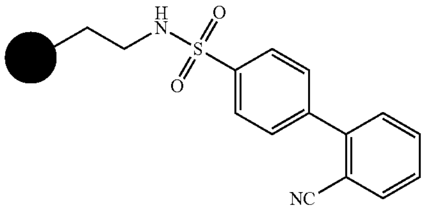
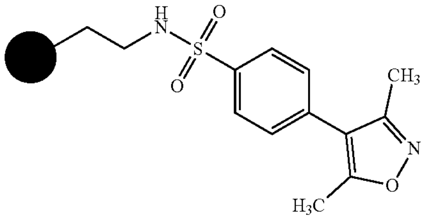
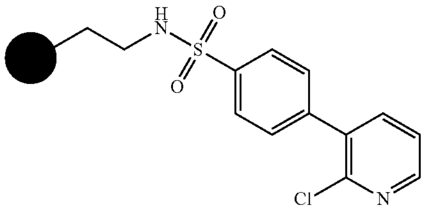
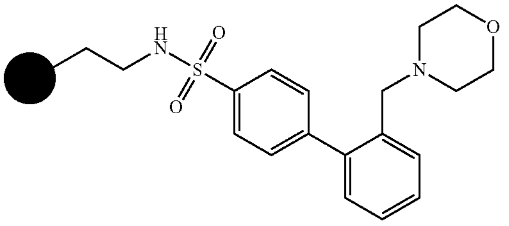
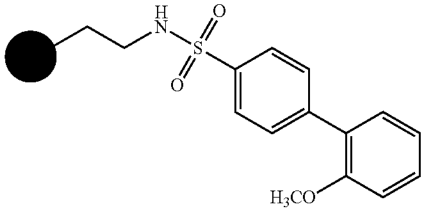
-continued
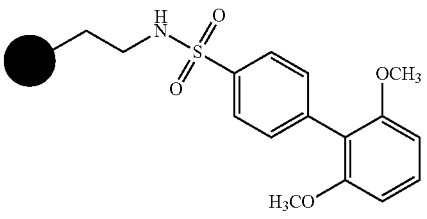
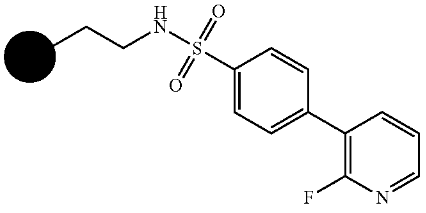
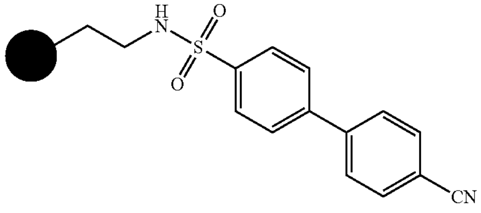
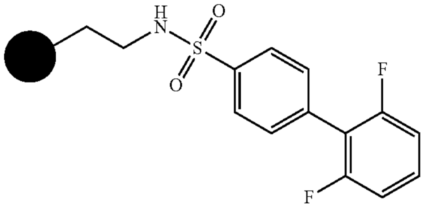
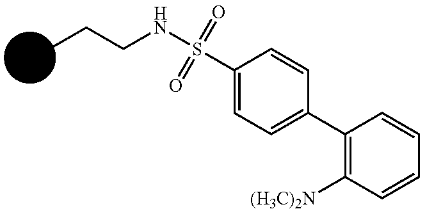
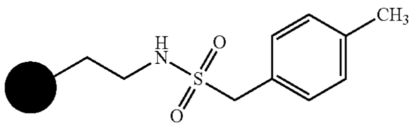
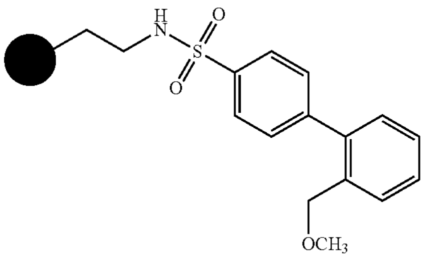
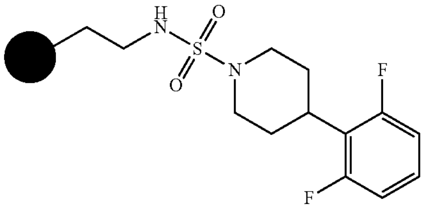

-continued
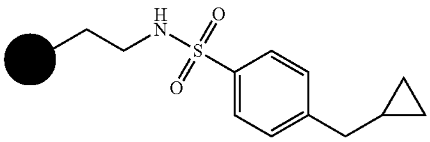
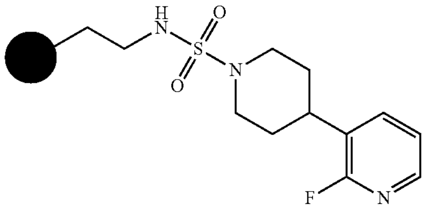
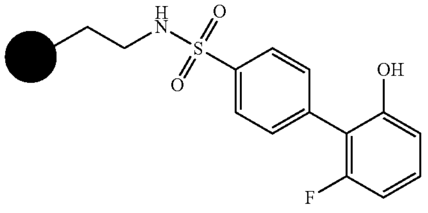
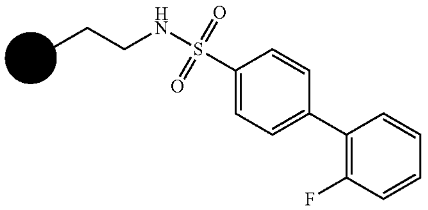
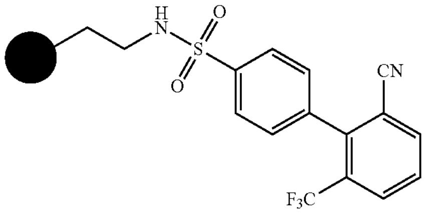
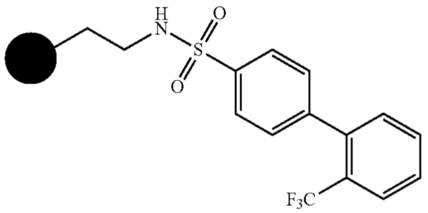
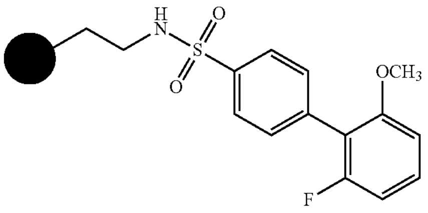
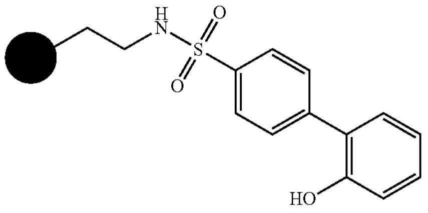
-continued
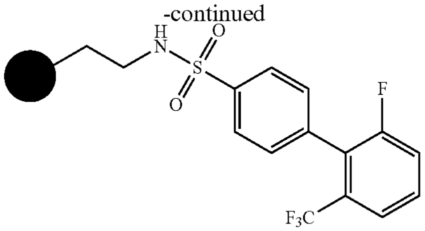
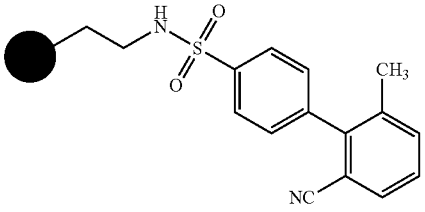
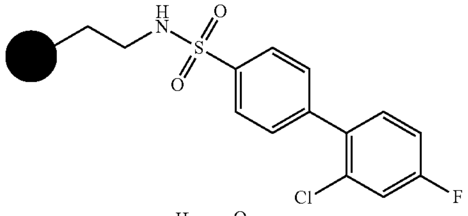
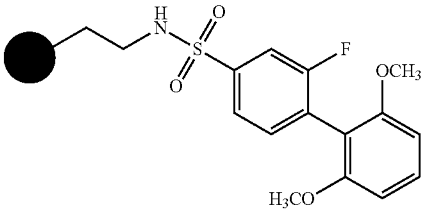
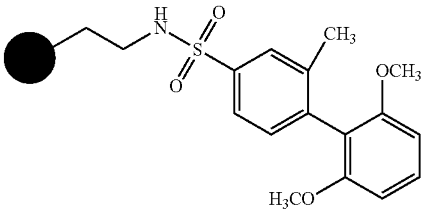
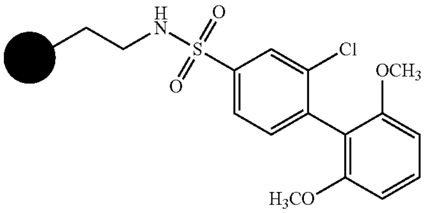
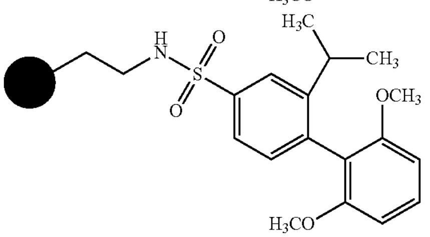
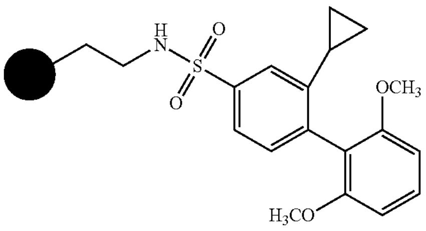

-continued
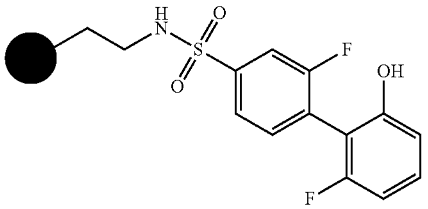
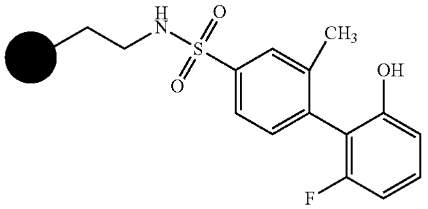
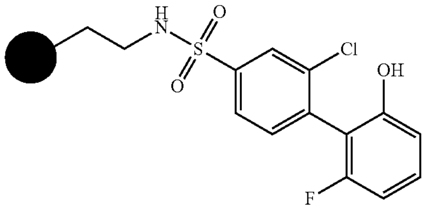
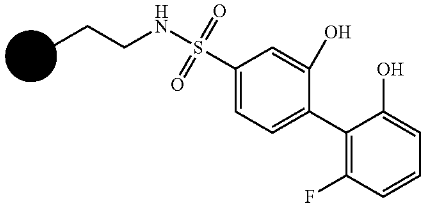
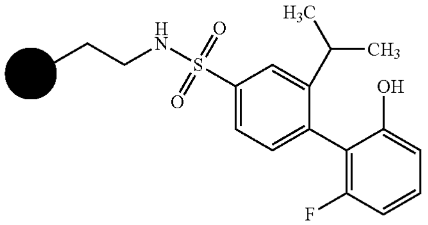
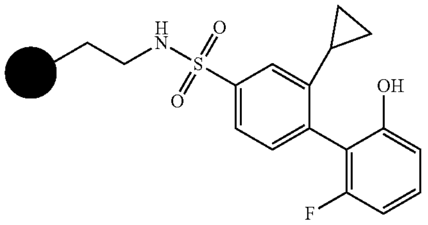
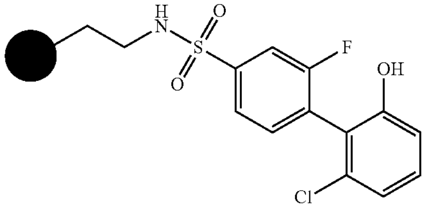
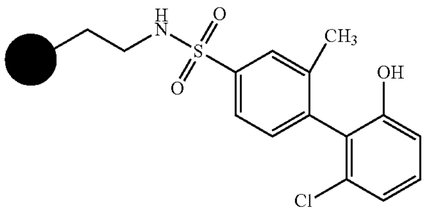
-continued
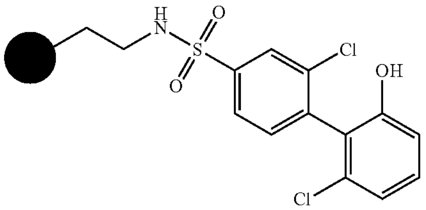
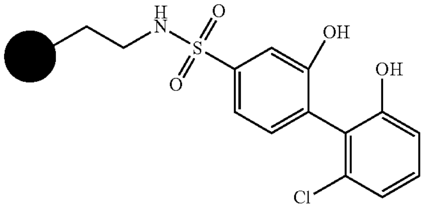
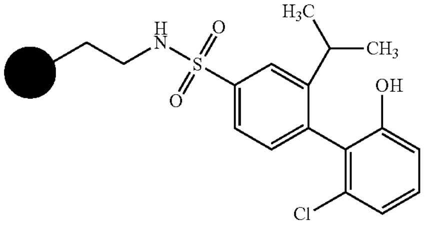
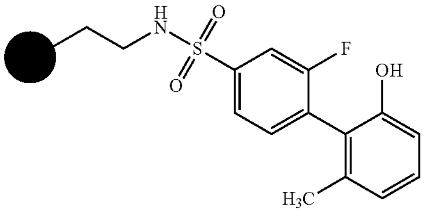
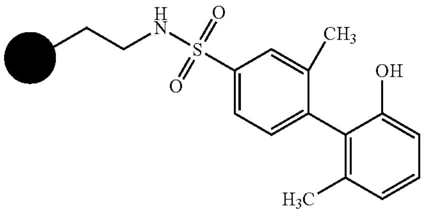
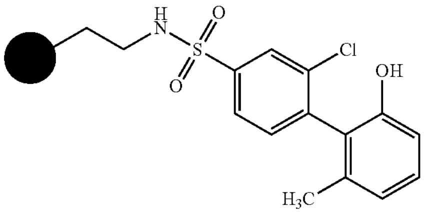
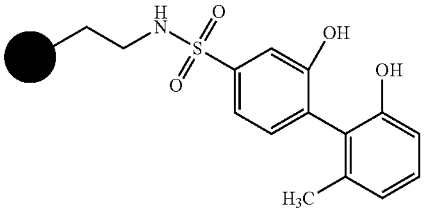
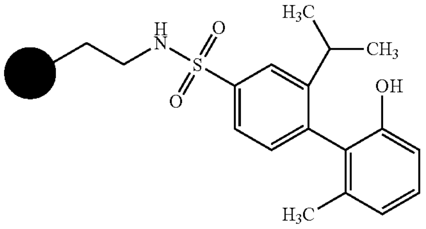

-continued
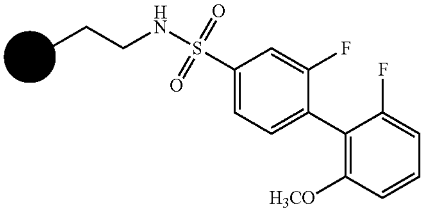
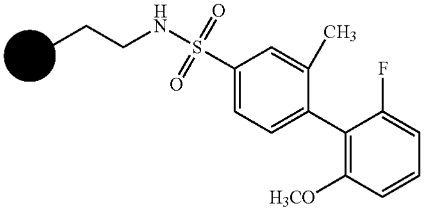
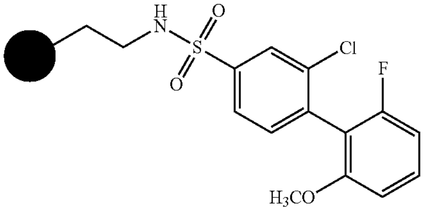
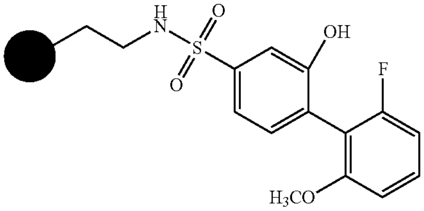
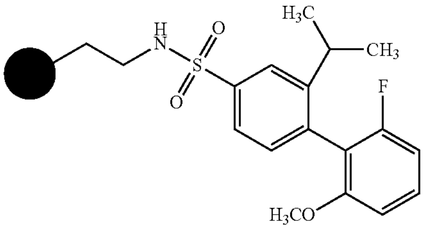
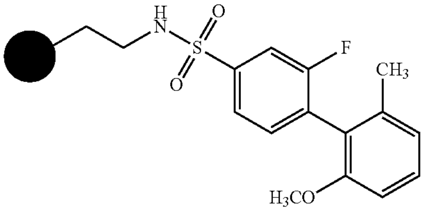
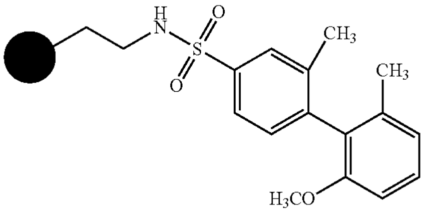
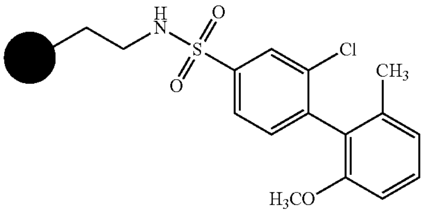
-continued
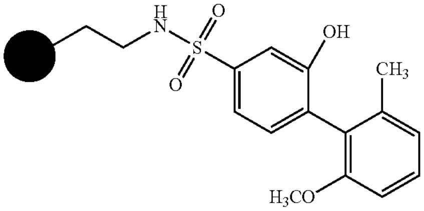
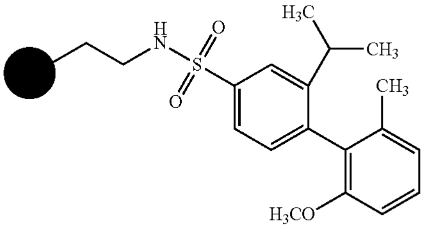
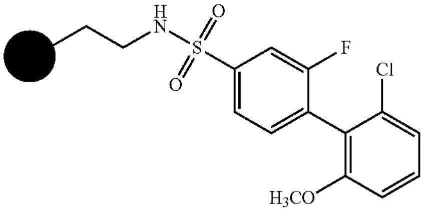
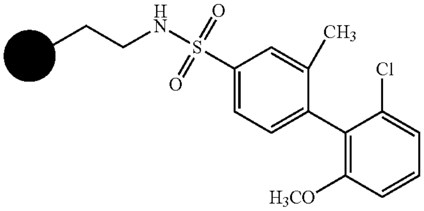
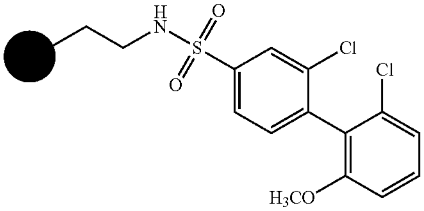
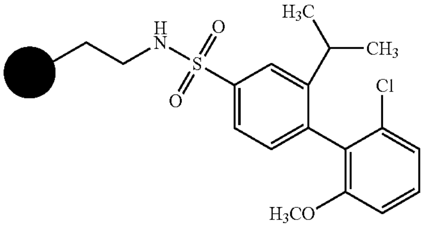
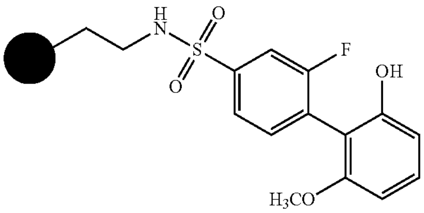
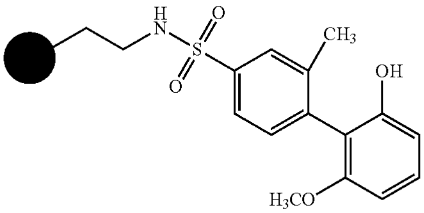

-continued

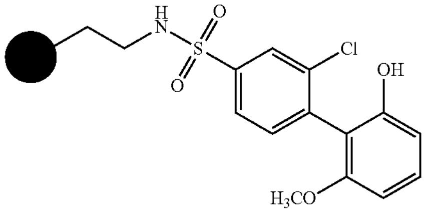

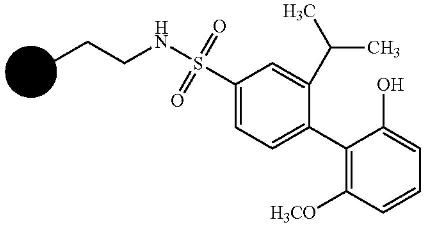

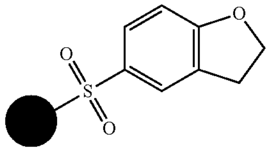

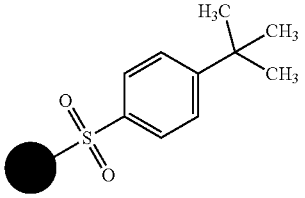

In a preferred embodiment, $R_4$ is a —$CH_2$—$CH_2$—NH—$SO_2$—$R_6$ group with $R_6$ being a phenyl or a naphtalenyl optionally substituted by a radical selected in the group consisting of:

a halogen, preferably a chlorine;

a ($C_1$-$C_6$)alkyl optionally substituted by at least one fluorine, preferably a methyl, a trifluoromethyl, an ethyl, or an isopropyl.

In a more preferred embodiment, wherein $R_4$ is a radical selected in the group consisting of a —$CH_2$—$CH_2$—NH—$SO_2$—$R_6$ group with $R_6$ being a phenyl substituted by a ($C_1$-$C_6$)alkyl.

Preferably, $R_6$ is

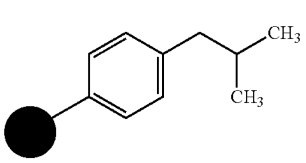

or

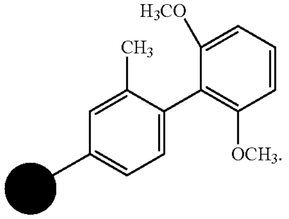

In a further particular embodiment, $R_4$ is a X—$R_7$ group in which:

X represents —$CH_2$—, —CO—, —NH—CO—NH—, or —$SO_2$—, and $R_7$ represents a 3-10 membered ring optionally substituted by at least one radical selected in the group consisting of:

a halogen, a ($C_1$-$C_6$)alkyl optionally substituted by at least one fluorine, a ($C_1$-$C_6$)alkyloxy, and a 3-10 membered ring, a —O-3-10 membered ring, a —$CH_2$-3-10 membered ring, or a —O—$CH_2$-3-10 membered ring, said rings are optionally substituted by at least one radical selected in the group consisting of:

a ($C_1$-$C_6$)alkyl optionally substituted by at least one ($C_1$-$C_6$)alkyloxy, a ($C_1$-$C_6$)alkyloxy, a halogen, a —$COR_8$ with $R_8$ being a hydrogen or a ($C_1$-$C_6$) alkyl, and an aryl.

In one aspect, $R_4$ is a X—$R_7$ group in which X represents —$CH_2$— and $R_7$ is as above defined.

In a particular embodiment, $R_7$ is a phenyl optionally substituted by at least one radical selected in the group consisting of:

a halogen, preferably a chlorine, a ($C_1$-$C_6$)alkyl optionally substituted by at least one fluorine, preferably an isopropyl, a ($C_1$-$C_6$)alkyloxy, preferably an isobutoxy or an isopentoxy, and a 3-10 membered ring, preferably an indolyl, a phenyl, or a dihydrobenzofuranyl, a —O-3-10 membered ring, preferably a —O-phenyl (phenoxy), a —O-indolyl, a —O-cyclopentyl, a —O-piperidinyl, a —O-cyclohexyl, or a —O-dihydrobenzofuranyl (dihydrobenzofuranoxy), a —$CH_2$-3-10 membered ring, preferably a —$CH_2$-piperidinyl, or a —O—$CH_2$-3-10 membered ring, preferably a —O—$CH_2$-cyclohexyl, said rings are optionally substituted by at least one radical selected in the group consisting of:

a ($C_1$-$C_6$)alkyl optionally substituted by at least one ($C_1$-$C_6$)alkyloxy or a fluorine, preferably a methoxymethyl, an isopropyl, a trifluoromethyl, or a methyl, a ($C_1$-$C_6$)alkyloxy, preferably an isopentoxy, a methoxy, or an isobutoxy, a halogen, preferably a chlorine, a —$COR_8$ with $R_8$ being a hydrogen or a ($C_1$-$C_6$)alkyl, preferably a methyl, and an aryl, preferably a phenyl.

In a more particular embodiment, $R_7$ a phenyl optionally substituted by at least one radical selected in the group consisting of:

a halogen, preferably a chlorine, a ($C_1$-$C_6$)alkyl optionally substituted by at least one fluorine, preferably an isopropyl, a ($C_1$-$C_6$)alkyloxy, preferably an isobutoxy or an isopentoxy, and a 3-10 membered ring, preferably an indolyl, a phenyl, or a dihydrobenzofuranyl, a —O-3-10 membered ring, preferably a —O-phenyl (phenoxy), a —O-indolyl, or a —O— dihydrobenzofuranyl (dihydrobenzofuranoxy), said rings are optionally substituted by at least one radical selected in the group consisting of:

a ($C_1$-$C_6$)alkyl optionally substituted by at least one ($C_1$-$C_6$)alkyloxy, preferably a methoxymethyl, an isopropyl, or a methyl, a $(C_1$-$C_6)$alkyloxy, preferably an isopentoxy, a methoxy, or an isobutoxy, and a —$COR_8$ with $R_8$ being a $(C_1$-$C_6)$alkyl, preferably a methyl.

In a further aspect, $R_4$ is a X—$R_7$ group in which X represents —CO— and $R_7$ is as above defined.

In a particular embodiment, $R_7$ is a phenyl optionally substituted by at least one radical selected in the group consisting of:

a halogen, preferably a chlorine, a $(C_1$-$C_6)$alkyl optionally substituted by at least one fluorine, preferably a trifluoromethyl, a 3-10 membered ring, preferably an indolyl or a phenyl, or a —O—$CH_2$-3-10 membered ring, preferably a —O—$CH_2$-cyclohexyl, said rings are optionally substituted by at least a $(C_1$-$C_6)$alkyl optionally substituted by at least one $(C_1$-$C_6)$alkyloxy, preferably a methoxymethyl.

In a more particular embodiment, $R_7$ a phenyl optionally substituted by at least one radical selected in the group consisting of:

a halogen, preferably a chlorine, a $(C_1$-$C_6)$alkyl optionally substituted by at least one fluorine, preferably a trifluoromethyl, a 3-10 membered ring, preferably an indolyl or a phenyl, said rings are optionally substituted by at least a $(C_1$-$C_6)$alkyl optionally substituted by at least one $(C_1$-$C_6)$alkyloxy, preferably a methoxymethyl.

In a further aspect, $R_4$ is a X—$R_7$ group in which X represents —NH—CO—NH—, and $R_7$ is as above defined.

In a particular embodiment, $R_7$ is a phenyl optionally substituted by at least one radical selected in the group consisting of:

a halogen, preferably a chlorine, and a 3-10 membered ring, preferably an indolyl.

In a further aspect, $R_4$ is a X—$R_7$ group in which X represents —$SO_2$—, and $R_7$ is as above defined.

In a particular embodiment, $R_7$ is a piperazinyl optionally substituted by at least a —$CH_2$-3-10 membered ring, preferably a —$CH_2$-phenyl (benzyl). In a further particular embodiment, $R_7$ is a dihydrobenzofuran or a phenyl optionally substituted by a $(C_1$-$C_6)$alkyl, preferably a tert-butyl More specifically, $R_4$ is a radical selected in the group consisting of:

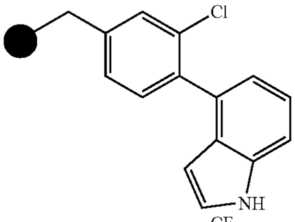

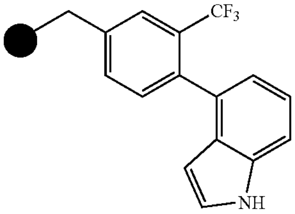

-continued

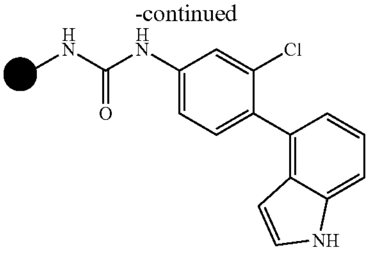

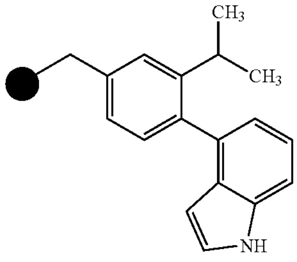

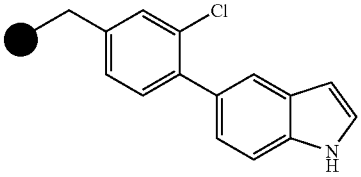

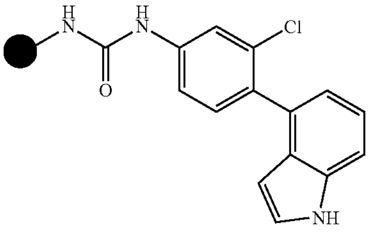

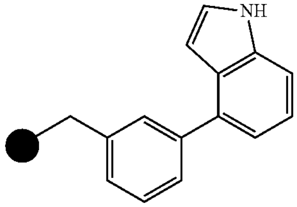

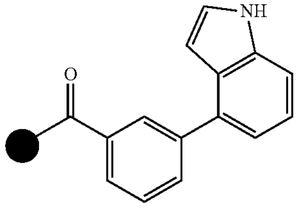

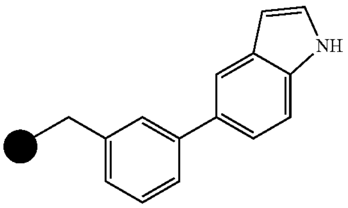

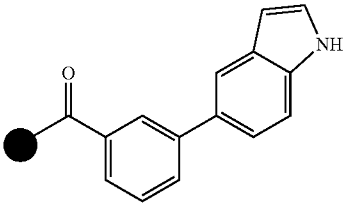

-continued
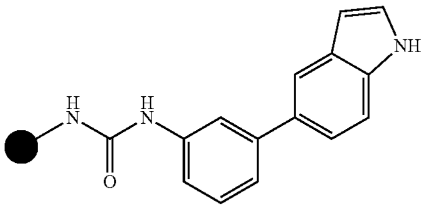
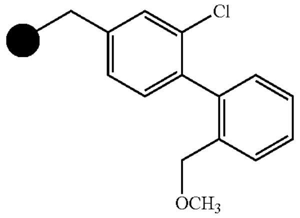
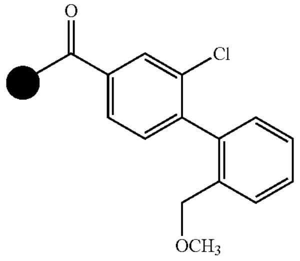
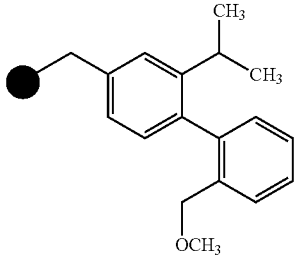
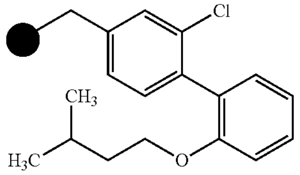
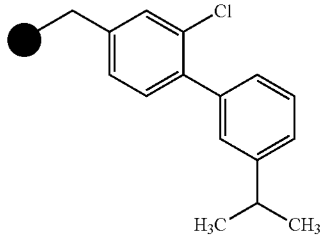
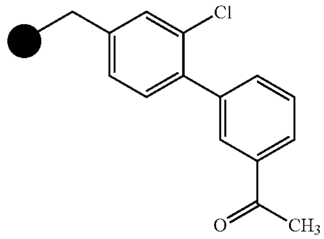
-continued
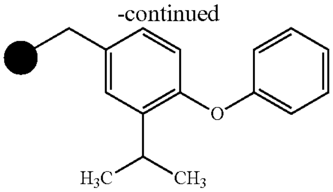
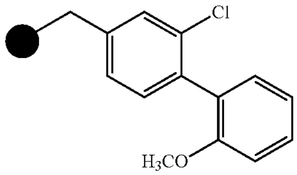
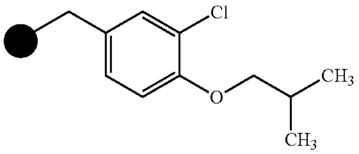
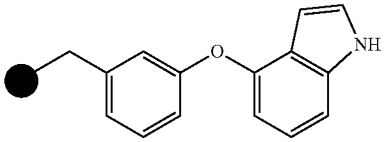
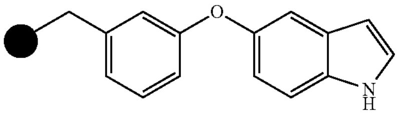
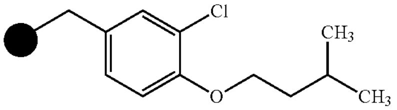
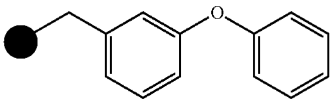
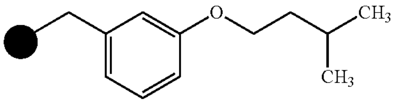
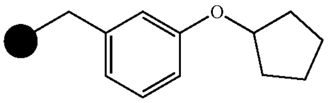
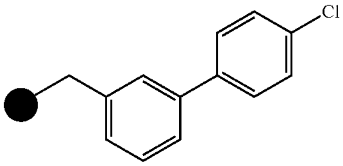
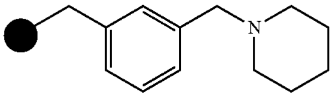
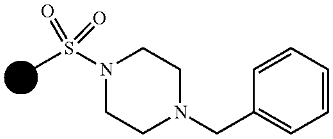
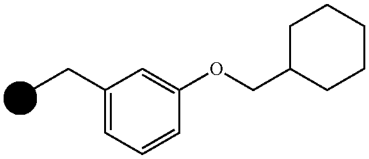

-continued

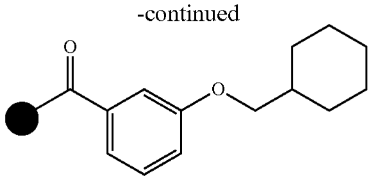

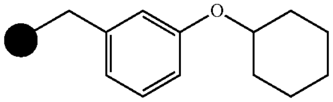

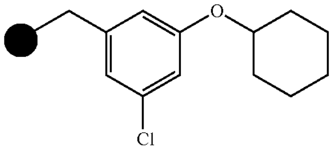

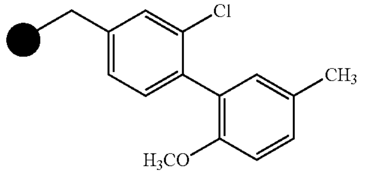

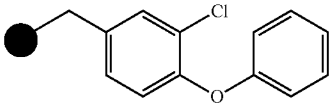

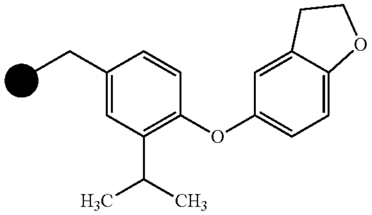

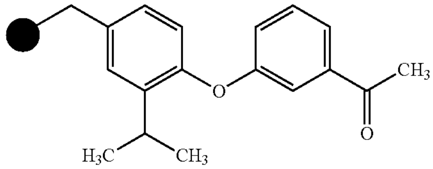

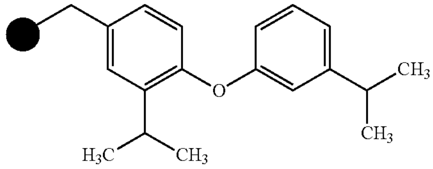

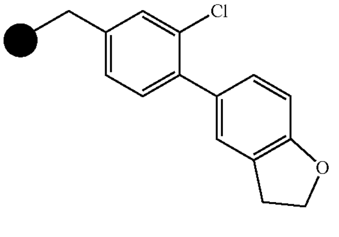

In a preferred embodiment, $R_4$ is a X—$R_7$ group $R_4$ is a X—$R_7$ group in which:

X represents —$CH_2$—, —CO—, or —$SO_2$—, and $R_7$ represents a phenyl, a dihydrobenzofuran or a piperazinyl optionally substituted by at least one radical selected in the group consisting of:

a halogen, preferably a chlorine, a ($C_1$-$C_6$)alkyl optionally substituted by at least one fluorine, preferably an isopropyl, a tert-butyl, or a trifluoromethyl, a ($C_1$-$C_6$)alkyloxy, preferably an isobutyloxy or an isopentyloxy, and a radical selected in the group consisting of a phenyl, an indolyl, a dihydrobenzofuranyl, a dihydrobenzofuranoxy, a phenoxy, and a benzyl, said radicals are optionally substituted by at least one radical selected in the group consisting of:

a ($C_1$-$C_6$)alkyl optionally substituted by at least one ($C_1$-$C_6$)alkyloxy or a halogen, preferably a methyl, an isopropyl, a methoxymethyl, or a trifluoromethyl, a ($C_1$-$C_6$)alkyloxy, preferably a methoxy or an isopentyloxy, and a —$COR_8$ with $R_8$ being ($C_1$-$C_6$)alkyl, preferably a methyl.

In a further preferred embodiment, $R_4$ is a X—$R_7$ group in which:

X represents —$CH_2$— or —CO—, and $R_7$ represents a phenyl disubstituted:

in meta position by a radical selected in the group consisting of:

a halogen, preferably a chlorine, and a ($C_1$-$C_6$)alkyl optionally substituted by at least one fluorine, preferably an isopropyl or a trifluoromethyl, a phenyl optionally substituted by ($C_1$-$C_6$)alkyl optionally substituted by at least one fluorine, preferably a trifluoromethyl, and in para position by a radical selected in the group consisting of:

a ($C_1$-$C_6$)alkyloxy, preferably an isobutyloxy or an isopentyloxy, and a phenyl, an indolyl, a dihydrobenzofuranyl, a dihydrobenzofuranoxy, a phenoxy, and a benzyl, said radicals are optionally substituted by at least one radical selected in the group consisting of:

a ($C_1$-$C_6$)alkyl optionally substituted by at least one ($C_1$-$C_6$)alkyloxy, preferably a methyl, an isopropyl, or a methoxymethyl, a ($C_1$-$C_6$)alkyloxy, preferably a methoxy or an isopentyloxy, and a —$COR_8$ with $R_8$ being ($C_1$-$C_6$)alkyl, preferably a methyl.

In a preferred embodiment, a compound of formula (I') or (I) is a compound selected in the group consisting of:

AB150: N-(2-(4-((4-(1H-indol-3-yl)-1H-1,2,3-triazol-1-yl)methyl)piperidin-1-yl)ethyl)benzenesulfonamide;

AB152: N-(2-(4-((4-(1H-indol-3-yl)-1H-1,2,3-triazol-1-yl)methyl)piperidin-1-yl)ethyl)-4-chlorobenzenesulfonamide;

AB153: 4-chloro-N-(2-(4-((4-(5-fluoro-1H-indol-3-yl)-1H-1,2,3-triazol-1-yl)methyl)piperidin-1-yl)ethyl)benzenesulfonamide;

AB201: 5-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB202: 6-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB401: ethyl 3-(1-((1-(2-((4-chlorophenyl)sulfonamido)ethyl)piperidin-4-yl)methyl)-1H-1,2,3-triazol-4-yl)-5-fluoro-1H-indole-2-carboxylate;

AB460: ethyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB433: ethyl 6-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB504: ethyl 5-fluoro-3-(1-((1-(2-((4-methylphenyl)sulfonamido)ethyl)piperidin-4-yl)methyl)-1H-1,2,3-triazol-4-yl)-1H-indole-2-carboxylate;

AB505: ethyl 5-chloro-3-(1-((1-(2-((4-methylphenyl)sulfonamido)ethyl)piperidin-4-yl)methyl)-1H-1,2,3-triazol-4-yl)-1H-indole-2-carboxylate;

AB503: ethyl 6-chloro-3-(1-((1-(2-((4-methylphenyl)sulfonamido)ethyl)piperidin-4-yl)methyl)-1H-1,2,3-triazol-4-yl)-1H-indole-2-carboxylate;

AB529: ethyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB550: ethyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB526: ethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB543: ethyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB536: ethyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB551: ethyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB579: ethyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB582 ethyl 5-chloro-3-(1-((1-(2-((4-isopropylphenyl)sulfonamido)ethyl)piperidin-4-yl)methyl)-1H-1,2,3-triazol-4-yl)-1H-indole-2-carboxylate;

AB577: isopropyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB578: isopropyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB498: isobutyl 3-(1-((1-(2-((4-chlorophenyl)sulfonamido)ethyl)piperidin-4-yl)methyl)-1H-1,2,3-triazol-4-yl)-5-fluoro-1H-indole-2-carboxylate;

AB499: isobutyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB600: isobutyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB601: isobutyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB556: isobutyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB557: isobutyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB598: isobutyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB599: isobutyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB603: isobutyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB668: isobutyl 5-fluoro-3-(1-((1-(2-((4-isobutylphenyl)sulfonamido)ethyl)piperidin-4-yl)methyl)-1H-1,2,3-triazol-4-yl)-1H-indole-2-carboxylate;

AB651: 3-(1-((1-(2-((4-ethylphenyl)sulfonamido)ethyl)piperidin-4-yl)methyl)-1H-1,2,3-triazol-4-yl)-5-fluoro-N-isobutyl-1H-indole-2-carboxamide;

AB652: 5-fluoro-N-isobutyl-3-(1-((1-(2-((4-isopropylphenyl)sulfonamido)ethyl)piperidin-4-yl)methyl)-1H-1,2,3-triazol-4-yl)-1H-indole-2-carboxamide;

AB663: isopentyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB664: isopentyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB669: isopentyl 5-fluoro-3-(1-((1-(2-((4-isobutylphenyl)sulfonamido)ethyl)piperidin-4-yl)methyl)-1H-1,2,3-triazol-4-yl)-1H-indole-2-carboxylate;

AB670: 3-(1-((1-(2-((4-ethylphenyl)sulfonamido)ethyl)piperidin-4-yl)methyl)-1H-1,2,3-triazol-4-yl)-5-fluoro-N-isopentyl-1H-indole-2-carboxamide;

AB671: 5-fluoro-N-isopentyl-3-(1-((1-(2-((4-isopropylphenyl)sulfonamido)ethyl)piperidin-4-yl)methyl)-1H-1,2,3-triazol-4-yl)-1H-indole-2-carboxamide;

AB597: 2-hydroxyethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB614: 2-aminoethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB680: isobutyl 3-(1-((1-((2-chloro-2'-(methoxymethyl)-[1,1'-biphenyl]-4-yl)methyl)piperidin-4-yl)methyl)-1H-1,2,3-triazol-4-yl)-5-fluoro-1H-indole-2-carboxylate;

AB681: isobutyl 3-(1-((1-(2-chloro-2'-(methoxymethyl)-[1,1'-biphenyl]-4-carbonyl)piperidin-4-yl)methyl)-1H-1,2,3-triazol-4-yl)-5-fluoro-1H-indole-2-carboxylate;

AB689: isobutyl 3-(1-((1-((2-chloro-2'-methoxy-[1,1'-biphenyl]-4-yl)methyl)piperidin-4-yl)methyl)-1H-1,2,3-triazol-4-yl)-5-fluoro-1H-indole-2-carboxylate;

AB690: isobutyl 3-(1-((1-(3-chloro-4-(1H-indol-4-yl)benzyl)piperidin-4-yl)methyl)-1H-1,2,3-triazol-4-yl)-5-fluoro-1H-indole-2-carboxylate;

AB691: isobutyl 3-(1-((1-(3-chloro-4-phenoxybenzyl)piperidin-4-yl)methyl)-1H-1,2,3-triazol-4-yl)-5-fluoro-1H-indole-2-carboxylate;

AB692: isobutyl 3-(1-((1-((2-chloro-2'-methoxy-5'-methyl-[1,1'-biphenyl]-4-yl)methyl)piperidin-4-yl)methyl)-1H-1,2,3-triazol-4-yl)-5-fluoro-1H-indole-2-carboxylate;

AB697: isobutyl 5-fluoro-3-(1-((1-(3-isopropyl-4-phenoxybenzyl)piperidin-4-yl)methyl)-1H-1,2,3-triazol-4-yl)-1H-indole-2-carboxylate;

AB703: isobutyl 3-(1-((1-(4-(1H-indol-4-yl)-3-isopropylbenzyl)piperidin-4-yl)methyl)-1H-1,2,3-triazol-4-yl)-5-fluoro-1H-indole-2-carboxylate;

AB704: isobutyl 5-fluoro-3-(1-((1-((2-isopropyl-2'-(methoxymethyl)-[1,1'-biphenyl]-4-yl)methyl)piperidin-4-yl)methyl)-1H-1,2,3-triazol-4-yl)-1H-indole-2-carboxylate;

AB717: isobutyl 3-(1-((1-(4-((2,3-dihydrobenzofuran-5-yl)oxy)-3-isopropylbenzyl)piperidin-4-yl)methyl)-1H-1,2,3-triazol-4-yl)-5-fluoro-1H-indole-2-carboxylate;

AB718: isobutyl 3-(1-((1-(4-(3-acetylphenoxy)-3-isopropylbenzyl)piperidin-4-yl)methyl)-1H-1,2,3-triazol-4-yl)-5-fluoro-1H-indole-2-carboxylate;

AB713: isobutyl 5-fluoro-3-(1-((1-(3-isopropyl-4-(3-isopropylphenoxy)benzyl)piperidin-4-yl)methyl)-1H-1,2,3-triazol-4-yl)-1H-indole-2-carboxylate;

AB753: isobutyl 3-(1-((1-(3-chloro-4-(1H-indol-5-yl)benzyl)piperidin-4-yl)methyl)-1H-1,2,3-triazol-4-yl)-5-fluoro-1H-indole-2-carboxylate;

AB731: isobutyl 3-(1-((1-(3-chloro-4-(2,3-dihydrobenzofuran-5-yl)benzyl)piperidin-4-yl)methyl)-1H-1,2,3-triazol-4-yl)-5-fluoro-1H-indole-2-carboxylate;

AB739: isobutyl 3-(1-((1-((3'-acetyl-2-chloro-[1,1'-biphenyl]-4-yl)methyl)piperidin-4-yl)methyl)-1H-1,2,3-triazol-4-yl)-5-fluoro-1H-indole-2-carboxylate;

AB758: isobutyl 3-(1-((1-((2-chloro-3'-isopropyl-[1,1'-biphenyl]-4-yl)methyl)piperidin-4-yl)methyl)-1H-1,2,3-triazol-4-yl)-5-fluoro-1H-indole-2-carboxylate;

AB760: isobutyl 3-(1-((1-(3-chloro-4-isobutoxybenzyl)piperidin-4-yl)methyl)-1H-1,2,3-triazol-4-yl)-5-fluoro-1H-indole-2-carboxylate;

AB746: isobutyl 3-(1-((1-(3-chloro-4-(isopentyloxy)benzyl)piperidin-4-yl)methyl)-1H-1,2,3-triazol-4-yl)-5-fluoro-1H-indole-2-carboxylate;

AB743: isobutyl 3-(1-((1-(2-chloro-2'-(isopentyloxy)-[1,1'-biphenyl]-4-carbonyl)piperidin-4-yl)methyl)-1H-1,2,3-triazol-4-yl)-5-fluoro-1H-indole-2-carboxylate;

AB756: isobutyl 3-(1-((1-(4-(1H-indol-4-yl)-3-(trifluoromethyl)benzoyl)piperidin-4-yl)methyl)-1H-1,2,3-triazol-4-yl)-5-fluoro-1H-indole-2-carboxylate; and AB755: isobutyl 3-(1-((1-((4-benzylpiperazin-1-yl)sulfonyl)piperidin-4-yl)methyl)-1H-1,2,3-triazol-4-yl)-5-fluoro-1H-indole-2-carboxylate;

AB912: isobutyl 5-fluoro-3-(1-((1-(2-((4-(trifluoromethoxy)phenyl)sulfonamido)ethyl) piperidin-4-yl) methyl)-1H-1,2,3-triazol-4-yl)-1H-indole-2-carboxylate;

AB913: isobutyl 3-(1-((1-(2-([1,1'-biphenyl]-4-sulfonamido)ethyl)piperidin-4-yl)methyl)-1H-1,2,3-triazol-4-yl)-5-fluoro-1H-indole-2-carboxylate;

AB914: isobutyl 3-(1-((1-(2-((4-cyclohexylphenyl)sulfonamido)ethyl)piperidin-4-yl)methyl)-1H-1,2,3-triazol-4-yl)-5-fluoro-1H-indole-2-carboxylate;

AB917: isobutyl 5-fluoro-3-(1-((1-(2-((4-isopropoxyphenyl)sulfonamido)ethyl)piperidin-4-yl)methyl)-1H-1,2,3-triazol-4-yl)-1H-indole-2-carboxylate;

AB918: isobutyl 3-(1-((1-(2-((4-benzylpiperidine)-1-sulfonamido)ethyl)piperidin-4-yl)methyl)-1H-1,2,3-triazol-4-yl)-5-fluoro-1H-indole-2-carboxylate;

AB929: isobutyl 5-fluoro-3-(1-((1-(2-((4-phenylpiperidine)-1-sulfonamido) ethyl)piperidin-4-yl)methyl)-1H-1,2,3-triazol-4-yl)-1H-indole-2-carboxylate;

AB930: isobutyl 3-(1-((1-(2-((2,3-dihydrobenzofuran)-5-sulfonamido)ethyl)piperidin-4-yl)methyl)-1H-1,2,3-triazol-4-yl)-5-fluoro-1H-indole-2-carboxylate;

AB931: isobutyl 3-(1-((1-(2-((4-(sec-butyl)phenyl)sulfonamido)ethyl)piperidin-4-yl)methyl)-1H-1,2,3-triazol-4-yl)-5-fluoro-1H-indole-2-carboxylate;

AB932: isobutyl 3-(1-((1-(2-((2,3-dihydro-1H-indene)-5-sulfonamido)ethyl)piperidin-4-yl)methyl)-1H-1,2,3-triazol-4-yl)-5-fluoro-1H-indole-2-carboxylate;

AB933: isobutyl 5-fluoro-3-(1-((1-(2-((4-phenoxyphenyl) sulfonamido)ethyl)piperidin-4-yl)methyl)-1H-1,2,3-triazol-4-yl)-1H-indole-2-carboxylate AB934: isobutyl 3-(1-((1-(2-((4-(tert-butyl)phenyl)sulfonamido)ethyl)piperidin-4-yl)methyl)-1H-1,2,3-triazol-4-yl)-5-fluoro-1H-indole-2-carboxylate;

AB935: isobutyl 5-fluoro-3-(1-((1-(2-(((4-(trifluoromethyl) phenyl)methyl) sulfonamido)ethyl) piperidin-4-yl) methyl)-1H-1,2,3-triazol-4-yl)-1H-indole-2-carboxylate;

AB936: isobutyl 3-(1-((1-(2-(((4-chlorophenyl)methyl) sulfonamido)ethyl)piperidin-4-yl)methyl)-1H-1,2,3-triazol-4-yl)-5-fluoro-1H-indole-2-carboxylate;

AB937: isobutyl 3-(1-((1-(2-(((3-chlorophenyl)methyl) sulfonamido)ethyl)piperidin-4-yl)methyl)-1H-1,2,3-triazol-4-yl)-5-fluoro-1H-indole-2-carboxylate;

AB938: isobutyl 3-(1-((1-((4-(tert-butyl)phenyl)sulfonyl)piperidin-4-yl)methyl)-1H-1,2,3-triazol-4-yl)-5-fluoro-1H-indole-2-carboxylate;

AB939: isobutyl 3-(1-((1-((2,3-dihydrobenzofuran-6-yl) sulfonyl)piperidin-4-yl)methyl)-1H-1,2,3-triazol-4-yl)-5-fluoro-1H-indole-2-carboxylate;

AB1030: isobutyl 3-(1-((1-(2-(((4-bromophenyl)methyl) sulfonamido)ethyl)piperidin-4-yl)methyl)-1H-1,2,3-triazol-4-yl)-5-fluoro-1H-indole-2-carboxylate;

AB1031: isobutyl 3-(1-((1-(2-(((3-bromophenyl)methyl) sulfonamido)ethyl)piperidin-4-yl)methyl)-1H-1,2,3-triazol-4-yl)-5-fluoro-1H-indole-2-carboxylate;

AB1032: isobutyl 3-(1-((1-(2-((4-(1H-pyrazol-4-yl)phenyl) sulfonamido)ethyl)piperidin-4-yl)methyl)-1H-1,2,3-triazol-4-yl)-5-fluoro-1H-indole-2-carboxylate;

AB1070: isobutyl 3-(1-((1-(2-((4',4'-difluoro-2',3',4',5'-tetrahydro-[1,1'-biphenyl])-4-sulfonamido)ethyl)piperidin-4-yl)methyl)-1H-1,2,3-triazol-4-yl)-5-fluoro-1H-indole-2-carboxylate;

AB1071: isobutyl 5-fluoro-3-(1-((1-(2-((4-(furan-3-yl)phenyl)sulfonamido)ethyl)piperidin-4-yl)methyl)-1H-1,2,3-triazol-4-yl)-1H-indole-2-carboxylate;

AB1072: isobutyl 3-(1-((1-(2-((3,4-dihydro-2H-benzo[b][1,4]dioxepine)-7-sulfonamido)ethyl)piperidin-4-yl) methyl)-1H-1,2,3-triazol-4-yl)-5-fluoro-1H-indole-2-carboxylate;

AB1073: isobutyl 5-fluoro-3-(1-((1-(2-((4-(2-(pyrrolidin-1-yl)pyridin-3-yl)phenyl) sulfonamido)ethyl)piperidin-4-yl)methyl)-1H-1,2,3-triazol-4-yl)-1H-indole-2-carboxylate;

AB1074: isobutyl 3-(1-((1-(2-((4-(3,6-dihydro-2H-pyran-4-yl)phenyl) sulfonamido)ethyl)piperidin-4-yl)methyl)-1H-1,2,3-triazol-4-yl)-5-fluoro-1H-indole-2-carboxylate;

AB1075: isobutyl 5-fluoro-3-(1-((1-(2-((2'-(morpholinomethyl)-[1,1'-biphenyl])-4-sulfonamido)ethyl)piperidin-4-yl)methyl)-1H-1,2,3-triazol-4-yl)-1H-indole-2-carboxylate;

AB1076: isobutyl 3-(1-((1-(2-((2'-cyano-[1,1'-biphenyl])-4-sulfonamido)ethyl)piperidin-4-yl)methyl)-1H-1,2,3-triazol-4-yl)-5-fluoro-1H-indole-2-carboxylate;

AB1130: isobutyl 3-(1-((1-(2-((4-(3,5-dimethylisoxazol-4-yl)phenyl)sulfonamido) ethyl)piperidin-4-yl)methyl)-1H-1,2,3-triazol-4-yl)-5-fluoro-1H-indole-2-carboxylate;

AB1133: isobutyl 3-(1-((1-(2-((4-(2-chloropyridin-3-yl) phenyl)sulfonamido)ethyl)piperidin-4-yl)methyl)-1H-1,2,3-triazol-4-yl)-5-fluoro-1H-indole-2-carboxylate;

AB1134: isobutyl 3-(1-((1-(2-((4'-cyano-[1,1'-biphenyl])-4-sulfonamido)ethyl)piperidin-4-yl)methyl)-1H-1,2,3-triazol-4-yl)-5-fluoro-1H-indole-2-carboxylate;

AB1205: isobutyl 5-fluoro-3-(1-((1-(2-((2'-methoxy-[1,1'-biphenyl])-4-sulfonamido)ethyl) piperidin-4-yl)methyl)-1H-1,2,3-triazol-4-yl)-1H-indole-2-carboxylate;

AB1206: isobutyl 3-(1-((1-(2-((2',6'-dimethoxy-[1,1'-biphenyl])-4-sulfonamido)ethyl) piperidin-4-yl)methyl)-1H-1,2,3-triazol-4-yl)-5-fluoro-1H-indole-2-carboxylate;

AB1207: isobutyl 5-fluoro-3-(1-((1-(2-((4-(2-fluoropyridin-3-yl)phenyl)sulfonamido) ethyl)piperidin-4-yl)methyl)-1H-1,2,3-triazol-4-yl)-1H-indole-2-carboxylate;

AB1208: isobutyl 3-(1-((1-(2-((2',6'-difluoro-[1,1'-biphenyl])-4-sulfonamido)ethyl)piperidin-4-yl)methyl)-1H-1,2,3-triazol-4-yl)-5-fluoro-1H-indole-2-carboxylate;

AB1209: isobutyl 3-(1-((1-(2-((2'-(dimethylamino)-[1,1'-biphenyl])-4-sulfonamido) ethyl)piperidin-4-yl)methyl)-1H-1,2,3-triazol-4-yl)-5-fluoro-1H-indole-2-carboxylate;

AB1210: isobutyl 5-fluoro-3-(1-((1-(2-((p-tolylmethyl)sulfonamido)ethyl)piperidin-4-yl)methyl)-1H-1,2,3-triazol-4-yl)-1H-indole-2-carboxylate;

AB1303: isobutyl 5-fluoro-3-(1-((1-(2-((2'-(methoxymethyl)-[1,1'-biphenyl])-4-sulfonamido)ethyl)piperidin-4-yl)methyl)-1H-1,2,3-triazol-4-yl)-1H-indole-2-carboxylate;

AB1131: N-(2-(4-((4-(5-fluoro-2-(pyrrolidine-1-carbonyl)-1H-indol-3-yl)-1H-1,2,3-triazol-1-yl)methyl)piperidin-1-yl)ethyl)-4-isobutylbenzenesulfonamide;

AB1132: N-(2-(4-((4-(5-fluoro-2-(morpholine-4-carbonyl)-1H-indol-3-yl)-1H-1,2,3-triazol-1-yl)methyl)piperidin-1-yl)ethyl)-4-isobutylbenzenesulfonamide;

AB1135: N-(2-(4-((4-(2-acetyl-5-fluoro-1H-indol-3-yl)-1H-1,2,3-triazol-1-yl)methyl) piperidin-1-yl)ethyl)-4-isobutylbenzenesulfonamide;

AB1145: N-(2-(4-((4-(5-fluoro-2-pentanoyl-1H-indol-3-yl)-1H-1,2,3-triazol-1-yl)methyl) piperidin-1-yl)ethyl)-4-isobutylbenzenesulfonamide;

AB1231: N-(2-(4-((4-(2-(cyclopropanecarbonyl)-5-fluoro-1H-indol-3-yl)-1H-1,2,3-triazol-1-yl)methyl)piperidin-1-yl)ethyl)-4-isobutylbenzenesulfonamide;

AB1232: 4-(2-chloropyridin-3-yl)-N-(2-(4-((4-(2-(cyclopropanecarbonyl)-5-fluoro-1H-indol-3-yl)-1H-1,2,3-triazol-1-yl)methyl)piperidin-1-yl)ethyl)benzenesulfonamide;

AB1233: N-(2-(4-((4-(2-butyryl-5-fluoro-1H-indol-3-yl)-1H-1,2,3-triazol-1-yl)methyl) piperidin-1-yl)ethyl)-4-(2-chloropyridin-3-yl)benzenesulfonamide;

AB1235: N-(2-(4-((4-(5-fluoro-2-fornyl-1H-indol-3-yl)-1H-1,2,3-triazol-1-yl)methyl) piperidin-1-yl)ethyl)-4-isobutylbenzenesulfonamide;

AB1281: N-(2-(4-((4-(5-fluoro-2-isobutyryl-1H-indol-3-yl)-1H-1,2,3-triazol-1-yl)methyl) piperidin-1-yl)ethyl)-4-isobutylbenzenesulfonamide;

AB1282: 4-(2-chloropyridin-3-yl)-N-(2-(4-((4-(5-fluoro-2-isobutyryl-1H-indol-3-yl)-1H-1,2,3-triazol-1-yl)methyl) piperidin-1-yl)ethyl)benzenesulfonamide;

AB1283: N-(2-(4-((4-(5-fluoro-2-(3-methylbutanoyl)-1H-indol-3-yl)-1H-1,2,3-triazol-1-yl)methyl)piperidin-1-yl) ethyl)-4-isobutylbenzenesulfonamide;

AB1284: 4-(2-chloropyridin-3-yl)-N-(2-(4-((4-(5-fluoro-2-(3-methylbutanoyl)-1H-indol-3-yl)-1H-1,2,3-triazol-1-yl)methyl)piperidin-1-yl)ethyl)benzenesulfonamide;

AB1285: N-(2-(4-((4-(2-(cyclopropanecarbonyl)-5-fluoro-1H-indol-3-yl)-1H-1,2,3-triazol-1-yl)methyl)piperidin-1-yl)ethyl)-4-(3,5-dimethylisoxazol-4-yl)benzenesulfonamide;

AB1286: N-(2-(4-((4-(2-acetyl-5-fluoro-1H-indol-3-yl)-1H-1,2,3-triazol-1-yl)methyl) piperidin-1-yl)ethyl)-4-(3,5-dimethylisoxazol-4-yl)benzenesulfonamide;

AB1287: N-(2-(4-((4-(2-acetyl-5-fluoro-1H-indol-3-yl)-1H-1,2,3-triazol-1-yl)methyl) piperidin-1-yl)ethyl)-2',6'-dimethoxy-[1,1'-biphenyl]-4-sulfonamide;

AB1288: N-(2-(4-((4-(2-acetyl-5-fluoro-1H-indol-3-yl)-1H-1,2,3-triazol-1-yl)methyl)piperidin-1-yl)ethyl)-2',6'-difluoro-[1,1'-biphenyl]-4-sulfonamide;

AB1289: N-(2-(4-((4-(2-acetyl-5-fluoro-1H-indol-3-yl)-1H-1,2,3-triazol-1-yl)methyl) piperidin-1-yl)ethyl)-4-(2-fluoropyridin-3-yl)benzenesulfonamide;

AB1301: N-(2-(4-((4-(5-fluoro-2-nicotinoyl-1H-indol-3-yl)-1H-1,2,3-triazol-1-yl)methyl) piperidin-1-yl)ethyl)-4-isobutylbenzenesulfonamide;

AB1302: N-(2-(4-((4-(5-fluoro-2-(2-methylbutanoyl)-1H-indol-3-yl)-1H-1,2,3-triazol-1-yl)methyl)piperidin-1-yl) ethyl)-4-isobutylbenzenesulfonamide;

AB1304: N-(2-(4-((4-(2-(cyclopropanecarbonyl)-5-fluoro-1H-indol-3-yl)-1H-1,2,3-triazol-1-yl)methyl)piperidin-1-yl)ethyl)-4-(2,6-difluorophenyl)piperidine-1-sulfonamide;

AB1305: N-(2-(4-((4-(2-(cyclopropanecarbonyl)-5-fluoro-1H-indol-3-yl)-1H-1,2,3-triazol-1-yl)methyl)piperidin-1-yl)ethyl)-1-(4-(trifluoromethyl)phenyl)methanesulfonamide;

AB1306: N-(2-(4-((4-(5-fluoro-2-(3-methylbutanoyl)-1H-indol-3-yl)-1H-1,2,3-triazol-1-yl)methyl)piperidin-1-yl) ethyl)-1-(4-(trifluoromethyl)phenyl)methanesulfonamide;

AB1307: N-(2-(4-((4-(2-butyryl-5-fluoro-1H-indol-3-yl)-1H-1,2,3-triazol-1-yl)methyl) piperidin-1-yl)ethyl)-1-(4-(trifluoromethyl)phenyl)methanesulfonamide;

AB1315: N-(2-(4-((4-(2-acetyl-5-fluoro-1H-indol-3-yl)-1H-1,2,3-triazol-1-yl)methyl) piperidin-1-yl)ethyl)-1-(4-(trifluoromethyl)phenyl)methanesulfonamide;

AB1316: N-(2-(4-((4-(2-acetyl-5-fluoro-1H-indol-3-yl)-1H-1,2,3-triazol-1-yl)methyl) piperidin-1-yl)ethyl)-4-(2,6-difluorophenyl)piperidine-1-sulfonamide AB1317: N-(2-(4-((4-(2-acetyl-5-fluoro-1H-indol-3-yl)-1H-1,2,3-triazol-1-yl)methyl) piperidin-1-yl)ethyl)-4-(cyclopropylmethyl)benzenesulfonamide;

AB1318: (S)—N-(2-(3-((4-(2-acetyl-5-fluoro-1H-indol-3-yl)-1H-1,2,3-triazol-1-yl)methyl) pyrrolidin-1-yl)ethyl)-4-isobutylbenzenesulfonamide;

AB1319: (R)—N-(2-(3-((4-(2-acetyl-5-fluoro-1H-indol-3-yl)-1H-1,2,3-triazol-1-yl)methyl) pyrrolidin-1-yl)ethyl)-4-isobutylbenzenesulfonamide;

AB1321: N-(2-(4-(4-(2-acetyl-5-fluoro-1H-indol-3-yl)-1H-1,2,3-triazol-1-yl)piperidin-1-yl)ethyl)-4-isobutylbenzenesulfonamide;

AB1322: N-(2-(4-((4-(2-acetyl-5-fluoro-1H-indol-3-yl)-1H-1,2,3-triazol-1-yl)methyl) piperidin-1-yl)ethyl)-4-(2-fluoropyridin-3-yl)piperidine-1-sulfonamide;

AB1381: N-(2-(4-((4-(2-acetyl-5-fluoro-1H-indol-3-yl)-1H-1,2,3-triazol-1-yl)methyl) piperidin-1-yl)ethyl)-2'-fluoro-6'-hydroxy-[1,1'-biphenyl]-4-sulfonamide;

AB1390: N-(2-(4-((4-(2-acetyl-5-fluoro-1H-indol-3-yl)-1H-1,2,3-triazol-1-yl)methyl) piperidin-1-yl)ethyl)-2'-fluoro-[1,1'-biphenyl]-4-sulfonamide;

AB1393: N-(2-(4-((4-(2-acetyl-5-fluoro-1H-indol-3-yl)-1H-1,2,3-triazol-1-yl)methyl) piperidin-1-yl)ethyl)-2'-cyano-6'-(trifluoromethyl)-[1,1'-biphenyl]-4-sulfonamide;

AB1394: N-(2-(4-((4-(2-acetyl-5-fluoro-1H-indol-3-yl)-1H-1,2,3-triazol-1-yl)methyl) piperidin-1-yl)ethyl)-2'-(trifluoromethyl)-[1,1'-biphenyl]-4-sulfonamide;

AB1401: N-(2-(4-((4-(2-acetyl-5-fluoro-1H-indol-3-yl)-1H-1,2,3-triazol-1-yl)methyl) piperidin-1-yl)ethyl)-2'-fluoro-6'-methoxy-[1,1'-biphenyl]-4-sulfonamide;

AB1402: isobutyl 5-fluoro-3-(1-((1-(2-((2'-fluoro-6'-hydroxy-[1,1'-biphenyl])-4-sulfonamido)ethyl)piperidin-4-yl)methyl)-1H-1,2,3-triazol-4-yl)-1H-indole-2-carboxylate;

AB1403: (S)—N-(2-(3-((4-(2-acetyl-5-fluoro-1H-indol-3-yl)-1H-1,2,3-triazol-1-yl)methyl) piperidin-1-yl)ethyl)-4-isobutylbenzenesulfonamide;

AB1404: N-(2-(3-((4-(2-acetyl-5-fluoro-1H-indol-3-yl)-1H-1,2,3-triazol-1-yl)methyl) azetidin-1-yl)ethyl)-4-isobutylbenzenesulfonamide;

AB1405: N-(2-(4-((4-(5-fluoro-2-(hydroxymethyl)-1H-indol-3-yl)-1H-1,2,3-triazol-1-yl)methyl)piperidin-1-yl) ethyl)-4-isobutylbenzenesulfonamide;

AB1406: 2'-fluoro-N-(2-(4-((4-(5-fluoro-2-(hydroxymethyl)-1H-indol-3-yl)-1H-1,2,3-triazol-1-yl)methyl)piperidin-1-yl)ethyl)-6'-hydroxy-[1,1'-biphenyl]-4-sulfonamide;

AB1415: 2'-fluoro-N-(2-(4-((4-(5-fluoro-2-propionyl-1H-indol-3-yl)-1H-1,2,3-triazol-1-yl)methyl)piperidin-1-yl) ethyl)-6'-hydroxy-[1,1'-biphenyl]-4-sulfonamide;

AB1416: N-(2-(4-((4-(5-fluoro-2-propionyl-1H-indol-3-yl)-1H-1,2,3-triazol-1-yl)methyl) piperidin-1-yl)ethyl)-2',6'-dimethoxy-[1,1'-biphenyl]-4-sulfonamide;

AB1417: N-(2-(4-((4-(5-fluoro-2-propionyl-1H-indol-3-yl)-1H-1,2,3-triazol-1-yl)methyl) piperidin-1-yl)ethyl)-1-(4-(trifluoromethyl)phenyl)methanesulfonamide;

AB1450: N-(2-(4-((4-(2-acetyl-5-fluoro-1H-indol-3-yl)-1H-1,2,3-triazol-1-yl)methyl) piperidin-1-yl)ethyl)-2'-hydroxy-[1,1'-biphenyl]-4-sulfonamide;

AB1451: N-(2-(4-((4-(2-acetyl-5-fluoro-1H-indol-3-yl)-1H-1,2,3-triazol-1-yl)methyl) piperidin-1-yl)ethyl)-2'-fluoro-6'-(trifluoromethyl)-[1,1'-biphenyl]-4-sulfonamide;

AB1452: N-(2-(4-((4-(2-acetyl-5-fluoro-1H-indol-3-yl)-1H-1,2,3-triazol-1-yl)methyl) piperidin-1-yl)ethyl)-2'-cyano-6'-methyl-[1,1'-biphenyl]-4-sulfonamide;

AB1453: N-(2-(4-((4-(2-acetyl-5-fluoro-1H-indol-3-yl)-1H-1,2,3-triazol-1-yl)methyl) piperidin-1-yl)ethyl)-2'-chloro-4'-fluoro-[1,1'-biphenyl]-4-sulfonamide;

AB1454: N-(2-(4-((4-(2-acetyl-5-fluoro-1H-indol-3-yl)-1H-1,2,3-triazol-1-yl)methyl) piperidin-1-yl)ethyl)-2-fluoro-2',6'-dimethoxy-[1,1'-biphenyl]-4-sulfonamide;

AB1455: N-(2-(4-((4-(2-acetyl-5-fluoro-1H-indol-3-yl)-1H-1,2,3-triazol-1-yl)methyl) piperidin-1-yl)ethyl)-2',6'-dimethoxy-2-methyl-[1,1'-biphenyl]-4-sulfonamide;

AB1456: N-(2-(4-((4-(2-acetyl-5-fluoro-1H-indol-3-yl)-1H-1,2,3-triazol-1-yl)methyl) piperidin-1-yl)ethyl)-2-chloro-2',6'-dimethoxy-[1,1'-biphenyl]-4-sulfonamide; and AB1457: N-(2-(4-((4-(2-acetyl-5-fluoro-1H-indol-3-yl)-1H-1,2,3-triazol-1-yl)methyl) piperidin-1-yl)ethyl)-2,2'-difluoro-6'-hydroxy-[1,1'-biphenyl]-4-sulfonamide.

In a particular preferred embodiment, a compound of formula (I') or (I) is selected in the group consisting of:

AB150: N-(2-(4-((4-(1H-indol-3-yl)-1H-1,2,3-triazol-1-yl) methyl)piperidin-1-yl)ethyl)benzenesulfonamide;

AB152: N-(2-(4-((4-(1H-indol-3-yl)-1H-1,2,3-triazol-1-yl) methyl)piperidin-1-yl)ethyl)-4-chlorobenzenesulfonamide;

AB153: 4-chloro-N-(2-(4-((4-(5-fluoro-1H-indol-3-yl)-1H-1,2,3-triazol-1-yl)methyl)piperidin-1-yl)ethyl)benzenesulfonamide;

AB201: 5-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB202: 6-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB401: ethyl 3-(1-((1-(2-((4-chlorophenyl)sulfonamido) ethyl)piperidin-4-yl)methyl)-1H-1,2,3-triazol-4-yl)-5-fluoro-1H-indole-2-carboxylate;

AB460: ethyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB433: ethyl 6-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB504: ethyl 5-fluoro-3-(1-((1-(2-((4-methylphenyl)sulfonamido)ethyl)piperidin-4-yl)methyl)-1H-1,2,3-triazol-4-yl)-1H-indole-2-carboxylate;

AB505: ethyl 5-chloro-3-(1-((1-(2-((4-methylphenyl)sulfonamido)ethyl)piperidin-4-yl)methyl)-1H-1,2,3-triazol-4-yl)-1H-indole-2-carboxylate;

AB503: ethyl 6-chloro-3-(1-((1-(2-((4-methylphenyl)sulfonamido)ethyl)piperidin-4-yl)methyl)-1H-1,2,3-triazol-4-yl)-1H-indole-2-carboxylate;

AB529: ethyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB550: ethyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB526: ethyl 3-(1-((1-(2-((4-ethylphenyl)sulfonamido) ethyl)piperidin-4-yl)methyl)-1H-1,2,3-triazol-4-yl)-5-fluoro-1H-indole-2-carboxylate;

AB543: ethyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB536: ethyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB551: ethyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB579: ethyl 5-fluoro-3-(1-((1-(2-((4-isopropylphenyl) sulfonamido)ethyl)piperidin-4-yl)methyl)-1H-1,2,3-triazol-4-yl)-1H-indole-2-carboxylate;

AB582 ethyl 5-chloro-3-(1-((1-(2-((4-isopropylphenyl) sulfonamido)ethyl)piperidin-4-yl)methyl)-1H-1,2,3-triazol-4-yl)-1H-indole-2-carboxylate;

AB577: isopropyl 3-(1-((1-(2-((4-ethylphenyl)sulfonamido) ethyl)piperidin-4-yl)methyl)-1H-1,2,3-triazol-4-yl)-5-fluoro-1H-indole-2-carboxylate;

AB578: isopropyl 5-chloro-3-(1-((1-(2-((4-ethylphenyl) sulfonamido)ethyl)piperidin-4-yl)methyl)-1H-1,2,3-triazol-4-yl)-1H-indole-2-carboxylate;

AB498: isobutyl 3-(1-((1-(2-((4-chlorophenyl)sulfonamido) ethyl)piperidin-4-yl)methyl)-1H-1,2,3-triazol-4-yl)-5-fluoro-1H-indole-2-carboxylate;

AB499: isobutyl 5-chloro-3-(1-((1-(2-((4-chlorophenyl) sulfonamido)ethyl)piperidin-4-yl)methyl)-1H-1,2,3-triazol-4-yl)-1H-indole-2-carboxylate;

AB600: isobutyl 5-fluoro-3-(1-((1-(2-((4-(trifluoromethyl) phenyl)sulfonamido)ethyl)piperidin-4-yl)methyl)-1H-1,2,3-triazol-4-yl)-1H-indole-2-carboxylate;

AB601: isobutyl 5-chloro-3-(1-((1-(2-((4-(trifluoromethyl) phenyl)sulfonamido)ethyl)piperidin-4-yl)methyl)-1H-1,2,3-triazol-4-yl)-1H-indole-2-carboxylate;

AB556: isobutyl 3-(1-((1-(2-((4-ethylphenyl)sulfonamido) ethyl)piperidin-4-yl)methyl)-1H-1,2,3-triazol-4-yl)-5-fluoro-1H-indole-2-carboxylate;

AB557: isobutyl 5-chloro-3-(1-((1-(2-((4-ethylphenyl) sulfonamido)ethyl)piperidin-4-yl)methyl)-1H-1,2,3-triazol-4-yl)-1H-indole-2-carboxylate;

AB598: isobutyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB599: isobutyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB603: isobutyl 5-fluoro-3-(1-((1-(2-((4-isopropylphenyl) sulfonamido)ethyl)piperidin-4-yl)methyl)-1H-1,2,3-triazol-4-yl)-1H-indole-2-carboxylate;

AB668: isobutyl 5-fluoro-3-(1-((1-(2-((4-isobutylphenyl) sulfonamido)ethyl)piperidin-4-yl)methyl)-1H-1,2,3-triazol-4-yl)-1H-indole-2-carboxylate;

AB651: 3-(1-((1-(2-((4-ethylphenyl)sulfonamido)ethyl)piperidin-4-yl)methyl)-1H-1,2,3-triazol-4-yl)-5-fluoro-N-isobutyl-1H-indole-2-carboxamide;

AB652: 5-fluoro-N-isobutyl-3-(1-((1-(2-((4-isopropylphenyl)sulfonamido)ethyl)piperidin-4-yl)methyl)-1H-1,2,3-triazol-4-yl)-1H-indole-2-carboxamide;

AB663: isopentyl 3-(1-((1-(2-((4-ethylphenyl)sulfonamido) ethyl)piperidin-4-yl)methyl)-1H-1,2,3-triazol-4-yl)-5-fluoro-1H-indole-2-carboxylate;

AB664: isopentyl 5-fluoro-3-(1-((1-(2-((4-isopropylphenyl) sulfonamido)ethyl)piperidin-4-yl)methyl)-1H-1,2,3-triazol-4-yl)-1H-indole-2-carboxylate;

AB669: isopentyl 5-fluoro-3-(1-((1-(2-((4-isobutylphenyl) sulfonamido)ethyl)piperidin-4-yl)methyl)-1H-1,2,3-triazol-4-yl)-1H-indole-2-carboxylate;

AB670: 3-(1-((1-(2-((4-ethylphenyl)sulfonamido)ethyl)piperidin-4-yl)methyl)-1H-1,2,3-triazol-4-yl)-5-fluoro-N-isopentyl-1H-indole-2-carboxamide;

AB671: 5-fluoro-N-isopentyl-3-(1-((1-(2-((4-isopropylphenyl)sulfonamido)ethyl)piperidin-4-yl)methyl)-1H-1,2,3-triazol-4-yl)-1H-indole-2-carboxamide;

AB597: 2-hydroxyethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate; and AB614: 2-aminoethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

In a particular preferred embodiment, a compound of formula (I') or (I) is selected in the group consisting of:

AB680: isobutyl 3-(1-((1-((2-chloro-2'-(methoxymethyl)-[1,1'-biphenyl]-4-yl)methyl)piperidin-4-yl)methyl)-1H-1,2,3-triazol-4-yl)-5-fluoro-1H-indole-2-carboxylate;

AB681: isobutyl 3-(1-((1-(2-chloro-2'-(methoxymethyl)-[1,1'-biphenyl]-4-carbonyl)piperidin-4-yl)methyl)-1H-1,2,3-triazol-4-yl)-5-fluoro-1H-indole-2-carboxylate;

AB689: isobutyl 3-(1-((1-((2-chloro-2'-methoxy-[1,1'-biphenyl]-4-yl)methyl)piperidin-4-yl)methyl)-1H-1,2,3-triazol-4-yl)-5-fluoro-1H-indole-2-carboxylate;

AB690: isobutyl 3-(1-((1-(3-chloro-4-(1H-indol-4-yl)benzyl)piperidin-4-yl)methyl)-1H-1,2,3-triazol-4-yl)-5-fluoro-1H-indole-2-carboxylate;

AB691: isobutyl 3-(1-((1-(3-chloro-4-phenoxybenzyl)piperidin-4-yl)methyl)-1H-1,2,3-triazol-4-yl)-5-fluoro-1H-indole-2-carboxylate;

AB692: isobutyl 3-(1-((1-((2-chloro-2'-methoxy-5'-methyl-[1,1'-biphenyl]-4-yl)methyl)piperidin-4-yl)methyl)-1H-1,2,3-triazol-4-yl)-5-fluoro-1H-indole-2-carboxylate;

AB697: isobutyl 5-fluoro-3-(1-((1-(3-isopropyl-4-phenoxybenzyl)piperidin-4-yl)methyl)-1H-1,2,3-triazol-4-yl)-1H-indole-2-carboxylate;

AB703: isobutyl 3-(1-((1-(4-(1H-indol-4-yl)-3-isopropylbenzyl)piperidin-4-yl)methyl)-1H-1,2,3-triazol-4-yl)-5-fluoro-1H-indole-2-carboxylate;

AB704: isobutyl 5-fluoro-3-(1-((1-((2-isopropyl-2'-(methoxymethyl)-[1,1'-biphenyl]-4-yl)methyl)piperidin-4-yl)methyl)-1H-1,2,3-triazol-4-yl)-1H-indole-2-carboxylate;

AB717: isobutyl 3-(1-((1-(4-((2,3-dihydrobenzofuran-5-yl) oxy)-3-isopropylbenzyl)piperidin-4-yl)methyl)-1H-1,2,3-triazol-4-yl)-5-fluoro-1H-indole-2-carboxylate;

AB718: isobutyl 3-(1-((1-(4-(3-acetylphenoxy)-3-isopropylbenzyl)piperidin-4-yl)methyl)-1H-1,2,3-triazol-4-yl)-5-fluoro-1H-indole-2-carboxylate;

AB713: isobutyl 5-fluoro-3-(1-((1-(3-isopropyl-4-(3-isopropylphenoxy)benzyl)piperidin-4-yl)methyl)-1H-1,2,3-triazol-4-yl)-1H-indole-2-carboxylate;

AB753: isobutyl 3-(1-((1-(3-chloro-4-(1H-indol-5-yl)benzyl)piperidin-4-yl)methyl)-1H-1,2,3-triazol-4-yl)-5-fluoro-1H-indole-2-carboxylate;

AB731: isobutyl 3-(1-((1-(3-chloro-4-(2,3-dihydrobenzofuran-5-yl)benzyl)piperidin-4-yl)methyl)-1H-1,2,3-triazol-4-yl)-5-fluoro-1H-indole-2-carboxylate;

AB739: isobutyl 3-(1-((1-((3'-acetyl-2-chloro-[1,1'-biphenyl]-4-yl)methyl)piperidin-4-yl)methyl)-1H-1,2,3-triazol-4-yl)-5-fluoro-1H-indole-2-carboxylate;

AB758: isobutyl 3-(1-((1-((2-chloro-3'-isopropyl-[1,1'-biphenyl]-4-yl)methyl)piperidin-4-yl)methyl)-1H-1,2,3-triazol-4-yl)-5-fluoro-1H-indole-2-carboxylate;

AB760: isobutyl 3-(1-((1-(3-chloro-4-isobutoxybenzyl)piperidin-4-yl)methyl)-1H-1,2,3-triazol-4-yl)-5-fluoro-1H-indole-2-carboxylate;

AB746: isobutyl 3-(1-((1-(3-chloro-4-(isopentyloxy)benzyl) piperidin-4-yl)methyl)-1H-1,2,3-triazol-4-yl)-5-fluoro-1H-indole-2-carboxylate;

AB743: isobutyl 3-(1-((1-(2-chloro-2'-(isopentyloxy)-[1,1'-biphenyl]-4-carbonyl)piperidin-4-yl)methyl)-1H-1,2,3-triazol-4-yl)-5-fluoro-1H-indole-2-carboxylate;

AB756: isobutyl 3-(1-((1-(4-(1H-indol-4-yl)-3-(trifluoromethyl)benzoyl)piperidin-4-yl)methyl)-1H-1,2,3-triazol-4-yl)-5-fluoro-1H-indole-2-carboxylate; and AB755: isobutyl 3-(1-((1-((4-benzylpiperazin-1-yl)sulfonyl)piperidin-4-yl)methyl)-1H-1,2,3-triazol-4-yl)-5-fluoro-1H-indole-2-carboxylate.

In a particular preferred embodiment, a compound of formula (I') or (I) is selected in the group consisting of:

AB913: isobutyl 3-(1-((1-(2-([1,1'-biphenyl]-4-sulfonamido)ethyl)piperidin-4-yl)methyl)-1H-1,2,3-triazol-4-yl)-5-fluoro-1H-indole-2-carboxylate;

AB929: isobutyl 5-fluoro-3-(1-((1-(2-((4-phenylpiperidine)-1-sulfonamido) ethyl)piperidin-4-yl)methyl)-1H-1,2,3-triazol-4-yl)-1H-indole-2-carboxylate;

AB935: isobutyl 5-fluoro-3-(1-((1-(2-(((4-(trifluoromethyl) phenyl)methyl) sulfonamido)ethyl) piperidin-4-yl) methyl)-1H-1,2,3-triazol-4-yl)-1H-indole-2-carboxylate;

AB1073: isobutyl 5-fluoro-3-(1-((1-(2-((4-(2-(pyrrolidin-1-yl)pyridin-3-yl)phenyl) sulfonamido)ethyl)piperidin-4-yl)methyl)-1H-1,2,3-triazol-4-yl)-1H-indole-2-carboxylate;

AB1076: isobutyl 3-(1-((1-(2-((2'-cyano-[1,1'-biphenyl])-4-sulfonamido)ethyl)piperidin-4-yl)methyl)-1H-1,2,3-triazol-4-yl)-5-fluoro-1H-indole-2-carboxylate;

AB1135: N-(2-(4-((4-(2-acetyl-5-fluoro-1H-indol-3-yl)-1H-1,2,3-triazol-1-yl)methyl) piperidin-1-yl)ethyl)-4-isobutylbenzenesulfonamide;

AB1206: isobutyl 3-(1-((1-(2-((2',6'-dimethoxy-[1,1'-biphenyl])-4-sulfonamido)ethyl) piperidin-4-yl)methyl)-1H-1,2,3-triazol-4-yl)-5-fluoro-1H-indole-2-carboxylate;

AB1286: N-(2-(4-((4-(2-acetyl-5-fluoro-1H-indol-3-yl)-1H-1,2,3-triazol-1-yl)methyl) piperidin-1-yl)ethyl)-4-(3,5-dimethylisoxazol-4-yl)benzenesulfonamide;

AB1287: N-(2-(4-((4-(2-acetyl-5-fluoro-1H-indol-3-yl)-1H-1,2,3-triazol-1-yl)methyl) piperidin-1-yl)ethyl)-2',6'-dimethoxy-[1,1'-biphenyl]-4-sulfonamide;

AB1288: N-(2-(4-((4-(2-acetyl-5-fluoro-1H-indol-3-yl)-1H-1,2,3-triazol-1-yl)methyl)piperidin-1-yl)ethyl)-2',6'-difluoro-[1,1'-biphenyl]-4-sulfonamide;

AB1381: N-(2-(4-((4-(2-acetyl-5-fluoro-1H-indol-3-yl)-1H-1,2,3-triazol-1-yl)methyl) piperidin-1-yl)ethyl)-2'-fluoro-6'-hydroxy-[1,1'-biphenyl]-4-sulfonamide;

AB1402: isobutyl 5-fluoro-3-(1-((1-(2-((2'-fluoro-6'-hydroxy-[1,1'-biphenyl])-4-sulfonamido)ethyl)piperidin-4-yl)methyl)-1H-1,2,3-triazol-4-yl)-1H-indole-2-carboxylate; and AB1455: N-(2-(4-((4-(2-acetyl-5-fluoro-1H-indol-3-yl)-1H-1,2,3-triazol-1-yl)methyl) piperidin-1-yl)ethyl)-2',6'-dimethoxy-2-methyl-[1,1'-biphenyl]-4-sulfonamide;

It is also disclosed herein compounds having the following formula (I0):

(I0)

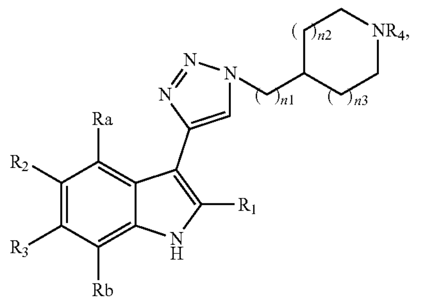

in which:

$R_1$, $R_2$, $R_3$, $R_4$, n1, n2, and n3 are such as defined herein; and

Ra and Rb represent independently a hydrogen, a halogen, or a ($C_1$-$C_6$)alkyl optionally substituted by at least one fluorine.

Therapeutic Applications

As illustrated by examples, the inventors have demonstrated the therapeutic interest of the compounds of the invention. Indeed, the inventors have shown that the compounds according to the present invention are capable of selectively inhibiting the protein kinase CK2, and more specifically have a CK2 $IC_{50}$ lower than 50 μM, thereby demonstrating the therapeutic interest of such compounds in therapies, more particularly in cancer therapies. Therefore, the compounds of the present invention are useful as a drug.

Accordingly, the present invention relates to a compound of formula (I') or (I) as defined herein, for use as a drug or a medicine. The present invention further relates to a pharmaceutical or veterinary composition comprising a compound according to the invention. Preferably, the pharmaceutical composition further comprises a pharmaceutically or veterinary acceptable carrier or excipient. The present invention relates to the use of a compound according to the invention as a drug or a medicine. The invention further relates to a method for treating a disease in a subject, wherein a therapeutically effective amount of a compound according to the invention, is administered to said subject in need thereof. The invention also relates to the use of a compound according to the invention, for the manufacture of a medicine. The invention also relates to a pharmaceutical composition comprising a compound according to the invention for use as a drug.

The present invention also concerns:

- a compound of formula (I') or (I) as defined above including anyone of the disclosed embodiments, or a pharmaceutical composition comprising such a compound for preventing and/or treating or for use for preventing and/or treating a cancer; and/or
- a pharmaceutical composition comprising a compound of formula (I') or (I) as defined above including anyone of the disclosed embodiments, and an antitumor drug, for the prevention and/or the treatment of cancer or for use in the prevention and/or the treatment of cancer; and/or
- a compound of formula (I') or (I) including anyone of the disclosed embodiments, or a pharmaceutical composition comprising such a compound, for preventing and/or treating a cancer or for use for preventing and/or treating a cancer in combination with radiotherapy, hyperthermia and/or other antitumor therapies, optionally before, simultaneously and/or after surgery (e.g., tumor resection); and/or
- a kit comprising (a) a compound of formula (I') or (I) as defined above including anyone of the disclosed embodiments; and (b) an antitumor drug as a combined preparation for simultaneous, separate or sequential use, for preventing and/or treating cancer or for use for preventing and/or treating a cancer; and/or
- the use of a compound of formula (I') or (I) as defined above including anyone of the disclosed embodiments, or a pharmaceutical composition comprising such a compound, for the manufacture of a medicament, a medicine or a drug for the prevention and/or the treatment of a cancer; and/or
- the use of a pharmaceutical composition comprising a compound of formula (I') or (I) as defined above including anyone of the disclosed embodiments, and an additional antitumor drug, for the manufacture of a medicament, a medicine or a drug for the prevention and/or the treatment of a cancer; and/or
- the use of a compound of formula (I') or (I) as defined above including anyone of the disclosed embodiments, or a pharmaceutical composition comprising such a compound, for the manufacture of a medicament, a medicine or a drug for the prevention and/or the treatment of a cancer in combination with radiotherapy, hyperthermia and/or other antitumor therapies, optionally before, simultaneously and/or after surgery (e.g., tumor resection); and/or
- a method for treating a cancer, in a subject in need thereof, comprising administering an effective amount of a compound of formula (I') or (I) as defined herein, or a pharmaceutical composition comprising such a compound;
- a method for treating a cancer, in a subject in need thereof, comprising administering an effective amount of a compound of formula (I') or (I) as defined herein, or a pharmaceutical composition comprising such a compound, and an additional antitumor drug;
- a method for treating a cancer, in a subject in need thereof, comprising administering an effective amount of a compound of formula (I') or (I) as defined herein, or a pharmaceutical composition comprising such a compound; the method further comprises radiotherapy, hyperthermia and/or other antitumor therapies, optionally before, simultaneously and/or after surgery (e.g., tumor resection).

The term "cancer", as used herein, refers to the presence of cells possessing characteristics typical of cancer-causing cells, such as uncontrolled proliferation, immortality, metastatic potential, rapid growth and proliferation rate, and certain characteristic morphological features. The cancer may be solid tumor or hematopoietic tumor. Examples of cancer include, for example, leukemia, lymphoma, blastoma, carcinoma, such as cholangiocarcinoma, and sarcoma. More particular examples of such cancers include chronic myeloid leukemia, acute lymphoblastic leukemia, Philadelphia chromosome positive acute lymphoblastic leukemia (Ph+ ALL), squamous cell carcinoma, lung cancer, smallcell lung cancer, non-small cell lung cancer, glioma, gastrointestinal cancer, renal cancer, ovarian cancer, liver cancer, colorectal cancer, endometrial cancer, kidney cancer, prostate cancer, melanoma, skin cancer, thyroid cancer, neuroblastoma, osteosarcoma, pancreatic cancer, glioblastoma multiforme, cervical cancer, stomach cancer, bladder cancer, hepatoma, breast cancer, oesophagal cancer, colon cancer, head and neck cancer, brain cancer, gastric cancer, germ cell tumor, pediatric sarcoma, sinonasal natural killer, multiple myeloma, acute myelogenous leukemia (AML), chronic lymphocytic leukemia, mastocytosis and any symptom associated with mastocytosis.

In a particular aspect, the cancer is chosen among multiple myeloma, lymphoma, cholangiocarcinoma, a brain cancer, a breast cancer, a colon cancer, a kidney cancer, a leukemia, a liver cancer, a lung cancer, an ovarian cancer, glioblastoma multiforme, melanoma, a skin cancer, and a pancreas cancer. In a preferred aspect, the cancer is chosen among a kidney cancer, a breast cancer, a lung cancer, glioblastoma multiforme, a pancreas cancer, melanoma, a skin cancer, and an ovarian cancer, more preferably a kidney cancer, a breast cancer, glioblastoma multiforme, a pancreas cancer, melanoma, a skin cancer, and a lung cancer.

The administration route can be topical, transdermal, oral, rectal, sublingual, intranasal, intrathecal, intratumor or parenteral (including subcutaneous, intramuscular, intravenous and/or intradermal). Preferably, the administration route is parental, oral or topical. The pharmaceutical composition is adapted for one or several of the above-mentioned routes. The pharmaceutical composition, kit, product or combined preparation is preferably administered by injection or by intravenous infusion or suitable sterile solutions, or in the form of liquid or solid doses via the alimentary canal.

The pharmaceutical composition can be formulated as solutions in pharmaceutically compatible solvents or as emulsions, suspensions or dispersions in suitable pharmaceutical solvents or vehicles, or as pills, tablets or capsules that contain solid vehicles in a way known in the art. Formulations of the present invention suitable for oral administration may be in the form of discrete units as capsules, sachets, tablets or lozenges, each containing a predetermined amount of the active ingredient; in the form of a powder or granules; in the form of a solution or a suspension in an aqueous liquid or non-aqueous liquid; or in the form of an oil-in-water emulsion or a water-in-oil emulsion. Formulations for rectal administration may be in the form of a suppository incorporating the active ingredient and carrier such as cocoa butter, or in the form of an enema. Formulations suitable for parenteral administration conveniently comprise a sterile oily or aqueous preparation of the active ingredient which is preferably isotonic with the blood of the recipient. Every such formulation can also contain other pharmaceutically compatible and nontoxic auxiliary agents, such as, e.g. stabilizers, antioxidants, binders, dyes, emulsifiers or flavoring substances. The formulations of the present invention comprise an active ingredient in association with a pharmaceutically acceptable carrier therefore and optionally other therapeutic ingredients. The carrier must be "acceptable" in the sense of being compatible with the other ingredients of the formulations and not deleterious to the recipient thereof. The pharmaceutical compositions are advantageously applied by injection or intravenous infusion of suitable sterile solutions or as oral dosage by the digestive tract. Methods for the safe and effective administration of most of these chemotherapeutic agents are known to those skilled in the art. In addition, their administration is described in the standard literature.

Pharmaceutical compositions according to the invention may be formulated to release the active drug substantially immediately upon administration or at any predetermined time or time period after administration.

Preferably, the treatment with the compound according to the invention or the pharmaceutical composition according to the invention starts no longer than a month, preferably no longer than a week, after the diagnosis of the disease. In a most preferred embodiment, the treatment starts the day of the diagnosis.

The compound according to the invention or the pharmaceutical composition according to the invention may be administered as a single dose or in multiple doses.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the compound according to the invention or the pharmaceutical composition according to the invention is preferably comprised between 1 day and 50 weeks, more preferably between 1 day and 30 weeks, still more preferably between 1 day and 15 weeks, even more preferably between 1 day and 10 weeks. In a particular embodiment, the duration of the treatment is of about 1 week. Alternatively, the treatment may last as long as the disease persists. The amount of compound according to the invention or of pharmaceutical composition according to the invention to be administered has to be determined by standard procedure well known by those of ordinary skills in the art. Physiological data of the patient (e.g. age, size, and weight) and the routes of administration have to be taken into account to determine the appropriate dosage, so as a therapeutically effective amount will be administered to the patient.

In a preferred embodiment, the total compound dose for each administration of the compound according to the invention or of the pharmaceutical composition according to the invention is comprised between 0.00001 and 1 g, preferably between 0.01 and 10 mg.

The form of the pharmaceutical compositions, the route of administration and the dose of administration of the compound according to the invention, or the pharmaceutical composition according to the invention can be adjusted by the man skilled in the art according to the type and severity of the disease, and to the patient, in particular its age, weight, sex, and general physical condition.

In one embodiment, the compound of the invention can be used in combination with another antitumor drug or antineoplastic agent.

The additional antitumor drug can be selected in the non-exhaustive list of antitumor agents consisting of an inhibitor of topoisomerases I or II, an anti-mitotic agent, a DNA alkylating agent, an agent causing crosslinking of DNA, an anti-metabolic agent, a targeted agent such as a kinase inhibitor, a histone deacetylase inhibitor and an anti-EGFR agent and/or a therapeutical antibody designed to mediate cytotoxicity against the cancer cells or to modulate one of their key biological functions.

Antimitotic agents include, but are not limited to, paclitaxel, docetaxel and analogs such as larotaxel (also called XRP9881; Sanofi-Aventis), XRP6258 (Sanofi-Aventis), BMS-184476 (Bristol-Meyer-Squibb), BMS-188797 (Bristol-Meyer-Squibb), BMS-275183 (Bristol-Meyer-Squibb), ortataxel (also called IDN 5109, BAY 59-8862 or SB-T-101131; Bristol-Meyer-Squibb), RPR 109881A (Bristol-Meyer-Squibb), RPR 116258 (Bristol-Meyer-Squibb), NBT-287 (TAPESTRY), PG-paclitaxel (also called CT-2103, PPX, paclitaxel poliglumex, paclitaxel polyglutamate or Xyotax™), ABRAXANE® (also called Nab-paclitaxel; ABRAXIS BIOSCIENCE), tesetaxel (also called DJ-927), IDN 5390 (INDENA), taxoprexin (also called docosahexanoic acid-paclitaxel; PROTARGA), DHA-paclitaxel (also called Taxoprexin®), and MAC-321 (WYETH). Preferably, antimitotic agents are docetaxel, paclitaxel, and is more preferably docetaxel.

Inhibitors of topoisomerases I and/or II include, but are not limited to etoposide, topotecan, camptothecin, irinotecan, amsacrine, intoplicin, anthracyclines such as doxorubicin, epirubicin, daunorubicin, idarubicin and mitoxantrone. Inhibitors of topoisomerase I and II include, but are not limited to intoplicin.

The additional antitumor agent can be alkylating agents including, without limitation, nitrogen mustards, ethylenimine derivatives, alkyl sulfonates, nitrosoureas, metal salts and triazenes. Non-exhaustive examples thereof include uracil mustard, chlormethine, cyclophosphamide (CYTOXAN®), ifosfamide, melphalan, chlorambucil, pipobroman, triethylenemelamine, triethylenethiophosphoramine, busulfan, carmustine, lomustine, cisplatin, carboplatin, fotemustine, oxaliplatin, thiotepa, streptozocin, dacarbazine, and temozolomide. In a preferred embodiment, the DNA alkylating agent is preferably cisplatin, carboplatin, temozolomide, fotemustine or dacarbazine.

Anti-metabolic agents block the enzymes responsible for nucleic acid synthesis or become incorporated into DNA, which produces an incorrect genetic code and leads to apoptosis. Non-exhaustive examples thereof include, without limitation, folic acid antagonists, pyrimidine analogs, purine analogs and adenosine deaminase inhibitors, and more particularly methotrexate, floxuridine, cytarabine, 6-mercaptopurine, 6-thioguanine, fludarabine phosphate, pentostatine, 5-fluorouracil, gemcitabine and capecitabine. In a preferred embodiment, such an agent is gemcitabine.

The additional anti-tumor agent can also be a targeted agent, in particular a kinase inhibitor. The kinase may be selected from the group consisting of intracellular tyrosine or serine/threonine kinases, receptors tyrosine or serine/threonine kinase. The kinase could be selected among EGFR family, ALK, B-Raf, MEK, and mTOR. For instance, the agents may have ability to inhibit angiogenesis based on the inhibitory activities on VEGFR and PDGFR kinases. In particular, the targeted agent can be selected among the multiple kinase inhibitor drugs which are already approved: Gleevec©, which inhibits Bcr-Abl and c-Kit, and Iressa® and Tarceva*, which both inhibit EGFR, sorafenib (Nexavar®, BAY 43-9006) which inhibits Raf, dasatinib (BMS-354825) and nilotinib (AMN-107, Tasigna®) which also inhibits Bcr-Abl, lapatinib which also inhibits EGFR, temsirolimus (Torisel®, CCI-779) which targets the mTOR pathway, sunitinib (Student®, SU11248) which inhibits several targets including VEGFR as well as specific antibodies inactivating kinase receptors: Herceptin® and Avastin®. The anti-EGFR agent can be selected among gefitinib, erlotinib, lapatinib, vandetanib, afatinib, osimertinib, neratinib, dacomitinib, brigatinib, canertinib, naquotinib, nazartinib, pelitinib, rociletinib, icotinib, AZD3759, AZ5104 (CAS No 1421373-98-9), poziotinib, WZ4002, preferably is erlotinib or cetuximab. The ALK inhibitor can be selected among crizotinib, entrectinib, ceritinib, alectinib, brigatinib, lorlatinib, TSR-011, CEP-37440, and ensartinib. The B-Raf inhibitor can be selected among vemurafenib, dabrafenib, regorafenib, and PLX4720. The MEK inhibitor can be selected among cobimetinib, trametinib, binimetinib, selumetinib, PD-325901, CI-1040, PD035901, U0126, TAK-733.

The additional drug can also be a checkpoint inhibitor, for instance an antibody targeting PD-1, PD-L1, CTLA-4 and the like.

The term "therapy", as used herein, refers to any type of treatment of cancer (i.e., antitumor therapy), including an adjuvant therapy and a neoadjuvant therapy. Therapy comprises radiotherapy and therapies, preferably systemic therapies such as hormone therapy, chemotherapy, immunotherapy and monoclonal antibody therapy.

The term "adjuvant therapy", as used herein, refers to any type of treatment of cancer given as additional treatment, usually after surgical resection of the primary tumor, in a patient affected with a cancer that is at risk of metastasizing and/or likely to recur. The aim of such an adjuvant treatment is to improve the prognosis. Adjuvant therapies comprise radiotherapy and therapy, preferably systemic therapy, such as hormone therapy, chemotherapy, immunotherapy and monoclonal antibody therapy.

The term "hormone therapy" or "hormonal therapy" refers to a cancer treatment having for purpose to block, add or remove hormones. For instance, in breast cancer, the female hormones estrogen and progesterone can promote the growth of some breast cancer cells. So, in these patients, hormone therapy is given to block estrogen and a non-exhaustive list commonly used drugs includes: tamoxifen, toremifene, anastrozole, exemestane, letrozole, goserelin, leuprolide, megestrol acetate, and fluoxymesterone.

As used herein, the term "chemotherapeutic treatment" or "chemotherapy" refers to a cancer therapeutic treatment using chemical or biological substances, in particular using one or several antineoplastic agents.

The term "radiotherapeutic treatment" or "radiotherapy" is a term commonly used in the art to refer to multiple types of radiation therapy including internal and external radiation therapies or radioimmunotherapy, and the use of various types of radiations including X-rays, gamma rays, alpha particles, beta particles, photons, electrons, neutrons, radioisotopes, and other forms of ionizing radiations.

The term "therapeutical antibody" refers to any antibody having an anti-tumoral effect. Preferably, the therapeutical antibody is a monoclonal antibody. Therapeutic antibodies are generally specific for surface antigens, e.g., membrane antigens. Most preferred therapeutic antibodies are specific for tumor antigens (e.g., molecules specifically expressed by tumor cells), such as CD20, CD52, ErbB2 (or HER2/Neu), CD33, CD22, CD25, MUC-1, CEA, KDR, aVb3, and the like. The therapeutical antibody include, but is not limited to, antibodies such as trastuzumab (anti-HER2 antibody), rituximab (anti-CD20 antibody), alemtuzumab, gemtuzamab, cetuximab, pertuzumab, epratuzumab, basiliximab, daclizumab, labetuzumab, sevirumab, tuvurimab, palivizumab, infliximab, omalizumab, efalizumab, natalizumab, clenoliximab, and bevacizumab.

Hyperthermia is a medical treatment in which is exposed to high temperatures to damage and kill cancer cells or to make cancer cells more sensitive to the effects of radiation and certain anti-cancer drugs. There are many techniques, well-known by the one skilled in the art, by which heat may be delivered. Some of the most common involve the use of focused ultrasound (FUS or HIFU), infrared sauna, microwave heating, induction heating, magnetic hyperthermia, infusion of warmed liquids, or direct application of heat such as through sitting in a hot room or wrapping a patient in hot blankets.

According to their high and selectively inhibition of CK2, the compounds of formula (I') or (I) of the invention are useful against chemoresistance phenomena. A further object of the invention is therefore a compound of formula (I') or (I) as defined above including anyone of the disclosed embodiments, or a pharmaceutical composition comprising such a compound for preventing and/or treating or for use for preventing and/or treating a cancer in a chemoresistant subject. Another object is a use of a compound of formula (I') or (I) as defined above including anyone of the disclosed embodiments, or a pharmaceutical composition comprising such a compound, for the manufacture of a medicament, a medicine or a drug for the prevention and/or the treatment of a cancer in a chemoresistant subject. Another object is a method for treating a cancer, in a chemoresistant subject, comprising administering an effective amount of a compound of formula (I') or (I) as defined herein, or a pharmaceutical composition comprising such a compound. As used herein, a "chemoresistant subject" is a subject for which chemotherapies currently used for treating a cancer are not efficient. Without limitation, a chemoresistant subject may be resistant, for instance, to chemotherapies using sunitinib. Resistance to a chemotherapy may occurred with primary resistance mediated by tumor intrinsic factors and by patient-specific factors and/or with acquired resistance after an initial response to the targeted therapy.

Further aspects and advantages of the invention will be disclosed in the following experimental section.

EXAMPLES

Example A—Chemistry

I. General Experimental Methods

All commercially available chemicals and solvents were purchased from Sigma-Aldrich, Acros Organics, Fischer Scientific, Alfa Aesar or Fluorochem and were used received unless otherwise stated. All reactions were carried out under argon atmosphere in flame-dried glassware as indicated and the reaction progress was monitored qualitatively using thin layer chromatography (TLC) aluminium plates precoated with Merck silica gel 60 F254. The spots were detected with UV light (254 nm or 356 nm) or by staining with ninhydrin (2% solution). The purification of products was performed on silica gel 60 (particle size 0.040-0.063 mm) from Merck 9385 Kieselgel using flash technique and under a positive pressure. The crude mixtures were adsorbed on silica gel 60 (particle size 0.040-0.063 mm) from Merck 9385 Kieselgel before chromatographic purification. Nuclear magnetic resonance spectra (NMR) were recorded on Bruker Avance 400 (400 MHz) and Bruker Avance 500 (500 MHz) spectrometers. Chemical shifts (δ) are referenced to the solvent residual peak and are quoted in parts per million (ppm) to the nearest 0.01 ppm for $\delta_H$ and to the nearest 0.1 ppm for $\delta_C$ and $\delta_F$. $d_6$-Acetone, $CDCl_3$ and $d_6$-DMSO were used as deuterated solvents and the resonances were locked as internal standards ($d_6$-Acetone $^1H$ δ=2.05, $^{13}C$ δ=29.8; $CDCl_3$ $^1H$ δ=7.26, $^{13}C$ δ=77.1 and $d_6$-DMSO $^1H$ δ=2.50, $^{13}C$ δ=39.5). The multiplicity of the signals is indicated by lower-case letters (s singlet, d doublet, t triplet, q quadruplet, m multiplet or overlap of non-equivalent resonances, br broad, br s singlet, or combination of letters) and coupling constants (J) are reported in Hertz to the nearest 0.1 Hz. Carbon multiplicity was determined by DEPT 135 experiments. Yields refer to isolated compounds, estimated to be >98% pure as determined by $^1H$ NMR or by high-performance liquid chromatography (HPLC). Liquid chromatography analyses were carried out Agilent 1290 Infinity system (Agilent Technologies) and chromatographic separations were performed on a reversed phase column Poroshell 120 SB-C18 Agilent (50 mm×2.1 mm/2.7 μm). High-resolution mass spectra (HRMS) were recorded on a Bruker Micromass Q-TOF spectrometer using electrospray ionisation (ESI). Melting points data (Mp) were collected on a Büchi B-545 and are uncorrected.

General methods for preparing compounds of the invention are illustrated by Schemes 1-12.

Scheme 1

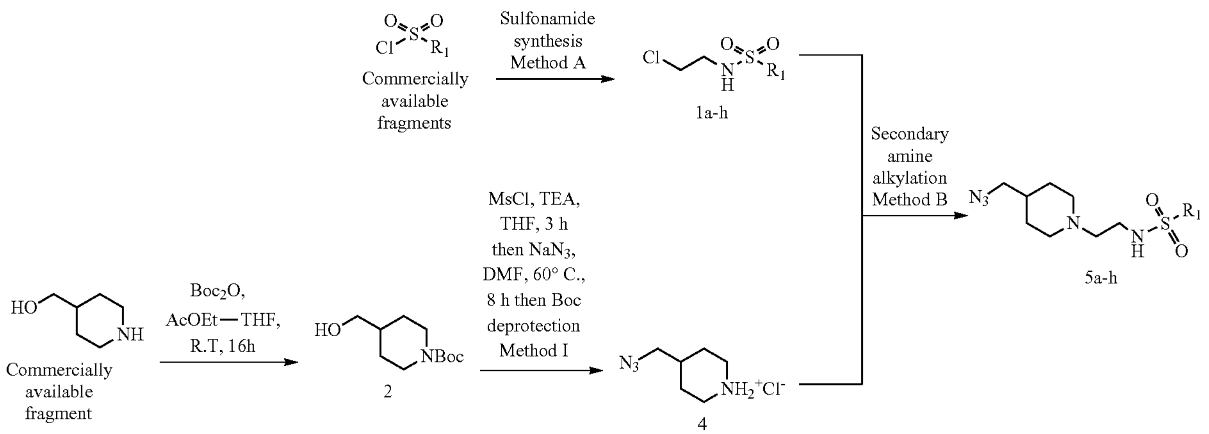

Scheme 2
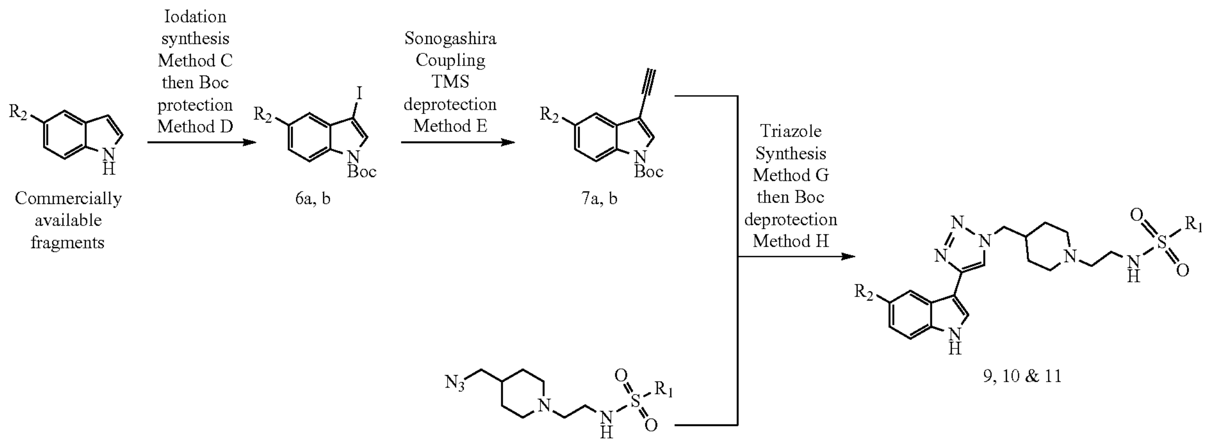
Commercially available fragments
6a, b
7a, b
5a or 5b
9, 10 & 11

Scheme 3
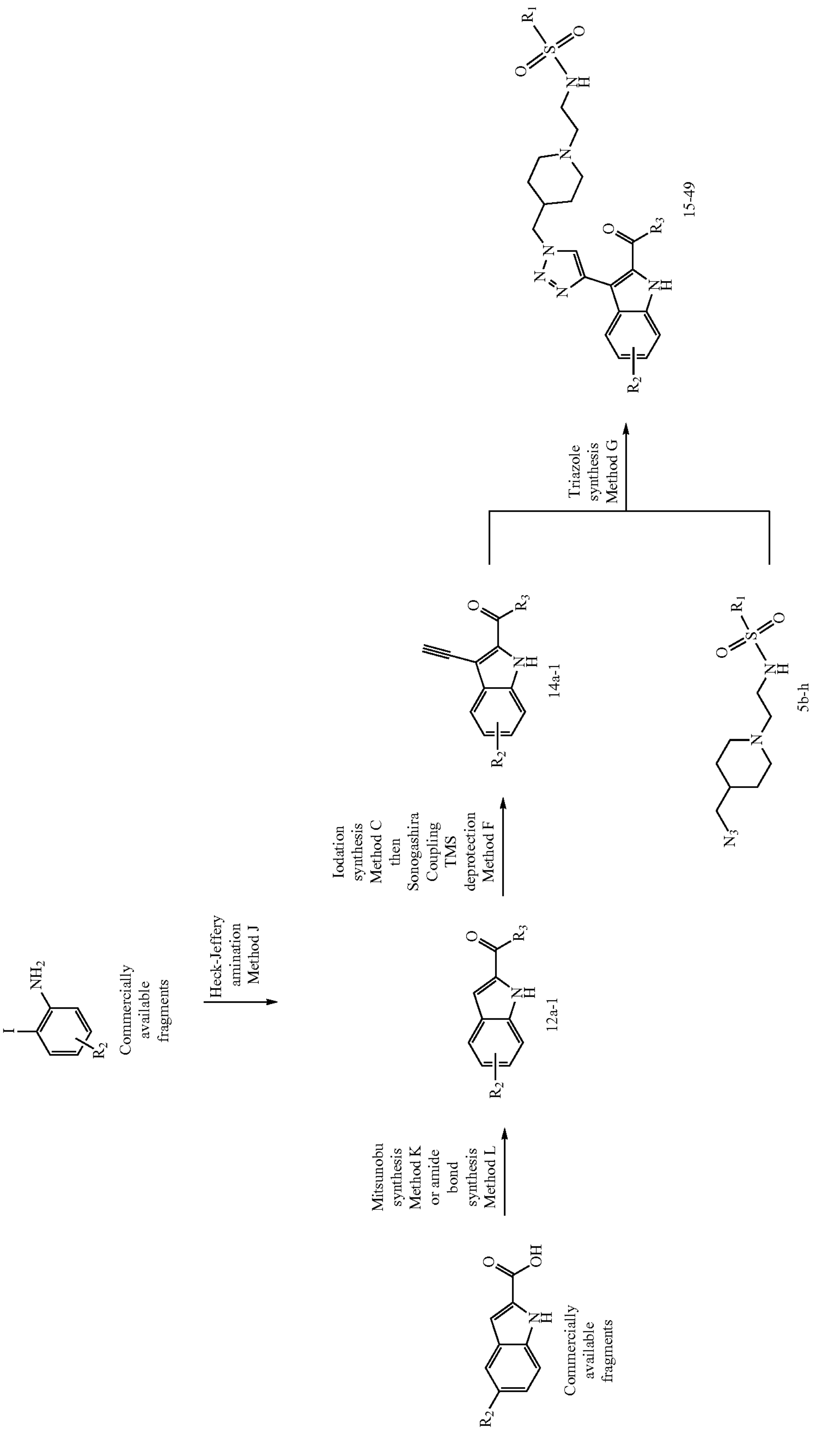

Scheme 4
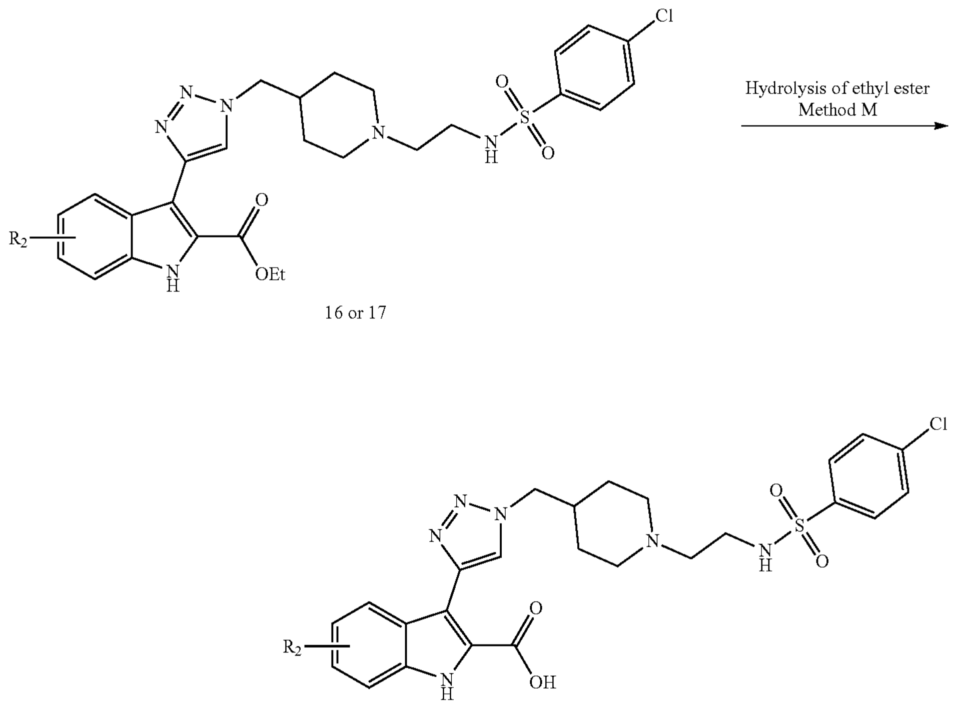
16 or 17
50 or 51
Scheme 5
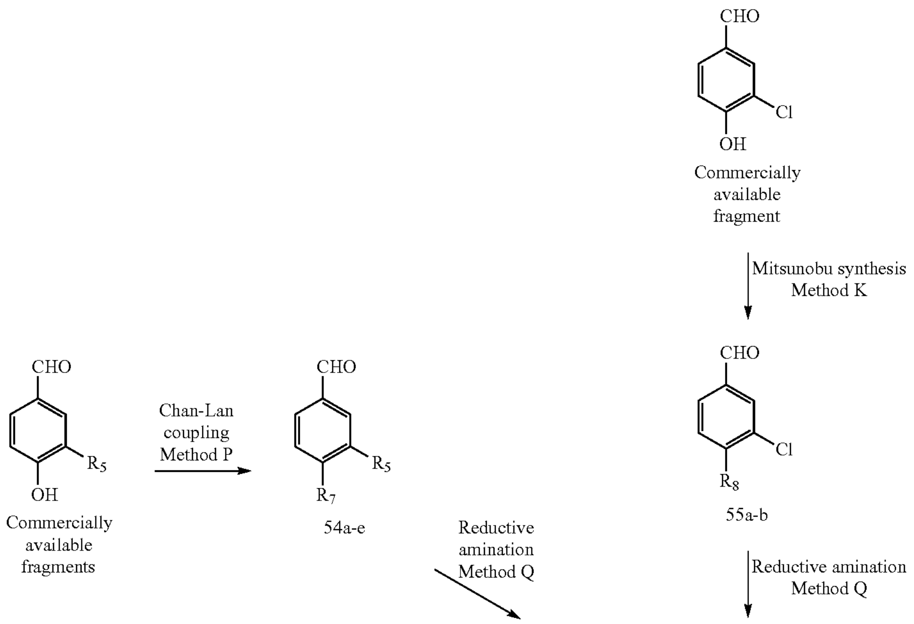
54a-e
55a-b

-continued
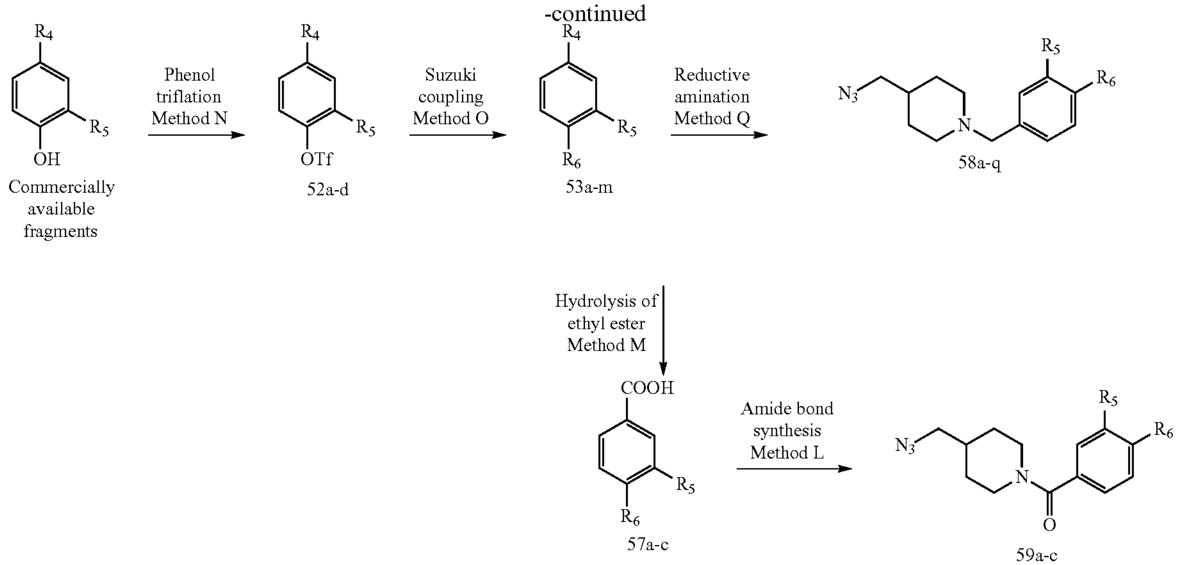
Commercially available fragments
52a-d
53a-m
58a-q
57a-c
59a-c
Scheme 6
-continued
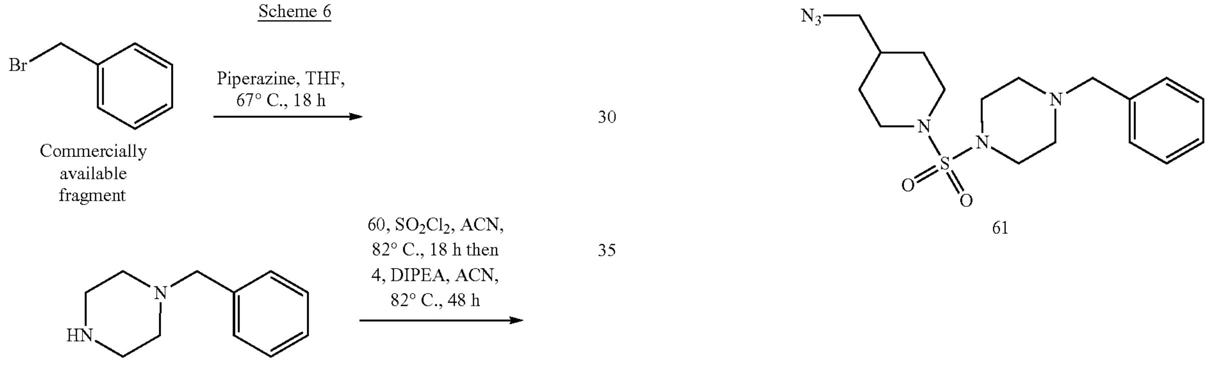
Commercially available fragment
60
61
Scheme 7
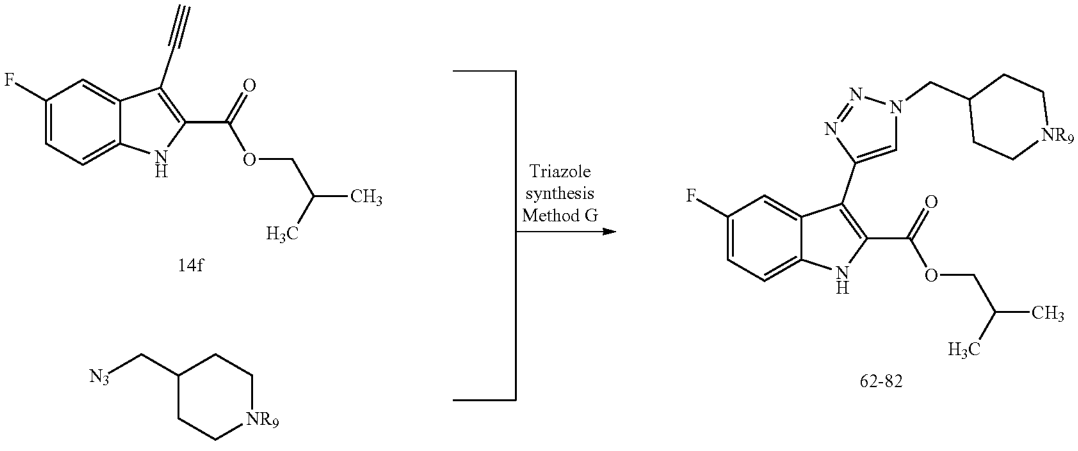
14f
58a-q, 59a-c or 61
62-82

Scheme 8
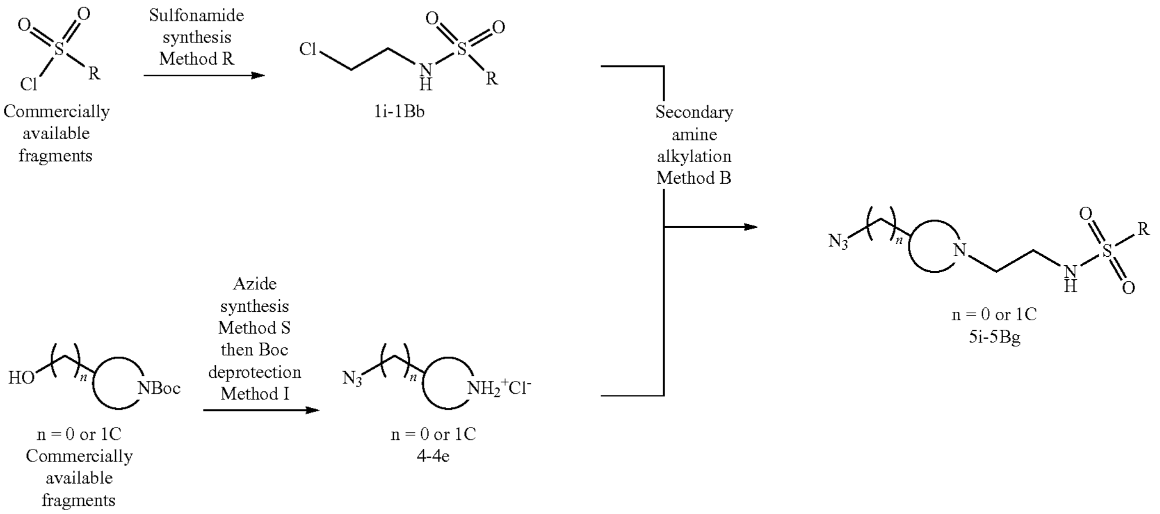

Scheme 9
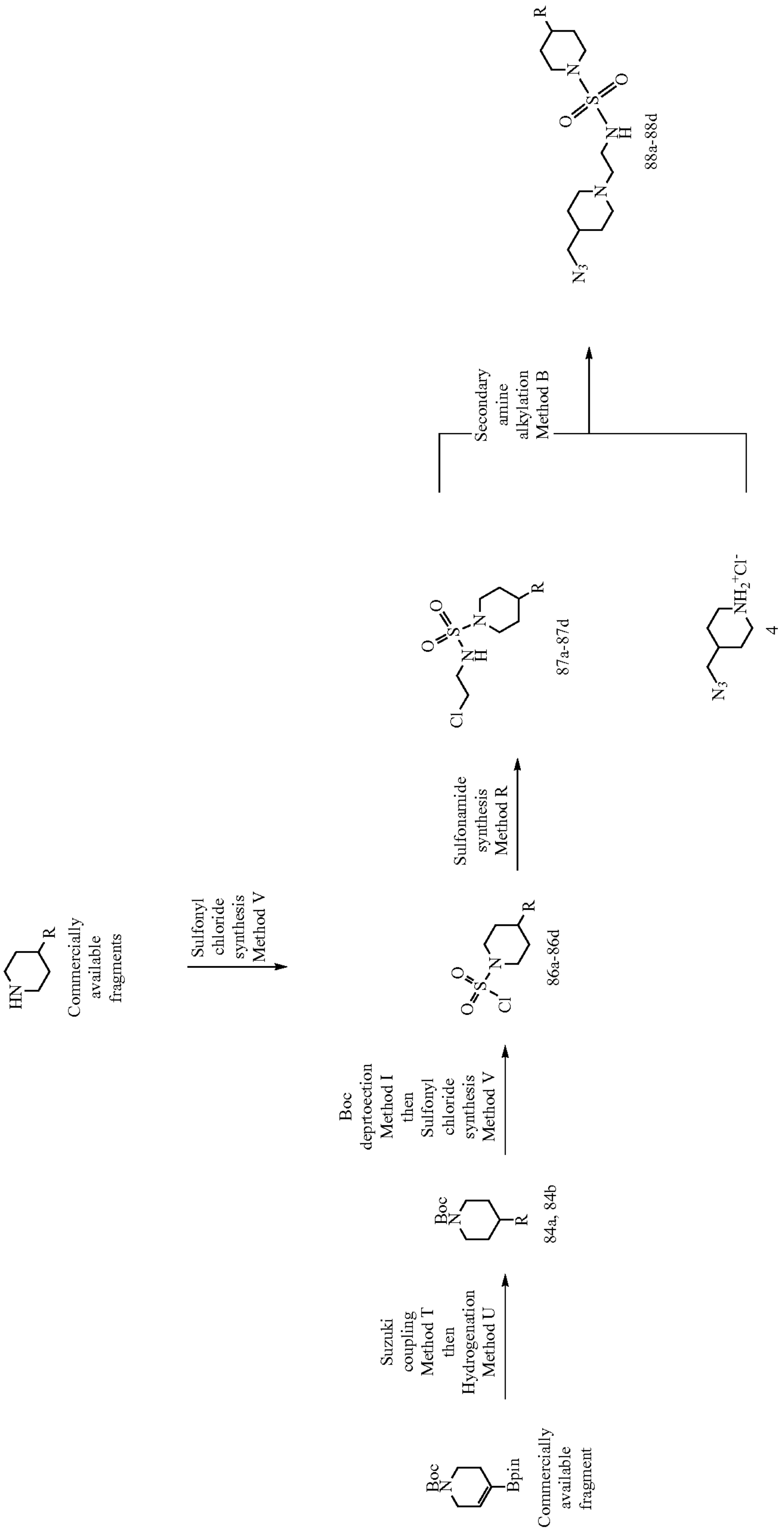
84a, 84b
86a-86d
87a-87d
4
88a-88d

Scheme 10
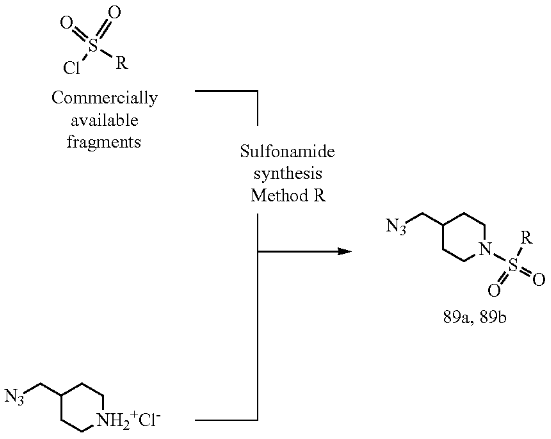
89a, 89b
4

Scheme 11
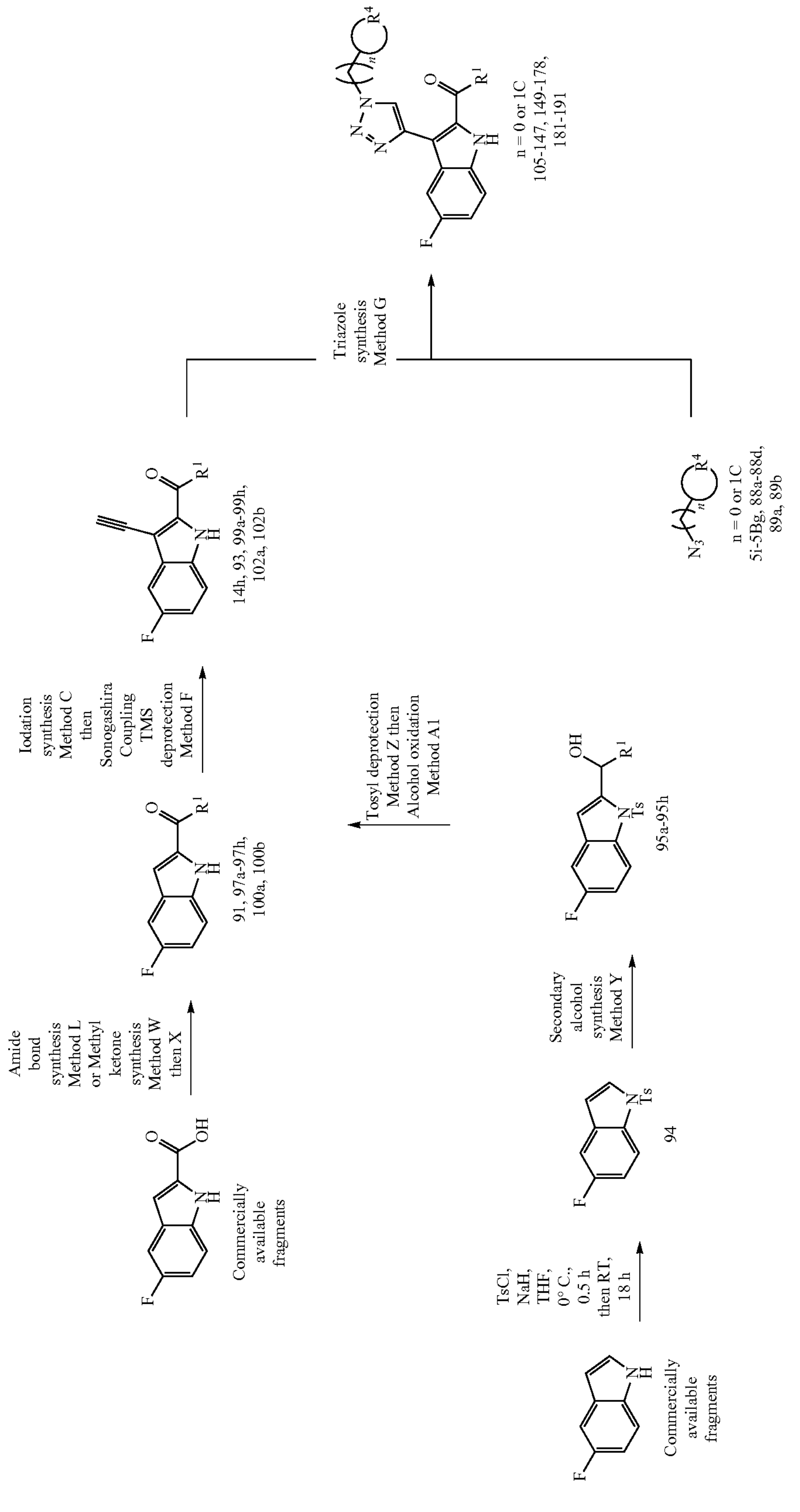

Scheme 12

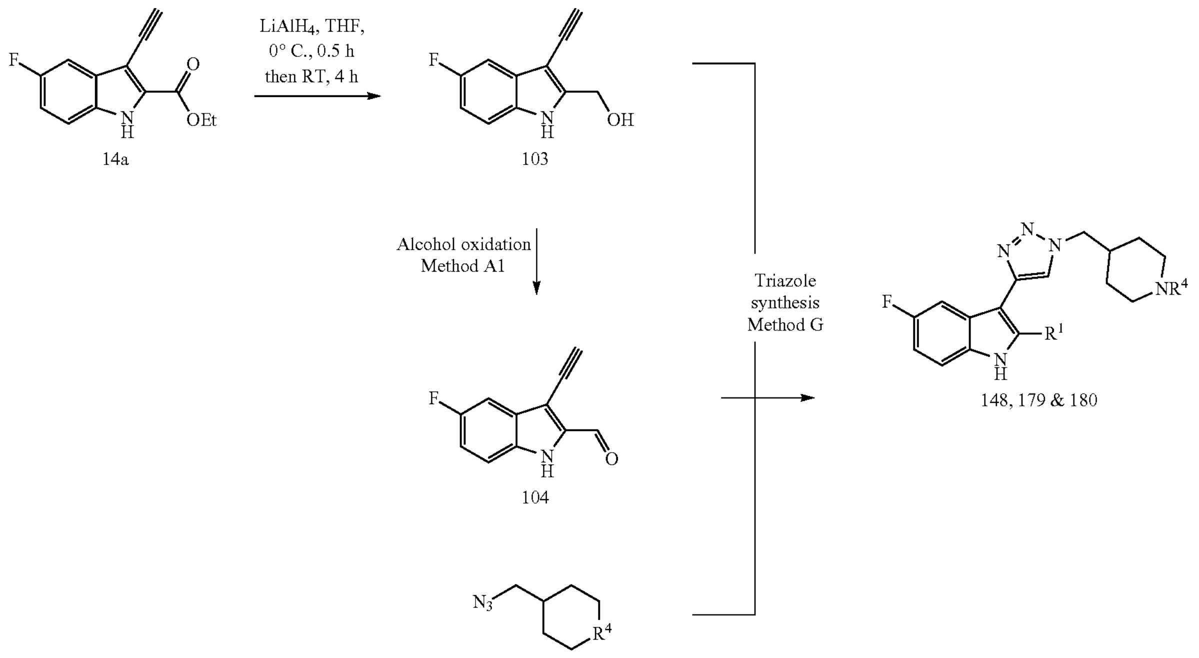

14a, 103, 104, 5h, 5Ap, 148, 179 & 180

General Method A—Sulfonamide Synthesis

In an oven-dried round bottom flask was added at 10° C. (ice bath) 2-chloroethylamine hydrochloride (1.00 equiv.), potassium carbonate (1.00 equiv.) and the corresponding sulfonyl chloride (1.00 equiv.) in dichloromethane-water (2:1, C~0.3 M). The reaction was stirred for 3 hours at 10±3° C. then allowed to warm up at room temperature and stirred for 12 hours (monitored by TLC). After completion, the pH value of the reaction was adjusted around 7-8 with a slow addition of potassium carbonate (1.00 equiv.). The mixture layers were partitioned and extracted with dichloromethane three times. The combined organic extracts were washed with brine, dried ($MgSO_4$) and filtered. The solvents were removed in vacuo and the residue was purified by column chromatography on silica gel or recrystallized from diisopropyl ether to yield the desired product.

General Method B—Secondary Amine Alkylation

In an oven-dried round bottom flask equipped with a reflux condenser and under argon atmosphere was dissolved the ammonium salt (1.00 equiv.) in dry acetonitrile (C~0.15 M) then treated with N,N-diisopropylethylamine (3.00 equiv.), added slowly through a syringe. The mixture was stirred for 10 minutes at room temperature before the addition in portion wise of the corresponding alkyl chloride (1.10 equiv.) and a catalytic amount of potassium iodide. The reaction was heated to 82° C. (preheated oil bath) for 18 hours. After the complete consumption of the starting material (monitored by TLC), the mixture was allowed to cool to room temperature and then poured into water and extracted with dichloromethane three times. The combined organic extracts were washed with brine, dried ($MgSO_4$) and filtered. The solvents were removed in vacuo and the residue was purified by column chromatography on silica gel to yield the desired product.

General Method C—Iodation Synthesis

In an oven-dried round bottom flask was dissolved the corresponding indole (1.00 equiv.) in N,N-dimethylformamide (C~0.6 M) and treated with potassium hydroxide (2.50-3.50 equiv.) during 10 minutes at room temperature. Then a solution of diiode (1.01 equiv.) in N,N-dimethylformamide (C~0.7 M) was added dropwise through a syringe and the mixture was stirred at room temperature for 1-4 hours until the complete consumption of the starting material (monitored by TLC). The reaction mixture was then poured into ice water (C~0.1 mM) containing 0.5% sodium bisulfite and 2.5% ammonia. The solution was placed in a refrigerator to ensure the complete precipitation then the resulting precipitate was filtered off, washed with ice water and dried in vacuo to yield the desired product used without further purification for the next step.

General Method D—Boc Protection

In an oven-dried round bottom flask were combined the corresponding 3-iodo-1H-indole (1.00 equiv.), 4-dimethylaminopyridine (10 mol %), di-tert-butyldicarbonate (1.50 equiv.) in dry dichloromethane (C~0.5 M). The reaction was stirred at room temperature for 0.5-2 hours until the complete consumption of the starting material (monitored by TLC). The organic layer was washed with 10% aqueous hydrochloride acid solution and the aqueous phase was extracted with dichloromethane three times. The combined organic extracts were washed with brine, dried ($MgSO_4$) and filtered. The solvents were removed in vacuo and the residue was purified by column chromatography on silica gel to yield the desired product.

General Method E—Sonogashira Coupling—TMS-Deprotection (1)

In an oven-dried round bottom flask equipped with a reflux condenser and under argon atmosphere, the corresponding 3-iodo-1H-indole (1.00 equiv.), bis(triphenylphosphine)palladium(II) dichloride (2 mol %) and copper(I) iodide (4 mol %) were combined in dry tetrahydrofuran (C~0.2 M). The reaction mixture was degassed with argon over 5 minutes before a slowly addition of trimethylsilylacetylene (1.50 equiv.) and dry triethylamine (2.00 equiv.). The reaction was stirred at room temperature for 12 hours (monitored by TLC), then 1M solution of tetrabutylammonium fluoride in tetrahydrofuran (1.50 equiv.) was added dropwise through a syringe and the mixture was stirred at room temperature for 0.5 hours until the complete deprotection (monitored by TLC). The resulting solution was quenched by addition of a saturated solution aqueous of ammonium chloride and extracted with ethyl acetate three times. The combined organic extracts were washed with brine, dried ($MgSO_4$) and filtered. The solvents were removed in vacuo and the residue was purified by column chromatography on silica gel to yield the desired product.

General Method F—Sonogashira Coupling—TMS-Deprotection (2)

In an oven-dried round bottom flask equipped with a reflux condenser and under argon atmosphere, the corresponding 3-iodo-1H-indole (1.00 equiv.), bis(triphenylphosphine)palladium(II) dichloride (5 mol %) and copper(I) iodide (10 mol %) were combined in dry tetrahydrofuran (C~0.2 M). The reaction mixture was degassed with argon over 5 minutes before a slowly addition of trimethylsilylacetylene (1.50 equiv.) and dry triethylamine (5.00 equiv.). The solution was then heated to 60° C. (preheated oil bath) for 18 hours (monitored by TLC). The mixture was allowed to cool to room temperature and 1M solution of tetrabutylammonium fluoride in tetrahydrofuran (1.50 equiv.) was added dropwise through a syringe over 10 minutes and stirred for 0.5 hour until the complete deprotection (monitored by TLC). The resulting solution was quenched by addition of a saturated solution aqueous of ammonium chloride and extracted with ethyl acetate three times. The combined organic extracts were washed with brine, dried ($MgSO_4$) and filtered. The solvents were removed in vacuo and the residue was purified by column chromatography on silica gel to yield the desired product.

General Method G—Copper-Catalyzed Synthesis of 1,2,3-Triazole

In an oven-dried round bottom flask was placed under argon atmosphere the corresponding 3-ethynyl-1H-indole (1.00 equiv.) and azide (1.05 equiv.) in tetrahydrofuran-tert-butanol (2:1, C~0.4 M). A freshly prepared 2M aqueous of sodium ascorbate (1.00-3.50 equiv.) and a 15% aqueous of copper(II) sulfate pentahydrate (0.25-0.87 equiv.) were added through syringes and the reaction mixture was stirred vigorously at room temperature for 8-20 h until the complete consumption of the starting material (monitored by TLC). After completion, the mixture was poured into water and extracted with ethyl acetate three times. The combined organic extracts were washed with brine, dried ($MgSO_4$) and filtered. The solvents were removed in vacuo and the residue was purified by column chromatography on silica gel to yield the desired product.

General Method H—Boc Deprotection (1)

In an oven-dried round bottom flask was dissolved the N-Boc protected triazolyl indole (1.00 equiv.) in methanol (C~0.2 M) then treated with potassium carbonate (2.50 equiv.). The mixture was stirred at room temperature until the complete consumption of the starting material (~2 hours, monitored by TLC). The solvents were removed in vacuo and the residue was purified by column chromatography on silica gel to yield the desired product.

General Method I—Boc Deprotection (2)

In an oven-dried round bottom flask was dissolved the appropriate N-Boc derivative (1.00 equiv.) in methanol (C~0.2 M). The solution was cooled to 0° C. and acetyl chloride (12.0 equiv.) added dropwise through a syringe over 30 minutes. The reaction was allowed to warm to room temperature and stirred for 18 hours until the complete consumption of the starting material (monitored by TLC). Excess of acetyl chloride and methanol were removed under reduced pressure and the residue was poured into diethyl ether and stirred at room temperature for 1 hour. The resulting precipitate was filtered off, washed with cold diethyl ether and dried in vacuo to yield the desired product.

General Method J—Heck-Jeffrey Amination

In an oven-dried round bottom flask equipped with a reflux condenser and under argon atmosphere were combined the corresponding 2-iodoaniline (1.00 equiv.), ethyl 2-ethoxyacrylate (2.00 equiv.), tetra-n-butylammonium bromide (2.00 equiv.), sodium bicarbonate (6.00 equiv.) and palladium(II) acetate (15 mol %) in dry acetonitrile (C~0.15 M). The reaction was stirred at 82° C. (preheated oil bath) for 96 hours. After the complete consumption of the starting material (monitored by TLC), the mixture was allowed to cool to room temperature and the solvents were removed under reduced pressure. The crude product was poured into water and extracted with ethyl acetate three times. The combined organic extracts were washed with brine, dried ($MgSO_4$) and filtered. The solvents were removed in vacuo and the residue was purified by column chromatography on silica gel to yield the desired product.

General Method K—Mitsunobu Synthesis

In an oven-dried round bottom flask was placed under argon atmosphere the appropriate indole-2-carboxylic acid (1.20 equiv.), triphenylphosphine (1.20 equiv.) and the corresponding alcohol (1.00 equiv.) in dry tetrahydrofuran (C~0.5 M). The reaction mixture was cooled to 0° C. and diisopropyl azodicarboxylate (1.20 equiv.) was added dropwise through a syringe over 10 minutes. The reaction was allowed to warm up to room temperature and stirred for 48 hours until the complete consumption of the starting material (monitored by TLC). The solvents were removed in vacuo and the crude was passed through a short silica gel column eluting with diethyl ether-dichloromethane (1:1) then purified by column chromatography to yield the desired product.

General Method L—Amide Bond Synthesis

In an oven-dried round bottom flask under argon atmosphere were combined the corresponding acid (1.00 equiv.) and the appropriate amine (1.00 equiv.) in N,N-dimethylformamide (C~0.3 M) then treated with N,N-diisopropylethylamine (3.00 equiv.), added slowly through a syringe. The mixture was stirred for 5 minutes at room temperature before the addition in portion wise of the O-(7-Azabenzotriazol-1-yl-N,N,N',N'-tetramethyluronium hexafluorophosphate (1.10 equiv.). The reaction was stirred for 18 hours and after the complete consumption of the starting material (monitored by TLC), the mixture was poured into water and extracted with ethyl acetate three times. The combined organics extracts were washed with water, brine, dried ($MgSO_4$) and filtered. The solvents were removed in vacuo and the residue was purified by column chromatography on silica gel to yield the desired product.

General Method M—Hydrolysis of Ethyl Ester

In an oven-dried round bottom flask equipped with a reflux condenser was dissolved the corresponding ethyl indole-2-carboxylate (1.00 equiv.) in tetrahydrofuran-water (1:1, C~0.1 M) then treated with lithium hydroxide (4.00 equiv.). The solution was heated to 70° C. (preheated oil bath) for 12 hours (monitored by TLC). The reaction mixture was allowed to cool to room temperature and then made acidic (pH~1) by addition of 10% aqueous hydrochloride acid solution. The stirring was continued for 15 minutes before the addition of ethyl acetate. Layers were separated and the aqueous solution was extracted with ethyl acetate three times. The combined organic extracts were washed with brine, dried ($MgSO_4$) and filtered. The solvents were removed in vacuo and the formed solid was collected and dried under high vacuum.

General Method N—Phenol Triflation

In an oven-dried round bottom flask, under argon atmosphere was added the corresponding phenol (1.00 equiv.) in dry dichloromethane (C~0.3 M) and treated with pyridine (3.00 equiv.), added slowly through a syringe. The solution was cooled to 0° C. and trifluoromethanesulfonic anhydride (1.10 equiv) was added dropwise over 30 minutes. The reaction was allowed to warm to room temperature and stirred for 18 hours until the complete consumption of the starting material (monitored by TLC). Excess of trifluoromethansulfonic acid and dichloromethane were removed under reduced pressure and the residue was poured into water and extracted with ethyl acetate three times. The combined organic extracts were washed with 10% aqueous hydrochloric acid solution, 5% aqueous sodium bicarbonate solution and brine, then dried ($MgSO_4$) and filtered. The solvents were removed in vacuo and the residue was purified by column chromatography on silica gel to yield the desired product.

General Method O—Suzuki Coupling

In an oven-dried round bottom flask equipped with a reflux condenser and under argon atmosphere were combined the aryl triflate (1.30-1.50 equiv.), the appropriate boronic acid (1.00 equiv.), anhydrous 1,2-dimethoxyethane (C~0.2 M) and 2M aqueous sodium carbonate (1.60 equiv.). The reaction mixture was degassed by bubbling argon through the solution for 15 minutes before the addition of tetrakis(triphenylphosphine)palladium(0) (6.25-25 mol %). The solution was degassed for a further 5 minutes and then heated to 85° C. (preheated oil bath) for 6-12 hours until the complete consumption of the starting material (monitored by TLC). The reaction was allowed to cool to room temperature, filtered through celite washing with diethyl ether and the solvents were removed under reduced pressure. The residue was poured into diethyl ether-water and extracted with diethyl ether three times. The combined organics extracts were washed with brine, dried ($MgSO_4$) and filtered. The solvents were removed in vacuo and the residue was purified by column chromatography on silica gel to yield the desired product.

General Method P—Chan-Lan Coupling

In an oven-dried round bottom flask were added in dry dichloromethane (C~0.1 M) the corresponding alcohol (1.00 equiv.), the boronic acid (2.00 equiv.), the powdered activated 4 Å molecular sieves (~1.00 g/mmol), copper(II) acetate (1.00 equiv.) and dry triethylamine (5.00 equiv.). The reaction mixture was stirred at room temperature for 18 hours under air atmosphere. After the complete consumption of the starting material (monitored by TLC), the mixture was quenched with an excess of n-hexane and precipitated catalyst and molecular sieves were separated by filtration. The solvents were removed under reduced pressure and the residue was purified by column chromatography on silica gel to yield the desired product.

General Method Q—Reductive Amination

In an oven-dried round bottom flask under argon atmosphere were combined the benzaldehyde (1.00 equiv.) and the corresponding amine (1.50 equiv.) in dry methanol (C~0.3 M) and stirred for 3 hours at room temperature. The reaction mixture was cooled to 0° C. and sodium triacetoxyborohydride (1.40 equiv.) was added in two portions with a 1-hour interval. The reaction was allowed to warm up to room temperature and stirred for 18 hours until the complete consumption of the starting material (monitored by TLC). The reaction mixture was poured into 2M aqueous sodium carbonate solution and extracted with dichloromethane three times. The combined organic extracts were washed with brine, dried ($MgSO_4$) and filtered. The solvents were removed in vacuo and the residue was purified by column chromatography on silica gel to yield the desired product.

General Method R—Sulfonamide Synthesis (2)

In an oven dried round bottom flask was dissolved 2-chloroethylamine hydrochloride (1.20 equiv.) in dry N,N-dimethylformamide (C~0.3 M) and treated with triethylamine (2.00 equiv.). The mixture was stirred for 5 minutes at room temperature before the addition in portion wise of the appropriate sulfonyl chloride (1.00 equiv.). The mixture was stirred for 16 hours at room temperature, until the complete consumption of the starting material (monitored by TLC). The reaction mixture was poured into a cold 5% aqueous hydrochloride acid solution and extracted with ethyl acetate three times. The combined organic extracts were washed with water, brine, then dried ($MgSO_4$) and filtered. The solvents were removed in vacuo and the residue was purified by column chromatography on silica gel to yield the desired product.

General Method S—Azide Synthesis

In an oven-dried round bottom flask were combined under argon atmosphere at 0° C. (ice bath), the corresponding alcohol (1.00 equiv.) and triethylamine (1.30 equiv.) in dry tetrahydrofuran (C~0.3 M). Methanesulfonyl chloride (1.00 equiv.) was added dropwise through a syringe over 10 minutes then the reaction was allowed to warm to room temperature and stirred for 3-5 hours. After the complete consumption of the starting material (monitored by TLC), the mixture was poured into ethyl acetate and water. The organic layer was extracted, washed with 10% aqueous hydrochloric acid solution, brine, dried ($MgSO_4$) and filtered. The solvents were removed under reduced pressure and the desired product used without further purification for the next step.

In an oven-dried round bottom flask equipped with a reflux condenser was dissolved the corresponding mesylate (1.00 equiv.) in N,N-dimethylformamide (C~0.15 M) and sodium azide (3.00 equiv.) was added in portion wise. The reaction mixture was heated to 60° C. and stirred for 8 hours until the complete consumption of the starting material (monitored by TLC). The reaction was allowed to cool to room temperature, poured into water and extracted with ethyl acetate three times. The combined organics extracts were washed with water three times, brine, dried ($MgSO_4$) and filtered. The solvents were removed in vacuo and the residue was purified by column chromatography on silica gel to yield the desired product.

General Method T—Suzuki Coupling (2)

In an oven-dried round bottom flask equipped with a reflux condenser and under argon atmosphere were combined the aryl bromide (1.00 equiv.), the appropriate boronic ester (1.20 equiv.), potassium carbonate (2.20 equiv.) in 1,4-dioxane-water (4:1, C~0.3 M). The reaction mixture was degassed by bubbling argon through the solution for 15 minutes before the addition of [1,1'-Bis(diphenylphosphino)ferrocene]dichloropalladium(II) (10 mol %). The solution was degassed for a further 5 minutes and then heated to 100° C. (preheated oil bath) for 16 hours until the complete consumption of the starting material (monitored by TLC).

The reaction was allowed to cool to room temperature, filtered through celite washing with ethyl acetate and the solvents were removed under reduced pressure. The residue was poured into ethyl acetate-water and extracted with ethyl acetate three times. The combined organics extracts were washed with brine, dried ($MgSO_4$) and filtered. The solvents were removed in vacuo and the residue was purified by column chromatography on silica gel to yield the desired product.

General Method U—Hydrogenation

In an oven-dried round bottom flask equipped with a reflux condenser were combined the corresponding dihydropyridine (1.00 equiv.) and ammonium formate (10.0 equiv.) in methanol (C~0.3 M). The mixture was stirred for 5 minutes at room temperature before the addition in portion wise of 10% palladium on carbon (0.10 equiv.). The reaction was heated to 80° C. (preheated oil bath) for 48 hours until the complete consumption of the starting material (monitored by TLC). The reaction was allowed to cool to room temperature, filtered through celite washing with ethyl acetate and the solvents were removed under reduced pressure. The residue was poured into ethyl acetate-water and extracted with ethyl acetate three times. The combined organics extracts were washed with brine, dried ($MgSO_4$) and filtered. The solvents were removed in vacuo and the residue was purified by column chromatography on silica gel to yield the desired product.

General Method V—Sulfonyl Chloride Synthesis

In an oven-dried round bottom flask under argon atmosphere was dissolved the corresponding ammonium salt (1.00 equiv.) in dry dichloromethane (C~0.15 M), then treated with N,N-diisopropylethylamine (1.00-2.50 equiv.), added slowly through a syringe. The reaction mixture was cooled to −30° C. and sulfuryl chloride (2.00 equiv.) in dry dichloromethane (C~0.1 M) was added dropwise through a syringe over 5 minutes. The mixture was stirred for 1 hour at −30° C., then 18 hours at room temperature, until the complete consumption of the starting material (monitored by TLC). The solvents were removed under reduced pressure and the residue was poured into ethyl acetate-water and extracted with ethyl acetate three times. The combined organic extracts were washed with 10% aqueous hydrochloric acid solution, brine, then dried ($MgSO_4$) and filtered. The solvents were removed in vacuo and the desired product used without further purification for the next step.

General Method W—Weinreb Amide Synthesis

In an oven-dried round bottom flask under argon atmosphere were combined the appropriate indole-2-carboxylic acid (1.00 equiv.) and N,O-dimethylhydroxylamine hydrochloride (1.20 equiv.) in dry dichloromethane (C~0.15 M). The reaction mixture was cooled to 0° C. and N,N-diisopropylethylamine (1.20 equiv.) was added dropwise through a syringe over 15 minutes. The mixture was stirred for 5 minutes at 0° C. before the addition in portion wise of the 1-Ethyl-3-(3-dimethylaminopropyl)carbodiimide (1.20 equiv.) and 4-dimethylaminopyridine (10 mol %). The reaction was allowed to warm up to room temperature and stirred for 16 hours until the complete consumption of the starting material (monitored by TLC). The mixture was poured into water, washed brine, dried ($MgSO_4$) and filtered. The solvents were removed in vacuo and the residue was purified by column chromatography on silica gel to yield the desired product.

General Method X—Methyl Ketone Synthesis

In an oven-dried round bottom flask under argon atmosphere was dissolved the corresponding indole (1.00 equiv.) in dry tetrahydrofuran (C~0.1 M). The reaction mixture was cooled to −78° C., then a solution of 1.6 M methyllithium in diethyl ether (3.00 equiv.) was added dropwise through a syringe over 15 minutes. The mixture was stirred for 3 hours at −78° C., until the complete consumption of the starting material (monitored by TLC). The mixture was poured into water and the solvents were remove in vacuo. The crude product was diluted into ethyl acetate, washed with aqueous ammonium chloride, brine, dried ($MgSO_4$) and filtered. The solvents were removed in vacuo and the residue was purified by column chromatography on silica gel to yield the desired product.

General Method Y—Secondary Alcohol Synthesis

In an oven-dried round bottom flask under argon atmosphere was dissolved the corresponding indole (1.80 equiv.) in dry tetrahydrofuran (C~0.15 M). The reaction mixture was cooled to −78° C., then a solution of 2.5 M n-butyllithium in n-hexane (1.80 equiv.) was added dropwise through a syringe over 15 minutes. The mixture was stirred for 1 hours at −78° C., before the slowly addition of the corresponding aldehyde (1.00 equiv.) in dry tetrahydrofuran (C~0.1 M). The reaction was stirred for 1 hour at the same temperature until the complete consumption of the starting material (monitored by TLC). The mixture was quenched with aqueous ammonium chloride, extracted with ethyl acetate three times, washed with brine, dried ($MgSO_4$) and filtered. The solvents were removed in vacuo and the residue was purified by column chromatography on silica gel to yield the desired product.

General Method Z—Tosyl Deprotection

In an oven-dried round bottom flask equipped with a reflux condenser and under argon atmosphere was dissolved the N-Ts protected indole (1.00 equiv.) in dry tetrahydrofuran-ethanol (1:10, C~0.1 M) then treated with potassium hydroxide (5.00 equiv.). The reaction was heated to 80° C. (preheated oil bath) for 2-4 hours. After the complete consumption of the starting material (monitored by TLC), the mixture was allowed to cool to room temperature then poured into water and extracted with ethyl acetate three times. The combined organic extracts were washed with brine, dried ($MgSO_4$) and filtered. The solvents were removed in vacuo and the residue was purified by column chromatography on silica gel to yield the desired product.

General Method A1—Alcohol Oxidation

In an oven-dried round bottom flask equipped with a reflux condenser and under argon atmosphere was dissolved the corresponding secondary alcohol (1.00 equiv.) in dry chloroform (C~0.1 M) then treated with manganese (IV) oxide (20.0 equiv.). The reaction was heated to 80° C. (preheated oil bath) for 4-8 hours until the complete consumption of the starting material (monitored by TLC). The reaction was allowed to cool to room temperature, filtered through celite washing with ethyl acetate. The solvents were removed in vacuo and the residue was purified by column chromatography on silica gel to yield the desired product.

II. Detailed Experimental Procedures and Characterization

N-(2-Chloroethyl)benzenesulfonamide (1a)

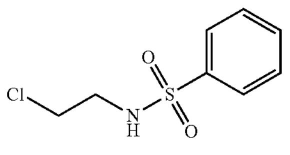 [SMILES: O=S(=O)(NCCCl)c1ccccc1]

Prepared by general method A using 2-chloroethylamine hydrochloride (500 mg, 4.31 mmol), benzenesulfonyl chloride (550 μL, 4.31 mmol), potassium carbonate (1.20 g, 8.62 mmol) and dichloromethane-water (15 mL). The crude residue was purified by recrystallization in diisopropyl ether and the title compound 1a was obtained as an off-white crystalline solid (741 mg, 78% yield). $^1$H-NMR (400 MHz, $d_6$-DMSO) δ=8.03 (t, J=5.9 Hz, 1H), 7.83-7.80 (m, 2H), 7.68-7.57 (m, 3H), 3.57 (t, J=6.1 Hz, 2H), 3.08 (q, J=6.1 Hz, 2H). $^{13}$C NMR (100 MHz, $d_6$-DMSO) δ=140.4 ($C_{quat}$), 132.5 (CH), 129.3 (CH), 126.4 (CH), 44.4 ($CH_2$), 43.5 ($CH_2$). Spectroscopic and physical data matched the ones reported in the literature.[1]

4-Chloro-N-(2-chloroethyl)benzenesulfonamide (1b)

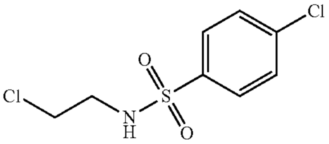 [SMILES: O=S(=O)(NCCCl)c1ccc(Cl)cc1]

Prepared by general method A using 2-chloroethylamine hydrochloride (500 mg, 4.31 mmol), 4-chlorobenzenesulfonyl chloride (910 mg, 4.31 mmol), potassium carbonate (1.20 g, 8.62 mmol) and dichloromethane-water (15 mL). The crude residue was purified by recrystallization in diisopropyl ether and the title compound 1b was obtained as an off-white crystalline solid (803 mg, 73% yield). $^1$H NMR (400 MHz, $d_6$-Acetone) δ=7.94-7.84 (m, 2H), 7.68-7.60 (m, 2H), 6.98 (s, 1H), 3.64 (t, J=6.2 Hz, 2H), 3.30 (q, J=6.2 Hz, 2H). $^{13}$C NMR (100 MHz, $d_6$-Acetone) δ=140.7 ($C_{quat}$), 139.0 ($C_{quat}$), 130.2 (CH), 129.5 (CH), 45.7 ($CH_2$), 44.1 ($CH_2$).

N-(2-Chloroethyl)-4-(trifluoromethyl)benzenesulfonamide (1c)

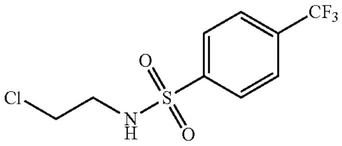 [SMILES: O=S(=O)(NCCCl)c1ccc(C(F)(F)F)cc1]

Prepared by general method A using 2-chloroethylamine hydrochloride (500 mg, 4.31 mmol), 4-(trifluoromethyl)-benzenesulfonyl chloride (1.05 g, 4.31 mmol), potassium carbonate (1.20 g, 8.62 mmol) and dichloromethane-water (15 mL). The crude product was purified chromatographically on silica gel (eluting cyclohexane-ethyl acetate 80:20) to provide the title compound 1c as an off-white crystalline solid (947 mg, 77% yield). $^1$H-NMR (400 MHz, $d_6$-DMSO) δ=8.31 (t, J=5.9 Hz, 1H), 8.01 (q, J=8.5 Hz, 4H), 3.59 (t, J=6.0 Hz, 2H), 3.14 (q, J=6.0 Hz, 2H). $^{13}$C NMR (100 MHz, $d_6$-DMSO) δ=144.5 (d, J=1.4 Hz, $C_{quat}$), 132.3 (q, J=32.5 Hz, $C_{quat}$) 127.5 (CH), 126.5 (q, J=3.8 Hz, $C_{quat}$), 123.5 (q, J=272.0 Hz, CH), 44.4 ($CH_2$), 43.59 ($CH_2$). $^{19}$F NMR (375 MHz, $d_6$-DMSO) δ=−61.7.

N-(2-Chloroethyl)naphthalene-2-sulfonamide (1d)

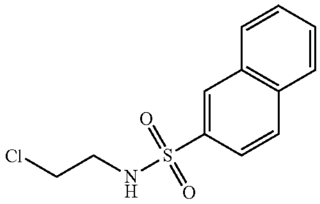 [SMILES: O=S(=O)(NCCCl)c1ccc2ccccc2c1]

Prepared by general method A using 2-chloroethylamine hydrochloride (500 mg, 4.31 mmol), naphthalene-2-sulfonyl chloride (977 mg, 4.31 mmol), potassium carbonate (1.20 g, 8.62 mmol) and dichloromethane-water (15 mL). The crude product was purified chromatographically on silica gel (eluting cyclohexane-ethyl acetate 85:15) to provide the title compound 1d as a white solid (739 mg, 64% yield). $^1$H NMR (400 MHz, $d_6$-DMSO) δ=8.48 (d, J=1.5 Hz, 1H), 8.20-8.09 (m, 3H), 8.06-8.00 (m, 1H), 7.85 (dd, J=8.6, 1.9 Hz, 1H), 7.67 (pd, J=6.9, 1.5 Hz, 2H), 3.59 (t, J=6.2 Hz, 2H), 3.13 (q, J=6.1 Hz, 2H). $^{13}$C NMR (100 MHz, $d_6$-DMSO) δ=137.4 ($C_{quat}$), 134.2 ($C_{quat}$), 131.7 ($C_{quat}$), 129.5 (CH), 129.2 (CH), 128.7 (CH), 127.8 (CH), 127.6 (CH), 127.4 (CH), 122.2 (CH), 44.4 ($CH_2$), 43.6 ($CH_2$).

N-(2-Chloroethyl)-4-methylbenzenesulfonamide (1e)

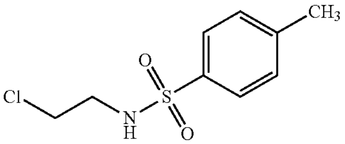

Prepared by general method A using 2-chloroethylamine hydrochloride (500 mg, 4.31 mmol), 4-methylbenzenesulfonyl chloride (822 mg, 4.31 mmol), potassium carbonate (1.20 g, 8.62 mmol) and dichloromethane-water (15 mL). The crude product was purified chromatographically on silica gel (eluting cyclohexane-ethyl acetate 80:20) to provide the tittle compound 1e as an off-white solid (754 mg, 75% yield). $^1$H NMR (400 MHz, $d_6$-Acetone) δ=7.79-7.71 (m, 2H), 7.44-7.39 (m, 2H), 6.78 (s, 1H), 3.61 (t, J=6.4 Hz, 2H), 3.25 (q, J=6.3 Hz, 2H), 2.42 (s, 3H). $^{13}$C NMR (100 MHz, $d_6$-Acetone) δ=144.1 ($C_{quat}$), 139.0 ($C_{quat}$), 130.5 (CH), 127.8 (CH), 45.7 ($CH_2$), 44.1 ($CH_2$), 21.4 ($CH_3$).

N-(2-Chloroethyl)-4-ethylbenzenesulfonamide (If)

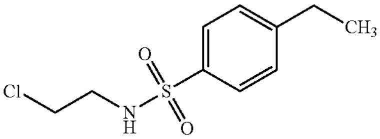

In an oven-dried round bottom flask were combined 2-chloroethylamine hydrochloride (500 mg, 4.31 mmol, 1.00 equiv.) and triethylamine (721 μL, 5.17 mmol, 1.20 equiv.) in dry N,N-dimethylformamide (14 mL, ~0.3 M). 4-ethylbenzenesulfonyl chloride (700 μL, 4.31 mmol, 1.00 equiv.) was gradually added through a syringe over 5 minutes and the solution was stirred at room temperature for 3 hours until the complete consumption of the starting material (monitored by TLC). The reaction mixture was poured into a cold 5% aqueous hydrochloride acid solution (50 mL). The solution was placed in a refrigerator to ensure the complete precipitation then the resulting precipitate was filtered off, washed with ice water and dried under reduced pressure to obtain the title compound 1f as an off-white solid (711 mg, 67% yield) used without further purification for the next step. $^{1}$H NMR (400 MHz, $d_6$-Acetone) δ=7.78-7.69 (m, 2H), 7.45-7.40 (m, 2H), 6.80 (s, 1H), 3.60 (t, J=6.4 Hz, 2H), 3.25 (q, J=6.4 Hz, 2H), 2.42 (q, J=6.8 Hz, 2H), 1.20 (d, J=6.8 Hz, 3H). $^{13}$C NMR (100 MHz, $d_6$-Acetone) δ=147.1 ($C_{quat}$), 140.0 ($C_{quat}$), 130.5 (CH), 127.8 (CH), 45.7 ($CH_2$), 44.1 ($CH_2$), 24.4 ($CH_2$), 16.2 ($CH_3$).

N-(2-Chloroethyl)-4-isopropylbenzenesulfonamide (1g)

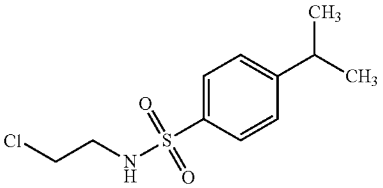 [SMILES: CC(C)c1ccc(S(=O)(=O)NCCCl)cc1]

Prepared by general method A using 2-chloroethylamine hydrochloride (500 mg, 4.31 mmol), 4-isopropylbenzenesulfonyl chloride (943 mg, 4.31 mmol), potassium carbonate (1.20 g, 8.62 mmol) and dichloromethane-water (15 mL). The crude product was purified chromatographically on silica gel (eluting cyclohexane-ethyl acetate 85:15) to provide the title compound 1g as a white solid (841 mg, 74%). $^{1}$H NMR (400 MHz, $d_6$-DMSO) δ=7.93 (t, J=5.9 Hz, 1H), 7.73 (d, J=8.3 Hz, 2H), 7.46 (d, J=8.3 Hz, 2H), 3.57 (t, J=6.2 Hz, 2H), 3.06 (q, J=6.1 Hz, 2H), 2.97 (p, J=6.9 Hz, 1H), 1.21 (d, J=6.9 Hz, 6H). $^{13}$C NMR (100 MHz, $d_6$-DMSO) δ=153.3 ($C_{quat}$), 137.9 ($C_{quat}$), 127.2 (CH), 126.6 (CH), 44.4 ($CH_2$), 43.5 ($CH_2$), 33.4 (CH), 23.5 ($CH_3$).

N-(2-Chloroethyl)-4-isobutylbenzenesulfonamide (1h)

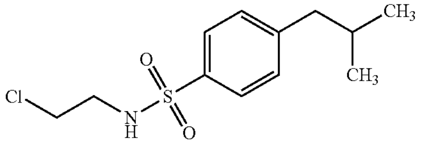 [SMILES: CC(C)Cc1ccc(S(=O)(=O)NCCCl)cc1]

Prepared by general method A using 2-chloroethylamine hydrochloride (500 mg, 4.31 mmol), 4-isobutylbenzenesulfonyl chloride (1.00 g, 4.31 mmol), potassium carbonate (1.20 g, 8.62 mmol) and dichloromethane-water (15 mL). The crude product was purified chromatographically on silica gel (eluting cyclohexane-ethyl acetate 85:15) to provide the title compound 1h as a white solid (835 mg, 70% yield). $^{1}$H NMR (400 MHz, $d_6$-DMSO) δ=7.91 (t, J=5.9 Hz, 1H), 7.72 (d, J=8.3 Hz, 2H), 7.46 (d, J=8.3 Hz, 2H), 3.56 (t, J=6.2 Hz, 2H), 3.06 (q, J=6.1 Hz, 2H), 1.48-1.35 (m, 1H), 1.10 (qd, J=12.1, 3.8 Hz, 2H), 0.91 (d, J=6.7 Hz, 6H). $^{13}$C NMR (100 MHz, $d_6$-DMSO) δ=144.5 ($C_{quat}$), 136.3 ($C_{quat}$) 129.5 (CH), 126.4 (CH), 44.2 ($CH_2$), 43.6 ($CH_2$), 29.5 (CH), 29.1 ($CH_2$), 22.0 ($CH_3$).

N-(2-chloroethyl)-4-(trifluoromethoxy)benzenesulfonamide (1i)

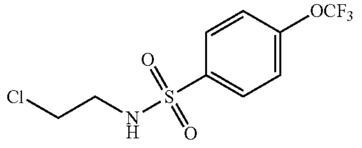 [SMILES: O=S(=O)(NCCCl)c1ccc(OC(F)(F)F)cc1]

Prepared by general method R using 2-chloroethylamine hydrochloride (534 mg, 4.60 mmol), 4-(trifluoromethoxy)benzenesulfonyl chloride (1.00 g, 3.84 mmol), triethylamine (1.07 mL, 7.67 mmol) and dry N,N-dimethylformamide (13 mL). The crude product was purified chromatographically on silica gel (eluting cyclohexane-ethyl acetate 80:20) to provide the title compound 1i as a white solid (815 mg, 69% yield). LC-MS (ESI+) Found: $[M+H]^+$, 303.9.

N-(2-chloroethyl)-[1,1'-biphenyl]-4-sulfonamide (1j)

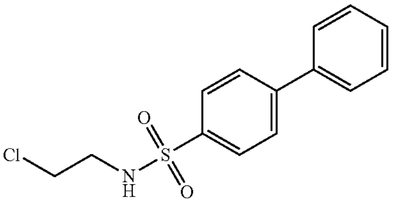 [SMILES: O=S(=O)(NCCCl)c1ccc(-c2ccccc2)cc1]

Prepared by general method R using 2-chloroethylamine hydrochloride (551 mg, 4.75 mmol), [1,1'-biphenyl]-4-sulfonyl chloride (1.00 g, 3.96 mmol), triethylamine (1.10 mL, 7.91 mmol) and dry N,N-dimethylformamide (14 mL). The crude product was purified chromatographically on silica gel (eluting cyclohexane-ethyl acetate 85:15) to provide the title compound 1j as a white solid (721 mg, 72% yield). LC-MS (ESI+) Found: $[M+H]^+$, 252.9.

N-(2-chloroethyl)-4-cyclohexylbenzenesulfonamide (1k)

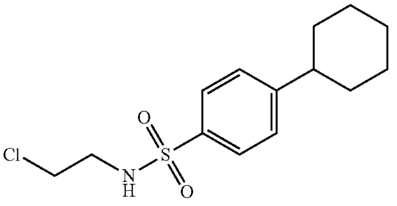 [SMILES: O=S(=O)(NCCCl)c1ccc(C2CCCCC2)cc1]

Prepared by general method R using 2-chloroethylamine hydrochloride (538 mg, 4.64 mmol), 4-cyclohexylbenzenesulfonyl chloride (1.00 g, 3.86 mmol), triethylamine (1.08 mL, 7.73 mmol) and dry N,N-dimethylfonnamide (15 mL).

The crude product was purified chromatographically on silica gel (eluting cyclohexane-ethyl acetate 85:15) to provide the title compound 1k as a white solid (886 mg, 76% yield). LC-MS (ESI+) Found: $[M+H]^+$, 302.1.

N-(2-chloroethyl)-4-isopropoxybenzenesulfonamide (1l)

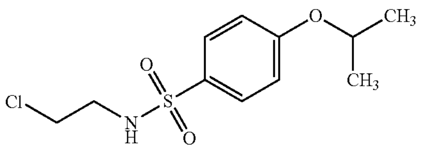 [SMILES: CC(C)Oc1ccc(S(=O)(=O)NCCCl)cc1]

Prepared by general method R using 2-chloroethylamine hydrochloride (593 mg, 5.11 mmol), 4-isopropoxybenzenesulfonyl chloride (1.00 g, 4.26 mmol), triethylamine (1.19 mL, 8.52 mmol) and dry N,N-dimethylformamide (14 mL). The crude product was purified chromatographically on silica gel (eluting cyclohexane-ethyl acetate 80:20) to provide the title compound 11 as a white solid (563 mg, 48% yield). LC-MS (ESI+) Found: $[M+H]^+$, 277.9.

N-(2-chloroethyl)-2,3-dihydrobenzofuran-5-sulfonamide (1m)

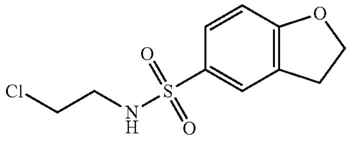 [SMILES: O=S(=O)(NCCCl)c1ccc2c(c1)CCO2]

Prepared by general method R using 2-chloroethylamine hydrochloride (637 mg, 5.49 mmol), 2,3-dihydrobenzofuran-6-sulfonyl chloride (1.00 g, 4.57 mmol), triethylamine (1.27 mL, 9.15 mmol) and dry N,N-dimethylformamide (15 mL). The crude product was purified chromatographically on silica gel (eluting cyclohexane-ethyl acetate 80:20) to provide the title compound 1m as a white solid (760 mg, 64% yield). $^1H$ NMR (300 MHz, $d_6$-DMSO) δ=7.77 (t, J=6.0 Hz, 1H), 7.74-7.62 (m, 1H), 7.56 (dd, J=8.4, 2.1 Hz, 1H), 6.92 (d, J=8.4 Hz, 1H), 4.64 (t, J=8.8 Hz, 2H), 3.56 (t, J=6.2 Hz, 2H), 3.25 (t, J=8.8 Hz, 2H), 3.03 (q, J=6.2 Hz, 2H). LC-MS (ESI+) Found: $[M+H]^+$, 261.9.

4-(sec-butyl)-N-(2-chloroethyl)benzenesulfonamide (1n)

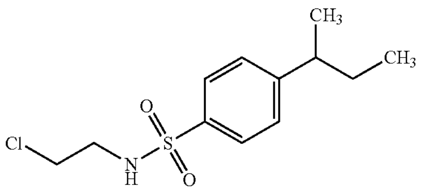 [SMILES: CCC(C)c1ccc(S(=O)(=O)NCCCl)cc1]

Prepared by general method R using 2-chloroethylamine hydrochloride (600 mg, 5.16 mmol), 4-(sec-butyl)benzenesulfonyl chloride (1.00 g, 4.30 mmol), triethylamine (1.20 mL, 8.59 mmol) and dry N,N-dimethylfonnamide (14 mL). The crude product was purified chromatographically on silica gel (eluting cyclohexane-ethyl acetate 80:20) to provide the title compound 1n as a white solid (794 mg, 67% yield). LC-MS (ESI+) Found: $[M+H]^+$, 275.9.

N-(2-chloroethyl)-2,3-dihydro-1H-indene-5-sulfonamide (1o)

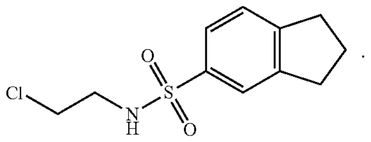 [SMILES: O=S(=O)(NCCCl)c1ccc2c(c1)CCC2]

Prepared by general method R using 2-chloroethylamine hydrochloride (642 mg, 5.54 mmol), 2,3-dihydro-1H-indene-5-sulfonyl chloride (1.00 g, 4.62 mmol), triethylamine (1.29 mL, 9.23 mmol) and dry N,N-dimethylformamide (15 mL). The crude product was purified chromatographically on silica gel (eluting cyclohexane-ethyl acetate 85:15) to provide the title compound 1o as a white solid (805 mg, 67% yield). $^1H$ NMR (300 MHz, $d_6$-DMSO) δ=7.87 (t, J=6.0 Hz, 1H), 7.64 (d, J=1.8 Hz, 1H), 7.57 (dd, J=7.9, 1.8 Hz, 1H), 7.42 (d, J=7.9 Hz, 1H), 3.56 (t, J=6.2 Hz, 2H), 3.04 (t, J=6.2 Hz, 2H), 2.92 (t, J=7.3 Hz, 4H), 2.05 (p, J=7.5 Hz, 21H). LC-MS (ESI+) Found: [M+H]+, 259.9.

N-(2-chloroethyl)-4-phenoxybenzenesulfonamide (1p)

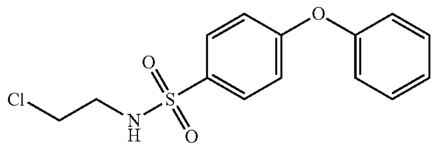 [SMILES: O=S(=O)(NCCCl)c1ccc(Oc2ccccc2)cc1]

Prepared by general method R using 2-chloroethylamine hydrochloride (518 mg, 4.47 mmol), 4-phenoxybenzenesulfonyl chloride (1.00 g, 3.72 mmol), triethylamine (1.04 mL, 7.44 mmol) and dry N,N-dimethylformamide (14 mL). The crude product was purified chromatographically on silica gel (eluting cyclohexane-ethyl acetate 80:20) to provide the title compound 1p as a white solid (648 mg, 56% yield). $^1H$ NMR (300 MHz, $d_6$-DMSO) δ=7.95 (t, J=5.9 Hz, 1H), 7.88-7.72 (m, 2H), 7.54-7.41 (m, 2H), 7.31-7.21 (m, 1H), 7.19-7.05 (m, 4H), 3.58 (t, J=6.2 Hz, 2H), 3.07 (q, J=6.1 Hz, 2H). LC-MS (ESI+) Found: $[M+H]^+$, 311.9.

4-(tert-butyl)-N-(2-chloroethyl)benzenesulfonamide (1q)

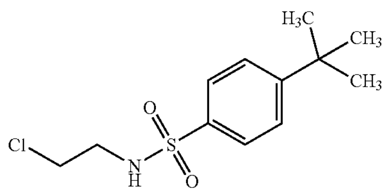 [SMILES: CC(C)(C)c1ccc(S(=O)(=O)NCCCl)cc1]

Prepared by general method R using 2-chloroethylamine hydrochloride (600 mg, 5.16 mmol), 4-(tert-butyl)-N-(2-chloroethyl)benzenesulfonamide (1.00 g, 4.30 mmol), triethylamine (1.20 mL, 8.60 mmol) and dry N,N-dimethylformamide (14 mL). The crude product was purified chromatographically on silica gel (eluting cyclohexane-ethyl acetate 80:20) to provide the title compound 1q as a white solid (946 mg, 79% yield). $^1$H NMR (300 MHz, $d_6$-DMSO) δ=7.93 (t, J=5.9 Hz, 1H), 7.76-7.70 (m, 2H), 7.65-7.58 (m, 2H), 3.57 (t, J=6.2 Hz, 2H), 3.05 (q, J=6.1 Hz, 2H), 1.30 (s, 9H). LC-MS (ESI+) Found: $[M+H]^+$, 275.9.

N-(2-chloroethyl)-1-(4-(trifluoromethyl)phenyl) methanesulfonamide (1r)

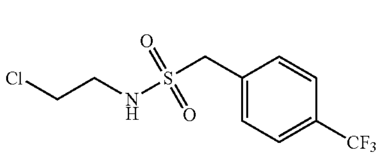 [SMILES: O=S(=O)(Cc1ccc(C(F)(F)F)cc1)NCCCl]

Prepared by general method R using 2-chloroethylamine hydrochloride (538 mg, 4.64 mmol), (4-(trifluoromethyl) phenyl)methanesulfonyl chloride (1.00 g, 3.87 mmol), triethylamine (1.08 mL, 7.73 mmol) and dry N,N-dimethylformamide (14 mL). The crude product was purified chromatographically on silica gel (eluting cyclohexane-ethyl acetate 85:15) to provide the title compound 1r as a white solid (804 mg, 69% yield). $^1$H NMR (300 MHz, $d_6$-DMSO) δ=8.30 (t, J=5.9 Hz, 1H), 8.16-7.92 (m, 4H), 3.59 (t, J=6.0 Hz, 2H), 3.14 (q, J=6.0 Hz, 2H). LC-MS (ESI+) Found: $[M+H]^+$, 302.1.

N-(2-chloroethyl)-1-(4-chlorophenyl)methanesulfonamide (1s)

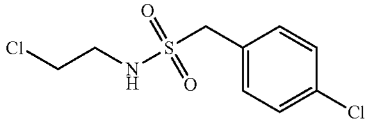 [SMILES: O=S(=O)(Cc1ccc(Cl)cc1)NCCCl]

Prepared by general method R using 2-chloroethylamine hydrochloride (618 mg, 5.33 mmol), (4-chlorophenyl)methanesulfonyl chloride (1.00 g, 4.44 mmol), triethylamine (1.24 mL, 8.89 mmol) and dry N,N-dimethylformamide (15 mL). The crude product was purified chromatographically on silica gel (eluting cyclohexane-ethyl acetate 85:15) to provide the title compound 1s as a white solid (915 mg, 77% yield). $^1$H NMR (300 MHz, $d_6$-DMSO) δ=7.76 (d, J=7.9 Hz, 2H), 7.62 (d, J=8.0 Hz, 2H), 7.55 (t, J=6.0 Hz, 1H), 4.53 (s, 2H), 3.59 (t, J=6.4 Hz, 2H), 3.25 (q, J=6.3 Hz, 2H). LC-MS (ESI+) Found: $[M+H]^+$, 267.9.

N-(2-chloroethyl)-1-(3-chlorophenyl)methanesulfonamide (1t)

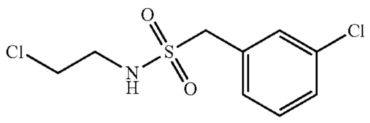 [SMILES: O=S(=O)(Cc1cccc(Cl)c1)NCCCl]

Prepared by general method R using 2-chloroethylamine hydrochloride (618 mg, 5.33 mmol), (3-chlorophenyl)methanesulfonyl chloride (1.00 g, 4.44 mmol), triethylamine (1.24 mL, 8.89 mmol) and dry N,N-dimethylformamide (15 mL). The crude product was purified chromatographically on silica gel (eluting cyclohexane-ethyl acetate 85:15) to provide the title compound 1t as a white solid (812 mg, 68% yield). LC-MS (ESI+) Found: $[M+H]^+$, 267.9.

1-(4-bromophenyl)-N-(2-chloroethyl)methanesulfonamide (1u)

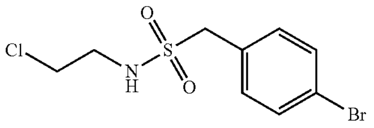 [SMILES: O=S(=O)(Cc1ccc(Br)cc1)NCCCl]

Prepared by general method R using 2-chloroethylamine hydrochloride (516 mg, 4.45 mmol), (4-bromophenyl)methanesulfonyl chloride (1.00 g, 3.71 mmol), triethylamine (1.03 mL, 7.42 mmol) and dry N,N-dimethylformamide (12 mL). The crude product was purified chromatographically on silica gel (eluting cyclohexane-ethyl acetate 85:15) to provide the title compound 1u as a white solid (833 mg, 71% yield). $^1$H NMR (300 MHz, $d_6$-DMSO) δ=7.64-7.54 (m, 2H), 7.48 (t, J=5.9 Hz, 1H), 7.38-7.27 (m, 2H), 4.39 (s, 2H), 3.57 (t, J=6.4 Hz, 2H), 3.20 (q, J=6.3 Hz, 2H). LC-MS (ESI+) Found: $[M+H]^+$, 311.9.

1-(3-bromophenyl)-N-(2-chloroethyl)methanesulfonamide (1v)

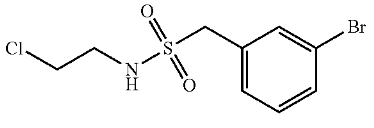 [SMILES: O=S(=O)(Cc1cccc(Br)c1)NCCCl]

Prepared by general method R using 2-chloroethylamine hydrochloride (516 mg, 4.45 mmol), (3-bromophenyl)methanesulfonyl chloride (1.00 g, 3.71 mmol), triethylamine (1.03 mL, 7.42 mmol) and dry N,N-dimethylformamide (12 mL). The crude product was purified chromatographically on silica gel (eluting cyclohexane-ethyl acetate 85:15) to provide the title compound 1v as a white solid (742 mg, 64% yield). $^1$H NMR (300 MHz, $d_6$-DMSO) δ=7.60 (d, J=1.8 Hz, 1H), 7.59-7.48 (m, 2H), 7.45-7.31 (m, 2H), 4.42 (s, 2H), 3.58 (t, J=6.4 Hz, 2H), 3.21 (q, J=6.3 Hz, 2H). LC-MS (ESI+) Found: $[M+H]^+$, 311.9.

N-(2-chloroethyl)-4-(1H-pyrazol-4-yl)benzenesulfonamide (1w)

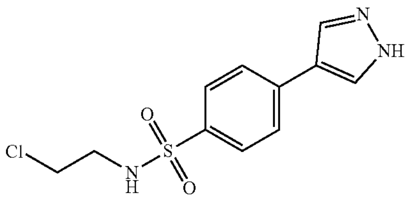 [SMILES: O=S(=O)(NCCCl)c1ccc(-c2cn[nH]c2)cc1]

Prepared by general method R using 2-chloroethylamine hydrochloride (344 mg, 2.97 mmol), 4-(1H-pyrazol-4-yl)benzenesulfonyl chloride (600 mg, 2.47 mmol), triethylamine (689 µL, 4.94 mmol) and dry N,N-dimethylformamide (10 mL). The crude product was purified chromatographically on silica gel (eluting cyclohexane-ethyl acetate 60:40) to provide the title compound 1w as a white solid (473 mg, 67% yield). LC-MS (ESI+) Found: $[M+H]^+$, 286.9.

N-(2-chloroethyl)-4',4'-difluoro-2',3',4',5'-tetrahydro-[1,1'-biphenyl]-4-sulfonamide (1x)

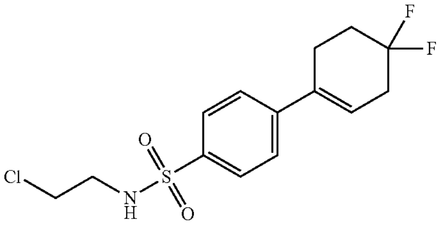 [SMILES: O=S(=O)(NCCCl)c1ccc(C2=CCC(F)(F)CC2)cc1]

Prepared by general method R using 2-chloroethylamine hydrochloride (238 mg, 2.05 mmol), 4',4'-difluoro-2',3',4',5'-tetrahydro-[1,1'-biphenyl]-4-sulfonyl chloride (500 mg, 1.71 mmol), triethylamine (476 µL, 3.42 mmol) and dry N,N-dimethylformamide (6.0 mL). The crude product was purified chromatographically on silica gel (eluting cyclohexane-ethyl acetate 85:15) to provide the title compound 1x as a white solid (389 mg, 68° a yield). LC-MS (ESI+) Found: $[M+H]^+$, 292.9.

N-(2-chloroethyl)-4-(furan-3-yl)benzenesulfonamide (1y)

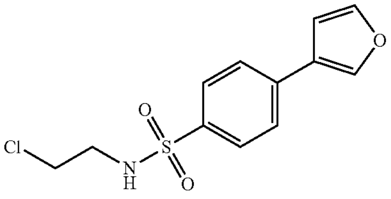 [SMILES: O=S(=O)(NCCCl)c1ccc(-c2ccoc2)cc1]

Prepared by general method R using 2-chloroethylamine hydrochloride (287 mg, 2.47 mmol), 4-(furan-3-yl)benzenesulfonyl chloride (500 mg, 2.06 mmol), triethylamine (574 µL, 4.12 mmol) and dry N,N-dimethylformamide (7.0 mL). The crude product was purified chromatographically on silica gel (eluting cyclohexane-ethyl acetate 80:20) to provide the title compound 1y as a white solid (489 mg, 83% yield). LC-MS (ESI+) Found: $[M+H]^+$, 285.9.

N-(2-chloroethyl)-3,4-dihydro-2H-benzo[b][1,4]dioxepine-7-sulfonamide (1z)

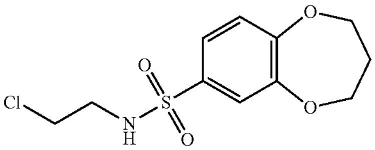 [SMILES: O=S(=O)(NCCCl)c1ccc2c(c1)OCCCO2]

Prepared by general method R using 2-chloroethylamine hydrochloride (560 mg, 4.83 mmol), 3,4-dihydro-2H-benzo[b][1,4]dioxepine-7-sulfonyl chloride (1.00 g, 4.02 mmol), triethylamine (1.12 mL, 8.04 mmol) and dry N,N-dimethylformamide (14 mL). The crude product was purified chromatographically on silica gel (eluting cyclohexane-ethyl acetate 80:20) to provide the title compound 1z as a white solid (849 mg, 73% yield). LC-MS (ESI+) Found: $[M+H]^+$, 291.9.

N-(2-chloroethyl)-4-(2-(pyrrolidin-1-yl)pyridin-3-yl)benzenesulfonamide (1Aa)

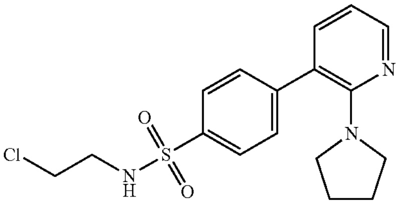 [SMILES: O=S(=O)(NCCCl)c1ccc(-c2cccnc2N2CCCC2)cc1]

Prepared by general method R using 2-chloroethylamine hydrochloride (216 mg, 1.86 mmol), 4-(2-(pyrrolidin-1-yl)pyridin-3-yl)benzenesulfonyl chloride (500 mg, 1.55 mmol), triethylamine (432 µL, 3.10 mmol) and dry N,N-dimethylformamide (5.0 mL). The crude product was purified chromatographically on silica gel (eluting dichloromethane-methanol 95:5) to provide the title compound 1Aa as a colorless oil (356 mg, 63% yield). LC-MS (ESI+) Found: $[M+H]^+$, 366.1.

N-(2-chloroethyl)-4-(3,6-dihydro-2H-pyran-4-yl)benzenesulfonamide (1Ab)

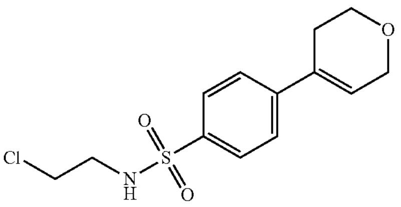 [SMILES: O=S(=O)(NCCCl)c1ccc(C2=CCOCC2)cc1]

Prepared by general method R using 2-chloroethylamine hydrochloride (267 mg, 2.32 mmol), 4-(3,6-dihydro-2H-pyran-4-yl)benzenesulfonyl chloride (500 mg, 1.93 mmol), triethylamine (540 µL, 3.87 mmol) and dry N,N-dimethylformamide (7.0 mL). The crude product was purified chromatographically on silica gel (eluting cyclohexane-ethyl acetate 80:20) to provide the title compound 1Ab as a white solid (389 mg, 67% yield). LC-MS (ESI+) Found: $[M+H]^+$, 302.1.

N-(2-chloroethyl)-2'-(morpholinomethyl)-[1,1'-biphenyl]-4-sulfonamide (1Ac)

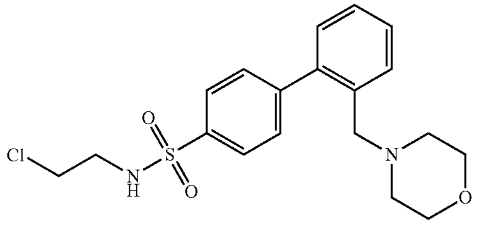 [SMILES: O=S(=O)(NCCCl)c1ccc(-c2ccccc2CN2CCOCC2)cc1]

Prepared by general method R using 2-chloroethylamine hydrochloride (100 mg, 0.85 mmol), 2'-(morpholinomethyl)-[1,1'-biphenyl]-4-sulfonyl chloride (250 mg, 0.71 mmol), triethylamine (200 μL, 1.42 mmol) and dry N,N-dimethylformamide (3.0 mL). The crude product was purified chromatographically on silica gel (eluting dichloromethane-methanol 95:5) to provide the title compound 1Ac as a colorless oil (187 mg, 53% yield). LC-MS (ESI+) Found: $[M+H]^+$, 395.1.

N-(2-chloroethyl)-2'-cyano-[1,1'-biphenyl]-4-sulfonamide (1Ad)

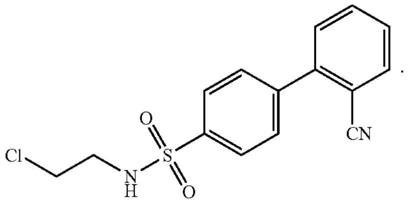 [SMILES: N#Cc1ccccc1-c1ccc(S(=O)(=O)NCCCl)cc1]

Prepared by general method R using 2-chloroethylamine hydrochloride (250 mg, 2.16 mmol), 2'-cyano-[1,1'-biphenyl]-4-sulfonyl chloride (500 mg, 1.80 mmol), triethylamine (500 μL, 3.60 mmol) and dry N,N-dimethylformamide (6.0 mL). The crude product was purified chromatographically on silica gel (eluting cyclohexane-ethyl acetate 80:20) to provide the title compound 1Ad as a white solid (413 mg, 71% yield). LC-MS (ESI+) Found: $[M+H]^+$, 320.9.

N-(2-chloroethyl)-4-(3,5-dimethylisoxazol-4-yl)benzenesulfonamide (1Ae)

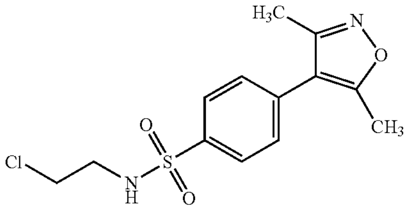 [SMILES: Cc1noc(C)c1-c1ccc(S(=O)(=O)NCCCl)cc1]

Prepared by general method R using 2-chloroethylamine hydrochloride (128 mg, 1.10 mmol), 4-(3,5-dimethylisoxazol-4-yl)benzenesulfonyl chloride (250 mg, 0.92 mmol), triethylamine (256 μL, 1.84 mmol) and dry N,N-dimethylformamide (3.0 mL). The crude product was purified chromatographically on silica gel (eluting cyclohexane-ethyl acetate 60:40) to provide the title compound 1Ae as a pale brown oil (206 mg, 71% yield). LC-MS (ESI+) Found: $[M+H]^+$, 314.9.

N-(2-chloroethyl)-4-(2-chloropyridin-3-yl)benzenesulfonamide (1Af)

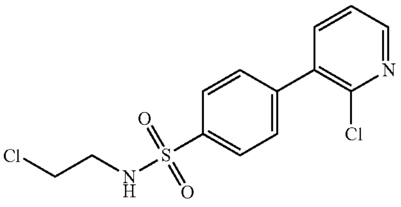 [SMILES: O=S(=O)(NCCCl)c1ccc(-c2cccnc2Cl)cc1]

Prepared by general method R using 2-chloroethylamine hydrochloride (120 mg, 1.04 mmol), 4-(2-chloropyridin-3-yl)benzenesulfonyl chloride (250 mg, 0.87 mmol), triethylamine (242 μL, 1.74 mmol) and dry N,N-dimethylformamide (3.0 mL). The crude product was purified chromatographically on silica gel (eluting cyclohexane-ethyl acetate 60:40) to provide the title compound 1Af as a pale brown oil (189 mg, 66% yield). $^1H$ NMR (300 MHz, $d_6$-DMSO) δ=8.49 (dd, J=4.8, 1.9 Hz, 1H), 8.14 (t, J=5.9 Hz, 1H), 7.98-7.89 (m, 3H), 7.79-7.68 (m, 2H), 7.57 (dd, J=7.6, 4.8 Hz, 1H), 3.62 (t, J=6.1 Hz, 2H), 3.16 (q, J=6.1 Hz, 2H). LC-MS (ESI+) Found: $[M+H]^+$, 330.9.

N-(2-chloroethyl)-4'-cyano-[1,1'-biphenyl]-4-sulfonamide (1Ag)

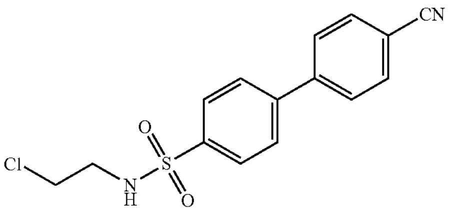 [SMILES: N#Cc1ccc(-c2ccc(S(=O)(=O)NCCCl)cc2)cc1]

Prepared by general method R using 2-chloroethylamine hydrochloride (250 mg, 2.16 mmol), 4'-cyano-[1,1'-biphenyl]-4-sulfonyl chloride (500 mg, 1.80 mmol), triethylamine (500 μL, 3.60 mmol) and dry N,N-dimethylformamide (6.0 mL). The crude product was purified chromatographically on silica gel (eluting cyclohexane-ethyl acetate 80:20) to provide the title compound 1Ag as a white solid (335 mg, 58% yield). LC-MS (ESI+) Found: $[M+H]^+$, 320.9.

N-(2-chloroethyl)-2'-methoxy-[1,1'-biphenyl]-4-sulfonamide (1Ah)

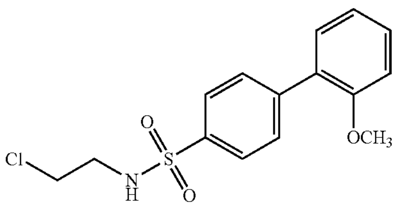 [SMILES: COc1ccccc1-c1ccc(S(=O)(=O)NCCCl)cc1]

Prepared by general method R using 2-chloroethylamine hydrochloride (246 mg, 2.12 mmol), 2'-methoxy-[1,1'-biphenyl]-4-sulfonyl chloride (500 mg, 1.77 mmol), triethylamine (493 μL, 3.54 mmol) and dry N,N-dimethylformamide (6.0 mL). The crude product was purified chromatographically on silica gel (eluting cyclohexane-ethyl acetate 80:20) to provide the title compound 1Ah as a white solid (429 mg, 74% yield). LC-MS (ESI+) Found: $[M+H]^+$, 326.1.

N-(2-chloroethyl)-2',6'-dimethoxy-[1,1'-biphenyl]-4-sulfonamide (1Ai)

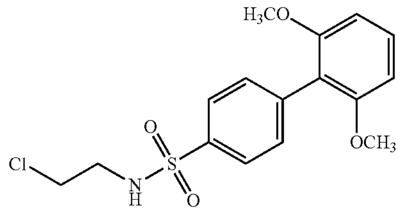 [SMILES: COc1cccc(OC)c1-c1ccc(S(=O)(=O)NCCCl)cc1]

Prepared by general method R using 2-chloroethylamine hydrochloride (223 mg, 1.92 mmol), 2',6'-dimethoxy-[1,1'-biphenyl]-4-sulfonyl chloride (500 mg, 1.60 mmol), triethylamine (446 μL, 3.20 mmol) and dry N,N-dimethylformamide (5.0 mL). The crude product was purified chromatographically on silica gel (eluting cyclohexane-ethyl acetate 80:20) to provide the title compound 1Ai as a white solid (411 mg, 72% yield). $^1H$ NMR (300 MHz, $d_6$-DMSO) δ=8.01 (t, J=6.0 Hz, 1H), 7.83-7.74 (m, 2H), 7.46-7.40 (m, 2H), 7.35 (t, J=8.4 Hz, 1H), 6.77 (d, J=8.4 Hz, 2H), 3.68 (s, 6H), 3.63 (t, J=6.2 Hz, 2H), 3.15 (q, J=6.1 Hz, 2H). LC-MS (ESI+) Found: $[M+H]^+$, 356.1.

N-(2-chloroethyl)-4-(2-fluoropyridin-3-yl)benzenesulfonamide (1Aj)

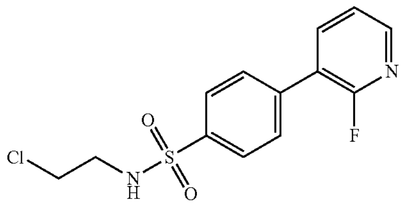 [SMILES: O=S(=O)(NCCCl)c1ccc(-c2cccnc2F)cc1]

Prepared by general method R using 2-chloroethylamine hydrochloride (128 mg, 1.10 mmol), 4-(2-fluoropyridin-3-yl)benzenesulfonyl chloride (250 mg, 0.92 mmol), triethylamine (257 μL, 1.84 mmol) and dry N,N-dimethylformamide (3.0 mL). The crude product was purified chromatographically on silica gel (eluting cyclohexane-ethyl acetate 60:40) to provide the title compound 1Aj a pale brown oil (187 mg, 65% yield). LC-MS (ESI+) Found: $[M+H]^+$, 314.9.

N-(2-chloroethyl)-2',6'-difluoro-[1,1'-biphenyl]-4-sulfonamide (1Ak)

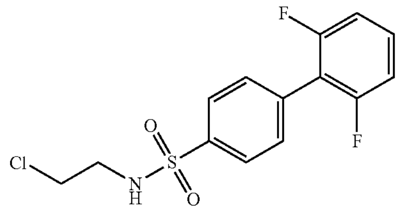 [SMILES: O=S(=O)(NCCCl)c1ccc(-c2c(F)cccc2F)cc1]

Prepared by general method R using 2-chloroethylamine hydrochloride (120 mg, 1.04 mmol), 2',6'-difluoro-[1,1'-biphenyl]-4-sulfonyl chloride (250 mg, 0.87 mmol), triethylamine (240 μL, 1.73 mmol) and dry N,N-dimethylformamide (3.0 mL). The crude product was purified chromatographically on silica gel (eluting cyclohexane-ethyl acetate 80:20) to provide the title compound 1Ak a colorless oil (206 mg, 71% yield). LC-MS (ESI+) Found: $[M+H]^+$, 331.9.

N-(2-chloroethyl)-2'-(dimethylamino)-[1,1'-biphenyl]-4-sulfonamide (1A)

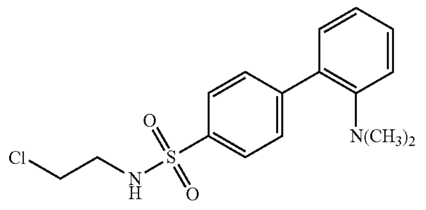 [SMILES: CN(C)c1ccccc1-c1ccc(S(=O)(=O)NCCCl)cc1]

Prepared by general method R using 2-chloroethylamine hydrochloride (118 mg, 1.01 mmol), 2'-(dimethylamino)-[1,1'-biphenyl]-4-sulfonyl chloride (250 mg, 0.85 mmol), triethylamine (236 μL, 1.69 mmol) and dry N,N-dimethylformamide (3.0 mL). The crude product was purified chromatographically on silica gel (eluting dichloromethane-methanol 95:5) to provide the title compound 1Al as a colorless oil (155 mg, 54% yield). LC-MS (ESI+) Found: $[M+H]^+$, 339.1.

N-(2-chloroethyl)-1-(p-tolyl)methanesulfonamide (1Am)

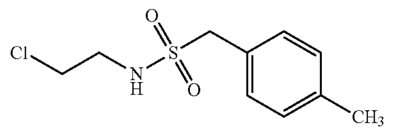

Prepared by general method R using 2-chloroethylamine hydrochloride (680 mg, 5.86 mmol), p-tolylmethanesulfonyl chloride (1.00 g, 4.89 mmol), triethylamine (1.36 mL, 9.77 mmol) and dry N,N-dimethylformamide (16 mL). The crude product was purified chromatographically on silica gel (eluting cyclohexane-ethyl acetate 85:15) to provide the title compound 1Am as a white solid (863 mg, 71% yield). $^1H$ NMR (300 MHz, $d_6$-DMSO) δ=7.41 (t, J=6.0 Hz, 1H), 7.27 (d, J=8.1 Hz, 2H), 7.19 (d, J=7.8 Hz, 2H), 4.32 (s, 2H), 3.55 (t, J=6.5 Hz, 2H), 3.17 (q, J=6.3 Hz, 2H), 2.31 (s, 3H). LC-MS (ESI+) Found: $[M+H]^+$, 247.9.

N-(2-chloroethyl)-2'-(methoxymethyl)-[1,1'-biphenyl]-4-sulfonamide (1An)

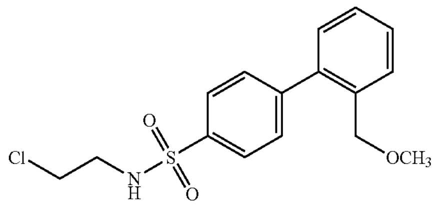 [SMILES: COCc1ccccc1-c1ccc(S(=O)(=O)NCCCl)cc1]

Prepared by general method R using 2-chloroethylamine hydrochloride (235 mg, 2.02 mmol), 2'-(methoxymethyl)-[1,1'-biphenyl]-4-sulfonyl chloride (500 mg, 1.68 mmol), triethylamine (470 μL, 3.37 mmol) and dry N,N-dimethylformamide (6.0 mL). The crude product was purified chromatographically on silica gel (eluting cyclohexane-ethyl acetate 80:20) to provide the title compound 1An as a white solid (404 mg, 71% yield). LC-MS (ESI+) Found: $[M+H]^+$, 340.1.

N-(2-chloroethyl)-4-(cyclopropylmethyl)benzenesulfonamide (1Ao)

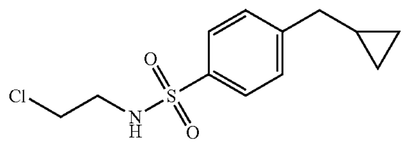 [SMILES: O=S(=O)(NCCCl)c1ccc(CC2CC2)cc1]

Prepared by general method R using 2-chloroethylamine hydrochloride (300 mg, 2.60 mmol), 4-(cyclopropylmethyl) benzenesulfonyl chloride (500 mg, 2.17 mmol), triethylamine (604 μL, 4.33 mmol) and dry N,N-dimethylformamide (7.0 mL). The crude product was purified chromatographically on silica gel (eluting cyclohexane-ethyl acetate 85:15) to provide the title compound 1Ao as a pale brown solid (402 mg, 68% yield). LC-MS (ESI+) Found: $[M+H]^+$, 273.9.

N-(2-chloroethyl)-2'-fluoro-6'-hydroxy-[1,1'-biphenyl]-4-sulfonamide (1Ap)

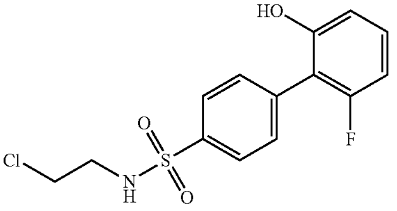 [SMILES: O=S(=O)(NCCCl)c1ccc(-c2c(O)cccc2F)cc1]

Prepared by general method R using 2-chloroethylamine hydrochloride (121 mg, 1.05 mmol), 2'-fluoro-6'-hydroxy-[1,1'-biphenyl]-4-sulfonyl chloride (250 mg, 0.87 mmol), triethylamine (243 μL, 1.74 mmol) and dry N,N-dimethylformamide (3.0 mL). The crude product was purified chromatographically on silica gel (eluting cyclohexane-ethyl acetate 60:40) to provide the title compound 1Ap a pale brown solid (203 mg, 70% yield). LC-MS (ESI+) Found: $[M+H]^+$, 329.1.

N-(2-chloroethyl)-2'-fluoro-[1,1'-biphenyl]-4-sulfonamide (1Aq)

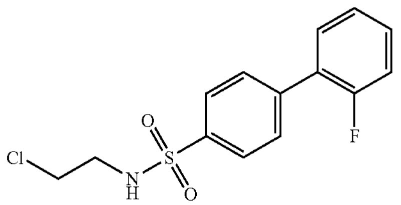 [SMILES: O=S(=O)(NCCCl)c1ccc(-c2ccccc2F)cc1]

Prepared by general method R using 2-chloroethylamine hydrochloride (257 mg, 2.22 mmol), 2'-fluoro-[1,1'-biphenyl]-4-sulfonyl chloride (500 mg, 1.85 mmol), triethylamine (515 μL, 3.69 mmol) and dry N,N-dimethylfonnamide (6.0 mL). The crude product was purified chromatographically on silica gel (eluting cyclohexane-ethyl acetate 80:20) to provide the title compound 1Aq a pale brown solid (421 mg, 72% yield). LC-MS (ESI+) Found: $[M+H]^+$, 313.9.

N-(2-chloroethyl)-2'-cyano-6'-(trifluoromethyl)-[1,1'-biphenyl]-4-sulfonamide (1Ar)

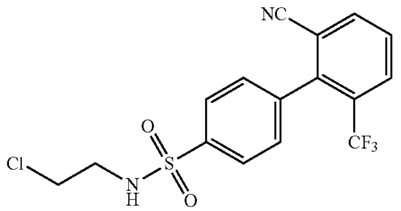 [SMILES: N#Cc1cccc(C(F)(F)F)c1-c1ccc(S(=O)(=O)NCCCl)cc1]

Prepared by general method R using 2-chloroethylamine hydrochloride (100 mg, 0.87 mmol), 2'-cyano-6'-(trifluoromethyl)-[1,1'-biphenyl]-4-sulfonyl chloride (250 mg, 0.72 mmol), triethylamine (202 μL, 1.45 mmol) and dry N,N-dimethylformamide (3.0 mL). The crude product was purified chromatographically on silica gel (eluting cyclohexane-ethyl acetate 80:20) to provide the title compound 1Ar a white solid (149 mg, 53% yield). LC-MS (ESI+) Found: $[M+H]^+$, 388.9.

N-(2-chloroethyl)-2'-(trifluoromethyl)-[1,1'-biphenyl]-4-sulfonamide (1As)

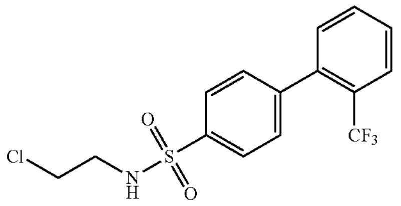 [SMILES: O=S(=O)(NCCCl)c1ccc(-c2ccccc2C(F)(F)F)cc1]

Prepared by general method R using 2-chloroethylamine hydrochloride (217 mg, 1.87 mmol), 2'-(trifluoromethyl)-[1,1'-biphenyl]-4-sulfonyl chloride (500 mg, 1.56 mmol), triethylamine (435 µL, 3.12 mmol) and dry N,N-dimethylformamide (5.0 mL). The crude product was purified chromatographically on silica gel (eluting cyclohexane-ethyl acetate 80:20) to provide the title compound 1As a pale brown solid (419 mg, 74% yield). $^1$H NMR (300 MHz, $d_6$-DMSO) δ=8.12 (t, J=5.9 Hz, 1H), 7.92-7.82 (m, 3H), 7.77 (tdd, J=7.6, 1.5, 0.7 Hz, 1H), 7.67 (dddd, J=9.4, 7.5, 1.9, 1.0 Hz, 1H), 7.61-7.51 (m, 2H), 7.46 (ddd, J=7.4, 1.5, 0.7 Hz, 1H), 3.60 (t, J=6.1 Hz, 2H), 3.15 (q, J=6.1 Hz, 2H). LC-MS (ESI+) Found: $[M+H]^+$, 363.9.

N-(2-chloroethyl)-2'-fluoro-6'-methoxy-[1,1'-biphenyl]-4-sulfonamide (1At)

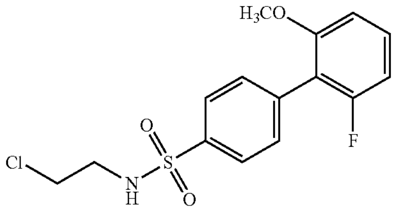 [SMILES: COc1cccc(F)c1-c1ccc(S(=O)(=O)NCCCl)cc1]

Prepared by general method R using 2-chloroethylamine hydrochloride (116 mg, 1.00 mmol), 2'-fluoro-6'-methoxy-[1,1'-biphenyl]-4-sulfonyl chloride (250 mg, 0.83 mmol), triethylamine (232 µL, 1.66 mmol) and dry N,N-dimethylformamide (3.0 mL). The crude product was purified chromatographically on silica gel (eluting cyclohexane-ethyl acetate 80:20) to provide the title compound 1At a colorless oil (201 mg, 70% yield). LC-MS (ESI+) Found: $[M+H]^+$, 343.9.

N-(2-chloroethyl)-2'-hydroxy-[1,1'-biphenyl]-4-sulfonamide (1Au)

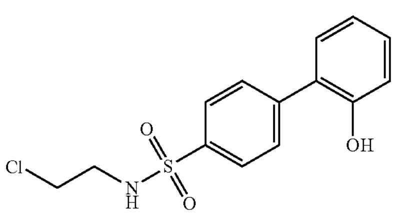 [SMILES: O=S(=O)(NCCCl)c1ccc(-c2ccccc2O)cc1]

Prepared by general method R using 2-chloroethylamine hydrochloride (260 mg, 2.23 mmol), 2'-hydroxy-[1,1'-biphenyl]-4-sulfonyl chloride (500 mg, 1.86 mmol), triethylamine (520 µL, 3.72 mmol) and dry N,N-dimethylformamide (6.0 mL). The crude product was purified chromatographically on silica gel (eluting cyclohexane-ethyl acetate 60:40) to provide the title compound 1Au a white solid (416 mg, 72% yield). $^1$H NMR (300 MHz, $d_6$-DMSO) δ=9.77 (s, 1H), 8.02 (t, J=5.9 Hz, 1H), 7.87-7.72 (m, 4H), 7.32 (dd, J=7.6, 1.7 Hz, 1H), 7.22 (ddd, J=8.2, 7.3, 1.7 Hz, 1H), 6.98 (dd, J=8.2, 1.2 Hz, 1H), 6.91 (td, J=7.4, 1.2 Hz, 1H), 3.61 (t, J=6.2 Hz, 2H), 3.12 (q, J=6.1 Hz, 2H). LC-MS (ESI+) Found: $[M+H]^+$, 311.9.

N-(2-chloroethyl)-2'-fluoro-6'-(trifluoromethyl)-[1,1'-biphenyl]-4-sulfonamide (1Av)

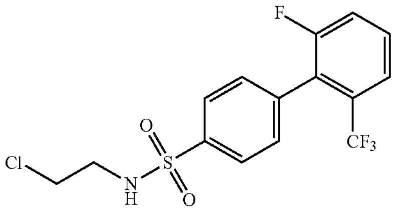 [SMILES: O=S(=O)(NCCCl)c1ccc(-c2c(F)cccc2C(F)(F)F)cc1]

Prepared by general method R using 2-chloroethylamine hydrochloride (103 mg, 0.89 mmol), 2'-fluoro-6'-(trifluoromethyl)-[1,1'-biphenyl]-4-sulfonyl chloride (250 mg, 0.74 mmol), triethylamine (206 µL, 1.48 mmol) and dry N,N-dimethylformamide (3.0 mL). The crude product was purified chromatographically on silica gel (eluting cyclohexane-ethyl acetate 80:20) to provide the title compound 1Av a pale yellow solid (163 mg, 58% yield). LC-MS (ESI+) Found: $[M+H]^+$, 381.9.

N-(2-chloroethyl)-2'-cyano-6'-methyl-[1,1'-biphenyl]-4-sulfonamide (1Aw)

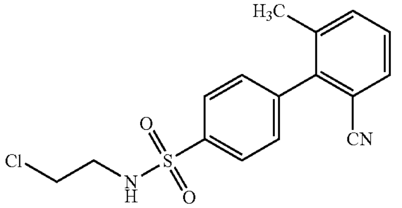 [SMILES: Cc1cccc(C#N)c1-c1ccc(S(=O)(=O)NCCCl)cc1]

Prepared by general method R using 2-chloroethylamine hydrochloride (120 mg, 1.03 mmol), 2'-cyano-6'-methyl-[1,1'-biphenyl]-4-sulfonyl chloride (250 mg, 0.86 mmol), triethylamine (240 µL, 1.71 mmol) and dry N,N-dimethylformamide (3.0 mL). The crude product was purified chromatographically on silica gel (eluting cyclohexane-ethyl acetate 80:20) to provide the title compound 1Aw a colorless oil (186 mg, 65% yield). LC-MS (ESI+) Found: $[M+H]^+$, 381.9.

2'-chloro-N-(2-chloroethyl)-4'-fluoro-[1,1'-biphenyl]-4-sulfonamide (1Ax)

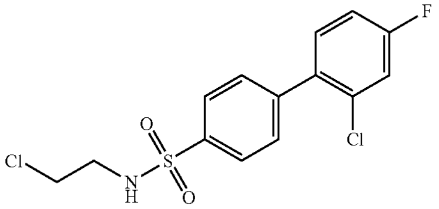 [SMILES: O=S(=O)(NCCCl)c1ccc(-c2ccc(F)cc2Cl)cc1]

Prepared by general method R using 2-chloroethylamine hydrochloride (114 mg, 0.98 mmol), 2'-chloro-4'-fluoro-[1,1'-biphenyl]-4-sulfonyl chloride (250 mg, 0.82 mmol), triethylamine (228 µL, 1.64 mmol) and dry N,N-dimethylformanide (3.0 mL). The crude product was purified chromatographically on silica gel (eluting cyclohexane-ethyl acetate 85:15) to provide the title compound 1Ax a colorless oil (201 mg, 71% yield). LC-MS (ESI+) Found: $[M+H]^+$, 348.1.

N-(2-chloroethyl)-2-fluoro-2',6'-dimethoxy-[1,1'-biphenyl]-4-sulfonamide (1Ay)

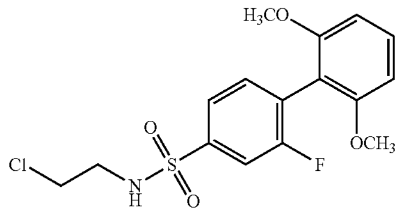 [SMILES: COc1cccc(OC)c1-c1ccc(S(=O)(=O)NCCCl)cc1F]

Prepared by general method R using 2-chloroethylamine hydrochloride (105 mg, 0.91 mmol), 2-fluoro-2',6'-dimethoxy-[1,1'-biphenyl]-4-sulfonyl chloride (250 mg, 0.76 mmol), triethylamine (210 μL, 1.51 mmol) and dry N,N-dimethylformamide (3.0 mL). The crude product was purified chromatographically on silica gel (eluting cyclohexane-ethyl acetate 80:20) to provide the title compound 1Ay a colorless oil (200 mg, 71% yield). LC-MS (ESI+) Found: $[M+H]^+$, 373.9.

N-(2-chloroethyl)-2',6'-dimethoxy-2-methyl-[1,1'-biphenyl]-4-sulfonamide (1Az)

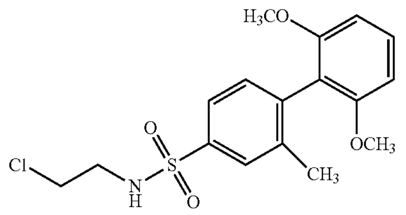 [SMILES: COc1cccc(OC)c1-c1ccc(S(=O)(=O)NCCCl)cc1C]

Prepared by general method R using 2-chloroethylamine hydrochloride (106 mg, 0.92 mmol), 2',6'-dimethoxy-2-methyl-[1,1'-biphenyl]-4-sulfonyl chloride (250 mg, 0.77 mmol), triethylamine (213 μL, 1.53 mmol) and dry N,N-dimethylformamide (3.0 mL). The crude product was purified chromatographically on silica gel (eluting cyclohexane-ethyl acetate 80:20) to provide the title compound 1Az a colorless oil (186 mg, 66% yield). LC-MS (ESI+) Found: $[M+H]^+$, 370.1.

2-chloro-N-(2-chloroethyl)-2',6'-dimethoxy-[1,1'-biphenyl]-4-sulfonamide (1Ba)

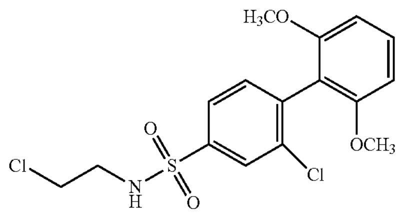 [SMILES: COc1cccc(OC)c1-c1ccc(S(=O)(=O)NCCCl)cc1Cl]

Prepared by general method R using 2-chloroethylamine hydrochloride (100 mg, 0.86 mmol), 2-chloro-2',6'-dimethoxy-[1,1'-biphenyl]-4-sulfonyl chloride (250 mg, 0.72 mmol), triethylamine (200 μL, 1.44 mmol) and dry N,N-dimethylformamide (3.0 mL). The crude product was purified chromatographically on silica gel (eluting cyclohexane-ethyl acetate 80:20) to provide the title compound 1Ba a colorless oil (177 mg, 63% yield). LC-MS (ESI+) Found: $[M+H]^+$, 389.9.

N-(2-chloroethyl)-2,2'-difluoro-6'-hydroxy-[1,1'-biphenyl]-4-sulfonamide (1Bb)

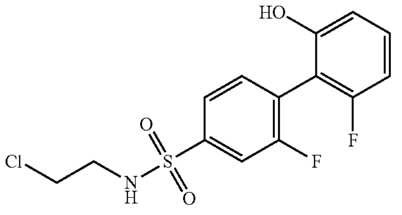 [SMILES: O=S(=O)(NCCCl)c1ccc(-c2c(O)cccc2F)c(F)c1]

Prepared by general method R using 2-chloroethylamine hydrochloride (114 mg, 0.98 mmol), 2,2'-difluoro-6'-hydroxy-[1,1'-biphenyl]-4-sulfonyl chloride (250 mg, 0.82 mmol), triethylamine (229 μL, 1.64 mmol) and dry N,N-dimethylformamide (3.0 mL). The crude product was purified chromatographically on silica gel (eluting cyclohexane-ethyl acetate 60:40) to provide the title compound 1Bb a colorless oil (194 mg, 68% yield). LC-MS (ESI+) Found: $[M+H]^+$, 347.9.

tert-Butyl 4-(hydroxymethyl)piperidine-1-carboxylate (2)

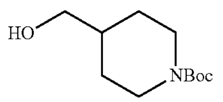 [SMILES: CC(C)(C)OC(=O)N1CCC(CO)CC1]

In an oven-dried round bottom flask was dissolved piperidin-4-ylmethanol (10.0 g, 86.8 mmol, 1.00 equiv.) in ethyl acetate-tetrahydrofuran (2:1, 160 mL, C~0.5 M). Di-tert-butyldicarbonate (19.9 g, 91.2 mmol, 1.05 equiv.) was added in portion wise and the reaction mixture was stirred at room temperature for 14 hours until the complete consumption of the starting material (monitored by TLC). The solvents were removed under reduced pressure and the residue was poured into ethyl acetate (400 mL) and saturated aqueous ammonium chloride solution (250 mL). The organic layer was washed with brine (100 mL), dried ($MgSO_4$) and filtered. The solvents were removed under reduced pressure and the residue was recrystallized in n-hexane-diethyl ether (1:1) to provide the title compound 2 as a colorless solid (18.2 g, 97% yield). $^1H$ NMR (400 MHz, $d_6$-Acetone) δ=4.06 (d, J=11.3 Hz, 2H), 3.61 (t, J=5.4 Hz, 1H), 3.41-3.36 (m, 2H), 2.68 (s, 2H), 1.74-1.65 (m, 2H), 1.65-1.53 (m, 1H), 1.51 (s, 1H), 1.42 (s, 9H). $^{13}C$ NMR (100 MHz, $d_6$-Acetone) δ=155.1 ($C_{quat}$), 79.1 ($C_{quat}$), 67.4 ($CH_2$), 39.9 (CH), 29.6 ($CH_2$), 28.6 ($CH_3$), 27.4 ($CH_2$). Spectroscopic and physical data matched the ones reported in the literature.[2]

tert-Butyl 4-(azidomethyl)piperidine-1-carboxylate (3)

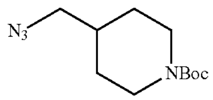

In an oven-dried round bottom flask were combined under argon atmosphere at 0° C. (ice bath) alcohol 2 (18.0 g, 83.6 mmol, 1.00 equiv.) and triethylamine (15.2 mL, 108.7 mmol, 1.30 equiv.) in dry tetrahydrofuran (250 mL, C~0.3 M). Methanesulfonyl chloride (6.47 mL, 83.6 mmol, 1.00 equiv.) was added dropwise through a syringe over 10 minutes then the reaction was allowed to warm to room temperature and stirred for 3 hours. After the complete consumption of the starting material (monitored by TLC), the mixture was poured into ethyl acetate (400 mL) and water (250 mL). The organic layer was extracted, washed with 10% aqueous hydrochloric acid solution (150 mL), brine (150 mL), dried ($MgSO_4$) and filtered. The solvents were removed under reduced pressure to obtain the product (23.6 g, 96% yield) as a white solid used without further purification for the next step.

In an oven-dried round bottom flask equipped with a reflux condenser was dissolved the tert-butyl 4-(((methylsulfonyl)oxy)methyl)piperidine-1-carboxylate (20.0 g, 68.2 mmol, 1.00 equiv.) in N,N-dimethylformamide (450 mL, C~0.15 M) and sodium azide (13.3 g, 0.2 M, 3.00 equiv.) was added in portion wise. The reaction mixture was heated to 60° C. and stirred for 8 hours until the complete consumption of the starting material (monitored by TLC). The reaction was allowed to cool to room temperature, poured into water (800 mL) and extracted with ethyl acetate (3×200 mL). The combined organics extracts were washed with water (3×200 mL), brine (100 mL), dried ($MgSO_4$) and filtered. The solvents were removed under reduced pressure and the residue was purified chromatographically on silica gel (eluting cyclohexane-ethyl acetate 90:10) to provide the tittle compound 3 as a colorless oil (15.6 g, 95% yield, 91% total yield over two steps). $^1H$ NMR (400 MHz, $CDCl_3$) δ=4.13 (bs, 2H), 3.19 (d, J=6.3 Hz, 2H), 2.69 (bs, 2H), 1.73-1.66 (m, 3H), 1.45 (s, 9H), 1.24-1.10 (m, 2H). $^{13}C$ NMR (100 MHz, $CDCl_3$) δ=154.6 ($C_{quat}$), 79.3 ($C_{quat}$), 56.9 ($CH_2$), 43.7 ($CH_2$), 42.9 (CH), 36.4 ($CH_2$), 29.5 ($CH_2$), 28.3 ($CH_3$). Spectroscopic and physical data matched the ones reported in the literature.[3]

tert-butyl 3-(azidomethyl)azetidine-1-carboxylate (3a)

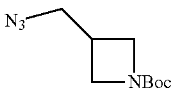

Prepared by general method S using tert-butyl 3-(hydroxymethyl)azetidine-1-carboxylate (1.00 g, 5.34 mmol), methanesulfonyl chloride (413 μL, 5.34 mmol), triethylamine (968 μL, 6.94 mmol) and dry tetrahydrofuran (18 mL). Then the corresponding mesylate (1.20 g, 4.52 mmol) was substituted with sodium azide (882 mg, 13.6 mmol) in N,N-dimethylformamide (30 mL). The crude product was purified chromatographically on silica gel (eluting cyclohexane-ethyl acetate 90:10) to provide the title compound 3a as a colorless oil (876 mg, 86% total yield over two steps). LC-MS (ESI+) Found: $[M+H]^+$, 213.1.

tert-butyl (R)-3-(azidomethyl)pyrrolidine-1-carboxylate (3b)

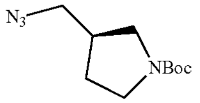 [SMILES: CC(C)(C)OC(=O)N1CC[C@@H](CN=[N+]=[N-])C1]

Prepared by general method S using tert-butyl (R)-3-(hydroxymethyl)pyrrolidine-1-carboxylate (1.00 g, 4.97 mmol), methanesulfonyl chloride (385 μL, 4.97 mmol), triethylamine (900 μL, 6.46 mmol) and dry tetrahydrofuran (17 mL). Then the corresponding mesylate (1.30 g, 4.65 mmol) was substituted with sodium azide (882 mg, 14.0 mmol) in N,N-dimethylformamide (30 mL). The crude product was purified chromatographically on silica gel (eluting cyclohexane-ethyl acetate 90:10) to provide the title compound 3b as a colorless oil (943 mg, 85% total yield over two steps). LC-MS (ESI+) Found: $[M+H]^+$, 227.1.

tert-butyl (S)-3-(azidomethyl)pyrrolidine-1-carboxylate (3c)

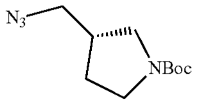

Prepared by general method S using tert-butyl (S)-3-(hydroxymethyl)pyrrolidine-1-carboxylate (1.00 g, 4.97 mmol), methanesulfonyl chloride (385 μL, 4.97 mmol), triethylamine (900 μL, 6.46 mmol) and dry tetrahydrofuran (17 mL). Then the corresponding mesylate (1.25 g, 4.47 mmol) was substituted with sodium azide (873 mg, 13.4 nmol) in N,N-dimethylformamide (30 mL). The crude product was purified chromatographically on silica gel (eluting cyclohexane-ethyl acetate 90:10) to provide the title compound 3c as a colorless oil (913 mg, 87% total yield over two steps). LC-MS (ESI+) Found: $[M+H]^+$, 227.1.

tert-butyl (S)-3-(azidomethyl)piperidine-1-carboxylate (3d)

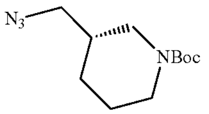

Prepared by general method S using tert-butyl (S)-3-(hydroxymethyl)piperidine-1-carboxylate (1.00 g, 4.64 mmol), methanesulfonyl chloride (385 μL, 4.64 mmol), triethylamine (842 μL, 6.04 mmol) and dry tetrahydrofuran (15 mL). Then the corresponding mesylate (1.20 g, 4.10 mmol) was substituted with sodium azide (800 mg, 12.3 mmol) in N,N-dimethylformamide (30 mL). The crude product was purified chromatographically on silica gel (eluting cyclohexane-ethyl acetate 90:10) to provide the title compound 3d as a colorless oil (881 mg, 86% total yield over two steps). LC-MS (ESI+) Found: $[M+H]^+$, 241.1.

tert-butyl 4-azidopiperidine-1-carboxylate (3e)

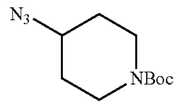

Prepared by general method S using tert-butyl 4-hydroxypiperidine-1-carboxylate (1.00 g, 4.97 mmol), methanesulfonyl chloride (385 μL, 4.97 mmol), triethylamine (900 μL, 6.46 mmol) and dry tetrahydrofuran (17 mL). Then the corresponding mesylate (1.30 g, 4.65 mmol) was substituted with sodium azide (800 mg, 14.0 mmol) in N,N-dimethylformamide (30 mL). The crude product was purified chromatographically on silica gel (eluting cyclohexane-ethyl acetate 90:10) to provide the title compound 3e as a colorless oil (861 mg, 84% total yield over two steps). LC-MS (ESI+) Found: $[M+H]^+$, 227.1.

4-(Azidomethyl)piperidine hydrochloride (4)

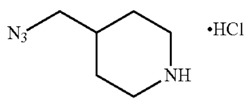

Prepared by general method I using azide 3 (15.2 g, 63.3 mmol), acetyl chloride (54.2 mL, 760 mmol) and methanol (210 mL). The hydrochloride salt 4 was obtained as a white crystalline solid (11.0 g, 98% yield). $^1H$ NMR (400 MHz, $d_6$-DMSO) δ=3.36 (s, 1H), 3.30 (d, J=6.2 Hz, 2H), 3.21 (d, J=12.6 Hz, 2H), 2.81 (t, J=12.2 Hz, 2H), 1.77 (d, J=12.7 Hz, 3H), 1.42 (qd, J=13.5, 3.9 Hz, 2H). $^{13}C$ NMR (100 MHz, $d_6$-DMSO) δ=55.4 ($CH_2$), 42.4 ($CH_2$), 33.4 (CH), 25.7 ($CH_2$).

3-(azidomethyl)azetidine hydrochloride (4a)

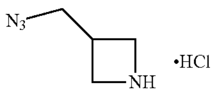

Prepared by general method I using azide 3a (800 mg, 3.77 mmol), acetyl chloride (3.23 mL, 45.2 mmol) and methanol (20 mL). The hydrochloride salt 4a was obtained as a white crystalline solid (511 mg, 91% yield). LC-MS (ESI+) Found: $[M+H]^+$, 112.9.

(R)-3-(azidomethyl)pyrrolidine hydrochloride (4b)

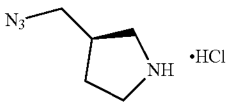

Prepared by general method I using azide 3b (900 mg, 3.98 mmol), acetyl chloride (3.41 mL, 47.7 mmol) and methanol (20 mL). The hydrochloride salt 4b was obtained as a white crystalline solid (598 mg, 92% yield). LC-MS (ESI+) Found: $[M+H]^+$, 127.1.

(S)-3-(azidomethyl)pyrrolidine hydrochloride (4c)

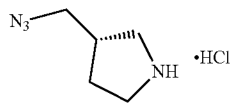

Prepared by general method I using azide 3c (850 mg, 3.76 mmol), acetyl chloride (3.21 mL, 45.1 mmol) and methanol (20 mL). The hydrochloride salt 4c was obtained as a white crystalline solid (586 mg, 96% yield). LC-MS (ESI+) Found: $[M+H]^+$, 127.1.

(S)-3-(azidomethyl)piperidine hydrochloride (4d)

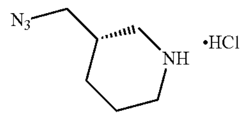

Prepared by general method I using azide 3d (850 mg, 3.54 mmol), acetyl chloride (3.03 mL, 42.4 mmol) and methanol (18 mL). The hydrochloride salt 4d was obtained as a white crystalline solid (591 mg, 95% yield). LC-MS (ESI+) Found: $[M+H]^+$, 141.1.

4-azidopiperidine hydrochloride (4e)

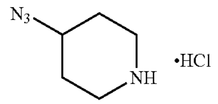

Prepared by general method I using azide 3e (800 mg, 3.54 mmol), acetyl chloride (3.03 mL, 42.4 mmol) and methanol (18 mL). The hydrochloride salt 4e was obtained as a white crystalline solid (511 mg, 89% yield). LC-MS (ESI+) Found: $[M+H]^+$, 127.1.

N-(2-(4-(Azidomethyl)piperidin-1-yl)ethyl)benzenesulfonamide (5a)

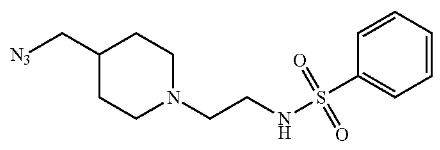 [SMILES: [N-]=[N+]=NCC1CCN(CCNS(=O)(=O)c2ccccc2)CC1]

Prepared by general method B using the ammonium salt 4 (300 mg, 1.70 mmol), the corresponding alkyl chloride 1a (410 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5a as a beige solid (364 mg, 66% yield). $^1$H NMR (400 MHz, $d_6$-DMSO) δ=7.81 (dd, J=8.0, 1.7, 2H), 7.61 (m, 4H), 4.40 (d, J=6.0, 1H), 3.19 (dd, J=3.8, 6.2, 2H), 2.86 (t, J=6.9, 2H), 2.73 (d, J=9.6, 2H), 2.33 (s, 2H), 1.97-1.70 (m, 2H), 1.60-1.55 (m, 2H), 1.25 (d, J=14.5, 2H). $^{13}$C NMR (100 MHz, $d_6$-DMSO) δ=140.6 ($C_{quat}$), 132.3 (CH), 129.4 (CH), 126.4 (CH), 66.0 ($CH_2$), 57.2 ($CH_2$), 53.1 ($CH_2$), 40.3 ($CH_2$), 37.0 (CH), 28.6 ($CH_2$).

N-(2-(4-(Azidomethyl)piperidin-1-yl)ethyl)-4-chlorobenzenesulfonamide (5b)

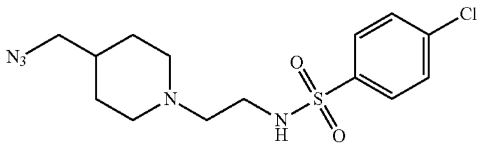 [SMILES: [N-]=[N+]=NCC1CCN(CCNS(=O)(=O)c2ccc(Cl)cc2)CC1]

Prepared by general method B using the ammonium salt 4 (300 mg, 1.70 mmol), the corresponding alkyl chloride 1b (475 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5b as a beige solid which solidifies upon storage in refrigerator (451 mg, 74% yield). $^1$H NMR (400 MHz, $d_6$-Acetone) 5=7.92-7.88 (m, 2H), 7.65-7.61 (m, 2H), 6.38 (s, 1H), 3.21 (d, J=6.6 Hz, 2H), 3.02 (t, J=6.3 Hz, 2H), 2.71 (d, J=11.6 Hz, 2H), 2.38 (t, J=6.3 Hz, 2H), 1.89 (td, J=11.7, 2.4 Hz, 2H), 1.61 (d, J=13.6 Hz, 2H), 1.49 (tdt, J=10.4, 6.8, 3.8 Hz, 1H), 1.20 (qd, J=12.1, 3.8 Hz, 2H). $^{13}$C NMR (100 MHz, $d_6$-Acetone) δ=140.7 ($C_{quat}$), 138.7 ($C_{quat}$), 130.0 (CH), 129.6 (CH), 57.6 ($CH_2$), 57.5 ($CH_2$), 53.7 ($CH_2$), 41.0 ($CH_2$), 37.0 (CH), 30.3 ($CH_2$).

N-(2-(4-(Azidomethyl)piperidin-1-yl)ethyl)-4-(trifluoromethyl)benzenesulfonamide (5c)

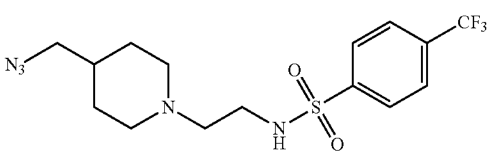 [SMILES: [N-]=[N+]=NCC1CCN(CCNS(=O)(=O)c2ccc(C(F)(F)F)cc2)CC1]

Prepared by general method B using the ammonium salt 4 (300 mg, 1.70 mmol), the corresponding alkyl chloride 1c (537 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5c as a white solid (501 mg, 75% yield). $^1$H NMR (400 MHz, $CDCl_3$) δ=8.00 (d, J=8.2 Hz, 2H), 7.78 (d, J=8.2 Hz, 2H), 5.29 (s, 1H), 3.15 (d, J=6.7 Hz, 2H), 3.05-2.97 (m, 2H), 2.61 (d, J=11.6 Hz, 2H), 2.43-2.34 (m, 2H), 1.90 (td, J=11.8, 2.4 Hz, 2H), 1.65 (d, J=13.5 Hz, 2H), 1.50 (ddq, J=14.5, 6.7, 3.5, 3.1 Hz, 1H), 1.17 (qd, J=12.2, 3.8 Hz, 2H). $^{13}$C NMR (100 MHz, $CDCl_3$) δ=144.5 (d, J=1.3 Hz, $C_{quat}$), 134.4 (q, J=32.9 Hz, $C_{quat}$), 127.7 (CH), 126.3 (q, J=3.7 Hz, C), 123.4 (q, J=272.9 Hz, $C_{quat}$), 57.1 ($CH_2$), 55.9 ($CH_2$), 52.8 ($CH_2$), 39.5 ($CH_2$), 36.2 (CH), 29.8 ($CH_2$). $^{19}$F NMR (375 MHz, $CDCl_3$) δ=−63.1.

N-(2-(4-(Azidomethyl)piperidin-1-yl)ethyl)naphthalene-2-sulfonamide (5d)

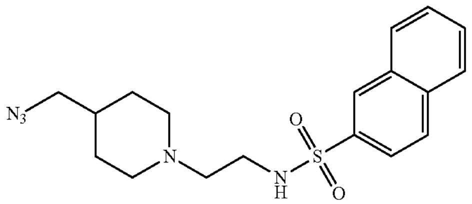 [SMILES: [N-]=[N+]=NCC1CCN(CCNS(=O)(=O)c2ccc3ccccc3c2)CC1]

Prepared by general method B using the ammonium salt 4 (300 mg, 1.70 mmol), the corresponding alkyl chloride 1d (504 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5d as a white solid (429 mg, 67% yield). $^1$H NMR (400 MHz, $CDCl_3$) 5=8.44 (d, J=1.5 Hz, 1H), 7.96 (dd, J=8.8, 3.2 Hz, 2H), 7.92-7.88 (m, 1H), 7.83 (dd, J=8.7, 1.9 Hz, 1H), 7.62 (pd, J=6.9, 1.5 Hz, 2H), 5.40 (s, 1H), 3.12 (d, J=6.7 Hz, 2H), 3.03-2.96 (m, 2H), 2.55 (d, J=11.6 Hz, 2H), 2.38-2.32 (m, 2H), 1.82 (td, J=11.7, 2.3 Hz, 2H), 1.58 (d, J=13.5 Hz, 2H), 1.45 (ddq, J=14.5, 6.8, 3.6, 3.2 Hz, 1H), 1.15 (qd, J=12.2, 3.8 Hz, 2H). $^{13}$C NMR (100 MHz, $CDCl_3$) δ=136.4 ($C_{quat}$), 134.8 ($C_{quat}$), 132.2 ($C_{quat}$), 129.5 (CH), 129.3 (CH), 128.9 (CH), 128.6 (CH), 128.0 (CH), 127.7 (CH), 122.3 (CH), 57.1 ($CH_2$), 55.7 ($CH_2$), 52.7 ($CH_2$), 39.5 ($CH_2$), 36.2 (CH), 29.8 ($CH_2$).

N-(2-(4-(Azidomethyl)piperidin-1-yl)ethyl)-4-methylbenzenesulfonamide (5e)

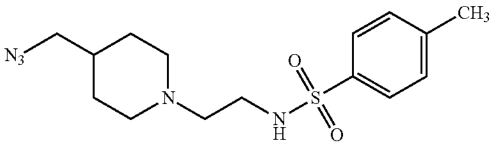 [SMILES: Cc1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1e (467 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5e as a colorless oil (394 mg, 68% yield). $^1$H NMR (400 MHz, $d_6$-DMSO) δ=7.78-7.65 (m, 2H), 7.45-7.36 (m, 2H), 5.76 (s, 2H), 3.69-3.52 (m, 1H), 3.52-3.40 (m, 1H), 3.40-3.29 (m, 1H), 3.27 (d, J=6.3 Hz, 2H), 3.23-2.89 (m, 4H), 2.39 (d, J=3.2 Hz, 3H), 1.77-1.59 (m, 2H), 1.33-1.21 (m, 3H), $^{13}$C NMR (100 MHz, $d_6$-DMSO) δ=142.8 ($C_{quat}$), 137.5 ($C_{quat}$), 129.7 (CH), 126.6 (CH), 64.1 ($CH_2$), 54.9 ($CH_2$), 49.0 (CH), 44.4 ($CH_2$), 43.4 ($CH_2$), 41.6 ($CH_2$), 40.4 ($CH_2$), 21.0 ($CH_3$).

N-(2-(4-(Azidomethyl)piperidin-1-yl)ethyl)-4-ethylbenzenesulfonamide (5f)

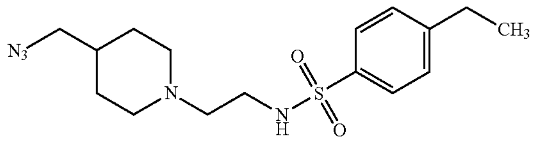 [SMILES: CCc1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1f (463 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5f as a colorless oil (433 mg, 73% yield). $^1$H NMR (400 MHz, $CDCl_3$) δ=7.76 (d, J=8.1 Hz, 2H), 7.31 (d, J=8.0 Hz, 2H), 5.23 (s, 1H), 3.13 (d, J=6.6 Hz, 2H), 2.94 (t, J=5.7 Hz, 2H), 2.70 (q, J=7.5 Hz, 2H), 2.56 (d, J=11.2 Hz, 2H), 2.34 (t, J=5.7 Hz, 2H), 1.85 (t, J=11.2 Hz, 2H), 1.61 (d, J=12.3 Hz, 2H), 1.47 (s, 1H), 1.24 (t, J=7.6 Hz, 3H), 1.18 (dd, J=12.1, 3.1 Hz, 2H). $^{13}$C NMR (100 MHz, $CDCl_3$) δ=149.6 ($C_{quat}$), 136.8 ($C_{quat}$), 128.6 (CH), 127.3 (CH), 57.1 ($CH_2$), 55.7 ($CH_2$), 52.7 ($CH_2$), 39.5 ($CH_2$), 36.2 (CH), 29.8 ($CH_2$), 28.9 ($CH_2$), 15.3 ($CH_3$).

N-(2-(4-(Azidomethyl)piperidin-1-yl)ethyl)-4-isopropylbenzenesulfonamide (5g)

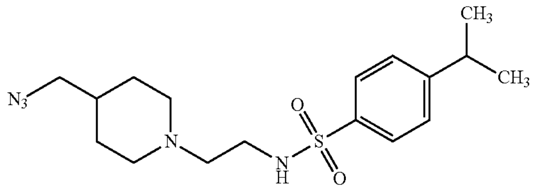 [SMILES: CC(C)c1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1g (489 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5g as a colorless oil (428 mg, 70% yield). $^1$H NMR (400 MHz, $CDCl_3$) δ=7.78-7.75 (m, 2H), 7.34 (d, J=8.2 Hz, 2H), 5.25 (d, J=29.8 Hz, 1H), 3.13 (d, J=6.7 Hz, 2H), 2.98-2.93 (m, 3H), 2.55 (d, J=11.6 Hz, 2H), 2.36-2.32 (m, 2H), 1.87-1.77 (m, 2H), 1.60 (d, J=13.5 Hz, 2H), 1.46 (ddq, J=15.1, 6.9, 4.1 Hz, 1H), 1.25 (d, J=6.9 Hz, 6H), 1.16 (td, J=12.4, 3.7 Hz, 2H). $^{13}$C NMR (400 MHz, $CDCl_3$) δ=154.2 ($C_{quat}$), 136.9 ($C_{quat}$), 127.3 (CH), 127.2 (CH), 57.1 ($CH_2$), 55.7 ($CH_2$), 52.7 ($CH_2$), 39.5 ($CH_2$), 36.2 (CH), 34.2 (CH), 29.8 ($CH_2$), 23.8 ($CH_3$).

N-(2-(4-(Azidomethyl)piperidin-1-yl)ethyl)-4-isobutylbenzenesulfonamide (5h)

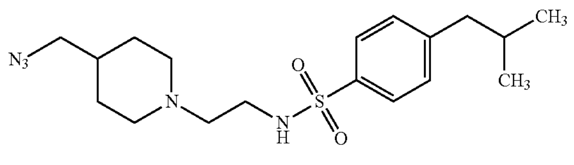 [SMILES: CC(C)Cc1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1h (515 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5h as a colorless oil (461 mg, 71% yield). $^1$H NMR (400 MHz, $d_6$-DMSO) δ=7.75-7.67 (m, 2H), 7.42-7.33 (m, 3H), 3.20 (d, J=6.6 Hz, 2H), 2.83 (dt, J=8.6, 4.3 Hz, 2H), 2.66 (dd, J=11.1, 4.0 Hz, 2H), 2.52 (d, J=7.1 Hz, 2H), 2.24 (dd, J=7.6, 6.2 Hz, 2H), 1.93-1.74 (m, 3H), 1.58-1.49 (m, 2H), 1.48-1.35 (m, 1H), 1.11 (qd, J=12.1, 3.9 Hz, 2H), 0.86 (d, J=6.6 Hz, 6H). $^{13}$C NMR (100 MHz, $d_6$-DMSO) δ=145.9 ($C_{quat}$), 138.1 ($C_{quat}$), 129.5 (CH), 126.4 (CH), 56.9 ($CH_2$), 56.2 ($CH_2$), 52.7 ($CH_2$), 44.2 ($CH_2$), 40.2 ($CH_2$), 35.6 (CH), 29.5 (CH), 29.1 ($CH_2$), 22.0 ($CH_3$).

N-(2-(4-(azidomethyl)piperidin-1-yl)ethyl)-4-(trifluoromethoxy)benzenesulfonamide (5i)

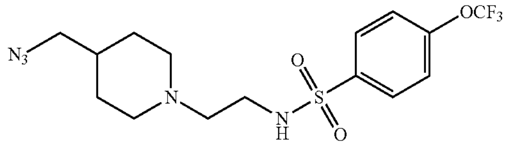 [SMILES: [N-]=[N+]=NCC1CCN(CCNS(=O)(=O)c2ccc(OC(F)(F)F)cc2)CC1]

Prepared by general method B using the ammonium salt 4 (300 mg, 1.70 mmol), the corresponding alkyl chloride 1i (567 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5i as a beige solid (483 mg, 70% yield). $^1$H NMR (300 MHz, $d_6$-DMSO) δ=7.99-7.90 (m, 2H), 7.71-7.63 (m, 1H), 7.58 (dq, J=7.8, 1.1 Hz, 2H), 3.19 (d, J=6.5 Hz, 2H), 2.88 (t, J=6.7 Hz, 2H), 2.67 (dt, J=11.8, 3.4 Hz, 2H), 2.26 (t, J=6.7 Hz, 2H), 1.80 (td, J=11.6, 2.4 Hz, 2H), 1.60-1.48 (m, 2H), 1.41 (ddq, J=14.4, 6.7, 3.7 Hz, 1H), 1.08 (qd, J=12.0, 3.9 Hz, 2H). LC-MS (ESI+) Found: $[M+H]^+$, 408.1.

N-(2-(4-(azidomethyl)piperidin-1-yl)ethyl)-[1,1'-biphenyl]-4-sulfonamide (5j)

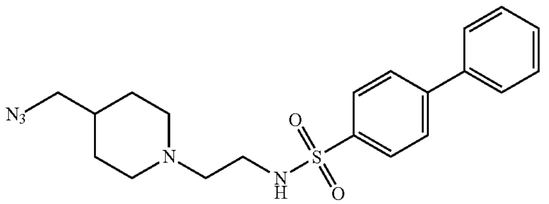 [SMILES: [N-]=[N+]=NCC1CCN(CCNS(=O)(=O)c2ccc(-c3ccccc3)cc2)CC1]

Prepared by general method B using the ammonium salt 4 (300 mg, 1.70 mmol), the corresponding alkyl chloride 1j (552 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5j as a colorless oil (453 mg, 67% yield). LC-MS (ESI+) Found: $[M+H]^+$, 340.2.

N-(2-(4-(azidomethyl)piperidin-1-yl)ethyl)-4-cyclohexylbenzenesulfonamide (5k)

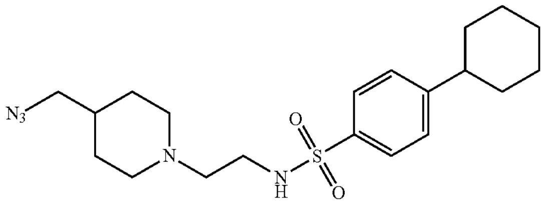 [SMILES: [N-]=[N+]=NCC1CCN(CCNS(=O)(=O)c2ccc(C3CCCCC3)cc2)CC1]

Prepared by general method B using the ammonium salt 4 (300 mg, 1.70 mmol), the corresponding alkyl chloride 1k (564 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5k as a colorless oil (421 mg, 61% yield). LC-MS (ESI+) Found: $[M+H]^+$, 406.2.

N-(2-(4-(azidomethyl)piperidin-1-yl)ethyl)-4-isopropoxybenzenesulfonamide (5l)

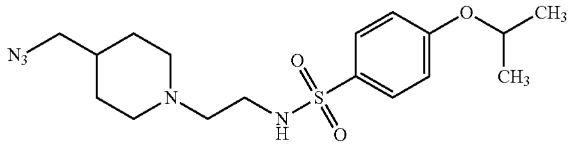 [SMILES: CC(C)Oc1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1l (518 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5l as a colorless oil (379 mg, 59% yield). LC-MS (ESI+) Found: $[M+H]^+$, 382.2.

N-(2-(4-(azidomethyl)piperidin-1-yl)ethyl)-2,3-dihydrobenzofuran-5-sulfonamide (5m)

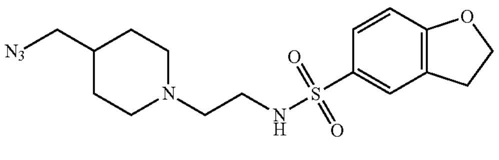 [SMILES: [N-]=[N+]=NCC1CCN(CCNS(=O)(=O)c2ccc3c(c2)CCO3)CC1]

Prepared by general method B using the ammonium salt 4 (300 mg, 1.70 mmol), the corresponding alkyl chloride 1m (489 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5m as a beige solid (379 mg, 74% yield). $^1H$ NMR (300 MHz, $d_6$-DMSO) δ=7.64 (q, J=1.4 Hz, 1H), 7.55 (dd, J=8.4, 2.1 Hz, 1H), 7.21 (d, J=5.6 Hz, 1H), 6.90 (d, J=8.4 Hz, 1H), 4.63 (t, J=8.8 Hz, 2H), 3.30-3.16 (m, 4H), 2.86-2.76 (m, 2H), 2.76-2.65 (m, 2H), 2.28 (dd, J=7.6, 6.2 Hz, 2H), 1.84 (td, J=11.6, 2.4 Hz, 2H), 1.64-1.53 (m, 2H), 1.42 (dp, J=10.4, 3.3 Hz, 1H), 1.13 (qd, J=12.0, 3.9 Hz, 2H). LC-MS (ESI+) Found: $[M+H]^+$, 366.2.

N-(2-(4-(azidomethyl)piperidin-1-yl)ethyl)-4-(sec-butyl)benzenesulfonamide (5n)

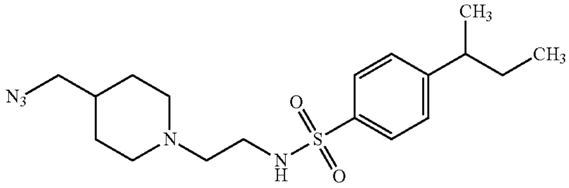 [SMILES: CCC(C)c1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1n (515 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5n as a colorless oil (455 mg, 63% yield). $^1H$ NMR (300 MHz, $d_6$-DMSO) δ=7.82-7.57 (m, 2H), 7.51-7.30 (m, 3H), 3.20 (d, J=6.5 Hz, 2H), 2.90-2.78 (m, 2H), 2.68 (ddd, J=14.1, 8.6, 5.5 Hz, 3H), 2.25 (t, J=6.9 Hz, 2H), 1.81 (td, J=11.5, 2.4 Hz, 2H), 1.72-1.49 (m, 4H), 1.41 (tq, J=10.6, 3.8 Hz, 1H), 1.20 (d, J=6.9 Hz, 3H), 1.16-1.02 (m, 2H), 0.75 (t, J=7.3 Hz, 3H). LC-MS (ESI+) Found: $[M+H]^+$, 380.2.

N-(2-(4-(azidomethyl)piperidin-1-yl)ethyl)-2,3-dihydro-1H-indene-5-sulfonamide (5o)

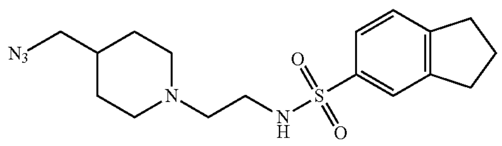 [SMILES: [N-]=[N+]=NCC1CCN(CCNS(=O)(=O)c2ccc3c(c2)CCC3)CC1]

Prepared by general method B using the ammonium salt 4 (300 mg, 1.70 mmol), the corresponding alkyl chloride to (485 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5o as a beige solid (398 mg, 64% yield). LC-MS (ESI+) Found: $[M+H]^+$, 363.2.

N-(2-(4-(azidomethyl)piperidin-1-yl)ethyl)-4-phenoxybenzenesulfonamide (5p)

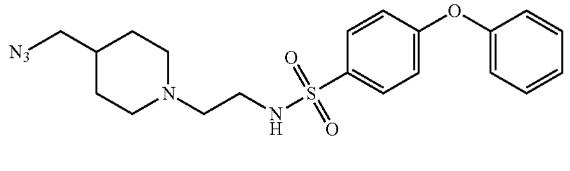 [SMILES: [N-]=[N+]=NCC1CCN(CCNS(=O)(=O)c2ccc(Oc3ccccc3)cc2)CC1]

Prepared by general method B using the ammonium salt 4 (300 mg, 1.70 mmol), the corresponding alkyl chloride 1p (582 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5p as a colorless oil (468 mg, 66% yield). $^1$H NMR (300 MHz, $d_6$-DMSO) δ=7.84-7.74 (m, 2H), 7.54-7.37 (m, 3H), 7.28-7.20 (m, 1H), 7.18-7.05 (m, 4H), 3.21 (d, J=6.5 Hz, 2H), 2.84 (t, J=7.0 Hz, 2H), 2.70 (dt, J=11.8, 3.0 Hz, 2H), 2.29 (t, J=6.9 Hz, 2H), 1.90-1.74 (m, 2H), 1.65-1.50 (m, 2H), 1.43 (tq, J=10.7, 4.0 Hz, 1H), 1.21-1.05 (m, 2H). LC-MS (ESI+) Found: $[M+H]^+$, 416.2.

N-(2-(4-(azidomethyl)piperidin-1-yl)ethyl)-4-(tert-butyl)benzenesulfonamide (5q)

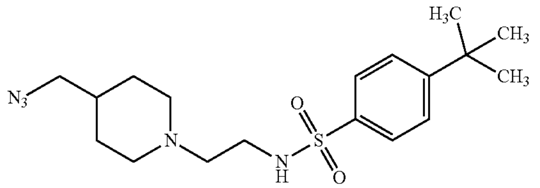 [SMILES: CC(C)(C)c1ccc(S(=O)(=O)NCCN2CCC(CN=[N+]=[N-])CC2)cc1]

Prepared by general method B using the ammonium salt 4 (300 mg, 1.70 mmol), the corresponding alkyl chloride 1q (515 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5q as a colorless oil (432 mg, 67% yield). $^1$H NMR (300 MHz, $d_6$-DMSO) δ=7.79-7.67 (m, 2H), 7.66-7.55 (m, 2H), 7.40 (s, 1H), 3.20 (d, J=6.5 Hz, 2H), 2.81 (d, J=7.5 Hz, 2H), 2.66 (dt, J=11.7, 3.4 Hz, 2H), 2.31-2.20 (m, 2H), 1.81 (td, J=11.7, 2.3 Hz, 2H), 1.59-1.49 (m, 2H), 1.48-1.35 (m, 1H), 1.30 (s, 9H), 1.10 (qd, J=12.0, 3.8 Hz, 2H). LC-MS (ESI+) Found: $[M+H]^+$, 380.2.

N-(2-(4-(azidomethyl)piperidin-1-yl)ethyl)-1-(4-(trifluoromethyl)phenyl)methane sulfonamide (5r)

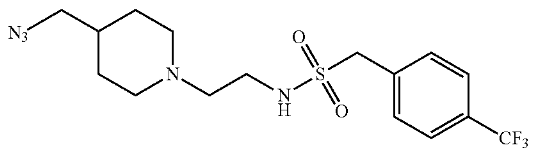 [SMILES: [N-]=[N+]=NCC1CCN(CCNS(=O)(=O)Cc2ccc(C(F)(F)F)cc2)CC1]

Prepared by general method B using the ammonium salt 4 (300 mg, 1.70 mmol), the corresponding alkyl chloride 1r (563 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5r as a beige solid (511 mg, 74% yield). $^1$H NMR (300 MHz, $d_6$-DMSO) δ=7.27 (d, J=8.1 Hz, 2H), 7.23-7.10 (m, 2H), 6.81 (d, J=5.3 Hz, 1H), 4.31 (s, 2H), 3.24 (d, J=6.5 Hz, 2H), 2.99 (q, J=6.1 Hz, 2H), 2.90-2.77 (m, 2H), 2.34 (d, J=6.8 Hz, 2H), 1.89 (td, J=11.6, 2.4 Hz, 2H), 1.72-1.57 (m, 2H), 1.48 (tq, J=10.3, 3.7 Hz, 1H), 1.31-1.08 (m, 2H). LC-MS (ESI+) Found: $[M+H]^+$, 406.2.

N-(2-(4-(azidomethyl)piperidin-1-yl)ethyl)-1-(4-chlorophenyl)methanesulfonamide (5s)

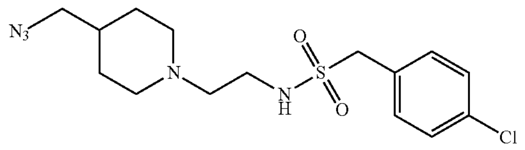 [SMILES: [N-]=[N+]=NCC1CCN(CCNS(=O)(=O)Cc2ccc(Cl)cc2)CC1]

Prepared by general method B using the ammonium salt 4 (300 mg, 1.70 mmol), the corresponding alkyl chloride 1s (501 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5s as a beige solid (406 mg, 64% yield). $^1$H NMR (300 MHz, $d_6$-DMSO) δ=7.75 (d, J=8.1 Hz, 2H), 7.63 (d, J=8.0 Hz, 2H), 7.03 (s, 1H), 4.53 (s, 2H), 3.24 (d, J=6.4 Hz, 2H), 3.05 (t, J=6.8 Hz, 2H), 2.85 (dt, J=11.8, 3.3 Hz, 2H), 2.35 (t, J=6.7 Hz, 2H), 1.90 (td, J=11.6, 2.4 Hz, 2H), 1.70-1.57 (m, 2H), 1.48 (ddq, J=14.1, 6.6, 3.7 Hz, 1H), 1.19 (qd, J=12.0, 3.9 Hz, 2H). LC-MS (ESI+) Found: $[M+H]^+$, 372.1.

N-(2-(4-(azidomethyl)piperidin-1-yl)ethyl)-1-(3-chlorophenyl)methanesulfonamide (5t)

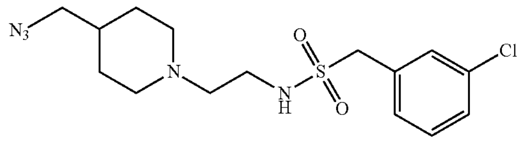 [SMILES: [N-]=[N+]=NCC1CCN(CCNS(=O)(=O)Cc2cccc(Cl)c2)CC1]

Prepared by general method B using the ammonium salt 4 (300 mg, 1.70 mmol), the corresponding alkyl chloride 1t (501 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5t as a beige solid (390 mg, 62% yield). $^1$H NMR (300 MHz, $d_6$-DMSO) δ=7.75 (d, J=8.1 Hz, 2H), 7.63 (d, J=8.0 Hz, 2H), 7.03 (s, 1H), 3.24 (d, J=6.5 Hz, 2H), 3.03 (d, J=7.0 Hz, 2H), 2.85 (dt, J=11.7, 3.4 Hz, 2H), 2.35 (t, J=6.7 Hz, 2H), 1.90 (td, J=11.7, 2.4 Hz, 2H), 1.72-1.58 (m, 2H), 1.47 (dddt, J=13.9, 10.2, 6.7, 4.0 Hz, 1H), 1.29-1.10 (m, 2H).

LC-MS (ESI+) Found: $[M+H]^+$, 372.1.

N-(2-(4-(azidomethyl)piperidin-1-yl)ethyl)-1-(4-bromophenyl)methanesulfonamide (5u)

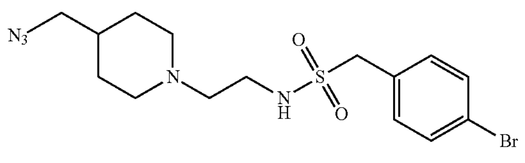 [SMILES: [N-]=[N+]=NCC1CCN(CCNS(=O)(=O)Cc2ccc(Br)cc2)CC1]

Prepared by general method B using the ammonium salt 4 (300 mg, 1.70 mmol), the corresponding alkyl chloride 1u (583 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5u as a beige solid (461 mg, 65% yield). $^1H$ NMR (300 MHz, $d_6$-DMSO) δ=7.61 (t, J=1.8 Hz, 1H), 7.55 (dt, J=7.7, 1.7 Hz, 1H), 7.40 (dt, J=7.7, 1.5 Hz, 1H), 7.34 (t, J=7.7 Hz, 1H), 6.98 (d, J=5.4 Hz, 1H), 4.41 (s, 2H), 3.24 (d, J=6.5 Hz, 2H), 3.02 (q, J=6.2 Hz, 2H), 2.85 (dt, J=11.8, 3.4 Hz, 2H), 2.34 (t, J=6.7 Hz, 2H), 1.90 (td, J=11.6, 2.4 Hz, 2H), 1.73-1.57 (m, 2H), 1.48 (dddd, J=15.1, 10.3, 6.9, 3.2 Hz, 1H), 1.20 (qd, J=12.0, 3.7 Hz, 2H), LC-MS (ESI+) Found: $[M+H]^+$, 416.1.

N-(2-(4-(azidomethyl)piperidin-1-yl)ethyl)-1-(3-bromophenyl)methanesulfonamide (5v)

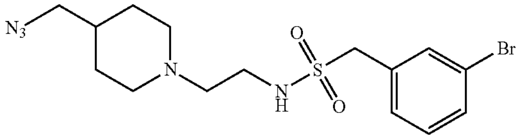 [SMILES: [N-]=[N+]=NCC1CCN(CCNS(=O)(=O)Cc2cccc(Br)c2)CC1]

Prepared by general method B using the ammonium salt 4 (300 mg, 1.70 mmol), the corresponding alkyl chloride 1v (583 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5v as a beige solid (409 mg, 58% yield). LC-MS (ESI+) Found: $[M+H]^+$, 416.1.

N-(2-(4-(azidomethyl)piperidin-1-yl)ethyl)-4-(1H-pyrazol-4-yl)benzenesulfonamide (5w)

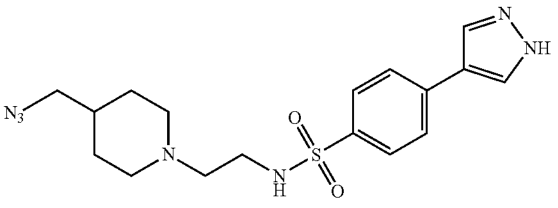 [SMILES: [N-]=[N+]=NCC1CCN(CCNS(=O)(=O)c2ccc(-c3cn[nH]c3)cc2)CC1]

Prepared by general method B using the ammonium salt 4 (120 mg, 0.68 mmol), the corresponding alkyl chloride 1w (214 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 9:2 to 95:5) to provide the title compound 5w as a colorless oil (159 mg, 60% yield). LC-MS (ESI+) Found: $[M+H]^+$, 390.2.

N-(2-(4-(azidomethyl)piperidin-1-yl)ethyl)-4',4'-difluoro-2',3',4',5'-tetrahydro-[1,1'-biphenyl]-4-sulfonamide (5x)

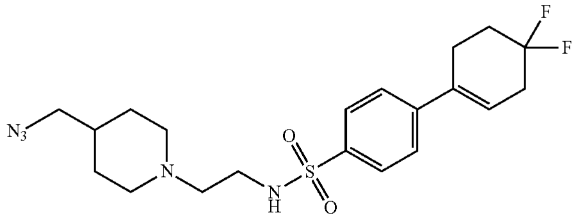 [SMILES: [N-]=[N+]=NCC1CCN(CCNS(=O)(=O)c2ccc(C3=CCC(F)(F)CC3)cc2)CC1]

Prepared by general method B using the ammonium salt 4 (120 mg, 0.68 mmol), the corresponding alkyl chloride 1x (251 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5x as a colorless oil (198 mg, 66% yield). LC-MS (ESI+) Found: $[M+H]^+$, 440.2.

N-(2-(4-(azidomethyl)piperidin-1-yl)ethyl)-4-(furan-3-yl)benzenesulfonamide (5y)

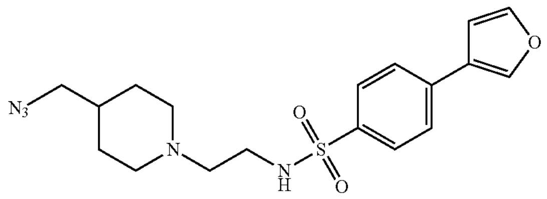 [SMILES: [N-]=[N+]=NCC1CCN(CCNS(=O)(=O)c2ccc(-c3ccoc3)cc2)CC1]

Prepared by general method B using the ammonium salt 4 (120 mg, 0.68 mmol), the corresponding alkyl chloride 1y (214 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5y as a colorless oil (163 mg, 62% yield). LC-MS (ESI+) Found: $[M+H]^+$, 390.2.

N-(2-(4-(azidomethyl)piperidin-1-yl)ethyl)-3,4-dihydro-2H-benzo[b][1,4]dioxepine-7-sulfonamide (5z)

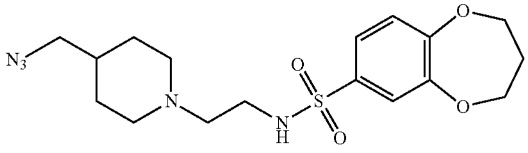 [SMILES: [N-]=[N+]=NCC1CCN(CCNS(=O)(=O)c2ccc3c(c2)OCCCO3)CC1]

Prepared by general method B using the ammonium salt 4 (300 mg, 1.70 mmol), the corresponding alkyl chloride 1z (545 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5z as a beige solid (461 mg, 69% yield). $^1H$ NMR (300 MHz, $d_6$-DMSO) δ=7.40 (d, J=3.9 Hz, 1H), 7.38-7.32 (m, 2H), 7.11 (dt, J=8.7, 1.2 Hz, 1H), 4.22 (qd, J=5.4, 2.2 Hz, 4H), 3.21 (d, J=6.5 Hz, 2H), 2.81 (d, J=7.2 Hz, 2H), 2.77-2.64 (m, 2H), 2.27 (dd, J=7.5, 6.2 Hz, 2H), 2.23-2.07 (m, 2H), 1.83 (td, J=11.6, 2.4 Hz, 2H), 1.63-1.51 (m, 2H), 1.43 (dddd, J=14.0, 10.4, 8.7, 5.0 Hz, 1H), 1.13 (qd, J=12.0, 3.9 Hz, 2H). LC-MS (ESI+) Found: $[M+H]^+$, 396.2.

N-(2-(4-(azidomethyl)piperidin-1-yl)ethyl)-4-(2-(pyrrolidin-1-yl)pyridin-3-yl)benzenesulfonamide (5Aa)

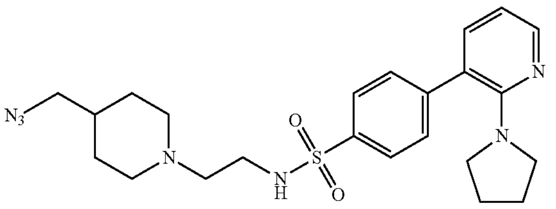 [SMILES: [N-]=[N+]=NCC1CCN(CCNS(=O)(=O)c2ccc(-c3cccnc3N3CCCC3)cc2)CC1]

Prepared by general method B using the ammonium salt 4 (120 mg, 0.68 mmol), the corresponding alkyl chloride 1Aa (273 mg, 0.75 mmol), N,N-diisopropylethylamine (355 L, 2.04 mmol) and dry acetonitrile (8.0 mL). The crude product was purified chromatographically on silica gel (eluting gradient dichloromethane-methanol 98:2 to 95:5) to provide the title compound 5Aa as a colorless oil (149 mg, 47% yield). LC-MS (ESI+) Found: $[M+H]^+$, 470.2.

N-(2-(4-(azidomethyl)piperidin-1-yl)ethyl)-4-(3,6-dihydro-2H-pyran-4-yl)benzenesulfonamide (5Ab)

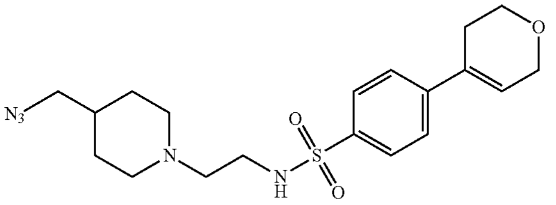 [SMILES: [N-]=[N+]=NCC1CCN(CCNS(=O)(=O)c2ccc(C3=CCOCC3)cc2)CC1]

Prepared by general method B using the ammonium salt 4 (120 mg, 0.68 mmol), the corresponding alkyl chloride 1Ab (226 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5Ab as a colorless oil (176 mg, 64% yield). LC-MS (ESI+) Found: $[M+H]^+$, 406.2.

N-(2-(4-(azidomethyl)piperidin-1-yl)ethyl)-2'-(morpholinomethyl)-[1,1'-biphenyl]-4-sulfonamide (5Ac)

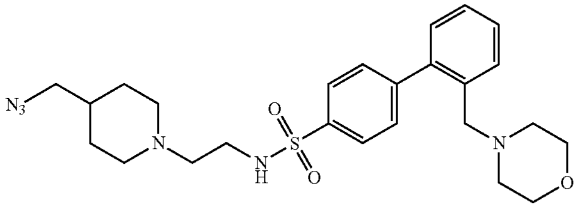 [SMILES: [N-]=[N+]=NCC1CCN(CCNS(=O)(=O)c2ccc(-c3ccccc3CN3CCOCC3)cc2)CC1]

Prepared by general method B using the ammonium salt 4 (70 mg, 0.40 mmol), the corresponding alkyl chloride 1Ac (172 mg, 0.44 mmol), NN-diisopropylethylamine (207 μL, 1.19 mmol) and dry acetonitrile (5.0 mL). The crude product was purified chromatographically on silica gel (eluting gradient dichloromethane-methanol 98:2 to 95:5) to provide the title compound 5Ac as a colorless oil (104 mg, 52% yield). LC-MS (ESI+) Found: $[M+H]^+$, 499.2.

N-(2-(4-(azidomethyl)piperidin-1-yl)ethyl)-2'-cyano-[1,1'-biphenyl]-4-sulfonamide (5Ad)

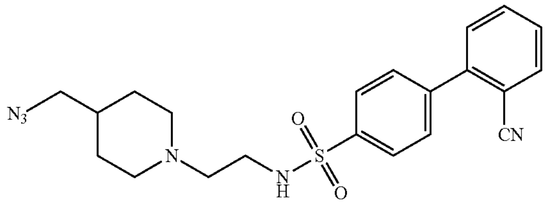

Prepared by general method B using the ammonium salt 4 (120 mg, 0.68 mmol), the corresponding alkyl chloride 1Ad (240 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5Ad as a beige solid (205 mg, 71% yield). LC-MS (ESI+) Found: $[M+H]^+$, 425.2.

N-(2-(4-(azidomethyl)piperidin-1-yl)ethyl)-4-(3,5-dimethylisoxazol-4-yl)benzenesulfonamide (5Ae)

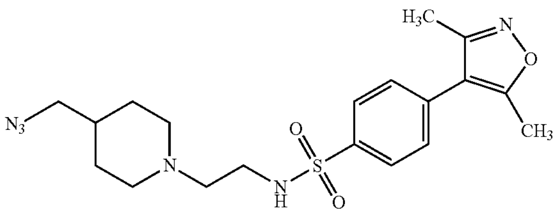 [SMILES: Cc1noc(C)c1-c1ccc(S(=O)(=O)NCCN2CCC(CN=[N+]=[N-])CC2)cc1]

Prepared by general method B using the ammonium salt 4 (80 mg, 0.45 mmol), the corresponding alkyl chloride 1Ae (157 mg, 0.50 mmol), N,N-diisopropylethylamine (237 L, 1.36 mmol) and dry acetonitrile (5.0 mL). The crude product was purified chromatographically on silica gel (eluting gradient dichloromethane-methanol 98:2 to 95:5) to provide the title compound 5Ae as a colorless oil (129 mg, 68% yield). $^1$H NMR (300 MHz, $d_6$-DMSO) δ=7.94-7.83 (m, 3H), 7.66-7.58 (m, 2H), 3.20 (d, J=6.5 Hz, 2H), 2.90 (t, J=6.8 Hz, 2H), 2.70 (dt, J=11.7, 3.5 Hz, 2H), 2.44 (s, 3H), 2.33-2.27 (m, 2H), 2.26 (s, 3H), 1.83 (td, J=11.6, 2.4 Hz, 2H), 1.62-1.51 (m, 2H), 1.49-1.33 (m, 1H), 1.19-1.02 (m, 2H). LC-MS (ESI+) Found: $[M+H]^+$, 419.2.

N-(2-(4-(azidomethyl)piperidin-1-yl)ethyl)-4-(2-chloropyridin-3-yl)benzenesulfonamide (5Af)

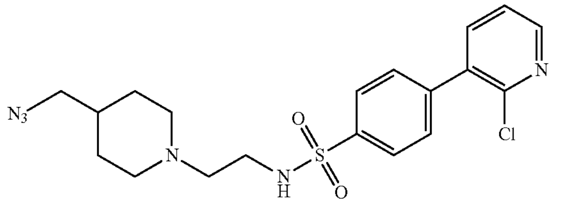

Prepared by general method B using the ammonium salt 4 (80 mg, 0.45 mmol), the corresponding alkyl chloride 1Af (165 mg, 0.50 mmol), N,N-diisopropylethylamine (237 μL, 1.36 mmol) and dry acetonitrile (5.0 mL). The crude product was purified chromatographically on silica gel (eluting gradient dichloromethane-methanol 98:2 to 95:5) to provide the title compound 5Af as a colorless oil (124 mg, 63% yield). LC-MS (ESI+) Found: $[M+H]^+$, 435.2.

N-(2-(4-(azidomethyl)piperidin-1-yl)ethyl)-4'-cyano-[1,1'-biphenyl]-4-sulfonamide (5Ag)

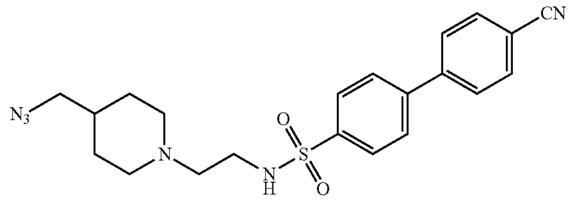 [SMILES: N#Cc1ccc(-c2ccc(S(=O)(=O)NCCN3CCC(CN=[N+]=[N-])CC3)cc2)cc1]

Prepared by general method B using the ammonium salt 4 (120 mg, 0.68 mmol), the corresponding alkyl chloride 1Ag (240 mg, 0.75 mmol), N,N-diisopropylethylamine (355 L, 2.04 mmol) and dry acetonitrile (8.0 mL). The crude product was purified chromatographically on silica gel (eluting gradient dichloromethane-methanol 98:2 to 96:4) to provide the title compound 5Ag as a white solid (196 mg, 68% yield). LC-MS (ESI+) Found: $[M+H]^+$, 425.2.

N-(2-(4-(azidomethyl)piperidin-1-yl)ethyl)-2'-methoxy-[1,1'-biphenyl]-4-sulfonamide (5Ah)

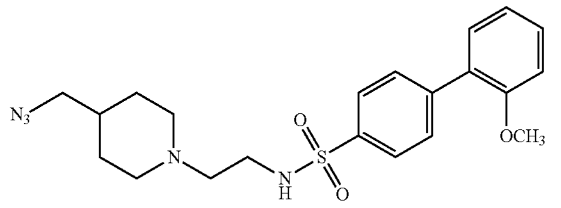 [SMILES: COc1ccccc1-c1ccc(S(=O)(=O)NCCN2CCC(CN=[N+]=[N-])CC2)cc1]

Prepared by general method B using the ammonium salt 4 (120 mg, 0.68 mmol), the corresponding alkyl chloride 1Ah (243 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5Ah as a beige solid (206 mg, 71% yield). $^1$H NMR (300 MHz, $d_6$-DMSO) δ=7.89-7.76 (m, 2H), 7.73-7.64 (m, 2H), 7.52 (s, 1H), 7.40 (ddd, J=8.3, 7.3, 1.8 Hz, 1H), 7.34 (dd, J=7.5, 1.7 Hz, 1H), 7.15 (dd, J=8.4, 1.1 Hz, 1H), 7.06 (td, J=7.4, 1.1 Hz, 1H), 3.78 (s, 3H), 3.20 (d, J=6.5 Hz, 2H), 2.89 (t, J=6.9 Hz, 2H), 2.71 (dt, J=10.9, 3.3 Hz, 2H), 2.31 (dd, J=7.5, 6.3 Hz, 2H), 1.84 (td, J=11.6, 2.4 Hz, 2H), 1.61-1.51 (m, 2H), 1.43 (ddd, J=11.3, 7.2, 3.9 Hz, 1H), 1.28-1.03 (m, 2H). LC-MS (ESI+) Found: $[M+H]^+$, 430.2.

N-(2-(4-(azidomethyl)piperidin-1-yl)ethyl)-2',6'-dimethoxy-[1,1'-biphenyl]-4-sulfonamide (5Ai)

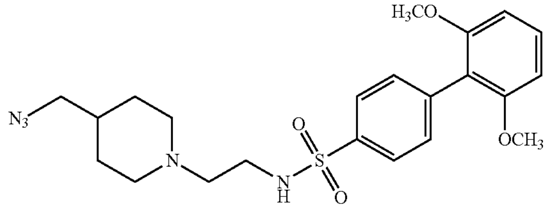 [SMILES: COc1cccc(OC)c1-c1ccc(S(=O)(=O)NCCN2CCC(CN=[N+]=[N-])CC2)cc1]

Prepared by general method B using the ammonium salt 4 (120 mg, 0.68 mmol), the corresponding alkyl chloride 1Ai (266 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5Ai as a beige solid (225 mg, 72% yield). $^1$H NMR (300 MHz, $d_6$-DMSO) δ=7.83-7.72 (m, 2H), 7.49 (s, 1H), 7.45-7.38 (m, 2H), 7.35 (t, J=8.4 Hz, 1H), 6.77 (d, J=8.4 Hz, 2H), 3.68 (s, 6H), 3.21 (d, J=6.5 Hz, 2H), 2.92 (t, J=6.9 Hz, 2H), 2.72 (dt, J=11.8, 3.3 Hz, 2H), 2.31 (dd, J=7.6, 6.2 Hz, 2H), 1.94-1.74 (m, 2H), 1.66-1.51 (m, 2H), 1.44 (ddq, J=14.5, 6.7, 3.7 Hz, 1H), 1.15 (qd, J=12.0, 3.8 Hz, 2H). LC-MS (ESI+) Found: $[M+H]^+$, 460.2.

N-(2-(4-(azidomethyl)piperidin-1-yl)ethyl)-4-(2-fluoropyridin-3-yl)benzenesulfonamide (5Aj)

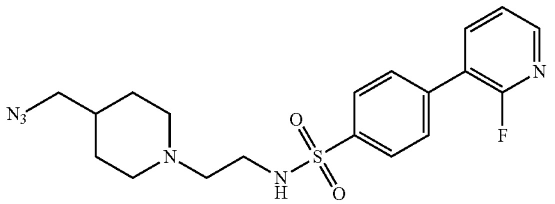 [SMILES: [N-]=[N+]=NCC1CCN(CCNS(=O)(=O)c2ccc(-c3cccnc3F)cc2)CC1]

Prepared by general method B using the ammonium salt 4 (80 mg, 0.45 mmol), the corresponding alkyl chloride 1Aj (157 mg, 0.50 mmol), N,N-diisopropylethylamine (237 μL, 1.36 mmol) and dry acetonitrile (5.0 mL). The crude product was purified chromatographically on silica gel (eluting gradient dichloromethane-methanol 98:2 to 95:5) to provide the title compound 5Aj as a colorless oil (115 mg, 61% yield). LC-MS (ESI+) Found: $[M+H]^+$, 419.2.

N-(2-(4-(azidomethyl)piperidin-1-yl)ethyl)-2',6'-difluoro-[1,1'-biphenyl]-4-sulfonamide (5Ak)

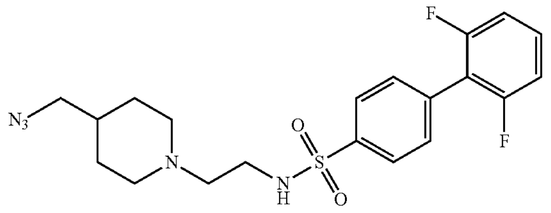 [SMILES: [N-]=[N+]=NCC1CCN(CCNS(=O)(=O)c2ccc(-c3c(F)cccc3F)cc2)CC1]

Prepared by general method B using the ammonium salt 4 (80 mg, 0.45 mmol), the corresponding alkyl chloride 1Ak (165 mg, 0.50 mmol), N,N-diisopropylethylamine (237 μL, 1.36 mmol) and dry acetonitrile (5.0 mL). The crude product was purified chromatographically on silica gel (eluting gradient dichloromethane-methanol 98:2 to 96:4) to provide the title compound 5Ak as a colorless oil (133 mg, 68% yield). $^1$H NMR (300 MHz, $d_6$-DMSO) δ=7.95-7.90 (m, 3H), 7.68 (dt, J=8.4, 1.4 Hz, 2H), 7.57-7.48 (m, 1H), 7.33-7.20 (m, 2H), 3.19 (d, J=6.6 Hz, 2H), 2.92 (t, J=6.8 Hz, 2H), 2.69 (dt, J=11.8, 3.7 Hz, 2H), 2.29 (t, J=6.8 Hz, 2H), 1.82 (td, J=11.6, 2.4 Hz, 2H), 1.65-1.49 (m, 2H), 1.40 (dtd, J=14.2, 6.9, 3.9 Hz, 1H), 1.11 (qd, J=12.0, 3.9 Hz, 2H). LC-MS (ESI+) Found: $[M+H]^+$, 436.2.

N-(2-(4-(azidomethyl)piperidin-1-yl)ethyl)-2'-(dimethylamino)-[1,1'-biphenyl]-4-sulfonamide (5Al)

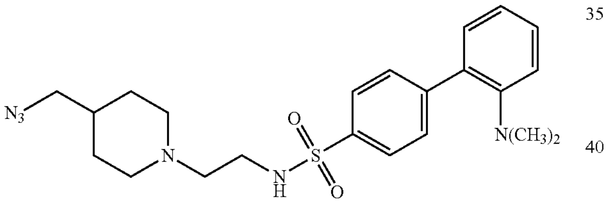

Prepared by general method B using the ammonium salt 4 (70 mg, 0.40 mmol), the corresponding alkyl chloride 1Al (145 mg, 0.44 mmol), N,N-diisopropylethylamine (207 μL, 1.19 mmol) and dry acetonitrile (5.0 mL). The crude product was purified chromatographically on silica gel (eluting gradient dichloromethane-methanol 98:2 to 95:5) to provide the title compound 5Al as a colorless oil (103 mg, 59% yield). LC-MS (ESI+) Found: $[M+H]^+$, 443.2.

N-(2-(4-(azidomethyl)piperidin-1-yl)ethyl)-1-(p-tolyl)methanesulfonamide (5Am)

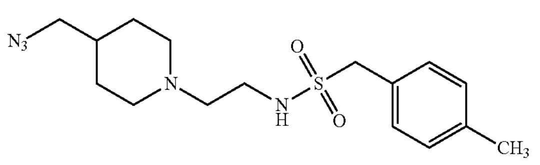 [SMILES: Cc1ccc(CS(=O)(=O)NCCN2CCC(CN=[N+]=[N-])CC2)cc1]

Prepared by general method B using the ammonium salt 4 (300 mg, 1.70 mmol), the corresponding alkyl chloride 1Am (463 mg, 1.87 mmol), N,N-diisopropylethylamine (887 μL, 5.10 mmol) and dry acetonitrile (15 mL). The crude product was purified chromatographically on silica gel (eluting gradient dichloromethane-methanol 98:2 to 96:4) to provide the title compound 5Am as a beige solid (409 mg, 69% yield). LC-MS (ESI+) Found: $[M+H]^+$, 352.2.

N-(2-(4-(azidomethyl)piperidin-1-yl)ethyl)-2'-(methoxymethyl)-[1,1'-biphenyl]-4-sulfonamide (5An)

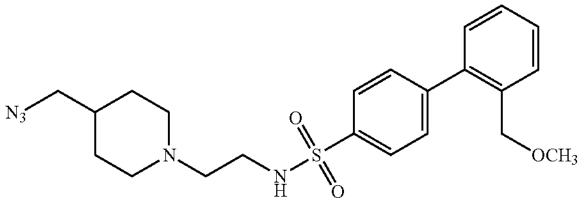 [SMILES: COCc1ccccc1-c1ccc(S(=O)(=O)NCCN2CCC(CN=[N+]=[N-])CC2)cc1]

Prepared by general method B using the ammonium salt 4 (120 mg, 0.68 mmol), the corresponding alkyl chloride 1An (254 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5An as a beige solid (216 mg, 72% yield). $^1$H NMR (300 MHz, $d_6$-DMSO) δ=7.91-7.83 (m, 3H), 7.63-7.56 (m, 2H), 7.55-7.50 (m, 1H), 7.46-7.39 (m, 2H), 7.33-7.27 (m, 1H), 4.28 (s, 2H), 3.22 (s, 3H), 3.20 (d, J=6.5 Hz, 2H), 2.92 (t, J=6.9 Hz, 2H), 2.71 (dt, J=11.8, 3.4 Hz, 2H), 2.30 (t, J=6.9 Hz, 2H), 1.94-1.75 (m, 2H), 1.56 (dd, J=12.2, 4.0 Hz, 2H), 1.43 (tq, J=10.5, 3.7 Hz, 1H), 1.23-1.08 (m, 2H). LC-MS (ESI+) Found: $[M+H]^+$, 440.1.

N-(2-(4-(azidomethyl)piperidin-1-yl)ethyl)-4-(cyclopropylmethyl)benzenesulfonamide (5Ao)

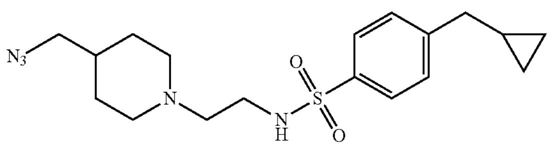 [SMILES: [N-]=[N+]=NCC1CCN(CCNS(=O)(=O)c2ccc(CC3CC3)cc2)CC1]

Prepared by general method B using the ammonium salt 4 (120 mg, 0.68 mmol), the corresponding alkyl chloride 1Ao (205 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 5Ao as a colorless oil (174 mg, 68% yield). LC-MS (ESI+) Found: $[M+H]^+$, 378.2.

N-(2-(4-(azidomethyl)piperidin-1-yl)ethyl)-2'-fluoro-6'-hydroxy-[1,1'-biphenyl]-4-sulfonamide (5Ap)

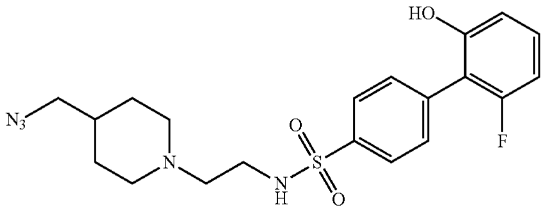

Prepared by general method B using the ammonium salt 4 (80 mg, 0.45 mmol), the corresponding alkyl chloride 1Ap (164 mg, 0.50 mmol), N,N-diisopropylethylamine (237 µL, 1.36 mmol) and dry acetonitrile (5.0 mL). The crude product was purified chromatographically on silica gel (eluting gradient dichloromethane-methanol 98:2 to 95:5) to provide the title compound 5Ap as a beige solid (138 mg, 70% yield). $^1$H NMR (300 MHz, $d_6$-DMSO) δ=10.02 (s, 1H), 7.88-7.78 (m, 3H), 7.59 (dq, J=8.6, 2.0 Hz, 2H), 7.23 (td, J=8.3, 6.8 Hz, 1H), 6.82 (dt, J=8.3, 1.0 Hz, 1H), 6.75 (ddd, J=9.5, 8.3, 1.0 Hz, 1H), 3.20 (d, J=6.5 Hz, 2H), 2.90 (dd, J=7.5, 6.2 Hz, 2H), 2.79-2.65 (m, 2H), 2.30 (dd, J=7.5, 6.2 Hz, 2H), 1.84 (td, J=11.7, 2.4 Hz, 2H), 1.63-1.49 (m, 2H), 1.42 (dddd, J=14.2, 10.3, 7.5, 3.9 Hz, 1H), 1.21-1.05 (m, 2H). LC-MS (ESI+) Found: $[M+H]^+$, 434.2.

N-(2-(4-(azidomethyl)piperidin-1-yl)ethyl)-2'-fluoro-[1,1'-biphenyl]-4-sulfonamide (5Aq)

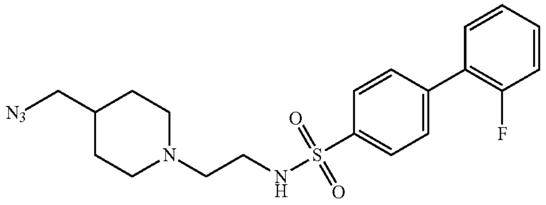 [SMILES: [N-]=[N+]=NCC1CCN(CCNS(=O)(=O)c2ccc(-c3ccccc3F)cc2)CC1]

Prepared by general method B using the ammonium salt 4 (120 mg, 0.68 mmol), the corresponding alkyl chloride 1Aq (234 mg, 0.75 mmol), N,N-diisopropylethylamine (355 L, 2.04 mmol) and dry acetonitrile (8.0 mL). The crude product was purified chromatographically on silica gel (eluting gradient dichloromethane-methanol 98:2 to 96:4) to provide the title compound 5Aq as a beige solid (205 mg, 72% yield). $^1$H NMR (300 MHz, $d_6$-DMSO) δ=7.98-7.86 (m, 2H), 7.76 (dq, J=8.6, 2.0 Hz, 2H), 7.58 (td, J=7.8, 1.7 Hz, 2H), 7.47 (tdd, J=7.0, 5.3, 2.6 Hz, 1H), 7.34 (ddt, J=11.9, 7.5, 1.1 Hz, 2H), 3.17 (d, J=6.5 Hz, 2H), 2.91 (t, J=6.8 Hz, 2H), 2.69 (dt, J=11.7, 3.4 Hz, 2H), 2.41-2.24 (m, 2H), 1.81 (td, J=11.6, 2.4 Hz, 2H), 1.63-1.47 (m, 2H), 1.40 (tq, J=10.3, 3.7 Hz, 1H), 1.10 (qd, J=12.0, 3.8 Hz, 2H). LC-MS (ESI+) Found: $[M+H]^+$, 418.2.

N-(2-(4-(azidomethyl)piperidin-1-yl)ethyl)-2'-cyano-6'-(trifluoromethyl)-[1,1'-biphenyl]-4-sulfonamide (5Ar)

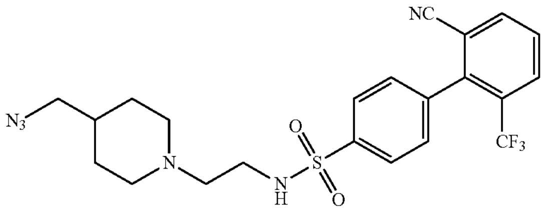 [SMILES: N#Cc1cccc(C(F)(F)F)c1-c1ccc(S(=O)(=O)NCCN2CCC(CN=[N+]=[N-])CC2)cc1]

Prepared by general method B using the ammonium salt 4 (50 mg, 0.28 mmol), the corresponding alkyl chloride 1Ar (124 mg, 0.31 mmol), N,N-diisopropylethylamine (145 µL, 0.83 mmol) and dry acetonitrile (2.5 mL). The crude product was purified chromatographically on silica gel (eluting gradient dichloromethane-methanol 98:2 to 96:4) to provide the title compound 5Ar as a colorless oil (96 mg, 69% yield). LC-MS (ESI+) Found: $[M+H]^+$, 493.2.

N-(2-(4-(azidomethyl)piperidin-1-yl)ethyl)-2'-(trifluoromethyl)-[1,1'-biphenyl]-4-sulfonamide (5As)

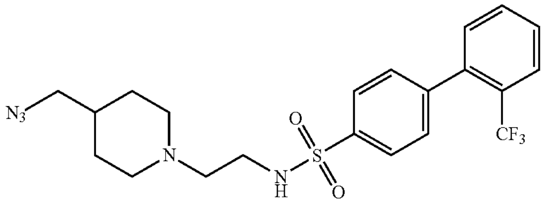 [SMILES: [N-]=[N+]=NCC1CCN(CCNS(=O)(=O)c2ccc(-c3ccccc3C(F)(F)F)cc2)CC1]

Prepared by general method B using the ammonium salt 4 (120 mg, 0.68 mmol), the corresponding alkyl chloride 1As (272 mg, 0.75 mmol), N,N-diisopropylethylamine (355 µL, 2.04 mmol) and dry acetonitrile (8.0 mL). The crude product was purified chromatographically on silica gel (eluting gradient dichloromethane-methanol 98:2 to 96:4) to provide the title compound 5As as a beige solid (229 mg, 72% yield). $^1$H NMR (300 MHz, $d_6$-DMSO) δ=7.93-7.83 (m, 3H), 7.76 (td, J=7.6, 1.5 Hz, 1H), 7.67 (tt, J=7.6, 1.2 Hz, 1H), 7.58-7.50 (m, 2H), 7.48-7.41 (m, 1H), 3.21 (d, J=6.5 Hz, 2H), 2.92 (t, J=6.9 Hz, 2H), 2.69 (dd, J=9.0, 6.0 Hz, 2H), 2.27 (dd, J=7.5, 6.2 Hz, 2H), 1.83 (td, J=11.6, 2.4 Hz, 2H), 1.60-1.52 (m, 2H), 1.42 (dddd, J=14.0, 10.2, 7.5, 3.9 Hz, 1H), 1.13 (qd, J=12.0, 3.9 Hz, 2H). LC-MS (ESI+) Found: $[M+H]^+$, 468.2.

N-(2-(4-(azidomethyl)piperidin-1-yl)ethyl)-2'-fluoro-6'-methoxy-[1,1'-biphenyl]-4-sulfonamide (5At)

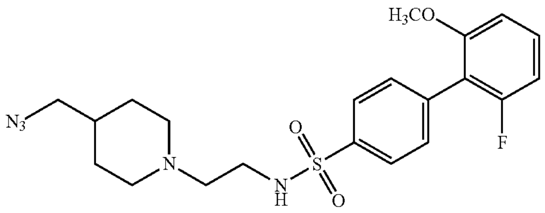 [SMILES: COc1cccc(F)c1-c1ccc(S(=O)(=O)NCCN2CCC(CN=[N+]=[N-])CC2)cc1]

Prepared by general method B using the ammonium salt 4 (80 mg, 0.45 mmol), the corresponding alkyl chloride 1At (171 mg, 0.50 mmol), N,N-diisopropylethylamine (237 μL, 1.36 mmol) and dry acetonitrile (5.0 mL). The crude product was purified chromatographically on silica gel (eluting gradient dichloromethane-methanol 98:2 to 96:4) to provide the title compound 5At as a beige solid (145 mg, 71% yield). $^1H$ NMR (300 MHz, $d_6$-DMSO) δ=7.91-7.82 (m, 2H), 7.64-7.52 (m, 2H), 7.42 (td, J=8.4, 6.8 Hz, 1H), 7.03-6.99 (m, 1H), 6.93 (ddd, J=9.4, 8.4, 0.9 Hz, 1H), 3.76 (s, 3H), 3.19 (d, J=6.5 Hz, 2H), 2.92 (t, J=6.8 Hz, 2H), 2.71 (dt, J=11.7, 3.4 Hz, 2H), 2.30 (dd, J=7.4, 6.2 Hz, 2H), 1.83 (td, J=11.6, 2.4 Hz, 2H), 1.63-1.52 (m, 2H), 1.41 (dtd, J=14.2, 6.9, 3.8 Hz, 1H), 1.14 (tt, J=11.7, 5.9 Hz, 2H). LC-MS (ESI+) Found: $[M+H]^+$, 448.2.

N-(2-(4-(azidomethyl)piperidin-1-yl)ethyl)-2'-hydroxy-[1,1'-biphenyl]-4-sulfonamide (5Au)

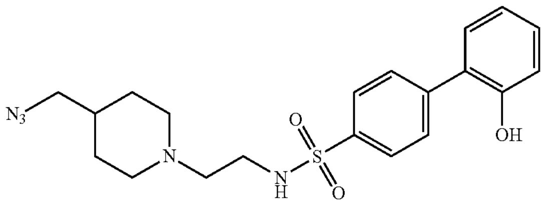 [SMILES: [N-]=[N+]=NCC1CCN(CCNS(=O)(=O)c2ccc(-c3ccccc3O)cc2)CC1]

Prepared by general method B using the ammonium salt 4 (120 mg, 0.68 mmol), the corresponding alkyl chloride 1Au (233 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 95:5) to provide the title compound 5Au as a colorless oil (198 mg, 70% yield). $^1H$ NMR (300 MHz, $d_6$-DMSO) δ=9.75 (s, 1H), 7.89-7.71 (m, 4H), 7.50 (s, 1H), 7.31 (dd, J=7.6, 1.7 Hz, 1H), 7.22 (ddd, J=8.2, 7.3, 1.7 Hz, 1H), 6.98 (dd, J=8.2, 1.2 Hz, 1H), 6.91 (td, J=7.4, 1.2 Hz, 1H), 3.20 (d, J=6.5 Hz, 2H), 2.99-2.84 (m, 2H), 2.72 (dd, J=11.5, 3.4 Hz, 2H), 2.36-2.27 (m, 2H), 1.84 (td, J=11.6, 2.4 Hz, 2H), 1.59-1.49 (m, 2H), 1.41 (ddt, J=14.2, 6.8, 3.3 Hz, 1H), 1.15 (ddd, J=15.8, 9.4, 3.8 Hz, 2H). LC-MS (ESI+) Found: $[M+H]^+$, 416.2.

N-(2-(4-(azidomethyl)piperidin-1-yl)ethyl)-2'-fluoro-6'-(trifluoromethyl)-[1,1'-biphenyl]-4-sulfonamide (5Av)

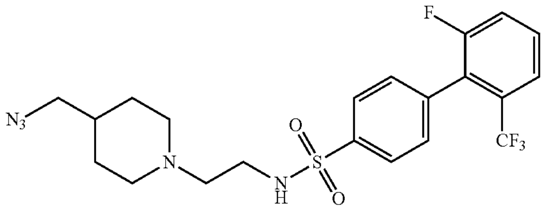 [SMILES: [N-]=[N+]=NCC1CCN(CCNS(=O)(=O)c2ccc(-c3c(F)cccc3C(F)(F)F)cc2)CC1]

Prepared by general method B using the ammonium salt 4 (50 mg, 0.28 mmol), the corresponding alkyl chloride 1Av (118 mg, 0.31 mmol), N,N-diisopropylethylamine (145 μL, 0.83 mmol) and dry acetonitrile (2.5 mL). The crude product was purified chromatographically on silica gel (eluting gradient dichloromethane-methanol 98:2 to 96:4) to provide the title compound 5Av as a colorless oil (89 mg, 65% yield). LC-MS (ESI+) Found: $[M+H]^+$, 486.2.

N-(2-(4-(azidomethyl)piperidin-1-yl)ethyl)-2'-cyano-6'-methyl-[1,1'-biphenyl]-4-sulfonamide (5Aw)

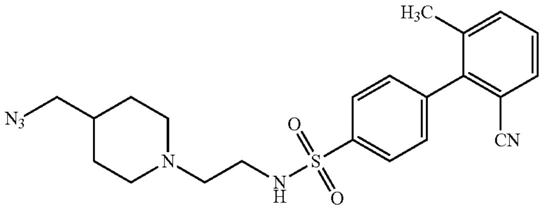 [SMILES: Cc1cccc(C#N)c1-c1ccc(S(=O)(=O)NCCN2CCC(CN=[N+]=[N-])CC2)cc1]

Prepared by general method B using the ammonium salt 4 (50 mg, 0.28 mmol), the corresponding alkyl chloride 1Aw (104 mg, 0.31 nmol), N,N-diisopropylethylamine (145 μL, 0.83 mmol) and dry acetonitrile (2.5 mL). The crude product was purified chromatographically on silica gel (eluting gradient dichloromethane-methanol 98:2 to 96:4) to provide the title compound 5Aw as a colorless oil (86 mg, 69% yield). LC-MS (ESI+) Found: $[M+H]^+$, 439.2.

N-(2-(4-(azidomethyl)piperidin-1-yl)ethyl)-2'-chloro-4'-fluoro-[1,1'-biphenyl]-4-sulfonamide (5Ax)

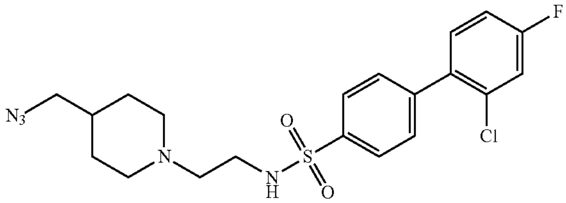 [SMILES: [N-]=[N+]=NCC1CCN(CCNS(=O)(=O)c2ccc(-c3ccc(F)cc3Cl)cc2)CC1]

Prepared by general method B using the ammonium salt 4 (80 mg, 0.45 mmol), the corresponding alkyl chloride 1Ax (173 mg, 0.50 mmol), N,N-diisopropylethylamine (237 L, 1.36 mmol) and dry acetonitrile (5.0 mL). The crude product was purified chromatographically on silica gel (eluting gradient dichloromethane-methanol 98:2 to 96:4) to provide the title compound 5Ax as a beige solid (143 mg, 70% yield). $^1H$ NMR (300 MHz, $d_6$-DMSO) δ=7.93-7.83 (m, 2H), 7.68-7.58 (m, 4H), 7.52 (dd, J=8.7, 6.2 Hz, 1H), 7.36 (td, J=8.5, 2.6 Hz, 1H), 3.20 (d, J=6.5 Hz, 2H), 2.91 (t, J=6.8 Hz, 2H), 2.80-2.65 (m, 2H), 2.30 (t, J=6.8 Hz, 2H), 1.84 (td, J=11.6, 2.4 Hz, 2H), 1.56 (dd, J=12.7, 3.9 Hz, 2H), 1.48-1.35 (m, 1H), 1.23-1.02 (m, 2H). LC-MS (ESI+) Found: $[M+H]^+$, 452.1.

N-(2-(4-(azidomethyl)piperidin-1-yl)ethyl)-2-fluoro-2',6'-dimethoxy-[1,1'-biphenyl]-4-sulfonamide (5Ay)

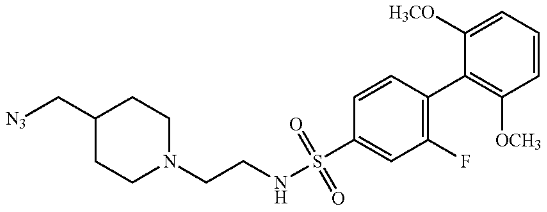 [SMILES: COc1cccc(OC)c1-c1ccc(S(=O)(=O)NCCN2CCC(CN=[N+]=[N-])CC2)cc1F]

Prepared by general method B using the ammonium salt 4 (50 mg, 0.28 mmol), the corresponding alkyl chloride 1Ay (116 mg, 0.31 mmol), N,N-diisopropylethylamine (145 μL, 0.83 mmol) and dry acetonitrile (2.5 mL). The crude product was purified chromatographically on silica gel (eluting gradient dichloromethane-methanol 98:2 to 96:4) to provide the title compound 5Ay as a colorless oil (85 mg, 63% yield). $^1$H NMR (300 MHz, $d_6$-DMSO) δ=7.63 (ddd, J=9.2, 4.3, 1.8 Hz, 2H), 7.51-7.33 (m, 3H), 6.78 (d, J=8.5 Hz, 2H), 3.69 (s, 6H), 3.21 (d, J=6.5 Hz, 2H), 2.97 (t, J=6.8 Hz, 2H), 2.81-2.68 (m, 2H), 2.30 (t, J=6.8 Hz, 2H), 1.85 (td, J=11.6, 2.4 Hz, 2H), 1.61-1.54 (m, 2H), 1.44 (dtd, J=10.5, 6.8, 3.6 Hz, 1H), 1.23-1.10 (m, 2H). LC-MS (ESI+) Found: $[M+H]^+$, 478.2.

N-(2-(4-(azidomethyl)piperidin-1-yl)ethyl)-2',6'-dimethoxy-2-methyl-[1,1'-biphenyl]-4-sulfonamide (5Az)

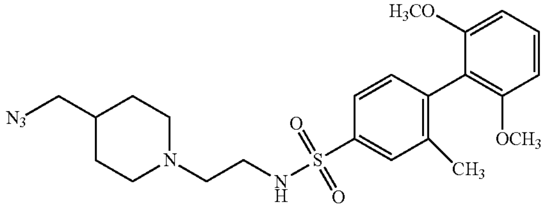 [SMILES: COc1cccc(OC)c1-c1ccc(S(=O)(=O)NCCN2CCC(CN=[N+]=[N-])CC2)cc1C]

Prepared by general method B using the ammonium salt 4 (50 mg, 0.28 mmol), the corresponding alkyl chloride 1Az (115 mg, 0.31 mmol), N,N-diisopropylethylamine (145 μL, 0.83 mmol) and dry acetonitrile (2.5 mL). The crude product was purified chromatographically on silica gel (eluting gradient dichloromethane-methanol 98:2 to 96:4) to provide the title compound 5Az as a colorless oil (87 mg, 65% yield). $^1$H NMR (300 MHz, $d_6$-DMSO) δ=7.66 (d, J=2.0 Hz, 1H), 7.64-7.54 (m, 1H), 7.42 (s, 1H), 7.35 (d, J=8.4 Hz, 1H), 7.20 (d, J=8.0 Hz, 1H), 6.77 (d, J=8.4 Hz, 2H), 3.65 (s, 6H), 3.22 (d, J=6.5 Hz, 2H), 2.91 (d, J=7.3 Hz, 2H), 2.77-2.67 (m, 2H), 2.30 (dd, J=7.6, 6.3 Hz, 2H), 2.03 (s, 3H), 1.85 (td, J=11.6, 2.4 Hz, 2H), 1.67-1.51 (m, 2H), 1.44 (ddp, J=10.6, 6.7, 3.7 Hz, 1H), 1.16 (d, J=12.2 Hz, 2H). LC-MS (ESI+) Found: [M+H]T, 474.2.

N-(2-(4-(azidomethyl)piperidin-1-yl)ethyl)-2-chloro-2',6'-dimethoxy-[1,1'-biphenyl]-4-sulfonamide (5Ba)

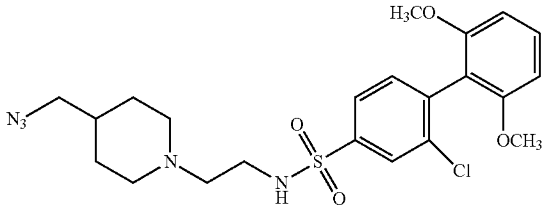 [SMILES: COc1cccc(OC)c1-c1ccc(S(=O)(=O)NCCN2CCC(CN=[N+]=[N-])CC2)cc1Cl]

Prepared by general method B using the ammonium salt 4 (50 mg, 0.28 mmol), the corresponding alkyl chloride 1Ba (122 mg, 0.31 mmol), N,N-diisopropylethylamine (145 μL, 0.83 mmol) and dry acetonitrile (2.5 mL). The crude product was purified chromatographically on silica gel (eluting gradient dichloromethane-methanol 98:2 to 96:4) to provide the title compound 5Ba as a colorless oil (94 mg, 67% yield). $^1$H NMR (300 MHz, $d_6$-DMSO) δ=7.87 (d, J=1.8 Hz, 1H), 7.75 (dd, J=8.0, 1.9 Hz, 1H), 7.45-7.34 (m, 3H), 6.77 (d, J=8.5 Hz, 2H), 3.67 (s, 6H), 3.20 (d, J=6.5 Hz, 2H), 2.97 (t, J=6.7 Hz, 2H), 2.82-2.66 (m, 2H), 2.30 (t, J=6.7 Hz, 2H), 1.85 (td, J=11.6, 2.4 Hz, 2H), 1.64-1.50 (m, 2H), 1.44 (ddq, J=14.8, 6.7, 3.7 Hz, 1H), 1.23-1.14 (m, 2H). LC-MS (ESI+) Found: $[M+H]^+$, 494.2.

N-(2-(4-(azidomethyl)piperidin-1-yl)ethyl)-2,2'-difluoro-6'-hydroxy-[1,1'-biphenyl]-4-sulfonamide (5Bb)

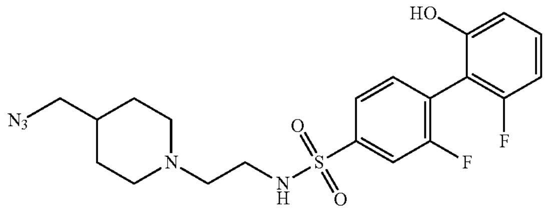 [SMILES: [N-]=[N+]=NCC1CCN(CCNS(=O)(=O)c2ccc(-c3c(O)cccc3F)c(F)c2)CC1]

Prepared by general method B using the ammonium salt 4 (50 mg, 0.28 mmol), the corresponding alkyl chloride 1Bb (108 mg, 0.31 mmol), N,N-diisopropylethylamine (145 μL, 0.83 mmol) and dry acetonitrile (2.5 mL). The crude product was purified chromatographically on silica gel (eluting gradient dichloromethane-methanol 98:2 to 95:5) to provide the title compound 5Bb as a colorless oil (86 mg, 67% yield). LC-MS (ESI+) Found: $[M+H]^+$, 452.2.

N-(2-(3-(azidomethyl)azetidin-1-yl)ethyl)-4-isobutylbenzenesulfonamide (5Bc)

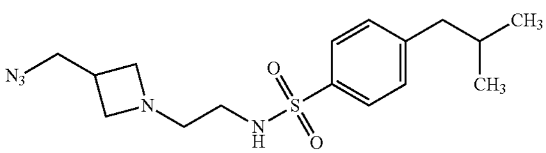 [SMILES: CC(C)Cc1ccc(S(=O)(=O)NCCN2CC(CN=[N+]=[N-])C2)cc1]

Prepared by general method B using the ammonium salt 4a (300 mg, 2.02 mmol), the corresponding alkyl chloride 1h (612 mg, 2.22 mmol), N,N-diisopropylethylamine (1.08 mL, 6.06 mmol) and dry acetonitrile (15 mL). The crude product was purified chromatographically on silica gel (eluting gradient dichloromethane-methanol 98:2 to 96:4) to provide the title compound 5Be as a colorless oil (484 mg, 68% yield). LC-MS (ESI+) Found: $[M+H]^+$, 352.2.

(R)—N-(2-(3-(azidomethyl)pyrrolidin-1-yl)ethyl)-4-isobutylbenzenesulfonamide (5Bd)

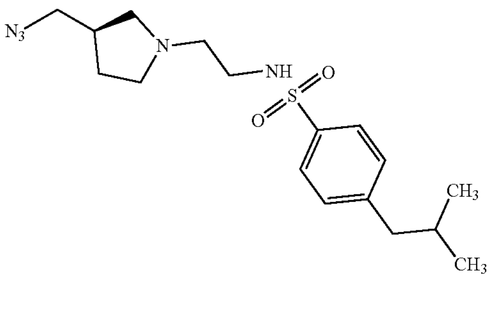

Prepared by general method B using the ammonium salt 4b (300 mg, 1.84 mmol), the corresponding alkyl chloride 1h (560 mg, 2.03 mmol), N,N-diisopropylethylamine (964 µL, 5.53 mmol) and dry acetonitrile (15 mL). The crude product was purified chromatographically on silica gel (eluting gradient dichloromethane-methanol 98:2 to 96:4) to provide the title compound 5Bd as a colorless oil (459 mg, 68% yield). $^1$H NMR (300 MHz, $d_6$-DMSO) δ=7.78-7.69 (m, 2H), 7.42-7.32 (m, 2H), 3.40-3.17 (m, 2H), 2.98-2.84 (m, 2H), 2.81 (d, J=10.1 Hz, 1H), 2.71-2.62 (m, 3H), 2.53 (d, J=7.2 Hz, 2H), 2.36 (dq, J=14.4, 6.8 Hz, 2H), 1.89 (ddt, J=16.7, 13.6, 7.1 Hz, 2H), 1.44 (tt, J=13.3, 6.4 Hz, 1H), 1.34-1.17 (m, 2H), 0.86 (d, J=6.6 Hz, 6H). LC-MS (ESI+) Found: $[M+H]^+$, 366.2.

(S)—N-(2-(3-(azidomethyl)pyrrolidin-1-yl)ethyl)-4-isobutylbenzenesulfonamide (5Be)

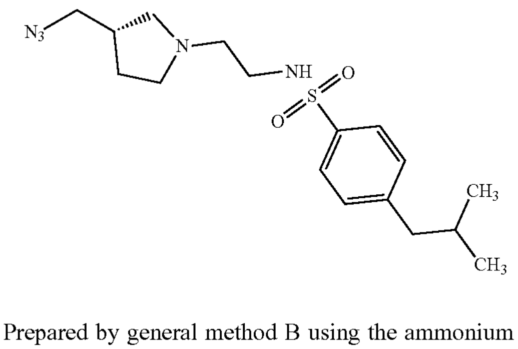

Prepared by general method B using the ammonium salt 4c (300 mg, 1.84 mmol), the corresponding alkyl chloride 1h (560 mg, 2.03 mmol), N,N-diisopropylethylamine (964 µL, 5.53 rmnol) and dry acetonitrile (15 mL). The crude product was purified chromatographically on silica gel (eluting gradient dichloromethane-methanol 98:2 to 96:4) to provide the title compound 5Be as a colorless oil (481 mg, 71% yield). $^1$H NMR (300 MHz, $d_6$-DMSO) δ=7.76-7.67 (m, 2H), 7.46 (d, J=5.3 Hz, 1H), 7.39-7.32 (m, 2H), 3.26 (dd, J=7.3, 2.5 Hz, 2H), 2.82 (t, J=6.9 Hz, 2H), 2.54 (s, 2H), 2.49-2.44 (m, 2H), 2.34 (ddd, J=7.5, 5.9, 4.2 Hz, 4H), 2.12 (dd, J=8.9, 5.5 Hz, 1H), 1.93-1.74 (m, 2H), 1.37-1.24 (m, 1H), 0.86 (d, J=6.6 Hz, 6H). LC-MS (ESI+) Found: $[M+H]^+$, 366.2.

(S)—N-(2-(3-(azidomethyl)piperidin-1-yl)ethyl)-4-isobutylbenzenesulfonamide (5Bf)

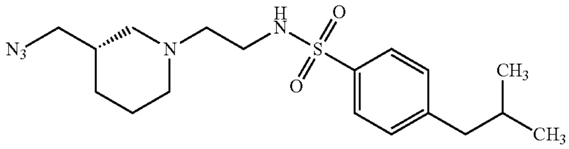 [SMILES: CC(C)Cc1ccc(S(=O)(=O)NCCN2CCC[C@H](CN=[N+]=[N-])C2)cc1]

Prepared by general method B using the ammonium salt 4d (300 mg, 1.70 mmol), the corresponding alkyl chloride 1h (515 mg, 1.87 mmol), N,N-diisopropylethylamine (887 µL, 5.09 mmol) and dry acetonitrile (15 mL). The crude product was purified chromatographically on silica gel (eluting gradient dichloromethane-methanol 98:2 to 96:4) to provide the title compound 5Bf as a colorless oil (402 mg, 62% yield). LC-MS (ESI+) Found: $[M+H]^+$, 380.2.

N-(2-(4-azidopiperidin-1-yl)ethyl)-4-isobutylbenzenesulfonamide (5Bg)

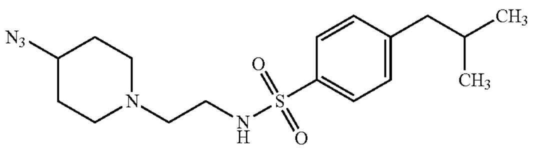 [SMILES: CC(C)Cc1ccc(S(=O)(=O)NCCN2CCC(N=[N+]=[N-])CC2)cc1]

Prepared by general method B using the ammonium salt 4e (300 mg, 1.84 mmol), the corresponding alkyl chloride 1h (560 mg, 2.03 mmol), N,N-diisopropylethylamine (964 µL, 5.53 mmol) and dry acetonitrile (15 mL). The crude product was purified chromatographically on silica gel (eluting gradient dichloromethane-methanol 98:2 to 96:4) to provide the title compound 5Bg as a colorless oil (453 mg, 67% yield). H NMR (300 MHz, $d_6$-DMSO)=7.75-7.68 (m, 2H), 7.38-7.31 (m, 3H), 3.43 (tt, J=9.0, 4.0 Hz, 1H), 2.88-2.76 (m, 2H), 2.53 (d, J=4.0 Hz, 4H), 2.25 (t, J=6.8 Hz, 2H), 2.00 (ddd, J=12.1, 9.9, 2.8 Hz, 2H), 1.85 (hept, J=6.8 Hz, 1H), 1.77-1.64 (m, 2H), 1.41 (dtd, J=13.2, 9.7, 3.7 Hz, 2H), 0.85 (d, J=6.6 Hz, 6H). LC-MS (ESI+) Found: $[M+H]^+$, 366.2.

tert-Butyl 3-iodo-1H-indole-1-carboxylate (6a)

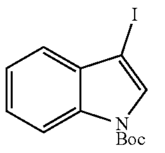 [SMILES: CC(C)(C)OC(=O)n1cc(I)c2ccccc21]

Prepared by general method C using a solution of iodine (1.75 g, 6.90 mmol) in N,N-dimethylformamide (10 mL) dropped to the solution of indole (800 mg, 6.83 mmol) and potassium hydroxide (958 mg, 17.1 mmol) in N,N-dimethylformamide (11 mL). The precipitate was dried at 50° C. under reduced pressure overnight and the beige solid obtained (1.31 g, 79% yield) was used without further purification for the next step. The corresponding 3-iodo-1H-indole (1.00 g, 6.17 mmol) was then protected according general method D, using 4-dimethylaminopyridine (75 mg, 0.62 mmol), di-tert-butyldicarbonate (2.02 g, 9.26 mmol) and dry dichloromethane (10 mL). The crude product was purified chromatographically on silica gel (eluting cyclo-hexane-ethyl acetate 95:5) to provide the title compound 6a as a pale brown oil (1.23 g, 87% yield, 69% total yield over two steps). $^{1}H$ NMR (400 MHz, $CDCl_3$) δ=8.14 (d, J=7.3 Hz, 1H), 7.75 (s, 1H), 7.41-7-38 (m, 1H), 7.36-7.33 (m, 1H), 7.32-7.26 (m, 1H), 1.69 (s, 9H). $^{13}C$ NMR (100 MHz, $CDCl_3$) δ=148.6 ($C_{quat}$), 134.6 ($C_{quat}$), 132.2 ($C_{quat}$), 130.1 (CH), 125.4 (CH), 123.3 (CH), 121.5 (CH), 115.2 (CH), 84.2 ($C_{quat}$), 65.5 ($C_{quat}$), 28.1 ($CH_3$). Spectroscopic and physical data matched the ones reported in the literature.[4]

tert-Butyl 5-fluoro-3-iodo-1H-indole-1-carboxylate (6b)

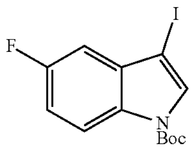

Prepared by general method C using a solution of iodine (1.52 g, 5.98 mmol) in N,N-dimethylformamide (8 mL) dropped to the solution of 5-fluoro-1H-indole (800 mg, 5.92 mmol) and potassium hydroxide (831 mg, 14.8 mmol) in N,N-dimethylformamide (10 mL). The precipitate was dried at 50° C. under reduced pressure overnight and the yellow solid obtained (1.41 g, 91% yield) was used without further purification for the next step. The corresponding 5-fluoro-3-iodo-1H-indole (1.20 g, 4.60 mmol) was then protected according general method D, using 4-dimethylaminopyridine (56 mg, 0.46 mmol), di-tert-butyldicarbonate (1.50 g, 6.90 mmol) and dry dichloromethane (9 mL). The crude product was purified chromatographically on silica gel (eluting cyclohexane-ethyl acetate 94:6) to provide the tittle compound 6b as a white solid (1.24 g, 75% yield, 68% total yield over two steps). $^{1}H$ NMR (400 MHz, $CDCl_3$) δ=8.11 (br, 1H), 7.78 (s, 1H), 7.12-7.05 (m, 2H), 1.66 (s, 9H). $^{13}C$ NMR (100 MHz, $CDCl_3$) δ=160.0 (d, J=240.6 Hz, $C_{quat}$), 148.4 ($C_{quat}$), 132.2 ($C_{quat}$), 116.5 (d, J=9.0 Hz, CH), 113.4 (d, J=25.1 Hz, CH), 107.3 (d, J=24.9 Hz, CH), 84.8 ($C_{quat}$), 64.4 (d, J=4.1 Hz, $C_{quat}$), 28.1 ($CH_3$). Spectroscopic and physical data matched the ones reported in the literature.[4]

tert-Butyl 3-ethynyl-1H-indole-1-carboxylate (7a)

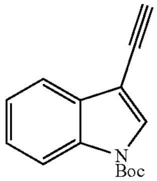 [SMILES: C#Cc1cn(C(=O)OC(C)(C)C)c2ccccc12]

Prepared by general method E using 6a (800 mg, 2.33 mmol), dry triethylamine (650 μL, 4.66 mmol), bis(triphenylphosphine)palladium(II) dichloride (33 mg, 0.046 mmol), copper(I) iodide (18 mg, 0.093 mmol), trimethylsilylacetylene (484 μL, 3.50 mmol) and dry tetrahydrofuran (12 mL). The TMS-deprotection was realized using 1M solution of tetrabutylammonium fluoride in tetrahydrofuran (350 μL, 3.50 mmol) and the crude product was purified chromatographically on silica gel (eluting cyclohexane-ethyl acetate 90:10) to provide the title compound 7a as a pale brown oil (496 mg, 95% yield). $^{1}H$ NMR (400 MHz, $CDCl_3$) δ=8.15 (d, J=8.2 Hz, 1H), 7.82 (s, 1H), 7.69 (dd, J=7.6 Hz, J=1.4 Hz, 1H), 7.40-7.34 (m, 1H), 7.33-7.29 (m, 1H), 3.25 (s, 1H), 1.67 (s, 9H). $^{13}C$ NMR (100 MHz, $CDCl_3$) δ=148.9 ($C_{quat}$), 134.5 ($C_{quat}$), 130.4 ($C_{quat}$), 129.9 (CH), 125.2 (CH), 123.2 (CH), 120.0 (CH), 115.2 (CH), 102.2 ($C_{quat}$), 84.4 ($C_{quat}$), 80.7 (CH), 75.8 ($C_{quat}$), 28.1 ($CH_3$).

tert-Butyl 3-ethynyl-5-fluoro-1H-indole-1-carboxylate (7b)

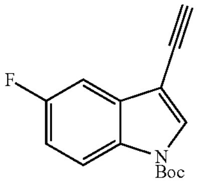 [SMILES: C#Cc1cn(C(=O)OC(C)(C)C)c2ccc(F)cc12]

Prepared by general method E using 6b (450 mg, 1.25 mmol), dry triethylamine (347 μL, 2.49 mmol), bis(triphenylphosphine)palladium(II) dichloride (18 mg, 0.025 mmol), copper(I) iodide (9 mg, 0.049 mmol), trimethylsilylacetylene (259 μL, 1.87 mmol) and dry tetrahydrofuran (6 mL). The TMS-deprotection was realized using 1M solution of tetrabutylammonium fluoride in tetrahydrofuran (188 μL, 1.88 mmol) and the crude product was purified chromatographically on silica gel (eluting cyclohexane:ethyl acetate 90:10) to provide the title compound 7b as a pale yellow oil (294 mg, 91% yield). $^{1}H$ NMR (400 MHz, $CDCl_3$) δ=8.10 (br, 1H), 7.82 (s, 1H), 7.24-7.15 (m, 2H), 3.31 (s, 1H), 1.66 (s, 9H). LC-MS (ESI+) Found: $[M+H]^+$, 260.1.

tert-Butyl 3-(1-((1-(2-(phenylsulfonamido)ethyl) piperidin-4-yl)methyl)-1H-1,2,3-triazol-4-yl)-1H-indole-1-carboxylate (8a)

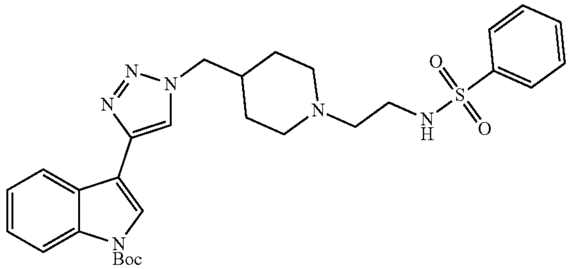 [SMILES: CC(C)(C)OC(=O)n1cc(-c2cn(CC3CCN(CCNS(=O)(=O)c4ccccc4)CC3)nn2)c2ccccc21]

Prepared by general method G using alkyne 7a (110 mg, 0.46 mmol), azide 5a (155 mg, 0.48 mmol), 2M aqueous of sodium ascorbate (228 μL, 0.46 mmol), 15% aqueous of copper(II) sulfate pentahydrate (190 μL, 0.11 mmol) and tetrahydrofuran-tert-butanol (1.14 mL). The crude product was purified chromatographically on silica gel (eluting gradient dichloromethane-methanol 100:0 to 96:4) to provide the title compound 8a as a white solid (211 mg, 82% yield). LC-MS (ESI+) Found: $[M+H]^+$, 565.3.

tert-Butyl 3-(1-((1-(2-((4-chlorophenyl)sulfonamido) ethyl)piperidin-4-yl)methyl)-1H-1,2,3-triazol-4-yl)-1H-indole-1-carboxylate (8b)

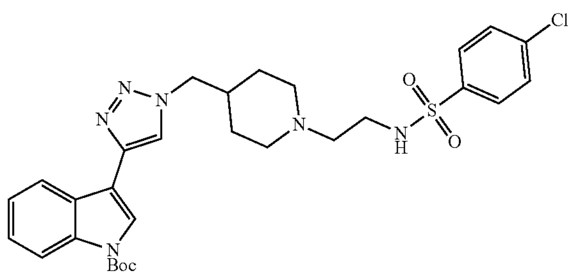 [SMILES: CC(C)(C)OC(=O)n1cc(-c2cn(CC3CCN(CCNS(=O)(=O)c4ccc(Cl)cc4)CC3)nn2)c2ccccc21]

Prepared by general method G using alkyne 7a (110 mg, 0.46 mmol), azide 5b (171 mg, 0.48 mmol), 2M aqueous of sodium ascorbate (228 μL, 0.46 mmol), 15% aqueous of copper(II) sulfate pentahydrate (190 μL, 0.11 mmol) and tetrahydrofuran-tert-butanol (1.14 mL). The crude product was purified chromatographically on silica gel (eluting gradient dichloromethane-methanol 98:2 to 96:4) to provide the title compound 8b as a white solid (214 mg, 78% yield). $^1$H NMR (400 MHz, $d_6$-Acetone) δ=8.42 (s, 1H), 8.27-8.19 (m, 2H), 8.07 (s, 1H), 7.92-7.84 (m, 2H), 7.68-7.57 (m, 2H), 7.44-7.29 (m, 2H), 6.33 (s, 1H), 4.38 (d, J=7.1 Hz, 2H), 3.02 (t, J=6.2 Hz, 2H), 2.78-2.69 (m, 2H), 2.39 (t, J=6.2 Hz, 2H), 2.02-1.85 (m, 3H), 1.71 (s, 9H), 1.56 (d, J=12.7 Hz, 2H), 1.36-1.26 (m, 2H). $^{13}$C NMR (100 MHz, $d_6$-Acetone) δ=150.2 ($C_{quat}$), 141.7 ($C_{quat}$), 140.8 ($C_{quat}$), 138.8 ($C_{quat}$), 136.6 ($C_{quat}$), 130.1 (CH), 129.6 (CH), 129.0 ($C_{quat}$), 125.6 (CH), 123.8 (CH), 123.5 (CH), 122.1 (CH), 122.0 (CH), 116.0 (CH), 113.1 ($C_{quat}$), 84.8 ($C_{quat}$), 57.5 ($CH_2$), 56.0 ($CH_2$), 53.6 ($CH_2$), 41.1 ($CH_2$), 37.9 (CH), 30.4 ($CH_2$), 28.2 ($CH_3$).

tert-Butyl 3-(1-((1-(2-((4-chlorophenyl)sulfonamido) ethyl)piperidin-4-yl)methyl)-1H-1,2,3-triazol-4-yl)-5-fluoro-1H-indole-1-carboxylate (8c)

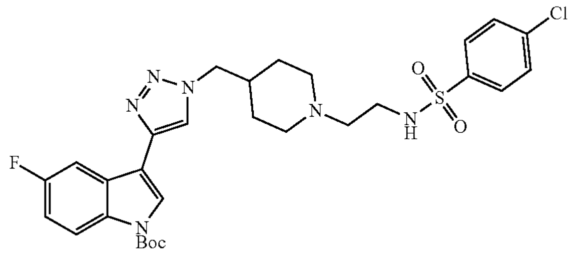 [SMILES: CC(C)(C)OC(=O)n1cc(-c2cn(CC3CCN(CCNS(=O)(=O)c4ccc(Cl)cc4)CC3)nn2)c2cc(F)ccc21]

Prepared by general method G using alkyne 7b (80 mg, 0.31 mmol), azide 5b (116 mg, 0.32 mmol), 2M aqueous of sodium ascorbate (154 μL, 0.31 mmol), 15% aqueous of copper(II) sulfate pentahydrate (129 μL, 0.08 mmol) and tetrahydrofuran-tert-butanol (771 μL). The crude product was purified chromatographically on silica gel (eluting gradient dichloromethane-methanol 100:0 to 96:4) to provide the title compound 8c as a pale yellow solid (164 mg, 86% yield). $^1$H NMR (400 MHz, $d_6$-Acetone) δ=8.44 (s, 1H), 8.21 (dd, J=9.1, 4.7 Hz, 1H), 8.13 (s, 1H), 7.99 (dd, J=9.4, 2.6 Hz, 1H), 7.92-7.84 (m, 2H), 7.67-7.57 (m, 2H), 7.19 (td, J=9.1, 2.7 Hz, 1H), 6.35 (s, 1H), 4.37 (d, J=7.1 Hz, 2H), 3.02 (t, J=6.2 Hz, 2H), 2.73 (dd, J=11.7, 3.4 Hz, 2H), 2.39 (t, J=6.3 Hz, 2H), 2.01-1.84 (m, 3H), 1.70 (s, 9H), 1.60-1.52 (m, 2H), 1.38-1.23 (m, 2H). $^{13}$C NMR (100 MHz, $d_6$-Acetone) δ=160.2 (d, J=238.1 Hz, $C_{quat}$), 150.0 ($C_{quat}$), 141.1 ($C_{quat}$), 140.8 ($C_{quat}$), 138.7 ($C_{quat}$), 133.0 ($C_{quat}$), 130.1 (CH), 129.9 (d, J=10.3 Hz, $C_{quat}$), 129.6 (CH), 125.1 (CH), 122.0 (CH), 117.2 (d, J=9.1 Hz, CH), 113.2 (d, J=25.4 Hz, CH), 112.8 (d, J=4.2 Hz, $C_{quat}$), 107.6 (d, J=24.9 Hz, CH), 85.1 ($C_{quat}$), 57.5 ($CH_2$), 56.0 ($CH_2$), 53.6 ($CH_2$), 41.1 ($CH_2$), 37.8 (CH), 30.4 ($CH_2$), 28.2 ($CH_3$). $^{19}$F NMR (376 MHz, $d_6$-Acetone) δ=−120.3.

N-(2-(4-((4-(1H-Indol-3-yl)-1H-1,2,3-triazol-1-yl) methyl)piperidin-1-yl)ethyl)benzenesulfonamide (9) (Code AB150)

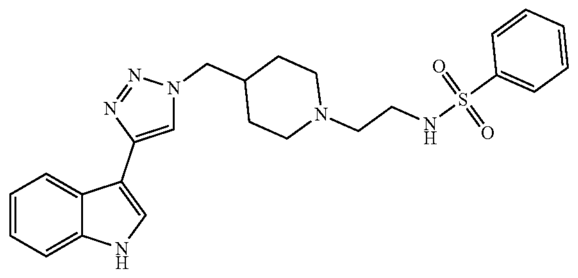 [SMILES: O=S(=O)(NCCN1CCC(Cn2cc(-c3c[nH]c4ccccc34)nn2)CC1)c1ccccc1]

Prepared by general method H using 8a (140 mg, 0.25 mmol), potassium carbonate (86 mg, 0.62 mmol) and methanol (1.24 mL). The crude product was purified chromatographically on silica gel (eluting gradient dichloromethane-methanol 100:0 to 95:5) to provide the title compound 9 as a white solid (83 mg, 72% yield). Mp 60° C. $^1$H NMR (400 MHz, $d_6$-DMSO) δ=11.41-11.27 (m, 1H), 8.38 (s, 1H), 8.05 (d, J=7.8 Hz, 1H), 7.85-7.75 (m, 3H), 7.62-7.55 (m, 3H), 7.51 (s, 1H), 7.45 (d, J=7.9 Hz, 1H), 7.19-7.14 (m, 1H), 7.11 (td, J=7.6, 7.1, 1.1 Hz, 1H), 4.27 (d, J=7.0 Hz, 2H), 2.85 (t, J=6.5 Hz, 2H), 2.69 (d, J=11.3 Hz, 2H), 2.27 (t, J=6.8 Hz, 2H), 1.81 (t, J=10.6 Hz, 3H), 1.45 (d, J=11.2 Hz, 2H), 1.20 (tt, J=11.7, 6.1 Hz, 2H). $^{13}$C NMR (100 MHz, $d_6$-DMSO) δ=142.4 ($C_{quat}$), 140.7 ($C_{quat}$), 136.4 ($C_{quat}$), 132.3 (CH), 129.1 (CH), 126.5 (CH), 124.7 ($C_{quat}$), 122.9 (CH), 121.6 (CH), 120.0 (CH), 119.8 (CH), 119.4 (CH), 111.8 (CH), 106.4 ($C_{quat}$), 57.0 ($CH_2$), 54.5 ($CH_2$), 52.6 ($CH_2$), 40.3 ($CH_2$), 36.4 (CH), 29.1 ($CH_2$). HRMS (ESI+): calcd. for $C_{24}H_{29}N_6O_2S$, 465.2068. Found: $[M+H]^+$, 465.2067 (−0.1 ppm error).

N-(2-(4-((4-(1H-Indol-3-yl)-1H-1,2,3-triazol-1-yl) methyl)piperidin-1-yl)ethyl)-4-chlorobenzenesulfonamide (10) (Code AB152)

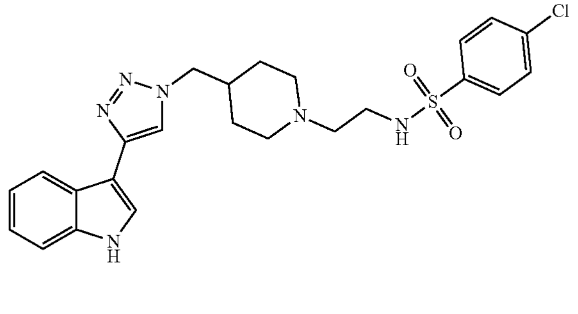 [SMILES: O=S(=O)(NCCN1CCC(Cn2cc(-c3c[nH]c4ccccc34)nn2)CC1)c1ccc(Cl)cc1]

Prepared by general method H using 8b (140 mg, 0.23 mmol), potassium carbonate (81 mg, 0.58 mmol) and methanol (1.20 mL). The crude product was purified chromatographically on silica gel (eluting gradient dichloromethane-methanol 100:0 to 95:5) to provide the title compound 10 as a white solid (94 mg, 81% yield). Mp 79° C. $^1$H NMR (400 MHz, $d_6$-DMSO) δ=11.31 (s, 1H), 8.38 (s, 1H), 8.02 (d, J=7.8 Hz, 1H), 7.87-7.74 (m, 3H), 7.66 (d, J=8.6 Hz, 3H), 7.43 (d, J=8.0 Hz, 1H), 7.18-7.12 (m, 1H), 7.12-7.06 (m, 1H), 4.27 (d, J=7.0 Hz, 2H), 2.85 (s, 2H), 2.70 (d, J=11.1 Hz, 2H), 2.28 (t, J=6.6 Hz, 2H), 1.83 (t, J=10.7 Hz, 3H), 1.46 (d, J=11.4 Hz, 2H), 1.26-1.17 (m, 2H). $^{13}$C NMR (100 MHz, $d_6$-DMSO) δ=142.4 ($C_{quat}$), 139.6 ($C_{quat}$), 137.1 ($C_{quat}$), 136.3 ($C_{quat}$), 129.3 (CH), 128.4 (CH), 124.7 ($C_{quat}$), 122.9 (CH), 121.6 (CH), 119.9 (CH), 119.8 (CH), 119.4 (CH), 111.7 (CH), 106.3 ($C_{quat}$), 57.0 ($CH_2$), 54.5 ($CH_2$), 52.6 ($CH_2$), 40.2 ($CH_2$), 36.4 (CH), 29.1 ($CH_2$). HRMS (ESI+): calcd. for $C_{24}H_{28}ClN_6O_2S$, 499.1667. Found: $[M+H]^+$, 499.1677 (2.2 ppm error).

4-Chloro-N-(2-(4-((4-(5-fluoro-1H-indol-3-yl)-1H-1,2,3-triazol-1-yl)methyl)piperidin-1-yl)ethyl)benzenesulfonamide (11) (Code AB153)

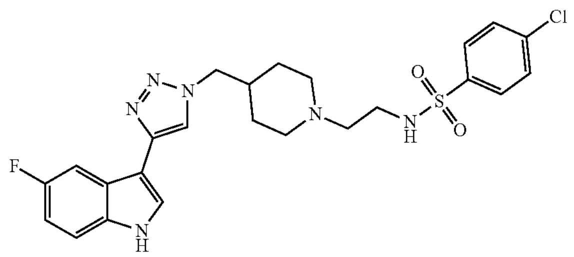 [SMILES: O=S(=O)(NCCN1CCC(Cn2cc(-c3c[nH]c4ccc(F)cc34)nn2)CC1)c1ccc(Cl)cc1]

Prepared by general method H using 8c (110 mg, 0.18 mmol), potassium carbonate (62 mg, 0.45 mmol) and methanol (1.0 mL). The crude product was purified chromatographically on silica gel (eluting gradient dichloromethane-methanol 100:0 to 95:5) to provide the title compound 11 as a white solid (81 mg, 88% yield). Mp 91° C. $^1$H NMR (400 MHz, $d_6$-DMSO) δ=11.43 (s, 1H), 8.43 (s, 1H), 7.86 (d, J=2.6 Hz, 1H), 7.83-7.75 (m, 3H), 7.66 (d, J=8.7 Hz, 3H), 7.44 (dd, J=8.9, 4.6 Hz, 1H), 7.00 (td, J=9.2, 2.5 Hz, 1H), 4.27 (d, J=7.0 Hz, 2H), 2.85 (s, 2H), 2.70 (d, J=11.2 Hz, 2H), 2.27 (t, J=6.6 Hz, 2H), 1.83 (t, J=10.8 Hz, 3H), 1.45 (d, J=11.3 Hz, 2H), 1.26-1.15 (m, 2H). $^{13}$C NMR (100 MHz, $d_6$-DMSO) δ=157.3 (d, J=233.2 Hz, $C_{quat}$), 142.0 ($C_{quat}$), 139.6 ($C_{quat}$), 137.1 ($C_{quat}$), 133.0 ($C_{quat}$), 129.3 (CH), 128.4 (CH), 124.9 (CH), 119.7 (CH), 112.8 (d, J=9.5 Hz, CH), 109.7 (d, J=26.1 Hz, CH), 106.7 (d, J=4.7 Hz, $C_{quat}$), 104.7 (d, J=24.0 Hz, CH), 57.0 ($CH_2$), 54.4 ($CH_2$), 52.6 ($CH_2$), 40.2 ($CH_2$), 36.3 (CH), 29.1 ($CH_2$). $^{19}$F NMR (376 MHz, $d_6$-DMSO) δ=−120.3. HRMS (ESI+): calcd. for $C_{24}H_{27}ClFN_6O_2S$, 517.1579. Found: $[M+H]^+$, 517.1583 (0.8 ppm error).

Ethyl 5-fluoro-1H-indole-2-carboxylate (12a)

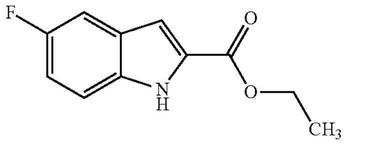

Prepared by general method J using 4-fluoro-2-iodoaniline (4.00 g, 16.9 mmol), ethyl 2-ethoxyacrylate-(4.87 g, 33.8 mmol), tetra-n-butylammonium bromide (10.9 g, 33.8 mmol), sodium bicarbonate (8.51 g, 0.10 mol) and palladium(II) acetate (568 mg, 2.53 mmol) in dry acetonitrile (110 mL). The crude product was purified chromatographically on silica gel (eluting cyclohexane-ethyl acetate 90:10) to provide the title compound 12a as a pale yellow solid (1.98 g, 50% yield). $^1$H NMR (400 MHz, $CDCl_3$) δ=9.00 (br. s, 1H), 7.36 (dd, J=8.9, 4.3 Hz, 1H), 7.32 (dd, J=9.2, 2.4 Hz, 1H), 7.18 (m, 1H), 7.09 (td, J=9.02, 2.48 Hz, 1H), 4.42 (q, J=7.10 Hz, 2H), 1.42 (t, J=7.10 Hz, 3H). $^{13}$C NMR (100 MHz, $CDCl_3$) δ=161.9 (C), 158.3 (d, J=237.6 Hz, $C_{quat}$), 129.2 ($C_{quat}$), 127.8 (d, J=10.4 Hz, $C_{quat}$), 114.6 (d, J=26.9 Hz, CH), 112.9 (d, J=9.6 Hz, CH), 108.6 (d, J=5.3 Hz, CH), 106.9 (d, J=23.3 Hz, $C_{quat}$), 61.3 ($CH_2$), 14.5 ($CH_3$). $^{19}$F NMR (376 MHz, $d_6$-DMSO) δ=−121.5. Spectroscopic and physical data matched the ones reported in the literature.[5]

Ethyl 5-chloro-1H-indole-2-carboxylate (12b)

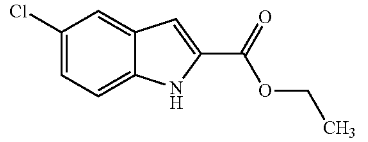

Prepared by general method J using 4-chloro-2-iodoaniline (4.00 g, 15.8 mmol), ethyl 2-ethoxyacrylate (4.55 g, 31.6 mmol), tetra-n-butylammonium bromide (10.2 g, 31.6 mmol), sodium bicarbonate (7.95 g, 94.7 mol) and palladium(II) acetate (541 mg, 2.38 mmol) in dry acetonitrile (105 mL). The crude product was purified chromatographically on silica gel (eluting cyclohexane-ethyl acetate 90:10) to provide the title compound 12b as a beige solid (2.25 g, 63% yield). $^1$H NMR (400 MHz, $CDCl_3$) δ=9.12 (br. s, 1H), 7.66 (d, J=1.83 Hz, 1H), 7.35 (d, J=8.35 Hz, 1H), 7.27 (dd, J=8.73, 1.92 Hz, 1H), 7.15 (m, 1H), 4.42 (q, J=7.10 Hz, 2H), 1.42 (t, J=7.10 Hz, 3H). $^{13}$C NMR (100 MHz, $CDCl_3$) δ 161.9 ($C_{quat}$), 135.2 ($C_{quat}$), 128.9 ($C_{quat}$), 128.6 ($C_{quat}$), 126.6 ($C_{quat}$), 126.0 ($C_{quat}$), 121.9 (CH), 113.1 (CH), 108.1 (CH), 61.4 ($CH_2$), 14.5 ($CH_3$). Spectroscopic and physical data matched the ones reported in the literature.[5]

Ethyl 6-chloro-1H-indole-2-carboxylate (12c)

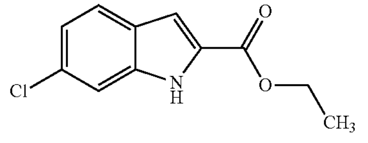

Prepared by general method J using 5-chloro-2-iodoaniline (1.00 g, 3.95 mmol), ethyl 2-ethoxyacrylate (1.14 g, 7.89 mmol), tetra-n-butylammonium bromide (2.54 g, 7.89 mmol), sodium bicarbonate (2.00 g, 23.7 mol) and palladium(II) acetate (135 mg, 0.60 mmol) in dry acetonitrile (25 mL). The crude product was purified chromatographically on silica gel (eluting cyclohexane-ethyl acetate 90:10) to provide the title compound 12c as a white solid (456 mg, 49% yield). $^1$H NMR (400 MHz, $CDCl_3$) δ=9.07 (br. s, 1H), 7.59 (d, J=8.50 Hz, 1H), 7.42 (s, 1H), 7.19 (s, 1H), 7.12 (dd, J=8.50, 1.8 Hz, 1H), 4.20 (q, J=7.10 Hz, 2H), 1.42 (t, J=7.10 Hz, 3H). $^{13}$C NMR (100 MHz, $CDCl_3$)=162.0 ($C_{quat}$), 137.2 ($C_{quat}$), 131.4 ($C_{quat}$), 128.4 ($C_{quat}$), 126.2 ($C_{quat}$), 123.7 (CH), 122.0 (CH), 111.8 (CH), 108.8 (CH), 61.4 ($CH_2$), 14.5 ($CH_3$). Spectroscopic and physical data matched the ones reported in the literature.[5]

Isopropyl 5-fluoro-1H-indole-2-carboxylate (12d)

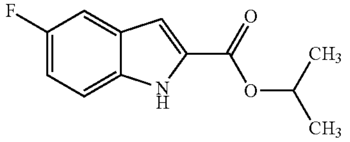 [SMILES: CC(C)OC(=O)c1cc2cc(F)ccc2[nH]1]

Prepared by general method K using isopropyl alcohol (143 μL, 1.86 mmol), 5-fluoro-1H-indole-2-carboxylic acid (400 mg, 2.24 mmol), triphenylphosphine (585 mg, 2.24 mmol), diisopropyl azodicarboxylate (440 μL, 2.24 mmol), in dry tetrahydrofuran (3.5 mL). The crude product was passed through a short silica gel column eluting with dichloromethane-diethyl ether (1:1) then purified chromatographically on silica gel (eluting cyclohexane-ethyl acetate 90:10) to provide the title compound 12d as a white solid (696 mg, 85% yield). $^{1}$H NMR (400 MHz, $d_6$-Acetone) δ=10.99 (s, 1H), 7.54 (dd, J=9.0, 4.5 Hz, 1H), 7.38 (dd, J=9.6, 2.5 Hz, 1H), 7.16 (dd, J=2.2, 0.9 Hz, 1H), 7.10 (td, J=9.2, 2.5 Hz, 1H), 5.22 (p, J=6.3 Hz, 1H), 1.36 (d, J=6.3 Hz, 6H). $^{13}$C NMR (100 MHz, $d_6$-Acetone) δ=161.5 ($C_{quat}$), 158.9 (d, J=241.61 Hz, $C_{quat}$), 135.0 ($C_{quat}$), 130.9 ($C_{quat}$), 128.5 (d, J=10.5 Hz, $C_{quat}$), 114.5 (d, J=3.2 Hz, CH), 114.3 (d, J=20.5 Hz, CH), 108.4 (d, J=5.4 Hz, CH), 107.0 (d, J=22.9 Hz, CH), 69.0 (CH), 22.1 ($CH_3$). $^{19}$F NMR (376 MHz, $d_6$-Acetone) δ=−124.9 (td, J=9.5, 4.6 Hz).

Isopropyl 5-chloro-1H-indole-2-carboxylate (12e)

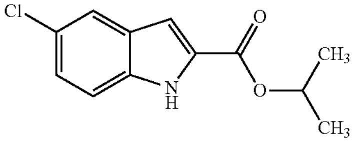 [SMILES: CC(C)OC(=O)c1cc2cc(Cl)ccc2[nH]1]

Prepared by general method K using isopropyl alcohol (131 μL, 3.41 mmol), 5-chloro-1H-indole-2-carboxylic acid (400 mg, 2.05 mmol), triphenylphosphine (535 mg, 2.05 mmol), diisopropyl azodicarboxylate (403 μL, 2.05 mmol), in dry tetrahydrofuran (3.5 mL). The crude product was passed through a short silica gel column eluting with dichloromethane-diethyl ether (1:1) then purified chromatographically on silica gel (eluting cyclohexane-ethyl acetate 90:10) to provide the title compound 12e as a white solid (614 mg, 76% yield). $^{1}$H NMR (400 MHz, $d_6$-DMSO) δ=12.03 (s, 1H), 7.71 (d, J=2.0 Hz, 1H), 7.46 (d, J=8.8 Hz, 1H), 7.25 (dd, J=8.8, 2.1 Hz, 1H), 7.12-7.07 (m, 1H), 5.16 (p, J=6.2 Hz, 1H), 1.34 (d, J=6.3 Hz, 6H). $^{13}$C NMR (100 MHz, $d_6$-DMSO) δ=160.6 ($C_{quat}$), 135.7 ($C_{quat}$), 129.1 ($C_{quat}$), 127.7 ($C_{quat}$), 124.7 ($C_{quat}$), 124.6 (CH), 121.0 (CH), 114.2 (CH), 107.1 (CH), 68.2 (CH), 21.7 ($CH_3$).

Isobutyl 5-fluoro-1H-indole-2-carboxylate (12f)

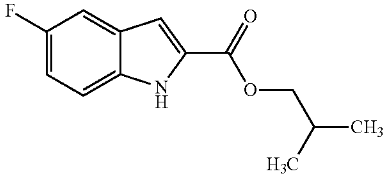 [SMILES: CC(C)COC(=O)c1cc2cc(F)ccc2[nH]1]

Prepared by general method K using isobutanol (1.08 mL, 11.6 mmol), 5-chloro-1H-indole-2-carboxylic acid (2.50 g, 13.9 mmol), triphenylphosphine (3.66 g, 13.9 mmol), diisopropyl azodicarboxylate (2.75 mL, 13.9 mmol), in dry tetrahydrofuran (23 mL). The crude product was passed through a short silica gel column eluting with dichloromethane-diethyl ether (1:1) then purified chromatographically on silica gel (eluting cyclohexane-ethyl acetate 90:10) to provide the title compound 12f as a pale yellow solid (2.78 g, 85% yield). $^{1}$H NMR (400 MHz, $CDCl_3$) δ=9.12 (s, 1H), 7.37 (dd, J=9.0, 4.4 Hz, 1H), 7.32 (dd, J=9.2, 2.4 Hz, 1H), 7.19 (dd, J=2.1, 0.9 Hz, 1H), 7.09 (td, J=9.1, 2.5 Hz, 1H), 4.16 (d, J=6.7 Hz, 2H), 2.10 (dq, J=13.4, 6.7 Hz, 1H), 1.04 (d, J=6.7 Hz, 6H). $^{13}$C NMR (100 MHz, $CDCl_3$) δ=162.1 ($C_{quat}$), 158.3 (d, J=236.6 Hz, $C_{quat}$), 133.6 ($C_{quat}$), 129.14 ($C_{quat}$), 127.8 (d, J=10.4 Hz, CH), 114.6 (d, J=27.1 Hz, CH), 113.0 (d, J=9.5 Hz, CH), 108.5 (d, J=5.0 Hz, CH), 106.8 (d, J=23.3 Hz, $C_{quat}$), 71.3 ($CH_2$), 21.1 (CH), 19.3 ($CH_3$). $^{19}$F NMR (376 MHz, $d_6$-DMSO) δ=−121.5.

Isobutyl 5-chloro-1H-indole-2-carboxylate (12g)

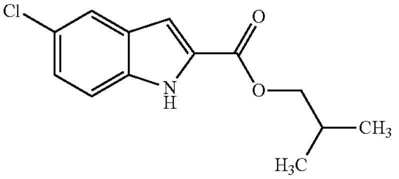 [SMILES: CC(C)COC(=O)c1cc2cc(Cl)ccc2[nH]1]

Prepared by general method K using isobutanol (987 μL, 10.6 mmol), 5-chloro-1H-indole-2-carboxylic acid (2.50 g, 12.8 mmol), triphenylphosphine (3.35 g, 12.8 mmol), diisopropyl azodicarboxylate (2.52 mL, 12.8 mmol), in dry tetrahydrofuran (21 mL). The crude product was passed through a short silica gel column eluting with dichloromethane-diethyl ether (1:1) then purified chromatographically on silica gel (eluting cyclohexane-ethyl acetate 90:10) to provide the title compound 12g as a pale yellow solid (2.08 g, 78% yield). $^{1}$H NMR (400 MHz, $CDCl_3$) δ=9.19 (s, 1H), 7.64 (d, J=2.0 Hz, 1H), 7.34 (d, J=8.8 Hz, 1H), 7.27-7.23 (m, 1H), 7.14 (dd, J=2.1, 0.9 Hz, 1H), 4.14 (d, J=6.7 Hz, 2H), 2.09 (dt, J=13.4, 6.7 Hz, 1H), 1.02 (d, J=6.7 Hz, 6H). $^{13}$C NMR (100 MHz, $CDCl_3$) δ=162.1 ($C_{quat}$), 135.3 ($C_{quat}$), 128.9 ($C_{quat}$), 128.5 ($C_{quat}$), 126.6 ($C_{quat}$), 126.0 (CH), 121.9 (CH), 113.2 (CH), 108.0 (CH), 71.4 ($CH_2$), 28.1 (CH), 19.3 ($CH_3$).

Isopentyl 5-fluoro-1H-indole-2-carboxylate (12h)

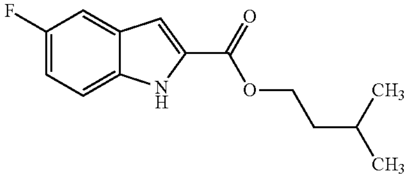 [SMILES: CC(C)CCOC(=O)c1cc2cc(F)ccc2[nH]1]

Prepared by general method K using isoamyl alcohol (152 µL, 1.40 mmol), 5-fluoro-1H-indole-2-carboxylic acid (300 mg, 1.67 mmol), triphenylphosphine (439 mg, 1.67 mmol), diisopropyl azodicarboxylate (329 µL, 1.67 mmol), in dry tetrahydrofuran (2.8 mL). The crude product was passed through a short silica gel column eluting with dichloromethane-diethyl ether (1:1) then purified chromatographically on silica gel (eluting cyclohexane-ethyl acetate 90:10) to provide the title compound 12h as a pale yellow solid (288 mg, 83% yield). $^1H$ NMR (400 MHz, $CDCl_3$) δ=9.11 (s, 1H), 7.39 (dd, J=9.0, 4.4 Hz, 1H), 7.30 (dd, J=9.3, 2.5 Hz, 1H), 7.20 (dd, J=2.1, 0.9 Hz, 1H), 7.10 (td, J=9.1, 2.4 Hz, 1H), 4.27 (m, 2H), 1.64 (dq, J=13.4, 6.6 Hz, 1H), 1.48-1.39 (m, 2H), 0.91 (d, J=6.7 Hz, 6H). $^{13}C$ NMR (100 MHz, $CDCl_3$) δ=162.1 ($C_{quat}$), 158.3 (d, J=236.6 Hz, $C_{quat}$), 133.6 ($C_{quat}$), 129.14 ($C_{quat}$), 127.8 (d, J=10.4 Hz, CH), 114.6 (d, J=27.1 Hz, CH), 113.0 (d, J=9.5 Hz, CH), 108.5 (d, J=5.0 Hz, CH), 106.8 (d, J=23.3 Hz, $C_{quat}$), 69.4 ($CH_2$), 35.2 ($CH_2$), 20.1 (CH), 19.3 ($CH_3$). $^{19}F$ NMR (376 MHz, $d_6$-DMSO) δ=−121.5.

2-((Triisopropylsilyl)oxy)ethyl 5-fluoro-1H-indole-2-carboxylate (12i)

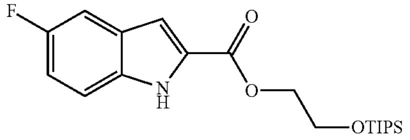

Prepared by general method K using 2-((trimethylsilyl)oxy)ethan-1-ol (188 mg, 1.40 mmol), 5-fluoro-1H-indole-2-carboxylic acid (300 mg, 1.67 mmol), triphenylphosphine (439 mg, 1.67 mmol), diisopropyl azodicarboxylate (329 µL, 1.67 mmol), in dry tetrahydrofuran (2.8 mL). The crude product was passed through a short silica gel column eluting with dichloromethane-diethyl ether (1:1) then purified chromatographically on silica gel (eluting cyclohexane-ethyl acetate 85:15) to provide the title compound 12i as a beige solid (417 mg, 79% yield). LC-MS (ESI+) Found: $[M+H]^+$, 380.2.

2-((tert-Butoxycarbonyl)amino)ethyl 5-fluoro-1H-indole-2-carboxylate (12j)

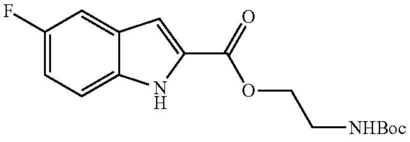 [SMILES: CC(C)(C)OC(=O)NCCOC(=O)c1cc2cc(F)ccc2[nH]1]

Prepared by general method K using N-Boc-ethanolamine (216 µL, 1.40 mmol), 5-fluoro-1H-indole-2-carboxylic acid (300 mg, 1.67 mmol), triphenylphosphine (439 mg, 1.67 mmol), diisopropyl azodicarboxylate (329 µL, 1.67 mmol), in dry tetrahydrofuran (2.8 mL). The crude product was passed through a short silica gel column eluting with dichloromethane-diethyl ether (1:1) then purified chromatographically on silica gel (eluting cyclohexane-ethyl acetate 70:30) to provide the title compound 12j as a white solid (339 mg, 75% yield). LC-MS (ESI+) Found: $[M+H]^+$, 323.1.

5-Fluoro-N-isobutyl-1H-indole-2-carboxamide (12k)

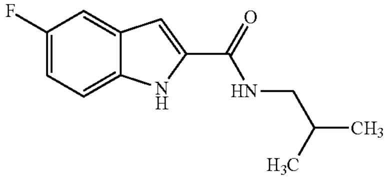 [SMILES: CC(C)CNC(=O)c1cc2cc(F)ccc2[nH]1]

Prepared by general method L using 5-fluoro-1H-indole-2-carboxylic acid (300 mg, 1.67 mmol), isobutylamine (166 µL, 1.67 mmol), N,N-diisopropylethylamine (875 µL, 5.02 mmol) and O-(7-azabenzotriazol-1-yl-N,N,N',N'-tetramethyluronium hexafluorophosphate (700 mg, 1.84 mmol) in N,N-dimethylformamide (5.6 mL). The crude product was purified chromatographically on silica gel (eluting cyclohexane-ethyl acetate 80:20) to provide the title compound 12k as a white solid (307 mg, 78% yield). $^1H$ NMR (400 MHz, $d_6$-DMSO) δ=11.65 (s, 1H), 8.49 (t, J=5.9 Hz, 1H), 7.51-7.25 (m, 2H), 7.21-7.10 (m, 1H), 7.02 (td, J=9.3, 2.6 Hz, 1H), 3.23-2.95 (m, 2H), 1.86 (h, J=6.8 Hz, 1H), 0.90 (d, J=6.7 Hz, 6H). $^{13}C$ NMR (100 MHz, $d_6$-DMSO) δ=160.8 ($C_{quat}$), 157.1 (d, J=232.3 Hz, $C_{quat}$), 133.7 ($C_{quat}$), 133.1 ($C_{quat}$), 127.2 (d, J=10.9 Hz, $C_{quat}$), 113.4 (d, J=10.0 Hz, CH), 111.8 (d, J=26.8 Hz, CH), 105.6 (d, J=22.6 Hz, CH), 102.3 (d, J=5.08 Hz, CH), 46.3 ($CH_2$), 28.2 (CH), 20.2 ($CH_3$). $^{19}F$ NMR (376 MHz, $d_6$-DMSO) δ=−124.1 (td, J=9.6, 4.7 Hz).

5-Fluoro-N-isopentyl-1H-indole-2-carboxamide (12l)

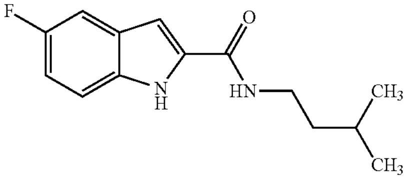 [SMILES: CC(C)CCNC(=O)c1cc2cc(F)ccc2[nH]1]

Prepared by general method L using 5-fluoro-1H-indole-2-carboxylic acid (300 mg, 1.67 mmol), isoamylamine (194 µL, 1.46 mmol), N,N-diisopropylethylainine (875 µL, 5.02 mmol) and O-(7-azabenzotriazol-1-yl-N,N,N',N'-tetramethyluronium hexafluorophosphate (700 mg, 1.84 mmol) in N,N-dimethylformamide (5.6 mL). The crude product was purified chromatographically on silica gel (eluting cyclohexane-ethyl acetate 85:15) to provide the title compound 12l as a white solid (303 mg, 73% yield). $^1H$ NMR (400 MHz, $d_6$-DMSO) δ=11.66-11.61 (m, 1H), 8.45 (t, J=5.7 Hz, 1H), 7.45-7.34 (m, 2H), 7.09 (dd, J=2.2, 0.9 Hz, 1H), 7.02

(ddd, J=9.6, 8.9, 2.6 Hz, 1H), 3.35-3.26 (m, 2H), 1.62 (dq, J=13.3, 6.7 Hz, 1H), 1.48-1.39 (m, 2H), 0.91 (d, J=6.6 Hz, 6H). $^{13}C$ NMR (100 MHz, $d_6$-DMSO) δ=160.6 ($C_{quat}$), 157.2 (d, J=232.2 Hz, $C_{quat}$), 133.7 ($C_{quat}$), 133.1 ($C_{quat}$), 127.2 (d, J=10.4 Hz, $C_{quat}$), 113.4 (d, J=9.3 Hz, CH), 111.7 (d, J=26.5 Hz, CH), 105.6 (d, J=23.3 Hz, CH), 102.2 (d, J=5.1 Hz, CH), 38.2 ($CH_2$), 37.0 ($CH_2$), 25.3 (CH), 22.4 ($CH_3$). $^{19}F$ NMR (376 MHz, $d_6$-DMSO) δ=−124.1 (td, J=9.6, 4.7 Hz).

Ethyl 5-fluoro-3-iodo-1H-indole-2-carboxylae (13a)

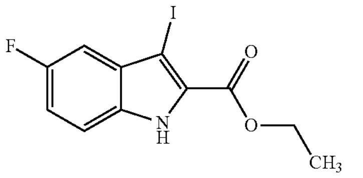 [SMILES: CCOC(=O)c1[nH]c2ccc(F)cc2c1I]

Prepared by general method C using iodine (2.35 g, 9.26 mmol) in N,N-dimethylformamide (13 mL) dropped to the solution of indole 12a (1.90 g, 9.17 mmol) and potassium hydroxide (1.80 g, 32.1 mmol) in N,N-dimethylformamide (15 mL). The mixture was stirred at room temperature for 3.5 hours. The precipitate was dried at 50° C. under reduced pressure during 72 hours and the beige solid obtained 13a (2.84 g, 92% yield) was used without further purification for the next step. $^{1}H$ NMR (400 MHz, $d_6$-DMSO) δ=12.37 (s, 1H), 7.50 (dd, J=9.0, 4.5 Hz, 1H), 7.21 (td, J=9.2, 2.5 Hz, 1H), 7.13 (dd, J=9.4, 2.4 Hz, 1H), 4.38 (q, J=7.1 Hz, 2H), 1.38 (t, J=7.1 Hz, 3H). $^{13}C$ NMR (100 MHz, $d_6$-DMSO) δ=160.1 ($C_{quat}$), 158.0 (d, J=235.8 Hz, $C_{quat}$), 133.6 ($C_{quat}$), 131.0 (d, J=11.2 Hz, $C_{quat}$), 128.6 ($C_{quat}$), 114.9 (d, J=33.4 Hz, CH), 114.8 (d, J=2.8 Hz, CH), 107.6 (d, J=24.1 Hz, CH), 65.0 (d, J=5.9 Hz, $C_{quat}$), 60.9 ($CH_2$), 14.2 2 ($CH_3$). $^{19}F$ NMR (376 MHz, $d_6$-DMSO) δ=−121.6 (td, J=9.5, 4.6 Hz).

Ethyl 5-chloro-3-iodo-1H-indole-2-carboxylate (13b)

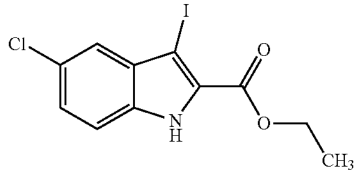 [SMILES: CCOC(=O)c1[nH]c2ccc(Cl)cc2c1I]

Prepared by general method C using a solution of iodine (2.29 g, 9.03 mmol) in N,N-dimethylformamide (13 mL) dropped to the solution of indole 12b (2.0 g, 8.94 mmol) and potassium hydroxide (1.76 g, 31.3 mmol) in N,N-dimethylformamide (15 mL). The mixture was stirred at room temperature for 4 hours. The precipitate was dried at 50° C. under reduced pressure during 72 hours and the beige solid obtained 13b (2.79 g, 89% yield) was used without further purification for the next step. $^{1}H$ NMR (400 MHz, $d_6$-DMSO) δ=12.36 (s, 1H), 7.48 (d, J=1.6 Hz, 1H), 7.43 (d, J=8.6 Hz, 1H), 7.19 (dd, J=8.6, 1.9 Hz, 1H), 4.38 (q, J=7.1 Hz, 2H), 1.38 (t, J=7.1 Hz, 3H). $^{13}C$ NMR (100 MHz, $d_6$-DMSO) δ=160.1 ($C_{quat}$), 136.9 ($C_{quat}$), 130.5 ($C_{quat}$), 129.5 ($C_{quat}$), 128.0 ($C_{quat}$), 124.1 (CH), 121.7 (CH), 112.3 (CH), 66.0 ($C_{quat}$), 61.0 ($CH_2$), 14.2 ($CH_3$).

Ethyl 6-chloro-3-iodo-1H-indole-2-carboxylate (13c)

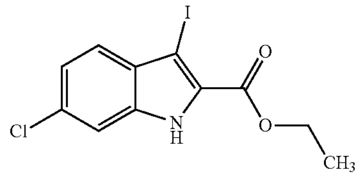 [SMILES: CCOC(=O)c1[nH]c2cc(Cl)ccc2c1I]

Prepared by general method C using a solution of iodine (573 mg, 2.26 mmol) in N,N-dimethylformamide (3.3 mL) dropped to the solution of indole 12c (500 mg, 2.24 mmol) and potassium hydroxide (440 mg, 7.83 mmol) in N,N-dimethylformamide (3.8 mL). The mixture was stirred at room temperature for 4 hours. The precipitate was dried at 50° C. under reduced pressure during 72 hours and the beige solid obtained 13c (728 mg, 93% yield) was used without further purification for the next step. $^{1}H$ NMR (400 MHz, $d_6$-DMSO) δ=12.44 (s, 1H), 7.49 (d, J=8.7 Hz, 1H), 7.40 (d, J=2.0 Hz, 1H), 7.33 (dd, J=8.8, 2.1 Hz, 1H), 4.38 (q, J=7.1 Hz, 2H), 1.38 (t, J=7.1 Hz, 3H). $^{13}C$ NMR (100 MHz, $d_6$-DMSO) δ=160.1 ($C_{quat}$), 135.4 ($C_{quat}$), 131.7 ($C_{quat}$), 128.5 ($C_{quat}$), 126.0 (CH), 125.8 ($C_{quat}$), 121.3 (CH), 114.9 (CH), 64.8 ($C_{quat}$), 61.0 ($CH_2$), 14.2 ($CH_3$).

Isopropyl 5-fluoro-3-iodo-1H-indole-2-carboxylate (13d)

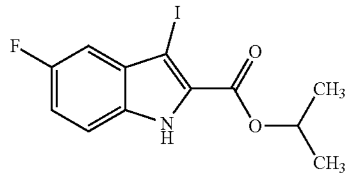 [SMILES: CC(C)OC(=O)c1[nH]c2ccc(F)cc2c1I]

Prepared by general method C using a solution of iodine (348 mg, 1.37 mmol) in N,N-dimethylformamide (2 mL) dropped to the solution of indole 12d (300 mg, 1.36 mmol) and potassium hydroxide (266 mg, 4.75 mmol) in N,N-dimethylformamide (2.3 mL). The mixture was stirred at room temperature for 4 hours. The precipitate was dried at 50° C. under reduced pressure during 72 hours and the pale yellow solid obtained 13d (421 mg, 90% yield) was used without further purification for the next step. $^{1}H$ NMR (400 MHz, $d_6$-DMSO) δ=12.30 (s, 1H), 7.50 (dd, J=8.9, 4.5 Hz, 1H), 7.21 (td, J=9.2, 2.3 Hz, 1H), 7.13 (dd, J=9.3, 2.1 Hz, 1H), 5.20 (p, J=6.2 Hz, 1H), 1.38 (d, J=6.2 Hz, 6H). $^{13}C$ NMR (100 MHz, $d_6$-DMSO) δ=159.7 ($C_{quat}$), 158.0 (d, J=236.2 Hz, $C_{quat}$), 133.5 ($C_{quat}$), 131.0 (d, J=10.6 Hz, $C_{quat}$), 128.9 ($C_{quat}$), 114.9 (d, J=19.5 Hz, CH), 114.7 (d, J=2.1 Hz, CH), 106.5 (d, J=24.4 Hz, CH), 68.7 (CH), 64.8 (d, J=5.6 Hz, $C_{quat}$), 21.8 ($CH_3$). $^{19}F$ NMR (376 MHz, $d_6$-DMSO) δ=−121.5 (td, J=9.5, 4.5 Hz).

Isopropyl 5-chloro-3-iodo-1H-indole-2-carboxylate (13e)

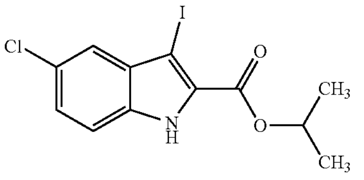 [SMILES: CC(C)OC(=O)c1[nH]c2ccc(Cl)cc2c1I]

Prepared by general method C using a solution of iodine (324 mg, 1.27 mmol) in N,N-dimethylformamide (1.8 mL) dropped to the solution of indole 12e (300 mg, 1.26 mmol) and potassium hydroxide (248 mg, 4.42 mmol) in N,N-dimethylformamide (2.1 mL). The mixture was stirred at room temperature for 4 hours. The precipitate was dried at 50° C. under reduced pressure during 72 hours and the pale yellow solid obtained 13e (396 mg, 86% yield) was used without further purification for the next step. $^{1}$H NMR (400 MHz, $d_6$-Acetone) δ=11.50 (s, 1H), 7.55 (d, J=8.8 Hz, 1H), 7.49 (d, J=2.0 Hz, 1H), 7.34 (dd, J=8.8, 2.0 Hz, 1H), 5.26 (h, J=6.2 Hz, 1H), 1.40 (d, J=6.3 Hz, 6H). $^{13}$C NMR (100 MHz, $d_6$-Acetone) δ=160.4 ($C_{quat}$), 136.2 ($C_{quat}$), 133.2 ($C_{quat}$), 130.1 ($C_{quat}$), 127.6 ($C_{quat}$), 127.2 (CH), 122.6 (CH), 115.4 (CH), 69.9 (CH), 63.9 ($C_{quat}$), 22.2 ($CH_3$).

Isobutyl 5-fluoro-3-iodo-1H-indole-2-carboxylate (13f)

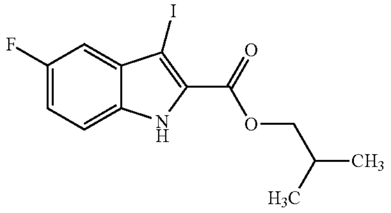 [SMILES: CC(C)COC(=O)c1[nH]c2ccc(F)cc2c1I]

Prepared by general method C using a solution of iodine (2.94 g, 11.60 mmol) in N,N-dimethylformamide (16.5 mL) dropped to the solution of indole 12f (2.70 g, 11.48 mmol) and potassium hydroxide (2.25 g, 40.17 mmol) in N,N-dimethylformamide (19 mL). The mixture was stirred at room temperature for 4 hours. The precipitate was dried at 50° C. under reduced pressure during 72 hours and the beige solid obtained 13f (3.82 g, 92% yield) was used without further purification for the next step. $^{1}$H NMR (400 MHz, $d_6$-DMSO) δ=12.34 (s, 1H), 7.51 (dd, J=9.0, 4.5 Hz, 1H), 7.21 (td, J=9.2, 2.5 Hz, 1H), 7.14 (dd, J=9.4, 2.4 Hz, 1H), 4.13 (d, J=6.4 Hz, 2H), 2.08 (dp, J=13.2, 6.6 Hz, 1H), 1.04 (d, J=6.7 Hz, 6H). $^{13}$C NMR (100 MHz, $d_6$-DMSO) δ=160.4 ($C_{quat}$), 158.0 (d, J=235.8 Hz, $C_{quat}$), 133.6 ($C_{quat}$), 131.0 (d, J=10.4 Hz, $C_{quat}$), 128.9 ($C_{quat}$), 114.9 (d, J=34.9 Hz, CH), 114.8 (d, J=1.80 Hz, CH), 106.6 (d, J=23.8 Hz, CH), 70.9 ($CH_2$), 64.8 (d, J=5.5 Hz, $C_{quat}$), 27.4 (CH), 19.1 ($CH_3$). $^{19}$F NMR (376 MHz, $d_6$-DMSO) δ=−121.5.

Isobutyl 5-chloro-3-iodo-1H-indole-2-carboxylate (13g)

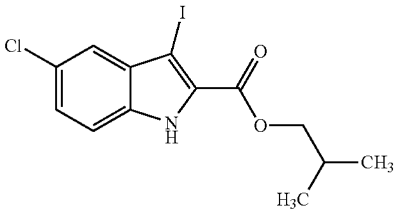 [SMILES: CC(C)COC(=O)c1[nH]c2ccc(Cl)cc2c1I]

Prepared by general method C using a solution of iodine (1.94 g, 7.62 mmol) in N,N-dimethylformamide (11 mL) dropped to the solution of indole 12g (1.90 g, 7.55 mmol) and potassium hydroxide (1.48 g, 26.42 mmol) in N,N-dimethylformamide (12.6 mL). The mixture was stirred at room temperature for 4 hours. The precipitate was dried at 50° C. under reduced pressure during 72 hours and the beige solid obtained 13g (2.57 g, 90% yield) was used without further purification for the next step. $^{1}$H NMR (400 MHz, $d_6$-DMSO) δ=12.43 (s, 1H), 7.50 (d, J=8.7 Hz, 1H), 7.41 (d, J=1.6 Hz, 1H), 7.34 (dd, J=8.8, 1.9 Hz, 1H), 4.14 (d, J=6.4 Hz, 2H), 2.08 (dp, J=13.2, 6.5 Hz, 1H), 1.05 (d, J=6.7 Hz, 6H). $^{13}$C NMR (100 MHz, $d_6$-DMSO) δ=160.3 ($C_{quat}$), 135.4 ($C_{quat}$), 131.8 ($C_{quat}$), 128.7 ($C_{quat}$), 126.1 (CH), 125.8 ($C_{quat}$), 121.4 (CH), 114.9 (CH), 71.0 ($CH_2$), 64.6 ($C_{quat}$), 27.4 (CH), 19.1 ($CH_3$).

Isopentyl 5-fluoro-3-iodo-1H-indole-2-carboxylate (13h)

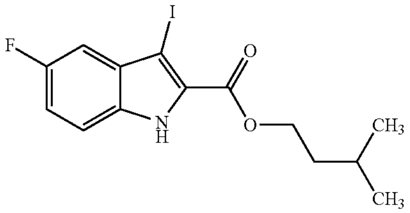 [SMILES: CC(C)CCOC(=O)c1[nH]c2ccc(F)cc2c1I]

Prepared by general method C using a solution of iodine (257 mg, 1.01 mmol) in N,N-dimethylformamide (1.4 mL) dropped to the solution of indole 12h (250 mg, 1.00 mmol) and potassium hydroxide (196 mg, 3.50 mmol) in N,N-dimethylformamide (1.7 mL). The mixture was stirred at room temperature for 4 hours. The precipitate was dried at 50° C. under reduced pressure during 72 hours and the beige solid obtained 13h (337 mg, 90% yield) was used without further purification for the next step. $^{1}$H NMR (400 MHz, $d_6$-DMSO) δ=12.34 (s, 1H), 7.51 (dd, J=9.0, 4.5 Hz, 1H), 7.21 (td, J=9.2, 2.5 Hz, 1H), 7.14 (dd, J=9.4, 2.4 Hz, 1H), 4.36 (m, 2H), 1.86 (dp, J=13.2, 6.6 Hz, 1H), 1.58-1.43 (m, 2H), 1.04 (d, J=6.7 Hz, 6H). $^{13}$C NMR (100 MHz, $d_6$-DMSO) δ=161.4 ($C_{quat}$), 158.0 (d, J=234.2 Hz, $C_{quat}$), 133.6 ($C_{quat}$), 131.0 (d, J=10.4 Hz, $C_{quat}$), 128.9 ($C_{quat}$), 114.9 (d, J=34.9 Hz, CH), 114.8 (d, J=1.80 Hz, CH), 106.6 (d, J=23.8 Hz, CH), 70.9 ($CH_2$), 66.8 (d, J=5.5 Hz, $C_{quat}$), 65.4 ($CH_2$), 36.2 ($CH_2$), 24.3 (CH), 22.3 ($CH_3$). $^{19}$F NMR (376 MHz, $d_6$-DMSO) δ=−122.5.

2-((Triisopropylsilyl)oxy)ethyl 5-fluoro-3-iodo-1H-indole-2-carboxylate (13i)

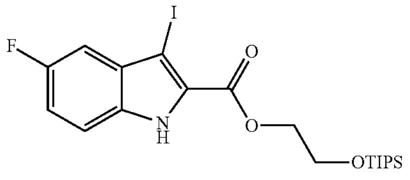

Prepared by general method C using a solution of iodine (169 mg, 0.67 mmol) in N,N-dimethylformamide (1 mL) dropped to the solution of indole 12i (250 mg, 0.66 mmol) and potassium hydroxide (129 mg, 2.30 mmol) in N,N-dimethylformamide (1.1 mL). The mixture was stirred at room temperature for 4 hours. The precipitate was dried at 50° C. under reduced pressure during 72 hours and the yellow solid obtained 13i (223 mg, 67% yield) was used without further purification for the next step. LC-MS (ESI+) Found: $[M+H]^+$, 506.1.

2-((tert-Butoxycarbonyl)amino)ethyl 5-fluoro-3-iodo-1H-indole-2-carboxylate (13j)

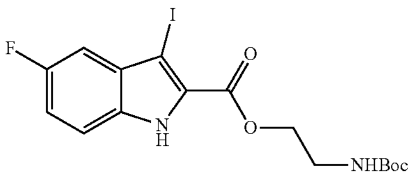 [SMILES: CC(C)(C)OC(=O)NCCOC(=O)c1[nH]c2ccc(F)cc2c1I]

Prepared by general method C using a solution of iodine (200 mg, 0.78 mmol) in NN-dimethylformamide (1.1 mL) dropped to the solution of indole 12j (250 mg, 0.78 mmol) and potassium hydroxide (152 mg, 2.71 mmol) in N,N-dimethylformamide (1.3 mL). The mixture was stirred at room temperature for 4 hours. The precipitate was dried at 50° C. under reduced pressure during 72 hours and the beige solid obtained 13j (196 mg, 56% yield) was used without further purification for the next step. LC-MS (ESI+) Found: $[M+H]^+$, 449.0.

5-Fluoro-3-iodo-N-isobutyl-1H-indole-2-carboxamide (13k)

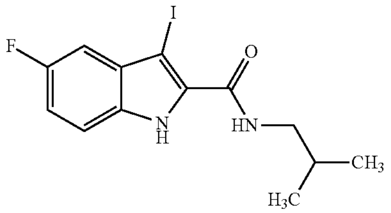 [SMILES: CC(C)CNC(=O)c1[nH]c2ccc(F)cc2c1I]

Prepared by general method C using a solution of iodine (274 mg, 1.08 mmol) in N,N-dimethylformamide (1.5 mL) dropped to the solution of indole 12k (250 mg, 1.07 mmol) and potassium hydroxide (210 mg, 3.74 mmol) in N,N-dimethylformamide (1.8 mL). The precipitate was dried at 50° C. under reduced pressure during 72 hours and the beige solid obtained 13k (316 mg, 82% yield) was used without further purification for the next step. $^1$H NMR (400 MHz, $d_6$-DMSO) δ=12.12 (s, 1H), 7.98 (t, J=5.6 Hz, 1H), 7.46 (dd, J=8.9, 4.5 Hz, 1H), 7.16-7.06 (m, 2H), 3.18 (t, J=6.3 Hz, 2H), 1.87 (dq, J=13.4, 6.7 Hz, 1H), 0.97 (d, J=6.7 Hz, 6H). $^{13}$C NMR (100 MHz, $d_6$-DMSO) δ=160.4 ($C_{quat}$), 157.8 (d, J=233.9 Hz, $C_{quat}$), 134.3 ($C_{quat}$), 132.6 ($C_{quat}$), 130.7 (d, J=10.7 Hz, $C_{quat}$), 114.1 (d, J=10.0 Hz, CH), 113.1 (d, J=26.5 Hz, CH), 106.0 (d, J=24.1 Hz, CH), 59.0 (d, J=5.1 Hz, $C_{quat}$), 46.5 ($CH_2$), 28.1 (CH), 20.2 ($CH_3$). $^{19}$F NMR (376 MHz, $d_6$-DMSO) δ=−122.3 (td, J=9.4, 4.5 Hz).

5-Fluoro-3-iodo-N-isopentyl-1H-indole-2-carboxamide (13l)

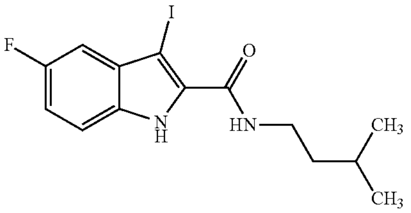

Prepared by general method C using a solution of iodine (258 mg, 1.02 mmol) in N,N-dimethylformamide (1.5 mL) dropped to the solution of indole 12l (250 mg, 1.01 mmol) and potassium hydroxide (198 mg, 3.52 mmol) in N,N-dimethylformamide (1.7 mL). The precipitate was dried at 50° C. under reduced pressure during 72 hours and the beige solid obtained 13l (297 mg, 79% yield) was used without further purification for the next step. $^1$H NMR (400 MHz, $d_6$-DMSO) δ=12.09 (s, 1H), 7.96 (t, J=5.6 Hz, 1H), 7.45 (dd, J=8.9, 4.5 Hz, 1H), 7.18-7.05 (m, 2H), 3.39-3.30 (m, 2H), 1.72 (dp, J=13.4, 6.7 Hz, 1H), 1.47 (dt, J=8.1, 7.0 Hz, 2H), 0.93 (d, J=6.6 Hz, 6H). $^{13}$C NMR (100 MHz, $d_6$-DMSO) δ=160.3 ($C_{quat}$), 157.8 (d, J=234.7 Hz, $C_{quat}$), 134.2 ($C_{quat}$), 132.6 ($C_{quat}$), 130.7 (d, J=10.3 Hz, $C_{quat}$), 114.1 (d, J=9.7 Hz, CH), 113.1 (d, J=26.3 Hz, CH), 59.0 (d, J=5.2 Hz, $C_{quat}$), 37.9 ($CH_2$), 37.3 ($CH_2$), 25.2 (CH), 22.4 ($CH_3$). $^{19}$F NMR (376 MHz, $d_6$-DMSO) δ=−122.3 (td, J=9.8, 4.5 Hz).

Ethyl 3-ethynyl-5-fluoro-1H-indole-2-carboxylate (14a)

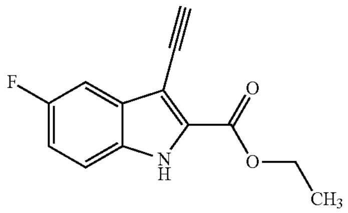 [SMILES: C#Cc1c(C(=O)OCC)[nH]c2ccc(F)cc12]

Prepared by general method F using 13a (2.50, 7.50 mmol), dry triethylamine (5.23 mL, 37.5 mmol), bis(triphenylphosphine)palladium(II) dichloride (263 mg, 0.38 mmol), copper(I) iodide (143 mg, 0.75 mmol), trimethylsilylacetylene (1.60 mL, 11.3 mmol) and dry tetrahydrofuran (38 mL). The TMS-deprotection was realized using 1M solution of tetrabutylammonium fluoride in tetrahydrofuran (11.3 mL, 11.3 mmol) and the crude product was purified chromatographically on silica gel (eluting cyclohexane-ethyl acetate 90:10) to provide the title compound 14a as a pale yellow solid (1.14 g, 66% yield). $^{1}$H NMR (400 MHz, $d_6$-DMSO) δ=12.32 (s, 1H), 7.51 (dd, J=9.2, 4.3 Hz, 1H), 7.34 (dd, J=9.0, 2.4 Hz, 1H), 7.22 (td, J=9.3, 2.6 Hz, 1H), 4.44 (s, 1H), 4.37 (q, J=7.1 Hz, 2H), 1.35 (t, J=7.1 Hz, 3H). $^{13}$C NMR (100 MHz, $d_6$-DMSO) δ=159.9 ($C_{quat}$), 158.0 (d, J=237.5 Hz, $C_{quat}$), 132.5 ($C_{quat}$), 130.5 ($C_{quat}$), 129.0 (d, J=10.3 Hz, $C_{quat}$), 115.8 (d, J=10.2 Hz, CH), 114.6 (d, J=6.7 Hz, CH), 104.6 (d, J=23.5 Hz, CH), 101.3 (d, J=5.2 Hz, $C_{quat}$), 86.5 (CH), 76.0 ($C_{quat}$), 60.9 ($CH_2$), 14.1 ($CH_3$). $^{19}$F NMR (375 MHz, $d_6$-DMSO) δ=−121.4.

Ethyl 5-chloro-3-ethynyl-1H-indole-2-carboxylate (14b)

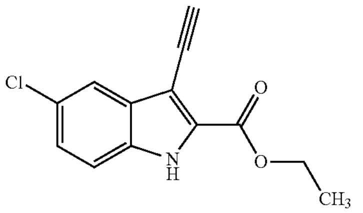 [SMILES: C#Cc1c(C(=O)OCC)[nH]c2ccc(Cl)cc12]

Prepared by general method F using 13b (2.50, 7.15 mmol), dry triethylamine (5 mL, 35.8 mmol), bis(triphenylphosphine)palladium(II) dichloride (251 mg, 0.36 mmol), copper(I) iodide (136 mg, 0.72 mmol), trimethylsilylacetylene (1.5 mL, 10.7 mmol) and dry tetrahydrofuran (36 mL). The TMS-deprotection was realized using 1M solution of tetrabutylammonium fluoride in tetrahydrofuran (10.7 mL, 10.7 mmol) and the crude product was purified chromatographically on silica gel (eluting cyclohexane-ethyl acetate 90:10) to provide the title compound 14b as a pale yellow solid (1.15 g, 65% yield). $^{1}$H NMR (400 MHz, $d_6$-DMSO) δ=12.31 (s, 1H), 7.65 (d, J=8.7 Hz, 1H), 7.50 (d, J=1.6 Hz, 1H), 7.20 (dd, J=8.6, 1.9 Hz, 1H), 4.43 (d, J=26.4 Hz, 1H), 4.42-4.35 (m, 2H), 1.35 (t, J=7.1 Hz, 3H). $^{13}$C NMR (100 MHz, $d_6$-DMSO) δ=159.9 ($C_{quat}$), 136.0 ($C_{quat}$), 130.3 ($C_{quat}$), 129.9 ($C_{quat}$), 127.4 ($C_{quat}$), 122.0 (CH), 121.8 (CH), 112.5 (CH), 101.5 ($C_{quat}$), 86.7 (CH), 75.9 ($C_{quat}$), 61.0 ($CH_2$), 14.2 ($CH_3$).

Ethyl 6-chloro-3-ethynyl-1H-indole-2-carboxylate (14c)

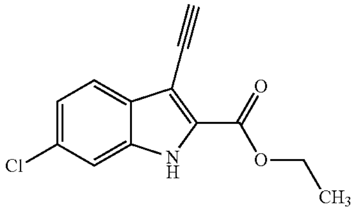 [SMILES: C#Cc1c(C(=O)OCC)[nH]c2cc(Cl)ccc12]

Prepared by general method F using 13c (680 mg, 1.95 mmol), dry triethylamine (1.36 mL, 9.73 mmol), bis(triphenylphosphine)palladium(II) dichloride (68 mg, 0.097 mmol), copper(I) iodide (37 mg, 0.19 mmol), trimethylsilylacetylene (404 μL, 2.92 mmol) and dry tetrahydrofuran (10 mL). The TMS-deprotection was realized using 1M solution of tetrabutylammonium fluoride in tetrahydrofuran (2.92 mL, 2.92 mmol) and the crude product was purified chromatographically on silica gel (eluting cyclohexane-ethyl acetate 90:10) to provide the title compound 14c as a pale yellow solid (306 mg, 63% yield). $^{1}$H NMR (400 MHz, $d_6$-DMSO) δ=12.32 (s, 1H), 7.65 (d, J=8.6 Hz, 1H), 7.52-7.47 (m, 1H), 7.20 (dd, J=8.6, 1.9 Hz, 1H), 4.48 (s, 1H), 4.38 (q, J=7.0 Hz, 2H), 1.36 (t, J=7.1 Hz, 3H). $^{13}$C NMR (100 MHz, $d_6$-DMSO) δ=159.9 ($C_{quat}$), 135.9 ($C_{quat}$), 130.2 ($C_{quat}$), 129.9 ($C_{quat}$), 127.4 ($C_{quat}$), 122.0 (CH), 121.8 (CH), 112.5 (CH), 101.5 ($C_{quat}$), 86.7 (CH), 75.9 ($C_{quat}$), 61.0 ($CH_2$), 14.1 ($CH_3$).

Isopropyl 3-ethynyl-5-fluoro-1H-indole-2-carboxylate (14d)

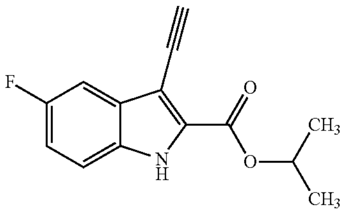 [SMILES: C#Cc1c(C(=O)OC(C)C)[nH]c2ccc(F)cc12]

Prepared by general method F using 13d (380 mg, 1.09 mmol), dry triethylamine (762 μL, 5.47 mmol), bis(triphenylphosphine)palladium(II) dichloride (38 mg, 0.055 mmol), copper(I) iodide (21 mg, 0.11 mmol), trimethylsilylacetylene (227 μL, 1.64 mmol) and dry tetrahydrofuran (5.5 mL). The TMS-deprotection was realized using 1M solution of tetrabutylammonium fluoride in tetrahydrofuran (1.64 mL, 1.64 mmol) and the crude product was purified chromatographically on silica gel (eluting cyclohexane-ethyl acetate 90:10) to provide the title compound 14d as a pale yellow solid (159 mg, 59% yield). $^{1}$H NMR (400 MHz, $d_6$-DMSO) δ=12.26 (s, 1H), 7.51 (dd, J=9.0, 4.5 Hz, 1H), 7.33 (dd, J=9.1, 2.4 Hz, 1H), 7.22 (td, J=9.2, 2.5 Hz, 1H), 5.18 (h, J=6.2 Hz, 1H), 4.43 (s, 1H), 1.36 (d, J=6.2 Hz, 6H). $^{13}$C NMR (100 MHz, $d_6$-DMSO) δ=159.5 ($C_{quat}$), 158.0 (d, J=237.1 Hz, $C_{quat}$), 132.4 ($C_{quat}$), 130.8 ($C_{quat}$), 129.0 (d, J=10.3 Hz, $C_{quat}$), 114.8 (d, J=4.9 Hz, CH), 114.6 (d, J=12.7 Hz, CH), 104.5 (d, J=23.6 Hz, C), 101.2 (d, J=5.2 Hz, $C_{quat}$), 86.4 (CH), 76.1 (CH), 68.7 (CH), 21.7 ($CH_3$). $^{19}$F NMR (375 MHz, $d_6$-DMSO) δ=−121.7 (td, J=9.3, 4.5 Hz).

Isopropyl 5-chloro-3-ethynyl-1H-indole-2-carboxylate (14e)

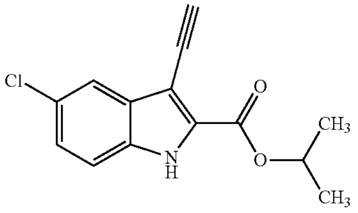 [SMILES: C#Cc1c(C(=O)OC(C)C)[nH]c2ccc(Cl)cc12]

Prepared by general method F using 13e (350 mg, 0.96 mmol), dry triethylamine (671 μL, 4.81 mmol), bis(triphenylphosphine)palladium(II) dichloride (34 mg, 0.048 mmol), copper(I) iodide (18 mg, 0.096 mmol), trimethylsilylacetylene (200 µL, 1.44 mmol) and dry tetrahydrofuran (5 mL). The TMS-deprotection was realized using 1M solution of tetrabutylammonium fluoride in tetrahydrofuran (1.44 mL, 1.44 mmol) and the crude product was purified chromatographically on silica gel (eluting cyclohexane-ethyl acetate 90:10) to provide the title compound 14e as a pale yellow solid (134 mg, 53% yield). $^1$H NMR (400 MHz, $d_6$-DMSO) δ=12.34 (s, 1H), 7.61 (d, J=1.9 Hz, 1H), 7.51 (d, J=8.8 Hz, 1H), 7.35 (dd, J=8.8, 2.0 Hz, 1H), 5.18 (p, J=6.2 Hz, 1H), 4.45 (s, 1H), 1.36 (d, J=6.2 Hz, 6H). $^{13}$C NMR (100 MHz, $d_6$-DMSO) δ=159.4 ($C_{quat}$), 134.1 ($C_{quat}$), 130.6 ($C_{quat}$), 129.6 ($C_{quat}$), 126.0 ($C_{quat}$), 126.0 (CH), 119.2 (CH), 114.9 (CH), 100.7 ($C_{quat}$), 86.6 (CH), 75.8 ($C_{quat}$), 68.8 (CH), 21.7 ($CH_3$).

Isobutyl 3-ethynyl-5-fluoro-1H-indole-2-carboxylate (14f)

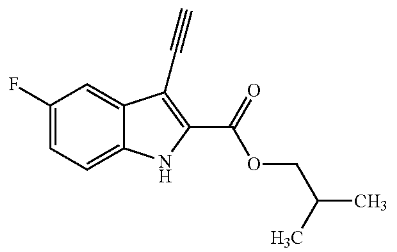 [SMILES: C#Cc1c(C(=O)OCC(C)C)[nH]c2ccc(F)cc12]

Prepared by general method F using 13f (3.70 g, 10.25 mmol), dry triethylamine (7.14 mL, 51.2 mmol), bis(triphenylphosphine)palladium(II) dichloride (360 mg, 0.51 mmol), copper(I) iodide (195 mg, 1.02 mmol), trimethylsilylacetylene (2.13 mL, 15.4 mmol) and dry tetrahydrofuran (50 mL). The TMS-deprotection was realized using 1M solution of tetrabutylammonium fluoride in tetrahydrofuran (15.4 mL, 15.4 mmol) and the crude product was purified chromatographically on silica gel (eluting cyclohexane-ethyl acetate 90:10) to provide the title compound 14f as a pale yellow solid (1.71 g, 65% yield). $^1$H NMR (400 MHz, $d_6$-DMSO) δ=12.78 (s, 1H), 8.02-7.94 (m, 1H), 7.81 (dd, J=9.1, 2.6 Hz, 1H), 7.69 (td, J=9.2, 2.6 Hz, 1H), 4.93 (s, 1H), 4.60 (d, J=6.3 Hz, 2H), 2.50 (h, J=6.6 Hz, 1H), 1.48 (d, J=6.7 Hz, 6H). $^{13}$C NMR (100 MHz, $d_6$-DMSO) δ=160.3 ($C_{quat}$), 158.0 (d, J=237.3 Hz, $C_{quat}$), 132.6 ($C_{quat}$), 130.5 ($C_{quat}$), 129.0 (d, J=10.8 Hz, $C_{quat}$), 114.8 (d, J=10.9 Hz, CH), 114.6 (d, J=6.2 Hz, CH), 104.6 (d, J=23.9 Hz, CH), 101.1 (d, J=5.5 Hz, $C_{quat}$), 86.5 (CH), 76.1 ($C_{quat}$), 70.8 ($CH_2$), 27.4 (CH), 19.0 ($CH_3$). $^{19}$F NMR (375 MHz, $d_6$-DMSO) δ=−121.8 (td, J=9.4, 4.5 Hz).

Isobutyl 5-chloro-3-ethynyl-1H-indole-2-carboxylate (14g)

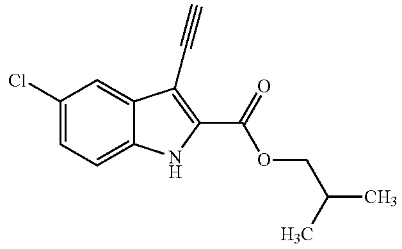 [SMILES: C#Cc1c(C(=O)OCC(C)C)[nH]c2ccc(Cl)cc12]

Prepared by general method F using 13g (2.40 g, 6.36 mmol), dry triethylamine (4.43 mL, 31.8 mmol), bis(triphenylphosphine)palladium(II) dichloride (223 mg, 0.32 mmol), copper(I) iodide (121 mg, 0.64 mmol), trimethylsilylacetylene (1.32 mL, 9.53 mmol) and dry tetrahydrofuran (32 mL). The TMS-deprotection was realized using 1M solution of tetrabutylammonium fluoride in tetrahydrofuran (9.53 mL, 9.53 mmol) and the crude product was purified chromatographically on silica gel (eluting cyclohexane-ethyl acetate 90:10) to provide the title compound 14g as a pale yellow solid (988 mg, 56% yield). $^1$H NMR (400 MHz, $d_6$-DMSO) δ=12.40 (s, 1H), 7.62 (d, J=2.0 Hz, 1H), 7.51 (d, J=8.8 Hz, 1H), 7.35 (dd, J=8.8, 2.1 Hz, 1H), 4.49 (s, 1H), 4.14 (d, J=6.3 Hz, 2H), 2.04 (dp, J=13.2, 6.6 Hz, 1H), 1.02 (d, J=6.7 Hz, 6H). $^{13}$C NMR (100 MHz, $d_6$-DMSO) δ=160.2 ($C_{quat}$), 134.2 ($C_{quat}$), 130.3 ($C_{quat}$), 129.7 ($C_{quat}$), 126.0 ($C_{quat}$), 126.0 (CH), 119.3 (CH), 114.9 (CH), 100.6 ($C_{quat}$), 86.6 (CH), 75.9 ($C_{quat}$), 70.9 ($CH_2$), 27.4 (CH), 19.0 ($CH_3$).

Isopentyl 3-ethynyl-5-fluoro-1H-indole-2-carboxylate (14h)

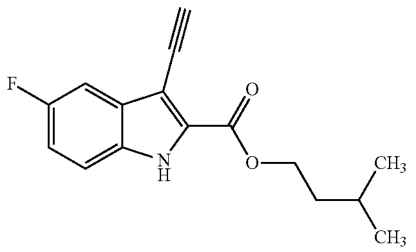 [SMILES: C#Cc1c(C(=O)OCCC(C)C)[nH]c2ccc(F)cc12]

Prepared by general method F using 13h (290 mg, 0.77 mmol), dry triethylamine (539 µL, 3.86 mmol), bis(triphenylphosphine)palladium(II) dichloride (27 mg, 0.039 mmol), copper(I) iodide (15 mg, 0.077 mmol), trimethylsilylacetylene (161 µL, 1.16 mmol) and dry tetrahydrofuran (4 mL). The TMS-deprotection was realized using 1M solution of tetrabutylammonium fluoride in tetrahydrofuran (1.16 mL, 1.16 mmol) and the crude product was purified chromatographically on silica gel (eluting cyclohexane-ethyl acetate 90:10) to provide the title compound 14h as a pale yellow solid (104 mg, 49% yield). $^1$H NMR (400 MHz, $d_6$-DMSO) δ=12.30 (s, 1H), 7.51 (dd, J=9.0, 4.5 Hz, 1H), 7.33 (dd, J=9.1, 2.3 Hz, 1H), 7.22 (td, J=9.3, 2.6 Hz, 1H), 4.45 (s, 1H), 4.36 (t, J=6.6 Hz, 2H), 1.84 (dq, J=13.4, 6.7 Hz, 1H), 1.62 (q, J=6.7 Hz, 2H), 0.94 (d, J=6.6 Hz, 6H). $^{13}$C NMR (100 MHz, $d_6$-DMSO) δ=160.0 ($C_{quat}$), 158.0 (d, J=237.4 Hz, $C_{quat}$), 132.5 ($C_{quat}$), 130.5 ($C_{quat}$), 129.0 (d, J=10.3 Hz, $C_{quat}$), 114.8 (d, J=11.3 Hz, CH), 114.6 (d, J=5.5 Hz, CH), 104.6 (d, J=23.3 Hz, CH), 101.2 (d, J=5.3 Hz, $C_{quat}$), 86.5 (CH), 76.0 ($C_{quat}$), 63.3 ($CH_2$), 36.9 ($CH_2$), 24.4 (CH), 22.3 ($CH_3$). $^{19}$F NMR (376 MHz, $d_6$-DMSO) δ=−121.4 (td, J=9.3, 4.5 Hz).

2-Hydroxyethyl 3-ethynyl-5-fluoro-1H-indole-2-carboxylate (14i)

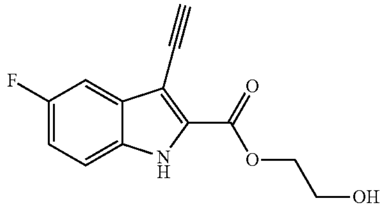 [SMILES: C#Cc1c(C(=O)OCCO)[nH]c2ccc(F)cc12]

Prepared by general method F using 13i (200 mg, 0.40 mmol), dry triethylamine (276 μL, 1.98 mmol), bis(triphenylphosphine)palladium(II) dichloride (14 mg, 0.020 mmol), copper(I) iodide (8 mg, 0.040 mmol), trimethylsilylacetylene (82 μL, 0.60 mmol) and dry tetrahydrofuran (2 mL). The TMS-deprotection was realized using 1M solution of tetrabutylammonium fluoride in tetrahydrofuran (1.19 mL, 1.19 mmol) and the crude product was purified chromatographically on silica gel (eluting dichloromethane-methanol 95:5) to provide the title compound 14i as a pale yellow solid (54 mg, 55% yield). LC-MS Found: $[M+H]^+$, 248.1.

2-((tert-Butoxycarbonyl)amino)ethyl 3-ethynyl-5-fluoro-1H-indole-2-carboxylate (14j)

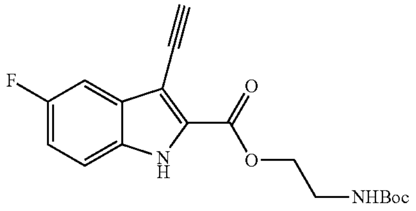 [SMILES: C#Cc1c(C(=O)OCCNC(=O)OC(C)(C)C)[nH]c2ccc(F)cc12]

Prepared by general method F using 13j (180 mg, 0.40 mmol), dry triethylamine (280 μL, 2.01 mmol), bis(triphenylphosphine)palladium(II) dichloride (14 mg, 0.020 mmol), copper(I) iodide (8 mg, 0.040 mmol), trimethylsilylacetylene (82 μL, 0.60 mmol) and dry tetrahydrofuran (2 mL). The TMS-deprotection was realized using 1M solution of tetrabutylammonium fluoride in tetrahydrofuran (1.20 mL, 1.20 mmol) and the crude product was purified chromatographically on silica gel (eluting cyclohexane-ethyl acetate 65:35) to provide the title compound 14j as a white solid (72 mg, 52% yield). LC-MS (ESI+) Found: $[M+H]^+$, 347.2.

3-Ethynyl-5-fluoro-N-isobutyl-1H-indole-2-carboxamide (14k)

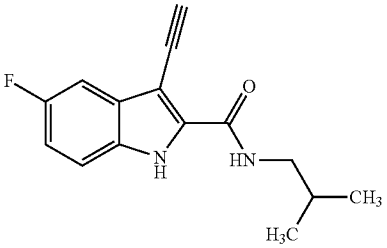 [SMILES: C#Cc1c(C(=O)NCC(C)C)[nH]c2ccc(F)cc12]

Prepared by general method F using 13k (250 mg, 0.69 mmol), dry triethylamine (484 μL, 3.47 mmol), bis(triphenylphosphine)palladium(II) dichloride (24 mg, 0.024 mmol), copper(I) iodide (13 mg, 0.069 mmol), trimethylsilylacetylene (144 μL, 1.04 mmol) and dry tetrahydrofuran (3.5 mL). The TMS-deprotection was realized using 1M solution of tetrabutylammonium fluoride in tetrahydrofuran (1.04 mL, 1.04 mmol) and the crude product was purified chromatographically on silica gel (eluting cyclohexane-ethyl acetate 85:15) to provide the title compound 14k as a white solid (110 mg, 61% yield). $^1$H NMR (400 MHz, $d_6$-DMSO) δ=12.56 (s, 1H), 7.98 (m, 1H), 7.83 (m, 1H), 7.21-7.13 (m, 2H), 4.97 (s, 1H), 4.62 (d, J=6.3 Hz, 2H), 1.88 (dq, J=13.4, 6.7 Hz, 1H), 1.07 (d, J=6.7 Hz, 6H). $^{13}$C NMR (100 MHz, $d_6$-DMSO) δ=160.3 ($C_{quat}$), 158.0 (d, J=234.3 Hz, $C_{quat}$), 133.6 ($C_{quat}$), 130.7 ($C_{quat}$), 129.0 (d, J=10.8 Hz, $C_{quat}$), 114.5 (d, J=10.9 Hz, CH), 114.4 (d, J=6.2 Hz, CH), 104.6 (d, J=23.9 Hz, CH), 101.1 (d, J=5.5 Hz, $C_{quat}$), 86.5 (CH), 76.1 ($C_{quat}$), 70.8 ($CH_2$), 27.4 (CH), 19.0 ($CH_3$). $^{19}$F NMR (375 MHz, $d_6$-DMSO) δ=−122.3 (td, J=9.4, 4.5 Hz).

3-Ethynyl-5-fluoro-N-isopentyl-1H-indole-2-carboxamide (14l)

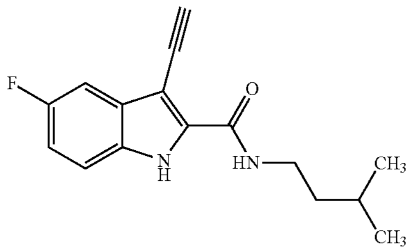 [SMILES: C#Cc1c(C(=O)NCCC(C)C)[nH]c2ccc(F)cc12]

Prepared by general method F using 13l (250 mg, 0.67 mmol), dry triethylamine (466 μL, 3.34 mmol), bis(triphenylphosphine)palladium(II) dichloride (23 mg, 0.033 mmol), copper(I) iodide (13 mg, 0.067 mmol), trimethylsilylacetylene (139 μL, 1.00 mmol) and dry tetrahydrofuran (3.5 mL). The TMS-deprotection was realized using 1M solution of tetrabutylammonium fluoride in tetrahydrofuran (1.00 mL, 1.00 mmol) and the crude product was purified chromatographically on silica gel (eluting cyclohexane-ethyl acetate 85:15) to provide the title compound 14l as a white solid (104 mg, 57% yield). $^1$H NMR (400 MHz, $d_6$-DMSO) δ=12.18 (s, 1H), 7.80 (t, J=5.7 Hz, 1H), 7.48 (ddd, J=8.9, 4.5, 0.6 Hz, 1H), 7.31 (dd, J=9.2, 2.6 Hz, 1H), 7.22-7.10 (m, 1H), 4.73 (s, 1H), 3.40 (td, J=7.2, 5.7 Hz, 2H), 1.68 (dp, J=13.4, 6.7 Hz, 1H), 1.46 (q, J=7.0 Hz, 2H), 0.92 (d, J=6.6 Hz, 6H). $^{13}$C NMR (100 MHz, $d_6$-DMSO) δ=159.4 ($C_{quat}$), 158.0 (d, J=235.3 Hz, $C_{quat}$), 135.8 ($C_{quat}$), 131.6 ($C_{quat}$), 128.7 (d, J=10.3 Hz, $C_{quat}$), 114.4 (d, J=9.5 Hz, CH), 113.4 (d, J=26.6 Hz, CH), 104.3 (d, J=23.7 Hz, CH), 95.2 (d, J=5.1 Hz, $C_{quat}$), 87.8 (CH), 76.4 ($C_{quat}$), 37.9 ($CH_2$), 37.3 ($CH_2$), 25.3 (CH), 22.4 ($CH_3$). $^{19}$F NMR (376 MHz, $d_6$-DMSO) δ=−121.8 (td, J=9.2, 4.6 Hz).

Ethyl 3-(1-((1-(2-((4-chlorophenyl)sulfonamido) ethyl)piperidin-4-yl)methyl)-1H-1,2,3-triazol-4-yl)-5-fluoro-1H-indole-2-carboxylate (15) (Code AB401)

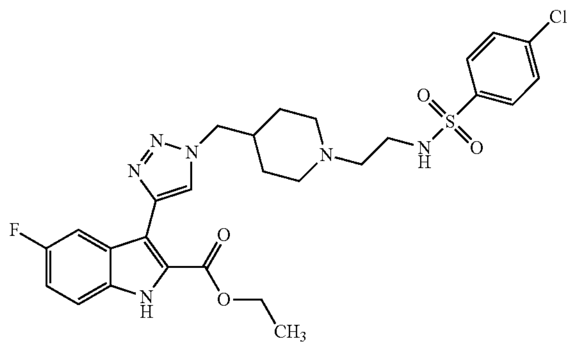 [SMILES: CCOC(=O)c1[nH]c2ccc(F)cc2c1-c1cn(CC2CCN(CCNS(=O)(=O)c3ccc(Cl)cc3)CC2)nn1]

Prepared by general method G using alkyne 14a (65 mg, 0.28 mmol), azide 5b (102 mg, 0.29 mmol), 2M aqueous of sodium ascorbate (492 μL, 0.98 mmol), 15% aqueous of copper(II) sulfate pentahydrate (410 μL, 0.25 mmol) and tetrahydrofuran-tert-butanol (703 μL). The crude product was purified chromatographically on silica gel (eluting gradient dichloromethane-methanol 98:2 to 96:4) to provide the title compound 15 as a pale yellow solid (121 mg, 73% yield). Mp 173° C. $^1$H NMR (400 MHz, $d_6$-DMSO) δ=12.07 (s, 1H), 8.56 (s, 1H), 8.08 (dd, J=10.3, 2.5 Hz, 1H), 7.83-7.78 (m, 2H), 7.70-7.58 (m, 3H), 7.52 (dd, J=9.0, 4.7 Hz, 1H), 7.24 (d, J=2.6 Hz, 1H), 4.37 (dt, J=14.0, 7.0 Hz, 4H), 2.85 (t, J=6.5 Hz, 2H), 2.70 (d, J=11.3 Hz, 2H), 2.27 (t, J=6.8 Hz, 2H), 1.82 (t, J=10.5 Hz, 3H), 1.46 (d, J=11.1 Hz, 2H), 1.35 (t, J=7.1 Hz, 3H), 1.24-1.17 (m, 2H). $^{13}$C NMR (100 MHz, $d_6$-DMSO) δ=160.9 ($C_{quat}$), 157.4 (d, J=234.3 Hz, $C_{quat}$), 140.3 ($C_{quat}$), 139.6 ($C_{quat}$), 137.1 ($C_{quat}$), 133.1 ($C_{quat}$), 129.3 (CH), 128.4 (CH), 125.9 (d, J=10.3 Hz, $C_{quat}$), 124.8 (CH), 123.8 ($C_{quat}$), 114.4 (d, J=26.3 Hz, CH), 113.9 (d, J=9.6 Hz, CH), 111.7 (d, J=5.8 Hz, $C_{quat}$), 107.4 (d, J=23.9 Hz, CH), 61.0 ($CH_2$), 57.0 ($CH_2$), 54.5 ($CH_2$), 52.6 ($CH_2$), 40.3 ($CH_2$), 36.5 (CH), 29.0 ($CH_2$), 14.2 ($CH_3$). $^{19}$F NMR (376 MHz, $d_6$-DMSO) δ=−122.4. HRMS (ESI+): calcd. for $C_{27}H_{31}ClFN_6O_4S$, 589.1799. Found: $[M+H]^+$, 589.1795 (−0.8 ppm error).

Ethyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate (16) (Code AB460)

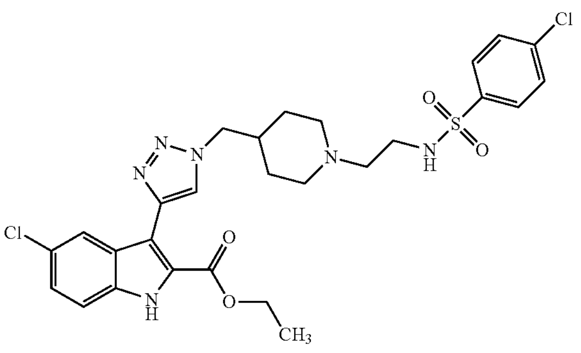 [SMILES: CCOC(=O)c1[nH]c2ccc(Cl)cc2c1-c1cn(CC2CCN(CCNS(=O)(=O)c3ccc(Cl)cc3)CC2)nn1]

Prepared by general method G using 14b (65 mg, 0.26 mmol), 5b (99 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 16 as a white solid (114 mg, 72% yield). Mp 68° C. $^1$H NMR (400 MHz, $d_6$-DMSO) δ=12.06 (s, 1H), 8.56 (s, 1H), 8.39 (d, J=8.7 Hz, 1H), 7.85-7.77 (m, 2H), 7.69-7.59 (m, 3H), 7.52 (dd, J=2.0, 0.6 Hz, 1H), 7.17 (dd, J=8.8, 2.0 Hz, 1H), 4.39 (t, J=7.1 Hz, 2H), 4.34 (d, J=6.8 Hz, 2H), 2.85 (t, J=6.7 Hz, 2H), 2.69 (dt, J=11.9, 3.5 Hz, 2H), 2.27 (t, J=6.8 Hz, 2H), 1.86-1.76 (m, 3H), 1.51-1.42 (m, 2H), 1.35 (t, J=7.1 Hz, 3H), 1.26-1.12 (m, 2H). $^{13}$C NMR (100 MHz, $d_6$-DMSO) δ 160.9 ($C_{quat}$), 140.1 ($C_{quat}$), 139.6 ($C_{quat}$), 137.1 ($C_{quat}$), 136.6 ($C_{quat}$), 130.0 ($C_{quat}$), 129.2 (CH), 128.4 (CH), 125.2 (CH), 125.1 (CH), 124.8 ($C_{quat}$), 123.1 ($C_{quat}$), 121.2 (CH), 112.0 ($C_{quat}$), 111.8 (CH), 60.9 ($CH_2$), 57.0 ($CH_2$), 54.5 ($CH_2$), 52.5 ($CH_2$), 40.2 ($CH_2$), 36.5 (CH), 29.0 ($CH_2$), 14.2 ($CH_3$). HRMS (ESI+) calcd. for $C_{27}H_{31}C_{12}N_6O_4S$, 605.1507. Found: $[M+H]^+$, 605.1499 (−1.4 ppm error).

Ethyl 6-chloro-3-(1-((1-(2-((4-chlorophenyl)sulfonamido)ethyl)piperidin-4-yl)methyl)-1H-1,2,3-triazol-4-yl)-1H-indole-2-carboxylate (17) (Code AB433)

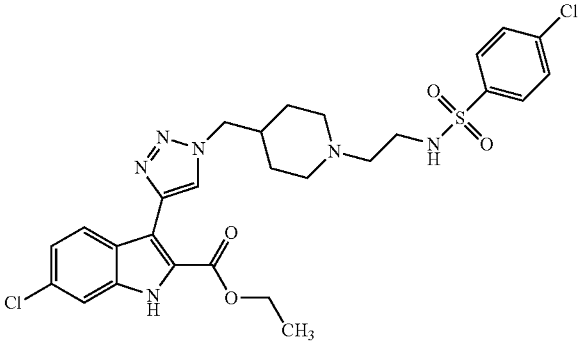 [SMILES: CCOC(=O)c1[nH]c2cc(Cl)ccc2c1-c1cn(CC2CCN(CCNS(=O)(=O)c3ccc(Cl)cc3)CC2)nn1]

Prepared by general method G using alkyne 14c (65 mg, 0.26 mmol), azide 5b (99 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 17 as a white solid (109 mg, 69% yield). Mp 94° C. $^1$H NMR (400 MHz, $d_6$-DMSO) δ=12.06 (s, 1H), 8.56 (s, 1H), 8.38 (d, J=8.8 Hz, 1H), 7.82-7.75 (m, 2H), 7.65 (dt, J=9.2, 2.4 Hz, 3H), 7.51 (d, J=1.8 Hz, 1H), 7.17 (d, J=10.7 Hz, 1H), 4.37 (dt, J=13.4, 6.8 Hz, 4H), 2.85 (t, J=6.2 Hz, 2H), 2.70 (d, J=11.2 Hz, 2H), 2.27 (t, J=6.7 Hz, 2H), 1.82 (t, J=10.5 Hz, 3H), 1.46 (d, J=11.1 Hz, 2H), 1.35 (t, J=7.1 Hz, 3H), 1.20 (dt, J=12.0, 6.0 Hz, 2H). $^{13}$C NMR (100 MHz, $d_6$-DMSO) δ=160.9 ($C_{quat}$), 140.0 ($C_{quat}$), 139.6 ($C_{quat}$), 137.1 ($C_{quat}$), 136.6 ($C_{quat}$), 130.1 ($C_{quat}$), 129.3 (CH), 128.4 (CH), 125.2 (CH), 125.1 (CH), 124.7 ($C_{quat}$), 123.1 ($C_{quat}$), 121.2 (CH), 111.9 ($C_{quat}$), 111.8 (CH), 60.9 ($CH_2$), 57.0 ($CH_2$), 54.5 ($CH_2$), 52.6 ($CH_2$), 40.3 ($CH_2$), 36.5 (CH), 29.0 ($CH_2$), 14.2 ($CH_3$). HRMS (ESI+): calcd. for $C_{27}H_{31}Cl_2N_6O_4S$, 605.1498. Found: $[M+H]^+$, 605.1499 (0.2 ppm error).

Ethyl 5-fluoro-3-(1-((1-(2-((4-methylphenyl)sulfonamido)ethyl)piperidin-4-yl)methyl)-1H-1,2,3-triazol-4-yl)-1H-indole-2-carboxylate (18) (Code AB504)

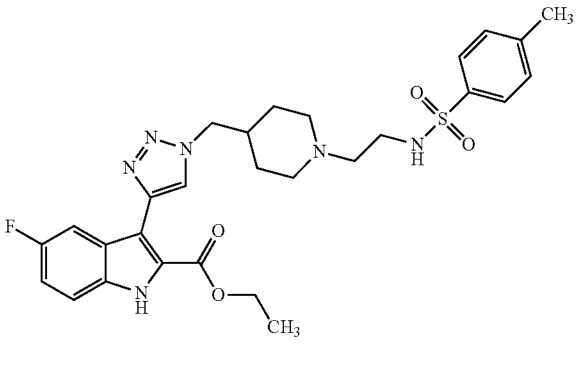 [SMILES: CCOC(=O)c1[nH]c2ccc(F)cc2c1-c1cn(CC2CCN(CCNS(=O)(=O)c3ccc(C)cc3)CC2)nn1]

Prepared by general method G using alkyne 14a (65 mg, 0.28 mmol), azide 5e (100 mg, 0.30 mmol), 2M aqueous of sodium ascorbate (492 μL, 0.98 mmol), 15% aqueous of copper(II) sulfate pentahydrate (410 μL, 0.25 mmol) and tetrahydrofuran-tert-butanol (703 μL). The crude product was purified chromatographically on silica gel (eluting gradient dichloromethane-methanol 98:2 to 96:4) to provide the title compound 18 as a white solid (94 mg, 59% yield). Mp 85° C. $^1$H NMR (400 MHz, $d_6$-DMSO) δ=12.09 (s, 1H), 8.60 (s, 1H), 8.09 (dd, J=10.4, 2.6 Hz, 1H), 7.70 (d, J=7.8 Hz, 2H), 7.53 (dd, J=9.0, 4.7 Hz, 1H), 7.40 (d, J=7.9 Hz, 3H), 7.22 (td, J=9.1, 2.7 Hz, 1H), 4.39 (q, J=6.8 Hz, 4H), 2.80 (q, J=6.4 Hz, 2H), 2.70 (d, J=10.9 Hz, 2H), 2.37 (s, 3H), 2.28 (t, J=6.9 Hz, 2H), 1.88-1.76 (m, 3H), 1.52-1.41 (m, 2H), 1.36 (t, J=7.1 Hz, 3H), 1.20 (qd, J=12.0, 3.8 Hz, 2H). $^{13}$C NMR (100 MHz, $d_6$-DMSO) δ=160.9 ($C_{quat}$), 157.4 (d, J=233.4 Hz, $C_{quat}$), 146.0 ($C_{quat}$), 140.4 ($C_{quat}$), 137.8 ($C_{quat}$), 133.1 ($C_{quat}$), 129.7 (CH), 126.6 (CH), 125.9 (d, J=10.3 Hz, $C_{quat}$), 124.9 (CH), 123.8 ($C_{quat}$), 114.5 (d, J=26.4 Hz, CH), 114.0 (d, J=10.3 Hz, CH), 111.6 (d, J=5.7 Hz, $C_{quat}$), 107.4 (d, J=24.8 Hz, CH), 60.9 ($CH_2$), 56.9 ($CH_2$), 54.2 ($CH_2$), 52.5 ($CH_2$), 40.3 ($CH_2$), 36.5 (CH), 29.1 ($CH_2$), 20.9 ($CH_3$), 14.2 ($CH_3$). $^{19}$F NMR (376 MHz, $d_6$-DMSO) δ=−122.4. HRMS (ESI+): calcd. for $C_{28}H_{34}FN_6O_4S$, 569.2336. Found: $[M+H]^+$, 569.2341 (0.8 ppm error).

Ethyl 5-chloro-3-(1-((1-(2-((4-methylphenyl)sulfonamido)ethyl)piperidin-4-yl)methyl)-1H-1,2,3-triazol-4-yl)-1H-indole-2-carboxylate (19) (Code AB505)

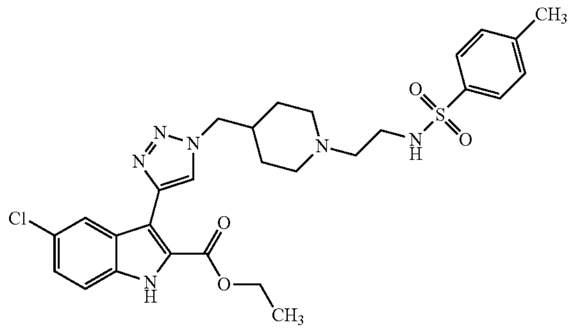 [SMILES: CCOC(=O)c1[nH]c2ccc(Cl)cc2c1-c1cn(CC2CCN(CCNS(=O)(=O)c3ccc(C)cc3)CC2)nn1]

Prepared by general method G using alkyne 14b (65 mg, 0.26 mmol), azide 5e (93 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 19 as a beige solid (103 mg, 67% yield). Mp 83° C. $^1$H NMR (400 MHz, $d_6$-Acetone) δ=11.15 (s, 1H), 8.69 (d, J=8.8 Hz, 1H), 8.65 (s, 1H), 7.78-7.72 (m, 2H), 7.56 (d, J=1.8 Hz, 1H), 7.42-7.37 (m, 2H), 7.20 (dd, J=8.8, 1.9 Hz, 1H), 6.07 (s, 1H), 4.46-4.38 (m, 4H), 2.97 (t, J=6.3 Hz, 2H), 2.70 (dt, J=12.0, 3.6 Hz, 2H), 2.40 (s, 3H), 2.37 (t, J=6.3 Hz, 2H), 1.99-1.85 (m, 3H), 1.57 (dt, J=14.1, 3.3 Hz, 2H), 1.38 (t, J=7.1 Hz, 3H), 1.36-1.27 (m, 2H). $^{13}$C NMR (100 MHz, $d_6$-Acetone) δ=161.8 ($C_{quat}$), 143.9 ($C_{quat}$), 141.7 ($C_{quat}$), 138.9 ($C_{quat}$), 137.7 ($C_{quat}$), 131.9 ($C_{quat}$), 130.4 (CH), 127.9 (CH), 126.9 (CH), 126.2 ($C_{quat}$), 125.8 (CH), 123.9 ($C_{quat}$), 122.2 (CH), 114.1 ($C_{quat}$), 112.5 (CH), 61.7 ($CH_2$), 57.4 ($CH_2$), 55.8 ($CH_2$), 53.6 ($CH_2$), 41.0 ($CH_2$), 38.0 (CH), 30.4 (CH), 21.4 ($CH_3$), 14.7 ($CH_3$). HRMS (ESI+): calcd. for $C_{28}H_{34}ClN_6O_4S$, 585.2041. Found: $[M+H]^+$, 585.2045 (0.7 ppm error).

Ethyl 6-chloro-3-(1-((1-(2-((4-methylphenyl)sulfonamido)ethyl)piperidin-4-yl)methyl)-1H-1,2,3-triazol-4-yl)-1H-indole-2-carboxylate (20) (Code AB503)

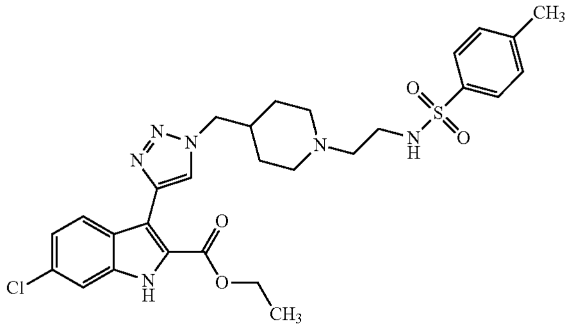 [SMILES: CCOC(=O)c1[nH]c2cc(Cl)ccc2c1-c1cn(CC2CCN(CCNS(=O)(=O)c3ccc(C)cc3)CC2)nn1]

Prepared by general method G using alkyne 14c (65 mg, 0.26 mmol), azide 5e (93 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 20 as a beige solid (104 mg, 68% yield). Mp 81° C. $^1$H NMR (400 MHz, $d_6$-DMSO) δ=12.06 (s, 1H), 8.56 (s, 1H), 8.38 (d, J=8.8 Hz, 1H), 7.71-7.64 (m, 2H), 7.51 (d, J=2.0 Hz, 1H), 7.38 (t, J=5.2 Hz, 3H), 7.17 (dd, J=8.8, 2.0 Hz, 1H), 4.42-4.32 (m, 4H), 2.80 (q, J=6.4 Hz, 2H), 2.70 (d, J=10.9 Hz, 2H), 2.37 (s, 3H), 2.27 (t, J=6.9 Hz, 2H), 1.86-1.77 (m, 3H), 1.50-1.43 (m, 2H), 1.35 (t, J=7.1 Hz, 3H), 1.20 (qd, J=12.0, 3.8 Hz, 2H). $^{13}$C NMR (100 MHz, $d_6$-DMSO) δ=160.9 ($C_{quat}$), 142.5 ($C_{quat}$), 140.0 ($C_{quat}$), 137.7 ($C_{quat}$), 136.6 ($C_{quat}$), 130.0 ($C_{quat}$), 129.6 (CH), 126.5 (CH), 125.2 (CH), 125.1 (CH), 124.7 ($C_{quat}$), 123.1 ($C_{quat}$), 121.2 (CH), 111.9 ($C_{quat}$), 111.8 (CH), 60.9 ($CH_2$), 56.9 ($CH_2$), 54.4 ($CH_2$), 52.6 ($CH_2$), 40.2 ($CH_2$), 36.5 (CH), 29.0 ($CH_2$), 20.9 ($CH_3$), 14.2 ($CH_2$). HRMS (ESI+): calcd. for $C_{28}H_{34}ClN_6O_4S$, 585.2043. Found: $[M+H]^+$, 585.2045 (0.3 ppm error).

Ethyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate (21) (Code AB529)

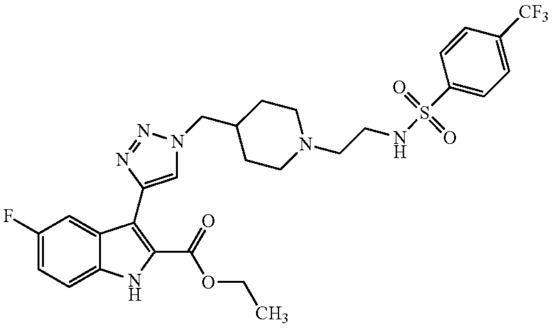 [SMILES: CCOC(=O)c1[nH]c2ccc(F)cc2c1-c1cn(CC2CCN(CCNS(=O)(=O)c3ccc(C(F)(F)F)cc3)CC2)nn1]

Prepared by general method G using alkyne 14a (65 mg, 0.28 mmol), azide 5c (116 mg, 0.30 mmol), 2M aqueous of sodium ascorbate (492 μL, 0.98 mmol), 15% aqueous of copper(II) sulfate pentahydrate (410 μL, 0.25 mmol) and tetrahydrofuran-tert-butanol (703 μL). The crude product was purified chromatographically on silica gel (eluting gradient dichloromethane-methanol 98:2 to 96:4) to provide the title compound 21 as a white solid (131 mg, 75% yield). Mp 162° C. $^1H$ NMR (400 MHz, $d_6$-DMSO) δ=12.06 (s, 1H), 8.55 (s, 1H), 8.08 (dd, J=10.3, 2.5 Hz, 1H), 8.05-7.95 (m, 4H), 7.82 (s, 1H), 7.52 (dd, J=9.0, 4.7 Hz, 1H), 7.21 (td, J=9.1, 2.6 Hz, 1H), 4.42-4.31 (m, 4H), 2.90 (t, J=6.4 Hz, 2H), 2.68 (d, J=11.2 Hz, 2H), 2.27 (t, J=6.6 Hz, 2H), 1.81 (t, J=10.8 Hz, 3H), 1.45 (d, J=11.3 Hz, 2H), 1.35 (t, J=7.1 Hz, 3H), 1.17 (dt, J=11.9, 5.9 Hz, 2H). $^{13}C$ NMR (100 MHz, $d_6$-DMSO) δ=160.9 ($C_{quat}$), 157.4 (d, J=234.2 Hz, $C_{quat}$), 144.8 (d, J=1.6 Hz, $C_{quat}$), 140.3 ($C_{quat}$), 133.1 ($C_{quat}$), 132.0 (q, J=32.7 Hz, $C_{quat}$), 127.4 (CH), 126.3 (q, J=3.8 Hz, CH), 126.0 (d, J=10.8 Hz, $C_{quat}$), 124.9 (CH), 123.8 ($C_{quat}$), 123.5 (q, J=274.2 Hz, $C_{quat}$), 114.4 (d, J=26.7 Hz, CH), 113.9 (d, J=10.1 Hz, CH), 111.6 (d, J=5.6 Hz, $C_{quat}$), 107.2 (d, J=24.1 Hz, CH), 60.8 ($CH_2$), 57.0 ($CH_2$), 54.4 ($CH_2$), 52.5 ($CH_2$), 40.2 ($CH_2$), 36.5 (CH), 29.0 ($CH_2$), 14.3 ($CH_3$). $^{19}F$ NMR (376 MHz, $d_6$-DMSO) δ=−61.6, −122.4. HRMS (ESI+): calcd. for $C_{28}H_{31}F_4N_6O_4S$, 623.2057. Found: $[M+H]^+$, 623.2058 (0.2 ppm error).

Ethyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate (22) (Code AB550)

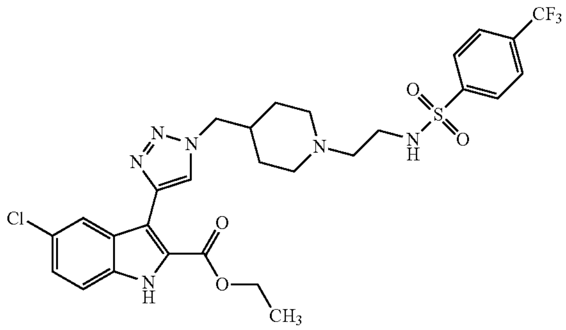 [SMILES: CCOC(=O)c1[nH]c2ccc(Cl)cc2c1-c1cn(CC2CCN(CCNS(=O)(=O)c3ccc(C(F)(F)F)cc3)CC2)nn1]

Prepared by general method G using alkyne 14b (65 mg, 0.26 mmol), azide 5c (108 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 22 as a white solid (119 mg, 71% yield). Mp 193° C. $^1H$ NMR (400 MHz, $d_6$-DMSO) δ=12.15 (s, 1H), 8.56 (s, 1H), 8.41 (d, J=1.9 Hz, 1H), 7.99 (q, J=8.5 Hz, 4H), 7.82 (s, 1H), 7.53 (d, J=8.8 Hz, 1H), 7.34 (dd, J=8.8, 2.1 Hz, 1H), 4.44-4.28 (m, 4H), 2.90 (t, J=6.5 Hz, 2H), 2.68 (d, J=11.2 Hz, 2H), 2.27 (t, J=6.6 Hz, 2H), 1.81 (t, J=10.7 Hz, 3H), 1.45 (d, J=11.2 Hz, 2H), 1.35 (t, J=7.1 Hz, 3H), 1.16 (qd, J=12.2, 3.2 Hz, 2H). $^{13}C$ NMR (100 MHz, $d_6$-DMSO) δ=160.9 ($C_{quat}$), 144.8 (d, J=1.5 Hz, $C_{quat}$), 140.1 ($C_{quat}$), 134.7 ($C_{quat}$), 132.0 (d, J=32.3 Hz, $C_{quat}$), 127.4 (CH), 126.8 ($C_{quat}$), 126.3 (q, J=3.8 Hz, CH), 125.5 (CH), 125.1 ($C_{quat}$), 124.9 (CH), 123.7 (q, J=273.3 Hz, $C_{quat}$), 123.6 ($C_{quat}$), 122.4 (CH), 114.3 (CH), 111.2 ($C_{quat}$), 60.9 ($CH_2$), 57.0 ($CH_2$), 54.5 ($CH_2$), 52.5 ($CH_2$), 40.3 ($CH_2$), 36.5 (CH), 29.0 ($CH_2$), 14.2 ($CH_3$). $^{19}F$ NMR (376 MHz, $d_6$-DMSO) δ=−61.6. HRMS (ESI+): calcd. for $C_{28}H_{31}ClF_3N_6O_4S$, 639.1762. Found: $[M+H]^+$, 639.1763 (0.1 ppm error).

Ethyl 5-fluoro-3-(1-((1-(2-(naphthalene-2-sulfonamido)ethyl)piperidin-4-yl)methyl)-1H-1,2,3-triazol-4-yl)-1H-indole-2-carboxylate (23) (Code AB536)

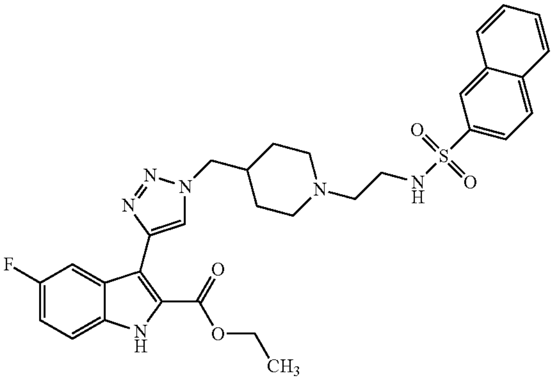 [SMILES: CCOC(=O)c1[nH]c2ccc(F)cc2c1-c1cn(CC2CCN(CCNS(=O)(=O)c3ccc4ccccc4c3)CC2)nn1]

Prepared by general method G using alkyne 14a (65 mg, 0.28 mmol), azide 5d (110 mg, 0.30 mmol), 2M aqueous of sodium ascorbate (492 μL, 0.98 mmol), 15% aqueous of copper(II) sulfate pentahydrate (410 μL, 0.25 mmol) and tetrahydrofuran-tert-butanol (703 μL). The crude product was purified chromatographically on silica gel (eluting gradient dichloromethane-methanol 98:2 to 96:4) to provide the title compound 23 as a white solid (116 mg, 69% yield). Mp 101° C. $^{1}$H NMR (400 MHz, $d_6$-Acetone) δ=11.14 (s, 1H), 8.62 (s, 1H), 8.49-8.45 (m, 1H), 8.41 (dd, J=10.4, 2.6 Hz, 1H), 8.16-8.08 (m, 2H), 8.06-8.00 (m, 1H), 7.90 (dd, J=8.6, 1.9 Hz, 1H), 7.74-7.63 (m, 2H), 7.56 (ddd, J=9.0, 4.6, 0.6 Hz, 1H), 7.18 (td, J=9.1, 2.6 Hz, 1H), 4.42 (q, J=7.1 Hz, 2H), 4.36 (d, J=7.1 Hz, 2H), 3.04 (d, J=12.5 Hz, 2H), 2.66 (dt, J=10.8, 3.9 Hz, 2H), 2.36 (td, J=6.2, 2.3 Hz, 2H), 1.87 (tddd, J=19.8, 10.9, 7.7, 2.9 Hz, 3H), 1.56-1.47 (m, 2H), 1.38 (t, J=7.1 Hz, 3H), 1.34-1.22 (m, 2H), 1.22-1.10 (m, 1H). $^{13}$C NMR (100 MHz, $d_6$-Acetone) δ=161.8 ($C_{quat}$), 159.0 (d, J=233.8 Hz, $C_{quat}$), 141.9 ($C_{quat}$), 138.9 ($C_{quat}$), 135.6 ($C_{quat}$), 134.1 ($C_{quat}$), 133.2 ($C_{quat}$), 130.2 (CH), 130.1 (CH), 129.4 (CH), 128.8 (CH), 128.7 (CH), 128.4 (CH), 127.6 (d, J=11.0 Hz, $C_{quat}$), 125.5 (CH), 124.7 ($C_{quat}$), 123.5 (CH), 115.4 (d, J=27.3 Hz, CH), 114.3 (d, J=9.3 Hz, CH), 113.8 (d, J=5.6 Hz, $C_{quat}$), 109.4 (d, J=24.6 Hz, CH), 61.7 ($CH_2$), 57.4 ($CH_2$), 55.8 ($CH_2$), 53.5 ($CH_2$), 41.1 ($CH_2$), 37.9 (CH), 30.3 ($CH_2$), 14.7 ($CH_3$). $^{19}$F NMR (376 MHz, $d_6$-Acetone) δ=−123.9. HRMS (ESI+): calcd. for $C_{31}H_{34}FN_6O_4S$, 605.2346. Found: $[M+H]^+$, 605.2341 (−0.9 ppm error).

Ethyl 5-chloro-3-(1-((1-(2-(naphthalene-2-sulfonamido)ethyl)piperidin-4-yl)methyl)-1H-1,2,3-triazol-4-yl)-1H-indole-2-carboxylate (24) (Code AB551)

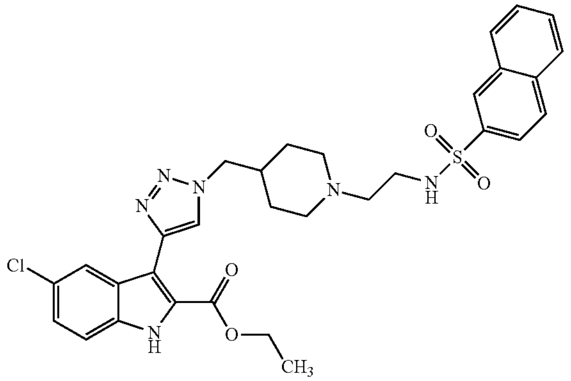 [SMILES: CCOC(=O)c1[nH]c2ccc(Cl)cc2c1-c1cn(CC2CCN(CCNS(=O)(=O)c3ccc4ccccc4c3)CC2)nn1]

Prepared by general method G using alkyne 14b (65 mg, 0.26 mmol), azide 5d (103 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 24 as a white solid (110 mg, 67% yield). Mp 106° C. $^{1}$H NMR (400 MHz, $d_6$-DMSO) δ=12.15 (s, 1H), 8.54 (s, 1H), 8.42 (dd, J=10.4, 1.6 Hz, 2H), 8.17-8.08 (m, 2H), 8.06-8.00 (m, 1H), 7.83 (dd, J=8.7, 1.8 Hz, 1H), 7.68 (qd, J=7.1, 1.5 Hz, 2H), 7.64-7.56 (m, 1H), 7.53 (d, J=8.8 Hz, 1H), 7.34 (dd, J=8.8, 2.1 Hz, 1H), 4.38 (q, J=7.1 Hz, 2H), 4.29 (d, J=7.0 Hz, 2H), 2.88 (t, J=6.3 Hz, 2H), 2.66 (d, J=11.3 Hz, 2H), 2.27 (t, J=6.8 Hz, 2H), 1.78 (t, J=10.5 Hz, 3H), 1.40 (d, J=11.1 Hz, 2H), 1.34 (t, J=7.1 Hz, 3H), 1.13 (qd, J=12.2, 3.2 Hz, 2H). $^{13}$C NMR (100 MHz, $d_6$-DMSO) δ=160.9 ($C_{quat}$), 140.1 ($C_{quat}$), 137.7 ($C_{quat}$), 134.7 ($C_{quat}$), 134.1 ($C_{quat}$), 131.7 ($C_{quat}$), 129.3 (CH), 129.2 (CH), 128.6 (CH), 127.8 (CH), 127.5 (CH), 127.2 (CH), 126.8 ($C_{quat}$), 125.5 (CH), 125.1 ($C_{quat}$), 124.9 (CH), 123.6 ($C_{quat}$), 122.4 (CH), 122.3 (CH), 114.3 (CH), 111.2 ($C_{quat}$), 60.9 ($CH_2$), 57.0 ($CH_2$), 54.4 ($CH_2$), 52.5 ($CH_2$), 40.3 ($CH_2$), 36.5 (CH), 29.0 ($CH_2$), 14.2 ($CH_3$). HRMS (ESI+): calcd. for $C_{31}H_{34}ClN_6O_4S$, 621.2048. Found: $[M+H]^+$, 621.2045 (−0.5 ppm error).

Ethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate (25) (Code AB526)

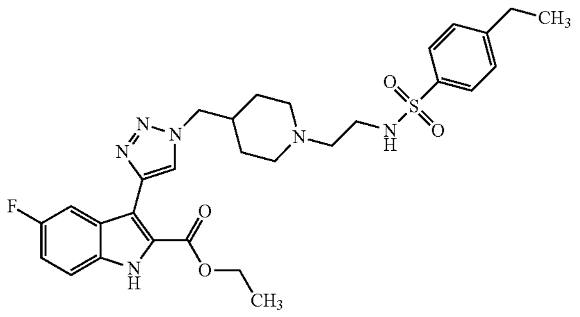 [SMILES: CCOC(=O)c1[nH]c2ccc(F)cc2c1-c1cn(CC2CCN(CCNS(=O)(=O)c3ccc(CC)cc3)CC2)nn1]

Prepared by general method G using alkyne 14a (65 mg, 0.28 mmol), azide 5f (100 mg, 0.30 mmol), 2M aqueous of sodium ascorbate (492 μL, 0.98 mmol), 15% aqueous of copper(II) sulfate pentahydrate (410 μL, 0.25 mmol) and tetrahydrofuran-tert-butanol (703 μL). The crude product was purified chromatographically on silica gel (eluting gradient dichloromethane-methanol 98:2 to 96:4) to provide the title compound 25 as a white solid (102 mg, 62% yield). Mp 79° C. $^{1}$H NMR (400 MHz, $d_6$-DMSO) δ=12.07 (s, 1H), 8.56 (s, 1H), 8.08 (dd, J=10.3, 2.6 Hz, 1H), 7.70 (d, J=8.3 Hz, 2H), 7.52 (dd, J=9.0, 4.7 Hz, 1H), 7.40 (d, J=8.4 Hz, 3H), 7.22 (td, J=9.1, 2.6 Hz, 1H), 4.41-4.31 (m, 4H), 2.85-2.78 (m, 2H), 2.67 (p, J=7.6, 6.6 Hz, 4H), 2.27 (t, J=6.8 Hz, 2H), 1.81 (t, J=11.3 Hz, 3H), 1.46 (d, J=11.3 Hz, 2H), 1.35 (t, J=7.1 Hz, 3H), 1.23-1.13 (m, 5H). $^{13}$C NMR (100 MHz, $d_6$-DMSO) δ=160.9 ($C_{quat}$), 157.4 (d, J=233.5 Hz, $C_{quat}$), 148.5 ($C_{quat}$), 140.3 ($C_{quat}$), 138.0 ($C_{quat}$), 133.1 ($C_{quat}$), 128.4 (CH), 126.6 (CH), 125.4 (d, J=10.9 Hz, $C_{quat}$), 124.8 (CH), 123.8 ($C_{quat}$), 114.4 (d, J=26.4 Hz, CH), 113.9 (d, J=10.4 Hz, CH), 111.7 (d, J=5.6 Hz, $C_{quat}$), 107.4 (d, J=24.8 Hz, CH), 60.9 ($CH_2$), 56.9 ($CH_2$), 54.2 ($CH_2$), 52.5 ($CH_2$), 40.2 ($CH_2$), 36.5 (CH), 29.0 ($CH_2$), 28.0 ($CH_2$), 15.2 ($CH_3$), 14.2 ($CH_3$). $^{19}$F NMR (376 MHz, $d_6$-DMSO) δ=−122.4. HRMS (ESI+): calcd. for $C_{29}H_{36}FN_6O_4S$, 583.2501. Found: $[M+H]^+$, 583.2497 (−0.7 ppm error).

Ethyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate (26) (Code AB543)

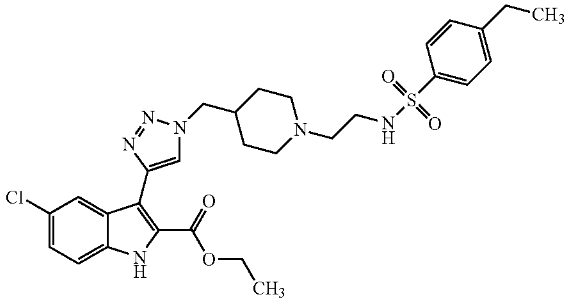 [SMILES: CCOC(=O)c1[nH]c2ccc(Cl)cc2c1-c1cn(CC2CCN(CCNS(=O)(=O)c3ccc(CC)cc3)CC2)nn1]

Prepared by general method G using alkyne 14b (65 mg, 0.26 mmol), azide 5f (97 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 26 as a white solid (96 mg, 61% yield). Mp 84° C. $^{1}$H NMR (400 MHz, $d_6$-DMSO) δ=12.06 (s, 1H), 8.56 (s, 1H), 8.37 (d, J=8.8 Hz, 1H), 7.73-7.67 (m, 2H), 7.51 (d, J=2.0 Hz, 1H), 7.41 (s, 2H), 7.40 (s, 1H), 7.17 (dd, J=8.7, 2.0 Hz, 1H), 4.42-4.32 (m, 4H), 2.81 (s, 2H), 2.71-2.62 (m, 4H), 2.27 (t, J=6.8 Hz, 2H), 1.81 (td, J=11.1, 6.0 Hz, 3H), 1.49-1.43 (m, 2H), 1.35 (t, J=7.1 Hz, 3H), 1.22-1.14 (m, 5H). $^{13}$C NMR (100 MHz, $d_6$-DMSO) δ=160.9 ($C_{quat}$), 148.5 ($C_{quat}$), 140.0 ($C_{quat}$), 138.0 ($C_{quat}$), 136.6 ($C_{quat}$), 130.0 ($C_{quat}$), 128.4 (CH), 126.6 (CH), 125.2 (CH), 125.1 (CH), 124.7 ($C_{quat}$), 123.1 ($C_{quat}$), 121.2 (CH), 111.9 ($C_{quat}$), 111.8 (CH), 60.9 ($CH_2$), 56.9 ($CH_2$), 54.4 ($CH_2$), 52.5 ($CH_2$), 40.3 ($CH_2$), 36.5 (CH), 29.0 ($CH_2$), 28.0 ($CH_2$), 15.2 ($CH_3$), 14.2 ($CH_3$). HRMS (ESI+): calcd. for $C_{29}H_{36}ClN_6O_4S$, 599.2199. Found: $[M+H]^+$, 599.2202 (0.5 ppm error).

Ethyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate (27) (Code AB579)

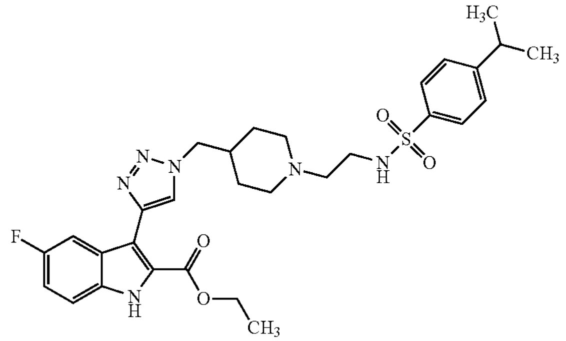 [SMILES: CCOC(=O)c1[nH]c2ccc(F)cc2c1-c1cn(CC2CCN(CCNS(=O)(=O)c3ccc(C(C)C)cc3)CC2)nn1]

Prepared by general method G using alkyne 14a (65 mg, 0.28 mmol), azide 5g (108 mg, 0.30 mmol), 2M aqueous of sodium ascorbate (492 μL, 0.98 mmol), 15% aqueous of copper(II) sulfate pentahydrate (410 μL, 0.25 mmol) and tetrahydrofuran-tert-butanol (703 μL). The crude product was purified chromatographically on silica gel (eluting gradient dichloromethane-methanol 98:2 to 96:4) to provide the title compound 27 as a white solid (106 mg, 63% yield). Mp 89° C. $^{1}$H NMR (400 MHz, $d_6$-DMSO) δ=12.07 (s, 1H), 8.56 (s, 1H), 8.08 (dd, J=10.3, 2.6 Hz, 1H), 7.74-7.67 (m, 2H), 7.52 (dd, J=9.0, 4.7 Hz, 1H), 7.46-7.41 (m, 2H), 7.38 (t, J=5.5 Hz, 1H), 7.22 (td, J=9.1, 2.7 Hz, 1H), 4.37 (dt, J=14.3, 7.1 Hz, 4H), 2.95 (h, J=6.9 Hz, 1H), 2.82 (q, J=6.3 Hz, 2H), 2.70-2.62 (m, 2H), 2.26 (t, J=6.8 Hz, 2H), 1.81 (dt, J=15.4, 5.8 Hz, 311), 1.45 (d, J=12.4 Hz, 2H), 1.35 (t, J=7.1 Hz, 3H), 1.19 (d, J=6.9 Hz, 8H). $^{13}$C NMR (100 MHz, $d_6$-DMSO) δ=160.9 ($C_{quat}$), 157.6 (d, J=233.9 Hz, $C_{quat}$), 153.0 ($C_{quat}$), 140.3 ($C_{quat}$), 138.1 ($C_{quat}$), 133.0 ($C_{quat}$), 127.0 (CH), 126.6 (CH), 126.0 (d, J=10.5 Hz, $C_{quat}$), 124.8 (CH), 123.8 ($C_{quat}$), 114.4 (d, J=26.2 Hz, CH), 113.9 (d, J=9.4 Hz, CH), 111.6 (d, J=5.8 Hz, $C_{quat}$), 107.4 (d, J=23.9 Hz, CH), 60.8 ($CH_2$), 56.9 ($CH_2$), 54.4 ($CH_2$), 52.5 ($CH_2$), 40.3 ($CH_2$), 36.5 (CH), 33.3 (CH), 29.0 ($CH_2$), 23.5 ($CH_3$), 14.2 ($CH_3$). $^{19}$F NMR (376 MHz, $d_6$-DMSO) δ=−122.4. HRMS (ESI+): calcd. for $C_{30}H_{38}FN_6O_4S$, 597.2659. Found: $[M+H]^+$, 597.2654 (−0.8 ppm error).

Ethyl 5-chloro-3-(1-((1-(2-((4-isopropylphenyl)sulfonamido)ethyl)piperidin-4-yl)methyl)-1H-1,2,3-triazol-4-yl)-1H-indole-2-carboxylate (28) (Code AB582)

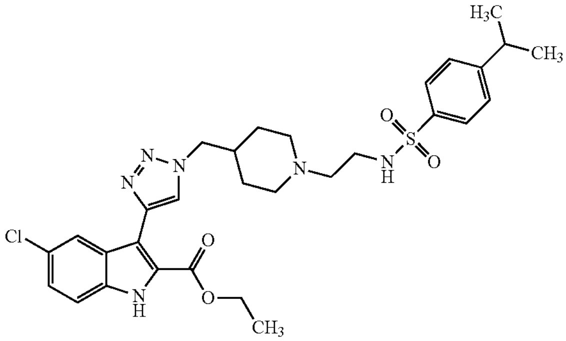 [SMILES: CCOC(=O)c1[nH]c2ccc(Cl)cc2c1-c1cn(CC2CCN(CCNS(=O)(=O)c3ccc(C(C)C)cc3)CC2)nn1]

Prepared by general method G using alkyne 14b (65 mg, 0.26 mmol), azide 5g (101 mg, 0.28 mmol), 2M aqueous of sodium ascorbate (459 μL, 0.92 mmol), 15% aqueous of copper(II) sulfate pentahydrate (383 μL, 0.23 mmol) and tetrahydrofuran-tert-butanol (656 μL). The crude product was purified chromatographically on silica gel (eluting gradient dichloromethane-methanol 98:2 to 96:4) to provide the title compound 28 as a white solid (99 mg, 61% yield). Mp 94° C. $^{1}$H NMR (400 MHz, $d_6$-DMSO) δ=12.15 (s, 1H), 8.57 (s, 1H), 8.43 (d, J=2.1 Hz, 1H), 7.71 (d, J=8.4 Hz, 2H), 7.55-7.51 (m, 1H), 7.42 (d, J=8.3 Hz, 2H), 7.37 (s, 1H), 7.35-7.30 (m, 1H), 4.37 (dd, J=14.6, 7.3 Hz, 4H), 2.99-2.91 (m, 1H), 2.85-2.79 (m, 2H), 2.66 (d, J=11.3 Hz, 2H), 2.26 (t, J=6.8 Hz, 2H), 1.86-1.76 (m, 3H), 1.45 (d, J=10.9 Hz, 2H), 1.35 (t, J=7.1 Hz, 3H), 1.18 (d, J=6.9 Hz, 8H). $^{13}$C NMR (100 MHz, $d_6$-DMSO) δ=160.9 ($C_{quat}$), 153.0 ($C_{quat}$), 140.1 ($C_{quat}$), 138.1 ($C_{quat}$), 134.7 ($C_{quat}$), 127.0 (CH), 126.8 ($C_{quat}$), 126.6 (CH), 125.5 (CH), 125.1 ($C_{quat}$), 124.9 (CH), 123.5 ($C_{quat}$), 122.4 (CH), 114.2 (CH), 111.2 ($C_{quat}$), 60.9 ($CH_2$), 56.9 ($CH_2$), 54.4 ($CH_2$), 52.5 ($CH_2$), 40.2 ($CH_2$), 36.5 (CH), 33.3 (CH), 29.0 ($CH_2$), 23.5 ($CH_3$), 14.2 ($CH_3$).

HRMS (ESI+): calcd. for $C_{30}H_{38}ClN_6O_4S$, 613.2362. Found: $[M+H]^+$, 613.2358 (−0.5 ppm error).

Isopropyl 3-(1-((1-(2-((4-ethylphenyl)sulfonamido) ethyl)piperidin-4-yl)methyl)-1H-1,2,3-triazol-4-yl)-5-fluoro-1H-indole-2-carboxylate (29) (Code AB577)

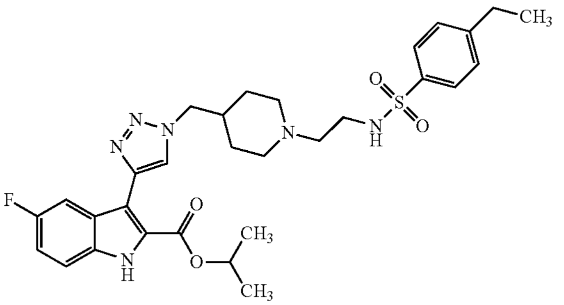 [SMILES: CCc1ccc(S(=O)(=O)NCCN2CCC(Cn3cc(-c4c(C(=O)OC(C)C)[nH]c5ccc(F)cc45)nn3)CC2)cc1]

Prepared by general method G using alkyne 14d (60 mg, 0.24 mmol), azide 5f (90 mg, 0.26 mmol), 2M aqueous of sodium ascorbate (428 μL, 0.86 mmol), 15% aqueous of copper(II) sulfate pentahydrate (357 μL, 0.21 mmol) and tetrahydrofuran-tert-butanol (612 μL). The crude product was purified chromatographically on silica gel (eluting gradient dichloromethane-methanol 98:2 to 96:4) to provide the title compound 29 as a white solid (86 mg, 59% yield). Mp 176° C. $^1$H NMR (400 MHz, $d_6$-DMSO) δ=11.99 (s, 1H), 8.54 (s, 1H), 8.06 (dd, J=10.3, 2.7 Hz, 1H), 7.73-7.67 (m, 2H), 7.53 (dd, J=9.0, 4.7 Hz, 1H), 7.44-7.33 (m, 3H), 7.22 (td, J=9.1, 2.7 Hz, 1H), 5.21 (h, J=6.3 Hz, 1H), 4.34 (d, J=7.0 Hz, 2H), 2.81 (t, J=6.9 Hz, 2H), 2.71-2.62 (m, 4H), 2.26 (t, J=6.9 Hz, 2H), 1.85-1.77 (m, 3H), 1.49-1.43 (m, 2H), 1.35 (d, J=6.2 Hz, 6H), 1.26-1.14 (m, 5H). $^{13}$C NMR (100 MHz, $d_6$-DMSO) δ=160.5 ($C_{quat}$), 157.5 (d, J=233.7 Hz, $C_{quat}$), 148.5 ($C_{quat}$), 140.3 ($C_{quat}$), 138.0 ($C_{quat}$), 133.0 ($C_{quat}$), 128.4 (CH), 126.6 (CH), 126.0 (d, J=10.7 Hz, $C_{quat}$), 124.7 (CH), 124.1 ($C_{quat}$), 114.3 (d, J=26.8 Hz, CH), 113.9 (d, J=9.7 Hz, CH), 111.5 (d, J=5.5 Hz, $C_{quat}$), 107.4 (d, J=24.3 Hz, CH), 68.6 (CH), 56.9 ($CH_2$), 54.5 ($CH_2$), 52.5 ($CH_2$), 40.3 ($CH_2$), 36.5 (CH), 29.1 ($CH_2$), 28.0 ($CH_2$), 21.7 ($CH_3$), 15.2 ($CH_3$). $^{19}$F NMR (376 MHz, $d_6$-DMSO) δ=−122.4. HRMS (ESI+): calcd. for $C_{30}H_{38}FN_6O_4S$, 597.2660. Found: $[M+H]^+$, 597.2654 (−1.0 ppm error).

Isopropyl 5-chloro-3-(1-((1-(2-((4-ethylphenyl) sulfonamido)ethyl)piperidin-4-yl)methyl)-1H-1,2,3-triazol-4-yl)-1H-indole-2-carboxylate (30) (Code AB578)

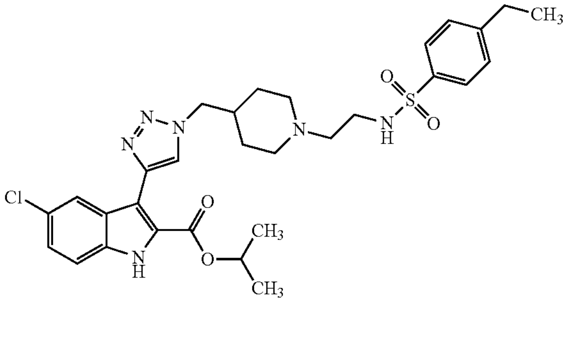 [SMILES: CCc1ccc(S(=O)(=O)NCCN2CCC(Cn3cc(-c4c(C(=O)OC(C)C)[nH]c5ccc(Cl)cc45)nn3)CC2)cc1]

Prepared by general method G using alkyne 14e (70 mg, 0.27 mmol), azide 5f (99 mg, 0.28 mmol), 2M aqueous of sodium ascorbate (468 μL, 0.94 mmol), 15% aqueous of copper(II) sulfate pentahydrate (390 μL, 0.23 mmol) and tetrahydrofuran-tert-butanol (669 μL). The crude product was purified chromatographically on silica gel (eluting gradient dichloromethane-methanol 98:2 to 96:4) to provide the title compound 30 as a white solid (94 mg, 57% yield). Mp 182° C. $^1$H NMR (400 MHz, $d_6$-DMSO) δ=12.01 (s, 1H), 8.55 (s, 1H), 8.38 (d, J=2.7 Hz, 1H), 7.75-7.69 (m, 2H), 7.53 (dd, J=2.0, 0.7 Hz, 1H), 7.44-7.33 (m, 3H), 7.17 (dd, J=8.8, 2.5 Hz, 1H), 5.35 (h, J=6.3 Hz, 1H), 4.34 (d, J=6.9 Hz, 2H), 2.83 (t, J=6.7 Hz, 2H), 2.71-2.65 (m, 4H), 2.27 (t, J=6.9 Hz, 2H), 1.86-1.76 (m, 3H), 1.50-1.42 (m, 2H), 1.35 (d, J=7.0 Hz, 6H), 1.26-1.14 (m, 5H). HRMS (ESI+): calcd. for $C_{30}H_{38}ClN_6O_4S$, 613.2347. Found: $[M+H]^+$, 613.2358 (1.8 ppm error).

Isobutyl 3-(1-((1-(2-((4-chlorophenyl)sulfonamido) ethyl)piperidin-4-yl)methyl)-1H-1,2,3-triazol-4-yl)-5-fluoro-1H-indole-2-carboxylate (31) (Code AB498)

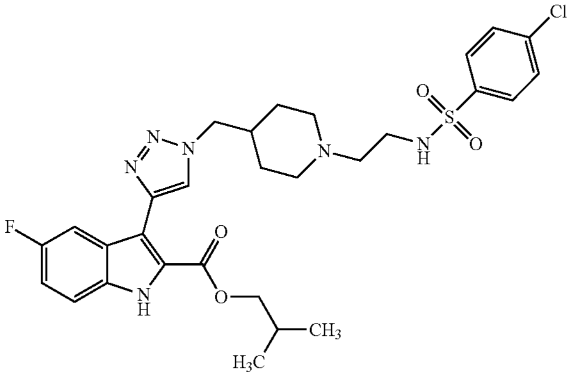 [SMILES: CC(C)COC(=O)c1[nH]c2ccc(F)cc2c1-c1cn(CC2CCN(CCNS(=O)(=O)c3ccc(Cl)cc3)CC2)nn1]

Prepared by general method G using alkyne 14f (60 mg, 0.23 mmol), azide 5b (87 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 31 as a pale yellow solid (96 mg, 67% yield). Mp 154° C. $^1$H NMR (400 MHz, $d_6$-DMSO) δ=12.01 (s, 1H), 8.55 (s, 1H), 8.04 (dd, J=10.3, 2.6 Hz, 1H), 7.83-7.76 (m, 2H), 7.68-7.57 (m, 3H), 7.55 (dd, J=9.0, 4.7 Hz, 1H), 7.22 (td, J=9.1, 2.7 Hz, 1H), 4.34 (d, J=6.9 Hz, 2H), 4.12 (d, J=6.7 Hz, 2H), 2.85 (t, J=6.4 Hz, 2H), 2.70 (d, J=11.3 Hz, 2H), 2.27 (t, J=6.7 Hz, 2H), 2.04 (dq, J=13.4, 6.5 Hz, 1H), 1.82 (t, J=10.6 Hz, 3H), 1.46 (d, J=11.2 Hz, 2H), 1.20 (tt, J=11.7, 6.1 Hz, 2H), 0.94 (d, J=6.7 Hz, 6H). $^{13}$C NMR (100 MHz, $d_6$-DMSO) δ=161.0 ($C_{quat}$), 157.4 (d, J=233.9 Hz, $C_{quat}$), 140.2 ($C_{quat}$), 139.6 ($C_{quat}$), 137.1 ($C_{quat}$), 133.1 ($C_{quat}$), 129.3 (CH), 128.4 (CH), 126.1 (d, J=10.7 Hz, $C_{quat}$), 124.8 (CH), 123.8 ($C_{quat}$), 114.4 (d, J=27.3 Hz, CH), 114.0 (d, J=9.9 Hz, CH), 111.8 (d, J=5.4 Hz, $C_{quat}$), 107.3 (d, J=24.2 Hz, CH), 70.6 ($CH_2$), 57.0 ($CH_2$), 54.5 ($CH_2$), 52.6 ($CH_2$), 40.2 ($CH_2$), 36.5 (CH), 29.0 ($CH_2$), 27.4 (CH), 18.9 ($CH_3$). $^{19}$F NMR (376 MHz, $d_6$-DMSO) δ=−122.3. HRMS (ESI+): calcd. for $C_{29}H_{35}ClFN_6O_4S$, 617.2104. Found: $[M+H]^+$, 617.2108 (0.6 ppm error).

Isobutyl 5-chloro-3-(1-((1-(2-((4-chlorophenyl) sulfonamido)ethyl)piperidin-4-yl)methyl)-1H-1,2,3-triazol-4-yl)-1H-indole-2-carboxylate (32) (Code AB499)

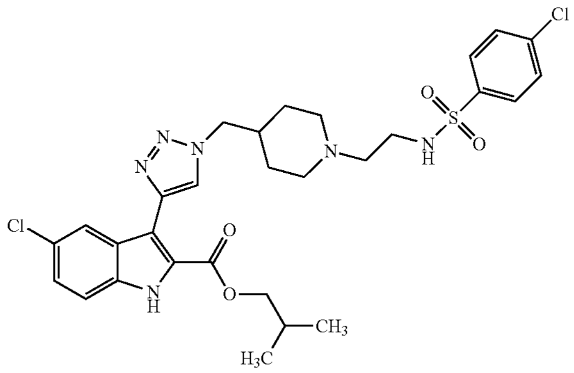 [SMILES: CC(C)COC(=O)c1[nH]c2ccc(Cl)cc2c1-c1cn(CC2CCN(CCNS(=O)(=O)c3ccc(Cl)cc3)CC2)nn1]

Prepared by general method G using alkyne 14g (70 mg, 0.25 mmol), azide 5b (95 mg, 0.27 mmol), 2M aqueous of sodium ascorbate (444 µL, 0.89 mmol), 15% aqueous of copper(II) sulfate pentahydrate (370 µL, 0.22 mmol) and tetrahydrofuran-tert-butanol (635 µL). The crude product was purified chromatographically on silica gel (eluting gradient dichloromethane-methanol 98:2 to 96:4) to provide the title compound 32 as a white solid (101 mg, 63% yield). Mp 162° C. $^{1}$H NMR (400 MHz, $d_6$-DMSO) δ=12.03 (s, 1H), 8.56 (s, 1H), 8.36 (d, J=2.3 Hz, 1H), 7.74-7.66 (m, 2H), 7.54 (d, J=8.0 Hz, 1H), 7.44-7.33 (m, 3H), 7.17 (dd, J=8.8, 2.5 Hz, 1H), 4.34 (d, J=6.9 Hz, 2H), 4.12 (d, J=6.7 Hz, 2H), 2.83 (t, J=6.4 Hz, 2H), 2.70 (d, J=11.3 Hz, 2H), 2.27 (t, J=6.8 Hz, 2H), 2.12 (dq, J=12.7, 6.4 Hz, 1H), 1.82 (t, J=10.6 Hz, 3H), 1.46 (d, J=11.2 Hz, 2H), 1.20 (tt, J=11.7, 6.2 Hz, 2H), 0.96 (d, J=6.8 Hz, 6H). HRMS (ESI+): calcd. for $C_{29}H_{35}Cl_2N_6O_4S$, 633.6204. Found: $[M+H]^+$, 633.6215 (1.8 ppm error).

Isobutyl 5-fluoro-3-(1-((1-(2-((4-(trifluoromethyl) phenyl)sulfonamido)ethyl)piperidin-4-yl)methyl)-1H-1,2,3-triazol-4-yl)-1H-indole-2-carboxylate (33) (Code AB600)

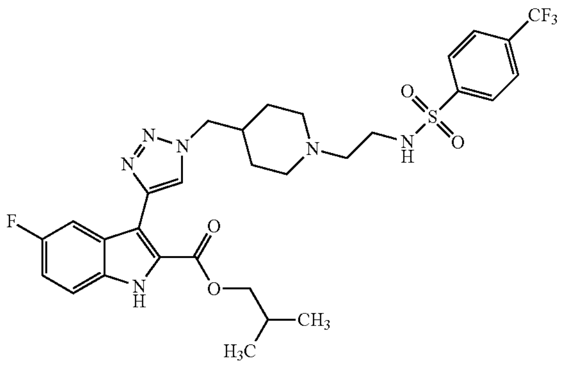 [SMILES: CC(C)COC(=O)c1[nH]c2ccc(F)cc2c1-c1cn(CC2CCN(CCNS(=O)(=O)c3ccc(C(F)(F)F)cc3)CC2)nn1]

Prepared by general method G using alkyne 14f (60 mg, 0.23 mmol), azide 5c (95 mg, 0.24 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (579 µL). The crude product was purified chromatographically on silica gel (eluting gradient dichloromethane-methanol 98:2 to 96:4) to provide the title compound 33 as a white solid (105 mg, 70% yield). Mp 177° C. $^{1}$H NMR (400 MHz, $d_6$-DMSO) δ=12.01 (s, 1H), 8.54 (s, 1H), 8.06-7.95 (m, 5H), 7.82 (s, 1H), 7.55 (dd, J=9.1, 4.7 Hz, 1H), 7.22 (td, J=9.1, 2.6 Hz, 1H), 4.32 (d, J=7.0 Hz, 2H), 4.11 (d, J=6.7 Hz, 2H), 2.90 (t, J=6.5 Hz, 2H), 2.68 (d, J=11.2 Hz, 2H), 2.27 (t, J=6.6 Hz, 2H), 2.10-1.99 (m, 1H), 1.80 (t, J=10.6 Hz, 3H), 1.45 (d, J=11.1 Hz, 2H), 1.21-1.12 (m, 2H), 0.94 (d, J=6.7 Hz, 6H). $^{13}$C NMR (100 MHz, $d_6$-DMSO) δ=161.0 ($C_{quat}$), 157.5 (d, J=234.2 Hz, $C_{quat}$), 144.8 (d, J=1.6 Hz, $C_{quat}$), 140.2 ($C_{quat}$), 133.1 ($C_{quat}$), 132.0 (q, J=32.5 Hz, $C_{quat}$), 127.4 (CH), 126.3 (q, J=3.6 Hz, CH), 126.0 (d, J=10.8 Hz, $C_{quat}$), 124.7 (CH), 123.8 ($C_{quat}$), 123.4 (q, J=272.7 Hz, $C_{quat}$), 114.4 (d, J=27.3 Hz, CH), 114.0 (d, J=9.6 Hz, CH), 111.8 (d, J=5.7 Hz, $C_{quat}$), 107.3 (d, J=24.2 Hz, CH), 70.6 ($CH_2$), 57.0 ($CH_2$), 54.4 ($CH_2$), 52.5 ($CH_2$), 40.2 ($CH_2$), 36.5 (CH), 29.0 ($CH_2$), 27.3 ($CH_2$), 18.9 ($CH_3$). $^{19}$F NMR (376 MHz, $d_6$-DMSO) δ=−61.6, −122.4. HRMS (ESI+): calcd. for $C_{30}H_{35}F_4N_6O_4S$, 651.2373. Found: $[M+H]^+$, 651.2371 (−0.2 ppm error).

Isobutyl 5-chloro-3-(1-((1-(2-((4-(trifluoromethyl) phenyl)sulfonamido)ethyl)piperidin-4-yl)methyl)-1H-1,2,3-triazol-4-yl)-1H-indole-2-carboxylate (34) (Code AB601)

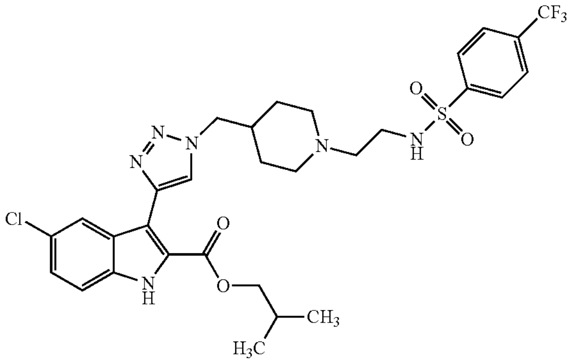 [SMILES: CC(C)COC(=O)c1[nH]c2ccc(Cl)cc2c1-c1cn(CC2CCN(CCNS(=O)(=O)c3ccc(C(F)(F)F)cc3)CC2)nn1]

Prepared by general method G using alkyne 14g (70 mg, 0.25 mmol), azide 5c (104 mg, 0.27 mmol), 2M aqueous of sodium ascorbate (444 µL, 0.89 mmol), 15% aqueous of copper(II) sulfate pentahydrate (370 µL, 0.22 mmol) and tetrahydrofuran-tert-butanol (635 µL). The crude product was purified chromatographically on silica gel (eluting gradient dichloromethane-methanol 98:2 to 96:4) to provide the title compound 34 as a white solid (113 mg, 67% yield). Mp 213° C. $^{1}$H NMR (400 MHz, $d_6$-DMSO) δ 12.09 (s, 1H), 8.55 (s, 1H), 8.38 (d, J=2.0 Hz, 1H), 8.06-7.96 (m, 4H), 7.82 (s, 1H), 7.55 (d, J=8.8 Hz, 1H), 7.34 (dd, J=8.8, 2.1 Hz, 1H), 4.33 (d, J=7.0 Hz, 2H), 4.12 (d, J=6.7 Hz, 2H), 2.90 (t, J=6.5 Hz, 2H), 2.68 (d, J=11.2 Hz, 2H), 2.27 (t, J=6.6 Hz, 2H), 2.03 (dt, J=13.4, 6.7 Hz, 1H), 1.80 (t, J=10.8 Hz, 3H), 1.45 (d, J=11.1 Hz, 2H), 1.21-1.12 (m, 2H), 0.93 (d, J=6.7 Hz, 6H). $^{13}$C NMR (100 MHz, $d_6$-DMSO) δ=160.9 ($C_{quat}$), 144.8 (d, J=1.4 Hz, $C_{quat}$), 140.0 ($C_{quat}$), 134.7 ($C_{quat}$), 132.0 (d, J=32.2 Hz, $C_{quat}$), 127.4 (CH), 126.9 ($C_{quat}$), 126.3 (q, J=3.7 Hz, CH), 125.5 (CH), 125.2 ($C_{quat}$), 124.9 (CH), 123.6 (q, J=273.2 Hz, $C_{quat}$), 123.5 ($C_{quat}$), 122.3 (CH), 114.3 (CH), 111.4 ($C_{quat}$), 70.6 ($CH_2$), 57.0 ($CH_2$), 54.5 ($CH_2$), 52.5 ($CH_2$), 40.2 ($CH_2$), 36.5 (CH), 29.0 ($CH_2$), 27.3 (CH), 18.9 ($CH_3$). $^{19}F$ NMR (376 MHz, $d_6$-DMSO) δ=−61.6. HRMS (ESI+): calcd. for $C_{30}H_{35}C_1F_3N_6O_4S$, 667.2082. Found: $[M+H]^+$, 667.2076 (−1.0 ppm error).

Isobutyl 5-fluoro-3-(1-((1-(2-(naphthalene-2-sulfonamido)ethyl)piperidin-4-yl)methyl)-1H-1,2,3-triazol-4-yl)-1H-indole-2-carboxylate (35) (Code AB598)

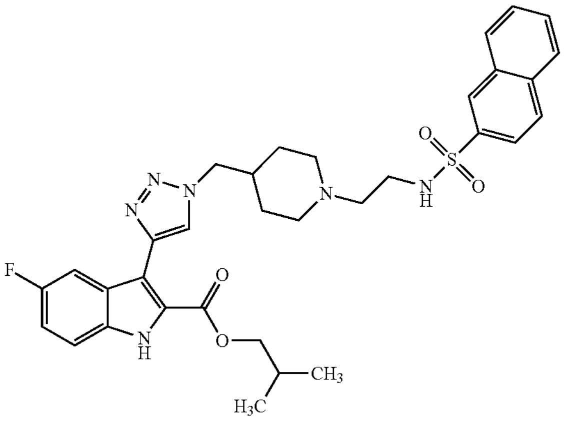 [SMILES: CC(C)COC(=O)c1[nH]c2ccc(F)cc2c1-c1cn(CC2CCN(CCNS(=O)(=O)c3ccc4ccccc4c3)CC2)nn1]

Prepared by general method G using alkyne 14f (60 mg, 0.23 mmol), azide 5d (91 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 35 as a white solid (98 mg, 67% yield). Mp 173° C. $^1H$ NMR (400 MHz, $d_6$-DMSO) δ=12.01 (s, 1H), 8.52 (s, 1H), 8.46-8.41 (m, 1H), 8.18-8.10 (m, 2H), 8.06-8.00 (m, 2H), 7.84 (dd, J=8.7, 1.8 Hz, 1H), 7.72-7.63 (m, 2H), 7.61 (d, J=12.4 Hz, 1H), 7.55 (dd, J=9.0, 4.7 Hz, 1H), 7.22 (td, J=9.1, 2.6 Hz, 1H), 4.27 (d, J=7.0 Hz, 2H), 4.11 (d, J=6.7 Hz, 2H), 2.89 (s, 2H), 2.66 (d, J=11.1 Hz, 2H), 2.28 (t, J=6.8 Hz, 2H), 2.05-1.94 (m, 1H), 1.78 (t, J=10.7 Hz, 3H), 1.41 (d, J=11.2 Hz, 2H), 1.22-1.10 (m, 2H), 0.93 (d, J=6.7 Hz, 6H). $^{13}C$ NMR (100 MHz, $d_6$-DMSO) δ=160.1 ($C_{quat}$), 157.5 (d, J=232.9 Hz, $C_{quat}$), 140.2 ($C_{quat}$), 137.7 ($C_{quat}$), 134.1 ($C_{quat}$), 133.1 ($C_{quat}$), 131.7 ($C_{quat}$), 129.2 (CH), 129.1 (CH), 128.6 (CH), 127.8 (CH), 127.5 (CH), 127.2 (CH), 126.0 (d, J=11.1 Hz, $C_{quat}$), 124.7 (CH), 123.8 ($C_{quat}$), 122.3 (CH), 114.4 (d, J=27.3 Hz, CH), 114.0 (d, J=9.8 Hz, CH), 111.8 (d, J=5.5 Hz, $C_{quat}$), 107.3 (d, J=24.7 Hz, CH), 70.6 ($CH_2$), 57.0 ($CH_2$), 54.4 ($CH_2$), 52.5 ($CH_2$), 40.3 ($CH_2$), 36.4 (CH), 29.0 ($CH_2$), 27.3 (CH), 18.9 ($CH_3$). $^{19}F$ NMR (376 MHz, $d_6$-DMSO) δ=−122.3. HRMS (ESI+): calcd. for $C_{33}H_{38}FN_6O_4S$, 633.2653. Found: $[M+H]^+$, 633.2654 (0.1 ppm error).

Isobutyl 5-chloro-3-(1-((1-(2-(naphthalene-2-sulfonamido)ethyl)piperidin-4-yl)methyl)-1H-1,2,3-triazol-4-yl)-1H-indole-2-carboxylate (36) (Code AB599)

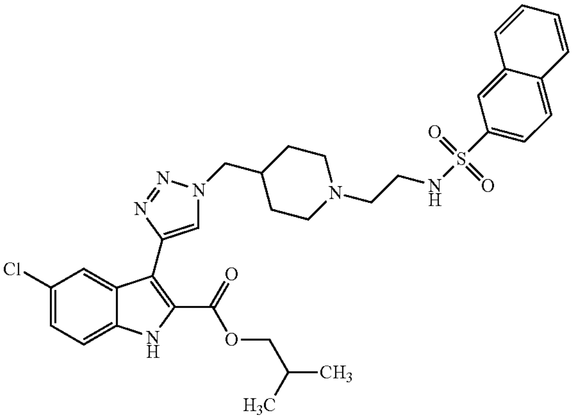 [SMILES: CC(C)COC(=O)c1[nH]c2ccc(Cl)cc2c1-c1cn(CC2CCN(CCNS(=O)(=O)c3ccc4ccccc4c3)CC2)nn1]

Prepared by general method G using alkyne 14g (70 mg, 0.25 mmol), azide 5d (100 mg, 0.27 mmol), 2M aqueous of sodium ascorbate (444 μL, 0.89 mmol), 15% aqueous of copper(II) sulfate pentahydrate (370 μL, 0.22 mmol) and tetrahydrofuran-tert-butanol (635 μL). The crude product was purified chromatographically on silica gel (eluting gradient dichloromethane-methanol 98:2 to 96:4) to provide the title compound 36 as a white solid (106 mg, 64% yield). Mp 96° C. $^1H$ NMR (400 MHz, $d_6$-DMSO) δ=12.09 (s, 1H), 8.53 (s, 1H), 8.44 (d, J=1.8 Hz, 1H), 8.38 (d, J=2.1 Hz, 1H), 8.18-8.08 (m, 2H), 8.02 (dd, J=7.3, 2.0 Hz, 1H), 7.84 (dd, J=8.6, 1.9 Hz, 1H), 7.66 (tt, J=7.1, 5.3 Hz, 2H), 7.59 (s, 1H), 7.55 (d, J=8.8 Hz, 1H), 7.35 (dd, J=8.8, 2.2 Hz, 1H), 4.28 (d, J=7.0 Hz, 2H), 4.11 (d, J=6.7 Hz, 2H), 2.88 (t, J=6.7 Hz, 2H), 2.67 (dd, J=9.5, 5.2 Hz, 2H), 2.27 (t, J=6.8 Hz, 2H), 2.02 (hept, J=6.6 Hz, 1H), 1.79 (d, J=11.1 Hz, 2H), 1.74 (s, 1H), 1.45-1.37 (m, 2H), 1.20-1.05 (m, 2H), 0.92 (d, J=6.7 Hz, 6H). $^{13}C$ NMR (100 MHz, $d_6$-DMSO) δ=160.9 ($C_{quat}$), 140.0 ($C_{quat}$), 137.7 ($C_{quat}$), 134.7 ($C_{quat}$), 134.1 ($C_{quat}$), 131.7 ($C_{quat}$), 129.2 (CH), 129.1 (CH), 128.6 (CH), 127.8 (CH), 127.5 (CH), 127.2 (CH), 126.9 ($C_{quat}$), 125.5 (CH), 125.2 ($C_{quat}$), 124.9 (CH), 123.5 ($C_{quat}$), 122.3 (CH), 122.2 (CH), 114.3 (CH), 111.4 ($C_{quat}$), 70.6 ($CH_2$), 57.0 ($CH_2$), 54.4 ($CH_2$), 52.5 ($CH_2$), 40.3 ($CH_2$), 36.4 (CH), 29.0 ($CH_2$), 27.3 (CH), 18.9 ($CH_3$). HRMS (ESI+): calcd. for $C_{33}H_{38}ClN_6O_4S$, 649.2351. Found: $[M+H]^+$, 649.2358 (1.2 ppm error).

Isobutyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate (37) (Code AB556)

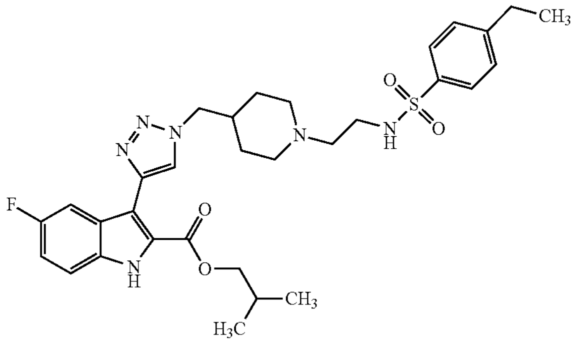

Prepared by general method G using alkyne 14f (60 mg, 0.23 mmol), azide 5f (85 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 37 as a pale yellow solid (84 mg, 60% yield). Mp 139° C. $^1H$ NMR (400 MHz, $d_6$-DMSO) δ=12.01 (s, 1H), 8.55 (s, 1H), 8.04 (dd, J=10.3, 2.6 Hz, 1H), 7.73-7.67 (m, 2H), 7.55 (dd, J=9.0, 4.7 Hz, 1H), 7.40 (d, J=8.1 Hz, 3H), 7.23 (td, J=9.1, 2.7 Hz, 1H), 4.33 (d, J=7.0 Hz, 2H), 4.12 (d, J=6.7 Hz, 2H), 2.81 (q, J=6.1 Hz, 2H), 2.72-2.61 (m, 4H), 2.27 (t, J=6.9 Hz, 2H), 2.03 (hept, J=6.7 Hz, 1H), 1.80 (dt, J=11.2, 5.8 Hz, 3H), 1.50-1.42 (m, 2H), 1.18 (q, J=8.2, 7.6 Hz, 5H), 0.94 (d, J=6.7 Hz, 6H). $^{13}C$ NMR (100 MHz, $d_6$-DMSO) δ=161.0 ($C_{quat}$), 157.6 (d, J=234.4 Hz, $C_{quat}$), 148.5 ($C_{quat}$), 140.2 ($C_{quat}$), 138.0 ($C_{quat}$), 133.1 ($C_{quat}$), 128.4 (CH), 126.6 (CH), 126.1 (d, J=11.0 Hz, $C_{quat}$), 124.7 (CH), 123.8 ($C_{quat}$), 114.4 (d, J=26.2 Hz, CH), 114.0 (d, J=10.1 Hz, CH), 111.8 (d, J=5.5 Hz, $C_{quat}$), 107.3 (d, J=24.4 Hz, CH), 70.6 ($CH_2$), 56.9 ($CH_2$), 54.4 ($CH_2$), 52.5 ($CH_2$), 40.2 ($CH_2$), 36.5 (CH), 29.0 ($CH_2$), 28.0 ($CH_2$), 27.3 (CH), 18.9 ($CH_3$), 15.2 ($CH_3$). $^{19}F$ NMR (376 MHz, $d_6$-DMSO) δ=−122.4. HRMS (ESI+): calcd. for $C_{31}H_{40}FN_6O_4S$, 611.2811. Found: $[M+H]^+$, 611.2810 (−0.1 ppm error).

Isobutyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate (38) (Code AB557)

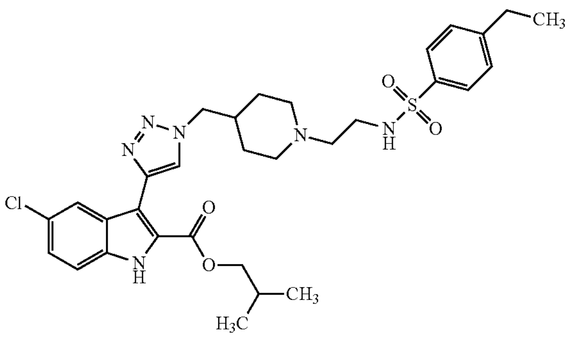 [SMILES: CCc1ccc(S(=O)(=O)NCCN2CCC(Cn3cc(-c4c(C(=O)OCC(C)C)[nH]c5ccc(Cl)cc45)nn3)CC2)cc1]

Prepared by general method G using alkyne 14g (70 mg, 0.25 mmol), azide 5f (94 mg, 0.27 mmol), 2M aqueous of sodium ascorbate (444 μL, 0.89 mmol), 15% aqueous of copper(II) sulfate pentahydrate (370 μL, 0.22 mmol) and tetrahydrofuran-tert-butanol (635 μL). The crude product was purified chromatographically on silica gel (eluting gradient dichloromethane-methanol 98:2 to 96:4) to provide the title compound 38 as a white solid (87 mg, 55% yield). Mp 146° C. $^1H$ NMR (400 MHz, $d_6$-DMSO) δ=12.09 (s, 1H), 8.56 (s, 1H), 8.37 (d, J=2.1 Hz, 1H), 7.74-7.67 (m, 2H), 7.55 (d, J=8.8 Hz, 1H), 7.41 (s, 1H), 7.41-7.32 (m, 3H), 4.34 (d, J=7.0 Hz, 2H), 4.12 (d, J=6.7 Hz, 2H), 2.81 (q, J=6.4 Hz, 2H), 2.66 (q, J=7.6 Hz, 4H), 2.27 (t, J=6.8 Hz, 2H), 2.03 (h, J=6.7 Hz, 1H), 1.85-1.75 (m, 3H), 1.49-1.43 (m, 2H), 1.26-1.13 (m, 5H), 0.94 (d, J=6.7 Hz, 6H). $^{13}C$ NMR (100 MHz, $d_6$-DMSO) δ=162.3 ($C_{quat}$), 160.9 ($C_{quat}$), 148.5 ($C_{quat}$), 140.0 ($C_{quat}$), 138.0 ($C_{quat}$), 134.7 ($C_{quat}$), 128.4 (CH), 126.9 ($C_{quat}$), 126.6 (CH), 125.6 (CH), 125.2 ($C_{quat}$), 124.9 (CH), 123.5 ($C_{quat}$), 122.2 (CH), 114.3 (CH), 111.4 ($C_{quat}$), 70.7 ($CH_2$), 56.9 ($CH_2$), 54.5 ($CH_2$), 52.5 ($CH_2$), 40.2 ($CH_2$), 36.5 (CH), 35.8 (CH), 30.8 (CH), 29.0 ($CH_2$), 28.0 ($CH_2$), 27.3 (CH), 18.9 ($CH_3$), 15.2 ($CH_3$). HRMS (ESI+): calcd. for $C_{31}H_{40}ClN_6O_4S$, 627.2518. Found: $[M+H]^+$, 627.2515 (−0.5 ppm error).

Isobutyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate (39) (Code AB603)

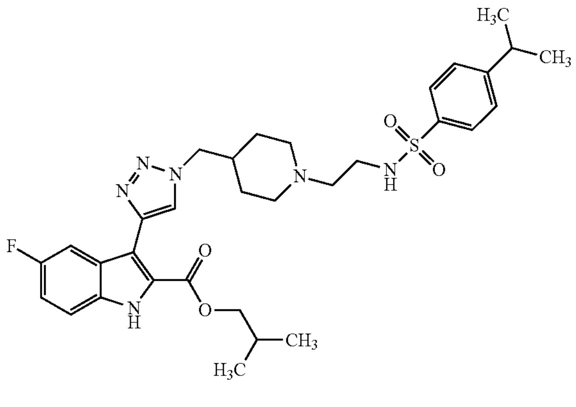 [SMILES: CC(C)COC(=O)c1[nH]c2ccc(F)cc2c1-c1cn(CC2CCN(CCNS(=O)(=O)c3ccc(C(C)C)cc3)CC2)nn1]

Prepared by general method G using alkyne 14f (60 mg, 0.23 mmol), azide 5g (89 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 39 as a white solid (88 mg, 61% yield). Mp 166° C. $^1H$ NMR (400 MHz, $d_6$-DMSO) δ=11.71 (s, 1H), 8.25 (s, 1H), 7.74 (dd, J=10.3, 2.7 Hz, 1H), 7.41 (d, J=8.0 Hz, 2H), 7.25 (dd, J=9.0, 4.7 Hz, 1H), 7.13 (d, J=7.9 Hz, 2H), 7.09 (t, J=5.2 Hz, 1H), 6.93 (td, J=9.1, 2.7 Hz, 1H), 4.04 (d, J=6.9 Hz, 2H), 3.82 (d, J=6.7 Hz, 2H), 2.66 (h, J=6.9 Hz, 1H), 2.37 (d, J=10.8 Hz, 2H), 2.23-2.17 (m, 4H), 1.96 (t, J=6.9 Hz, 2H), 1.73 (h, J=6.8 Hz, 1H), 1.50 (t, J=11.2 Hz, 3H), 1.15 (d, J=12.4 Hz, 2H), 0.89 (d, J=6.9 Hz, 6H), 0.64 (d, J=6.7 Hz, 6H). $^{13}C$ NMR (100 MHz, $d_6$-DMSO) δ=161.0 ($C_{quat}$), 157.5 (d, J=233.4 Hz, $C_{quat}$), 153.0 ($C_{quat}$), 140.2 ($C_{quat}$), 138.1 ($C_{quat}$), 133.1 ($C_{quat}$), 127.0 (CH), 126.6 (CH), 126.0 (d, J=11.2 Hz, $C_{quat}$), 124.8 (CH), 123.8 ($C_{quat}$), 114.4 (d, J=25.5 Hz, CH), 114.0 (d, J=9.4 Hz, CH), 111.9 (d, J=5.6 Hz, $C_{quat}$), 107.3 (d, J=24.6 Hz, CH), 70.6 ($CH_2$), 56.9 ($CH_2$), 54.4 ($CH_2$), 52.5 ($CH_2$), 40.3 ($CH_2$), 36.5 (CH), 33.3 (CH), 29.1 ($CH_2$) 27.4 (CH), 23.5 ($CH_3$), 18.9 ($CH_3$). $^{19}F$ NMR (376 MHz, $d_6$-DMSO) δ=−122.4. HRMS (ESI+): calcd. for $C_{32}H_{42}FN_6O_4S$, 625.2964. Found: $[M+H]^+$, 625.2967 (0.5 ppm error).

Isobutyl 5-fluoro-3-(1-((1-(2-((4-isobutylphenyl) sulfonamido)ethyl)piperidin-4-yl)methyl)-1H-1,2,3-triazol-4-yl)-1H-indole-2-carboxylate (40) (Code AB668)

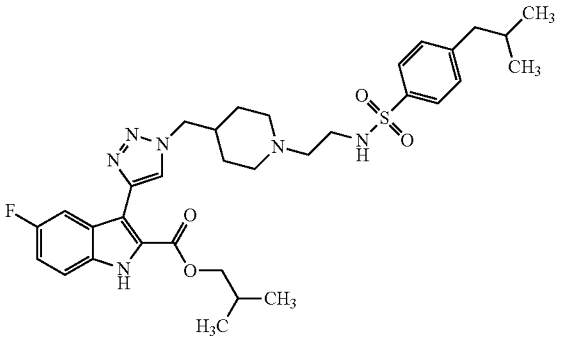 [SMILES: CC(C)COC(=O)c1[nH]c2ccc(F)cc2c1-c1cn(CC2CCN(CCNS(=O)(=O)c3ccc(CC(C)C)cc3)CC2)nn1]

Prepared by general method G using alkyne 14f (60 mg, 0.23 mmol), azide 5h (92 mg, 0.24 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (579 µL). The crude product was purified chromatographically on silica gel (eluting gradient dichloromethane-methanol 98:2 to 96:4) to provide the title compound 40 as a white solid (91 mg, 62% yield). Mp 163° C. $^1$H NMR (400 MHz, $d_6$-DMSO) δ=12.01 (s, 1H), 8.55 (s, 1H), 8.05 (dd, J=10.2, 2.5 Hz, 1H), 7.70 (d, J=8.3 Hz, 2H), 7.55 (dd, J=9.0, 4.7 Hz, 1H), 7.34 (t, J=8.4 Hz, 3H), 7.22 (td, J=9.1, 2.6 Hz, 1H), 4.33 (d, J=7.0 Hz, 2H), 4.12 (d, J=6.7 Hz, 2H), 2.86-2.78 (m, 2H), 2.65 (d, J=11.2 Hz, 2H), 2.48 (s, 2H), 2.23 (t, J=6.8 Hz, 2H), 2.03 (dq, J=13.4, 6.7 Hz, 1H), 1.81 (tt, J=16.5, 9.0 Hz, 4H), 1.44 (d, J=11.3 Hz, 2H), 1.25-1.16 (m, 2H), 0.94 (d, J=6.7 Hz, 6H), 0.81 (d, J=6.6 Hz, 6H). $^{13}$C NMR (100 MHz, $d_6$-DMSO) δ=161.0 ($C_{quat}$), 157.5 (d, J=234.1 Hz, $C_{quat}$), 145.9 ($C_{quat}$), 140.2 ($C_{quat}$), 138.0 ($C_{quat}$), 133.1 ($C_{quat}$), 129.5 (CH), 126.4 (CH), 126.0 (d, J=10.3 Hz, $C_{quat}$), 124.7 (CH), 123.7 ($C_{quat}$), 114.4 (d, J=26.7 Hz, CH), 114.0 (d, J=9.4 Hz, CH), 111.9 (d, J=5.6 Hz, $C_{quat}$), 107.3 (d, J=24.6 Hz, CH), 70.6 ($CH_2$), 56.8 ($CH_2$), 54.4 ($CH_2$), 52.5 ($CH_2$), 44.1 ($CH_2$), 40.2 ($CH_2$), 36.5 ($CH_2$), 29.5 (CH), 29.0 ($CH_2$), 27.4 (CH), 22.0 ($CH_3$), 18.9 ($CH_3$). $^{19}$F NMR (376 MHz, $d_6$-DMSO) δ=−122.4 (td, J=9.7, 4.7 Hz). HRMS (ESI+): calcd. for $C_{33}H_{44}FN_6O_4S$, 639.3122. Found: $[M+H]^+$, 639.3123 (0.2 ppm error).

Isopentyl 3-(1-((1-(2-((4-ethylphenyl)sulfonamido) ethyl)piperidin-4-yl)methyl)-1H-1,2,3-triazol-4-yl)-5-fluoro-1H-indole-2-carboxylate (41) (Code AB663)

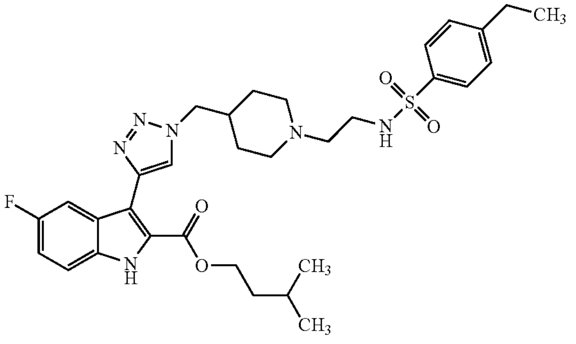 [SMILES: CCc1ccc(S(=O)(=O)NCCN2CCC(Cn3cc(-c4c(C(=O)OCCC(C)C)[nH]c5ccc(F)cc45)nn3)CC2)cc1]

Prepared by general method G using alkyne 14h (70 mg, 0.26 mmol), azide 5f (95 mg, 0.27 mmol), 2M aqueous of sodium ascorbate (448 µL, 0.90 mmol), 15% aqueous of copper(II) sulfate pentahydrate (374 µL, 0.22 mmol) and tetrahydrofuran-tert-butanol (640 µL). The crude product was purified chromatographically on silica gel (eluting gradient dichloromethane-methanol 98:2 to 96:4) to provide the title compound 41 as a white solid (95 mg, 59% yield). Mp 157° C. $^1$H NMR (400 MHz, $d_6$-DMSO) δ=12.02 (s, 1H), 8.55 (s, 1H), 8.06 (d, J=12.8 Hz, 1H), 7.70 (d, J=8.3 Hz, 2H), 7.53 (dd, J=9.0, 4.7 Hz, 1H), 7.40 (d, J=8.3 Hz, 3H), 7.22 (td, J=9.1, 2.6 Hz, 1H), 4.40-4.30 (m, 4H), 2.85-2.77 (m, 2H), 2.66 (q, J=7.7 Hz, 4H), 2.26 (t, J=6.8 Hz, 2H), 1.81 (t, J=10.5 Hz, 3H), 1.71 (dt, J=13.2, 6.6 Hz, 1H), 1.62 (q, J=6.9 Hz, 2H), 1.46 (d, J=11.1 Hz, 2H), 1.25-1.14 (m, 5H), 0.91 (d, J=6.5 Hz, 6H). $^{13}$C NMR (100 MHz, $d_6$-DMSO) δ=161.0 ($C_{quat}$), 157.5 (d, J=233.1 Hz, $C_{quat}$), 148.5 ($C_{quat}$), 140.2 ($C_{quat}$), 138.0 ($C_{quat}$), 133.1 ($C_{quat}$), 128.4 (CH), 126.6 (CH), 126.0 (d, J=10.8 Hz, $C_{quat}$), 124.7 (CH), 123.8 ($C_{quat}$), 114.4 (d, J=26.8 Hz, CH), 114.0 (d, J=9.3 Hz, CH), 111.7 (d, J=5.6 Hz, $C_{quat}$), 107.4 (d, J=24.9 Hz, CH), 63.3 ($CH_2$), 56.9 ($CH_2$), 54.5 ($CH_2$), 52.5 ($CH_2$), 40.2 ($CH_2$), 36.9 ($CH_2$), 36.5 (CH), 29.1 ($CH_2$), 28.0 ($CH_2$), 24.4 (CH), 22.3 ($CH_3$), 15.2 ($CH_3$). $^{19}$F NMR (376 MHz, $d_6$-DMSO) δ=−122.4. HRMS (ESI+): calcd. for $C_{32}H_{42}FN_6O_4S$, 625.2970. Found: $[M+H]^+$, 625.2967 (−0.6 ppm error).

Isopentyl 5-fluoro-3-(1-((1-(2-((4-isopropylphenyl) sulfonamido)ethyl)piperidin-4-yl)methyl)-1H-1,2,3-triazol-4-yl)-1H-indole-2-carboxylate (42) (Code AB664)

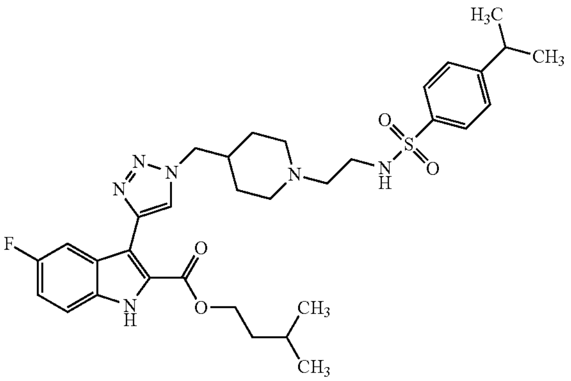 [SMILES: CC(C)CCOC(=O)c1[nH]c2ccc(F)cc2c1-c1cn(CC2CCN(CCNS(=O)(=O)c3ccc(C(C)C)cc3)CC2)nn1]

Prepared by general method G using alkyne 14h (70 mg, 0.26 mmol), azide 5g (98 mg, 0.27 mmol), 2M aqueous of sodium ascorbate (448 µL, 0.90 mmol), 15% aqueous of copper(II) sulfate pentahydrate (374 µL, 0.22 mmol) and tetrahydrofuran-tert-butanol (640 µL). The crude product was purified chromatographically on silica gel (eluting gradient dichloromethane-methanol 98:2 to 96:4) to provide the title compound 42 as a white solid (98 mg, 60% yield). Mp 171° C. $^1$H NMR (400 MHz, $d_6$-DMSO) δ=12.02 (s, 1H), 8.55 (s, 1H), 8.07 (dd, J=10.3, 2.6 Hz, 1H), 7.74-7.67 (m, 2H), 7.53 (dd, J=9.0, 4.7 Hz, 1H), 7.46-7.39 (m, 2H), 7.38 (s, 1H), 7.22 (td, J=9.1, 2.7 Hz, 1H), 4.40-4.31 (m, 4H), 2.94 (h, J=6.9 Hz, 1H), 2.82 (s, 2H), 2.66 (dt, J=11.4, 3.6 Hz, 2H), 2.26 (t, J=6.8 Hz, 2H), 1.85-1.75 (m, 3H), 1.75-1.68 (m, 1H), 1.61 (q, J=6.9 Hz, 2H), 1.45 (d, J=12.0 Hz, 2H), 1.18 (d, J=6.9 Hz, 8H), 0.91 (d, J=6.5 Hz, 6H). $^{13}$C NMR (100 MHz, $d_6$-DMSO) δ=161.0 ($C_{quat}$), 157.5 (d, J=233.1 Hz, $C_{quat}$), 153.0 ($C_{quat}$), 140.3 ($C_{quat}$), 138.1 ($C_{quat}$), 133.1 ($C_{quat}$), 127.0 (CH), 126.6 (CH), 126.0 (d, J=10.9 Hz, $C_{quat}$), 124.7 (CH), 123.8 ($C_{quat}$), 114.4 (d, J=26.8 Hz, CH), 114.0 (d, J=9.4 Hz, CH), 111.7 (d, J=5.5 Hz, $C_{quat}$), 107.4 (d, J=24.7 Hz, CH), 63.2 ($CH_2$), 56.9 ($CH_2$), 54.4 ($CH_2$), 52.5 ($CH_2$), 40.2 ($CH_2$), 36.9 ($CH_2$), 36.5 (CH), 33.3 (CH), 29.1 ($CH_2$), 24.5 (CH), 23.5 ($CH_3$), 22.3 ($CH_3$). $^{19}F$ NMR (376 MHz, $d_6$-DMSO) δ=−122.4. HRMS (ESI+): calcd. for $C_{33}H_{44}FN_6O_4S$, 639.3124. Found: $[M+H]^+$, 639.3123 (−0.1 ppm error).

Isopentyl 5-fluoro-3-(1-((1-(2-((4-isobutylphenyl) sulfonamido)ethyl)piperidin-4-yl)methyl)-1H-1,2,3-triazol-4-yl)-1H-indole-2-carboxylate (43) (Code AB669)

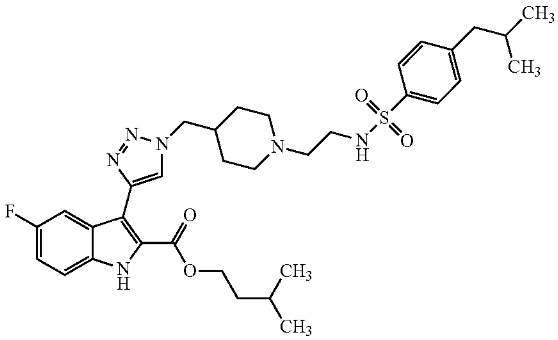 [SMILES: CC(C)CCOC(=O)c1[nH]c2ccc(F)cc2c1-c1cn(CC2CCN(CCNS(=O)(=O)c3ccc(CC(C)C)cc3)CC2)nn1]

Prepared by general method G using alkyne 14h (70 mg, 0.26 mmol), azide 5h (102 mg, 0.27 mmol), 2M aqueous of sodium ascorbate (448 μL, 0.90 mmol), 15% aqueous of copper(II) sulfate pentahydrate (374 μL, 0.22 mmol) and tetrahydrofuran-tert-butanol (640 μL). The crude product was purified chromatographically on silica gel (eluting gradient dichloromethane-methanol 98:2 to 96:4) to provide the title compound 43 as a beige solid (94 mg, 56% yield). Mp 145° C. $^1H$ NMR (400 MHz, $d_6$-DMSO) δ=12.02 (s, 1H), 8.55 (s, 1H), 8.06 (dd, J=10.3, 2.6 Hz, 1H), 7.73-7.66 (m, 2H), 7.53 (dd, J=9.0, 4.7 Hz, 1H), 7.38-7.31 (m, 3H), 7.22 (td, J=9.1, 2.6 Hz, 1H), 4.40-4.31 (m, 4H), 2.82 (q, J=6.2 Hz, 2H), 2.65 (dt, J=12.0, 3.3 Hz, 2H), 2.48 (s, 2H), 2.24 (t, J=6.9 Hz, 2H), 1.90-1.57 (m, 7H), 1.44 (d, J=12.4 Hz, 2H), 1.20 (qd, J=12.3, 11.7, 3.5 Hz, 2H), 0.91 (d, J=6.5 Hz, 6H), 0.82 (d, J=6.6 Hz, 6H). $^{13}C$ NMR (100 MHz, $d_6$-DMSO) δ=161.0 ($C_{quat}$), 157.5 (d, J=234.6 Hz, $C_{quat}$), 145.9 ($C_{quat}$), 140.2 ($C_{quat}$), 138.0 ($C_{quat}$), 133.1 ($C_{quat}$), 129.5 (CH), 126.4 (CH), 126.0 (d, J=10.8 Hz, $C_{quat}$), 124.7 (CH), 123.8 ($C_{quat}$), 114.4 (d, J=26.5 Hz, CH), 114.0 (d, J=9.6 Hz, CH), 111.7 (d, J=5.9 Hz, $C_{quat}$), 107.4 (d, J=24.1 Hz, CH), 63.2 ($CH_2$), 56.8 ($CH_2$), 54.4 ($CH_2$), 52.5 ($CH_2$), 44.1 ($CH_2$), 40.2 ($CH_2$), 36.9 ($CH_2$), 36.5 (CH), 29.5 (CH), 29.0 ($CH_2$), 24.4 (CH), 22.3 ($CH_3$), 22.0 ($CH_3$). $^{19}F$ NMR (376 MHz, $d_6$-DMSO) δ=−122.4. HRMS (ESI+): calcd. for $C_{34}H_{46}FN_6O_4S$, 653.3275. Found: $[M+H]^+$, 653.3280 (0.8 ppm error).

2-Hydroxyethyl 3-(1-((1-(2-((4-ethylphenyl)sulfonamido)ethyl)piperidin-4 yl)methyl)-1H-1,2,3-triazol-4-yl)-5-fluoro-1H-indole-2-carboxylate (44) (Code AB597)

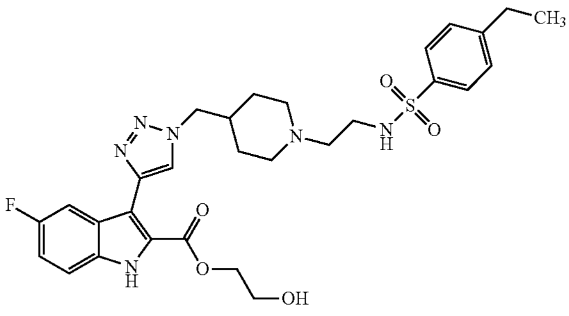 [SMILES: CCc1ccc(S(=O)(=O)NCCN2CCC(Cn3cc(-c4c(C(=O)OCCO)[nH]c5ccc(F)cc45)nn3)CC2)cc1]

Prepared by general method G using alkyne 14i (40 mg, 0.16 mmol), azide 5f (60 mg, 0.17 mmol), 2M aqueous of sodium ascorbate (283 μL, 0.57 mmol), 15% aqueous of copper(II) sulfate pentahydrate (236 μL, 0.14 mmol) and tetrahydrofuran-tert-butanol (404 μL). The crude product was purified chromatographically on silica gel (eluting gradient dichloromethane-methanol 98:2 to 95:5) to provide the title compound 44 as a white solid (56 mg, 58% yield). $^1H$ NMR (400 MHz, $d_6$-DMSO) δ=12.01 (s, 1H), 8.54 (s, 1H), 8.01 (dd, J=10.2, 2.6 Hz, 1H), 7.54 (dd, J=9.0, 4.7 Hz, 1H), 7.30 (d, J=2.0 Hz, 1H), 7.27-7.12 (m, 2H), 7.05 (d, J=8.5 Hz, 1H), 4.37 (d, J=7.0 Hz, 2H), 4.12 (d, J=6.7 Hz, 2H), 3.80 (d, J=6.4 Hz, 2H), 3.37 (s, 2H), 2.78 (d, J=11.3 Hz, 2H), 2.08-1.97 (m, 2H), 1.88 (t, J=11.1 Hz, 3H), 1.53 (d, J=12.5 Hz, 2H), 1.28 (q, J=13.2, 12.4 Hz, 3H), 0.96 (dd, J=21.5, 6.7 Hz, 5H). $^{13}C$ NMR (100 MHz, $d_6$-DMSO) δ=160.6 ($C_{quat}$), 157.8 (d, J=233.4 Hz, $C_{quat}$), 148.6 ($C_{quat}$), 140.3 ($C_{quat}$), 137.9 ($C_{quat}$), 132.0 ($C_{quat}$), 130.2 ($C_{quat}$), 128.4 (CH), 126.6 (CH), 125.6 (d, J=10.1 Hz, $C_{quat}$), 123.3 (CH), 113.9 (d, J=10.6 Hz, CH), 112.7 (d, J=26.5 Hz, CH), 105.4 (d, J=24.1 Hz, CH), 104.7 (d, J=5.0 Hz, $C_{quat}$), 59.7 ($CH_2$), 56.9 ($CH_2$), 54.9 ($CH_2$), 52.5 ($CH_2$), 42.2 ($CH_2$), 40.2 ($CH_2$), 36.2 (CH), 29.1 ($CH_2$), 28.0 ($CH_2$), 15.2 ($CH_3$). $^{19}F$ NMR (376 MHz, $d_6$-DMSO) δ=−122.5. HRMS (ESI+): calcd. for $C_{29}H_{36}FN_6O_5S$, 599.2444. Found: $[M+H]^+$, 599.2446 (0.5 ppm error).

2-Aminoethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate (45) (Code AB614)

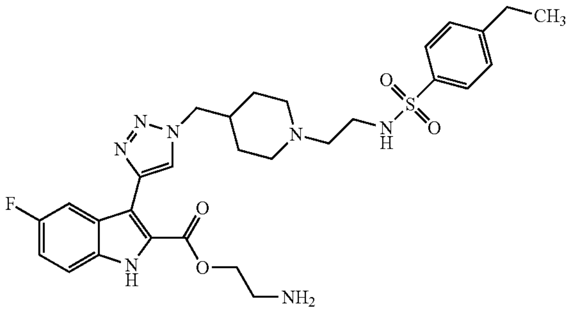 [SMILES: CCc1ccc(S(=O)(=O)NCCN2CCC(Cn3cc(-c4c(C(=O)OCCN)[nH]c5ccc(F)cc45)nn3)CC2)cc1]

Prepared by general method G using alkyne 14j (50 mg, 0.14 mmol), azide 5f (53 mg, 0.15 mmol), 2M aqueous of sodium ascorbate (253 µL, 0.51 mmol), 15% aqueous of copper(II) sulfate pentahydrate (211 µL, 0.13 mmol) and tetrahydrofuran-tert-butanol (361 µL). The crude product was purified chromatographically on silica gel (eluting gradient dichloromethane-methanol 97:3 to 94:6) to give the N-Boc derivative (63 mg, 62% yield). The product (50 mg, 0.072 mmol) was converted to the hydrochloride salt according general method method I, using acetyl chloride (61 µL, 0.86 mmol) and methanol (400 µL). The hydrochloride salt 45 was obtained as a white cristalline solid (45 mg, 94% yield). HRMS (ESI+): calcd. for $C_{29}H_{37}FN_7O_4S$, 598.2600. Found: $[M+H]^+$, 598.2606 (1.0 ppm error).

3-(1-((1-(2-((4-Ethylphenyl)sulfonamido)ethyl)piperidin-4-yl)methyl)-1H-1,2,3-triazol-4-yl)-5-fluoro-N-isobutyl-1H-indole-2-carboxamide (46) (Code AB651)

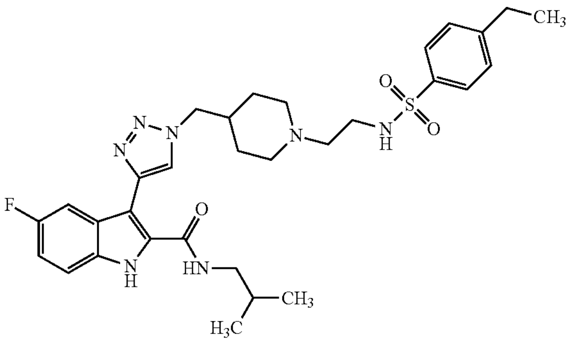 [SMILES: CCc1ccc(S(=O)(=O)NCCN2CCC(Cn3cc(-c4c(C(=O)NCC(C)C)[nH]c5ccc(F)cc45)nn3)CC2)cc1]

Prepared by general method G using alkyne 14k (60 mg, 0.23 mmol), azide 5f (86 mg, 0.24 mmol), 2M aqueous of sodium ascorbate (407 µL, 0.81 mmol), 15% aqueous of copper(II) sulfate pentahydrate (339 µL, 0.20 mmol) and tetrahydrofuran-tert-butanol (581 µL). The crude product was purified chromatographically on silica gel (eluting gradient dichloromethane-methanol 98:2 to 95:5) to provide the title compound 46 as a pale yellow solid (76 mg, 54% yield). Mp 198° C. $^1$H NMR (400 MHz, $d_6$-DMSO) δ=11.97 (s, 1H), 10.78 (t, J=5.5 Hz, 1H), 8.81 (s, 1H), 7.70 (dd, J=8.8, 2.3 Hz, 2H), 7.67-7.59 (m, 1H), 7.54 (dd, J=9.0, 4.8 Hz, 1H), 7.48-7.37 (m, 3H), 7.15 (td, J=9.2, 2.5 Hz, 1H), 4.37 (d, J=7.1 Hz, 2H), 3.29-3.17 (m, 2H), 2.81 (q, J=6.2 Hz, 2H), 2.72-2.61 (m, 4H), 2.27 (t, J=6.9 Hz, 2H), 1.84 (ddd, J=12.7, 10.5, 6.6 Hz, 3H), 1.45 (d, J=12.5 Hz, 2H), 1.37 (s, 1H), 1.28-1.13 (m, 5H), 0.94 (d, J=6.7 Hz, 6H). $^{13}$C NMR (100 MHz, $d_6$-DMSO) δ=160.3 ($C_{quat}$), 157.8 (d, J=233.5 Hz, $C_{quat}$), 148.5 ($C_{quat}$), 140.2 ($C_{quat}$), 138.0 ($C_{quat}$), 131.9 ($C_{quat}$), 130.4 ($C_{quat}$), 128.4 (CH), 126.6 (CH), 125.6 (d, J=10.0 Hz, $C_{quat}$), 123.4 (CH), 114.0 (d, J=9.8 Hz, CH), 112.7 (d, J=26.8 Hz, CH), 105.1 (d, J=24.2 Hz, CH), 104.3 (d, J=5.0 Hz, $C_{quat}$), 56.9 ($CH_2$), 54.9 ($CH_2$), 52.5 ($CH_2$), 46.8 ($CH_2$), 40.2 ($CH_2$), 36.3 (CH), 29.0 ($CH_2$), 28.0 ($CH_2$), 20.2 ($CH_3$), 15.2 ($CH_3$). $^{19}$F NMR (376 MHz, $d_6$-DMSO) δ=−122.5. HRMS (ESI+): calcd. for $C_{31}H_{41}FN_7O_3S$, 610.2961. Found: $[M+H]^+$, 610.2970 (1.5 ppm error).

5-Fluoro-N-isobutyl-3-(1-((1-(2-((4-isopropylphenyl)sulfonamido)ethyl)piperidin-4-yl)methyl)-1H-1,2,3-triazol-4-yl)-1H-indole-2-carboxamide (47) (Code AB652)

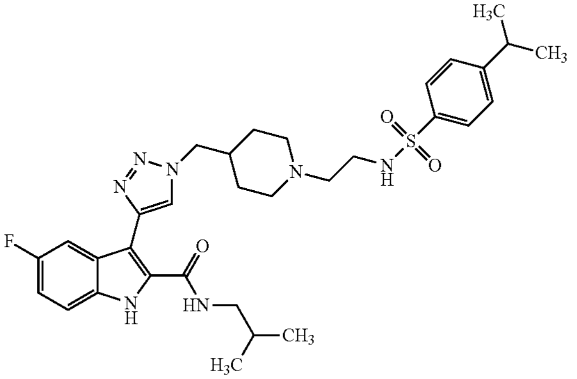 [SMILES: CC(C)CNC(=O)c1[nH]c2ccc(F)cc2c1-c1cn(CC2CCN(CCNS(=O)(=O)c3ccc(C(C)C)cc3)CC2)nn1]

Prepared by general method G using alkyne 14k (60 mg, 0.23 mmol), azide 5g (89 mg, 0.24 mmol), 2M aqueous of sodium ascorbate (407 µL, 0.81 mmol), 15% aqueous of copper(II) sulfate pentahydrate (339 µL, 0.20 mmol) and tetrahydrofuran-tert-butanol (581 µL). The crude product was purified chromatographically on silica gel (eluting gradient dichloromethane-methanol 100:0 to 95:5) to provide the title compound 47 as a pale yellow solid (76 mg, 52% yield). Mp 85° C. $^1$H NMR (400 MHz, $d_6$-DMSO) δ=11.95 (s, 1H), 10.76 (t, J=5.5 Hz, 1H), 8.80 (s, 1H), 7.73-7.68 (m, 2H), 7.66 (dd, J=10.3, 2.5 Hz, 1H), 7.54 (dd, J=9.0, 4.8 Hz, 1H), 7.48-7.41 (m, 2H), 7.15 (td, J=9.1, 2.5 Hz, 1H), 4.36 (d, J=7.1 Hz, 2H), 3.31-3.13 (m, 4H), 2.95 (dq, J=13.7, 6.7 Hz, 1H), 2.82 (t, J=6.8 Hz, 2H), 2.66 (d, J=11.2 Hz, 2H), 2.26 (t, J=6.8 Hz, 2H), 1.94-1.77 (m, 4H), 1.44 (d, J=12.0 Hz, 2H), 1.20 (dd, J=14.1, 6.9 Hz, 8H), 0.93 (d, J=6.7 Hz, 5H). $^{13}$C NMR (100 MHz, $d_6$-DMSO) δ=160.4 ($C_{quat}$), 157.8 (d, J=234.6 Hz, $C_{quat}$), 153.1 ($C_{quat}$), 140.2 ($C_{quat}$), 138.1 ($C_{quat}$), 132.0 ($C_{quat}$), 130.4 ($C_{quat}$), 127.1 (CH), 126.7 (CH), 125.7 (d, J=10.3 Hz, $C_{quat}$), 123.4 (CH), 114.0 (d, J=9.8 Hz, CH), 112.7 (d, J=26.7 Hz, CH), 105.1 (d, J=24.0 Hz, CH), 104.3 (d, J=5.1 Hz, $C_{quat}$), 56.9 ($CH_2$), 54.9 ($CH_2$), 52.5 ($CH_2$), 46.8 ($CH_2$), 40.3 ($CH_2$), 36.3 (CH), 33.4 (CH), 29.1 ($CH_2$), 28.1 (CH), 23.5 ($CH_3$), 20.2 ($CH_3$). $^{19}$F NMR (376 MHz, $d_6$-DMSO) δ=−122.4. HRMS (ESI+): calcd. for $C_{32}H_{43}FN_7O_3S$, 624.3122. Found: $[M+H]^+$, 624.3127 (0.7 ppm error).

3-(1-((1-(2-((4-Ethylphenyl)sulfonamido)ethyl)piperidin-4-yl)methyl)-1H-1,2,3-triazol-4-yl)-5-fluoro-N-isopentyl-1H-indole-2-carboxamide (48) (Code AB670)

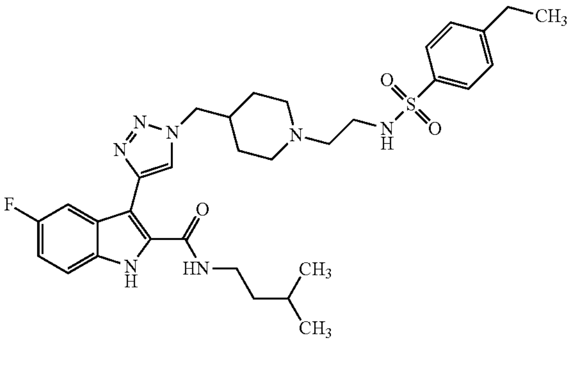 [SMILES: CCc1ccc(S(=O)(=O)NCCN2CCC(Cn3cc(-c4c(C(=O)NCCC(C)C)[nH]c5ccc(F)cc45)nn3)CC2)cc1]

Prepared by general method G using alkyne 14l (65 mg, 0.24 mmol), azide 5f (88 mg, 0.25 mmol), 2M aqueous of sodium ascorbate (418 μL, 0.84 mmol), 15% aqueous of copper(II) sulfate pentahydrate (348 μL, 0.21 mmol) and tetrahydrofuran-tert-butanol (597 μL). The crude product was purified chromatographically on silica gel (eluting gradient dichloromethane-methanol 100:0 to 95:5) to provide the title compound 48 as a pale yellow solid (83 mg, 56% yield). HRMS (ESI+): calcd. for $C_{32}H_{43}FN_7O_3S$, 624.3120. Found: $[M+H]^+$, 624.3127 (1.1 ppm error).

5-Fluoro-N-isopentyl-3-(1-((1-(2-((4-isopropylphenyl)sulfonamido)ethyl)piperidin-4-yl)methyl)-1H-1,2,3-triazol-4-yl)-1H-indole-2-carboxamide (49) (Code AB671)

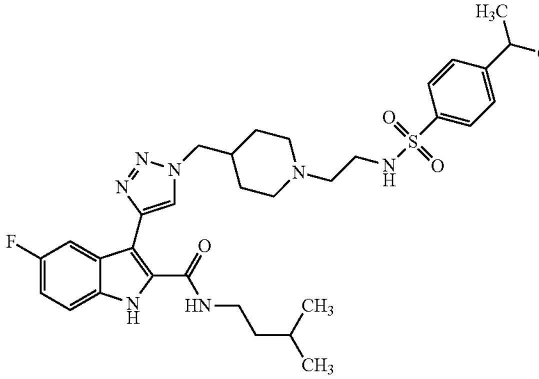

Prepared by general method G using alkyne 14j (65 mg, 0.24 mmol), 5g (92 mg, 0.25 mmol), 2M aqueous of sodium ascorbate (418 μL, 0.84 mmol), 15% aqueous of copper(II) sulfate pentahydrate (348 μL, 0.21 mmol) and tetrahydrofuran-tert-butanol (597 μL). The crude product was purified chromatographically on silica gel (eluting gradient dichloromethane-methanol 98:2 to 95:5) to provide the title compound 49 as a pale yellow solid (81 mg, 53% yield). HRMS (ESI+): calcd. for $C_{33}H_{45}FN_7O_3S$, 638.3277. Found: $[M+H]^+$, 638.3283 (0.9 ppm error).

5-Chloro-3-(1-((1-(2-((4-chlorophenyl)sulfonamido)ethyl)piperidin-4-yl)methyl)-1H-1,2,3-triazol-4-yl)-1H-indole-2-carboxylic acid (50) (Code AB201)

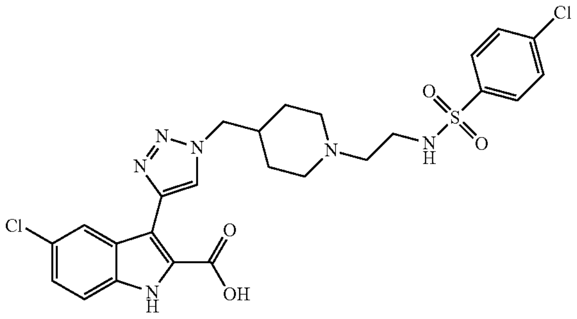 [SMILES: O=C(O)c1[nH]c2ccc(Cl)cc2c1-c1cn(CC2CCN(CCNS(=O)(=O)c3ccc(Cl)cc3)CC2)nn1]

Prepared by general method M using ester 16 (80 mg, 0.13 mmol), lithium hydroxide (13 mg, 0.52 mmol) and tetrahydrofuran-water (1.3 mL). The product was then dried at 35° C. under reduced pressure for 72 hours to obtain the title compound 50 as a white solid (70 mg, 92% yield). HRMS (ESI+): calcd. for $C_{25}H_{27}C_2N_6O_4S$, 577.1189. Found: $[M+H]^+$, 577.1186 (−0.6 ppm error).

6-Chloro-3-(1-((1-(2-((4-chlorophenyl)sulfonamido)ethyl)piperidin-4-yl)methyl)-1H-1,2,3-triazol-4-yl)-1H-indole-2-carboxylic acid (51) (Code AB202)

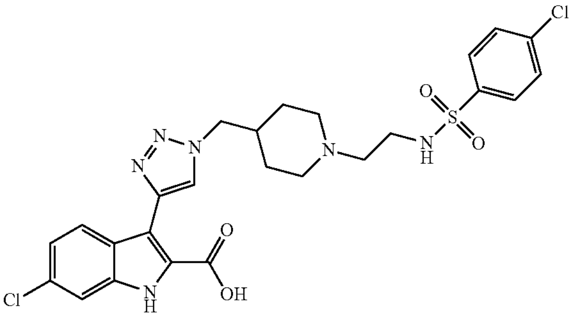 [SMILES: O=C(O)c1[nH]c2cc(Cl)ccc2c1-c1cn(CC2CCN(CCNS(=O)(=O)c3ccc(Cl)cc3)CC2)nn1]

Prepared by general method M using ester 17 (80 mg, 0.13 mmol), lithium hydroxide (13 mg, 0.52 mmol) and tetrahydrofuran-water (1.3 mL). The product was then dried at 35° C. under reduced pressure for 72 hours to obtain the title compound 51 as a white solid (71 mg, 93% yield). HRMS (ESI+): calcd. for $C_{25}H_{27}Cl_2N_6O_4S$, 577.1189. Found: $[M+H]^+$, 577.1186 (−0.6 ppm error).

2-Chloro-4-formylphenyl trifluoromethanesulfonate (52a)

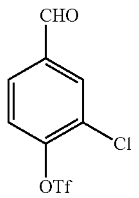 [SMILES: O=Cc1ccc(OS(=O)(=O)C(F)(F)F)c(Cl)c1]

Prepared by general method N using 3-chloro-4-hydroxybenzaldehyde (2.00 g, 12.8 mmol), pyridine (3.09 mL, 38.2 mmol), trifluoromethanesulfonic anhydride (2.36 mL, 14.1 mmol), in dry dichloromethane (43 mL). The crude product was purified chromatographically on silica gel (eluting cyclohexane-ethyl acetate 90:10) to provide the title compound 52a as a white solid which solidifies upon storage in refrigerator (3.29 g, 89% yield). $^1H$ NMR (400 MHz, $CDCl_3$) δ=10.02 (1H, s), 8.29 (1H, d, J=1.9 Hz), 8.06 (1H, dd, J=8.5, 2.0 Hz), 7.90 (1H, d, J=8.5 Hz). $^{13}C$ NMR (100 MHz, $CDCl_3$) δ=190.9 (CH), 148.2 ($C_{quat}$), 137.1 ($C_{quat}$), 132.1 (CH), 130.1 (CH), 127.0 (CH), 124.5 ($C_{quat}$), 118.1 (q, J=320.6 Hz, $C_{quat}$). $^{19}F$ NMR (376 MHz, $CDCl_3$) δ=−73.3. Spectroscopic and physical data matched the ones reported in the literature.[6]

4-Formyl-2-isopropylphenyl trifluoromethanesulfonate (52b)

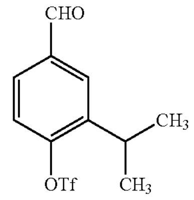

Prepared by general method N using 4-hydroxy-3-isopropylbenzaldehyde (2.00 g, 12.2 mmol), pyridine (2.94 mL, 36.5 mmol), trifluoromethanesulfonic anhydride (2.25 mL, 13.4 mmol), in dry dichloromethane (40 mL). The crude product was purified chromatographically on silica gel (eluting cyclohexane-ethyl acetate 90:10) to provide the title compound 52b as a red oil (2.57 g, 71% yield). LC-MS (ESI+) Found: $[M+H]^+$, 297.1.

Ethyl 3-chloro-4-(((trifluoromethyl)sulfonyl)oxy)benzoate (52c)

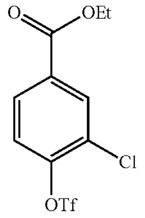 [SMILES: CCOC(=O)c1ccc(OS(=O)(=O)C(F)(F)F)c(Cl)c1]

Prepared by general method N using ethyl 3-chloro-4-hydroxybenzoate (1.00 g, 4.98 mmol), pyridine (1.20 mL, 14.9 mmol), trifluoromethanesulfonic anhydride (921 µL, 5.48 mmol), in dry dichloromethane (17 mL). The crude product was purified chromatographically on silica gel (eluting cyclohexane-ethyl acetate 90:10) to provide the title compound 52c as a white solid which solidifies upon storage in refrigerator (1.24 g, 75% yield). LC-MS (ESI+) Found: $[M+H]^+$, 332.8.

Ethyl 3-(trifluoromethyl)-4-(((trifluoromethyl)sulfonyl)oxy)benzoate (52d)

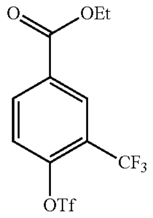 [SMILES: CCOC(=O)c1ccc(OS(=O)(=O)C(F)(F)F)c(C(F)(F)F)c1]

Prepared by general method N using ethyl 4-hydroxy-3-(trifluoromethyl)benzoate (1.00 g, 4.27 mmol), pyridine (1.03 mL, 12.8 mmol), trifluoromethanesulfonic anhydride (789 µL, 4.70 mmol), in dry dichloromethane (14 mL). The crude product was purified chromatographically on silica gel (eluting cyclohexane-ethyl acetate 90:10) to provide the title compound 52d as a white solid which solidifies upon storage in refrigerator (1.27 g, 81% yield). LC-MS (ESI+) Found: $[M+H]^+$, 367.0.

2-Chloro-2'-methoxy-[1,1'-biphenyl]-4-carbaldehyde (53a)

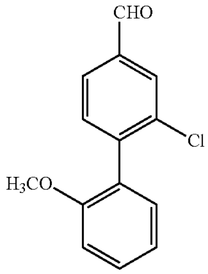 [SMILES: COc1ccccc1-c1ccc(C=O)cc1Cl]

Prepared by general method O using 52a (420 mg, 1.28 mmol), (2-methoxyphenyl)boronic acid (150 mg, 0.99 mmol), 2M aqueous sodium carbonate (790 µL, 1.58 mmol), tetrakis(triphenylphosphine)palladium(0) (114 mg, 0.10 mmol), in dry 1,2-dimethoxyethane (5 mL). The crude product was purified chromatographically on silica gel (eluting gradient cyclohexane-ethyl acetate 95:5 to 85:15) to provide the title compound 53a as a white solid (191 mg, 78% yield). LC-MS (ESI+) Found: $[M+H]^+$, 247.1.

2-Chloro-2'-(methoxymethyl)-[1,1'-biphenyl]-4-carbaldehyde (53b)

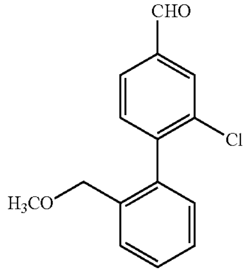 [SMILES: COCc1ccccc1-c1ccc(C=O)cc1Cl]

Prepared by general method O using 52a (407 mg, 1.41 mmol), (2-(methoxymethyl)phenyl)boronic acid (180 mg, 1.08 mmol), 2M aqueous sodium carbonate (868 µL, 1.76 mmol), tetrakis(triphenylphosphine)palladium(0) (125 mg, 0.11 mmol), in dry 1,2-dimethoxyethane (5.4 mL). The crude product was purified chromatographically on silica gel (eluting gradient cyclohexane-ethyl acetate 95:5 to 85:15) to provide the title compound 53b as a white solid (223 mg, 79% yield). LC-MS (ESI+) Found: $[M+H]^+$, 261.1.

2-Chloro-2'-methoxy-5'-methyl-[1,1'-biphenyl]-4-carbaldehyde (53c)

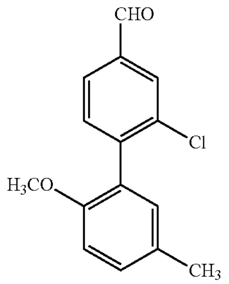 [SMILES: COc1ccc(C)cc1-c1ccc(C=O)cc1Cl]

Prepared by general method O using 52a (407 mg, 1.41 mmol), (2-methoxy-5-methylphenyl)boronic acid (180 mg, 1.08 mmol), 2M aqueous sodium carbonate (868 μL, 1.76 mmol), tetrakis(triphenylphosphine)palladium(0) (125 mg, 0.11 mmol), in dry 1,2-dimethoxyethane (5.4 mL). The crude product was purified chromatographically on silica gel (eluting gradient cyclohexane-ethyl acetate 95:5 to 85:15) to provide the title compound 53c as a white solid (197 mg, 70% yield). LC-MS (ESI+) Found: $[M+H]^+$, 261.1.

3-Chloro-4-(1H-indol-4-yl)benzaldehyde (53d)

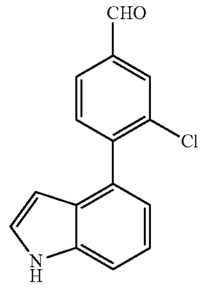 [SMILES: O=Cc1ccc(-c2cccc3[nH]ccc23)c(Cl)c1]

Prepared by general method O using 52a (407 mg, 1.45 mmol), (1H-indol-4-yl)boronic acid (180 mg, 1.12 mmol), 2M aqueous sodium carbonate (895 μL, 1.79 mmol), tetrakis (triphenylphosphine)palladium(0) (129 mg, 0.11 mmol), in dry 1,2-dimethoxyethane (5.6 mL). The crude product was purified chromatographically on silica gel (eluting gradient cyclohexane-ethyl acetate 90:10 to 70:30) to provide the title compound 53d as a white solid (198 mg, 69% yield). LC-MS (ESI+) Found: $[M+H]^+$, 255.9.

3-Chloro-4-(1H-indol-5-yl)benzaldehyde (53e)

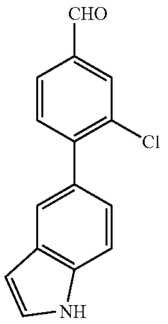 [SMILES: O=Cc1ccc(-c2ccc3[nH]ccc3c2)c(Cl)c1]

Prepared by general method O using 52a (407 mg, 1.45 mmol), (1H-indol-5-yl)boronic acid (180 mg, 1.12 mmol), 2M aqueous sodium carbonate (895 μL, 1.79 mmol), tetrakis (triphenylphosphine)palladium(0) (129 mg, 0.11 mmol), in dry 1,2-dimethoxyethane (5.6 mL). The crude product was purified chromatographically on silica gel (eluting gradient cyclohexane-ethyl acetate 90:10 to 70:30) to provide the title compound 53e as a colorless oil (179 mg, 63% yield). LC-MS (ESI+) Found: $[M+H]^+$, 255.9.

3-Chloro-4-(2,3-dihydrobenzofuran-5-yl)benzaldehyde (53f)

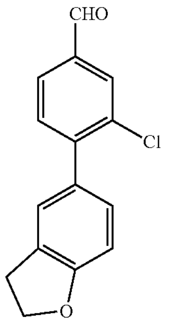 [SMILES: O=Cc1ccc(-c2ccc3c(c2)CCO3)c(Cl)c1]

Prepared by general method O using 53f (343 mg, 1.19 mmol), (2,3-dihydrobenzofuran-5-yl)boronic acid (150 mg, 0.91 mmol), 2M aqueous sodium carbonate (732 μL, 1.46 mmol), tetrakis(triphenylphosphine)palladium(0) (106 mg, 0.091 mmol)), in dry 1,2-dimethoxyethane (4.6 mL). The crude product was purified chromatographically on silica gel (eluting gradient cyclohexane-ethyl acetate 95:5 to 80:20) to provide the title compound 53f as a colorless oil (161 mg, 68% yield). LC-MS (ESI+) Found: $[M+H]^+$, 259.0.

3'-Acetyl-2-chloro-[1,1'-biphenyl]-4-carbaldehyde (53g)

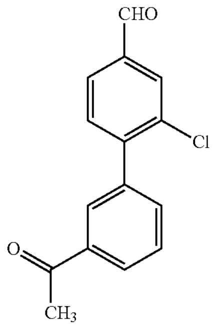 [SMILES: CC(=O)c1cccc(-c2ccc(C=O)cc2Cl)c1]

Prepared by general method O using 52a (343 mg, 1.19 mmol), (3-acetylphenyl)boronic acid (150 mg, 0.91 mmol), 2M aqueous sodium carbonate (732 μL, 1.46 mmol), tetrakis (triphenylphosphine)palladium(0) (106 mg, 0.091 mmol), in dry 1,2-dimethoxyethane (4.6 mL). The crude product was purified chromatographically on silica gel (eluting gradient cyclohexane-ethyl acetate 95:5 to 80:20) to provide the title compound 53g as a colorless oil (153 mg, 64% yield). LC-MS (ESI+) Found: $[M+H]^+$, 259.0.

2-Chloro-3'-isopropyl-[1,1'-biphenyl]-4-carbaldehyde (53h)

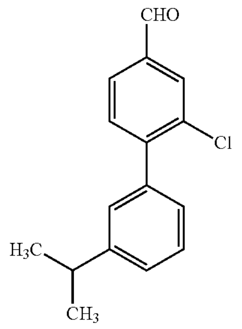 [SMILES: CC(C)c1cccc(-c2ccc(C=O)cc2Cl)c1]

Prepared by general method O using 52a (343 mg, 1.19 mmol), (3-isopropylphenyl)boronic acid (150 mg, 0.91 mmol), 2M aqueous sodium carbonate (732 μL, 1.46 mmol), tetrakis(triphenylphosphine)palladium(0) (106 mg, 0.091 mmol), in dry 1,2-dimethoxyethane (4.6 mL). The crude product was purified chromatographically on silica gel (eluting gradient cyclohexane-ethyl acetate 95:5 to 85:15) to provide the title compound 53h as a colorless oil (168 mg, 71% yield). LC-MS (ESI+) Found: $[M+H]^+$, 259.1.

2-Isopropyl-2'-(methoxymethyl)-[1,1'-biphenyl]-4-carbaldehyde (53i)

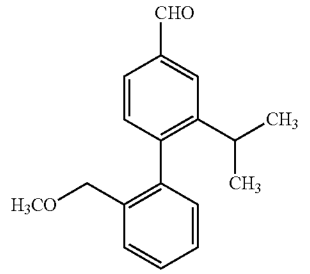 [SMILES: COCc1ccccc1-c1ccc(C=O)cc1C(C)C]

Prepared by general method O using 52b (482 mg, 1.63 mmol), (2-(methoxymethyl)phenyl)boronic acid (180 mg, 1.08 mmol), 2M aqueous sodium carbonate (868 μL, 1.74 mmol), tetrakis(triphenylphosphine)palladium(0) (313 mg, 0.27 mmol), in dry 1,2-dimethoxyethane (5.4 mL). The crude product was purified chromatographically on silica gel (eluting gradient cyclohexane-ethyl acetate 95:5 to 80:20) to provide the title compound 53i as a colorless oil (214 mg, 74% yield). LC-MS (ESI+) Found: $[M+H]^+$, 268.2.

4-(1H-Indol-4-yl)-3-isopropylbenzaldehyde (53j)

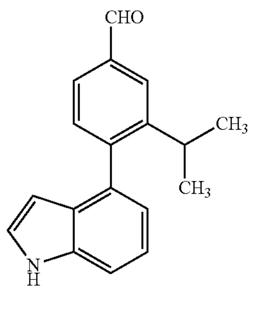 [SMILES: CC(C)c1cc(C=O)ccc1-c1cccc2[nH]ccc12]

Prepared by general method O using 52b (497 mg, 1.68 mmol), (1H-indol-4-yl)boronic acid (180 mg, 1.12 mmol), 2M aqueous sodium carbonate (895 μL, 1.79 mmol), tetrakis(triphenylphosphine)palladium(0) (323 mg, 0.28 mmol), in dry 1,2-dimethoxyethane (5.6 mL). The crude product was purified chromatographically on silica gel (eluting gradient cyclohexane-ethyl acetate 90:10 to 70:30) to provide the title compound 53j as a white solid (198 mg, 67% yield). LC-MS (ESI+) Found: $[M+H]^+$, 264.1.

Ethyl 2-chloro-2'-(methoxymethyl)-[1,1'-biphenyl]-4-carboxylate (53k)

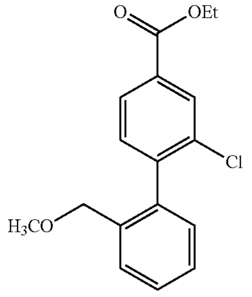

Prepared by general method O using 52c (521 mg, 1.57 mmol), (2-(methoxymethyl)phenyl)boronic acid (200 mg, 1.20 mmol), 2M aqueous sodium carbonate (964 μL, 1.93 mmol), tetrakis(triphenylphosphine)palladium(0) (139 mg, 0.12 mmol), in dry 1,2-dimethoxyethane (6 mL). The crude product was purified chromatographically on silica gel (eluting gradient cyclohexane-ethyl acetate 95:5 to 80:20) to provide the title compound 53k as a colorless oil (294 mg, 80% yield). LC-MS (ESI+) Found: $[M+H]^+$, 305.1.

Ethyl 2-chloro-2'-hydroxy-[1,1'-biphenyl]-4-carboxylate (53l)

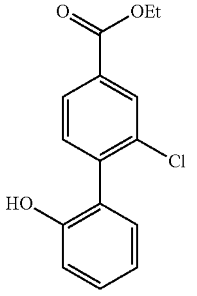 [SMILES: CCOC(=O)c1ccc(-c2ccccc2O)c(Cl)c1]

Prepared by general method O using 52c (470 mg, 1.41 mmol), (2-hydroxyphenyl)boronic acid (150 mg, 1.09 mmol), 2M aqueous sodium carbonate (870 μL, 1.74 mmol), tetrakis(triphenylphosphine)palladium(0) (126 mg, 0.11 mmol), in dry 1,2-dimethoxyethane (6 mL). The crude product was purified chromatographically on silica gel (eluting gradient cyclohexane-ethyl acetate 90:10 to 70:30) to provide the title compound 53l as a white solid (221 mg, 73% yield). LC-MS (ESI+) Found: $[M+H]^+$, 277.1.

Ethyl 4-(1H-indol-4-yl)-3-(trifluoromethyl)benzoate (53m)

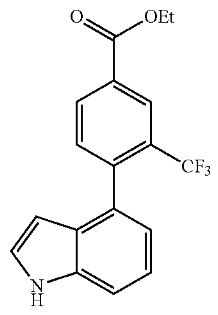

Prepared by general method O using 52d (591 mg, 1.62 mmol), (2-hydroxyphenyl)boronic acid (200 mg, 1.24 mmol), 2M aqueous sodium carbonate (994 μL, 1.99 mmol), tetrakis(triphenylphosphine)palladium(0) (144 mg, 0.12 mmol), in dry 1,2-dimethoxyethane (6.2 mL). The crude product was purified chromatographically on silica gel (eluting gradient cyclohexane-ethyl acetate 90:10 to 70:30) to provide the title compound 53m as a white solid (262 mg, 63% yield). LC-MS (ESI+) Found: $[M+H]^+$, 334.1.

3-Chloro-4-phenoxybenzaldehyde (54a)

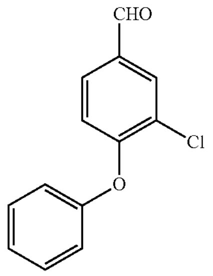 [SMILES: O=Cc1ccc(Oc2ccccc2)c(Cl)c1]

Prepared by general method P using 3-chloro-4-hydroxybenzaldehyde (200 mg, 1.28 mmol), phenylboronic acid (312 mg, 2.55 mmol), copper(II) acetate (232 mg, 1.28 mmol), triethylamine (890 μL, 6.39 mmol), powdered activated 4 Å molecular sieves (1.30 g), in dry dichloromethane (13 mL). The crude product was purified chromatographically on silica gel (eluting cyclohexane-ethyl acetate 85:15) to provide the title compound 54a as a colorless oil (179 mg, 60% yield). LC-MS (ESI+) Found: $[M+H]^+$, 233.1.

3-Isopropyl-4-phenoxybenzaldehyde (54b)

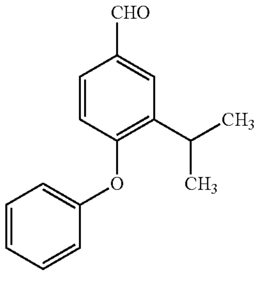 [SMILES: CC(C)c1cc(C=O)ccc1Oc1ccccc1]

Prepared by general method P using 4-hydroxy-3-isopropylbenzaldehyde (200 mg, 1.22 mmol), phenylboronic acid (297 mg, 2.43 mmol), copper(II) acetate (221 mg, 1.22 mmol), triethylamine (849 μL, 6.09 mmol), powdered activated 4 Å molecular sieves (1.20 g), in dry dichloromethane (12 mL). The crude product was purified chromatographically on silica gel (eluting cyclohexane-ethyl acetate 80:20) to provide the title compound 54b as a colorless oil (164 mg, 56% yield). LC-MS (ESI+) Found: $[M+H]^+$, 241.2.

4-((2,3-Dihydrobenzofuran-5-yl)oxy)-3-isopropylbenzaldehyde (54c)

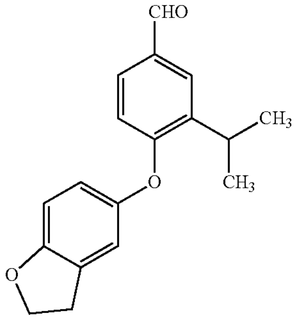 [SMILES: CC(C)c1cc(C=O)ccc1Oc1ccc2c(c1)CCO2]

Prepared by general method P using 4-hydroxy-3-isopropylbenzaldehyde (200 mg, 1.22 mmol), (2,3-dihydrobenzofuran-6-yl)boronic acid (400 mg, 2.44 mmol), copper(II) acetate (221 mg, 1.22 mmol), triethylamine (849 μL, 6.09 mmol), powdered activated 4 Å molecular sieves (1.20 g), in dry dichloromethane (12 mL). The crude product was purified chromatographically on silica gel (eluting cyclohexane-ethyl acetate 80:20) to provide the title compound 54c as a colorless oil (159 mg, 46% yield). LC-MS (ESI+) Found: $[M+H]^+$, 283.2.

4-(3-Acetylphenoxy)-3-isopropylbenzaldehyde (54d)

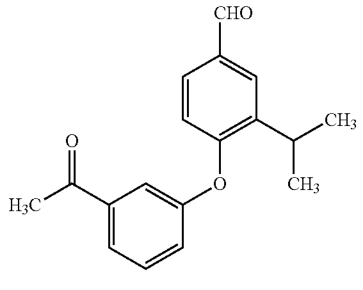 [SMILES: CC(=O)c1cccc(Oc2ccc(C=O)cc2C(C)C)c1]

Prepared by general method P using 4-hydroxy-3-isopropylbenzaldehyde (200 mg, 1.22 mmol), (3-acetylphenyl) boronic acid (400 mg, 2.44 mmol), copper(II) acetate (221 mg, 1.22 mmol), triethylamine (849 μL, 6.09 mmol), powdered activated 4 Å molecular sieves (1.20 g), in dry dichloromethane (12 mL). The crude product was purified chromatographically on silica gel (eluting cyclohexane-ethyl acetate 80:20) to provide the title compound 54d as a colorless oil (135 mg, 39% yield). LC-MS (ESI+) Found: $[M+H]^+$, 283.2.

3-Isopropyl-4-(3-isopropylphenoxy)benzaldehyde (54e)

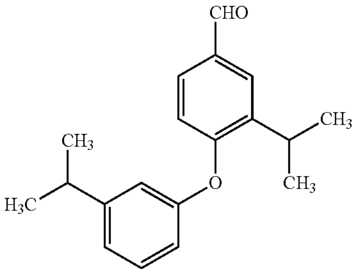 [SMILES: CC(C)c1cccc(Oc2ccc(C=O)cc2C(C)C)c1]

Prepared by general method P using 4-hydroxy-3-isopropylbenzaldehyde (200 mg, 1.22 mmol), (3-isopropylphenyl) boronic acid (400 mg, 2.44 mmol), copper(II) acetate (221 mg, 1.22 mmol), triethylamine (849 μL, 6.09 mmol), powdered activated 4 Å molecular sieves (1.20 g), in dry dichloromethane (12 mL). The crude product was purified chromatographically on silica gel (eluting cyclohexane-ethyl acetate 80:20) to provide the title compound 54e as a colorless oil (127 mg, 37% yield). LC-MS (ESI+) Found: $[M+H]^+$, 283.3.

3-Chloro-4-isobutoxybenzaldehyde (55a)

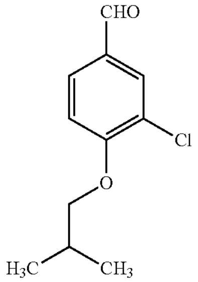

Prepared by general method K using isobutanol (89 μL, 0.96 mmol), 4-hydroxy-3-isopropylbenzaldehyde (180 mg, 1.15 mmol), triphenylphosphine (302 mg, 1.15 mmol), diisopropyl azodicarboxylate (226 μL, 1.15 mmol), in dry tetrahydrofuran (2 mL). The crude product was passed through a short silica gel column eluting with dichloromethane-diethyl ether (1:1) then purified chromatographically on silica gel (eluting cyclohexane-ethyl acetate 80:20) to provide the title compound 55a as a colorless oil (181 mg, 89% yield). LC-MS (ESI+) Found: $[M+H]^+$, 213.1.

3-Chloro-4-(isopentyloxy)benzaldehyde (55b)

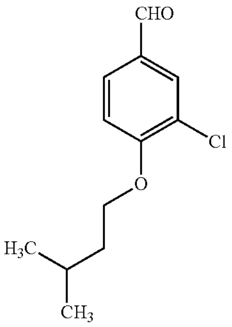

Prepared by general method K using isoamyl alcohol (104 μL, 0.96 mmol), 4-hydroxy-3-isopropylbenzaldehyde (180 mg, 1.15 mmol), triphenylphosphine (302 mg, 1.15 mmol), diisopropyl azodicarboxylate (226 μL, 1.15 mmol), in dry tetrahydrofuran (2 mL). The crude product was passed through a short silica gel column eluting with dichloromethane-diethyl ether (1:1) then purified chromatographically on silica gel (eluting cyclohexane-ethyl acetate 80:20) to provide the title compound 55b as a colorless oil (186 mg, 86% yield). LC-MS (ESI+) Found: $[M+H]^+$, 227.1.

Ethyl 2-chloro-2'-(isopentyloxy)-[1,1'-biphenyl]-4-carboxylate (56)

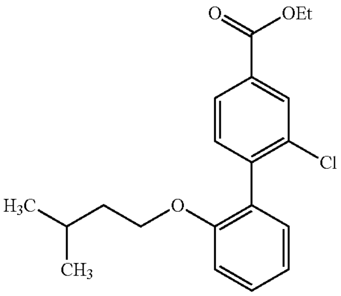

Prepared by general method K using isoamyl alcohol (66 μL, 0.60 mmol), 531 (200 mg, 0.72 mmol), triphenylphosphine (190 mg, 0.72 mmol), diisopropyl azodicarboxylate (142 μL, 0.72 mmol), in dry tetrahydrofuran (1.2 mL). The crude product was passed through a short silica gel column eluting with dichloromethane-diethyl ether (1:1) then purified chromatographically on silica gel (eluting cyclohexane-ethyl acetate 85:15) to provide the title compound 56 as a colorless oil (177 mg, 85% yield). LC-MS (ESI+) Found: $[M+H]^+$, 347.2.

2-Chloro-2'-(methoxymethyl)-[1,1'-biphenyl]-4-carboxylic acid (57a)

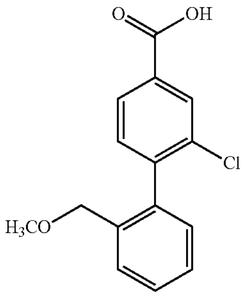 [SMILES: COCc1ccccc1-c1ccc(C(=O)O)cc1Cl]

Prepared by general method M using ester 53k (250 mg, 0.82 mmol), lithium hydroxide (79 mg, 3.28 mmol) and tetrahydrofuran-water (8.2 mL). The product was then dried at 35° C. under reduced pressure for 72 hours to obtain the title compound 57a as a white solid (211 mg, 93% yield). LC-MS (ESI+) Found: $[M+H]^+$, 277.1.

2-Chloro-2'-(isopentyloxy)-[1,1'-biphenyl]-4-carboxylic acid (57b)

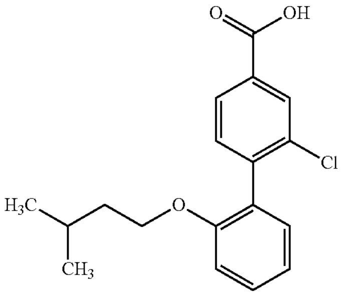 [SMILES: CC(C)CCOc1ccccc1-c1ccc(C(=O)O)cc1Cl]

Prepared by general method M using ester 56 (140 mg, 0.40 mmol), lithium hydroxide (39 mg, 1.61 mmol) and tetrahydrofuran-water (4 mL). The product was then dried at 35° C. under reduced pressure for 72 hours to obtain the title compound 57b as a white solid (115 mg, 89% yield). LC-MS (ESI+) Found: $[M+H]^+$, 319.1.

4-(1H-Indol-4-yl)-3-(trifluoromethyl)benzoic acid (57c)

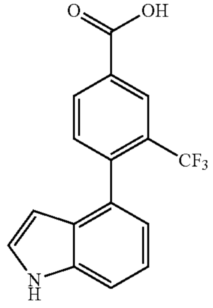 [SMILES: O=C(O)c1ccc(-c2cccc3[nH]ccc23)c(C(F)(F)F)c1]

Prepared by general method M using ester 53m (210 mg, 0.63 mmol), lithium hydroxide (60 mg, 2.52 nmol) and tetrahydrofuran-water (6.3 mL). The product was then dried at 35° C. under reduced pressure for 72 hours to obtain the title compound 57c as a white solid (174 mg, 91% yield). LC-MS (ESI+) Found: $[M+H]^+$, 306.1.

4-(Azidomethyl)-1-((2-chloro-2'-methoxy-[1,1'-biphenyl]-4-yl)methyl)piperidine (58a)

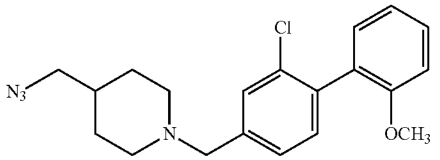 [SMILES: COc1ccccc1-c1ccc(CN2CCC(CN=[N+]=[N-])CC2)cc1Cl]

Prepared by general method Q using the ammonium salt 4 (161 mg, 0.91 mmol), the corresponding aldehyde 53a (150 mg, 0.61 mmol), triethylamine (170 μL, 1.22 mmol), sodium triacetoxyborohydride (180 mg, 0.85 mmol), in dry methanol (2 mL). The crude product was purified chromatographically on silica gel (eluting gradient dichloromethane-methanol 98:2 to 96:4) to provide the title compound 58a as a colorless oil (131 mg, 58% yield). LC-MS (ESI+) Found: $[M+H]^+$, 371.2.

4-(Azidomethyl)-1-((2-chloro-2'-(methoxymethyl)-[1,1'-biphenyl]-4-yl)methyl)piperidine (58b)

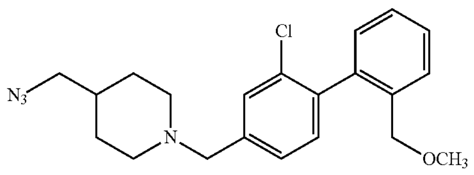 [SMILES: COCc1ccccc1-c1ccc(CN2CCC(CN=[N+]=[N-])CC2)cc1Cl]

Prepared by general method Q using the ammonium salt 4 (183 mg, 1.04 mmol), the corresponding aldehyde 53b (180 mg, 0.69 mmol), triethylamine (192 μL, 1.38 mmol), sodium triacetoxyborohydride (205 mg, 0.97 mmol), in dry methanol (2.3 mL). The crude product was purified chromatographically on silica gel (eluting gradient dichloromethane-methanol 98:2 to 96:4) to provide the title compound 58b as a colorless oil (138 mg, 52% yield). LC-MS (ESI+) Found: $[M+H]^+$, 385.2.

4-(Azidomethyl)-1-((2-chloro-2'-methoxy-5'-methyl-[1,1'-biphenyl]-4-yl)methyl)piperidine (58c)

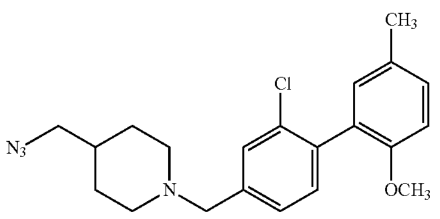 [SMILES: COc1ccc(C)cc1-c1ccc(CN2CCC(CN=[N+]=[N-])CC2)cc1Cl]

Prepared by general method Q using the ammonium salt 4 (152 mg, 0.86 mmol), the corresponding aldehyde 53c (150 mg, 0.58 mmol), triethylamine (160 μL, 1.15 mmol), sodium triacetoxyborohydride (171 mg, 0.81 mmol), in dry methanol (2 mL). The crude product was purified chromatographically on silica gel (eluting gradient dichloromethane-methanol 98:2 to 96:4) to provide the title compound 58c as a colorless oil (123 mg, 56% yield). LC-MS (ESI+) Found: $[M+H]^+$, 385.2.

4-(4-((4-(Azidomethyl)piperidin-1-yl)methyl)-2-chlorophenyl)-1H-indole (58d)

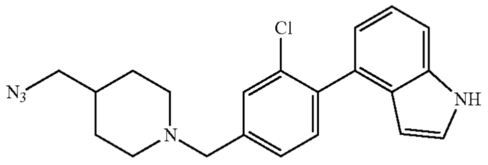 [SMILES: [N-]=[N+]=NCC1CCN(Cc2ccc(-c3cccc4[nH]ccc34)c(Cl)c2)CC1]

Prepared by general method Q using the ammonium salt 4 (155 mg, 0.88 mmol), the corresponding aldehyde 53d (150 mg, 0.59 mmol), triethylamine (164 μL, 1.17 mmol), sodium triacetoxyborohydride (174 mg, 0.82 mmol), in dry methanol (2 mL). The crude product was purified chromatographically on silica gel (eluting gradient dichloromethane-methanol 98:2 to 95:5) to provide the title compound 58d as a colorless oil (106 mg, 48% yield). LC-MS (ESI+) Found: $[M+H]^+$, 380.2.

5-(4-((4-(Azidomethyl)piperidin-1-yl)methyl)-2-chlorophenyl)-1H-indole (58e)

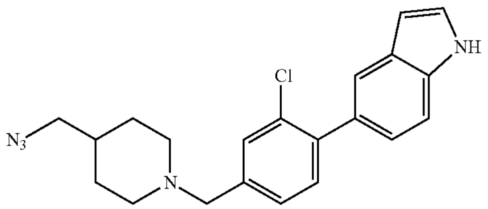 [SMILES: [N-]=[N+]=NCC1CCN(Cc2ccc(-c3ccc4[nH]ccc4c3)c(Cl)c2)CC1]

Prepared by general method Q using the ammonium salt 4 (155 mg, 0.88 mmol), the corresponding aldehyde 53e (150 mg, 0.59 mmol), triethylamine (164 μL, 1.17 mmol), sodium triacetoxyborohydride (174 mg, 0.82 mmol), in dry methanol (2 mL). The crude product was purified chromatographically on silica gel (eluting gradient dichloromethane-methanol 98:2 to 95:5) to provide the title compound 58e as a colorless oil (115 mg, 52% yield). LC-MS (ESI+) Found: $[M+H]^+$, 380.2.

4-(Azidomethyl)-1-(3-chloro-4-(2,3-dihydrobenzofuran-5-yl)benzyl)piperidine (58f)

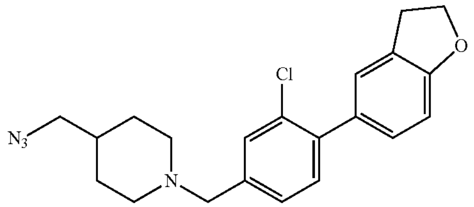 [SMILES: [N-]=[N+]=NCC1CCN(Cc2ccc(-c3ccc4c(c3)CCO4)c(Cl)c2)CC1]

Prepared by general method Q using the ammonium salt 4 (143 mg, 0.81 mmol), the corresponding aldehyde 53f (140 mg, 0.54 mmol), triethylamine (151 μL, 1.08 mmol), sodium triacetoxyborohydride (161 mg, 0.76 mmol), in dry methanol (1.8 mL). The crude product was purified chromatographically on silica gel (eluting gradient dichloromethane-methanol 98:2 to 96:4) to provide the title compound 58f as a colorless oil (134 mg, 65% yield). LC-MS (ESI+) Found: $[M+H]^+$, 383.2.

1-(4'-((4-(Azidomethyl)piperidin-1-yl)methyl)-2'-chloro-[1,1'-biphenyl]-3-yl)ethan-1-one (58g)

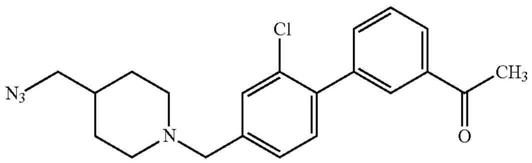 [SMILES: CC(=O)c1cccc(-c2ccc(CN3CCC(CN=[N+]=[N-])CC3)cc2Cl)c1]

Prepared by general method Q using the ammonium salt 4 (143 mg, 0.81 mmol), the corresponding aldehyde 53g (140 mg, 0.54 mmol), triethylamine (151 μL, 1.08 mmol), sodium triacetoxyborohydride (161 mg, 0.76 mmol), in dry methanol (1.8 mL). The crude product was purified chromatographically on silica gel (eluting gradient dichloromethane-methanol 98:2 to 96:4) to provide the title compound 58g as a colorless oil (91 mg, 44% yield). LC-MS (ESI+) Found: $[M+H]^+$, 383.2.

4-(Azidomethyl)-1-((2-chloro-3'-isopropyl-[1,1'-biphenyl]-4-yl)methyl)piperidine (58h)

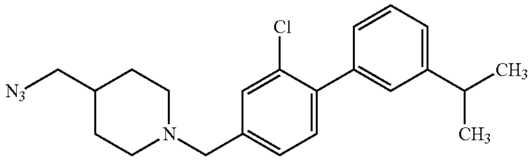 [SMILES: CC(C)c1cccc(-c2ccc(CN3CCC(CN=[N+]=[N-])CC3)cc2Cl)c1]

Prepared by general method Q using the ammonium salt 4 (154 mg, 0.87 mmol), the corresponding aldehyde 53h (150 mg, 0.58 mmol), triethylamine (162 μL, 1.16 mmol), sodium triacetoxyborohydride (172 mg, 0.81 mmol), in dry methanol (1.9 mL). The crude product was purified chromatographically on silica gel (eluting gradient dichloromethane-methanol 98:2 to 96:4) to provide the title compound 58h as a colorless oil (119 mg, 54% yield). LC-MS (ESI+) Found: $[M+H]^+$, 383.2.

4-(Azidomethyl)-1-((2-isopropyl-2'-(methoxymethyl)-[1,1'-biphenyl]-4-yl)methyl)piperidine (58i)

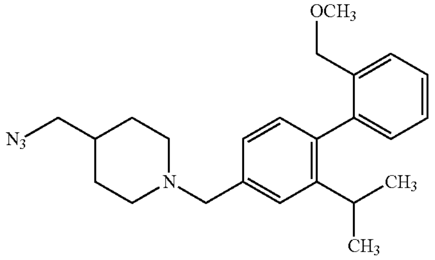 [SMILES: COCc1ccccc1-c1ccc(CN2CCC(CN=[N+]=[N-])CC2)cc1C(C)C]

Prepared by general method Q using the ammonium salt 4 (178 mg, 1.01 mmol), the corresponding aldehyde 53i (180 mg, 0.67 mmol), triethylamine (187 μL, 1.34 mmol), sodium triacetoxyborohydride (200 mg, 0.94 mmol), in dry methanol (2.2 mL). The crude product was purified chromatographically on silica gel (eluting gradient dichloromethane-methanol 98:2 to 96:4) to provide the title compound 58i as a colorless oil (157 mg, 60% yield). LC-MS (ESI+) Found: $[M+H]^+$, 393.2.

4-(4-((4-(Azidomethyl)piperidin-1-yl)methyl)-2-isopropylphenyl)-1H-indole (58j)

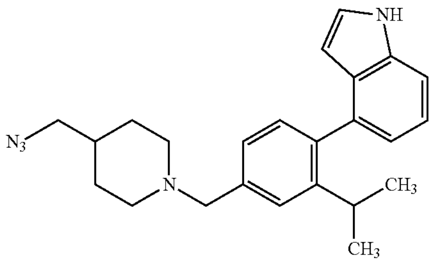 [SMILES: CC(C)c1cc(CN2CCC(CN=[N+]=[N-])CC2)ccc1-c1cccc2[nH]ccc12]

Prepared by general method Q using the ammonium salt 4 (161 mg, 0.91 mmol), the corresponding aldehyde 53j (160 mg, 0.61 mmol), triethylamine (170 μL, 1.22 mmol), sodium triacetoxyborohydride (180 mg, 0.85 mmol), in dry methanol (2 mL). The crude product was purified chromatographically on silica gel (eluting gradient dichloromethane-methanol 98:2 to 95:5) to provide the title compound 58j as a colorless oil (124 mg, 53% yield). LC-MS (ESI+) Found: $[M+H]^+$, 388.2.

4-(Azidomethyl)-1-(3-chloro-4-phenoxybenzyl)piperidine (58k)

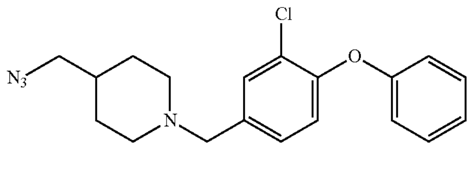 [SMILES: [N-]=[N+]=NCC1CCN(Cc2ccc(Oc3ccccc3)c(Cl)c2)CC1]

Prepared by general method Q using the ammonium salt 4 (171 mg, 0.97 mmol), the corresponding aldehyde 54a (150 mg, 0.64 mmol), triethylamine (180 μL, 1.29 mmol), sodium triacetoxyborohydride (191 mg, 0.90 mmol), in dry methanol (2.1 mL). The crude product was purified chromatographically on silica gel (eluting gradient dichloromethane-methanol 98:2 to 96:4) to provide the title compound 58k as a white solid (160 mg, 70% yield). LC-MS (ESI+) Found: $[M+H]^+$, 357.1.

4-(Azidomethyl)-1-(3-isopropyl-4-phenoxybenzyl)piperidine (58l)

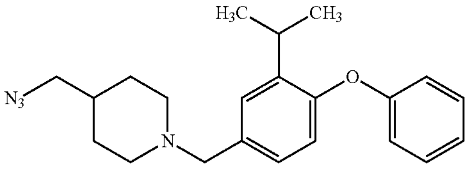 [SMILES: CC(C)c1cc(CN2CCC(CN=[N+]=[N-])CC2)ccc1Oc1ccccc1]

Prepared by general method Q using the ammonium salt 4 (154 mg, 0.87 mmol), the corresponding aldehyde 54b (140 mg, 0.58 mmol), triethylamine (162 μL, 1.17 mmol), sodium triacetoxyborohydride (173 mg, 0.82 mmol), in dry methanol (1.9 mL). The crude product was purified chromatographically on silica gel (eluting gradient dichloromethane-methanol 98:2 to 96:4) to provide the title compound 58l as a colorless oil (144 mg, 68% yield). LC-MS (ESI+) Found: $[M+H]^+$, 365.2.

4-(Azidomethyl)-1-(4-((2,3-dihydrobenzofuran-5-yl)oxy)-3-isopropylbenzyl)piperidine (58m)

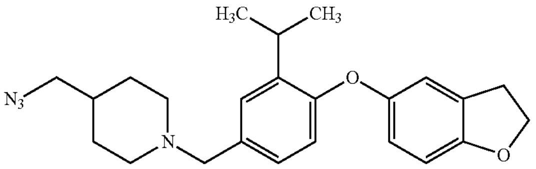 [SMILES: CC(C)c1cc(CN2CCC(CN=[N+]=[N-])CC2)ccc1Oc1ccc2c(c1)CCO2]

Prepared by general method Q using the ammonium salt 4 (131 mg, 0.74 mmol), the corresponding aldehyde 54c (140 mg, 0.50 mmol), triethylamine (138 μL, 1.00 mmol), sodium triacetoxyborohydride (147 mg, 0.69 mmol), in dry methanol (1.7 mL). The crude product was purified chromatographically on silica gel (eluting gradient dichloromethane-methanol 98:2 to 96:4) to provide the title compound 58m as a colorless oil (107 mg, 53% yield). LC-MS (ESI+) Found: $[M+H]^+$, 407.2.

1-(3-(4-((4-(Azidomethyl)piperidin-1-yl)methyl)-2-isopropylphenoxy)phenyl)ethan-1-one (58n)

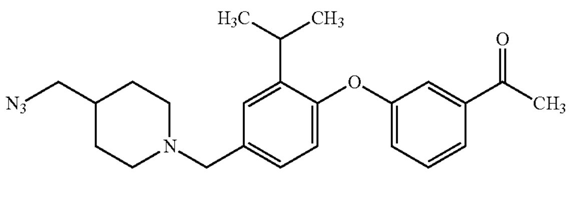 [SMILES: CC(=O)c1cccc(Oc2ccc(CN3CCC(CN=[N+]=[N-])CC3)cc2C(C)C)c1]

Prepared by general method Q using the ammonium salt 4 (113 mg, 0.64 mmol), the corresponding aldehyde 54d (120 mg, 0.43 mmol), triethylamine (118 μL, 0.85 mmol), sodium triacetoxyborohydride (126 mg, 0.60 mmol), in dry methanol (1.4 mL). The crude product was purified chromatographically on silica gel (eluting gradient dichloromethane-methanol 98:2 to 96:4) to provide the title compound 58n as a colorless oil (102 mg, 59% yield). LC-MS (ESI+) Found: $[M+H]^+$, 407.2.

4-(Azidomethyl)-1-(3-isopropyl-4-(3-isopropylphenoxy)benzyl)piperidine (58o)

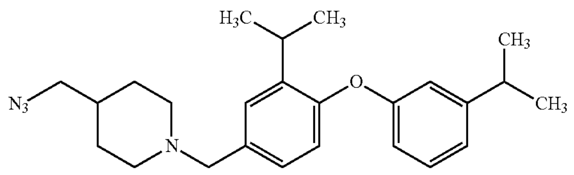 [SMILES: CC(C)c1cccc(Oc2ccc(CN3CCC(CN=[N+]=[N-])CC3)cc2C(C)C)c1]

Prepared by general method Q using the ammonium salt 4 (113 mg, 0.64 mmol), the corresponding aldehyde 54e (120 mg, 0.42 mmol), triethylamine (118 μL, 0.85 mmol), sodium triacetoxyborohydride (126 mg, 0.59 mmol), in dry methanol (1.4 mL). The crude product was purified chromatographically on silica gel (eluting gradient dichloromethane-methanol 98:2 to 96:4) to provide the title compound 58o as a colorless oil (78 mg, 45% yield). LC-MS (ESI+) Found: $[M+H]^+$, 407.3.

4-(Azidomethyl)-1-(3-chloro-4-isobutoxybenzyl) piperidine (58p)

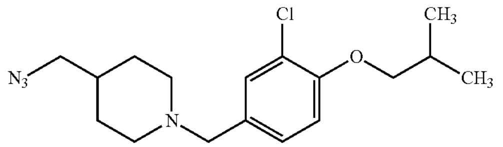 [SMILES: CC(C)COc1ccc(CN2CCC(CN=[N+]=[N-])CC2)cc1Cl]

Prepared by general method Q using the ammonium salt 4 (187 mg, 1.06 mmol), the corresponding aldehyde 55a (150 mg, 0.71 mmol), triethylamine (197 μL, 1.41 mmol), sodium triacetoxyborohydride (209 mg, 0.99 mmol), in dry methanol (2.4 mL). The crude product was purified chromatographically on silica gel (eluting gradient dichloromethane-methanol 98:2 to 96:4) to provide the title compound 58p as a colorless oil (149 mg, 63% yield). LC-MS (ESI+) Found: $[M+H]^+$, 337.2.

4-(Azidomethyl)-1-(3-chloro-4-(isopentyloxy)benzyl)piperidine (58q)

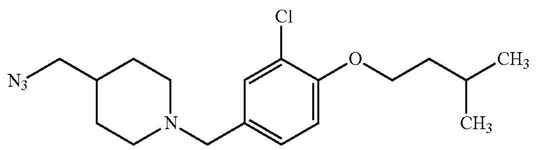 [SMILES: CC(C)CCOc1ccc(CN2CCC(CN=[N+]=[N-])CC2)cc1Cl]

Prepared by general method Q using the ammonium salt 4 (175 mg, 0.99 mmol), the corresponding aldehyde 55b (150 mg, 0.66 mmol), triethylamine (184 μL, 1.32 mmol), sodium triacetoxyborohydride (196 mg, 0.93 mmol), in dry methanol (2.2 mL). The crude product was purified chromatographically on silica gel (eluting gradient dichloromethane-methanol 98:2 to 96:4) to provide the title compound 58q as a colorless oil (135 mg, 58% yield). LC-MS (ESI+) Found: $[M+H]^+$, 351.2.

(4-(Azidomethyl)piperidin-1-yl)(2-chloro-2'-(methoxymethyl)-[1,1'-biphenyl]-4-yl)methanone (59a)

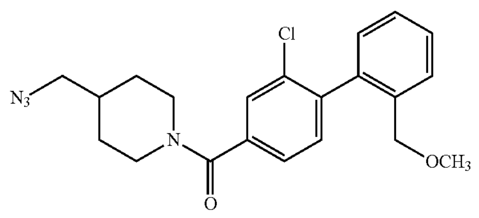 [SMILES: COCc1ccccc1-c1ccc(C(=O)N2CCC(CN=[N+]=[N-])CC2)cc1Cl]

Prepared by general method L using the corresponding acid 57a (180 mg, 0.65 mmol), the ammonium salt 4 (115 mg, 0.65 mmol), N,N-diisopropylethylamine (453 μL, 2.60 mmol) and O-(7-Azabenzotriazol-1-yl-N,N,N',N'-tetramethyluronium hexafluorophosphate (272 mg, 0.72 mmol) in N,N-dimethylformamide (2.2 mL). The crude product was purified chromatographically on silica gel (eluting gradient dichloromethane-methanol 99:1 to 96:4) to provide the title compound 59a as a colorless oil (186 mg, 72% yield). LC-MS (ESI+) Found: $[M+H]^+$, 399.2.

(4-(Azidomethyl)piperidin-1-yl)(2-chloro-2'-(isopentyloxy)-[1,1'-biphenyl]-4-yl)methanone (59b)

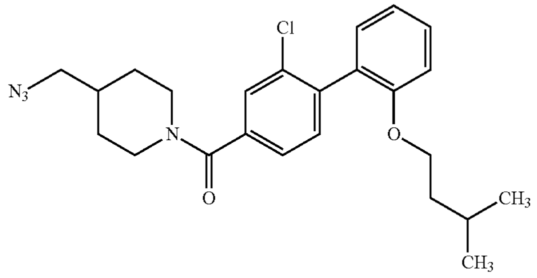 [SMILES: CC(C)CCOc1ccccc1-c1ccc(C(=O)N2CCC(CN=[N+]=[N-])CC2)cc1Cl]

Prepared by general method L using the corresponding acid 57b (100 mg, 0.31 mmol), the ammonium salt 4 (55 mg, 0.31 mmol), N,N-diisopropylethylamine (219 μL, 1.25 mmol) and O-(7-Azabenzotriazol-1-yl-N,N,N',N'-tetramethyluronium hexafluorophosphate (131 mg, 0.35 mmol) in N,N-dimethylformamide (1 mL). The crude product was purified chromatographically on silica gel (eluting gradient dichloromethane-methanol 99:1 to 96:4) to provide the title compound 59b as a colorless oil (96 mg, 70% yield). LC-MS (ESI+) Found: $[M+H]^+$, 440.2.

(4-(1H-Indol-4-yl)-3-(trifluoromethyl)phenyl)(4-(azidomethyl)piperidin-1-yl)methanone (59c)

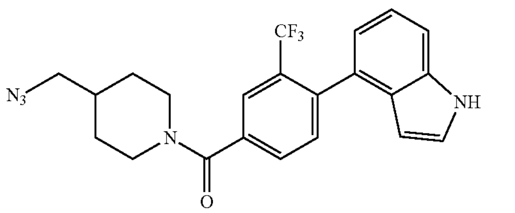 [SMILES: [N-]=[N+]=NCC1CCN(C(=O)c2ccc(-c3cccc4[nH]ccc34)c(C(F)(F)F)c2)CC1]

Prepared by general method L using the corresponding acid 57c (160 mg, 0.52 mmol), the ammonium salt 4 (93 mg, 0.31 mmol), N,N-diisopropylethylamine (365 μL, 2.10 mmol) and O-(7-Azabenzotriazol-1-yl-N,N,N',N'-tetramethyluronium hexafluorophosphate (219 mg, 0.58 mmol) in N,N-dimethylformamide (1.7 mL). The crude product was purified chromatographically on silica gel (eluting gradient dichloromethane-methanol 98:2 to 95:5) to provide the title compound 59c as a colorless oil (146 mg, 65% yield). LC-MS (ESI+) Found: $[M+H]^+$, 428.2.

1-Benzylpiperazine (60)

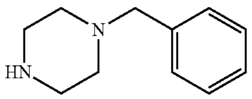 [SMILES: c1ccc(CN2CCNCC2)cc1]

In an oven-dried round bottom flask equipped with a reflux condenser and under argon atmosphere, piperazine (1.27 g, 14.7 mmol, 7.00 equiv.) was dissolved in dry tetrahydrofuran (7 mL, C~0.3 M) by heating. Benzyl bromide (250 μL, 2.10 mmol, 1.00 equiv.) was added dropwise over 10 minutes then the reaction was heated to 67° C. for 18 hours. After the complete consumption of the starting material (monitored by TLC), the mixture was allowed to cool to room temperature and the solvents were removed under reduced pressure. The residue was poured into 2M aqueous sodium carbonate (50 mL) and extracted with ethyl acetate (3×40 mL). The combined organic extracts were washed with brine (50 mL), then dried ($MgSO_4$) and filtered. The solvents were removed under reduced pressure and the crude product was purified chromatographically on silica gel (eluting ethyl acetate-methanol 95:5) to provide the title compound 60 as a yellow oil (302 mg, 82% yield). LC-MS (ESI+) Found: $[M+H]^+$, 177.2.

1-((4-(Azidomethyl)piperidin-1-yl)sulfonyl)-4-benzylpiperazine (61)

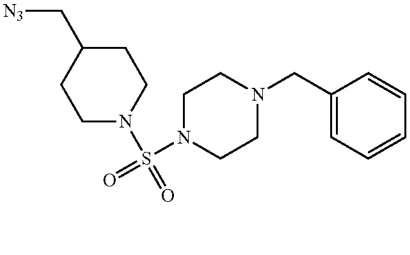 [SMILES: [N-]=[N+]=NCC1CCN(S(=O)(=O)N2CCN(Cc3ccccc3)CC2)CC1]

In an oven-dried round bottom flask equipped with a reflux condenser and under argon atmosphere, 1-Benzylpiperazine 60 (280 mg, 1.59 mmol, 1.00 equiv.) was dissolved in dry acetonitrile (3 mL, C~0.5 M). The solution was treated with a solution of sulphuryl chloride (385 μL, 4.77 mmol, 3.00 equiv.) in dry acetonitrile (1.5 mL), added dropwise over 10 minutes, then the reaction was heated to 82° C. for 18 hours. After the complete consumption of the starting material (monitored by TLC), the mixture was allowed to cool to room temperature and the solvents were removed under reduced pressure. The residue was triturated with diethyl ether (10×5 mL) and the resulting precipitate was filtered off, washed with cold diethyl ether and dried under reduced pressure to obtain the product (331 mg, 76% yield) as a white solid used without further purification for the next step. In an oven-dried round bottom flask equipped with a reflux condenser were combined the sulfonamide chloride (320 mg, 1.16 mmol, 1.00 equiv.) and the ammonium salt 4 (309 mg, 1.75 mmol, 1.50 equiv.) in dry acetonitrile (4 mL, C~0.3 M). The solution was treated with N,N-diisopropylethylamine (609 μL, 3.50 mmol, 3.00 equiv.), added slowly through a syringe and the reaction was heated to 82° C. for 48 hours. After the complete consumption of the starting material (monitored by TLC), the mixture was allowed to cool to room temperature and then poured into water (50 mL) and extracted with dichloromethane (3×30 mL). The combined organic extracts were washed with brine (50 mL), dried ($MgSO_4$) and filtered. The solvents were removed under reduced pressure and the crude product was purified chromatographically on silica gel (eluting gradient dichloromethane-methanol 98:2 to 95:5) to provide the title compound 61 as a colorless oil (269 mg, 61% yield). LC-MS (ESI+) Found: $[M+H]^+$, 379.3.

Isobutyl 3-(1-((1-((2-chloro-2'-methoxy-[1,1'-biphenyl]-4-yl)methyl)piperidin-4-yl)methyl)-1H-1,2,3-triazol-4-yl)-5-fluoro-1H-indole-2-carboxylate (62) (Code AB689)

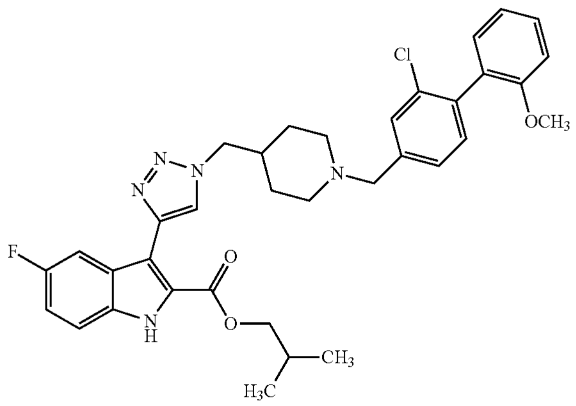 [SMILES: COc1ccccc1-c1ccc(CN2CCC(Cn3cc(-c4c(C(=O)OCC(C)C)[nH]c5ccc(F)cc45)nn3)CC2)cc1Cl]

Prepared by general method G using alkyne 14f (60 mg, 0.23 mmol), azide 58a (90 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 62 as a white solid (98 mg, 67% yield). Mp 176° C. $^1H$ NMR (400 MHz, $d_6$-Acetone) δ=11.10 (s, 1H), 8.65 (s, 1H), 8.38 (dd, J=10.4, 2.6 Hz, 1H), 7.52 (dd, J=9.0, 4.6 Hz, 1H), 7.43 (d, J=1.6 Hz, 1H), 7.36 (ddd, J=8.3, 7.4, 1.8 Hz, 1H), 7.28 (dd, J=7.8, 1.6 Hz, 1H), 7.21 (d, J=7.8 Hz, 1H), 7.16 (td, J=9.0, 2.6 Hz, 1H), 7.13 (dd, J=7.4, 1.7 Hz, 1H), 7.06 (dd, J=8.5, 1.0 Hz, 1H), 6.99 (td, J=7.4, 1.0 Hz, 1H), 4.45 (d, J=7.1 Hz, 2H), 4.15 (d, J=6.7 Hz, 2H), 3.74 (s, 3H), 3.51 (s, 2H), 2.93 (dt, J=11.5, 3.5 Hz, 2H), 2.14-1.97 (m, 3H), 1.71-1.64 (m, 2H), 1.51-1.39 (m, 2H), 1.30-1.23 (m, 1H), 0.98 (d, J=6.8 Hz, 6H). $^{13}$C NMR (100 MHz, $d_6$-Acetone) δ=161.9 ($C_{quat}$), 159.0 (d, J=236.9 Hz, $C_{quat}$), 157.8 ($C_{quat}$), 141.9 ($C_{quat}$), 141.3 ($C_{quat}$), 137.3 ($C_{quat}$), 134.2 ($C_{quat}$), 134.1 ($C_{quat}$), 132.4 (CH), 131.7 (CH), 130.2 (CH), 129.9 (CH), 129.2 ($C_{quat}$), 127.7 (d, J=10.6 Hz, $C_{quat}$), 127.7 (CH), 125.6 (CH), 124.6 ($C_{quat}$), 121.1 (CH), 115.4 (d, J=27.6 Hz, CH), 114.3 (d, J=9.7 Hz, CH), 114.0 (d, J=5.5 Hz, $C_{quat}$), 112.0 (CH), 109.3 (d, J=24.8 Hz, CH), 71.6 ($CH_2$), 62.7 ($CH_2$), 55.9 ($CH_2$), 55.8 (CH), 54.0 ($CH_2$), 38.1 (CH), 30.6 ($CH_2$), 28.6 ($CH_3$), 19.4 ($CH_3$). $^{19}$F NMR (376 MHz, $d_6$-Acetone) δ=−123.8. HRMS (ESI+): calcd. for $C_{35}H_{38}ClFN_5O_3$, 630.2640. Found: $[M+H]^+$, 630.2642 (0.3 ppm error).

Isobutyl 3-(1-((1-((2-chloro-2'-(methoxymethyl)-[1,1'-biphenyl]-4-yl)methyl)piperidin-4-yl)methyl)-1H-1,2,3-triazol-4-yl)-5-fluoro-1H-indole-2-carboxylate (63) (Code AB680)

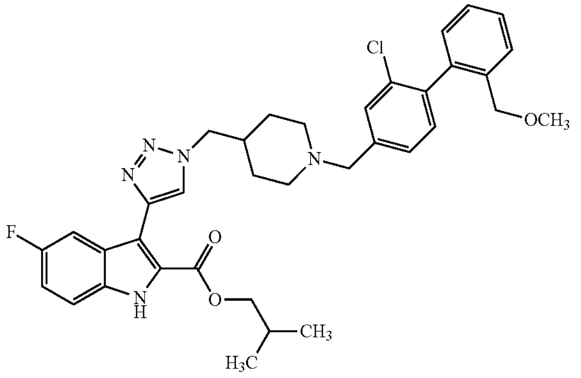 [SMILES: COCc1ccccc1-c1ccc(CN2CCC(Cn3cc(-c4c(C(=O)OCC(C)C)[nH]c5ccc(F)cc45)nn3)CC2)cc1Cl]

Prepared by general method G using alkyne 14f (60 mg, 0.23 mmol), azide 58b (94 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 63 as a pale yellow solid (101 mg, 68% yield). Mp 150° C. $^1$H NMR (400 MHz, $CDCl_3$) δ=9.06 (s, 1H), 8.49 (s, 1H), 8.39 (dd, J=9.9, 2.5 Hz, 1H), 7.53 (dd, J=7.8, 1.4 Hz, 1H), 7.50-7.29 (m, 6H), 7.29-7.08 (m, 4H), 4.34 (s, 1H), 4.33-4.21 (m, 3H), 4.21-4.10 (m, 4H), 3.61 (s, 1H), 3.23 (s, 3H), 3.03 (s, 1H), 2.10 (dq, J=13.4, 6.8 Hz, 3H), 1.72 (d, J=12.2 Hz, 2H), 1.60 (s, 1H), 1.01 (d, J=6.7 Hz, 6H). $^{13}$C NMR (100 MHz, $CDCl_3$) δ=161.0 ($C_{quat}$), 158.5 (d, J=236.8 Hz, $C_{quat}$), 154.7 ($C_{quat}$), 141.3 ($C_{quat}$), 138.3 ($C_{quat}$), 136.5 ($C_{quat}$), 133.4 ($C_{quat}$), 132.5 ($C_{quat}$), 131.4 (CH), 129.9 (CH), 128.2 (CH), 128.1 (CH), 127.4 (CH), 127.2 ($C_{quat}$), 127.1 (d, J=11.2 Hz, $C_{quat}$), 124.9 (CH), 123.4 ($C_{quat}$), 115.7 (d, J=27.1 Hz, CH), 113.7 (d, J=5.4 Hz, $C_{quat}$), 112.4 (d, J=9.4 Hz, CH), 109.4 (d, J=24.8 Hz, CH), 72.2 ($CH_2$), 71.4 ($CH_2$), 58.3 (CH), 55.4 ($CH_2$), 53.0 ($CH_2$), 38.1 (CH), 30.3 ($CH_2$), 28.0 ($CH_3$), 19.3 ($CH_3$). $^{19}$F NMR (376 MHz, $CDCl_3$) δ=−121.6. HRMS (ESI+): calcd. for $C_{36}H_{40}ClFN_5O_3$, 644.2795. Found: $[M+H]^+$, 644.2798 (0.5 ppm error).

Isobutyl 3-(1-((1-((2-chloro-2'-methoxy-5'-methyl-[1,1'-biphenyl]-4-yl)methyl)piperidin-4-yl)methyl)-1H-1,2,3-triazol-4-yl)-5-fluoro-1H-indole-2-carboxylate (64) (Code AB692)

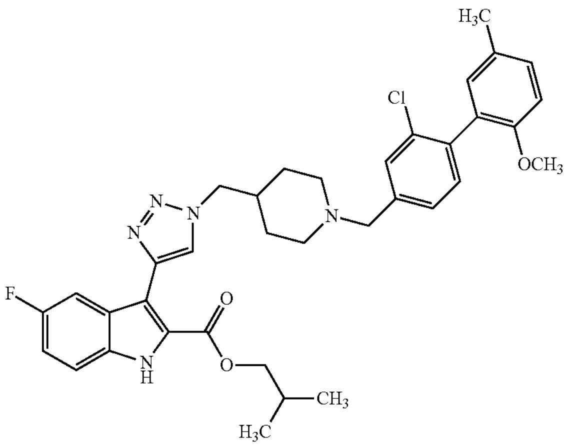 [SMILES: COc1ccc(C)cc1-c1ccc(CN2CCC(Cn3cc(-c4c(C(=O)OCC(C)C)[nH]c5ccc(F)cc45)nn3)CC2)cc1Cl]

Prepared by general method G using alkyne 14f (60 mg, 0.23 mmol), azide 58c (94 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 64 as a white solid (95 mg, 64% yield). Mp 175° C. $^1$H NMR (400 MHz, $d_6$-Acetone) δ=11.57 (s, 1H), 9.12 (s, 1H), 8.85 (dd, J=10.4, 2.6 Hz, 1H), 8.02-7.96 (m, 1H), 7.88 (d, J=1.6 Hz, 1H), 7.74 (dd, J=7.8, 1.6 Hz, 1H), 7.66 (d, J=7.8 Hz, 1H), 7.63 (td, J=9.1, 2.7 Hz, 2H), 7.43-7.38 (m, 2H), 4.91 (d, J=7.1 Hz, 2H), 4.62 (d, J=6.7 Hz, 2H), 4.17 (s, 3H), 3.97 (s, 2H), 3.39 (dt, J=11.7, 3.5 Hz, 2H), 2.74 (s, 3H), 2.60-2.49 (m, 3H), 2.47 (d, J=2.7 Hz, 1H), 2.17-2.10 (m, 2H), 1.97-1.85 (m, 2H), 1.45 (d, J=6.7 Hz, 6H). $^{13}$C NMR (100 MHz, $d_6$-Acetone) δ=161.4 ($C_{quat}$), 158.7 (d, J=234.3 Hz, $C_{quat}$), 155.3 ($C_{quat}$), 141.5 ($C_{quat}$), 140.7 ($C_{quat}$), 137.0 ($C_{quat}$), 133.8 ($C_{quat}$), 133.7 ($C_{quat}$), 132.0 (CH), 131.8 (CH), 130.0 (CH), 129.6 ($C_{quat}$), 129.4 (CH), 128.6 ($C_{quat}$), 127.3 ($C_{quat}$), 127.3 (CH), 125.1 (CH), 124.2 ($C_{quat}$), 115.0 (d, J=26.8 Hz, CH), 113.9 (d, J=9.7 Hz, CH), 113.6 (d, J=5.5 Hz, $C_{quat}$), 111.5 (CH), 108.9 (d, J=24.8 Hz, CH), 71.2 ($CH_2$), 62.3 ($CH_2$), 55.5 ($CH_2$), 55.4 (CH), 53.5 ($CH_2$), 37.7 (CH), 30.2 ($CH_2$), 28.2 ($CH_3$), 20.0 ($CH_3$), 19.0 ($CH_3$). $^{19}$F NMR (376 MHz, $d_6$-Acetone) δ=−123.9. HRMS (ESI+): calcd. for $C_{36}H_{40}ClFN_5O_3$, 644.2793. Found: $[M+H]^+$, 644.2798 (0.8 ppm error).

Isobutyl 3-(1-((1-(3-chloro-4-(1H-indol-4-yl)benzyl)piperidin-4-yl)methyl)-1H-1,2,3-triazol-4-yl)-5-fluoro-1H-indole-2-carboxylate (65) (Code AB690)

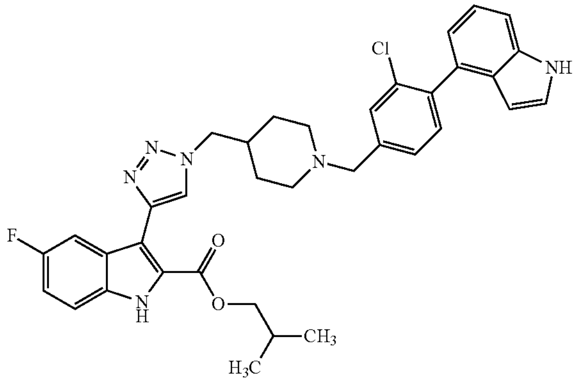 [SMILES: CC(C)COC(=O)c1[nH]c2ccc(F)cc2c1-c1cn(CC2CCN(Cc3ccc(-c4cccc5[nH]ccc45)c(Cl)c3)CC2)nn1]

Prepared by general method G using alkyne 14f (55 mg, 0.21 mmol), azide 58d (85 mg, 0.22 mmol), 2M aqueous of sodium ascorbate (371 μL, 0.74 mmol), 15% aqueous of copper(II) sulfate pentahydrate (309 μL, 0.19 mmol) and tetrahydrofuran-tert-butanol (530 μL). The crude product was purified chromatographically on silica gel (eluting gradient dichloromethane-methanol 98:2 to 95:5) to provide the title compound 65 as a white solid (98 mg, 72% yield). Mp 153° C. $^{1}$H NMR (400 MHz, $d_6$-Acetone) δ=11.13 (s, 1H), 10.36 (s, 1H), 8.67 (s, 1H), 8.41 (ddt, J=10.5, 2.6, 0.7 Hz, 1H), 7.58-7.50 (m, 2H), 7.47 (dt, J=8.2, 0.9 Hz, 1H), 7.41 (d, J=7.7 Hz, 1H), 7.38-7.31 (m, 2H), 7.23-7.13 (m, 2H), 7.01 (dd, J=7.2, 0.9 Hz, 1H), 6.23 (ddd, J=3.1, 2.0, 0.9 Hz, 1H), 4.46 (d, J=7.1 Hz, 2H), 4.17 (d, J=6.7 Hz, 2H), 3.55 (s, 2H), 3.00-2.91 (m, 2H), 2.17-2.06 (m, 2H), 2.03 (d, J=8.1 Hz, 2H), 1.73-1.64 (m, 2H), 1.54-1.39 (m, 2H), 1.00 (d, J=6.7 Hz, 6H). $^{13}$C NMR (100 MHz, $d_6$-Acetone) δ=161.9 ($C_{quat}$), 159.1 (d, J=234.2 Hz, $C_{quat}$), 141.9 ($C_{quat}$), 141.1 ($C_{quat}$), 139.4 ($C_{quat}$), 137.2 ($C_{quat}$), 134.1 ($C_{quat}$), 133.4 ($C_{quat}$), 132.5 (CH), 132.1 ($C_{quat}$), 130.5 (CH), 128.1 ($C_{quat}$), 127.9 (CH), 127.7 (d, J=10.7 Hz, $C_{quat}$), 125.9 (CH), 125.6 (CH), 124.6 ($C_{quat}$), 121.8 (CH), 121.1 (CH), 115.4 (d, J=27.0 Hz, CH), 114.3 (d, J=10.1 Hz, CH), 114.0 (d, J=5.5 Hz, $C_{quat}$), 111.8 (CH), 109.3 (d, J=25.0 Hz, CH), 102.0 (CH), 71.6 ($CH_2$), 62.7 ($CH_2$), 55.9 ($CH_2$), 53.9 ($CH_2$), 38.1 (CH), 30.6 ($CH_2$), 28.6 ($CH_3$), 19.4 ($CH_3$). $^{19}$F NMR (376 MHz, $d_6$-Acetone) δ=−123.8. HRMS (ESI+): calcd. for $C_{36}H_{37}ClFN_6O_2$, 639.2658. Found: $[M+H]^+$, 639.2645 (−0.2 ppm error).

Isobutyl 3-(1-((1-(3-chloro-4-(1H-indol-5-yl)benzyl)piperidin-4-yl)methyl)-1H-1,2,3-triazol-4-yl)-5-fluoro-1H-indole-2-carboxylate (66) (Code AB753)

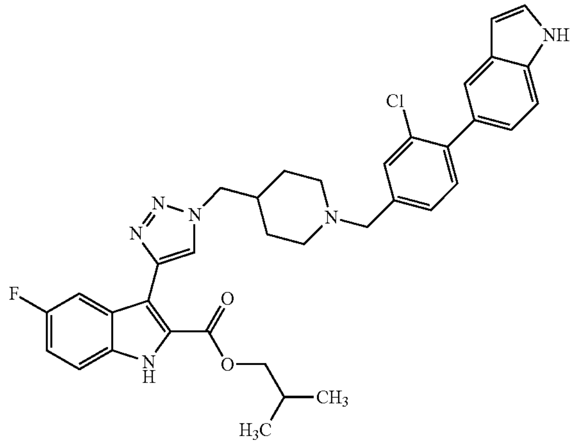 [SMILES: CC(C)COC(=O)c1[nH]c2ccc(F)cc2c1-c1cn(CC2CCN(Cc3ccc(-c4ccc5[nH]ccc5c4)c(Cl)c3)CC2)nn1]

Prepared by general method G using alkyne 14f (60 mg, 0.23 mmol), azide 58e (92 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 95:5) to provide the title compound 66 as a white solid (43 mg, 36% yield). Mp 179° C. HRMS (ESI+): calcd. for $C_{36}H_{37}ClFN_6O_2$, 639.2644. Found: $[M+H]^+$, 639.2645 (0.1 ppm error).

Isobutyl 3-(1-((1-(3-chloro-4-(2,3-dihydrobenzofuran-5-yl)benzyl)piperidin-4-yl)methyl)-1H-1,2,3-triazol-4-yl)-5-fluoro-1H-indole-2-carboxylate (67) (Code AB731)

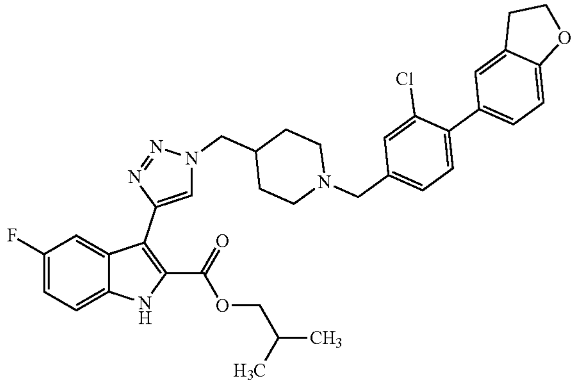

Prepared by general method G using alkyne 14f (60 mg, 0.23 mmol), azide 58f (93 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 67 as a pale yellow solid (88 mg, 59% yield).

Mp 173° C. HRMS (ESI+): calcd. for $C_{36}H_{38}ClFN_5O_3$, 642.2639. Found: $[M+H]^+$, 642.2642 (0.4 ppm error).

Isobutyl 3-(1-((1-((3'-acetyl-2-chloro-[1,1'-biphenyl]-4-yl)methyl)piperidin-4-yl)methyl)-1H-1,2,3-triazol-4-yl)-5-fluoro-1H-indole-2-carboxylate (68) (Code AB739)

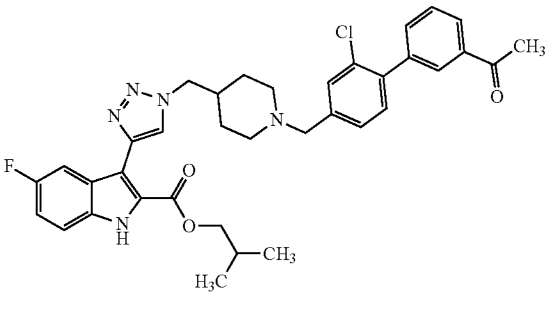 [SMILES: CC(=O)c1cccc(-c2ccc(CN3CCC(Cn4cc(-c5c(C(=O)OCC(C)C)[nH]c6ccc(F)cc56)nn4)CC3)cc2Cl)c1]

Prepared by general method G using alkyne 14f (45 mg, 0.17 mmol), azide 58g (70 mg, 0.18 mmol), 2M aqueous of sodium ascorbate (304 µL, 0.61 mmol), 15% aqueous of copper(II) sulfate pentahydrate (253 µL, 0.15 mmol) and tetrahydrofuran-tert-butanol (434 µL). The crude product was purified chromatographically on silica gel (eluting gradient dichloromethane-methanol 98:2 to 96:4) to provide the title compound 68 as a white solid (64 mg, 58% yield). Mp 190° C. HRMS (ESI+): calcd. for $C_{36}H_{38}ClFN_5O_3$, 642.2658. Found: $[M+H]^+$, 642.2642 (−2.6 ppm error).

Isobutyl 3-(1-((1-((2-chloro-3'-isopropyl-[1,1'-biphenyl]-4-yl)methyl)piperidin-4-yl)methyl)-1H-1,2,3-triazol-4-yl)-5-fluoro-1H-indole-2-carboxylate (69) (Code AB758)

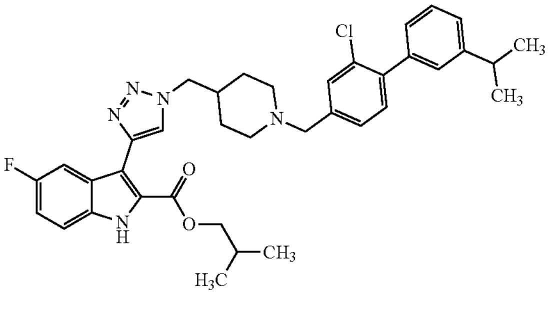 [SMILES: CC(C)COC(=O)c1[nH]c2ccc(F)cc2c1-c1cn(CC2CCN(Cc3ccc(-c4cccc(C(C)C)c4)c(Cl)c3)CC2)nn1]

Prepared by general method G using alkyne 14f (60 mg, 0.23 mmol), azide 58h (93 mg, 0.24 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (578 µL). The crude product was purified chromatographically on silica gel (eluting gradient dichloromethane-methanol 100:0 to 96:4) to provide the title compound 69 as a white solid (89 mg, 60% yield). Mp 177° C. $^1H$ NMR (400 MHz, $d_6$-DMSO) δ=12.01 (s, 1H), 8.56 (s, 1H), 8.02 (dd, J=10.3, 2.6 Hz, 1H), 7.54 (dd, J=9.1, 4.7 Hz, 1H), 7.45 (d, J=1.5 Hz, 1H), 7.40-7.30 (m, 3H), 7.29-7.19 (m, 4H), 4.39 (d, J=7.0 Hz, 2H), 4.12 (d, J=6.7 Hz, 2H), 3.49 (s, 2H), 2.94 (h, J=6.9 Hz, 1H), 2.84 (d, J=11.1 Hz, 2H), 2.10-1.93 (m, 3H), 1.93 (s, 1H), 1.56 (d, J=12.0 Hz, 2H), 1.34 (t, J=10.6 Hz, 2H), 1.23 (d, J=6.9 Hz, 6H), 0.94 (d, J=6.7 Hz, 6H). $^{19}F$ NMR (376 MHz, $d_6$-DMSO) δ=−122.3. HRMS (ESI+): calcd. for $C_{37}H_{42}ClFN_5O_2$, 642.3001. Found: $[M+H]^+$, 642.3006 (0.7 ppm error).

Isobutyl 5-fluoro-3-(1-((1-((2-isopropyl-2'-(methoxymethyl)-[1,1'-biphenyl]-4-yl)methyl)piperidin-4-yl)methyl)-1H-1,2,3-triazol-4-yl)-1H-indole-2-carboxylate (70) (Code AB704)

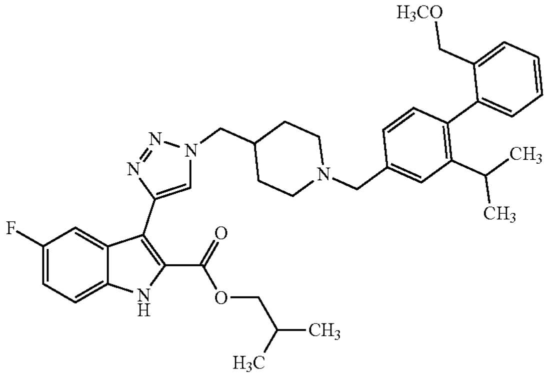 [SMILES: COCc1ccccc1-c1ccc(CN2CCC(Cn3cc(-c4c(C(=O)OCC(C)C)[nH]c5ccc(F)cc45)nn3)CC2)cc1C(C)C]

Prepared by general method G using alkyne 14f (65 mg, 0.25 mmol), azide 58i (103 mg, 0.26 mmol), 2M aqueous of sodium ascorbate (439 µL, 0.88 mmol), 15% aqueous of copper(II) sulfate pentahydrate (366 µL, 0.22 mmol) and tetrahydrofuran-tert-butanol (627 µL). The crude product was purified chromatographically on silica gel (eluting gradient dichloromethane-methanol 98:2 to 96:4) to provide the title compound 70 as a beige solid (89 mg, 67% yield). Mp 146° C. HRMS (ESI+): calcd. for $C_{39}H_{47}FN_5O_3$, 652.3658. Found: $[M+H]^+$, 652.3657 (−0.1 ppm error).

Isobutyl 3-(1-((1-(4-(1H-indol-4-yl)-3-isopropylbenzyl)piperidin-4-yl)methyl)-1H-1,2,3-triazol-4-yl)-5-fluoro-1H-indole-2-carboxylate (71) (Code AB703)

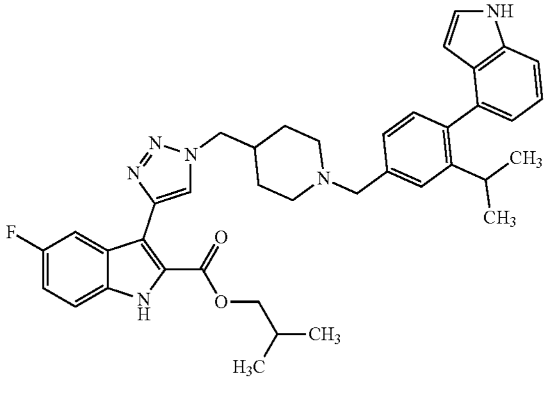 [SMILES: CC(C)COC(=O)c1[nH]c2ccc(F)cc2c1-c1cn(CC2CCN(Cc3ccc(-c4cccc5[nH]ccc45)c(C(C)C)c3)CC2)nn1]

Prepared by general method G using alkyne 14f (60 mg, 0.23 mmol), azide 58j (94 mg, 0.24 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (579 µL). The crude product was purified chromatographically on silica gel (eluting gradient dichloromethane-methanol 98:2 to 95:5) to provide the title compound 71 as a white solid (89 mg, 67% yield). Mp 114° C. HRMS (ESI+): calcd. for $C_{39}H_{44}FN_6O_2$, 647.3529. Found: $[M+H]^+$, 647.3504 (−3.8 ppm error).

Isobutyl 3-(1-((1-(2-chloro-2'-(methoxymethyl)-[1,1'-biphenyl]-4-carbonyl)piperidin-4-yl)methyl)-1H-1,2,3-triazol-4-yl)-5-fluoro-1H-indole-2-carboxylate (72) (Code AB681)

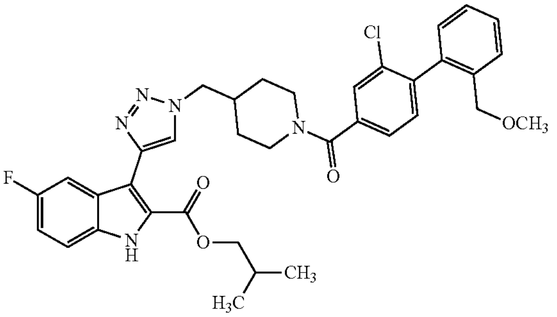 [SMILES: COCc1ccccc1-c1ccc(C(=O)N2CCC(Cn3cc(-c4c(C(=O)OCC(C)C)[nH]c5ccc(F)cc45)nn3)CC2)cc1Cl]

Prepared by general method G using alkyne 14f (60 mg, 0.23 mmol), azide 59a (97 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 72 as a pale yellow solid (83 mg, 55% yield). Mp 124° C. HRMS (ESI+): calcd. for $C_{36}H_{37}ClFN_5NaO_4$, 680.2416. Found: $[M+Na]^+$, 680.2410 (−0.8 ppm error).

Isobutyl 3-(1-((1-(2-chloro-2'-(isopentyloxy)-[1,1'-biphenyl]-4-carbonyl)piperidin-4-yl)methyl)-1H-1,2,3-triazol-4-yl)-5-fluoro-1H-indole-2-carboxylate (73) (Code AB743)

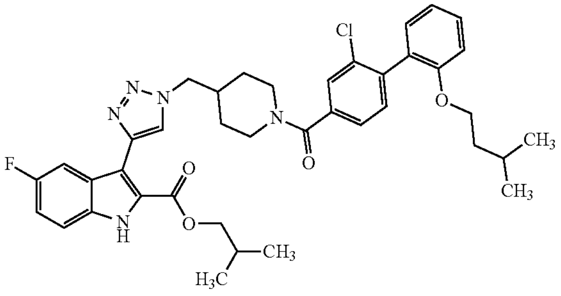 [SMILES: CC(C)CCOc1ccccc1-c1ccc(C(=O)N2CCC(Cn3cc(-c4c(C(=O)OCC(C)C)[nH]c5ccc(F)cc45)nn3)CC2)cc1Cl]

Prepared by general method G using alkyne 14f (45 mg, 0.17 mmol), azide 59b (80 mg, 0.18 mmol), 2M aqueous of sodium ascorbate (304 μL, 0.61 mmol), 15% aqueous of copper(II) sulfate pentahydrate (253 μL, 0.15 mmol) and tetrahydrofuran-tert-butanol (434 μL). The crude product was purified chromatographically on silica gel (eluting gradient dichloromethane-methanol 98:2 to 96:4) to provide the title compound 73 as a pale yellow solid (79 mg, 65% yield). Mp 91° C. $^1$H NMR (400 MHz, $d_6$-DMSO) δ=12.01 (s, 1H), 8.59 (s, 1H), 8.03 (dd, J=10.3, 2.7 Hz, 1H), 7.54 (dd, J=9.1, 4.7 Hz, 1H), 7.50 (t, J=1.0 Hz, 1H), 7.38 (ddd, J=8.3, 7.4, 1.8 Hz, 1H), 7.34 (d, J=1.1 Hz, 2H), 7.23 (td, J=9.1, 2.6 Hz, 1H), 7.17 (dd, J=7.5, 1.8 Hz, 1H), 7.11 (dd, J=8.4, 1.1 Hz, 1H), 7.01 (td, J=7.4, 1.0 Hz, 1H), 4.44 (d, J=7.2 Hz, 3H), 4.12 (d, J=6.7 Hz, 2H), 3.96 (t, J=6.3 Hz, 2H), 2.28-2.19 (m, 1H), 2.03 (dp, J=13.3, 6.7, 6.3 Hz, 1H), 1.70 (s, 1H), 1.52 (dt, J=13.1, 6.6 Hz, 2H), 1.42 (q, J=6.5 Hz, 2H), 1.32 (d, J=11.4 Hz, 2H), 1.18 (dd, J=21.0, 14.8 Hz, 3H), 0.95 (d, J=6.7 Hz, 6H), 0.74 (d, J=6.5 Hz, 6H). $^{19}$F NMR (376 MHz, $d_6$-DMSO) δ=−122.4. HRMS (ESI+): calcd. for $C_{39}H_{44}ClFN_5O_4$, 700.3067. Found: $[M+H]^+$, 700.3060 (−1.0 ppm error).

Isobutyl 3-(1-((1-(4-(1H-indol-4-yl)-3-(trifluoromethyl)benzoyl)piperidin-4-yl)methyl)-1H-1,2,3-triazol-4-yl)-5-fluoro-1H-indole-2-carboxylate (74) (Code AB756)

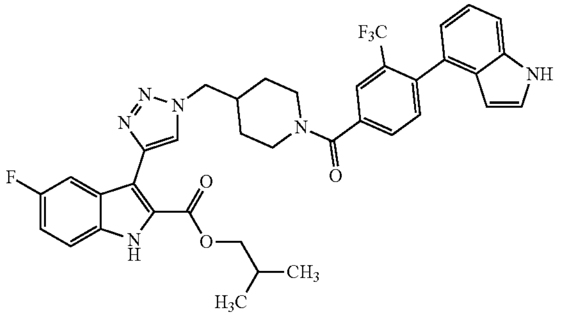 [SMILES: CC(C)COC(=O)c1[nH]c2ccc(F)cc2c1-c1cn(CC2CCN(C(=O)c3ccc(-c4cccc5[nH]ccc45)c(C(F)(F)F)c3)CC2)nn1]

Prepared by general method G using alkyne 14f (60 mg, 0.23 mmol), azide 59c (104 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 74 as a pale yellow solid (102 mg, 64% yield). Mp 153° C. $^1$H NMR (400 MHz, $d_6$-DMSO) δ=12.02 (s, 1H), 11.27 (s, 1H), 8.60 (s, 1H), 8.04 (dd, J=10.3, 2.6 Hz, 1H), 7.83 (d, J=1.7 Hz, 1H), 7.72 (dd, J=7.8, 1.8 Hz, 1H), 7.62-7.42 (m, 3H), 7.34 (t, J=2.8 Hz, 1H), 7.28-7.10 (m, 2H), 6.91-6.85 (m, 1H), 6.02 (ddd, J=3.0, 2.0, 0.9 Hz, 1H), 4.53 (s, 1H), 4.45 (d, J=7.1 Hz, 2H), 4.12 (d, J=6.7 Hz, 2H), 3.68 (s, 1H), 3.15 (s, 1H), 2.85 (s, 1H), 2.27 (s, 1H), 2.14-1.96 (m, 1H), 1.71 (s, 1H), 1.58 (s, 1H), 1.35 (d, J=12.2 Hz, 2H), 0.94 (d, J=6.7 Hz, 6H). $^{19}$F NMR (376 MHz, $d_6$-DMSO) δ=−56.4, −122.3. HRMS (ESI+): calcd. for $C_{37}H_{35}F_4N_6O_3$, 687.2717. Found: $[M+H]^+$, 687.2701 (−2.2 ppm error).

Isobutyl 3-(1-((1-(3-chloro-4-phenoxybenzyl)piperidin-4-yl)methyl)-1H-1,2,3-triazol-4-yl)-5-fluoro-1H-indole-2-carboxylate (75) (Code AB691)

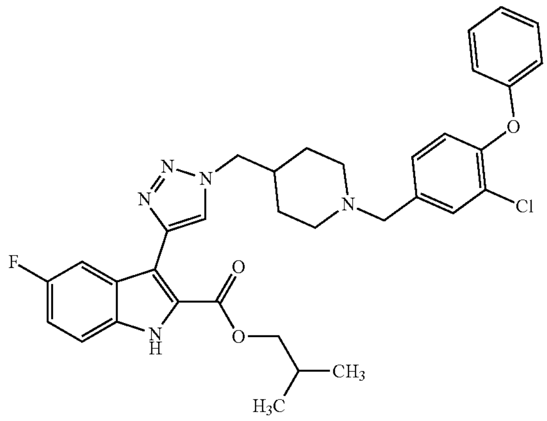 [SMILES: CC(C)COC(=O)c1[nH]c2ccc(F)cc2c1-c1cn(CC2CCN(Cc3ccc(Oc4ccccc4)c(Cl)c3)CC2)nn1]

Prepared by general method G using 14f (60 mg, 0.23 mmol), 58k (87 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 75 as a white solid (112 mg, 78% yield). Mp 197° C. $^1$H NMR (400 MHz, $d_6$-DMSO) δ=12.01 (s, 1H), 8.55 (s, 1H), 8.02 (dd, J=10.2, 2.6 Hz, 1H), 7.54 (dd, J=9.0, 4.7 Hz, 1H), 7.48 (d, J=2.0 Hz, 1H), 7.41-7.33 (m, 2H), 7.30-7.24 (m, 1H), 7.22 (dd, J=9.1, 2.6 Hz, 1H), 7.16-7.07 (m, 1H), 7.04 (d, J=8.3 Hz, 1H), 6.97-6.88 (m, 2H), 4.38 (d, J=7.0 Hz, 2H), 4.12 (d, J=6.7 Hz, 2H), 3.45 (s, 2H), 2.82 (d, J=11.1 Hz, 2H), 2.03 (dt, J=13.4, 6.7 Hz, 1H), 1.93 (t, J=11.6 Hz, 3H), 1.55 (d, J=12.2 Hz, 2H), 1.38-1.24 (m, 2H), 0.94 (d, J=6.7 Hz, 6H). $^{13}$C NMR (100 MHz, $d_6$-DMSO) δ=161.5 ($C_{quat}$), 157.9 (d, J=234.3 Hz, $C_{quat}$), 157.1 ($C_{quat}$), 150.5 ($C_{quat}$), 143.3 ($C_{quat}$), 140.6 ($C_{quat}$), 136.9 ($C_{quat}$), 133.5 ($C_{quat}$), 130.9 (CH), 130.5 (CH), 129.3 ($C_{quat}$), 125.3 (CH), 124.3 ($C_{quat}$), 123.7 (CH), 121.5 (CH), 117.6 (CH), 115.8 (d, J=26.9 Hz, CH), 114.1 (d, J=5.6 Hz, $C_{quat}$), 112.3 (d, J=9.3 Hz, CH), 109.5 (d, J=25.3 Hz, CH), 71.1 ($CH_2$), 61.3 ($CH_2$), 54.9 ($CH_2$), 52.9 ($CH_2$), 37.0 (CH), 29.7 ($CH_2$), 27.8 (CH), 19.4 ($CH_3$). $^{19}$F NMR (376 MHz, $d_6$-DMSO) δ=−122.3. HRMS (ESI+): calcd. for $C_{34}H_{36}ClFN_5O_3$, 616.2474. Found: $[M+H]^+$, 616.2485 (1.8 ppm error).

Isobutyl 5-fluoro-3-(1-((1-(3-isopropyl-4-phenoxybenzyl)piperidin-4-yl)methyl)-1H-1,2,3-triazol-4-yl)-1H-indole-2-carboxylate (76) (Code AB697)

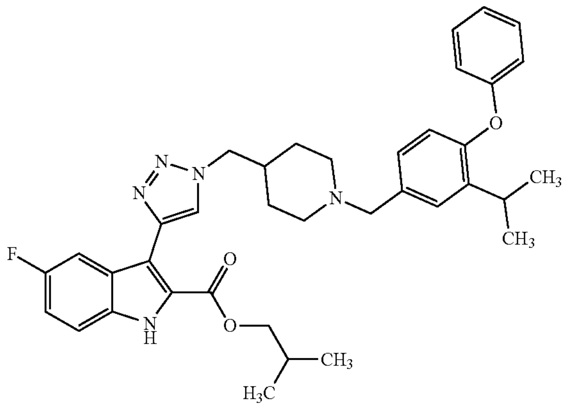 [SMILES: CC(C)COC(=O)c1[nH]c2ccc(F)cc2c1-c1cn(CC2CCN(Cc3ccc(Oc4ccccc4)c(C(C)C)c3)CC2)nn1]

Prepared by general method G using alkyne 14f (70 mg, 0.27 mmol), azide 581 (103 mg, 0.28 mmol), 2M aqueous of sodium ascorbate (472 μL, 0.94 mmol), 15% aqueous of copper(II) sulfate pentahydrate (394 μL, 0.24 mmol) and tetrahydrofuran-tert-butanol (675 μL). The crude product was purified chromatographically on silica gel (eluting gradient dichloromethane-methanol 98:2 to 96:4) to provide the title compound 76 as a pale yellow solid (116 mg, 69% yield). Mp 196° C. $^1$H NMR (400 MHz, $CDCl_3$) δ=9.07 (s, 1H), 8.46 (s, 1H), 8.38 (dd, J=10.0, 2.6 Hz, 1H), 7.36-7.19 (m, 4H), 7.16-6.96 (m, 3H), 6.93-6.85 (m, 2H), 6.79 (d, J=8.2 Hz, 1H), 4.30 (d, J=7.2 Hz, 2H), 4.13 (d, J=6.7 Hz, 2H), 3.46 (s, 2H), 3.23 (h, J=6.9 Hz, 1H), 2.91 (dt, J=12.0, 3.4 Hz, 2H), 2.14-2.04 (m, 1H), 2.04-1.90 (m, 3H), 1.66 (d, J=3.5 Hz, 2H), 1.42 (qd, J=12.1, 3.7 Hz, 2H), 1.22 (d, J=12.7 Hz, 1H), 1.20 (s, 2H), 1.18 (s, 3H), 0.99 (d, J=6.7 Hz, 6H). $^{13}$C NMR (100 MHz, $CDCl_3$) δ=161.1 ($C_{quat}$), 158.6 (d, J=236.8 Hz, $C_{quat}$), 158.5 ($C_{quat}$), 152.6 ($C_{quat}$), 141.2 ($C_{quat}$), 140.0 ($C_{quat}$), 134.0 ($C_{quat}$), 132.4 ($C_{quat}$), 129.7 (CH), 127.8 (CH), 127.7 (CH), 127.2 (d, J=10.9 Hz, $C_{quat}$), 124.8 (CH), 123.4 ($C_{quat}$), 122.3 (CH), 119.7 (CH), 117.5 (CH), 115.6 (d, J=27.7 Hz, CH), 113.8 (d, J=5.5 Hz, $C_{quat}$), 112.4 (d, J=9.3 Hz, CH), 109.4 (d, J=24.6 Hz, CH), 71.4 ($CH_2$), 63.0 ($CH_2$), 55.9 ($CH_2$), 53.0 ($CH_2$), 37.3 (CH), 29.9 ($CH_2$), 28.0 (CH), 27.3 (CH), 23.1 ($CH_3$), 19.3 ($CH_3$). $^{19}$F NMR (376 MHz, $CDCl_3$) δ=−121.6. HRMS (ESI+): calcd. for $C_{37}H_{43}FN_5O_3$, 624.3351. Found: $[M+H]^+$, 624.3344 (−1.0 ppm error).

Isobutyl 3-(1-((1-(4-((2,3-dihydrobenzofuran-5-yl)oxy)-3-isopropylbenzyl)piperidin-4-yl)methyl)-1H-1,2,3-triazol-4-yl)-5-fluoro-1H-indole-2-carboxylate (77) (Code AB717)

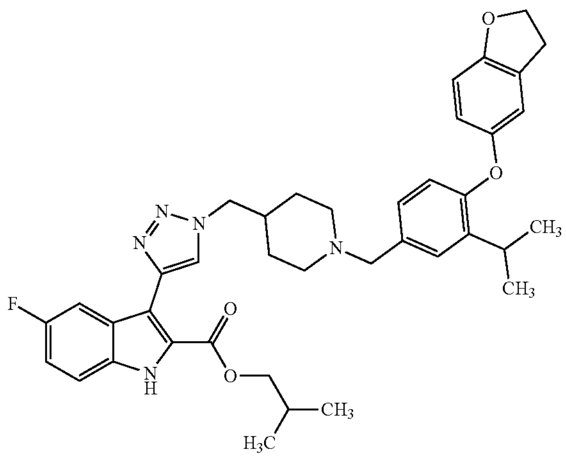 [SMILES: CC(C)COC(=O)c1[nH]c2ccc(F)cc2c1-c1cn(CC2CCN(Cc3ccc(Oc4ccc5c(c4)CCO5)c(C(C)C)c3)CC2)nn1]

Prepared by general method G using alkyne 14f (50 mg, 0.19 mmol), azide 58m (82 mg, 0.20 mmol), 2M aqueous of sodium ascorbate (337 μL, 0.67 mmol), 15% aqueous of copper(II) sulfate pentahydrate (281 μL, 0.17 mmol) and tetrahydrofuran-tert-butanol (482 μL). The crude product was purified chromatographically on silica gel (eluting gradient dichloromethane-methanol 98:2 to 95:5) to provide the title compound 77 as a white solid (91 mg, 71% yield). Mp 211° C. $^1$H NMR (400 MHz, $CDCl_3$) δ=9.04 (s, 1H), 8.47 (s, 1H), 8.40 (dd, J=10.0, 2.6 Hz, 1H), 7.38-7.27 (m, 1H), 7.21 (d, J=2.2 Hz, 1H), 7.19-7.12 (m, 1H), 7.12-7.02 (m, 1H), 6.82 (tt, J=2.7, 1.4 Hz, 1H), 6.75-6.67 (m, 3H), 4.57 (td, J=8.8, 4.5 Hz, 2H), 4.33 (dd, J=10.8, 7.2 Hz, 2H), 4.15 (dd, J=6.8, 3.7 Hz, 2H), 3.53 (s, 2H), 3.42-3.25 (m, J=6.9 Hz, 1H), 3.18 (tdd, J=8.7, 3.6, 1.1 Hz, 2H), 2.98 (d, J=11.3 Hz, 2H), 2.20-1.94 (m, 4H), 1.68 (d, J=12.4 Hz, 2H), 1.53 (s, 2H), 1.25 (dd, J=8.9, 6.9 Hz, 6H), 1.06-0.98 (in, 6H). $^{13}$C NMR (100 MHz, $CDCl_3$) δ=161.8 ($C_{quat}$), 161.0 ($C_{quat}$), 158.5 (d, J=238.7 Hz, $C_{quat}$), 158.5 ($C_{quat}$), 155.9 ($C_{quat}$), 141.2 ($C_{quat}$), 138.9 ($C_{quat}$), 132.4 ($C_{quat}$), 128.4 ($C_{quat}$), 127.8 ($C_{quat}$), 127.2 (d, J=10.9 Hz, $C_{quat}$), 124.8 (CH), 123.4 (CH), 118.3 (CH), 117.7 (CH), 116.0 (CH), 115.8 (CH), 115.5 (d, J=27.7 Hz, CH), 113.8 (d, J=5.5 Hz, $C_{quat}$), 112.4 (d, J=9.3 Hz, CH), 109.6 (CH), 109.5 (d, J=24.8 Hz, CH), 71.6 ($CH_2$), 71.4 ( ), 63.0 ($CH_2$), 55.7 ($CH_2$), 52.8 ($CH_2$), 30.2 (CH), 28.0 ($CH_2$), 27.3 (CH), 23.0 (CH), 22.9 ($CH_3$), 19.3 ($CH_3$). $^{19}$F NMR (376 MHz, $CDCl_3$) δ=−121.6. HRMS (ESI+): calcd. for $C_{39}H_{45}FN_5O_4$, 666.3461. Found: $[M+H]^+$, 666.3450 (−1.6 ppm error).

Isobutyl 3-(1-((1-(4-(3-acetylphenoxy)-3-isopropylbenzyl)piperidin-4-yl)methyl)-1H-1,2,3-triazol-4-yl)-5-fluoro-1H-indole-2-carboxylate (78) (Code AB718)

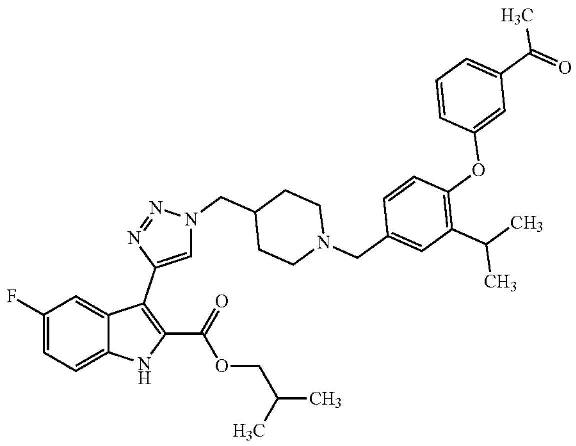 [SMILES: CC(=O)c1cccc(Oc2ccc(CN3CCC(Cn4cc(-c5c(C(=O)OCC(C)C)[nH]c6ccc(F)cc56)nn4)CC3)cc2C(C)C)c1]

Prepared by general method G using alkyne 14f (50 mg, 0.19 mmol), azide 58n (82 mg, 0.20 mmol), 2M aqueous of sodium ascorbate (337 μL, 0.67 mmol), 15% aqueous of copper(II) sulfate pentahydrate (281 μL, 0.17 mmol) and tetrahydrofuran-tert-butanol (482 μL). The crude product was purified chromatographically on silica gel (eluting gradient dichloromethane-methanol 98:2 to 96:4) to provide the title compound 78 as a white solid (63 mg, 49% yield). Mp 150° C. $^1$H NMR (400 MHz, $d_6$-DMSO) δ=12.01 (s, 1H), 8.56 (s, 1H), 8.02 (dd, J=10.2, 2.6 Hz, 1H), 7.67 (d, J=7.7 Hz, 1H), 7.59-7.45 (m, 2H), 7.37 (t, J=2.2 Hz, 1H), 7.31 (d, J=2.2 Hz, 1H), 7.22 (td, J=9.1, 2.6 Hz, 1H), 7.14 (dd, J=8.1, 2.4 Hz, 2H), 6.86 (d, J=8.2 Hz, 1H), 4.38 (d, J=7.0 Hz, 2H), 4.12 (d, J=6.8 Hz, 2H), 3.46 (s, 2H), 3.10 (p, J=6.8 Hz, 1H), 2.84 (d, J=10.9 Hz, 2H), 2.55 (s, 3H), 2.10-1.93 (m, 2H), 1.93-1.87 (m, 2H), 1.55 (d, J=12.5 Hz, 2H), 1.32 (q, J=11.1 Hz, 2H), 1.14 (d, J=6.9 Hz, 6H), 0.93 (d, J=6.7 Hz, 6H). $^{19}$F NMR (376 MHz, $d_6$-DMSO) δ=−122.4. HRMS (ESI+): calcd. for $C_{39}H_{45}FN_5O_4$, 666.3455. Found: $[M+H]^+$, 666.3450 (−0.7 ppm error).

Isobutyl 5-fluoro-3-(1-((1-(3-isopropyl-4-(3-isopropylphenoxy)benzyl)piperidin-4-yl)methyl)-1H-1,2,3-triazol-4-yl)-1H-indole-2-carboxylate (79) (Code AB713)

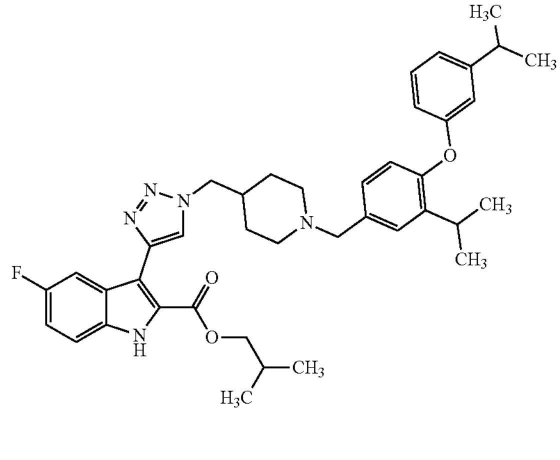 [SMILES: CC(C)COC(=O)c1[nH]c2ccc(F)cc2c1-c1cn(CC2CCN(Cc3ccc(Oc4cccc(C(C)C)c4)c(C(C)C)c3)CC2)nn1]

Prepared by general method G using alkyne 14f (40 mg, 0.15 mmol), azide 58o (66 mg, 0.16 mmol), 2M aqueous of sodium ascorbate (270 μL, 0.54 mmol), 15% aqueous of copper(II) sulfate pentahydrate (225 μL, 0.13 mmol) and tetrahydrofuran-tert-butanol (386 μL,). The crude product was purified chromatographically on silica gel (eluting gradient dichloromethane-methanol 98:2 to 96:4) to provide the title compound 79 as a pale yellow solid (63 mg, 61% yield). Mp 158° C. HRMS (ESI+): calcd. for $C_{40}H_{49}FN_5O_3$, 666.3815. Found: $[M+H]^+$, 666.3814 (−0.2 ppm error).

Isobutyl 3-(1-((1-(3-chloro-4-isobutoxybenzyl)piperidin-4-yl)methyl)-1H-1,2,3-triazol-4-yl)-5-fluoro-1H-indole-2-carboxylate (80) (Code AB760)

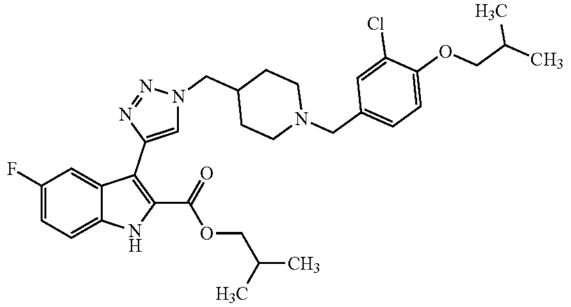 [SMILES: CC(C)COC(=O)c1[nH]c2ccc(F)cc2c1-c1cn(CC2CCN(Cc3ccc(OCC(C)C)c(Cl)c3)CC2)nn1]

Prepared by general method G using alkyne 14f (60 mg, 0.23 mmol), azide 58p (82 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 80 as a white solid (94 mg, 68% yield). Mp 177° C. $^1H$ NMR (400 MHz, $d_6$-DMSO) δ=12.01 (s, 1H), 8.54 (s, 1H), 8.01 (dd, J=10.2, 2.6 Hz, 1H), 7.54 (dd, J=9.0, 4.7 Hz, 1H), 7.30 (d, J=2.0 Hz, 1H), 7.27-7.12 (m, 2H), 7.05 (d, J=8.5 Hz, 1H), 4.37 (d, J=7.0 Hz, 2H), 4.12 (d, J=6.7 Hz, 2H), 3.80 (d, J=6.4 Hz, 2H), 3.37 (s, 2H), 2.78 (d, J=11.3 Hz, 2H), 2.08-1.97 (m, 2H), 1.88 (t, J=11.1 Hz, 3H), 1.53 (d, J=12.5 Hz, 2H), 1.28 (q, J=13.2, 12.4 Hz, 3H), 0.96 (dd, J=21.5, 6.7 Hz, 1H). $^{19}F$ NMR (376 MHz, $d_6$-DMSO) δ=−122.3. HRMS (ESI+): calcd. for $C_{32}H_{40}ClFN_5O_3$, 596.2805. Found: $[M+H]^+$, 596.2798 (−1.2 ppm error).

Isobutyl 3-(1-((1-(3-chloro-4-(isopentyloxy)benzyl)piperidin-4-yl)methyl)-1H-1,2,3-triazol-4-yl)-5-fluoro-1H-indole-2-carboxylate (81) (Code AB746)

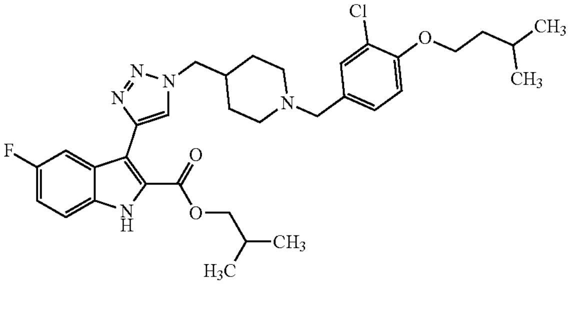 [SMILES: CC(C)CCOc1ccc(CN2CCC(Cn3cc(-c4c(C(=O)OCC(C)C)[nH]c5ccc(F)cc45)nn3)CC2)cc1Cl]

Prepared by general method G using alkyne 14f (60 mg, 0.23 mmol), azide 58q (82 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 81 as a pale yellow solid (92 mg, 65% yield). Mp 175° C. $^1H$ NMR (400 MHz, $d_6$-DMSO) δ=12.01 (s, 1H), 8.55 (s, 1H), 8.02 (dd, J=10.2, 2.6 Hz, 1H), 7.54 (dd, J=9.0, 4.7 Hz, 1H), 7.30 (d, J=2.0 Hz, 1H), 7.27-7.12 (m, 2H), 7.06 (d, J=8.6 Hz, 1H), 4.38 (d, J=7.1 Hz, 2H), 4.12 (d, J=6.8 Hz, 2H), 3.80 (d, J=6.5 Hz, 2H), 3.37 (s, 2H), 2.78 (d, J=11.3 Hz, 2H), 2.08-1.97 (m, 2H), 1.85 (m, 5H), 1.53 (d, J=12.5 Hz, 2H), 1.29 (m, 3H), 0.98 (dd, J=21.6, 6.8 Hz, 1H). $^{19}F$ NMR (376 MHz, $d_6$-DMSO) δ=−122.4. HRMS (ESI+): calcd. for $C_{33}H_{42}ClFN_5O_3$, 610.2950. Found: $[M+H]^+$, 610.2955 (0.7 ppm error).

Isobutyl 3-(1-((1-((4-benzylpiperazin-1-yl)sulfonyl)piperidin-4-yl)methyl)-1H-1,2,3-triazol-4-yl)-5-fluoro-1H-indole-2-carboxylate (82) (Code AB755)

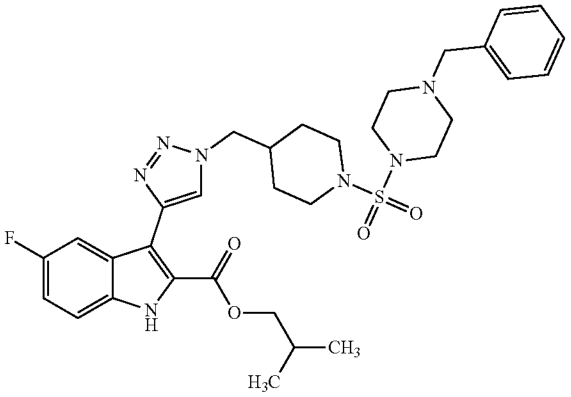 [SMILES: CC(C)COC(=O)c1[nH]c2ccc(F)cc2c1-c1cn(CC2CCN(S(=O)(=O)N3CCN(Cc4ccccc4)CC3)CC2)nn1]

Prepared by general method G using alkyne 14f (60 mg, 0.23 mmol), azide 61 (91 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (579 μL). The crude product was purified chromatographically on silica gel (eluting gradient dichloromethane-methanol 98:2 to 96:4) to provide the title compound 81 as a pale yellow solid (94 mg, 64% yield). HRMS (ESI+): calcd. for $C_{32}H_{41}FN_7O_4S$, 638.2903. Found: $[M+H]^+$, 638.2919 (2.5 ppm error).

tert-butyl 4-(2,6-difluorophenyl)-3,6-dihydropyridine-1(2H)-carboxylate (83a)

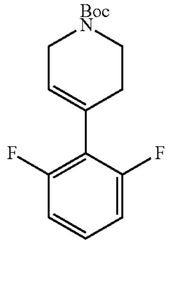 [SMILES: CC(C)(C)OC(=O)N1CC=C(c2c(F)cccc2F)CC1]

Prepared by general method T using 2-bromo-1,3-difluorobenzene (800 mg, 4.15 mmol), tert-butyl 4-(4,4,5,5-tetramethyl-1,3,2-dioxaborolan-2-yl)-3,6-dihydropyridine-1(2H)-carboxylate (1.54 g, 4.97 mmol), potassium carbonate (1.26 g, 9.12 mmol), [1,1'-Bis(diphenylphosphino)ferrocene]dichloropalladium(II) (339 mg, 0.41 mmol), in 1,4-dioxane-water (14 mL). The crude product was purified chromatographically on silica gel (eluting cyclohexane-ethyl acetate 80:20) to provide the title compound 83a as a yellow solid (980 mg, 80% yield). LC-MS (ESI+) Found: $[M+H]^+$, 296.2.

tert-butyl 2-fluoro-3',6'-dihydro-[3,4'-bipyridine]-1'(2'H)-carboxylate (83b)

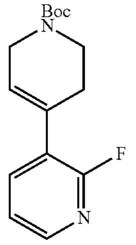 [SMILES: CC(C)(C)OC(=O)N1CC=C(c2cccnc2F)CC1]

Prepared by general method T using 3-bromo-2-fluoropyridine (800 mg, 4.55 mmol), tert-butyl 4-(4,4,5,5-tetramethyl-1,3,2-dioxaborolan-2-yl)-3,6-dihydropyridine-1(2H)-carboxylate (1.69 g, 5.45 mmol), potassium carbonate (1.38 g, 10.0 mmol), [1,1'-Bis(diphenylphosphino)ferrocene]dichloropalladium(II) (371 mg, 0.45 mmol), in 1,4-dioxane-water (15 mL). The crude product was purified chromatographically on silica gel (eluting cyclohexane-ethyl acetate 60:40) to provide the title compound 83b as a colorless oil (894 mg, 71% yield). LC-MS (ESI+) Found: $[M+H]^+$, 279.2.

tert-butyl 4-(2,6-difluorophenyl)piperidine-1-carboxylate (84a)

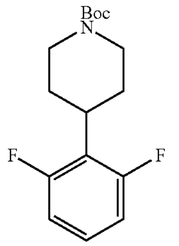 [SMILES: CC(C)(C)OC(=O)N1CCC(c2c(F)cccc2F)CC1]

Prepared by general method U using 83a (900 mg, 3.05 mmol), ammonium formate (1.92 g, 30.5 mmol), 10% palladium on carbon (32 mg, 0.30 mmol), in methanol (10 mL). The crude product was purified chromatographically on silica gel (eluting cyclohexane-ethyl acetate 80:20) to provide the title compound 84a as a colorless oil (704 mg, 77% yield). LC-MS (ESI+) Found: $[M+H]^+$, 298.2.

tert-butyl 4-(2-fluoropyridin-3-yl)piperidine-1-carboxylate (84b)

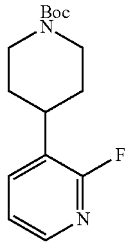 [SMILES: CC(C)(C)OC(=O)N1CCC(c2cccnc2F)CC1]

Prepared by general method U using 83b (850 mg, 3.05 mmol), ammonium formate (1.92 g, 30.5 mmol), 10% palladium on carbon (32 mg, 0.30 mmol), in methanol (10 mL). The crude product was purified chromatographically on silica gel (eluting cyclohexane-ethyl acetate 60:40) to provide the title compound 84b as a colorless oil (726 mg, 85% yield). LC-MS (ESI+) Found: $[M+H]^+$, 281.2.

4-(2,6-difluorophenyl)piperidine hydrochloride (85a)

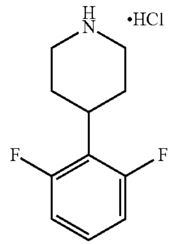 [SMILES: Cl ; Fc1cccc(F)c1C1CCNCC1]

Prepared by general method I using 84a (650 mg, 2.19 mmol), acetyl chloride (1.87 mL, 26.2 mmol) and methanol (10 mL). The hydrochloride salt 85a was obtained as a white crystalline solid (486 mg, 91% yield). LC-MS (ESI+) Found: $[M+H]^+$, 198.2.

2-fluoro-3-(piperidin-4-yl)pyridine hydrochloride (85b)

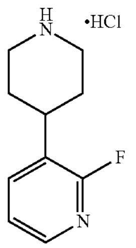 [SMILES: Cl ; Fc1ncccc1C1CCNCC1]

Prepared by general method I using 84b (700 mg, 2.50 mmol), acetyl chloride (2.14 mL, 30.0 mmol) and methanol (12 mL). The hydrochloride salt 85b was obtained as a white crystalline solid (503 mg, 93% yield). LC-MS (ESI+) Found: $[M+H]^+$, 181.1.

4-(2,6-difluorophenyl)piperidine-1-sulfonyl chloride (86a)

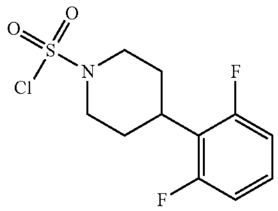 [SMILES: O=S(=O)(Cl)N1CCC(c2c(F)cccc2F)CC1]

Prepared by general method V using a solution of sulfuryl chloride (311 μL, 3.85 mmol) in dry dichloromethane (40 mL) dropped to the solution of the ammonium salt 85a (450 mg, 1.93 mmol) and N,N-diisopropylethylamine (839 μL, 4.81 mmol) in dry dichloromethane (12 mL). The solid compound was dried at 45° C. under reduced pressure during 24 hours and the brown solid obtained 86a (468 mg, 82% yield) was used without further purification for the next step. LC-MS (ESI+) Found: $[M+H]^+$, 296.1.

4-(2-fluoropyridin-3-yl)piperidine-1-sulfonyl chloride (86b)

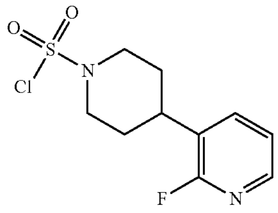 [SMILES: O=S(=O)(Cl)N1CCC(c2cccnc2F)CC1]

Prepared by general method V using a solution of sulfuryl chloride (335 μL, 4.15 mmol) in dry dichloromethane (40 mL) dropped to the solution of the ammonium salt 85b (450 mg, 2.08 mmol) and N,N-diisopropylethylamine (904 μL, 5.19 mmol) in dry dichloromethane (12 mL). The solid compound was dried at 45° C. under reduced pressure during 24 hours and the brown solid obtained 86b (443 mg, 76% yield) was used without further purification for the next step. LC-MS (ESI+) Found: $[M+H]^+$, 279.1.

4-benzylpiperidine-1-sulfonyl chloride (86c)

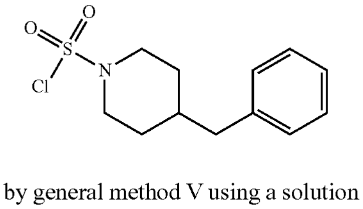

Prepared by general method V using a solution of sulfuryl chloride (461 μL, 5.71 mmol) in dry dichloromethane (55 mL) dropped to the solution of 4-benzylpiperidine (500 μL, 2.85 mmol) and N,N-diisopropylethylamine (500 μL, 2.85 mmol) in dry dichloromethane (20 mL). The solid compound was dried at 45° C. under reduced pressure during 24 hours and the brown solid obtained 86c (602 mg, 77% yield) was used without further purification for the next step. LC-MS (ESI+) Found: $[M+H]^+$, 274.1.

4-phenylpiperidine-1-sulfonyl chloride (86d)

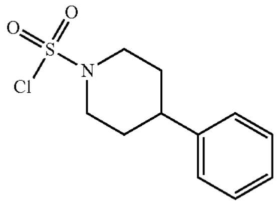 [SMILES: O=S(=O)(Cl)N1CCC(c2ccccc2)CC1]

Prepared by general method V using a solution of sulfuryl chloride (501 μL, 6.20 mmol) in dry dichloromethane (60 mL) dropped to the solution of 4-benzylpiperidine (500 mg, 3.10 mmol) and N,N-diisopropylethylamine (540 μL, 3.10 mmol) in dry dichloromethane (20 mL). The solid compound was dried at 45° C. under reduced pressure during 24 hours and the brown solid obtained 86d (633 mg, 79% yield) was used without further purification for the next step. LC-MS (ESI+) Found: $[M+H]^+$, 260.1.

N-(2-chloroethyl)-4-(2,6-difluorophenyl)piperidine-1-sulfonamide (87a)

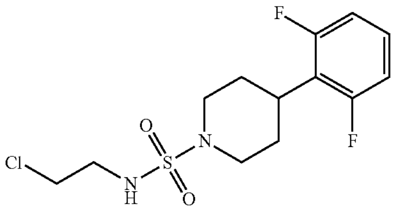 [SMILES: O=S(=O)(NCCCl)N1CCC(c2c(F)cccc2F)CC1]

Prepared by general method R using 2-chloroethylamine hydrochloride (198 mg, 1.70 mmol), compound 86a (450 mg, 1.42 mmol), triethylamine (395 μL, 2.84 mmol) and dry N,N-dimethylformamide (5.0 mL). The crude product was purified chromatographically on silica gel (eluting cyclohexane-ethyl acetate 50:50) to provide the title compound 87a as a colorless oil (302 mg, 63% yield). LC-MS (ESI+) Found: $[M+H]^+$, 339.1.

N-(2-chloroethyl)-4-(2-fluoropyridin-3-yl)piperidine-1-sulfonamide (87b)

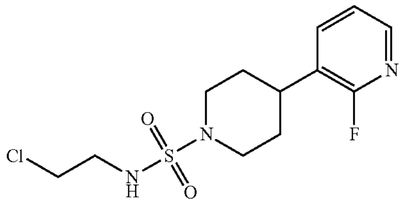 [SMILES: O=S(=O)(NCCCl)N1CCC(c2cccnc2F)CC1]

Prepared by general method R using 2-chloroethylamine hydrochloride (210 mg, 1.81 mmol), compound 86b (420 mg, 1.51 mmol), triethylamine (420 μL, 3.01 mmol) and dry N,N-dimethylformamide (5.0 mL). The crude product was purified chromatographically on silica gel (eluting cyclohexane-ethyl acetate 50:50) to provide the title compound 87b as a colorless oil (296 mg, 61% yield). LC-MS (ESI+) Found: $[M+H]^+$, 322.1.

4-benzyl-N-(2-chloroethyl)piperidine-1-sulfonamide (87c)

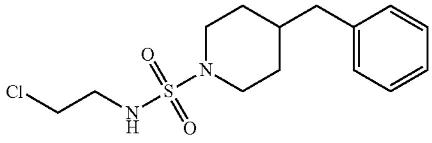 [SMILES: O=S(=O)(NCCCl)N1CCC(Cc2ccccc2)CC1]

Prepared by general method R using 2-chloroethylamine hydrochloride (254 mg, 2.19 mmol), compound 86c (500 mg, 1.83 mmol), triethylamine (510 μL, 3.65 mmol) and dry N,N-dimethylformamide (6.0 mL). The crude product was purified chromatographically on silica gel (eluting cyclohexane-ethyl acetate 50:50) to provide the title compound 87c as a white solid (439 mg, 76% yield). LC-MS (ESI+) Found: $[M+H]^+$, 317.1.

N-(2-chloroethyl)-4-phenylpiperidine-1-sulfonamide (87d)

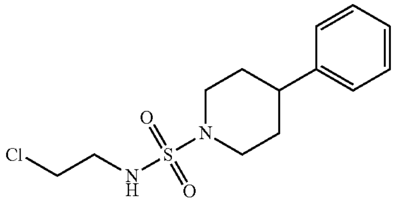 [SMILES: O=S(=O)(NCCCl)N1CCC(c2ccccc2)CC1]

Prepared by general method R using 2-chloroethylamine hydrochloride (268 mg, 2.31 mmol), compound 86d (500 mg, 1.92 mmol), triethylamine (537 μL, 3.85 mmol) and dry N,N-dimethylformamide (6.0 mL). The crude product was purified chromatographically on silica gel (eluting cyclohexane-ethyl acetate 50:50) to provide the title compound 87d as a white solid (414 mg, 71% yield). $^1$H NMR (300 MHz, $d_6$-DMSO) δ=7.49 (t, J=5.9 Hz, 1H), 7.33-7.24 (m, 2H), 7.18 (td, J=7.1, 1.2 Hz, 3H), 3.61 (t, J=6.3 Hz, 2H), 3.56-3.45 (m, 2H), 3.19 (q, J=6.2 Hz, 2H), 2.66-2.53 (m, 2H), 1.60 (tdd, J=14.1, 6.2, 3.3 Hz, 3H), 1.29-1.06 (m, 2H). LC-MS (ESI+) Found: $[M+H]^+$, 303.1.

N-(2-(4-(azidomethyl)piperidin-1-yl)ethyl)-4-(2,6-difluorophenyl)piperidine-1-sulfonamide (88a)

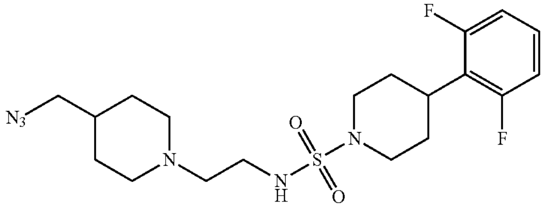 [SMILES: [N-]=[N+]=NCC1CCN(CCNS(=O)(=O)N2CCC(c3c(F)cccc3F)CC2)CC1]

Prepared by general method B using the ammonium salt 4 (120 mg, 0.68 mmol), the corresponding alkyl chloride 87a (254 mg, 0.75 mmol), N,N-diisopropylethylamine (355 L, 2.04 mmol) and dry acetonitrile (8.0 mL). The crude product was purified chromatographically on silica gel (eluting gradient dichloromethane-methanol 98:2 to 96:4) to provide the title compound 88a as a beige solid (206 mg, 68% yield). LC-MS (ESI+) Found: $[M+H]^+$, 443.2.

N-(2-(4-(azidomethyl)piperidin-1-yl)ethyl)-4-(2-fluoropyridin-3-yl)piperidine-1-sulfonamide (88b)

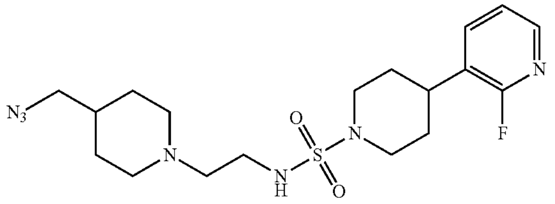 [SMILES: [N-]=[N+]=NCC1CCN(CCNS(=O)(=O)N2CCC(c3cccnc3F)CC2)CC1]

Prepared by general method B using the ammonium salt 4 (120 mg, 0.68 mmol), the corresponding alkyl chloride 87b (241 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 88b as a colorless oil (189 mg, 65% yield). LC-MS (ESI+) Found: $[M+H]^+$, 426.2.

N-(2-(4-(azidomethyl)piperidin-1-yl)ethyl)-4-benzylpiperidine-1-sulfonamide (88c)

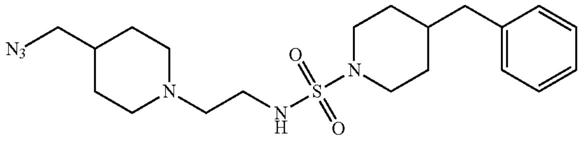 [SMILES: [N-]=[N+]=NCC1CCN(CCNS(=O)(=O)N2CCC(Cc3ccccc3)CC2)CC1]

Prepared by general method B using the ammonium salt 4 (120 mg, 0.68 mmol), the corresponding alkyl chloride 87c (238 mg, 0.75 mmol), N,N-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 88c as a colorless oil (195 mg, 68% yield). LC-MS (ESI+) Found: $[M+H]^+$, 421.2.

N-(2-(4-(azidomethyl)piperidin-1-yl)ethyl)-4-phenylpiperidine-1-sulfonamide (88d)

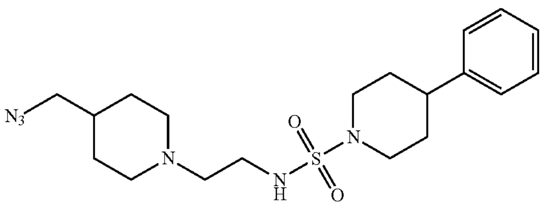 [SMILES: [N-]=[N+]=NCC1CCN(CCNS(=O)(=O)N2CCC(c3ccccc3)CC2)CC1]

Prepared by general method B using the ammonium salt 4 (120 mg, 0.68 mmol), the corresponding alkyl chloride 87d (227 mg, 0.75 mmol), NN-diisopropylethylamine (355 μL, 2.04 mmol) and dry acetonitrile (8.0 mL). The crude product was purified chromatographically on silica gel (eluting gradient dichloromethane-methanol 98:2 to 96:4) to provide the title compound 88d as a colorless oil (183 mg, 66% yield). LC-MS (ESI+) Found: $[M+H]^+$, 407.2.

4-(azidomethyl)-1-((4-(tert-butyl)phenyl)sulfonyl) piperidine (89a)

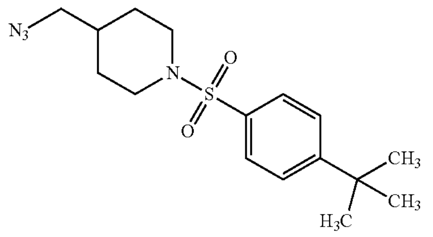 [SMILES: CC(C)(C)c1ccc(S(=O)(=O)N2CCC(CN=[N+]=[N-])CC2)cc1]

Prepared by general method R using the ammonium salt 4 (179 mg, 1.55 mmol), 4-(tert-butyl)benzenesulfonyl chloride (300 mg, 1.29 mmol), triethylamine (360 μL, 2.58 mmol) and dry N,N-dimethylformamide (5.0 mL). The crude product was purified chromatographically on silica gel (eluting cyclohexane-ethyl acetate 50:50) to provide the title compound 89a a white solid (302 mg, 70% yield). $^1H$ NMR (300 MHz, $d_6$-DMSO) δ=7.65 (s, 4H), 3.66 (dt, J=11.5, 2.6 Hz, 2H), 3.22 (d, J=6.5 Hz, 2H), 2.21 (td, J=12.0, 2.5 Hz, 2H), 1.76-1.63 (m, 2H), 1.56-1.39 (m, 1H), 1.30 (s, 9H), 1.25-1.07 (m, 2H). LC-MS (ESI+) Found: $[M+H]^+$, 337.2.

4-(azidomethyl)-1-((2,3-dihydrobenzofuran-6-yl) sulfonyl)piperidine (89b)

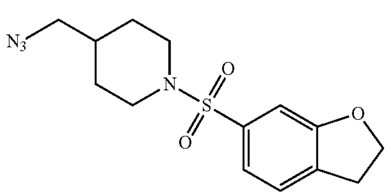 [SMILES: [N-]=[N+]=NCC1CCN(S(=O)(=O)c2ccc3c(c2)OCC3)CC1]

Prepared by general method R using the ammonium salt 4 (191 mg, 1.65 mmol), 2,3-dihydrobenzofuran-6-sulfonyl chloride (300 mg, 1.37 mmol), triethylamine (382 μL, 2.74 mmol) and dry N,N-dimethylformamide (5.0 mL). The crude product was purified chromatographically on silica gel (eluting cyclohexane-ethyl acetate 50:50) to provide the title compound 89b a beige solid (292 mg, 66% yield). $^1H$ NMR (300 MHz, $d_6$-DMSO) δ=7.58 (dt, J=2.2, 1.2 Hz, 1H), 7.48 (dd, J=8.4, 2.1 Hz, 1H), 6.95 (d, J=8.4 Hz, 1H), 4.65 (t, J=8.8 Hz, 2H), 3.61 (dt, J=11.2, 2.6 Hz, 2H), 3.32-3.18 (m, 4H), 2.17 (td, J=12.0, 2.5 Hz, 2H), 1.79-1.64 (m, 2H), 1.48 (ddp, J=13.7, 10.2, 3.8 Hz, 1H), 1.21 (qd, J=12.3, 4.1 Hz, 2H). LC-MS (ESI+) Found: [M+H], 323.1.

5-fluoro-N-methoxy-N-methyl-1H-indole-2-carboxamide (90)

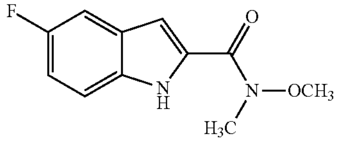

Prepared by general method W using 5-fluoro-1H-indole-2-carboxylic acid (10.0 g, 55.8 mmol), N,O-dimethylhydroxylamine hydrochloride (6.53 g, 67.0 mmol), N,N-diisopropylethylamine (11.67 mL, 67.0 mmol), 1-Ethyl-3-(3-dimethylaminopropyl)carbodiimide (11.86 mL, 67.0 mmol) and 4-dimethylaminopyridine (682 mg, 5.58 mmol), in dry dichloromethane (370 mL). The crude product was purified chromatographically on silica gel (eluting cyclohexane-ethyl acetate 60:40) to provide the title compound 90 a pale yellow solid (8.12 g, 65% yield). $^1H$ NMR (300 MHz, $d_6$-DMSO) δ=11.6 (s, 1H), 7.44 (m, 1H), 7.38 (d, J=2.6 Hz, 1H), 7.12 (d, J=1.5 Hz, 1H), 7.06 (dt, J=9.5, 2.6 Hz, 1H), 3.78 (s, 3H), 3.32 (s, 3H). LC-MS (ESI+) Found: $[M+H]^+$, 223.1.

1-(5-fluoro-1H-indol-2-yl)ethan-1-one (91)

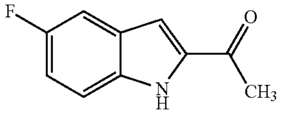

Prepared by general method X using a solution of 1.6 μM methyllithium in diethyl ether (42.2 mL, 67.5 mmol) dropped to the solution of indole 90 (5.00 g, 22.5 mmol) in dry tetrahydrofuran (220 mL). The crude product was purified chromatographically on silica gel (eluting cyclohexane-ethyl acetate 90:10) to provide the title compound 91 a pale yellow solid (3.26 g, 82% yield). $^1H$ NMR (300 MHz, $d_6$-DMSO) δ=9.16 (s, 1H), 7.41-7.35 (m, 2H), 7.19-7.11 (m, 2H), 2.65 (s, 3H). LC-MS (ESI+) Found: $[M+H]^+$, 178.1.

1-(5-fluoro-3-iodo-1H-indol-2-yl)ethan-1-one (92)

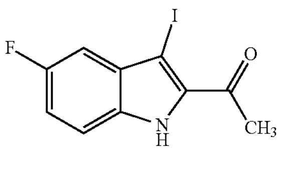

Prepared by general method C using a solution of iodine (4.49 g, 17.8 mmol) in N,N-dimethylformamide (25 mL) dropped to the solution of indole 91 (3.10 g, 17.5 mmol) and potassium hydroxide (3.44 g, 61.2 mmol) in N,N-dimethylformamide (30 mL). The mixture was stirred at room temperature for 6 hours, extracted with ethyl acetate three times and dried at 35° C. under reduced pressure during 48 hours. The brown solid obtained 92 (4.17 g, 79% yield) was used without further purification for the next step. LC-MS (ESI+) Found: $[M+H]^+$, 304.0.

1-(3-ethynyl-5-fluoro-1H-indol-2-yl)ethan-1-one (93)

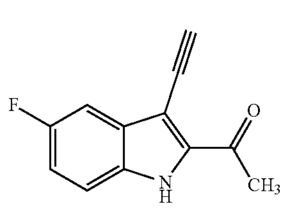

Prepared by general method F using 92 (4.00 g, 13.2 mmol), dry triethylamine (9.20 mL, 66.0 mmol), bis(triphenylphosphine)palladium(II) dichloride (463 mg, 0.66 mmol), copper(I) iodide (251 mg, 1.32 mmol), trimethylsilylacetylene (2.82 mL, 19.8 mmol) and dry tetrahydrofuran (65 mL). The TMS-deprotection was realized using 1M solution of tetrabutylammonium fluoride in tetrahydrofuran (19.8 mL, 19.8 mmol) and the crude product was purified chromatographically on silica gel (eluting cyclohexane-ethyl acetate 90:10) to provide the title compound 93 as a pale yellow solid (1.89 g, 71% yield). LC-MS (ESI+) Found: $[M+H]^+$, 202.1.

5-fluoro-1-tosyl-1H-indole (94)

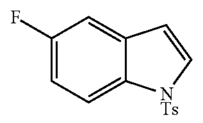 [SMILES: Cc1ccc(S(=O)(=O)n2ccc3cc(F)ccc32)cc1]

In an oven-dried round bottom flask under argon atmosphere was dissolved the 5-fluoro-1H-indole (10.0 g, 74.0 mmol, 1.00 equiv.) in dry tetrahydrofuran (250 mL, C~0.3 M). The reaction mixture was cooled to 0° C. and sodium hydride (~60% dispersion in mineral oil, 4.44 g, 110.0 mmol, 1.50 equiv.) was added in portion wise over 5 minutes. The mixture was stirred for 0.5 hour at 0° C. before the addition in portion wise of the p-toluenesulfonyl chloride (16.9 g, 88.8 mmol, 1.20 equiv.). The reaction was allowed to warm up to room temperature and stirred for 18 hours until the complete consumption of the starting material (monitored by TLC). The mixture was washed with 3M aqueous sodium hydroxide solution (150 mL), extracted with diethyl ether (3×100 mL). The combined organic extracts were washed with brine (75 mL), dried ($MgSO_4$) and filtered. The solvents were removed in vacuo and the residue was purified by column chromatography on silica gel (eluting cyclohexane-ethyl acetate 90:10) to provide the title compound 94 as pale yellow solid (18.6 g, 87% yield). $^1H$ NMR (300 MHz, $d_6$-DMSO) δ=7.97-7.86 (m, 2H), 7.85 (d, J=8.7 Hz, 2H), 7.43 (d, J=2.6 Hz, 1H), 7.39 (d, J=8.8 Hz, 2H), 7.17 (td, J=11.0 Hz, 9.3, 2.5 Hz, 1H), 6.83-6.81 (m, 1H), 2.33 (s, 3H). LC-MS (ESI+) Found: $[M+H]^+$, 290.1.

1-(5-fluoro-1-tosyl-1H-indol-2-yl)propan-1-ol (95a)

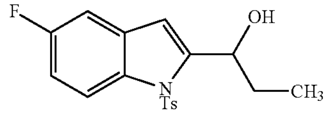

Prepared by general method Y using propionaldehyde (290 μL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95a as a colorless oil (905 mg, 65% yield). LC-MS (ESI+) Found: $[M+H]^+$, 348.2.

1-(5-fluoro-1-tosyl-1H-indol-2-yl)-2-methylpropan-1-ol (95b)

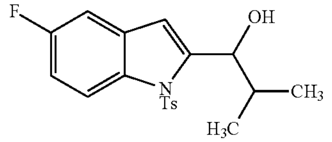

Prepared by general method Y using isobutyraldehyde (368 μL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95b as a colorless oil (887 mg, 61% yield). LC-MS (ESI+) Found: $[M+H]^+$, 362.1.

1-(5-fluoro-1-tosyl-1H-indol-2-yl)-3-methylbutan-1-ol (95c)

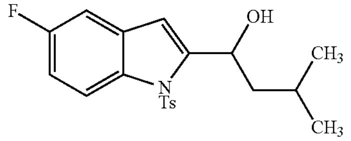 [SMILES: Cc1ccc(S(=O)(=O)n2c(C(O)CC(C)C)cc3cc(F)ccc32)cc1]

Prepared by general method Y using isovaleraldehyde (442 μL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95c as a colorless oil (769 mg, 51% yield). LC-MS (ESI+) Found: $[M+H]^+$, 376.1.

1-(5-fluoro-1-tosyl-1H-indol-2-yl)-2-methylbutan-1-ol (95d)

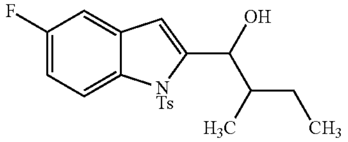 [SMILES: CCC(C)C(O)c1cc2cc(F)ccc2n1S(=O)(=O)c1ccc(C)cc1]

Prepared by general method Y using 2-methylbutyraldehyde (430 µL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95d as a colorless oil (852 mg, 56% yield). LC-MS (ESI+) Found: $[M+H]^+$, 376.1.

cyclopropyl(5-fluoro-1-tosyl-1H-indol-2-yl)methanol (95e)

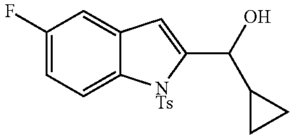 [SMILES: Cc1ccc(S(=O)(=O)n2c(C(O)C3CC3)cc3cc(F)ccc32)cc1]

Prepared by general method Y using cyclopropanecarbaldehyde (301 µL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95e as a colorless oil (916 mg, 63% yield). LC-MS (ESI+) Found: $[M+H]^+$, 360.1.

1-(5-fluoro-1-tosyl-1H-indol-2-yl)butan-1-ol (95f)

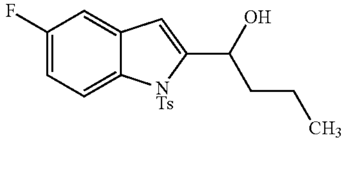

Prepared by general method Y using butyraldehyde (363 µL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95f as a colorless oil (848 mg, 56% yield). LC-MS (ESI+) Found: $[M+H]^+$, 376.1.

1-(5-fluoro-1-tosyl-1H-indol-2-yl)pentan-1-ol (95g)

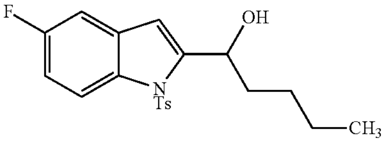 [SMILES: CCCCC(O)c1cc2cc(F)ccc2n1S(=O)(=O)c1ccc(C)cc1]

Prepared by general method Y using pentanal (429 µL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 80:20) to provide the title compound 95g as a colorless oil (755 mg, 52% yield). LC-MS (ESI+) Found: $[M+H]^+$, 362.1.

(5-fluoro-1-tosyl-1H-indol-2-yl)(pyridin-3-yl)methanol (95h)

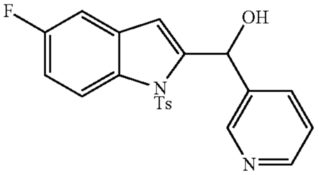 [SMILES: Cc1ccc(S(=O)(=O)n2c(C(O)c3cccnc3)cc3cc(F)ccc32)cc1]

Prepared by general method Y using 3-Pyridinecarboxaldehyde (379 µL, 4.03 mmol) in dry tetrahydrofuran (40 mL) dropped to the solution of indole 94 (2.10 g, 7.26 mmol) in dry tetrahydrofuran (50 mL), previously treated with a solution of 2.5 M n-butyllithium in n-hexane (2.90 mL, 7.26 mmol). The crude product was purified chromatographically on silica gel (eluting cyclohexane-ethyl acetate 60:40) to provide the title compound 95h as a colorless oil (861 mg, 54% yield). LC-MS (ESI+) Found: $[M+H]^+$, 397.1.

1-(5-fluoro-1H-indol-2-yl)propan-1-ol (96a)

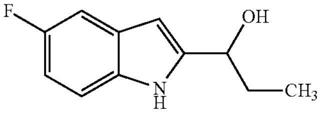

Prepared by general method Z using the N-Ts protected indole 95a (850 mg, 2.45 mmol), potassium hydroxide (686 mg, 12.2 mmol) and dry tetrahydrofuran-ethanol (25 mL). The crude product was purified chromatographically on silica gel (eluting cyclohexane-ethyl acetate 60:40) to provide the title compound 96a as a colorless oil (403 mg, 85% yield). LC-MS (ESI+) Found: $[M+H]^+$, 194.1.

1-(5-fluoro-1H-indol-2-yl)-2-methylpropan-1-ol (96b)

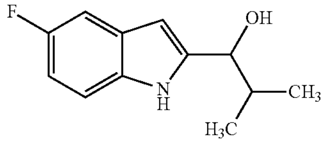

Prepared by general method Z using the N-Ts protected indole 95b (850 mg, 2.35 mmol), potassium hydroxide (660 mg, 11.8 mmol) and dry tetrahydrofuran-ethanol (25 mL). The crude product was purified chromatographically on silica gel (eluting cyclohexane-ethyl acetate 60:40) to provide the title compound 96b as a colorless oil (410 mg, 84% yield). LC-MS (ESI+) Found: $[M+H]^+$, 208.1.

1-(5-fluoro-1H-indol-2-yl)-3-methylbutan-1-ol (96c)

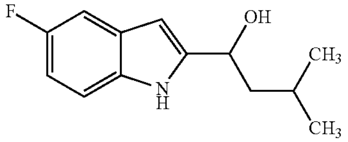 [SMILES: CC(C)CC(O)c1cc2cc(F)ccc2[nH]1]

Prepared by general method Z using the N-Ts protected indole 95c (750 mg, 2.00 mmol), potassium hydroxide (560 mg, 10.0 mmol) and dry tetrahydrofuran-ethanol (20 mL). The crude product was purified chromatographically on silica gel (eluting cyclohexane-ethyl acetate 60:40) to provide the title compound 96c as a colorless oil (397 mg, 90% yield). LC-MS (ESI+) Found: $[M+H]^+$, 222.1.

1-(5-fluoro-1H-indol-2-yl)-2-methylbutan-1-ol (96d)

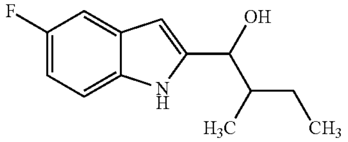

Prepared by general method Z using the N-Ts protected indole 95d (800 mg, 2.13 mmol), potassium hydroxide (600 mg, 10.7 mmol) and dry tetrahydrofuran-ethanol (20 mL). The crude product was purified chromatographically on silica gel (eluting cyclohexane-ethyl acetate 60:40) to provide the title compound 96d as a colorless oil (388 mg, 82% yield). LC-MS (ESI+) Found: $[M+H]^+$, 222.1.

cyclopropyl(5-fluoro-1H-indol-2-yl)methanol (96e)

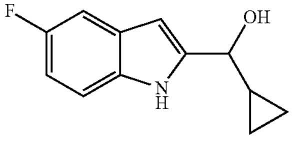 [SMILES: OC(c1cc2cc(F)ccc2[nH]1)C1CC1]

Prepared by general method Z using the N-Ts protected indole 95e (850 mg, 2.36 mmol), potassium hydroxide (663 mg, 11.8 mmol) and dry tetrahydrofuran-ethanol (24 mL). The crude product was purified chromatographically on silica gel (eluting cyclohexane-ethyl acetate 60:40) to provide the title compound 96e as a colorless oil (432 mg, 89% yield). LC-MS (ESI+) Found: $[M+H]^+$, 206.1.

1-(5-fluoro-1H-indol-2-yl)butan-1-ol (96f)

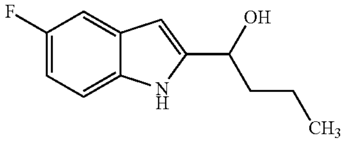

Prepared by general method Z using the N-Ts protected indole 95f (800 mg, 2.21 mmol), potassium hydroxide (621 mg, 11.1 mmol) and dry tetrahydrofuran-ethanol (22 mL). The crude product was purified chromatographically on silica gel (eluting cyclohexane-ethyl acetate 60:40) to provide the title compound 96f as a colorless oil (401 mg, 87% yield). LC-MS (ESI+) Found: $[M+H]^+$, 208.1.

1-(5-fluoro-1H-indol-2-yl)pentan-1-ol (96g)

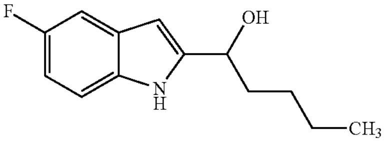

Prepared by general method Z using the N-Ts protected indole 95g (700 mg, 1.86 mmol), potassium hydroxide (523 mg, 9.32 mmol) and dry tetrahydrofuran-ethanol (22 mL). The crude product was purified chromatographically on silica gel (eluting cyclohexane-ethyl acetate 60:40) to provide the title compound 96g as a colorless oil (355 mg, 86% yield). LC-MS (ESI+) Found: $[M+H]^+$, 222.1.

(5-fluoro-1H-indol-2-yl)(pyridin-3-yl)methanol (96h)

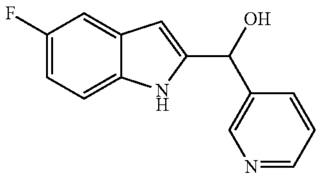 [SMILES: OC(c1cccnc1)c1cc2cc(F)ccc2[nH]1]

Prepared by general method Z using the N-Ts protected indole 95h (850 mg, 2.14 mmol), potassium hydroxide (601 mg, 10.7 mmol) and dry tetrahydrofuran-ethanol (22 mL). The crude product was purified chromatographically on silica gel (eluting cyclohexane-ethyl acetate 50:50) to provide the title compound 96h as a colorless oil (423 mg, 82% yield). LC-MS (ESI+) Found: $[M+H]^+$, 243.1.

1-(5-fluoro-1H-indol-2-yl)propan-1-one (97a)

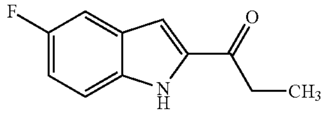

Prepared by general method A1 using the indole 96a (370 mg, 1.91 mmol), manganese (IV) oxide (3.33 g, 38.3 mmol) and dry chloroform (20 mL). The crude product was purified chromatographically on silica gel (eluting cyclohexane-ethyl acetate 80:20) to provide the title compound 97a as a pale yellow solid (296 mg, 81% yield). LC-MS (ESI+) Found: $[M+H]^+$, 192.1.

1-(5-fluoro-1H-indol-2-yl)-2-methylpropan-1-one (97b)

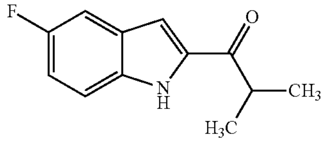

Prepared by general method A1 using the indole 96b (390 mg, 1.88 mmol), manganese (IV) oxide (3.27 g, 37.6 mmol) and dry chloroform (20 mL). The crude product was purified chromatographically on silica gel (eluting cyclohexane-ethyl acetate 80:20) to provide the title compound 97b as a pale yellow solid (292 mg, 76% yield). LC-MS (ESI+) Found: $[M+H]^+$, 206.1.

1-(5-fluoro-1H-indol-2-yl)-3-methylbutan-1-one (97c)

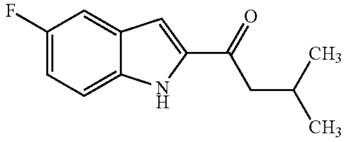 [SMILES: CC(C)CC(=O)c1cc2cc(F)ccc2[nH]1]

Prepared by general method A1 using the indole 96c (380 mg, 1.72 mmol), manganese (IV) oxide (3.00 g, 34.3 mmol) and dry chloroform (18 mL). The crude product was purified chromatographically on silica gel (eluting cyclohexane-ethyl acetate 80:20) to provide the title compound 97c as a pale yellow solid (302 mg, 80% yield). LC-MS (ESI+) Found: $[M+H]^+$, 220.1.

1-(5-fluoro-1H-indol-2-yl)-2-methylbutan-1-one (97d)

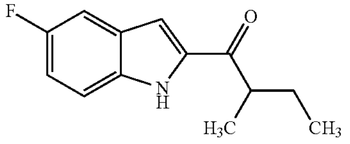

Prepared by general method A1 using the indole 96d (370 mg, 1.67 mmol), manganese (IV) oxide (2.91 g, 33.4 mmol) and dry chloroform (17 mL). The crude product was purified chromatographically on silica gel (eluting cyclohexane-ethyl acetate 80:20) to provide the title compound 97d as a pale yellow solid (255 mg, 69% yield). LC-MS (ESI+) Found: $[M+H]^+$, 220.1.

cyclopropyl(5-fluoro-1H-indol-2-yl)methanone (97e)

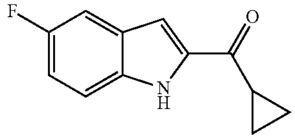 [SMILES: O=C(c1cc2cc(F)ccc2[nH]1)C1CC1]

Prepared by general method A1 using the indole 96e (410 mg, 2.00 mmol), manganese (IV) oxide (3.47 g, 40.0 mmol) and dry chloroform (20 mL). The crude product was purified chromatographically on silica gel (eluting cyclohexane-ethyl acetate 80:20) to provide the title compound 97e as a pale yellow solid (351 mg, 86% yield). LC-MS (ESI+) Found: $[M+H]^+$, 204.1.

1-(5-fluoro-1H-indol-2-yl)butan-1-one (97f)

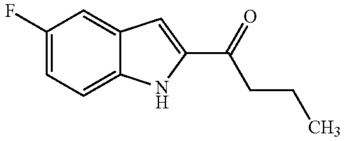

Prepared by general method A1 using the indole 96f (380 mg, 1.83 mmol), manganese (IV) oxide (3.19 g, 36.7 mmol) and dry chloroform (18 mL). The crude product was purified chromatographically on silica gel (eluting cyclohexane-ethyl acetate 80:20) to provide the title compound 97f as a pale yellow solid (311 mg, 83% yield). LC-MS (ESI+) Found: $[M+H]^+$, 206.1.

1-(5-fluoro-1H-indol-2-yl)pentan-1-one (97g)

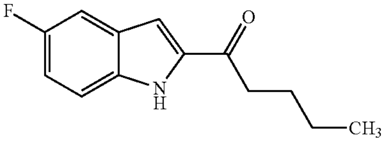 [SMILES: CCCCC(=O)c1cc2cc(F)ccc2[nH]1]

Prepared by general method A1 using the indole 96g (330 mg, 1.49 mmol), manganese (IV) oxide (2.59 g, 29.8 mmol) and dry chloroform (15 mL). The crude product was purified chromatographically on silica gel (eluting cyclohexane-ethyl acetate 80:20) to provide the title compound 97g as a pale yellow solid (246 mg, 75% yield). LC-MS (ESI+) Found: $[M+H]^+$, 220.1.

(5-fluoro-1H-indol-2-yl)(pyridin-3-yl)methanone (97h)

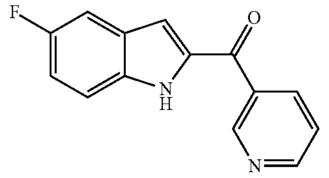 [SMILES: O=C(c1cccnc1)c1cc2cc(F)ccc2[nH]1]

Prepared by general method A1 using the indole 96h (400 mg, 1.65 mmol), manganese (IV) oxide (2.87 g, 33.0 mmol) and dry chloroform (17 mL). The crude product was purified chromatographically on silica gel (eluting cyclohexane-ethyl acetate 60:40) to provide the title compound 97h as a yellow solid (277 mg, 70% yield). LC-MS (ESI+) Found: $[M+H]^+$, 241.1.

1-(5-fluoro-3-iodo-1H-indol-2-yl)propan-1-one (98a)

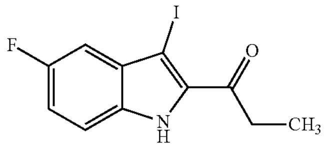

Prepared by general method C using a solution of iodine (375 mg, 1.48 mmol) in N,N-dimethylformamide (2 mL) dropped to the solution of indole 97a (280 mg, 1.46 mmol) and potassium hydroxide (288 mg, 5.13 mmol) in N,N-dimethylformamide (3 mL). The mixture was stirred at room temperature for 6 hours. The precipitate was dried at 50° C. under reduced pressure during 48 hours and the pale yellow solid obtained 98a (354 mg, 76% yield) was used without further purification for the next step. LC-MS (ESI+) Found: $[M+H]^+$, 318.1.

1-(5-fluoro-3-iodo-1H-indol-2-yl)-2-methylpropan-1-one (98b)

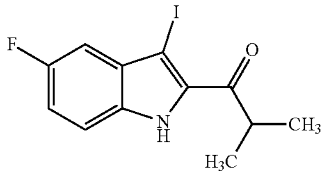 [SMILES: CC(C)C(=O)c1[nH]c2ccc(F)cc2c1I]

Prepared by general method C using a solution of iodine (350 mg, 1.38 mmol) in N,N-dimethylformamide (2 mL) dropped to the solution of indole 97b (280 mg, 1.36 mmol) and potassium hydroxide (268 mg, 4.76 mmol) in N,N-dimethylformamide (2.5 mL). The mixture was stirred at room temperature for 6 hours. The precipitate was dried at 50° C. under reduced pressure during 48 hours and the brown solid obtained 98b (346 mg, 77% yield) was used without further purification for the next step. LC-MS (ESI+) Found: $[M+H]^+$, 332.0.

1-(5-fluoro-3-iodo-1H-indol-2-yl)-3-methylbutan-1-one (98c)

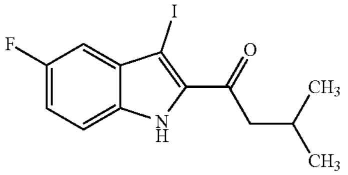

Prepared by general method C using a solution of iodine (327 mg, 1.29 mmol) in N,N-dimethylformamide (2 mL) dropped to the solution of indole 97c (280 mg, 1.28 mmol) and potassium hydroxide (251 mg, 4.47 mmol) in N,N-dimethylformamide (2.5 mL). The mixture was stirred at room temperature for 6 hours, extracted with ethyl acetate three times and dried at 35° C. under reduced pressure during 48 hours. The brown solid obtained 98c (312 mg, 71% yield) was used without further purification for the next step. LC-MS (ESI+) Found: $[M+H]^+$, 346.1.

1-(5-fluoro-3-iodo-1H-indol-2-yl)-2-methylbutan-1-one (98d)

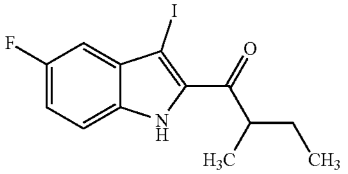 [SMILES: CCC(C)C(=O)c1[nH]c2ccc(F)cc2c1I]

Prepared by general method C using a solution of iodine (281 mg, 1.11 mmol) in N,N-dimethylformamide (2 mL) dropped to the solution of indole 97d (240 mg, 1.09 mmol) and potassium hydroxide (215 mg, 3.83 mmol) in N,N-dimethylformamide (2.5 mL). The mixture was stirred at room temperature for 6 hours, extracted with ethyl acetate three times and dried at 35° C. under reduced pressure during 48 hours. The brown solid obtained 98d (256 mg, 68% yield) was used without further purification for the next step. LC-MS (ESI+) Found: $[M+H]^+$, 346.1.

cyclopropyl(5-fluoro-3-iodo-1H-indol-2-yl)methanone (98e)

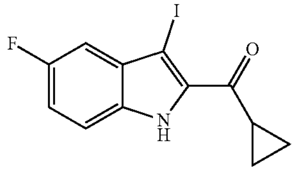 [SMILES: O=C(c1[nH]c2ccc(F)cc2c1I)C1CC1]

Prepared by general method C using a solution of iodine (404 mg, 1.59 mmol) in N,N-dimethylformamide (2.5 mL) dropped to the solution of indole 97e (320 mg, 1.57 mmol) and potassium hydroxide (309 mg, 5.51 mmol) in N,N-dimethylformamide (3 mL). The mixture was stirred at room temperature for 5 hours. The precipitate was dried at 50° C.

under reduced pressure during 48 hours and the yellow solid obtained 98e (426 mg, 82% yield) was used without further purification for the next step. LC-MS (ESI+) Found: $[M+H]^+$, 330.0.

1-(5-fluoro-3-iodo-1H-indol-2-yl)butan-1-one (98f)

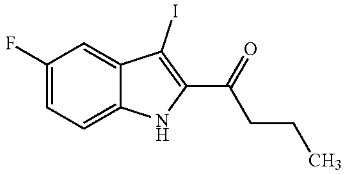

Prepared by general method C using a solution of iodine (362 mg, 1.43 mmol) in N,N-dimethylformamide (2 mL) dropped to the solution of indole 97f (290 mg, 1.41 mmol) and potassium hydroxide (277 mg, 4.95 mmol) in N,N-dimethylformamide (2.5 mL). The mixture was stirred at room temperature for 6 hours, extracted with ethyl acetate three times and dried at 35° C. under reduced pressure during 48 hours. The brown solid obtained 98f (366 mg, 78% yield) was used without further purification for the next step. LC-MS (ESI+) Found: $[M+H]^+$, 332.0.

1-(5-fluoro-3-iodo-1H-indol-2-yl)pentan-1-one (98g)

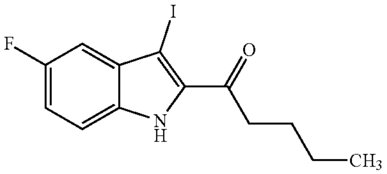 [SMILES: CCCCC(=O)c1[nH]c2ccc(F)cc2c1I]

Prepared by general method C using a solution of iodine (269 mg, 1.06 mmol) in N,N-dimethylformamide (1.5 mL) dropped to the solution of indole 97g (230 mg, 1.05 mmol) and potassium hydroxide (206 mg, 3.67 mmol) in N,N-dimethylformamide (2 mL). The mixture was stirred at room temperature for 6 hours, extracted with ethyl acetate three times and dried at 35° C. under reduced pressure during 48 hours. The brown solid obtained 98g (366 mg, 71% yield) was used without further purification for the next step. LC-MS (ESI+) Found: $[M+H]^+$, 346.1.

(5-fluoro-3-iodo-1H-indol-2-yl)(pyridin-3-yl)methanone (98h)

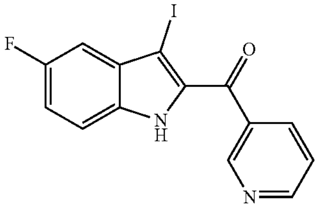 [SMILES: O=C(c1cccnc1)c1[nH]c2ccc(F)cc2c1I]

Prepared by general method C using a solution of iodine (267 mg, 1.05 mmol) in N,N-dimethylformamide (1.5 mL) dropped to the solution of indole 97h (250 mg, 1.04 mmol) and potassium hydroxide (204 mg, 3.64 mmol) in N,N-dimethylformamide (2 mL). The mixture was stirred at room temperature for 6 hours, extracted with ethyl acetate three times and dried at 35° C. under reduced pressure during 48 hours. The brown solid obtained 98h (366 mg, 57% yield) was used without further purification for the next step. LC-MS (ESI+) Found: $[M+H]^+$, 367.0

1-(3-ethynyl-5-fluoro-1H-indol-2-yl)propan-1-one (99a)

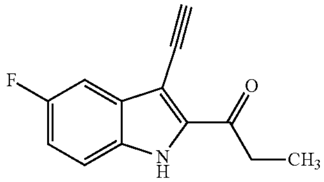 [SMILES: C#Cc1c(C(=O)CC)[nH]c2ccc(F)cc12]

Prepared by general method F using 98a (330 mg, 1.04 mmol), dry triethylamine (725 µL, 5.20 mmol), bis(triphenylphosphine)palladium(II) dichloride (36 mg, 0.052 mmol), copper(I) iodide (20 mg, 0.10 mmol), trimethylsilylacetylene (222 µL, 1.56 mmol) and dry tetrahydrofuran (5 mL). The TMS-deprotection was realized using 1M solution of tetrabutylammonium fluoride in tetrahydrofuran (1.56 mL, 1.56 mmol) and the crude product was purified chromatographically on silica gel (eluting cyclohexane-ethyl acetate 90:10) to provide the title compound 99a as a pale yellow solid (146 mg, 65% yield). LC-MS (ESI+) Found: $[M+H]^+$, 216.1.

1-(3-ethynyl-5-fluoro-1H-indol-2-yl)-2-methylpropan-1-one (99b)

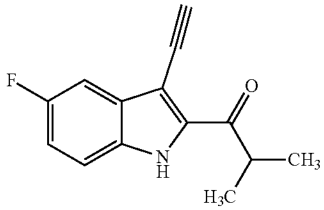 [SMILES: C#Cc1c(C(=O)C(C)C)[nH]c2ccc(F)cc12]

Prepared by general method F using 98b (330 mg, 1.00 mmol), dry triethylamine (694 µL, 5.00 mmol), bis(triphenylphosphine)palladium(II) dichloride (35 mg, 0.050 mmol), copper(I) iodide (19 mg, 0.10 mmol), trimethylsilylacetylene (213 µL, 1.50 mmol) and dry tetrahydrofuran (5 mL). The TMS-deprotection was realized using 1M solution of tetrabutylammonium fluoride in tetrahydrofuran (1.50 mL, 1.50 mmol) and the crude product was purified chromatographically on silica gel (eluting cyclohexane-ethyl acetate 90:10) to provide the title compound 99b as a pale yellow solid (129 mg, 56% yield). LC-MS (ESI+) Found: $[M+H]^+$, 230.1.

1-(3-ethynyl-5-fluoro-1H-indol-2-yl)-3-methylbutan-1-one (99c)

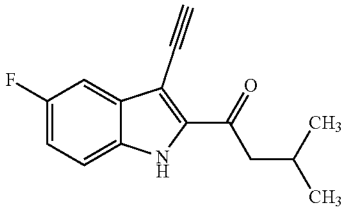 [SMILES: C#Cc1c(C(=O)CC(C)C)[nH]c2ccc(F)cc12]

Prepared by general method F using 98c (290 mg, 0.84 mmol), dry triethylamine (586 μL, 4.20 mmol), bis(triphenylphosphine)palladium(II) dichloride (29 mg, 0.042 mmol), copper(I) iodide (16 mg, 0.084 mmol), trimethylsilylacetylene (179 μL, 1.26 mmol) and dry tetrahydrofuran (5 mL). The TMS-deprotection was realized using 1M solution of tetrabutylammonium fluoride in tetrahydrofuran (1.26 mL, 1.26 mmol) and the crude product was purified chromatographically on silica gel (eluting cyclohexane-ethyl acetate 90:10) to provide the title compound 99c as a pale yellow solid (120 mg, 59% yield). LC-MS (ESI+) Found: $[M+H]^+$, 244.1.

1-(3-ethynyl-5-fluoro-1H-indol-2-yl)-2-methylbutan-1-one (99d)

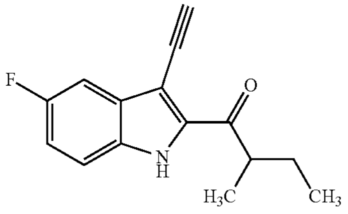 [SMILES: C#Cc1c(C(=O)C(C)CC)[nH]c2ccc(F)cc12]

Prepared by general method F using 98d (240 mg, 0.70 mmol), dry triethylamine (485 μL, 3.50 mmol), bis(triphenylphosphine)palladium(II) dichloride (25 mg, 0.035 mmol), copper(I) iodide (13 mg, 0.070 mmol), trimethylsilylacetylene (102 μL, 1.04 mmol) and dry tetrahydrofuran (3.5 mL). The TMS-deprotection was realized using 1M solution of tetrabutylammonium fluoride in tetrahydrofuran (1.04 mL, 1.04 mmol) and the crude product was purified chromatographically on silica gel (eluting cyclohexane-ethyl acetate 90:10) to provide the title compound 99d as a pale yellow solid (106 mg, 63% yield). LC-MS (ESI+) Found: $[M+H]^+$, 244.1.

cyclopropyl(3-ethynyl-5-fluoro-1H-indol-2-yl) methanone (99e)

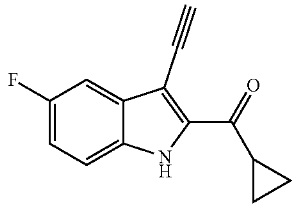 [SMILES: C#Cc1c(C(=O)C2CC2)[nH]c2ccc(F)cc12]

Prepared by general method F using 98e (400 mg, 1.22 mmol), dry triethylamine (847 μL, 6.08 mmol), bis(triphenylphosphine)palladium(II) dichloride (43 mg, 0.061 mmol), copper(I) iodide (23 mg, 0.12 mmol), trimethylsilylacetylene (260 μL, 1.82 mmol) and dry tetrahydrofuran (6 mL). The TMS-deprotection was realized using 1M solution of tetrabutylammonium fluoride in tetrahydrofuran (1.82 mL, 1.82 mmol) and the crude product was purified chromatographically on silica gel (eluting cyclohexane-ethyl acetate 90:10) to provide the title compound 99e as a beige solid (169 mg, 61% yield). LC-MS (ESI+) Found: $[M+H]^+$, 228.1.

1-(3-ethynyl-5-fluoro-1H-indol-2-yl)butan-1-one (99f)

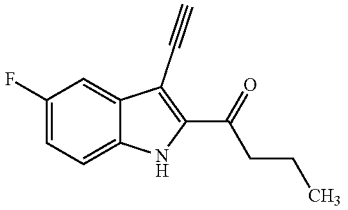 [SMILES: C#Cc1c(C(=O)CCC)[nH]c2ccc(F)cc12]

Prepared by general method F using 98f (350 mg, 1.06 mmol), dry triethylamine (737 μL, 5.28 mmol), bis(triphenylphosphine)palladium(II) dichloride (37 mg, 0.053 mmol), copper(I) iodide (20 mg, 0.11 mmol), trimethylsilylacetylene (226 μL, 1.59 mmol) and dry tetrahydrofuran (5 mL). The TMS-deprotection was realized using 1M solution of tetrabutylammonium fluoride in tetrahydrofuran (1.59 mL, 1.59 mmol) and the crude product was purified chromatographically on silica gel (eluting cyclohexane-ethyl acetate 90:10) to provide the title compound 99f as a pale yellow solid (142 mg, 59% yield). LC-MS (ESI+) Found: $[M+H]^+$, 230.1.

1-(3-ethynyl-5-fluoro-1H-indol-2-yl)pentan-1-one (99g)

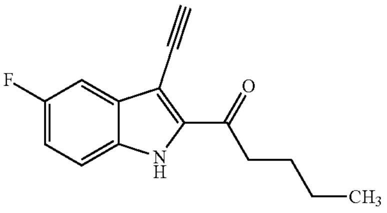 [SMILES: C#Cc1c(C(=O)CCCC)[nH]c2ccc(F)cc12]

Prepared by general method F using 98g (350 mg, 1.01 mmol), dry triethylamine (707 μL, 5.07 mmol), bis(triphenylphosphine)palladium(II) dichloride (36 mg, 0.051 mmol), copper(I) iodide (19 mg, 0.10 mmol), trimethylsilylacetylene (217 μL, 1.52 mmol) and dry tetrahydrofuran (5 mL). The TMS-deprotection was realized using 1M solution of tetrabutylammonium fluoride in tetrahydrofuran (1.52 mL, 1.52 mmol) and the crude product was purified chromatographically on silica gel (eluting cyclohexane-ethyl acetate 90:10) to provide the title compound 99g as a pale yellow solid (151 mg, 61% yield). LC-MS (ESI+) Found: $[M+H]^+$, 244.1.

(3-ethynyl-5-fluoro-1H-indol-2-yl)(pyridin-3-yl)methanone (99h)

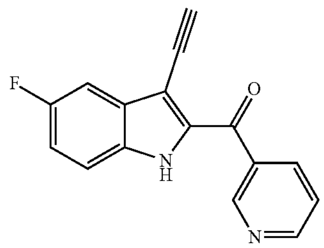 [SMILES: C#Cc1c(C(=O)c2cccnc2)[nH]c2ccc(F)cc12]

Prepared by general method F using 98h (350 mg, 0.96 mmol), dry triethylamine (667 µL, 4.78 mmol), bis(triphenylphosphine)palladium(II) dichloride (34 mg, 0.048 mmol), copper(I) iodide (18 mg, 0.096 mmol), trimethylsilylacetylene (204 µL, 1.43 mmol) and dry tetrahydrofuran (5 mL). The TMS-deprotection was realized using 1M solution of tetrabutylammonium fluoride in tetrahydrofuran (1.43 mL, 1.43 mmol) and the crude product was purified chromatographically on silica gel (eluting cyclohexane-ethyl acetate 60:40) to provide the title compound 99h as a yellow solid (115 mg, 45% yield). LC-MS (ESI+) Found: $[M+H]^+$, 265.1.

(5-fluoro-1H-indol-2-yl)(pyrrolidin-1-yl)methanone (100a)

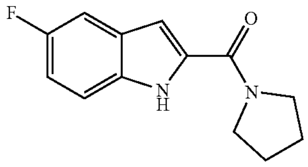 [SMILES: O=C(c1cc2cc(F)ccc2[nH]1)N1CCCC1]

Prepared by general method L using 5-fluoro-1H-indole-2carboxylic acid (500 mg, 2.79 mmol), pyrrolidine (229 µL, 2.79 mmol), N,N-diisopropylethylamine (1.46 mL, 8.37 mmol) and O-(7-azabenzotriazol-1-yl-N,N,N',N'-tetramethyluronium hexafluorophosphate (1.17 g, 3.07 mmol) in N,N-dimethylformamide (10 mL). The crude product was purified chromatographically on silica gel (eluting cyclohexane-ethyl acetate 60:40) to provide the title compound 100a as a yellow solid (469 mg, 72% yield). LC-MS (ESI+) Found: $[M+H]^+$, 233.1.

(5-fluoro-1H-indol-2-yl)(morpholino)methanone (100b)

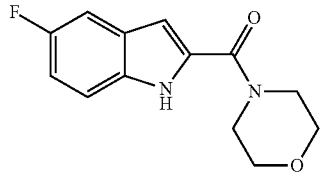 [SMILES: O=C(c1cc2cc(F)ccc2[nH]1)N1CCOCC1]

Prepared by general method L using 5-fluoro-1H-indole-2carboxylic acid (500 mg, 2.79 mmol), morpholine (241 µL, 2.79 mmol), N,N-diisopropylethylamine (1.46 mL, 8.37 mmol) and O-(7-azabenzotriazol-1-yl-N,N,N',N'-tetramethyluronium hexafluorophosphate (1.17 g, 3.07 mmol) in N,N-dimethylformamide (10 mL). The crude product was purified chromatographically on silica gel (eluting cyclohexane-ethyl acetate 60:40) to provide the title compound 100b as a yellow solid (488 mg, 71% yield). LC-MS (ESI+) Found: $[M+H]^+$, 249.1.

(5-fluoro-3-iodo-1H-indol-2-yl)(pyrrolidin-1-yl)methanone (101a)

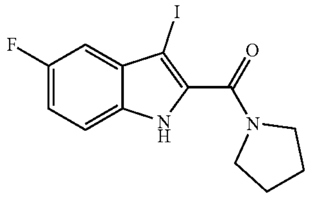 [SMILES: O=C(c1[nH]c2ccc(F)cc2c1I)N1CCCC1]

Prepared by general method C using a solution of iodine (497 mg, 1.96 mmol) in N,N-dimethylformamide (3 mL) dropped to the solution of indole 100a (450 mg, 1.94 mmol) and potassium hydroxide (380 mg, 6.78 mmol) in N,N-dimethylformamide (4 mL). The mixture was stirred at room temperature for 6 hours, extracted with ethyl acetate three times and dried at 35° C. under reduced pressure during 48 hours. The brown oil obtained 101a (483 mg, 71% yield) was used without further purification for the next step. LC-MS (ESI+) Found: $[M+H]^+$, 359.0.

(5-fluoro-3-iodo-1H-indol-2-yl)(morpholino)methanone (101b)

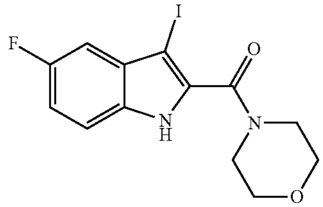 [SMILES: O=C(c1[nH]c2ccc(F)cc2c1I)N1CCOCC1]

Prepared by general method C using a solution of iodine (475 mg, 1.87 mmol) in N,N-dimethylformamide (3 mL) dropped to the solution of indole 100b (460 mg, 1.85 mmol) and potassium hydroxide (364 mg, 6.49 mmol) in N,N-dimethylformamide (4 mL). The mixture was stirred at room temperature for 6 hours, extracted with ethyl acetate three times and dried at 35° C. under reduced pressure during 48 hours. The brown solid obtained 101b (513 mg, 74% yield) was used without further purification for the next step. LC-MS (ESI+) Found: $[M+H]^+$, 375.0.

(3-ethynyl-5-fluoro-1H-indol-2-yl)(pyrrolidin-1-yl) methanone (102a)

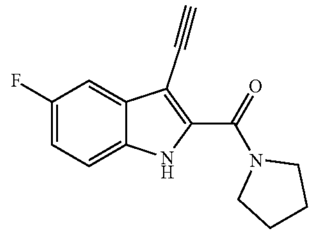 [SMILES: C#Cc1c(C(=O)N2CCCC2)[nH]c2ccc(F)cc12]

Prepared by general method F using 101a (450 mg, 1.26 mmol), dry triethylamine (876 μL, 6.28 mmol), bis(triphenylphosphine)palladium(II) dichloride (44 mg, 0.063 mmol), copper(I) iodide (24 mg, 0.13 mmol), trimethylsilylacetylene (268 μL, 1.88 mmol) and dry tetrahydrofuran (7 mL). The TMS-deprotection was realized using 1M solution of tetrabutylammonium fluoride in tetrahydrofuran (1.88 mL, 1.88 mmol) and the crude product was purified chromatographically on silica gel (eluting cyclohexane-ethyl acetate 60:40) to provide the title compound 102a as a yellow solid (196 mg, 61% yield). LC-MS (ESI+) Found: $[M+H]^+$, 257.1.

(3-ethynyl-5-fluoro-1H-indol-2-yl)(morpholino) methanone (102b)

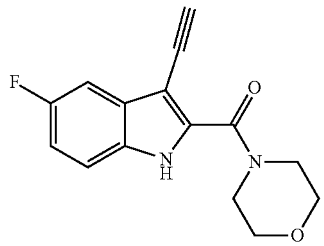 [SMILES: C#Cc1c(C(=O)N2CCOCC2)[nH]c2ccc(F)cc12]

Prepared by general method F using 101b (500 mg, 1.34 mmol), dry triethylamine (931 μL, 6.68 mmol), bis(triphenylphosphine)palladium(II) dichloride (47 mg, 0.067 mmol), copper(I) iodide (25 mg, 0.13 mmol), trimethylsilylacetylene (285 μL, 1.52 mmol) and dry tetrahydrofuran (7 mL). The TMS-deprotection was realized using 1M solution of tetrabutylammonium fluoride in tetrahydrofuran (2.00 mL, 2.00 mmol) and the crude product was purified chromatographically on silica gel (eluting cyclohexane-ethyl acetate 60:40) to provide the title compound 102b as a yellow solid (198 mg, 54% yield). LC-MS (ESI+) Found: $[M+H]^+$, 273.1.

(3-ethynyl-5-fluoro-1H-indol-2-yl)methanol (103)

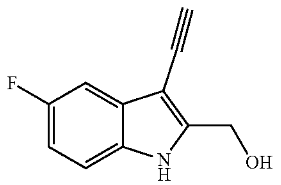

In an oven-dried round bottom flask was dissolved under argon atmosphere at 0° C. (ice bath), indole 14a (300 mg, 1.30 mmol, 1.00 equiv.) in tetrahydrofuran (5 mL, C~0.3 M). Lithium aluminium hydride (74 mg, 0.1.95 mmol, 1.50 equiv.) was added slowly over 5 minutes then the reaction was allowed to warm to room temperature and stirred for 4 hours. After the complete consumption of the starting material (monitored by TLC), the mixture was quenched by the addition of water-ammonia (2:1) (1 mL). The reaction was stirred vigorously at room temperature 30 minutes, filtered through celite and extracted with diethyl ether three times. The combined organics extracts were washed with brine, dried ($MgSO_4$) and filtered. The solvents were removed in vacuo and the residue was purified by column chromatography on silica gel (eluting cyclohexane-ethyl acetate 80:20) to provide the tittle compound 103 as a brown solid (203 mg, 83% yield). LC-MS (ESI+) Found: $[M+H]^+$, 190.1.

3-ethynyl-5-fluoro-1H-indole-2-carbaldehyde (104)

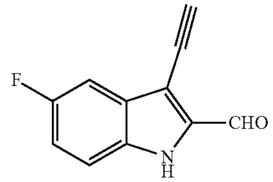

Prepared by general method A1 using the indole 103 (80 mg, 0.42 mmol), manganese (IV) oxide (735 mg, 8.46 mmol) and dry chloroform (5 mL). The crude product was purified chromatographically on silica gel (eluting cyclohexane-ethyl acetate 80:20) to provide the title compound 104 as a brown solid (64 mg, 81% yield). LC-MS (ESI+) Found: [M+H], 188.1.

isobutyl 5-fluoro-3-(1-((1-(2-((4-(trifluoromethoxy) phenyl)sulfonamido)ethyl)piperidin-4-yl)methyl)-1H-1,2,3-triazol-4-yl)-1H-indole-2-carboxylate (105) (Code AB912)

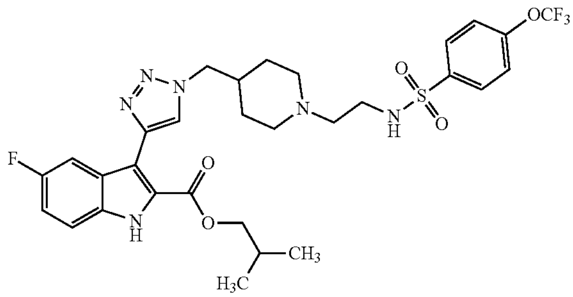 [SMILES: CC(C)COC(=O)c1[nH]c2ccc(F)cc2c1-c1cn(CC2CCN(CCNS(=O)(=O)c3ccc(OC(F)(F)F)cc3)CC2)nn1]

Prepared by general method G using alkyne 14f (60 mg, 0.23 mmol), azide 5i (100 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 105 as a white solid (96 mg, 62% yield). $^1H$ NMR (400 MHz, $d_6$-DMSO) δ=12.01 (s, 1H), 8.54 (s, 1H), 8.04 (dd, J=10.3, 2.6 Hz, 1H), 7.99-7.90 (m, 2H), 7.68 (s, 1H), 7.66-7.50 (m, 3H), 7.22 (td, J=9.1, 2.6 Hz, 1H), 4.33 (d, J=7.0 Hz, 2H), 4.12 (d, J=6.6 Hz, 2H), 2.88 (t, J=6.7 Hz, 2H), 2.78-2.63 (m, 2H), 2.26 (t, J=6.7 Hz, 2H), 2.03 (hept, J=6.7 Hz, 1H), 1.90-1.74 (m, 3H), 1.53-1.40 (m, 2H), 1.30-1.11 (m, 2H), 0.94 (d, J=6.7 Hz, 6H). $^{13}$C NMR (101 MHz, $d_6$-DMSO) δ=161.0 ($C_{quat}$), 156.5 (d, J=233.6 Hz, $C_{quat}$), 150.7 ($C_{quat}$), 140.2 ($C_{quat}$), 139.8 ($C_{quat}$), 133.1 ($C_{quat}$), 129.0 (CH), 126.0 (d, J=11.6 Hz, $C_{quat}$), 124.7 (CH), 123.7 ($C_{quat}$), 121.4 (CH), 118.6 ($C_{quat}$), 114.4 (d, J=26.8 Hz, CH), 114.0 (d, J=10.4 Hz, CH), 111.9 (d, J=5.6 Hz, $C_{quat}$), 107.4 (d, J=24.6 Hz, CH), 70.6 ($CH_2$), 56.9 ($CH_2$), 54.4 ($CH_2$), 52.5 ($CH_2$), 40.2 ($CH_2$), 36.5 (CH), 27.3 (CH), 29.0 ($CH_2$), 18.9 ($CH_3$). $^{19}$F NMR (376 MHz, $d_6$-DMSO) δ=−62.7, −122.4. LC-MS (ESI+) Found: $[M+H]^+$, 667.2.

isobutyl 3-(1-((1-(2-([1,1'-biphenyl]-4-sulfonamido) ethyl)piperidin-4-yl)methyl)-1H-1,2,3-triazol-4-yl)-5-fluoro-1H-indole-2-carboxylate (106) (Code AB913)

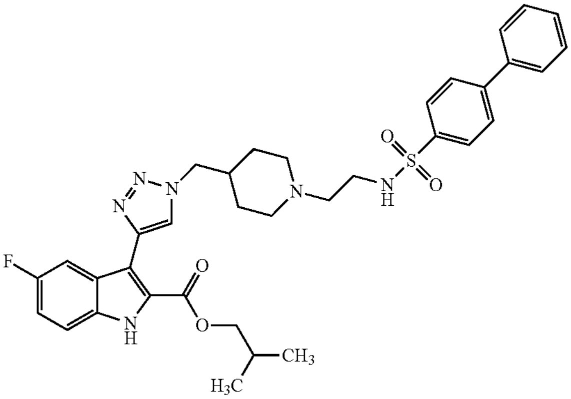 [SMILES: CC(C)COC(=O)c1[nH]c2ccc(F)cc2c1-c1cn(CC2CCN(CCNS(=O)(=O)c3ccc(-c4ccccc4)cc3)CC2)nn1]

Prepared by general method G using alkyne 14f (60 mg, 0.23 mmol), azide 5j (97 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 106 as a white solid (103 mg, 68% yield). $^{1}$H NMR (400 MHz, $d_6$-DMSO) δ=12.01 (s, 1H), 8.53 (s, 1H), 8.03 (dd, J=10.3, 2.7 Hz, 1H), 7.87 (s, 4H), 7.75-7.70 (m, 2H), 7.54 (dd, J=9.0, 4.7 Hz, 2H), 7.49 (dd, J=8.3, 6.7 Hz, 2H), 7.45-7.38 (m, 1H), 7.23 (td, J=9.2, 2.7 Hz, 1H), 4.33 (d, J=7.0 Hz, 2H), 4.11 (d, J=6.7 Hz, 2H), 2.88 (q, J=6.2 Hz, 2H), 2.70 (dd, J=11.4, 4.2 Hz, 2H), 2.30 (t, J=6.9 Hz, 2H), 2.02 (dt, J=13.3, 6.7 Hz, 1H), 1.83 (t, J=11.2 Hz, 3H), 1.46 (d, J=13.1 Hz, 2H), 1.20 (qt, J=12.5, 6.2 Hz, 2H), 0.93 (d, J=6.7 Hz, 6H). $^{19}$F NMR (376 MHz, $d_6$-DMSO) δ=−122.5. LC-MS (ESI+) Found: $[M+H]^+$, 659.3.

isobutyl 3-(1-((1-(2-((4-cyclohexylphenyl)sulfonamido)ethyl)piperidin-4-yl)methyl)-1H-1,2,3-triazol-4-yl)-5-fluoro-1H-indole-2-carboxylate (107) (Code AB914)

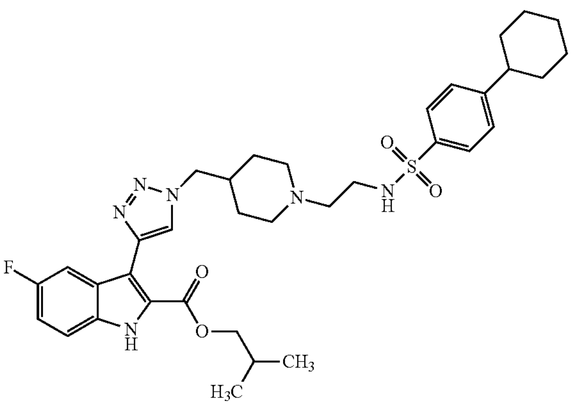

Prepared by general method G using alkyne 14f (60 mg, 0.23 mmol), azide 5k (99 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 107 as a white solid (106 mg, 69% yield). $^{1}$H NMR (400 MHz, $d_6$-DMSO) δ=12.01 (s, 1H), 8.55 (s, 1H), 8.05 (dd, J=10.3, 2.6 Hz, 1H), 7.74-7.67 (m, 2H), 7.55 (dd, J=9.0, 4.7 Hz, 1H), 7.44-7.37 (m, 2H), 7.36 (d, J=5.5 Hz, 1H), 7.22 (td, J=9.1, 2.6 Hz, 1H), 4.33 (d, J=7.0 Hz, 2H), 4.12 (d, J=6.7 Hz, 2H), 2.82 (q, J=6.0 Hz, 2H), 2.64 (dt, J=11.3, 3.0 Hz, 2H), 2.59-2.53 (m, 1H), 2.25 (t, J=6.8 Hz, 2H), 2.09-1.95 (m, 1H), 1.88-1.60 (m, 8H), 1.52-1.42 (m, 2H), 1.41-1.27 (m, 4H), 1.28-1.16 (m, 3H), 0.94 (d, J=6.7 Hz, 6H). $^{13}$C NMR (101 MHz, $d_6$-DMSO) δ=161.0 ($C_{quat}$), 158.7 ($C_{quat}$), 157.5 (d, J=231.5 Hz, $C_{quat}$), 140.2 ($C_{quat}$), 138.1 ($C_{quat}$), 133.1 ($C_{quat}$), 127.3 (CH), 126.6 (CH), 126.0 (d, J=10.3 Hz, $C_{quat}$), 124.7 (CH), 123.7 ($C_{quat}$), 114.4 (d, J=26.9 Hz, CH), 114.0 (d, J=9.1 Hz, CH), 111.9 (d, J=5.8 Hz, $C_{quat}$), 107.2 (d, J=24.8 Hz, CH), 70.6 ($CH_2$), 56.8 ($CH_2$), 54.4 ($CH_2$), 52.5 ($CH_2$), 43.6 (CH), 40.2 ($CH_2$), 36.5 (CH), 33.5 ($CH_2$), 29.0 ($CH_2$), 27.4 (CH), 26.1 ($CH_2$), 25.4 ($CH_2$), 18.9 ($CH_3$). $^{19}$F NMR (376 MHz, $d_6$-DMSO) δ=−122.5. LC-MS (ESI+) Found: $[M+H]^+$, 665.3.

isobutyl 5-fluoro-3-(1-((1-(2-((4-isopropoxyphenyl) sulfonamido)ethyl)piperidin-4-yl)methyl)-1H-1,2,3-triazol-4-yl)-1H-indole-2-carboxylate (108) (Code AB917)

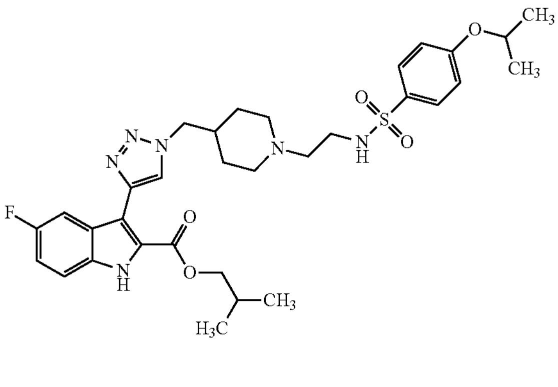 [SMILES: CC(C)COC(=O)c1[nH]c2ccc(F)cc2c1-c1cn(CC2CCN(CCNS(=O)(=O)c3ccc(OC(C)C)cc3)CC2)nn1]

Prepared by general method G using alkyne 14f (60 mg, 0.23 mmol), azide 51 (93 mg, 0.23 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (580 µL). The crude product was purified chromatographically on silica gel (eluting gradient dichloromethane-methanol 98:2 to 96:4) to provide the title compound 108 as a white solid (93 ng, 63% yield). $^1$H NMR (400 MHz, $d_6$-DMSO) δ=12.01 (s, 1H), 8.55 (d, J=3.6 Hz, 1H), 8.04 (dt, J=10.3, 3.1 Hz, 1H), 7.85-7.71 (m, 1H), 7.71-7.67 (m, 1H), 7.54 (dd, J=9.0, 4.7 Hz, 1H), 7.33-7.19 (m, 2H), 7.15-6.93 (m, 2H), 4.71 (dp, J=12.1, 6.0 Hz, 1H), 4.34 (d, J=7.0 Hz, 2H), 4.12 (dd, J=6.7, 2.4 Hz, 2H), 2.81 (dd, J=12.6, 6.0 Hz, 2H), 2.77-2.64 (m, 2H), 2.27 (t, J=7.0 Hz, 2H), 2.03 (dp, J=13.4, 7.1 Hz, 1H), 1.82 (dd, J=14.0, 6.4 Hz, 3H), 1.47 (d, J=12.6 Hz, 2H), 1.26 (d, J=6.0 Hz, 6H), 1.23-1.13 (m, 2H), 0.94 (d, J=6.7 Hz, 6H). $^{19}$F NMR (376 MHz, $d_6$-DMSO) δ=−122.4. LC-MS (ESI+) Found: $[M+H]^+$, 641.3.

isobutyl 3-(1-((1-(2-((4-benzylpiperidine)-1-sulfonamido)ethyl)piperidin-4-yl)methyl)-1H-1,2,3-triazol-4-yl)-5-fluoro-1H-indole-2-carboxylate (109) (Code AB918)

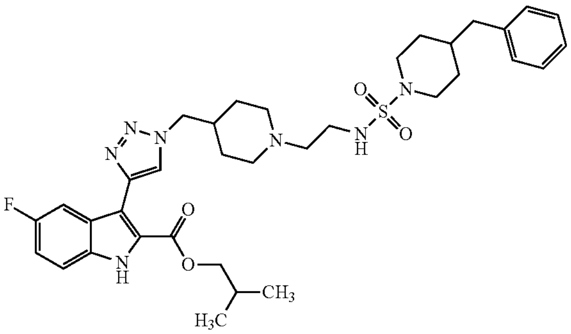 [SMILES: CC(C)COC(=O)c1[nH]c2ccc(F)cc2c1-c1cn(CC2CCN(CCNS(=O)(=O)N3CCC(Cc4ccccc4)CC3)CC2)nn1]

Prepared by general method G using alkyne 14f (60 mg, 0.23 mmol), azide 88c (102 mg, 0.24 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (580 µL). The crude product was purified chromatographically on silica gel (eluting gradient dichloromethane-methanol 98:2 to 96:4) to provide the title compound 109 as a pale yellow solid (104 mg, 65% yield). $^1$H NMR (400 MHz, $d_6$-DMSO) δ=12.01 (s, 1H), 8.56 (s, 1H), 8.04 (dd, J=10.3, 2.6 Hz, 1H), 7.55 (dd, J=9.1, 4.7 Hz, 1H), 7.44-7.12 (m, 6H), 6.98 (t, J=5.8 Hz, 1H), 4.36 (d, J=7.0 Hz, 2H), 4.12 (d, J=6.7 Hz, 2H), 3.55-3.42 (m, 2H), 2.93 (q, J=6.5 Hz, 2H), 2.81 (d, J=11.1 Hz, 2H), 2.69-2.56 (m, 3H), 2.35 (t, J=6.8 Hz, 2H), 2.04 (dq, J=13.4, 6.5 Hz, 1H), 1.96-1.77 (m, 3H), 1.60 (t, J=7.1 Hz, 3H), 1.52 (d, J=12.6 Hz, 2H), 1.37-1.07 (m, 5H), 0.95 (d, J=6.7 Hz, 6H). $^{13}$C NMR (101 MHz, $d_6$-DMSO) δ=161.0 ($C_{quat}$), 160.4 ($C_{quat}$), 157.3 (d, J=267.7 Hz, $C_{quat}$), 140.2 ($C_{quat}$), 133.1 ($C_{quat}$), 131.8 ($C_{quat}$), 129.8 ($C_{quat}$), 128.7 (CH), 126.0 (d, J=10.4 Hz, $C_{quat}$), 115.4 (CH), 114.4 (d, J=24.6 Hz, CH), 114.0 (d, J=8.6 Hz, CH), 111.2 (d, J=5.4 Hz, $C_{quat}$), 107.2 (d, J=22.8 Hz, CH), 70.6 ($CH_2$), 69.8 ($CH_2$), 52.5 ($CH_2$), 40.2 ($CH_2$), 36.5 ($CH_2$), 29.0 ($CH_2$), 27.3 (CH), 21.6 ($CH_3$), 18.9 ($CH_3$). $^{19}$F NMR (376 MHz, $d_6$-DMSO) δ=−122.5. LC-MS (ESI+) Found: $[M+H]^+$, 680.3.

isobutyl 5-fluoro-3-(1-((1-(2-((4-phenylpiperidine)-1-sulfonamido)ethyl)piperidin-4-yl)methyl)-1H-1,2,3-triazol-4-yl)-1H-indole-2-carboxylate (110) (Code AB929)

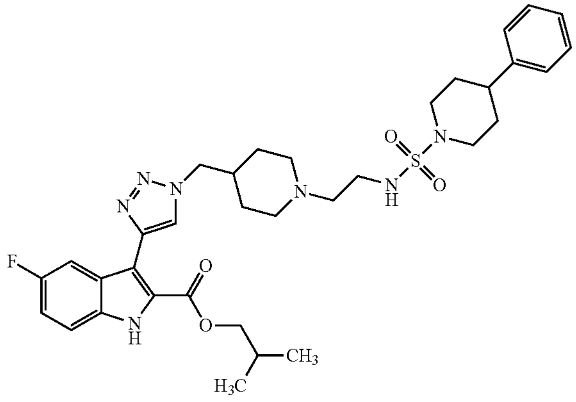 [SMILES: CC(C)COC(=O)c1[nH]c2ccc(F)cc2c1-c1cn(CC2CCN(CCNS(=O)(=O)N3CCC(c4ccccc4)CC3)CC2)nn1]

Prepared by general method G using alkyne 14f (60 mg, 0.23 mmol), azide 88d (100 mg, 0.24 mmol), 2M aqueous of sodium ascorbate (405 µL, 0.81 mmol), 15% aqueous of copper(II) sulfate pentahydrate (337 µL, 0.20 mmol) and tetrahydrofuran-tert-butanol (580 µL). The crude product was purified chromatographically on silica gel (eluting gradient dichloromethane-methanol 98:2 to 96:4) to provide the title compound 110 as a pale yellow solid (98 mg, 62% yield). $^1$H NMR (400 MHz, $d_6$-DMSO) δ=12.02 (s, 1H), 8.57 (s, 1H), 8.03 (dd, J=10.3, 2.6 Hz, 1H), 7.55 (dd, J=9.0, 4.6 Hz, 1H), 7.47-7.14 (m, 6H), 7.09 (t, J=5.8 Hz, 1H), 4.38 (d, J=7.0 Hz, 2H), 4.13 (d, J=6.7 Hz, 2H), 3.63 (d, J=11.9 Hz, 2H), 3.01 (q, J=6.5 Hz, 2H), 2.86 (d, J=10.9 Hz, 2H), 2.82-2.69 (m, 3H), 2.40 (t, J=7.0 Hz, 2H), 2.05 (dq, J=13.4, 6.8 Hz, 1H), 1.96-1.88 (m, 2H), 1.84 (d, J=13.0 Hz, 2H), 1.64 (tt, J=12.5, 6.2 Hz, 2H), 1.55 (d, J=12.3 Hz, 2H), 1.39-1.20 (m, 3H), 0.96 (d, J=6.7 Hz, 6H). $^{19}$F NMR (376 MHz, $d_6$-DMSO) δ=−122.5. LC-MS (ESI+) Found: $[M+H]^+$, 666.3.

isobutyl 3-(1-((1-(2-((2,3-dihydrobenzofuran)-5-sulfonamido)ethyl)piperidin-4-yl)methyl)-1H-1,2,3-triazol-4-yl)-5-fluoro-1H-indole-2-carboxylate (111) (Code AB930)

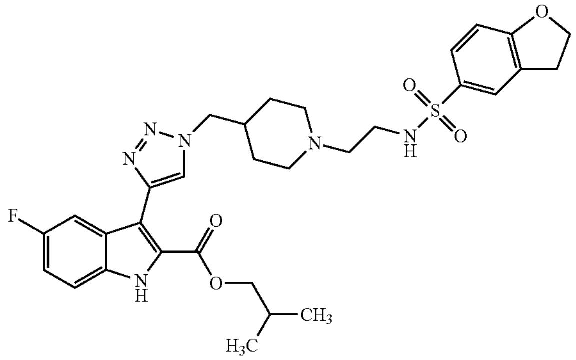 [SMILES: CC(C)COC(=O)c1[nH]c2ccc(F)cc2c1-c1cn(CC2CCN(CCNS(=O)(=O)c3ccc4c(c3)CCO4)CC2)nn1]

Prepared by general method G using alkyne 14f (60 mg, 0.23 mmol), azide 5m (89 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 111 as a white solid (91 mg, 63% yield). $^1$H NMR (400 MHz, $d_6$-DMSO) δ=12.01 (s, 1H), 8.55 (s, 1H), 8.04 (dd, J=10.2, 2.6 Hz, 1H), 7.64 (d, J=1.9 Hz, 1H), 7.57-7.48 (m, 2H), 7.31-7.16 (m, 2H), 6.90 (d, J=8.4 Hz, 1H), 4.62 (t, J=8.8 Hz, 2H), 4.34 (d, J=7.0 Hz, 2H), 4.12 (d, J=6.7 Hz, 2H), 3.24 (t, J=8.8 Hz, 2H), 2.79 (q, J=6.4 Hz, 2H), 2.76-2.65 (m, 2H), 2.28 (t, J=6.9 Hz, 2H), 2.03 (dp, J=13.3, 6.6 Hz, 1H), 1.90-1.75 (m, 3H), 1.56-1.39 (m, 2H), 1.22 (qd, J=12.1, 3.7 Hz, 2H), 0.94 (d, J=6.7 Hz, 6H). $^{13}$C NMR (101 MHz, $d_6$-DMSO) δ=162.8 ($C_{quat}$), 160.9 ($C_{quat}$), 157.5 (d, J=234.4 Hz, $C_{quat}$), 140.2 ($C_{quat}$), 133.1 ($C_{quat}$), 132.1 ($C_{quat}$), 128.7 ($C_{quat}$), 127.8 (CH), 126.1 (d, J=10.8 Hz, $C_{quat}$), 124.7 (CH), 123.9 (CH), 114.5 (d, J=26.0 Hz, CH), 114.0 (d, J=10.3 Hz, CH), 111.8 (d, J=4.0 Hz, $C_{quat}$), 108.9 ($C_{quat}$), 107.5 (d, J=23.5 Hz, CH), 72.1 ($CH_2$), 70.6 ($CH_2$), 56.9 ($CH_2$), 54.5 ($CH_2$), 52.6 ($CH_2$), 40.2 ($CH_2$), 39.6 (CH), 36.5 (CH), 29.1 ($CH_2$), 28.5 ($CH_2$), 27.4 (CH), 18.9 ($CH_3$). $^{19}$F NMR (376 MHz, $d_6$-DMSO) δ=−122.4. LC-MS (ESI+) Found: $[M+H]^+$, 625.3.

isobutyl 3-(1-((1-(2-((4-(sec-butyl)phenyl)sulfonamido)ethyl)piperidin-4-yl)methyl)-1H-1,2,3-triazol-4-yl)-5-fluoro-1H-indole-2-carboxylate (112) (Code AB931)

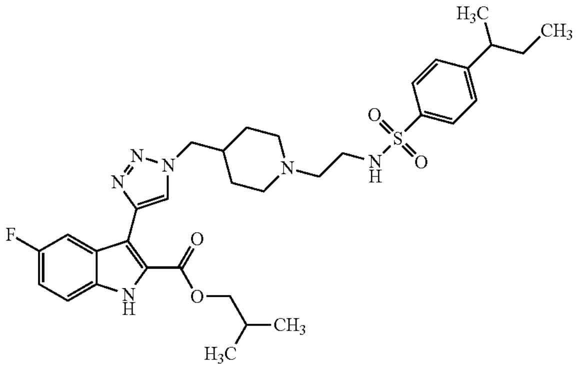 [SMILES: CCC(C)c1ccc(S(=O)(=O)NCCN2CCC(Cn3cc(-c4c(C(=O)OCC(C)C)[nH]c5ccc(F)cc45)nn3)CC2)cc1]

Prepared by general method G using alkyne 14f (60 mg, 0.23 mmol), azide 5n (92 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 112 as a pale yellow solid (101 mg, 68% yield). $^1$H NMR (400 MHz, $d_6$-DMSO) δ=12.01 (s, 1H), 8.54 (s, 1H), 8.04 (dd, J=10.3, 2.6 Hz, 1H), 7.79-7.69 (m, 2H), 7.63-7.50 (m, 3H), 7.39 (d, J=5.7 Hz, 1H), 7.22 (td, J=9.1, 2.6 Hz, 1H), 4.33 (d, J=7.0 Hz, 2H), 4.12 (d, J=6.7 Hz, 2H), 2.91-2.76 (m, 2H), 2.65 (dt, J=11.5, 3.2 Hz, 2H), 2.26 (t, J=6.8 Hz, 2H), 2.04 (td, J=13.4, 6.7 Hz, 1H), 1.88-1.69 (m, 3H), 1.45 (dd, J=13.0, 3.4 Hz, 2H), 1.27 (s, 9H), 1.24-1.12 (m, 2H), 0.94 (d, J=6.7 Hz, 6H). $^{13}$C NMR (101 MHz, $d_6$-DMSO) δ=160.9 ($C_{quat}$), 157.5 (d, J=233.0 Hz, $C_{quat}$), 155.19 ($C_{quat}$), 140.2 ($C_{quat}$), 137.7 ($C_{quat}$), 133.1 ($C_{quat}$), 126.4 (CH), 126.1 (d, J=11.5 Hz, $C_{quat}$), 125.9 (CH), 124.7 (CH), 123.8 ($C_{quat}$), 114.5 (d, J=26.7 Hz, CH), 114.0 (d, J=9.3 Hz, CH), 111.8 (d, J=6.3 Hz, $C_{quat}$), 107.3 (d, J=24.1 Hz, CH), 70.6 ($CH_2$), 56.9 ($CH_2$), 54.5 ($CH_2$), 52.6 ($CH_2$), 40.2 ($CH_2$), 39.6 (CH), 36.5 (CH), 34.8 (CH), 30.8 ($CH_3$), 29.1 ($CH_2$), 27.4 (CH), 18.9 ($CH_3$). $^{19}$F NMR (376 MHz, $d_6$-DMSO) δ=−122.4. LC-MS (ESI+) Found: $[M+H]^+$, 639.3.

isobutyl 3-(1-((1-(2-((2,3-dihydro-1H-indene)-5-sulfonamido)ethyl)piperidin-4-yl)methyl)-1H-1,2,3-triazol-4-yl)-5-fluoro-1H-indole-2-carboxylate (113) (Code AB932)

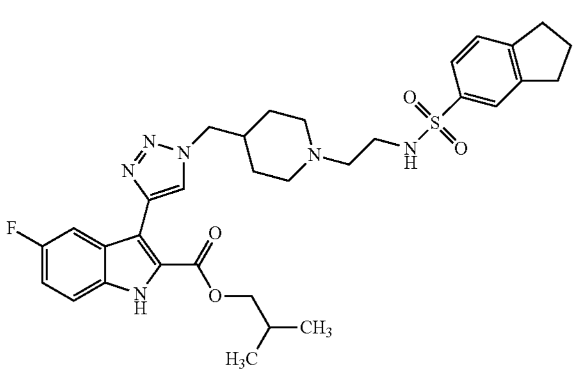 [SMILES: CC(C)COC(=O)c1[nH]c2ccc(F)cc2c1-c1cn(CC2CCN(CCNS(=O)(=O)c3ccc4c(c3)CCC4)CC2)nn1]

Prepared by general method G using alkyne 14f (60 mg, 0.23 mmol), azide 5o (88 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 113 as a pale yellow solid (97 mg, 67% yield). $^1$H NMR (400 MHz, $d_6$-DMSO) δ=12.01 (s, 1H), 8.55 (s, 1H), 8.04 (dd, J=10.3, 2.7 Hz, 1H), 7.63 (d, J=1.7 Hz, 1H), 7.54 (dd, J=7.9, 5.9 Hz, 2H), 7.39 (d, J=7.9 Hz, 1H), 7.33 (d, J=5.5 Hz, 1H), 7.22 (td, J=9.1, 2.6 Hz, 1H), 4.33 (d, J=7.0 Hz, 2H), 4.12 (d, J=6.7 Hz, 2H), 2.91 (dd, J=7.5, 5.4 Hz, 4H), 2.80 (q, J=6.3 Hz, 2H), 2.69 (dt, J=11.5, 3.4 Hz, 2H), 2.28 (t, J=6.8 Hz, 2H), 2.15-1.96 (m, 3H), 1.88-1.73 (m, 3H), 1.59-1.39 (m, 2H), 1.20 (qd, J=13.7, 5.2 Hz, 2H), 0.94 (d, J=6.7 Hz, 6H). $^{13}$C NMR (101 MHz, $d_6$-DMSO) δ 161.0 ($C_{quat}$), 157.5 (d, J=234.6 Hz, $C_{quat}$), 148.7 ($C_{quat}$), 144.9 ($C_{quat}$), 140.2 ($C_{quat}$), 138.5 ($C_{quat}$), 133.1 ($C_{quat}$), 126.0 (d, J=10.8 Hz, $C_{quat}$), 124.8 (CH), 124.6 (CH), 123.8 ($C_{quat}$), 122.3 (CH), 114.4 (d, J=26.6 Hz, CH), 114.0 (d, J=9.5 Hz, CH), 111.8 (d, J=5.5 Hz, $C_{quat}$), 107.2 (d, J=24.9 Hz, CH), 70.6 ($CH_2$), 56.9 ($CH_2$), 54.4 ($CH_2$), 52.5 ($CH_2$), 40.2 ($CH_2$), 39.7 (CH), 36.5 (CH), 32.2 ($CH_2$), 32.1 ($CH_2$), 29.1 ($CH_2$), 27.4 (CH), 25.0 ($CH_2$), 18.9 ($CH_3$). $^{19}$F NMR (376 MHz, $d_6$-DMSO) δ=−122.5. LC-MS (ESI+) Found: $[M+H]^+$, 623.3.

isobutyl 5-fluoro-3-(1-((1-(2-((4-phenoxyphenyl) sulfonamido)ethyl)piperidin-4-yl)methyl)-1H-1,2,3-triazol-4-yl)-1H-indole-2-carboxylate (114) (Code AB933)

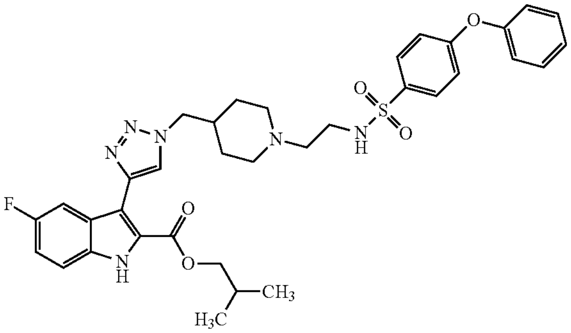 [SMILES: CC(C)COC(=O)c1[nH]c2ccc(F)cc2c1-c1cn(CC2CCN(CCNS(=O)(=O)c3ccc(Oc4ccccc4)cc3)CC2)nn1]

Prepared by general method G using alkyne 14f (60 mg, 0.23 mmol), azide 5p (101 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 114 as a white solid (105 mg, 67% yield). $^1H$ NMR (400 MHz, $d_6$-DMSO) δ=12.01 (s, 1H), 8.55 (s, 1H), 8.03 (dd, J=10.2, 2.6 Hz, 1H), 7.82-7.75 (m, 2H), 7.54 (dd, J=9.0, 4.7 Hz, 1H), 7.44 (dt, J=7.8, 6.6 Hz, 3H), 7.26-7.18 (m, 2H), 7.17-7.01 (m, 4H), 4.34 (d, J=7.0 Hz, 2H), 4.12 (d, J=6.7 Hz, 2H), 2.83 (q, J=6.5 Hz, 2H), 2.71 (d, J=11.2 Hz, 2H), 2.28 (t, J=6.9 Hz, 2H), 2.03 (dt, J=13.3, 6.6 Hz, 1H), 1.83 (t, J=11.2 Hz, 3H), 1.48 (d, J=12.3 Hz, 2H), 1.28 (d, J=2.1 Hz, 2H), 0.94 (d, J=6.7 Hz, 6H). $^{19}F$ NMR (376 MHz, $d_6$-DMSO) δ=−122.4. LC-MS (ESI+) Found: $[M+H]^+$, 675.3.

isobutyl 3-(1-((1-(2-((4-(tert-butyl)phenyl)sulfonamido)ethyl)piperidin-4-yl)methyl)-1H-1,2,3-triazol-4-yl)-5-fluoro-1H-indole-2-carboxylate (115) (Code AB934)

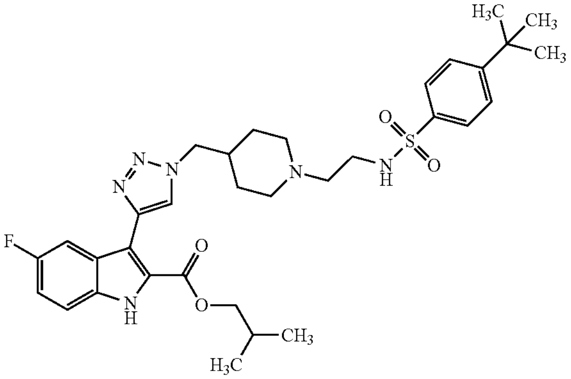 [SMILES: CC(C)COC(=O)c1[nH]c2ccc(F)cc2c1-c1cn(CC2CCN(CCNS(=O)(=O)c3ccc(C(C)(C)C)cc3)CC2)nn1]

Prepared by general method G using alkyne 14f (60 mg, 0.23 mmol), azide 5q (92 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 115 as a pale yellow solid (95 mg, 64% yield). $^1H$ NMR (400 MHz, $d_6$-DMSO) δ=12.01 (s, 1H), 8.55 (s, 1H), 8.05 (dd, J=10.3, 2.6 Hz, 1H), 7.90-7.64 (m, 2H), 7.55 (dd, J=9.0, 4.7 Hz, 1H), 7.49-7.29 (m, 3H), 7.22 (td, J=9.1, 2.6 Hz, 1H), 4.33 (d, J=6.9 Hz, 2H), 4.12 (d, J=6.7 Hz, 2H), 2.83 (q, J=6.1 Hz, 2H), 2.69-2.59 (m, 2H), 2.24 (t, J=6.8 Hz, 2H), 2.04 (dq, J=13.3, 6.5 Hz, 1H), 1.79 (tdd, J=11.7, 7.9, 4.2 Hz, 3H), 1.59-1.47 (m, 2H), 1.49-1.39 (m, 2H), 1.29-1.06 (m, 6H), 0.94 (d, J=6.7 Hz, 6H), 0.71 (t, J=7.4 Hz, 3H). $^{19}F$ NMR (376 MHz, $d_6$-DMSO) δ=−122.4. LC-MS (ESI+) Found: $[M+H]^+$, 639.3.

isobutyl 5-fluoro-3-(1-((1-(2-(((4-(trifluoromethyl) phenyl)methyl)sulfonamido)ethyl) piperidin-4-yl) methyl)-1H-1,2,3-triazol-4-yl)-1H-indole-2-carboxylate (116) (AB935)

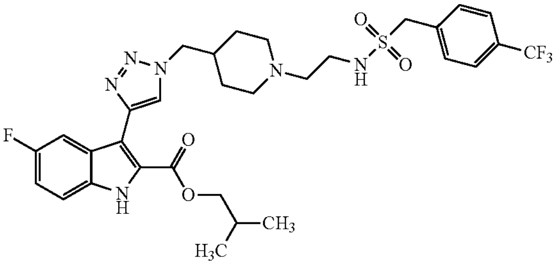 [SMILES: CC(C)COC(=O)c1[nH]c2ccc(F)cc2c1-c1cn(CC2CCN(CCNS(=O)(=O)Cc3ccc(C(F)(F)F)cc3)CC2)nn1]

Prepared by general method G using alkyne 14f (60 mg, 0.23 mmol), azide 5r (100 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 116 as a white solid (107 mg, 69% yield). $^1H$ NMR (400 MHz, $d_6$-DMSO) δ=12.01 (s, 1H), 8.56 (s, 1H), 8.03 (dd, J=10.3, 2.7 Hz, 1H), 7.74 (d, J=8.0 Hz, 2H), 7.67-7.47 (m, 3H), 7.23 (td, J=9.1, 2.7 Hz, 1H), 7.04 (t, J=5.8 Hz, 1H), 4.52 (s, 2H), 4.37 (d, J=7.0 Hz, 2H), 4.12 (d, J=6.7 Hz, 2H), 3.04 (q, J=6.4 Hz, 2H), 2.86 (d, J=10.6 Hz, 2H), 2.34 (t, J=6.7 Hz, 2H), 2.04 (tt, J=13.1, 6.5 Hz, 1H), 1.89 (q, J=10.1 Hz, 3H), 1.54 (d, J=12.3 Hz, 2H), 1.27 (qd, J=11.9, 3.9 Hz, 2H), 0.95 (d, J=6.6 Hz, 6H). $^{19}F$ NMR (376 MHz, $d_6$-DMSO) δ=−72.6, −122.4. LC-MS (ESI+) Found: $[M+H]^+$, 665.3.

isobutyl 3-(1-((1-(2-(((4-chlorophenyl)methyl)sulfonamido)ethyl)piperidin-4-yl)methyl)-1H-1,2,3-triazol-4-yl)-5-fluoro-1H-indole-2-carboxylate (117) (AB936)

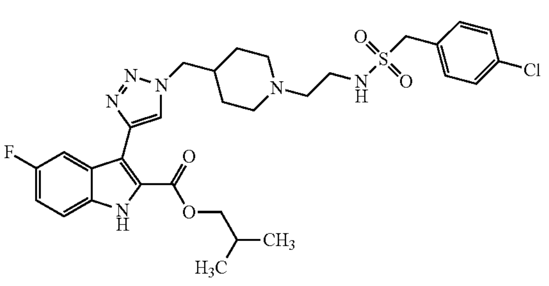

Prepared by general method G using alkyne 14f (60 mg, 0.23 mmol), azide 5s (90 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 117 as a white solid (95 mg, 65% yield). $^1H$ NMR (400 MHz, $d_6$-DMSO) δ=12.01 (s, 1H), 8.57 (s, 1H), 8.05 (dd, J=10.2, 2.6 Hz, 1H), 7.55 (dd, J=9.0, 4.7 Hz, 1H), 7.51-7.35 (m, 4H), 7.23 (td, J=9.1, 2.6 Hz, 1H), 6.95 (t, J=5.6 Hz, 1H), 4.37 (d, J=9.9 Hz, 4H), 4.12 (d, J=6.7 Hz, 2H), 3.01 (q, J=6.3 Hz, 2H), 2.85 (dt, J=11.7, 3.4 Hz, 2H), 2.33 (t, J=6.7 Hz, 2H), 2.04 (hept, J=6.7 Hz, 1H), 1.94-1.81 (m, 3H), 1.61-1.49 (m, 2H), 1.27 (qd, J=12.2, 3.8 Hz, 2H), 0.95 (d, J=6.7 Hz, 6H). $^{13}C$ NMR (101 MHz, $d_6$-DMSO) δ=161.0 ($C_{quat}$), 157.5 (d, J=233.8 Hz, $C_{quat}$), 140.2 ($C_{quat}$), 133.1 ($C_{quat}$), 132.8 ($C_{quat}$), 132.6 (CH), 129.7 ($C_{quat}$), 128.3 (CH), 126.1 (d, J=10.5 Hz, $C_{quat}$), 124.6 (CH), 123.8 ($C_{quat}$), 114.4 (d, J=26.4 Hz, CH), 114.0 (d, J=10.4 Hz, CH), 111.9 (d, J=5.3 Hz, $C_{quat}$), 107.3 (d, J=25.8 Hz, CH), 70.6 ($CH_2$), 57.9 ($CH_2$), 56.5 ($CH_2$), 54.5 ($CH_2$), 52.7 ($CH_2$), 40.2 ($CH_2$), 36.6 (CH), 29.2 ($CH_2$), 27.4 (CH), 18.9 ($CH_3$). $^{19}F$ NMR (376 MHz, $d_6$-DMSO) δ=−122.5. LC-MS (ESI+) Found: $[M+H]^+$, 631.2.

isobutyl 3-(1-((1-(2-(((3-chlorophenyl)methyl)sulfonamido)ethyl)piperidin-4-yl)methyl)-1H-1,2,3-triazol-4-yl)-5-fluoro-1H-indole-2-carboxylate (118) (AB937)

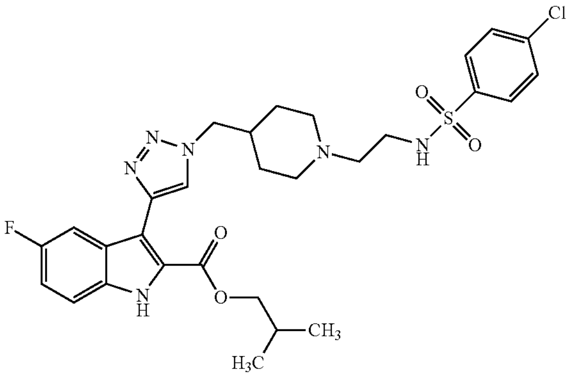 [SMILES: CC(C)COC(=O)c1[nH]c2ccc(F)cc2c1-c1cn(CC2CCN(CCNS(=O)(=O)c3ccc(Cl)cc3)CC2)nn1]

Prepared by general method G using alkyne 14f (60 mg, 0.23 mmol), azide 5t (90 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 118 as a white solid (88 mg, 60% yield). $^1H$ NMR (400 MHz, $d_6$-DMSO) δ=12.01 (s, 1H), 8.56 (s, 1H), 8.03 (dd, J=10.3, 2.7 Hz, 1H), 7.54 (dd, J=9.0, 4.6 Hz, 1H), 7.47 (q, J=1.4 Hz, 1H), 7.44-7.37 (m, 2H), 7.35 (ddd, J=5.9, 4.4, 2.0 Hz, 1H), 7.23 (td, J=9.1, 2.6 Hz, 1H), 6.99 (t, J=5.7 Hz, 1H), 4.39 (m, 3H), 4.12 (d, J=6.7 Hz, 2H), 3.02 (q, J=6.4 Hz, 2H), 2.86 (d, J=11.2 Hz, 2H), 2.35 (d, J=6.7 Hz, 2H), 2.04 (dp, J=13.2, 6.7 Hz, 2H), 1.90 (t, J=11.4 Hz, 3H), 1.55 (d, J=12.3 Hz, 2H), 1.36-1.25 (m, 2H), 0.95 (d, J=6.7 Hz, 6H). $^{19}F$ NMR (376 MHz, $d_6$-DMSO) δ=−122.5. LC-MS (ESI+) Found: $[M+H]^+$, 631.2.

isobutyl 3-(1-((1-((4-(tert-butyl)phenyl)sulfonyl)piperidin-4-yl)methyl)-1H-1,2,3-triazol-4-yl)-5-fluoro-1H-indole-2-carboxylate (119) (Code AB938)

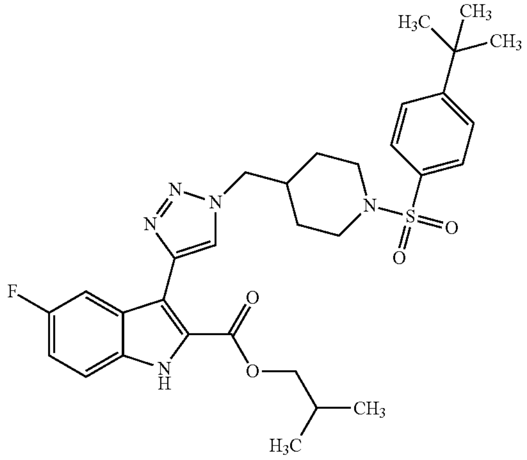 [SMILES: CC(C)COC(=O)c1[nH]c2ccc(F)cc2c1-c1cn(CC2CCN(S(=O)(=O)c3ccc(C(C)(C)C)cc3)CC2)nn1]

Prepared by general method G using alkyne 14f (60 mg, 0.23 mmol), azide 89a (82 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 119 as a pale yellow solid (102 mg, 74% yield). LC-MS (ESI+) Found: $[M+H]^+$, 596.3.

isobutyl 3-(1-((1-((2,3-dihydrobenzofuran-6-yl)sulfonyl)piperidin-4-yl)methyl)-1H-1,2,3-triazol-4-yl)-5-fluoro-1H-indole-2-carboxylate (120) (Code AB939)

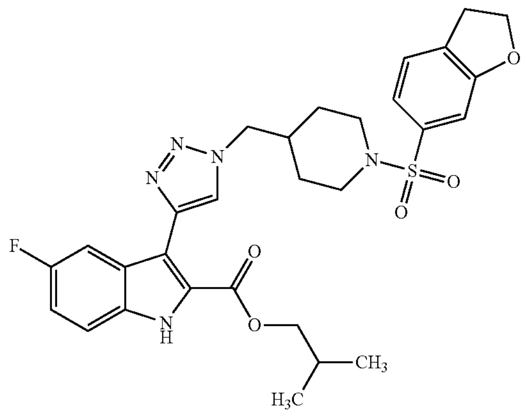 [SMILES: CC(C)COC(=O)c1[nH]c2ccc(F)cc2c1-c1cn(CC2CCN(S(=O)(=O)c3ccc4c(c3)OCC4)CC2)nn1]

Prepared by general method G using alkyne 14f (60 mg, 0.23 mmol), azide 89b (78 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 120 as a pale yellow solid (91 mg, 67% yield). LC-MS (ESI+) Found: $[M+H]^+$, 582.2.

isobutyl 3-(1-((1-(2-(((4-bromophenyl)methyl)sulfonamido)ethyl)piperidin-4-yl)methyl)-1H-1,2,3-triazol-4-yl)-5-fluoro-1H-indole-2-carboxylate (121) (Code AB1030)

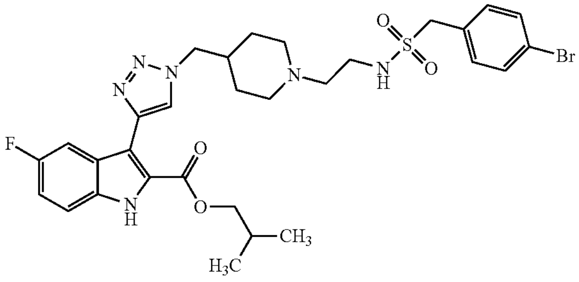 [SMILES: CC(C)COC(=O)c1[nH]c2ccc(F)cc2c1-c1cn(CC2CCN(CCNS(=O)(=O)Cc3ccc(Br)cc3)CC2)nn1]

Prepared by general method G using alkyne 14f (60 mg, 0.23 mmol), azide 5u (101 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 121 as a white solid (86 mg, 55% yield). $^1H$ NMR (400 MHz, $d_6$-DMSO) δ=12.01 (s, 1H), 8.56 (s, 1H), 8.05 (dd, J=10.3, 2.6 Hz, 1H), 7.70-7.49 (m, 3H), 7.41-7.29 (m, 2H), 7.23 (td, J=9.1, 2.7 Hz, 1H), 6.95 (t, J=5.7 Hz, 1H), 4.55-4.32 (m, 4H), 4.12 (d, J=6.7 Hz, 2H), 3.01 (q, J=6.3 Hz, 2H), 2.85 (dt, J=11.8, 3.4 Hz, 2H), 2.33 (t, J=6.7 Hz, 2H), 2.04 (hept, J=6.8 Hz, 1H), 1.88 (qd, J=9.8, 3.0 Hz, 3H), 1.65-1.50 (m, 2H), 1.27 (qd, J=12.1, 3.7 Hz, 2H), 0.95 (d, J=6.7 Hz, 6H). $^{13}C$ NMR (101 MHz, $d_6$-DMSO) δ=166.0 ($C_{quat}$), 161.0 ($C_{quat}$), 158.0 ($C_{quat}$), 157.5 (d, J=233.6 Hz, $C_{quat}$), 140.2 ($C_{quat}$), 139.6 ($C_{quat}$), 134.0 ($C_{quat}$), 133.1 ($C_{quat}$), 129.4 (CH), 126.9 ($C_{quat}$), 126.1 (d, J=10.8 Hz, $C_{quat}$), 124.7 (CH), 123.7 ($C_{quat}$), 114.4 (d, J=27.4 Hz, CH), 114.1 (d, J=10.9 Hz, CH), 111.8 (d, J=6.2 Hz, $C_{quat}$), 107.3 (d, J=23.3 Hz, CH), 70.6 ($CH_2$), 56.9 ($CH_2$), 54.4 ($CH_2$), 52.6 ($CH_2$), 40.2 ($CH_2$), 39.6 (CH), 36.5 (CH), 29.1 ($CH_2$), 27.4 (CH), 18.9 ($CH_3$), 11.4 ($CH_3$), 10.4 ($CH_3$). $^{19}F$ NMR (376 MHz, $d_6$-DMSO) δ=−122.4. LC-MS (ESI+) Found: $[M+H]^+$, 675.2.

isobutyl 3-(1-((1-(2-(((3-bromophenyl)methyl)sulfonamido)ethyl)piperidin-4-yl)methyl)-1H-1,2,3-triazol-4-yl)-5-fluoro-1H-indole-2-carboxylate (122) (Code AB1031)

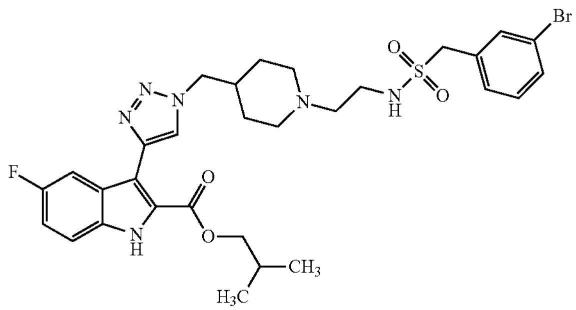 [SMILES: CC(C)COC(=O)c1[nH]c2ccc(F)cc2c1-c1cn(CC2CCN(CCNS(=O)(=O)Cc3cccc(Br)c3)CC2)nn1]

Prepared by general method G using alkyne 14f (60 mg, 0.23 mmol), azide 5v (101 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 122 as a white solid (93 mg, 60% yield). $^1H$ NMR (400 MHz, $d_6$-DMSO) δ=12.01 (s, 1H), 8.56 (s, 1H), 8.05 (dd, J=10.3, 2.6 Hz, 1H), 7.70-7.49 (m, 3H), 7.41-7.29 (m, 2H), 7.23 (td, J=9.1, 2.7 Hz, 1H), 6.95 (t, J=5.7 Hz, 1H), 4.55-4.32 (m, 4H), 4.12 (d, J=6.7 Hz, 2H), 3.01 (q, J=6.3 Hz, 2H), 2.85 (dt, J=11.8, 3.4 Hz, 2H), 2.33 (t, J=6.7 Hz, 2H), 2.04 (hept, J=6.8 Hz, 1H), 1.88 (qd, J=9.8, 3.0 Hz, 3H), 1.65-1.50 (m, 2H), 1.27 (qd, J=12.1, 3.7 Hz, 2H), 0.95 (d, J=6.7 Hz, 6H). $^{13}C$ NMR (101 MHz, $d_6$-DMSO) δ=161.0 ($C_{quat}$), 157.5 (d, J=234.3 Hz, $C_{quat}$), 140.2 ($C_{quat}$), 133.4 (CH), 133.1 ($C_{quat}$), 130.8 (CH), 130.4 ($C_{quat}$), 129.9 (CH), 126.1 (d, J=10.3 Hz, $C_{quat}$), 124.8 (CH), 123.8 ($C_{quat}$), 121.3 ($C_{quat}$), 114.4 (d, J=25.9 Hz, CH), 114.0 (d, J=10.2 Hz, CH), 111.9 (d, J=4.7 Hz, $C_{quat}$), 107.2 (d, J=24.7 Hz, CH), 70.6 ($CH_2$), 57.9 ($CH_2$), 56.5 ($CH_2$), 54.5 ($CH_2$), 52.7 ($CH_2$), 40.2 ($CH_2$), 36.6 (CH), 29.1 ($CH_2$), 27.4 (CH), 18.9 ($CH_3$). $^{19}F$ NMR (376 MHz, $d_6$-DMSO) δ=−122.4. LC-MS (ESI+) Found: $[M+H]^+$, 675.2.

isobutyl 3-(1-((1-(2-((4-(1H-pyrazol-4-yl)phenyl)sulfonamido)ethyl)piperidin-4-yl)methyl)-1H-1,2,3-triazol-4-yl)-5-fluoro-1H-indole-2-carboxylate (123) (Code AB1032)

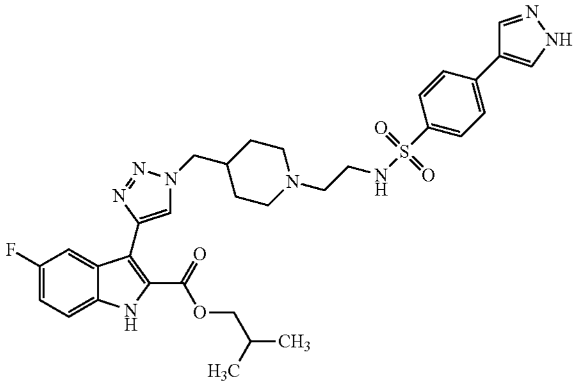 [SMILES: CC(C)COC(=O)c1[nH]c2ccc(F)cc2c1-c1cn(CC2CCN(CCNS(=O)(=O)c3ccc(-c4cn[nH]c4)cc3)CC2)nn1]

Prepared by general method G using alkyne 14f (60 mg, 0.23 mmol), azide 5w (95 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 95:5) to provide the title compound 123 as a pale yellow solid (84 mg, 56% yield). $^1H$ NMR (400 MHz, $d_6$-DMSO) δ=13.09 (s, 1H), 12.01 (s, 1H), 8.53 (s, 1H), 8.16-7.96 (m, 3H), 7.92-7.78 (m, 3H), 7.59-7.53 (m, 1H), 7.50 (d, J=15.0 Hz, 1H), 7.23 (td, J=9.1, 2.7 Hz, 1H), 6.84 (d, J=2.3 Hz, 1H), 4.32 (d, J=7.1 Hz, 2H), 4.11 (d, J=6.7 Hz, 3H), 2.86 (s, 2H), 2.75-2.67 (m, 2H), 2.29 (t, J=6.9 Hz, 2H), 2.02 (tt, J=13.4, 6.5 Hz, 1H), 1.95-1.76 (m, 2H), 1.46 (d, J=12.0 Hz, 2H), 1.29-1.18 (m, 2H), 0.94 (d, J=6.7 Hz, 6H). $^{19}F$ NMR (376 MHz, $d_6$-DMSO) δ=−122.5. LC-MS (ESI+) Found: $[M+H]^+$, 649.3.

isobutyl 3-(1-((1-(2-((4',4'-difluoro-2',3',4',5'-tetrahydro-[1,1'-biphenyl])-4-sulfonamido)ethyl)piperidin-4-yl)methyl)-1H-1,2,3-triazol-4-yl)-5-fluoro-1H-indole-2-carboxylate (124) (Code AB1070)

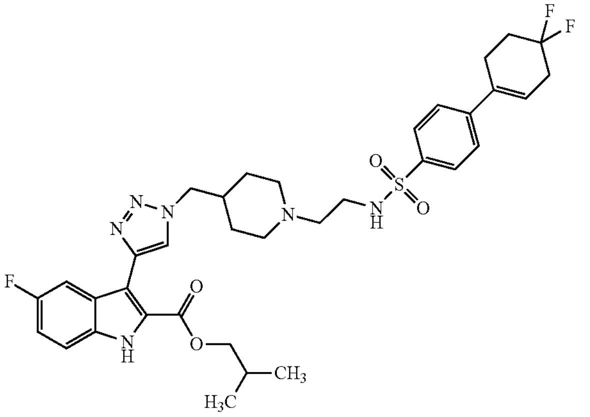 [SMILES: CC(C)COC(=O)c1[nH]c2ccc(F)cc2c1-c1cn(CC2CCN(CCNS(=O)(=O)c3ccc(C4=CCC(F)(F)CC4)cc3)CC2)nn1]

Prepared by general method G using alkyne 14f (60 mg, 0.23 mmol), azide 5x (107 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 124 as a pale yellow solid (105 mg, 65% yield). $^{1}$H NMR (400 MHz, $d_6$-DMSO) δ=12.01 (s, 1H), 8.54 (s, 1H), 8.02 (dd, J=10.3, 2.6 Hz, 1H), 7.79-7.72 (m, 2H), 7.64 (dq, J=8.7, 2.1 Hz, 2H), 7.54 (dd, J=9.0, 4.7 Hz, 1H), 7.48 (d, J=5.7 Hz, 1H), 7.23 (td, J=9.1, 2.7 Hz, 1H), 6.29-6.06 (m, 1H), 4.33 (d, J=7.0 Hz, 2H), 4.12 (d, J=6.7 Hz, 2H), 2.92-2.75 (m, 4H), 2.75-2.64 (in, 411), 2.28 (td, J=7.0, 3.0 Hz, 2H), 2.18 (tt, J=13.7, 6.6 Hz, 2H), 2.11-2.00 (m, 1H), 1.82 (t, J=11.0 Hz, 3H), 1.46 (d, J=12.0 Hz, 2H), 1.25-1.18 (m, 2H), 0.94 (d, J=6.7 Hz, 6H). LC-MS (ESI+) Found: $[M+H]^+$, 699.3.

isobutyl 5-fluoro-3-(1-((1-(2-((4-(furan-3-yl)phenyl)sulfonamido)ethyl)piperidin-4-yl)methyl)-1H-1,2,3-triazol-4-yl)-1H-indole-2-carboxylate (125) (Code AB1071)

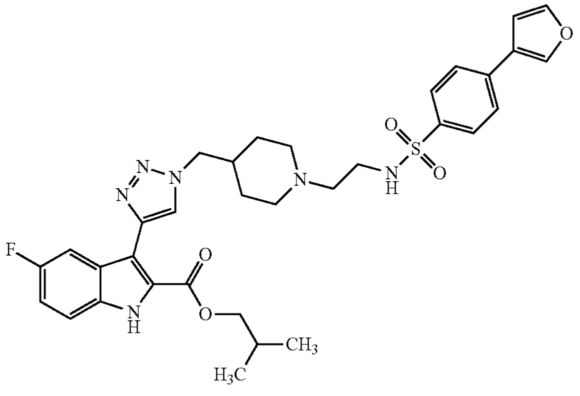 [SMILES: CC(C)COC(=O)c1[nH]c2ccc(F)cc2c1-c1cn(CC2CCN(CCNS(=O)(=O)c3ccc(-c4ccoc4)cc3)CC2)nn1]

Prepared by general method G using alkyne 14f (60 mg, 0.23 mmol), azide 5y (95 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 125 as a white solid (102 mg, 68% yield). $^{1}$H NMR (400 MHz, $d_6$-DMSO) δ=12.01 (s, 1H), 8.54 (s, 1H), 8.33 (t, J=1.2 Hz, 1H), 8.03 (dd, J=10.2, 2.6 Hz, 1H), 7.94-7.72 (m, 5H), 7.54 (dd, J=9.0, 4.7 Hz, 1H), 7.51-7.44 (m, 1H), 7.23 (td, J=9.1, 2.6 Hz, 1H), 7.04 (dd, J=2.0, 0.9 Hz, 1H), 4.33 (d, J=7.0 Hz, 2H), 4.11 (d, J=6.7 Hz, 2H), 2.85 (q, J=6.5 Hz, 2H), 2.71 (d, J=11.2 Hz, 2H), 2.29 (t, J=6.9 Hz, 2H), 2.02 (dt, J=13.4, 6.7 Hz, 1H), 1.83 (t, J=10.9 Hz, 3H), 1.46 (d, J=12.6 Hz, 2H), 1.30-1.15 (m, 2H), 0.94 (d, J=6.7 Hz, 6H). $^{13}$C NMR (101 MHz, $d_6$-DMSO) δ=161.0 ($C_{quat}$), 157.5 (d, J=233.6 Hz, $C_{quat}$), 146.8 ($C_{quat}$), 144.8 (CH), 140.8 (CH), 140.2 ($C_{quat}$), 138.6 ($C_{quat}$), 135.9 ($C_{quat}$), 133.1 (CH), 127.1 (CH), 125.9 (CH), 126.0 (d, J=10.2 Hz, $C_{quat}$), 124.8 (CH), 124.7 ($C_{quat}$), 123.7 ($C_{quat}$), 114.4 (d, J=25.8 Hz, CH), 114.0 (d, J=9.2 Hz, CH), 111.9 (d, J=5.7 Hz, $C_{quat}$), 107.4 (d, J=25.5 Hz, CH), 70.6 ($CH_2$), 57.0 ($CH_2$), 54.4 ($CH_2$), 52.6 ($CH_2$), 40.2 ($CH_2$), 29.0 ($CH_2$), 27.3 (CH), 18.9 ($CH_3$). $^{19}$F NMR (376 MHz, $d_6$-DMSO) δ=−122.3. LC-MS (ESI+) Found: $[M+H]^+$, 649.2.

isobutyl 3-(1-((1-(2-((3,4-dihydro-2H-benzo[b][1,4]dioxepine)-7-sulfonamido)ethyl)piperidin-4-yl)methyl)-1H-1,2,3-triazol-4-yl)-5-fluoro-1H-indole-2-carboxylate (126) (Code AB1072)

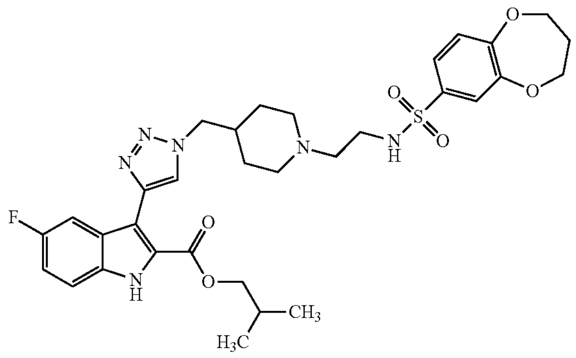 [SMILES: CC(C)COC(=O)c1[nH]c2ccc(F)cc2c1-c1cn(CC2CCN(CCNS(=O)(=O)c3ccc4c(c3)OCCCO4)CC2)nn1]

Prepared by general method G using alkyne 14f (60 mg, 0.23 mmol), azide 5z (96 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 126 as a white solid (96 mg, 63% yield). $^{1}$H NMR (400 MHz, $d_6$-DMSO) δ=12.01 (s, 1H), 8.55 (s, 1H), 8.03 (dd, J=10.3, 2.6 Hz, 1H), 7.54 (dd, J=9.0, 4.7 Hz, 1H), 7.49-7.31 (m, 3H), 7.27-7.21 (m, 1H), 7.15-7.02 (m, 1H), 4.34 (d, J=7.0 Hz, 2H), 4.21 (dt, J=7.7, 5.5 Hz, 4H), 4.12 (d, J=6.7 Hz, 2H), 2.82 (q, J=6.4 Hz, 2H), 2.76-2.65 (m, 2H), 2.28 (d, J=6.9 Hz, 2H), 2.21-2.10 (m, 2H), 2.07-1.97 (m, 1H), 1.93-1.73 (m, 3H), 1.48 (d, J=12.0 Hz, 2H), 1.33-1.18 (m, 2H), 0.95 (d, J=6.7 Hz, 6H). $^{19}$F NMR (376 MHz, $d_6$-DMSO) δ=−122.4. LC-MS (ESI+) Found: $[M+H]^+$, 655.3.

isobutyl 5-fluoro-3-(1-((1-(2-((4-(2-(pyrrolidin-1-yl) pyridin-3-yl)phenyl)sulfonamido)ethyl)piperidin-4-yl)methyl)-1H-1,2,3-triazol-4-yl)-1H-indole-2-carboxylate (127) (Code AB1073)

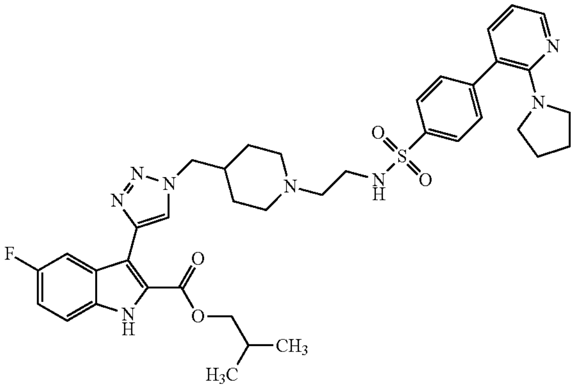 [SMILES: CC(C)COC(=O)c1[nH]c2ccc(F)cc2c1-c1cn(CC2CCN(CCNS(=O)(=O)c3ccc(-c4cccnc4N4CCCC4)cc3)CC2)nn1]

Prepared by general method G using alkyne 14f (60 mg, 0.23 mmol), azide 5Aa (114 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:5) to provide the title compound 127 as a pale yellow solid (76 mg, 45% yield). LC-MS (ESI+) Found: $[M+H]^+$, 729.3.

isobutyl 3-(1-((1-(2-((4-(3,6-dihydro-2H-pyran-4-yl) phenyl)sulfonamido)ethyl)piperidin-4-yl)methyl)-1H-1,2,3-triazol-4-yl)-5-fluoro-1H-indole-2-carboxylate (128) (Code AB1074)

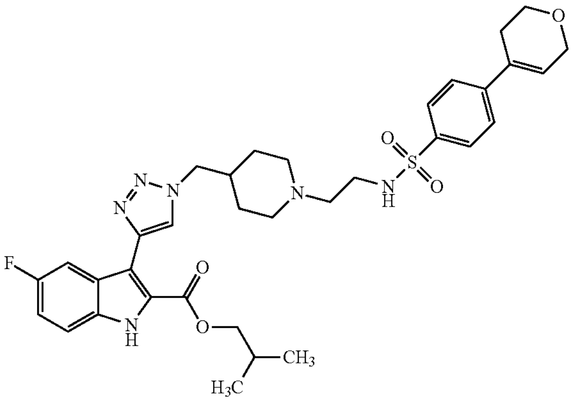 [SMILES: CC(C)COC(=O)c1[nH]c2ccc(F)cc2c1-c1cn(CC2CCN(CCNS(=O)(=O)c3ccc(C4=CCOCC4)cc3)CC2)nn1]

Prepared by general method G using alkyne 14f (60 mg, 0.23 mmol), azide 5Ab (98 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 128 as a white solid (103 mg, 67% yield). $^1H$ NMR (400 MHz, $d_6$-DMSO) δ=12.01 (s, 1H), 8.54 (s, 1H), 8.02 (dd, J=10.3, 2.7 Hz, 1H), 7.80-7.68 (m, 2H), 7.71-7.60 (m, 2H), 7.54 (dd, J=9.0, 4.7 Hz, 1H), 7.46 (s, 1H), 7.23 (td, J=9.1, 2.7 Hz, 1H), 6.43 (dt, J=3.1, 1.6 Hz, 1H), 4.33 (d, J=6.9 Hz, 2H), 4.23 (q, J=2.8 Hz, 2H), 4.12 (d, J=6.6 Hz, 2H), 3.81 (t, J=5.5 Hz, 2H), 2.83 (s, 2H), 2.70 (s, 2H), 2.28 (t, J=6.9 Hz, 2H), 2.10-1.94 (m, 3H), 1.82 (t, J=11.2 Hz, 3H), 1.46 (d, J=12.4 Hz, 2H), 1.29 (d, J=6.1 Hz, 2H), 0.98-0.86 (m, 6H). $^{19}F$ NMR (376 MHz, $d_6$-DMSO) δ=−122.5. LC-MS (ESI+) Found: $[M+H]^+$, 665.3.

isobutyl 5-fluoro-3-(1-((1-(2-((2'-(morpholinomethyl)-[1,1'-biphenyl])-4-sulfonamido)ethyl)piperidin-4-yl)methyl)-1H-1,2,3-triazol-4-yl)-1H-indole-2-carboxylate (129) (Code AB1075)

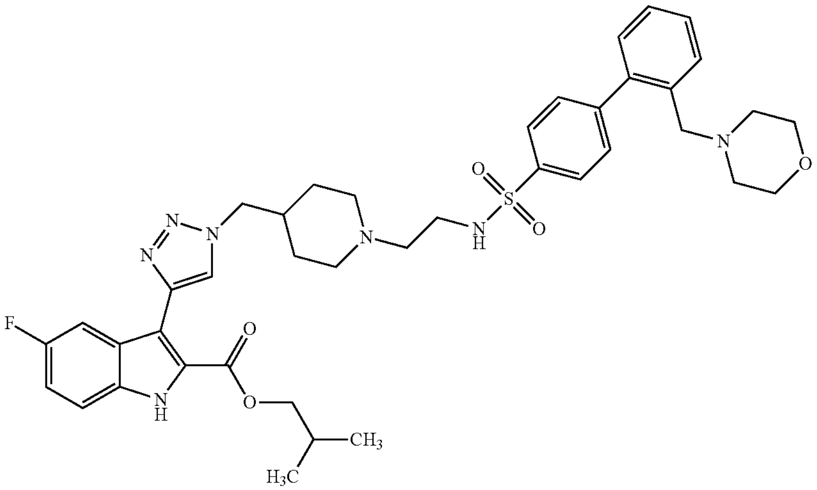 [SMILES: CC(C)COC(=O)c1[nH]c2ccc(F)cc2c1-c1cn(CC2CCN(CCNS(=O)(=O)c3ccc(-c4ccccc4CN4CCOCC4)cc3)CC2)nn1]

Prepared by general method G using alkyne 14f (45 mg, 0.17 mmol), azide 5Ac (91 mg, 0.18 mmol), 2M aqueous of sodium ascorbate (300 μL, 0.60 mmol), 15% aqueous of copper(II) sulfate pentahydrate (250 μL, 0.15 mmol) and tetrahydrofuran-tert-butanol (430 μL). The crude product was purified chromatographically on silica gel (eluting gradient dichloromethane-methanol 98:2 to 95:5) to provide the title compound 129 as a pale yellow solid (54 mg, 41% yield). $^1$H NMR (400 MHz, $d_6$-DMSO) δ=12.00 (s, 1H), 8.54 (s, 1H), 8.04 (dd, J=10.3, 2.6 Hz, 1H), 7.87-7.80 (m, 2H), 7.66-7.59 (m, 2H), 7.54 (dt, J=9.6, 4.8 Hz, 2H), 7.48-7.44 (m, 1H), 7.40-7.32 (m, 2H), 7.28-7.19 (m, 2H), 4.34 (d, J=7.0 Hz, 2H), 4.10 (d, J=6.7 Hz, 2H), 3.44 (t, J=4.6 Hz, 6H), 2.97-2.84 (m, 2H), 2.82-2.67 (m, 2H), 2.29 (t, J=7.0 Hz, 2H), 2.19 (q, J=6.7 Hz, 4H), 2.02 (dt, J=13.4, 6.7 Hz, 1H), 1.83 (t, J=11.4 Hz, 3H), 1.53-1.40 (m, 2H), 1.24 (td, J=11.9, 3.4 Hz, 2H), 0.94 (d, J=6.7 Hz, 6H). $^{19}$F NMR (376 MHz, $d_6$-DMSO) δ=−122.4. LC-MS (ESI+) Found: $[M+H]^+$, 758.3.

isobutyl 3-(1-((1-(2-((2'-cyano-[1,1'-biphenyl])-4-sulfonamido)ethyl)piperidin-4-yl)methyl)-1H-1,2,3-triazol-4-yl)-5-fluoro-1H-indole-2-carboxylate (130) (Code AB1076)

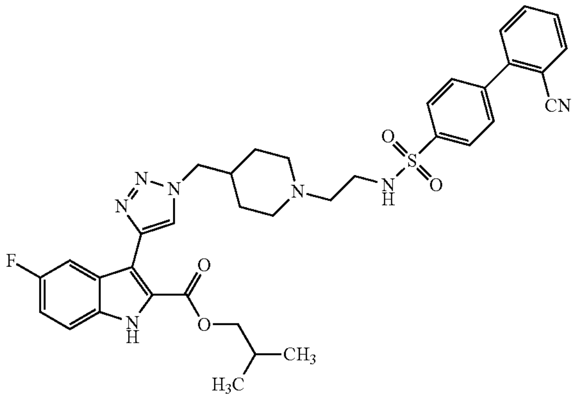 [SMILES: CC(C)COC(=O)c1[nH]c2ccc(F)cc2c1-c1cn(CC2CCN(CCNS(=O)(=O)c3ccc(-c4ccccc4C#N)cc3)CC2)nn1]

Prepared by general method G using alkyne 14f (60 mg, 0.23 mmol), azide 5Ad (103 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 130 as a white solid (107 mg, 68% yield). $^1$H NMR (400 MHz, $d_6$-DMSO) δ=12.00 (s, 1H), 8.53 (s, 1H), 8.14-7.89 (m, 4H), 7.88-7.73 (m, 3H), 7.74-7.59 (m, 3H), 7.54 (dd, J=9.0, 4.7 Hz, 1H), 7.22 (td, J=9.1, 2.7 Hz, 1H), 4.33 (d, J=7.0 Hz, 2H), 4.11 (d, J=6.7 Hz, 2H), 2.93 (t, J=7.0 Hz, 2H), 2.72 (dt, J=11.5, 3.2 Hz, 2H), 2.30 (t, J=6.9 Hz, 2H), 2.02 (hept, J=6.8 Hz, 1H), 1.94-1.76 (m, 3H), 1.56-1.41 (m, 2H), 1.32-1.21 (m, 2H), 0.94 (d, J=6.7 Hz, 6H). $^{19}$F NMR (376 MHz, $d_6$-DMSO) δ=−122.4. LC-MS (ESI+) Found: $[M+H]^+$, 683.3.

isobutyl 3-(1-((1-(2-((4-(3,5-dimethylisoxazol-4-yl)phenyl)sulfonamido)ethyl)piperidin-4-yl)methyl)-1H-1,2,3-triazol-4-yl)-5-fluoro-1H-indole-2-carboxylate (131) (Code AB1130)

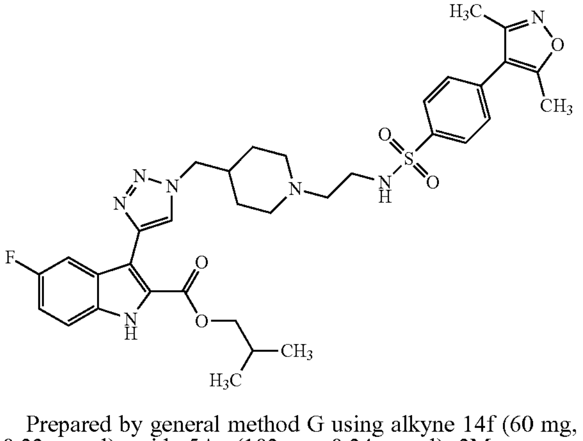

Prepared by general method G using alkyne 14f (60 mg, 0.23 mmol), azide 5Ae (102 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 131 as a pale yellow solid (95 mg, 61% yield). $^1$H NMR (400 MHz, $d_6$-DMSO) δ=12.00 (s, 1H), 8.54 (s, 1H), 8.04 (dd, J=10.3, 2.6 Hz, 1H), 7.93-7.84 (in, 211), 7.70-7.51 (m, 4H), 7.22 (td, J=9.1, 2.7 Hz, 1H), 4.34 (d, J=6.9 Hz, 2H), 4.11 (d, J=6.7 Hz, 2H), 2.91 (d, J=7.6 Hz, 2H), 2.70 (dt, J=12.2, 3.4 Hz, 2H), 2.42 (s, 3H), 2.29 (t, J=6.9 Hz, 2H), 2.24 (s, 3H), 2.09-1.98 (m, 1H), 1.89-1.75 (m, 3H), 1.56-1.43 (m, 2H), 1.21 (qd, J=11.8, 3.3 Hz, 2H), 0.94 (d, J=6.7 Hz, 6H). $^{13}$C NMR (101 MHz, $d_6$-DMSO) δ=168.0 ($C_{quat}$), 161.0 ($C_{quat}$), 158.0 ($C_{quat}$), 157.4 (d, J=234.4 Hz, $C_{quat}$), 140.2 ($C_{quat}$), 139.6 ($C_{quat}$), 134.0 ($C_{quat}$), 133.1 ($C_{quat}$), 129.4 (CH), 127.0 (CH), 126.0 (d, J=11.2 Hz, $C_{quat}$), 124.8 (CH), 123.8 ($C_{quat}$), 114.9 ($C_{quat}$), 114.4 (d, J=26.3 Hz, CH), 114.0 (d, J=9.6 Hz, CH), 111.8 (d, J=5.5 Hz, $C_{quat}$), 107.4 (d, J=23.4 Hz, CH), 70.6 ($CH_2$), 57.0 ($CH_2$), 54.4 ($CH_2$), 52.6 ($CH_2$), 40.2 ($CH_2$), 29.0 ($CH_2$), 27.4 (CH), 18.9 ($CH_3$), 11.4 ($CH_3$), 10.5 ($CH_3$). $^{19}$F NMR (376 MHz, $d_6$-DMSO) δ=−122.5. LC-MS (ESI+) Found: $[M+H]^+$, 678.3.

isobutyl 3-(1-((1-(2-((4-(2-chloropyridin-3-yl)phenyl)sulfonamido)ethyl)piperidin-4-yl)methyl)-1H-1,2,3-triazol-4-yl)-5-fluoro-1H-indole-2-carboxylate (132) (Code AB1133)

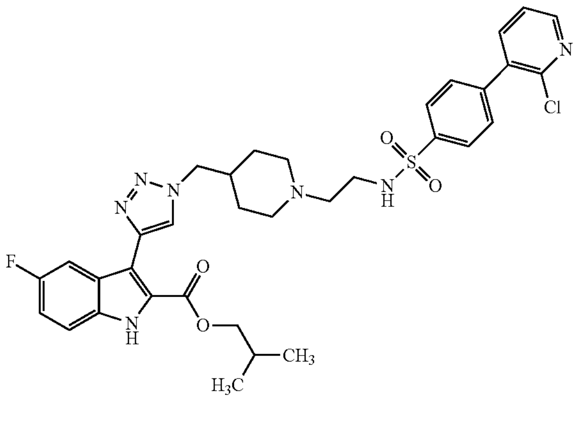 [SMILES: CC(C)COC(=O)c1[nH]c2ccc(F)cc2c1-c1cn(CC2CCN(CCNS(=O)(=O)c3ccc(-c4cccnc4Cl)cc3)CC2)nn1]

Prepared by general method G using alkyne 14f (60 mg, 0.23 mmol), azide 5Af (106 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 132 as a pale yellow solid (104 mg, 65% yield). $^1$H NMR (400 MHz, $d_6$-DMSO) δ=12.01 (d, J=2.1 Hz, 1H), 8.54 (d, J=0.9 Hz, 1H), 8.47 (dt, J=4.8, 2.0 Hz, 1H), 8.03 (dd, J=10.2, 2.6 Hz, 1H), 7.95-7.83 (m, 3H), 7.83-7.68 (m, 2H), 7.63 (d, J=10.4 Hz, 1H), 7.58-7.46 (m, 2H), 7.23 (td, J=9.1, 2.6 Hz, 1H), 4.33 (t, J=7.2 Hz, 2H), 4.11 (dd, J=6.7, 2.3 Hz, 2H), 2.91 (d, J=6.6 Hz, 2H), 2.71 (dd, J=10.7, 5.4 Hz, 2H), 2.29 (q, J=6.6 Hz, 2H), 2.02 (dt, J=13.4, 6.7 Hz, 1H), 1.90-1.68 (m, 3H), 1.55-1.43 (m, 2H), 1.20 (pd, J=13.0, 6.0 Hz, 2H), 0.94 (d, J=6.7 Hz, 6H). $^{13}$C NMR (101 MHz, $d_6$-DMSO) δ=161.0 ($C_{quat}$), 157.5 (d, J=233.0 Hz, $C_{quat}$), 149.4 (CH), 148.1 ($C_{quat}$), 140.9 ($C_{quat}$), 140.4 (CH), 140.2 ($C_{quat}$), 137.8 ($C_{quat}$), 134.8 ($C_{quat}$), 133.1 (CH), 130.1 (CH), 129.5 (CH), 127.1 (CH), 126.0 (d, J=10.8 Hz, $C_{quat}$), 126.5 (CH), 124.7 (CH), 123.6 (CH), 123.7 ($C_{quat}$), 114.4 (d, J=24.4 Hz, CH), 114.0 (d, J=11.5 Hz, CH), 111.8 (d, J=5.7 Hz, $C_{quat}$) 107.2 (d, J=27.2 Hz, CH), 70.6 ($CH_2$), 56.9 ($CH_2$), 54.4 ($CH_2$), 52.6 ($CH_2$), 44.1 ($CH_2$), 40.3 ($CH_2$), 27.3 (CH), 18.9 ($CH_3$). $^{19}$F NMR (376 MHz, $d_6$-DMSO) δ=−122.4. LC-MS (ESI+) Found: $[M+H]^+$, 694.2.

isobutyl 3-(1-((1-(2-((4'-cyano-[1,1'-biphenyl])-4-sulfonamido)ethyl)piperidin-4-yl)methyl)-1H-1,2,3-triazol-4-yl)-5-fluoro-1H-indole-2-carboxylate (133) (Code AB1134)

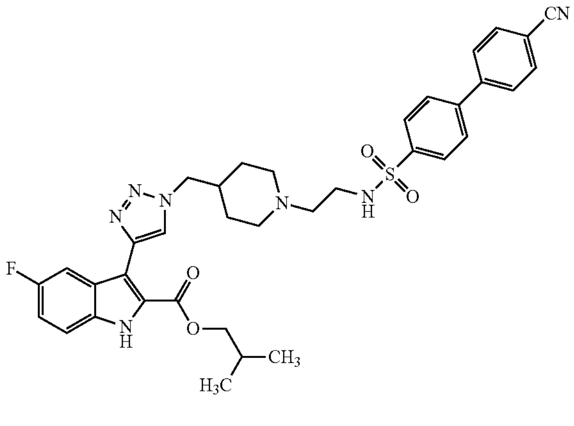 [SMILES: CC(C)COC(=O)c1[nH]c2ccc(F)cc2c1-c1cn(CC2CCN(CCNS(=O)(=O)c3ccc(-c4ccc(C#N)cc4)cc3)CC2)nn1]

Prepared by general method G using alkyne 14f (60 mg, 0.23 mmol), azide 5Ag (103 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 133 as a white solid (71 mg, 45% yield). $^1$H NMR (400 MHz, $d_6$-DMSO) δ=12.01 (s, 1H), 8.54 (s, 1H), 8.02 (dd, J=10.2, 2.6 Hz, 1H), 7.99-7.94 (m, 5H), 7.95-7.88 (m, 3H), 7.62 (s, 1H), 7.54 (dd, J=9.0, 4.7 Hz, 1H), 7.23 (td, J=9.1, 2.6 Hz, 1H), 4.33 (d, J=7.0 Hz, 2H), 4.11 (d, J=6.6 Hz, 2H), 2.88 (s, 2H), 2.71 (d, J=11.3 Hz, 3H), 2.29 (d, J=6.7 Hz, 2H), 2.10-1.95 (m, 1H), 1.89-1.69 (m, 2H), 1.46 (d, J=11.6 Hz, 2H), 1.38-1.14 (m, 2H), 0.93 (d, J=6.7 Hz, 6H). $^{19}$F NMR (376 MHz, $d_6$-DMSO) δ=−122.4. LC-MS (ESI+) Found: $[M+H]^+$, 684.3.

isobutyl 5-fluoro-3-(1-((1-(2-((2'-methoxy-[1,1'-biphenyl])-4-sulfonamido)ethyl)piperidin-4-yl)methyl)-1H-1,2,3-triazol-4-yl)-1H-indole-2-carboxylate (134) (Code AB1205)

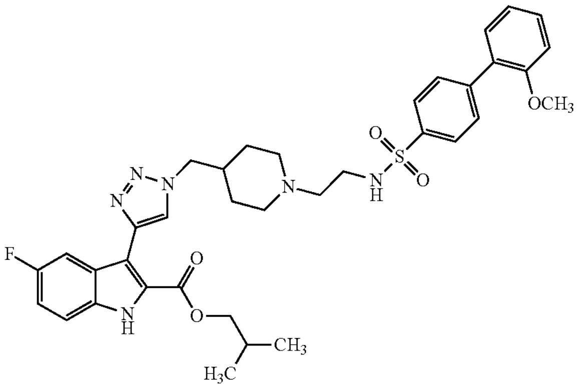 [SMILES: COc1ccccc1-c1ccc(S(=O)(=O)NCCN2CCC(Cn3cc(-c4c(C(=O)OCC(C)C)[nH]c5ccc(F)cc45)nn3)CC2)cc1]

Prepared by general method G using alkyne 14f (60 mg, 0.23 mmol), azide 5Ah (104 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 134 as a pale yellow solid (112 mg, 70% yield). $^1$H NMR (400 MHz, $d_6$-DMSO) δ=11.56 (s, 1H), 8.09 (s, 1H), 7.58 (dd, J=10.3, 2.6 Hz, 1H), 7.46-7.34 (m, 2H), 7.31-7.18 (m, 2H), 7.09 (dd, J=9.0, 4.7 Hz, 2H), 6.93 (ddd, J=8.7, 7.4, 1.8 Hz, 1H), 6.88 (dd, J=7.6, 1.7 Hz, 1H), 6.78 (td, J=9.1, 2.6 Hz, 1H), 6.68 (dd, J=8.4, 1.0 Hz, 1H), 6.59 (td, J=7.4, 1.1 Hz, 1H), 3.89 (d, J=7.0 Hz, 2H), 3.66 (d, J=6.7 Hz, 2H), 2.88 (s, 3H), 2.44 (q, J=6.8 Hz, 2H), 2.26 (dd, J=9.1, 5.9 Hz, 2H), 1.86 (t, J=6.9 Hz, 2H), 1.57 (hept, J=6.7 Hz, 1H), 1.50-1.31 (m, 3H), 1.11-0.97 (m, 2H), 0.78 (qd, J=12.0, 3.8 Hz, 2H), 0.49 (d, J=6.7 Hz, 6H). $^{19}$F NMR (376 MHz, $d_6$-DMSO) δ=−122.4. LC-MS (ESI+) Found: $[M+H]^+$, 698.3.

isobutyl 3-(1-((1-(2-((2',6'-dimethoxy-[1,1'-biphenyl])-4-sulfonamido)ethyl)piperidin-4-yl)methyl)-1H-1,2,3-triazol-4-yl)-5-fluoro-1H-indole-2-carboxylate (135) (Code AB1206)

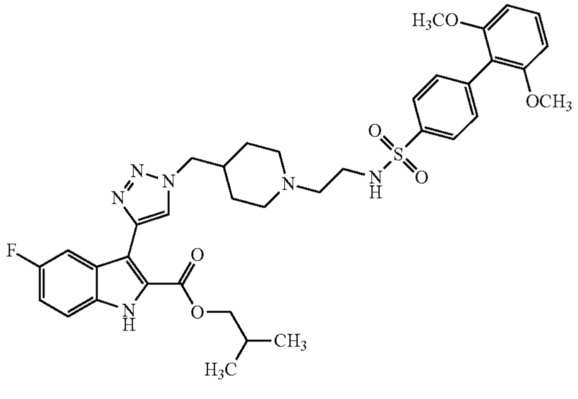 [SMILES: COc1cccc(OC)c1-c1ccc(S(=O)(=O)NCCN2CCC(Cn3cc(-c4c(C(=O)OCC(C)C)[nH]c5ccc(F)cc45)nn3)CC2)cc1]

Prepared by general method G using alkyne 14f (60 mg, 0.23 mmol), azide 5Ai (112 mg, 0.24 nmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 135 as a pale yellow solid (114 mg, 69% yield). $^1$H NMR (400 MHz, $d_6$-DMSO) δ=12.01 (s, 1H), 8.55 (s, 1H), 8.04 (dd, J=10.3, 2.6 Hz, 1H), 7.81-7.74 (m, 2H), 7.55 (dd, J=9.0, 4.7 Hz, 1H), 7.49 (s, 1H), 7.45-7.38 (m, 2H), 7.32 (t, J=8.4 Hz, 1H), 7.23 (td, J=9.1, 2.7 Hz, 1H), 6.74 (d, J=8.4 Hz, 2H), 4.34 (d, J=6.9 Hz, 2H), 4.11 (d, J=6.7 Hz, 2H), 3.65 (s, 6H), 2.93 (d, J=7.4 Hz, 2H), 2.86-2.72 (m, 2H), 2.32 (q, J=7.2 Hz, 2H), 2.15-1.95 (m, 1H), 1.84 (q, J=9.3 Hz, 3H), 1.63-1.39 (m, 2H), 1.38-1.16 (m, 2H), 0.94 (d, J=6.7 Hz, 6H). $^{13}$C NMR (101 MHz, $d_6$-DMSO) δ=161.0 ($C_{quat}$), 157.5 (d, J=233.9 Hz, $C_{quat}$), 156.9 ($C_{quat}$), 140.2 ($C_{quat}$), 138.5 ($C_{quat}$), 133.1 ($C_{quat}$), 131.5 (CH), 126.2 (d, J=10.0 Hz, $C_{quat}$), 129.7 (CH), 125.7 (CH), 124.8 (CH), 123.8 ($C_{quat}$), 117.1 ($C_{quat}$), 114.4 (d, =25.8 Hz, CH), 114.0 (d, J=9.6 Hz, CH), 107.4 (d, J=23.8 Hz, CH), 111.8 (d, J=5.6 Hz, $C_{quat}$), 70.6 ($CH_2$), 57.0 ($CH_2$), 55.7 (CH), 54.5 ($CH_2$), 52.6 ($CH_2$), 40.3 ($CH_2$), 29.0 ($CH_2$), 27.4 ($CH_3$), 36.6 (CH), 18.9 ($CH_3$). $^{19}$F NMR (376 MHz, $d_6$-DMSO) δ=−122.4. LC-MS (ESI+) Found: $[M+H]^+$, 719.3.

isobutyl 5-fluoro-3-(1-((1-(2-((4-(2-fluoropyridin-3-yl)phenyl)sulfonamido)ethyl)piperidin-4-yl)methyl)-1H-1,2,3-triazol-4-yl)-1H-indole-2-carboxylate (136) (Code AB1207)

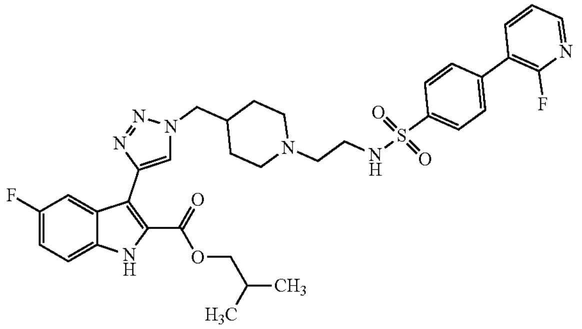 [SMILES: CC(C)COC(=O)c1[nH]c2ccc(F)cc2c1-c1cn(CC2CCN(CCNS(=O)(=O)c3ccc(-c4cccnc4F)cc3)CC2)nn1]

Prepared by general method G using alkyne 14f (60 mg, 0.23 mmol), azide 5Aj (102 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 136 as a pale yellow solid (91 mg, 58% yield). $^1$H NMR (400 MHz, $d_6$-DMSO) δ=12.00 (s, 1H), 8.54 (s, 1H), 8.29 (dt, J=4.9, 1.6 Hz, 1H), 8.20-8.09 (m, 1H), 8.03 (dd, J=10.3, 2.6 Hz, 1H), 7.95-7.89 (m, 2H), 7.82 (dq, J=8.5, 2.0 Hz, 2H), 7.63 (s, 111), 7.57-7.51 (m, 1H), 7.50 (td, J=5.0, 2.4 Hz, 1H), 7.22 (td, J=9.1, 2.7 Hz, 1H), 4.33 (d, J=7.0 Hz, 2H), 4.11 (d, J=6.7 Hz, 2H), 2.90 (t, J=6.9 Hz, 2H), 2.72 (dd, J=11.0, 3.6 Hz, 2H), 2.31 (t, J=6.9 Hz, 2H), 2.01 (dh, J=12.9, 6.5 Hz, 1H), 1.83 (t, J=10.8 Hz, 3H), 1.53-1.42 (m, 2H), 1.21 (h, J=8.4 Hz, 2H), 0.93 (d, J=6.7 Hz, 6H). $^{13}$C NMR (101 MHz, $d_6$-DMSO) δ=161.0 ($C_{quat}$), 158.3 ($C_{quat}$), 157.5 (d, J=233.4 Hz, $C_{quat}$), 147.5 ($C_{quat}$), 147.3 ($C_{quat}$), 140.5 ($C_{quat}$), 140.2 ($C_{quat}$), 137.1 ($C_{quat}$), 133.1 ($C_{quat}$), 141.7 (CH), 129.7 (CH), 129.6 (CH), 126.9 (CH), 126.0 (d, J=11.0 Hz, $C_{quat}$), 124.8 (CH), 122.8 (CH), 122.7 (CH), 114.4 (d, J=28.1 Hz, CH), 114.0 (d, J=10.4 Hz, CH), 111.9 (d, J=11.6 Hz, $C_{quat}$), 107.2 (d, J=23.9 Hz, CH), 70.6 ($CH_2$), 55.8 ($CH_2$), 54.4 ($CH_2$), 52.6 ($CH_2$), 40.3 ($CH_2$), 29.0 ($CH_2$), 27.3 (CH), 18.9 ($CH_3$). LC-MS (ESI+) Found: $[M+H]^+$, 678.3.

isobutyl 3-(1-((1-(2-((2',6'-difluoro-[1,1'-biphenyl])-4-sulfonamido)ethyl)piperidin-4-yl)methyl)-1H-1,2,3-triazol-4-yl)-5-fluoro-1H-indole-2-carboxylate (137) (Code AB1208)

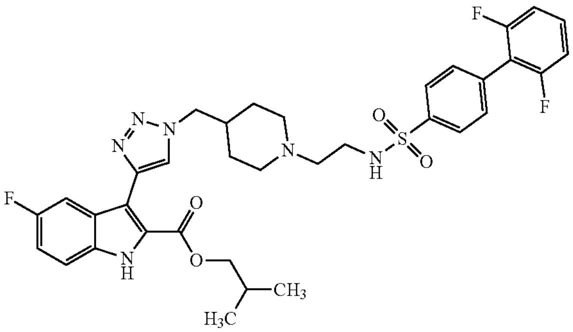 [SMILES: CC(C)COC(=O)c1[nH]c2ccc(F)cc2c1-c1cn(CC2CCN(CCNS(=O)(=O)c3ccc(-c4c(F)cccc4F)cc3)CC2)nn1]

Prepared by general method G using alkyne 14f (60 mg, 0.23 mmol), azide 5Ak (106 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 137 as a pale yellow solid (107 mg, 66% yield). $^1$H NMR (400 MHz, $d_6$-DMSO) δ=12.01 (d, J=2.3 Hz, 1H), 8.54 (d, J=5.3 Hz, 1H), 8.04 (dt, J=10.3, 2.3 Hz, 1H), 7.96-7.90 (m, 1H), 7.83-7.78 (m, 1H), 7.76-7.71 (m, 1H), 7.71-7.65 (m, 1H), 7.63 (s, 1H), 7.59-7.46 (m, 2H), 7.29-7.18 (m, 2H), 4.33 (dd, J=7.0, 2.7 Hz, 2H), 4.11 (dd, J=6.7, 5.2 Hz, 2H), 3.05-2.82 (m, 3H), 2.77-2.66 (m, 2H), 2.28 (q, J=7.0 Hz, 2H), 2.02 (dd, J=6.5, 3.7 Hz, 1H), 1.91-1.70 (m, 3H), 1.58-1.45 (m, 2H), 1.21 (tdd, J=12.2, 9.7, 4.9 Hz, 2H), 0.94 (dd, J=6.7, 3.5 Hz, 6H). $^{13}$C NMR (101 MHz, $d_6$-DMSO) δ=161.0 ($C_{quat}$), 157.9 ($C_{quat}$), 157.5 (d, J=233.7 Hz, $C_{quat}$), 140.7 ($C_{quat}$), 140.2 ($C_{quat}$), 140.0 ($C_{quat}$), 133.1 ($C_{quat}$), 132.5 ($C_{quat}$), 132.2 (CH), 130.8 ($C_{quat}$), 130.9 (CH), 128.5 (CH), 126.6 (CH), 126.0 (d, J=10.6 Hz, $C_{quat}$), 124.8 (CH), 114.4 (d, J=27.3 Hz, CH), 114.0 (d, J=10.4 Hz, CH), 112.3 (CH), 112.0 (CH), 111.9 (d, J=5.3 Hz, $C_{quat}$), 107.2 (d, J=23.4 Hz, CH), 70.6 ($CH_2$), 57.0 ($CH_2$), 54.5 ($CH_2$), 52.6 ($CH_2$), 40.2 ($CH_2$), 29.0 ($CH_2$), 27.4 (CH), 18.9 ($CH_3$). LC-MS (ESI+) Found: $[M+H]^+$, 695.2.

isobutyl 3-(1-((1-(2-((2'-(dimethylamino)-[1,1'-biphenyl])-4-sulfonamido)ethyl)piperidin-4-yl)methyl)-1H-1,2,3-triazol-4-yl)-5-fluoro-1H-indole-2-carboxylate (138) (Code AB1209)

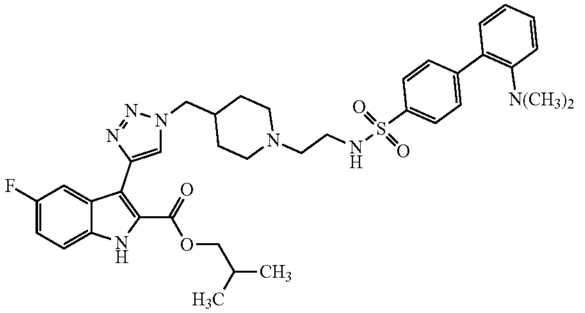 [SMILES: CC(C)COC(=O)c1[nH]c2ccc(F)cc2c1-c1cn(CC2CCN(CCNS(=O)(=O)c3ccc(-c4ccccc4N(C)C)cc3)CC2)nn1]

Prepared by general method G using alkyne 14f (45 mg, 0.17 mmol), azide 5A1 (80 mg, 0.18 mmol), 2M aqueous of sodium ascorbate (300 μL, 0.60 mmol), 15% aqueous of copper(II) sulfate pentahydrate (250 μL, 0.15 mmol) and tetrahydrofuran-tert-butanol (430 μL). The crude product was purified chromatographically on silica gel (eluting gradient dichloromethane-methanol 98:2 to 95:5) to provide the title compound 138 as a pale yellow solid (72 mg, 59% yield). $^1$H NMR (400 MHz, $d_6$-DMSO) δ=12.00 (s, 1H), 8.54 (s, 1H), 8.02 (dd, J=10.2, 2.7 Hz, 1H), 7.92-7.78 (m, 2H), 7.76-7.69 (m, 2H), 7.59-7.51 (m, 1H), 7.48 (s, 1H), 7.30 (ddd, J=8.1, 7.3, 1.7 Hz, 1H), 7.26-7.16 (m, 2H), 7.08 (dd, J=8.2, 1.2 Hz, 1H), 7.03 (td, J=7.4, 1.1 Hz, 1H), 4.41-4.27 (m, 2H), 4.26-4.01 (m, 2H), 2.89 (s, 2H), 2.70 (d, J=11.4 Hz, 2H), 2.45 (s, 6H), 2.28 (t, J=6.9 Hz, 3H), 2.07-1.99 (m, 1H), 1.87-1.75 (m, 2H), 1.47 (d, J=11.4 Hz, 2H), 1.30-1.20 (m, 2H), 0.95 (dd, J=8.4, 6.6 Hz, 6H). LC-MS (ESI+) Found: $[M+H]^+$, 702.3.

isobutyl 5-fluoro-3-(1-((1-(2-((p-tolylmethyl)sulfonamido)ethyl)piperidin-4-yl)methyl)-1H-1,2,3-triazol-4-yl)-1H-indole-2-carboxylate (139) (Code AB1210)

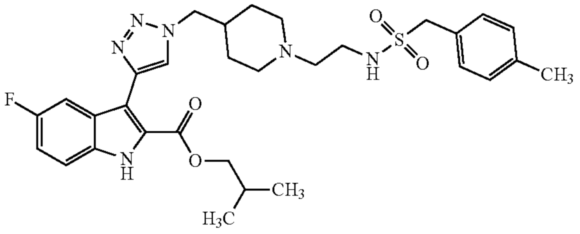 [SMILES: Cc1ccc(CS(=O)(=O)NCCN2CCC(Cn3cc(-c4c(C(=O)OCC(C)C)[nH]c5ccc(F)cc45)nn3)CC2)cc1]

Prepared by general method G using alkyne 14f (60 mg, 0.23 mmol), azide 5Am (85 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 139 as a white solid (98 mg, 70% yield). $^1$H NMR (400 MHz, $d_6$-DMSO) δ=12.01 (s, 1H), 8.56 (s, 1H), 8.03 (dd, J=10.3, 2.6 Hz, 1H), 7.55 (dd, J=9.0, 4.7 Hz, 1H), 7.29-7.19 (m, 3H), 7.19-7.11 (m, 2H), 6.82 (t, J=5.6 Hz, 1H), 4.37 (d, J=6.9 Hz, 2H), 4.30 (s, 3H), 4.12 (d, J=6.7 Hz, 2H), 3.05-2.96 (m, 2H), 2.84 (d, J=11.1 Hz, 2H), 2.31 (s, 2H), 2.28 (s, 2H), 2.01 (dd, J=13.2, 6.5 Hz, 1H), 1.89 (t, J=11.3 Hz, 3H), 1.54 (d, J=12.1 Hz, 2H), 1.29 (d, J=7.3 Hz, 2H), 0.95 (d, J=6.7 Hz, 6H). LC-MS (ESI+) Found: $[M+H]^+$, 611.3.

isobutyl 5-fluoro-3-(1-((1-(2-((2'-(methoxymethyl)-[1,1'-biphenyl])-4-sulfonamido)ethyl)piperidin-4-yl)methyl)-1H-1,2,3-triazol-4-yl)-1H-indole-2-carboxylate (140) (Code AB1303)

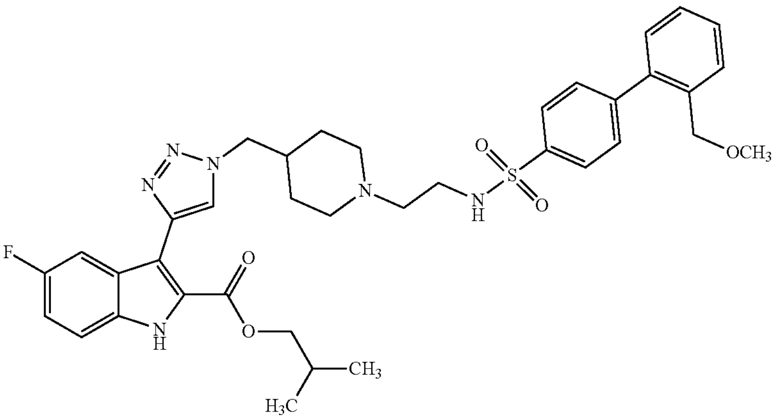 [SMILES: COCc1ccccc1-c1ccc(S(=O)(=O)NCCN2CCC(Cn3cc(-c4c(C(=O)OCC(C)C)[nH]c5ccc(F)cc45)nn3)CC2)cc1]

Prepared by general method G using alkyne 14f (60 mg, 0.23 mmol), azide 5An (108 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 140 as a pale yellow solid (113 mg, 70% yield). $^{1}$H NMR (400 MHz, $d_6$-DMSO) δ=12.01 (s, 1H), 8.54 (s, 1H), 8.03 (dd, J=10.3, 2.6 Hz, 1H), 7.89-7.83 (m, 2H), 7.62-7.52 (m, 4H), 7.52-7.48 (m, 1H), 7.42 (qt, J=6.5, 3.6 Hz, 2H), 7.36-7.28 (m, 1H), 7.23 (td, J=9.1, 2.6 Hz, 1H), 4.34 (d, J=7.0 Hz, 2H), 4.26 (s, 2H), 4.11 (d, J=6.6 Hz, 2H), 3.19 (s, 3H), 2.91 (t, J=6.9 Hz, 2H), 2.82-2.68 (m, 2H), 2.29 (t, J=6.9 Hz, 2H), 2.02 (dt, J=13.4, 6.7 Hz, 1H), 1.96-1.74 (m, 3H), 1.50-1.44 (m, 2H), 1.25-1.19 (m, 2H), 0.94 (d, J=6.7 Hz, 6H). $^{19}$F NMR (376 MHz, $d_6$-DMSO) δ=−122.4. LC-MS (ESI+) Found: $[M+H]^+$, 703.3.

N-(2-(4-((4-(5-fluoro-2-(pyrrolidine-1-carbonyl)-1H-indol-3-yl)-1H-1,2,3-triazol-1-yl)methyl)piperidin-1-yl)ethyl)-4-isobutylbenzenesulfonamide (141) (Code AB1131)

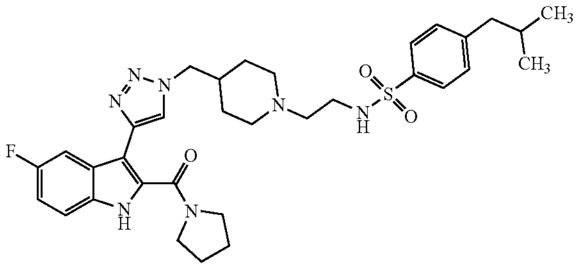 [SMILES: CC(C)Cc1ccc(S(=O)(=O)NCCN2CCC(Cn3cc(-c4c(C(=O)N5CCCC5)[nH]c5ccc(F)cc45)nn3)CC2)cc1]

Prepared by general method G using alkyne 102a (100 mg, 0.39 mmol), azide 5h (155 mg, 0.41 mmol), 2M aqueous of sodium ascorbate (683 μL, 1.37 mmol), 15% aqueous of copper(II) sulfate pentahydrate (566 μL, 0.34 mmol) and tetrahydrofuran-tert-butanol (975 μL). The crude product was purified chromatographically on silica gel (eluting gradient dichloromethane-methanol 98:2 to 90:10) to provide the title compound 141 as a pale yellow solid (128 mg, 52% yield). $^{1}$H NMR (400 MHz, $d_6$-DMSO) δ=11.86 (s, 1H), 8.20 (s, 1H), 7.82 (dd, J=10.1, 2.6 Hz, 1H), 7.75-7.67 (m, 2H), 7.41 (dt, J=10.0, 5.1 Hz, 1H), 7.40-7.25 (m, 3H), 7.08 (td, J=9.1, 2.6 Hz, 1H), 4.30 (d, J=6.9 Hz, 2H), 3.54 (t, J=7.0 Hz, 2H), 3.10 (t, J=6.8 Hz, 2H), 2.82 (dt, J=10.6, 5.4 Hz, 2H), 2.72-2.59 (m, 2H), 2.24 (t, J=6.9 Hz, 2H), 1.82 (dq, J=17.0, 8.8 Hz, 6H), 1.69 (p, J=6.8 Hz, 2H), 1.45-1.35 (m, 2H), 1.28-1.10 (m, 4H), 0.83 (d, J=6.6 Hz, 6H). $^{19}$F NMR (376 MHz, $d_6$-DMSO) δ=−122.5. LC-MS (ESI+) Found: $[M+H]^+$, 636.3. N-(2-(4-((4-(5-fluoro-2-(morpholine-4-carbonyl)-1H-indol-3-yl)-1H-1,2,3-triazol-1-yl)methyl)piperidin-1-yl)ethyl)-4-isobutylbenzenesulfonamide (142) (Code AB1132)

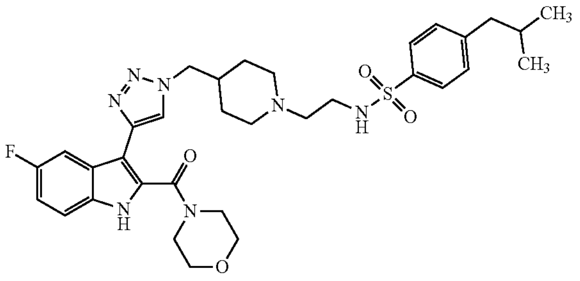 [SMILES: CC(C)Cc1ccc(S(=O)(=O)NCCN2CCC(Cn3cc(-c4c(C(=O)N5CCOCC5)[nH]c5ccc(F)cc45)nn3)CC2)cc1]

Prepared by general method G using alkyne 102b (80 mg, 0.29 mmol), azide 5h (117 mg, 0.31 mmol), 2M aqueous of sodium ascorbate (514 μL, 1.03 mmol), 15% aqueous of copper(II) sulfate pentahydrate (426 μL, 0.26 mmol) and tetrahydrofuran-tert-butanol (735 μL). The crude product was purified chromatographically on silica gel (eluting gradient dichloromethane-methanol 98:2 to 90:10) to provide the title compound 142 as a pale yellow solid (115 mg, 60% yield). $^{1}$H NMR (400 MHz, $d_6$-DMSO) δ=11.94 (s, 1H), 8.27 (s, 1H), 7.78 (dd, J=10.1, 2.6 Hz, 1H), 7.75-7.67 (m, 2H), 7.51-7.30 (m, 4H), 7.10 (tt, J=9.1, 4.2 Hz, 1H), 4.31 (d, J=7.0 Hz, 2H), 3.91-3.41 (m, 6H), 3.18 (d, J=4.9 Hz, 3H), 2.82 (d, J=7.0 Hz, 2H), 2.67 (d, J=11.1 Hz, 2H), 2.25 (t, J=7.0 Hz, 2H), 1.96-1.68 (m, 4H), 1.51-1.39 (m, 2H), 1.30-1.12 (m, 3H), 0.82 (d, J=6.6 Hz, 6H). $^{13}$C NMR (101 MHz, $d_6$-DMSO) δ=162.6 ($C_{quat}$), 157.5 (d, J=233.1 Hz, $C_{quat}$), 146.0 ($C_{quat}$), 140.2 ($C_{quat}$), 138.0 ($C_{quat}$), 132.3 ($C_{quat}$), 129.7 ($C_{quat}$), 127.8 (CH), 125.0 (d, J=9.8 Hz, $C_{quat}$), 129.6 (CH), 126.4 (CH), 121.5 (CH), 113.1 (d, J=8.8 Hz, CH), 111.3 (d, J=26.2 Hz, CH), 105.4 (d, J=24.0 Hz, CH), 105.0 (d, J=4.4 Hz, $C_{quat}$), 65.9 ($CH_2$), 56.8 ($CH_2$), 55.8 ($CH_2$), 54.5 ($CH_2$), 52.5 ($CH_2$), 44.1 ($CH_2$), 40.2 ($CH_2$), 36.4 (CH), 29.0 ($CH_2$), 29.5 (CH), 22.0 ($CH_3$). $^{19}$F NMR (376 MHz, $d_6$-DMSO) δ=−122.4. LC-MS (ESI+) Found: $[M+H]^+$, 652.3.

N-(2-(4-((4-(2-acetyl-5-fluoro-1H-indol-3-yl)-1H-1,2,3-triazol-1-yl)methyl)piperidin-1-yl)ethyl)-4-isobutylbenzenesulfonamide (143) (Code AB1135)

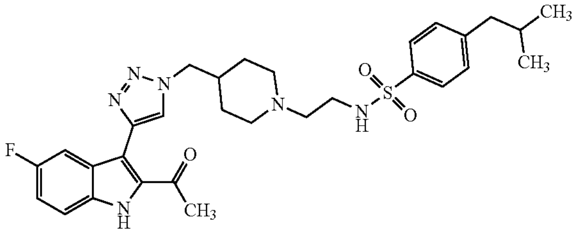 [SMILES: CC(=O)c1[nH]c2ccc(F)cc2c1-c1cn(CC2CCN(CCNS(=O)(=O)c3ccc(CC(C)C)cc3)CC2)nn1]

Prepared by general method G using alkyne 93 (60 mg, 0.30 mmol), azide 5h (117 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 143 as a pale yellow solid (124 mg, 72% yield). $^{1}$H NMR (400 MHz, $d_6$-DMSO) δ=12.07 (d, J=6.2 Hz, 1H), 8.61 (d, J=6.6 Hz, 1H), 7.80 (ddd, J=10.0, 6.6, 2.6 Hz, 1H), 7.76-7.67 (m, 2H), 7.60-7.49 (m, 1H), 7.35 (t, J=7.5 Hz, 3H), 7.24 (tdd, J=9.1, 6.6, 2.7 Hz, 1H), 4.34 (d, J=7.0 Hz, 2H), 2.83 (q, J=6.6 Hz, 2H), 2.66 (d, J=11.2 Hz, 2H), 2.52 (s, 3H), 2.24 (t, J=6.6 Hz, 2H), 1.89-1.72 (m, 4H), 1.48-1.38 (m, 2H), 1.27-1.15 (m, 4H), 0.82 (t, J=6.6 Hz, 6H). $^{13}$C NMR (101 MHz, $d_6$-DMSO) δ=191.0 ($C_{quat}$), 157.5 (d, J=234.3 Hz, $C_{quat}$), 146.0 ($C_{quat}$), 140.0 ($C_{quat}$), 133.0 ($C_{quat}$), 132.9 ($C_{quat}$), 129.7 ($C_{quat}$), 126.6 (d, J=10.1 Hz, $C_{quat}$), 129.5 (CH), 126.4 (CH), 125.0 (CH), 114.8 (d, J=27.5 Hz, CH), 114.2 (d, J=10.6 Hz, CH), 110.8 (d, J=5.5 Hz, $C_{quat}$), 106.8 (d, J=23.1 Hz, CH), 56.8 ($CH_2$), 54.5 ($CH_2$), 52.5 ($CH_2$), 44.1 ($CH_2$), 40.2 ($CH_2$), 36.4 (CH), 29.0 ($CH_2$), 28.7 ($CH_3$), 29.5 (CH), 22.0 ($CH_3$). $^{19}$F NMR (376 MHz, $d_6$-DMSO) δ=−122.4. LC-MS (ESI+) Found: $[M+H]^+$, 581.3.

N-(2-(4-((4-(5-fluoro-2-pentanoyl-1H-indol-3-yl)-1H-1,2,3-triazol-1-yl)methyl)piperidin-1-yl)ethyl)-4-isobutylbenzenesulfonamide (144) (Code AB1145)

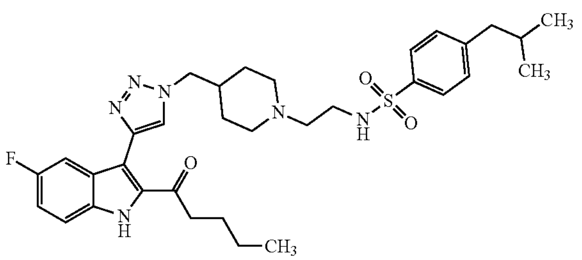 [SMILES: CCCCC(=O)c1[nH]c2ccc(F)cc2c1-c1cn(CC2CCN(CCNS(=O)(=O)c3ccc(CC(C)C)cc3)CC2)nn1]

Prepared by general method G using alkyne 99g (60 mg, 0.25 mmol), azide 5h (100 mg, 0.26 mmol), 2M aqueous of sodium ascorbate (415 μL, 0.83 mmol), 15% aqueous of copper(II) sulfate pentahydrate (343 μL, 0.21 mmol) and tetrahydrofuran-tert-butanol (592 μL). The crude product was purified chromatographically on silica gel (eluting gradient dichloromethane-methanol 98:2 to 96:4) to provide the title compound 144 as a pale yellow solid (91 mg, 61% yield). $^1$H NMR (400 MHz, $d_6$-DMSO) δ=12.04 (s, 1H), 8.61 (s, 1H), 7.83-7.73 (m, 1H), 7.73-7.65 (m, 2H), 7.53 (dd, J=9.0, 4.7 Hz, 1H), 7.43-7.30 (m, 3H), 7.23 (td, J=9.1, 2.6 Hz, 1H), 4.35 (d, J=7.0 Hz, 2H), 2.98-2.85 (m, 3H), 2.83 (s, 2H), 2.66 (d, J=11.6 Hz, 3H), 2.24 (t, J=6.9 Hz, 2H), 1.87-1.76 (m, 3H), 1.55 (p, J=7.4 Hz, 2H), 1.44 (d, J=12.2 Hz, 2H), 1.31-1.15 (m, 5H), 0.94-0.75 (m, 9H). $^{19}$F NMR (376 MHz, $d_6$-DMSO) δ=−122.3. LC-MS (ESI+) Found: $[M+H]^+$, 623.3.

N-(2-(4-((4-(2-(cyclopropanecarbonyl)-5-fluoro-1H-indol-3-yl)-1H-1,2,3-triazol-1-yl)methyl)piperidin-1-yl)ethyl)-4-isobutylbenzenesulfonamide (145) (Code AB1231)

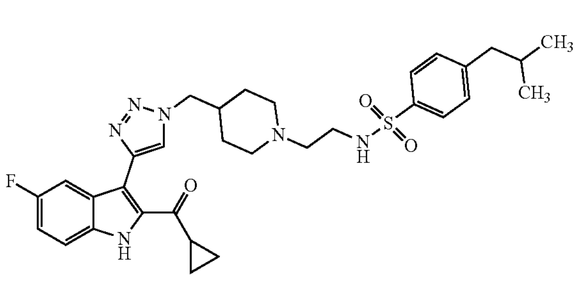 [SMILES: CC(C)Cc1ccc(S(=O)(=O)NCCN2CCC(Cn3cc(-c4c(C(=O)C5CC5)[nH]c5ccc(F)cc45)nn3)CC2)cc1]

Prepared by general method G using alkyne 99e (60 mg, 0.26 mmol), azide 5h (105 mg, 0.28 mmol), 2M aqueous of sodium ascorbate (462 μL, 0.92 mmol), 15% aqueous of copper(II) sulfate pentahydrate (382 μL, 0.23 mmol) and tetrahydrofuran-tert-butanol (660 μL). The crude product was purified chromatographically on silica gel (eluting gradient dichloromethane-methanol 98:2 to 96:4) to provide the title compound 145 as a white solid (103 mg, 64% yield). $^1$H NMR (400 MHz, $d_6$-DMSO) δ=12.20 (s, 1H), 8.57 (s, 1H), 7.81 (dd, J=10.1, 2.6 Hz, 1H), 7.79-7.60 (m, 2H), 7.54 (dd, J=8.9, 4.6 Hz, 1H), 7.50-7.32 (m, 3H), 7.24 (td, J=9.1, 2.6 Hz, 1H), 4.33 (d, J=6.9 Hz, 2H), 2.82 (d, J=5.8 Hz, 2H), 2.73-2.58 (m, 5H), 2.23 (t, J=6.9 Hz, 2H), 1.90-1.73 (m, 3H), 1.46-1.37 (m, 2H), 1.25-1.17 (m, 2H), 1.16 (d, J=3.7 Hz, 1H), 1.13-1.09 (m, 2H), 1.00 (dt, J=8.1, 3.4 Hz, 2H), 0.83 (d, J=6.7 Hz, 6H). $^{19}$F NMR (376 MHz, $d_6$-DMSO) δ=−122.4. LC-MS (ESI+) Found: $[M+H]^+$, 607.3.

4-(2-chloropyridin-3-yl)-N-(2-(4-((4-(2-(cyclopropanecarbonyl)-5-fluoro-1H-indol-3-yl)-1H-1,2,3-triazol-1-yl)methyl)piperidin-1-yl)ethyl)benzenesulfonamide (146) (Code AB1232)

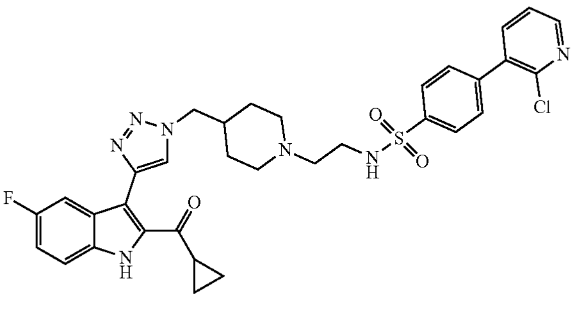 [SMILES: O=C(c1[nH]c2ccc(F)cc2c1-c1cn(CC2CCN(CCNS(=O)(=O)c3ccc(-c4cccnc4Cl)cc3)CC2)nn1)C1CC1]

Prepared by general method G using alkyne 99e (60 mg, 0.26 mmol), azide 5Af (120 mg, 0.28 mmol), 2M aqueous of sodium ascorbate (462 μL, 0.92 mmol), 15% aqueous of copper(II) sulfate pentahydrate (382 μL, 0.23 mmol) and tetrahydrofuran-tert-butanol (660 μL). The crude product was purified chromatographically on silica gel (eluting gradient dichloromethane-methanol 98:2 to 96:4) to provide the title compound 146 as a white solid (109 mg, 62% yield). $^1$H NMR (400 MHz, $d_6$-DMSO) δ=12.19 (s, 1H), 8.57 (s, 1H), 8.47 (dd, J=4.8, 1.9 Hz, 1H), 7.92 (td, J=7.1, 1.9 Hz, 3H), 7.81 (dd, J=10.1, 2.6 Hz, 1H), 7.74-7.67 (m, 2H), 7.64 (s, 1H), 7.56 (d, J=4.8 Hz, 1H), 7.54 (dd, J=4.7, 1.7 Hz, 1H), 7.23 (td, J=9.1, 2.6 Hz, 1H), 4.34 (d, J=7.0 Hz, 2H), 2.92 (t, J=6.8 Hz, 2H), 2.80-2.67 (m, 2H), 2.59 (td, J=7.8, 4.0 Hz, 1H), 2.30 (t, J=7.0 Hz, 2H), 2.01-1.75 (m, 3H), 1.48-1.39 (m, 2H), 1.22 (td, J=12.8, 3.9 Hz, 2H), 1.12-1.05 (m, 2H), 0.99 (dt, J=8.2, 3.4 Hz, 2H). $^{19}$F NMR (376 MHz, $d_6$-DMSO) δ=−122.4. LC-MS (ESI+) Found: $[M+H]^+$, 662.2.

N-(2-(4-((4-(2-butyryl-5-fluoro-1H-indol-3-yl)-1H-1,2,3-triazol-1-yl)methyl)piperidin-1-yl)ethyl)-4-(2-chloropyridin-3-yl)benzenesulfonamide (147) (Code AB1233)

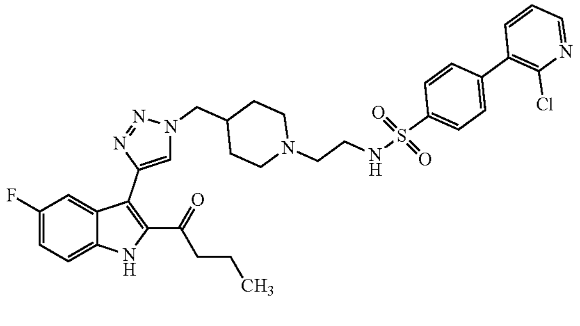 [SMILES: CCCC(=O)c1[nH]c2ccc(F)cc2c1-c1cn(CC2CCN(CCNS(=O)(=O)c3ccc(-c4cccnc4Cl)cc3)CC2)nn1]

Prepared by general method G using alkyne 99f (60 mg, 0.26 mmol), azide 5Af (120 mg, 0.27 mmol), 2M aqueous of sodium ascorbate (458 μL, 0.92 mmol), 15% aqueous of copper(II) sulfate pentahydrate (380 μL, 0.23 mmol) and tetrahydrofuran-tert-butanol (654 μL). The crude product was purified chromatographically on silica gel (eluting gradient dichloromethane-methanol 98:2 to 96:4) to provide the title compound 147 as a pale yellow solid (109 mg, 63% yield). $^{1}H$ NMR (400 MHz, $d_6$-DMSO) δ=12.04 (s, 1H), 8.61 (s, 1H), 8.47 (dd, J=4.8, 2.0 Hz, 1H), 7.98-7.87 (m, 3H), 7.76 (dd, J=10.1, 2.6 Hz, 1H), 7.73-7.69 (m, 2H), 7.64 (s, 1H), 7.59-7.50 (m, 2H), 7.23 (td, J=9.1, 2.6 Hz, 1H), 4.36 (d, J=7.0 Hz, 2H), 2.92 (t, J=6.9 Hz, 2H), 2.86 (t, J=7.3 Hz, 2H), 2.72 (d, J=11.2 Hz, 2H), 2.30 (t, J=6.8 Hz, 2H), 1.90-1.79 (m, 2H), 1.59 (h, J=7.4 Hz, 2H), 1.47 (d, J=12.4 Hz, 2H), 1.36-1.22 (m, 3H), 0.85 (t, J=7.4 Hz, 3H). $^{19}F$ NMR (376 MHz, $d_6$-DMSO) δ=−122.3. LC-MS (ESI+) Found: $[M+H]^+$, 664.2.

N-(2-(4-((4-(5-fluoro-2-formyl-1H-indol-3-yl)-1H-1,2,3-triazol-1-yl)methyl)piperidin-1-yl)ethyl)-4-isobutylbenzenesulfonamide (148) (AB1235)

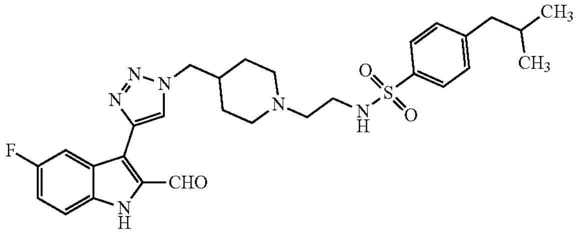 [SMILES: CC(C)Cc1ccc(S(=O)(=O)NCCN2CCC(Cn3cc(-c4c(C=O)[nH]c5ccc(F)cc45)nn3)CC2)cc1]

Prepared by general method G using alkyne 104 (60 mg, 0.32 mmol), azide 5h (128 mg, 0.34 mmol), 2M aqueous of sodium ascorbate (560 μL, 1.12 mmol), 15% aqueous of copper(II) sulfate pentahydrate (465 μL, 0.28 mmol) and tetrahydrofuran-tert-butanol (800 μL). The crude product was purified chromatographically on silica gel (eluting gradient dichloromethane-methanol 98:2 to 96:4) to provide the title compound 148 as a pale brown solid (120 mg, 66% yield). $^{1}H$ NMR (400 MHz, $d_6$-DMSO) δ=12.24 (s, 1H), 10.44 (s, 1H), 8.83 (s, 1H), 7.85 (dd, J=9.9, 2.6 Hz, 1H), 7.75-7.63 (m, 3H), 7.52 (dd, J=9.1, 4.6 Hz, 1H), 7.39-7.33 (m, 2H), 7.29 (td, J=9.1, 2.5 Hz, 1H), 4.33 (d, J=7.0 Hz, 2H), 2.83 (q, J=6.2 Hz, 2H), 2.73-2.61 (m, 3H), 2.25 (t, J=6.8 Hz, 2H), 1.96-1.69 (m, 4H), 1.46 (d, J=12.0 Hz, 2H), 1.27-1.16 (m, 3H), 0.82 (d, J=6.6 Hz, 6H). $^{19}F$ NMR (376 MHz, $d_6$-DMSO) δ=−122.4. LC-MS (ESI+) Found: $[M+H]^+$, 567.2.

N-(2-(4-((4-(5-fluoro-2-isobutyryl-1H-indol-3-yl)-1H-1,2,3-triazol-1-yl)methyl)piperidin-1-yl)ethyl)-4-isobutylbenzenesulfonamide (149) (AB1281)

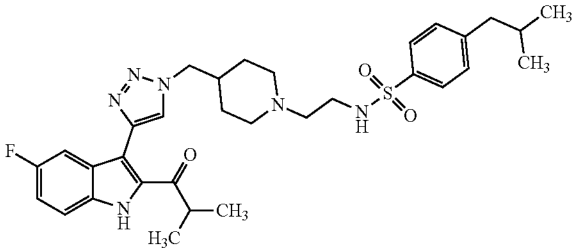 [SMILES: CC(C)Cc1ccc(S(=O)(=O)NCCN2CCC(Cn3cc(-c4c(C(=O)C(C)C)[nH]c5ccc(F)cc45)nn3)CC2)cc1]

Prepared by general method G using alkyne 99b (60 mg, 0.26 mmol), azide 5h (104 mg, 0.27 mmol), 2M aqueous of sodium ascorbate (458 μL, 0.92 mmol), 15% aqueous of copper(II) sulfate pentahydrate (380 μL, 0.23 mmol) and tetrahydrofuran-tert-butanol (654 μL). The crude product was purified chromatographically on silica gel (eluting gradient dichloromethane-methanol 98:2 to 96:4) to provide the title compound 149 as a white solid (103 mg, 65% yield). $^{1}H$ NMR (400 MHz, $d_6$-DMSO) δ=12.06 (s, 1H), 8.62 (s, 1H), 7.78 (dd, J=10.1, 2.6 Hz, 1H), 7.74-7.65 (m, 2H), 7.54 (dd, J=9.0, 4.6 Hz, 1H), 7.43-7.32 (m, 3H), 7.23 (td, J=9.1, 2.6 Hz, 1H), 4.35 (d, J=7.0 Hz, 2H), 3.49 (h, J=6.8 Hz, 1H), 2.83 (q, J=6.0 Hz, 2H), 2.73-2.62 (m, 2H), 2.25 (q, J=6.6 Hz, 2H), 1.97-1.74 (m, 4H), 1.52-1.38 (m, 2H), 1.32-1.18 (m, 3H), 1.06 (d, J=6.9 Hz, 6H), 0.97-0.87 (m, 1H), 0.82 (d, J=6.6 Hz, 6H). $^{13}C$ NMR (101 MHz, $d_6$-DMSO) δ=197.7 ($C_{quat}$), 157.5 (d, J=233.4 Hz, $C_{quat}$), 146.0 ($C_{quat}$), 140.1 ($C_{quat}$), 138.0 ($C_{quat}$), 133.0 ($C_{quat}$), 131.8 ($C_{quat}$), 129.5 (CH), 126.4 (CH), 126.0 (d, J=10.2 Hz, $C_{quat}$), 124.9 (CH), 114.4 (d, J=26.6 Hz, CH), 114.0 (d, J=9.6 Hz, CH), 111.9 (d, J=5.3 Hz, $C_{quat}$), 107.2 (d, J=23.7 Hz, CH), 56.8 ($CH_2$), 54.4 ($CH_2$), 52.5 ($CH_2$), 44.1 ($CH_2$), 40.2 ($CH_2$), 29.5 (CH), 29.0 ($CH_2$), 22.0 ($CH_3$), 18.8 ($CH_3$). $^{19}F$ NMR (376 MHz, $d_6$-DMSO) δ=−122.4. LC-MS (ESI+) Found: $[M+H]^+$, 609.3.

4-(2-chloropyridin-3-yl)-N-(2-(4-((4-(5-fluoro-2-isobutyryl-1H-indol-3-yl)-1H-1,2,3-triazol-1-yl)methyl)piperidin-1-yl)ethyl)benzenesulfonamide (150) (Code AB1282)

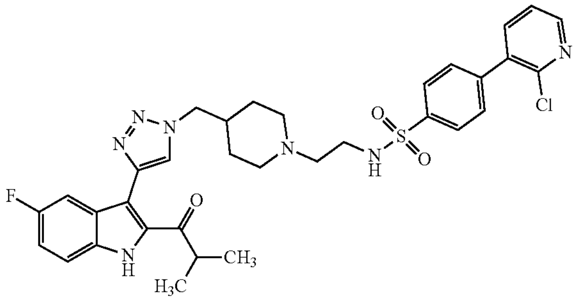 [SMILES: CC(C)C(=O)c1[nH]c2ccc(F)cc2c1-c1cn(CC2CCN(CCNS(=O)(=O)c3ccc(-c4cccnc4Cl)cc3)CC2)nn1]

Prepared by general method G using alkyne 99b (60 mg, 0.26 mmol), azide 5Af (120 mg, 0.27 mmol), 2M aqueous of sodium ascorbate (458 μL, 0.92 mmol), 15% aqueous of copper(II) sulfate pentahydrate (380 μL, 0.23 mmol) and tetrahydrofuran-tert-butanol (654 μL). The crude product was purified chromatographically on silica gel (eluting gradient dichloromethane-methanol 98:2 to 96:4) to provide the title compound 150 as a white solid (110 mg, 63% yield). $^1H$ NMR (400 MHz, $d_6$-DMSO) δ=12.06 (s, 1H), 8.61 (s, 1H), 8.47 (dd, J=4.7, 1.9 Hz, 1H), 8.07-7.83 (m, 3H), 7.77 (dd, J=10.1, 2.6 Hz, 1H), 7.74-7.67 (m, 2H), 7.64 (s, 1H), 7.60-7.44 (m, 2H), 7.23 (td, J=9.1, 2.6 Hz, 1H), 4.36 (d, J=7.0 Hz, 2H), 3.47 (hept, J=6.7 Hz, 1H), 2.91 (q, J=7.2 Hz, 2H), 2.73 (d, J=11.3 Hz, 2H), 2.30 (q, J=4.7 Hz, 2H), 1.85 (t, J=11.4 Hz, 3H), 1.46 (d, J=12.3 Hz, 2H), 1.22 (dtd, J=15.8, 12.1, 3.8 Hz, 2H), 1.05 (d, J=6.8 Hz, 6H). 19F NMR (376 MHz, $d_6$-DMSO) δ=−122.4. LC-MS (ESI+) Found: $[M+H]^+$, 664.2.

N-(2-(4-((4-(5-fluoro-2-(3-methylbutanoyl)-1H-indol-3-yl)-1H-1,2,3-triazol-1-yl)methyl)piperidin-1-yl)ethyl)-4-isobutylbenzenesulfonamide (151) (Code AB1283)

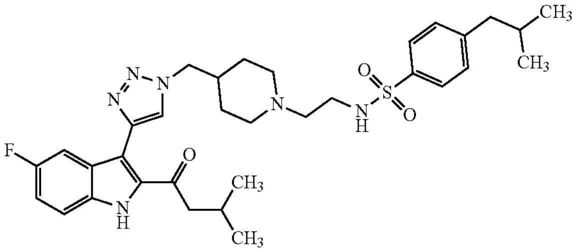 [SMILES: CC(C)CC(=O)c1[nH]c2ccc(F)cc2c1-c1cn(CC2CCN(CCNS(=O)(=O)c3ccc(CC(C)C)cc3)CC2)nn1]

Prepared by general method G using alkyne 99c (60 mg, 0.25 mmol), azide 5h (98 mg, 0.26 mmol), 2M aqueous of sodium ascorbate (432 μL, 0.86 mmol), 15% aqueous of copper(II) sulfate pentahydrate (358 μL, 0.21 mmol) and tetrahydrofuran-tert-butanol (617 μL). The crude product was purified chromatographically on silica gel (eluting gradient dichloromethane-methanol 98:2 to 96:4) to provide the title compound 151 as a white solid (94 mg, 61% yield). $^1H$ NMR (400 MHz, $d_6$-DMSO) δ=12.04 (s, 1H), 8.60 (s, 1H), 7.71 (ddt, J=10.4, 8.6, 2.4 Hz, 3H), 7.53 (dd, J=9.0, 4.6 Hz, 1H), 7.41-7.31 (m, 3H), 7.22 (td, J=9.1, 2.6 Hz, 1H), 4.36 (d, J=7.0 Hz, 2H), 2.89-2.80 (m, 2H), 2.77 (d, J=6.9 Hz, 2H), 2.72-2.61 (m, 2H), 2.25 (q, J=7.9 Hz, 2H), 2.20-2.02 (m, 1H), 1.81 (ddt, J=13.8, 11.1, 4.6 Hz, 4H), 1.45 (dd, J=13.3, 3.7 Hz, 2H), 1.31-1.09 (m, 3H), 1.03-0.92 (m, 1H), 0.93-0.78 (m, 12H). $^{13}C$ NMR (101 MHz, $d_6$-DMSO) δ=193.3 ($C_{quat}$), 157.6 (d, J=233.4 Hz, $C_{quat}$), 145.9 ($C_{quat}$), 140.0 ($C_{quat}$), 138.3 ($C_{quat}$), 133.1 ($C_{quat}$), 132.9 ($C_{quat}$), 129.5 (CH), 126.7 (d, J=10.1 Hz, $C_{quat}$), 126.4 (CH), 125.0 (CH), 114.7 (d, J=25.8 Hz, CH), 114.2 (d, J=9.9 Hz, CH), 110.5 (d, J=6.0 Hz, $C_{quat}$), 107.2 (d, J=25.8 Hz, CH), 56.8 ($CH_2$), 54.5 ($CH_2$), 52.5 ($CH_2$), 48.6 ($CH_2$), 44.1 ($CH_2$), 40.2 ($CH_2$), 29.5 (CH), 29.0 ($CH_2$), 24.5 (CH), 22.3 ($CH_3$), 22.0 ($CH_3$). $^{19}F$ NMR (376 MHz, $d_6$-DMSO) δ=−122.5. LC-MS (ESI+) Found: $[M+H]^+$, 623.3.

4-(2-chloropyridin-3-yl)-N-(2-(4-((4-(5-fluoro-2-(3-methylbutanoyl)-1H-indol-3-yl)-1H-1,2,3-triazol-1-yl)methyl)piperidin-1-yl)ethyl)benzenesulfonamide (152) (Code AB1284)

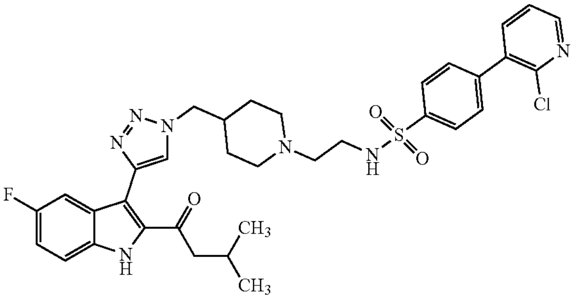 [SMILES: CC(C)CC(=O)c1[nH]c2ccc(F)cc2c1-c1cn(CC2CCN(CCNS(=O)(=O)c3ccc(-c4cccnc4Cl)cc3)CC2)nn1]

Prepared by general method G using alkyne 99c (60 mg, 0.25 mmol), azide 5Af (113 mg, 0.26 mmol), 2M aqueous of sodium ascorbate (432 μL, 0.86 mmol), 15% aqueous of copper(II) sulfate pentahydrate (358 μL, 0.21 mmol) and tetrahydrofuran-tert-butanol (617 μL). The crude product was purified chromatographically on silica gel (eluting gradient dichloromethane-methanol 98:2 to 96:4) to provide the title compound 152 as a pale yellow solid (105 mg, 63% yield). $^1H$ NMR (400 MHz, $d_6$-DMSO) δ=12.03 (s, 1H), 8.59 (s, 1H), 8.47 (dd, J=4.8, 1.9 Hz, 1H), 7.98-7.90 (m, 2H), 7.86-7.67 (m, 4H), 7.64 (s, 1H), 7.54 (ddd, J=9.1, 7.0, 4.7 Hz, 2H), 7.22 (td, J=9.1, 2.6 Hz, 1H), 4.36 (d, J=7.0 Hz, 2H), 2.92 (t, J=6.9 Hz, 2H), 2.80-2.68 (m, 4H), 2.30 (t, J=6.9 Hz, 2H), 2.19-2.03 (m, 1H), 1.93-1.79 (m, 3H), 1.62-1.44 (m, 2H), 1.35-1.16 (m, 2H), 0.83 (d, J=6.6 Hz, 6H). $^{13}C$ NMR (101 MHz, $d_6$-DMSO) δ=193.3 ($C_{quat}$), 157.6 (d, J=233.9 Hz, $C_{quat}$), 148.1 ($C_{quat}$), 140.7 ($C_{quat}$), 140.6 ($C_{quat}$), 140.0 ($C_{quat}$), 135.0 ($C_{quat}$), 133.1 ($C_{quat}$), 133.0 ($C_{quat}$), 130.1 (CH), 126.7 (d, J=9.8 Hz, $C_{quat}$), 126.5 (CH), 125.0 (CH), 123.5 (CH), 114.7 (d, J=25.9 Hz, CH), 114.1 (d, J=10.1 Hz, CH), 110.5 (d, J=4.7 Hz, $C_{quat}$), 106.7 (d, J=22.2 Hz, CH), 57.0 ($CH_2$), 54.5 ($CH_2$), 52.6 ($CH_2$), 48.6 ($CH_2$), 40.3 ($CH_2$), 36.6 (CH), 29.1 ($CH_2$), 24.5 (CH), 22.3 ($CH_3$). $^{19}F$ NMR (376 MHz, $d_6$-DMSO) δ=−122.4. LC-MS (ESI+) Found: $[M+H]^+$, 678.2.

N-(2-(4-((4-(2-(cyclopropanecarbonyl)-5-fluoro-1H-indol-3-yl)-1H-1,2,3-triazol-1-yl)methyl)piperidin-1-yl)ethyl)-4-(3,5-dimethylisoxazol-4-yl)benzenesulfonamide (153) (Code AB1285)

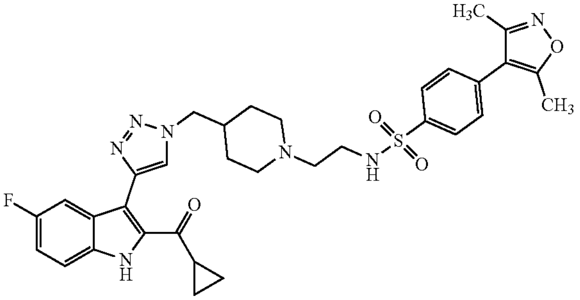 [SMILES: Cc1noc(C)c1-c1ccc(S(=O)(=O)NCCN2CCC(Cn3cc(-c4c(C(=O)C5CC5)[nH]c5ccc(F)cc45)nn3)CC2)cc1]

Prepared by general method G using alkyne 99e (60 mg, 0.26 mmol), azide 5Ae (116 mg, 0.28 mmol), 2M aqueous of sodium ascorbate (462 μL, 0.92 mmol), 15% aqueous of copper(II) sulfate pentahydrate (382 μL, 0.23 mmol) and tetrahydrofuran-tert-butanol (660 μL). The crude product was purified chromatographically on silica gel (eluting gradient dichloromethane-methanol 98:2 to 96:4) to provide the title compound 153 as a white solid (112 mg, 65% yield). $^1H$ NMR (400 MHz, $d_6$-DMSO) δ=12.20 (s, 1H), 8.57 (s, 1H), 7.91-7.85 (m, 2H), 7.82 (dd, J=10.1, 2.6 Hz, 1H), 7.66-7.57 (m, 3H), 7.55 (dd, J=9.0, 4.6 Hz, 1H), 7.24 (td, J=9.1, 2.6 Hz, 1H), 4.34 (d, J=7.0 Hz, 2H), 2.89 (t, J=6.8 Hz, 2H), 2.71 (dd, J=12.0, 3.5 Hz, 2H), 2.67-2.61 (m, 1H), 2.42 (s, 3H), 2.30 (d, J=6.9 Hz, 2H), 2.24 (s, 3H), 1.96-1.75 (m, 3H), 1.44 (dd, J=13.2, 3.5 Hz, 2H), 1.20 (qd, J=12.0, 3.9 Hz, 2H), 1.14-1.07 (m, 2H), 0.99 (dt, J=8.2, 3.4 Hz, 2H). $^{19}F$ NMR (376 MHz, $d_6$-DMSO) δ=−122.3. LC-MS (ESI+) Found: $[M+H]^+$, 646.3.

N-(2-(4-((4-(2-acetyl-5-fluoro-1H-indol-3-yl)-1H-1,2,3-triazol-1-yl)methyl)piperidin-1-yl)ethyl)-4-(3,5-dimethylisoxazol-4-yl)benzenesulfonamide (154) (Code AB1286)

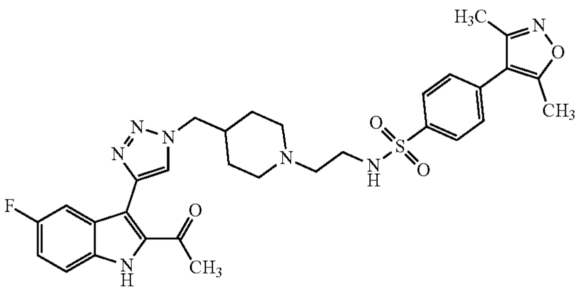 [SMILES: CC(=O)c1[nH]c2ccc(F)cc2c1-c1cn(CC2CCN(CCNS(=O)(=O)c3ccc(-c4c(C)noc4C)cc3)CC2)nn1]

Prepared by general method G using alkyne 93 (60 mg, 0.30 mmol), azide 5Ae (131 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 154 as a pale yellow solid (121 mg, 65% yield). $^1H$ NMR (400 MHz, $d_6$-DMSO) δ=12.06 (s, 1H), 8.60 (s, 1H), 7.93-7.83 (m, 2H), 7.79 (dd, J=10.1, 2.6 Hz, 1H), 7.71-7.57 (m, 3H), 7.54 (dd, J=9.0, 4.6 Hz, 1H), 7.23 (td, J=9.1, 2.6 Hz, 1H), 4.35 (d, J=7.0 Hz, 2H), 2.90 (t, J=6.8 Hz, 2H), 2.71 (dt, J=11.9, 3.0 Hz, 2H), 2.50 (s, 3H), 2.42 (s, 3H), 2.30 (t, J=6.8 Hz, 2H), 2.24 (s, 3H), 2.01-1.77 (m, 3H), 1.55-1.39 (m, 2H), 1.27-1.18 (m, 2H). $^{13}C$ NMR (101 MHz, $d_6$-DMSO) δ=191.0 ($C_{quat}$), 166.0 ($C_{quat}$), 158.0 ($C_{quat}$), 157.5 (d, J=235.7 Hz, $C_{quat}$), 140.0 ($C_{quat}$), 139.6 ($C_{quat}$), 133.9 ($C_{quat}$), 133.0 ($C_{quat}$), 132.9 ($C_{quat}$), 126.6 (d, J=10.9 Hz, $C_{quat}$), 129.5 (CH), 127.0 (CH), 125.0 (CH), 115.0 ($C_{quat}$), 114.8 (d, J=19.8 Hz, CH), 114.1 (d, J=10.3 Hz, CH), 110.7 (d, J=6.7 Hz, $C_{quat}$), 107.0 (d, J=23.9 Hz, CH), 57.0 ($CH_2$), 54.5 ($CH_2$), 52.6 ($CH_2$), 40.3 ($CH_2$), 29.0 ($CH_2$), 28.7 ($CH_2$), 28.7 (CH), 11.4 ($CH_3$), 10.5 ($CH_3$). $^{19}F$ NMR (376 MHz, $d_6$-DMSO) δ=−122.3. LC-MS (ESI+) Found: $[M+H]^+$, 620.2.

N-(2-(4-((4-(2-acetyl-5-fluoro-1H-indol-3-yl)-1H-1,2,3-triazol-1-yl)methyl)piperidin-1-yl)ethyl)-2',6'-dimethoxy-[1,1'-biphenyl]-4-sulfonamide (155) (Code AB1287)

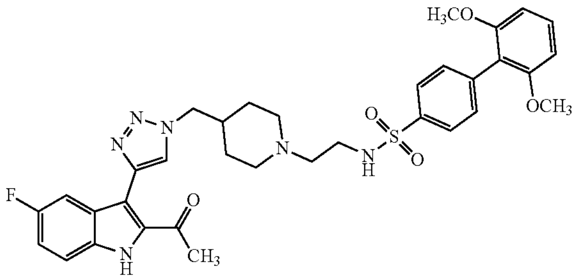 [SMILES: COc1cccc(OC)c1-c1ccc(S(=O)(=O)NCCN2CCC(Cn3cc(-c4c(C(C)=O)[nH]c5ccc(F)cc45)nn3)CC2)cc1]

Prepared by general method G using alkyne 93 (60 mg, 0.30 mmol), azide 5Ai (144 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 155 as a pale yellow solid (135 mg, 69% yield). $^1H$ NMR (400 MHz, $d_6$-DMSO) δ=12.06 (s, 1H), 8.61 (s, 1H), 7.90-7.73 (m, 3H), 7.54 (dd, J=9.0, 4.7 Hz, 1H), 7.50 (s, 1H), 7.48-7.38 (m, 2H), 7.32 (t, J=8.4 Hz, 1H), 7.24 (td, J=9.1, 2.6 Hz, 1H), 6.74 (d, J=8.4 Hz, 2H), 4.36 (d, J=7.0 Hz, 2H), 3.66 (s, 6H), 3.36 (s, 2H), 2.92 (t, J=6.8 Hz, 2H), 2.81-2.70 (m, 2H), 2.32 (q, J=5.9 Hz, 2H), 1.86 (t, J=11.3 Hz, 3H), 1.61-1.40 (m, 2H), 1.40-1.09 (m, 3H). $^{13}C$ NMR (101 MHz, $d_6$-DMSO) δ=191.0 ($C_{quat}$), 157.6 (d, J=234.4 Hz, $C_{quat}$), 140.0 ($C_{quat}$), 138.7 ($C_{quat}$), 138.5 ($C_{quat}$), 133.0 (d, J=8.0 Hz, $C_{quat}$), 135.1 (CH), 129.7 (CH), 126.6 (d, J=11.1 Hz, $C_{quat}$), 125.7 (CH), 125.0 (CH), 117.0 ($C_{quat}$), 114.8 (d, J=27.0 Hz, CH), 114.2 (d, J=10.0 Hz, CH), 110.8 ($C_{quat}$), 110.7 ($C_{quat}$), 106.9 (d, J=22.1 Hz, CH), 104.4 (CH), 57.7 ($CH_3$), 57.0 ($CH_2$), 54.3 ($CH_2$), 52.5 ($CH_2$), 40.7 ($CH_2$), 36.5 (CH), 30.8 ($CH_3$), 29.4 ($CH_2$), 36.5 (CH), 28.7 ($CH_3$). LC-MS (ESI+) Found: $[M+H]^+$, 661.3.

N-(2-(4-((4-(2-acetyl-5-fluoro-1H-indol-3-yl)-1H-1,2,3-triazol-1-yl)methyl)piperidin-1-yl)ethyl)-2',6'-difluoro-[1,1'-biphenyl]-4-sulfonamide (156) (Code AB1288)

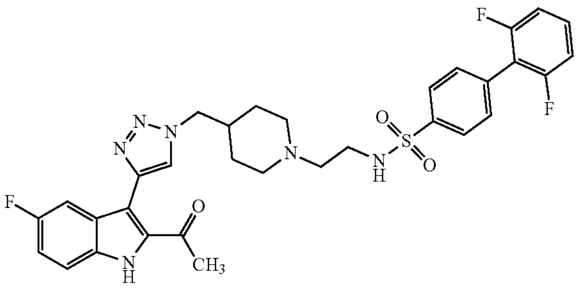 [SMILES: CC(=O)c1[nH]c2ccc(F)cc2c1-c1cn(CC2CCN(CCNS(=O)(=O)c3ccc(-c4c(F)cccc4F)cc3)CC2)nn1]

Prepared by general method G using alkyne 93 (60 mg, 0.30 mmol), azide 5Ak (136 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 156 as a pale yellow solid (116 mg, 61% yield). $^1H$ NMR (400 MHz, $d_6$-DMSO) δ=12.05 (s, 1H), 8.59 (s, 1H), 7.98-7.87 (m, 2H), 7.77 (dd, J=10.0, 2.6 Hz, 1H), 7.75-7.61 (in, 311), 7.61-7.49 (m, 2H), 7.38-7.18 (m, 3H), 4.35 (d, J=7.0 Hz, 2H), 3.26 (s, 3H), 2.92 (s, 2H), 2.76-2.65 (m, 2H), 2.30 (t, J=6.8 Hz, 2H), 1.91-1.75 (m, 3H), 1.46 (d, J=12.4 Hz, 2H), 1.34-1.17 (m, 2H). LC-MS (ESI+) Found: $[M+H]^+$, 637.2.

N-(2-(4-((4-(2-acetyl-5-fluoro-1H-indol-3-yl)-1H-1,2,3-triazol-1-yl)methyl)piperidin-1-yl)ethyl)-4-(2-fluoropyridin-3-yl)benzenesulfonamide (157) (Code AB1289)

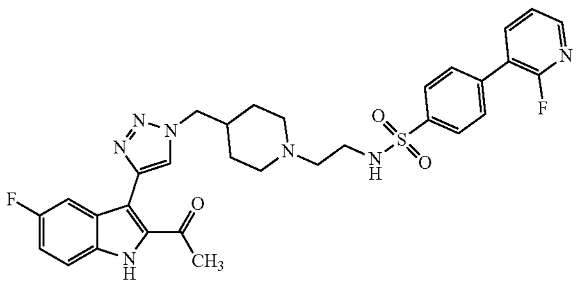 [SMILES: CC(=O)c1[nH]c2ccc(F)cc2c1-c1cn(CC2CCN(CCNS(=O)(=O)c3ccc(-c4cccnc4F)cc3)CC2)nn1]

Prepared by general method G using alkyne 93 (60 mg, 0.30 mmol), azide 5Aj (131 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 157 as a pale yellow solid (119 mg, 64% yield). LC-MS (ESI+) Found: $[M+H]^+$, 620.2.

N-(2-(4-((4-(5-fluoro-2-nicotinoyl-1H-indol-3-yl)-1H-1,2,3-triazol-1-yl)methyl)piperidin-1-yl)ethyl)-4-isobutylbenzenesulfonamide (158) (Code AB1301)

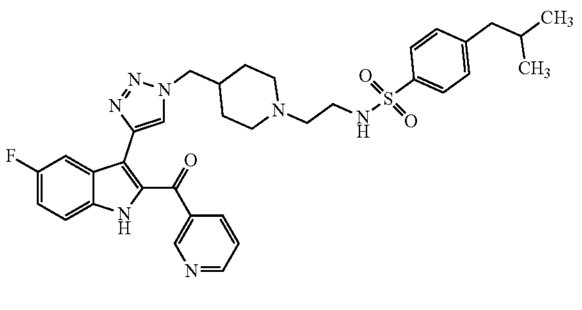 [SMILES: CC(C)Cc1ccc(S(=O)(=O)NCCN2CCC(Cn3cc(-c4c(C(=O)c5cccnc5)[nH]c5ccc(F)cc45)nn3)CC2)cc1]

Prepared by general method G using alkyne 99h (60 mg, 0.23 mmol), azide 5h (90 mg, 0.24 mmol), 2M aqueous of sodium ascorbate (397 μL, 0.79 mmol), 15% aqueous of copper(II) sulfate pentahydrate (330 μL, 0.20 mmol) and tetrahydrofuran-tert-butanol (568 μL). The crude product was purified chromatographically on silica gel (eluting gradient dichloromethane-methanol 98:2 to 95:5) to provide the title compound 158 as a yellow solid (86 mg, 59% yield). $^1H$ NMR (400 MHz, $d_6$-DMSO) δ=12.24 (s, 1H), 8.76 (d, J=2.2 Hz, 1H), 8.64 (dd, J=4.8, 1.7 Hz, 1H), 8.21 (s, 1H), 8.00 (dt, J=7.9, 2.0 Hz, 1H), 7.83-7.59 (m, 3H), 7.56 (dd, J=9.0, 4.6 Hz, 1H), 7.53-7.29 (m, 4H), 7.33-7.24 (m, 1H), 4.15 (d, J=7.0 Hz, 2H), 2.91-2.78 (m, 4H), 2.71-2.63 (m, 3H), 2.27 (t, J=6.8 Hz, 2H), 1.84 (dd, J=13.5, 6.8 Hz, 1H), 1.61 (d, J=4.0 Hz, 2H), 1.26 (dd, J=14.8, 10.9 Hz, 2H), 1.15-0.97 (m, 2H), 0.84 (d, J=6.7 Hz, 6H). LC-MS (ESI+) Found: $[M+H]^+$, 644.3.

N-(2-(4-((4-(5-fluoro-2-(2-methylbutanoyl)-1H-indol-3-yl)-1H-1,2,3-triazol-1-yl)methyl)piperidin-1-yl)ethyl)-4-isobutylbenzenesulfonamide (159) (Code AB1302)

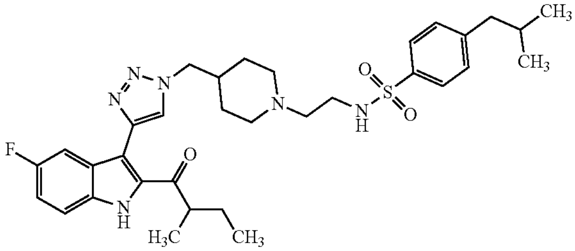 [SMILES: CCC(C)C(=O)c1[nH]c2ccc(F)cc2c1-c1cn(CC2CCN(CCNS(=O)(=O)c3ccc(CC(C)C)cc3)CC2)nn1]

Prepared by general method G using alkyne 99d (60 mg, 0.25 mmol), azide 5h (98 mg, 0.26 mmol), 2M aqueous of sodium ascorbate (432 μL, 0.86 mmol), 15% aqueous of copper(II) sulfate pentahydrate (358 μL, 0.21 mmol) and tetrahydrofuran-tert-butanol (617 μL). The crude product was purified chromatographically on silica gel (eluting gradient dichloromethane-methanol 98:2 to 96:4) to provide the title compound 159 as a white solid (103 mg, 67% yield). $^1H$ NMR (400 MHz, $d_6$-DMSO) δ=12.05 (s, 1H), 8.60 (s, 1H), 7.78-7.65 (m, 3H), 7.54 (dd, J=9.0, 4.6 Hz, 1H), 7.43-7.31 (m, 3H), 7.23 (td, J=9.1, 2.6 Hz, 1H), 4.35 (d, J=7.0 Hz, 2H), 2.83 (s, 3H), 2.66 (d, J=11.2 Hz, 2H), 2.24 (t, J=6.9 Hz, 2H), 1.90-1.76 (m, 4H), 1.65 (ddd, J=13.7, 7.6, 6.4 Hz, 1H), 1.44 (d, J=12.5 Hz, 2H), 1.33 (dt, J=13.9, 7.2 Hz, 1H), 1.29-1.16 (m, 4H), 1.04 (d, J=6.8 Hz, 3H), 0.91-0.80 (m, 6H), 0.75 (t, J=7.4 Hz, 3H). 19F NMR (376 MHz, $d_6$-DMSO) δ=−122.4. LC-MS (ESI+) Found: $[M+H]^+$, 623.3.

N-(2-(4-((4-(2-(cyclopropanecarbonyl)-5-fluoro-1H-indol-3-yl)-1H-1,2,3-triazol-1-yl)methyl)piperidin-1-yl)ethyl)-4-(2,6-difluorophenyl)piperidine-1-sulfonamide (160) (Code AB1304)

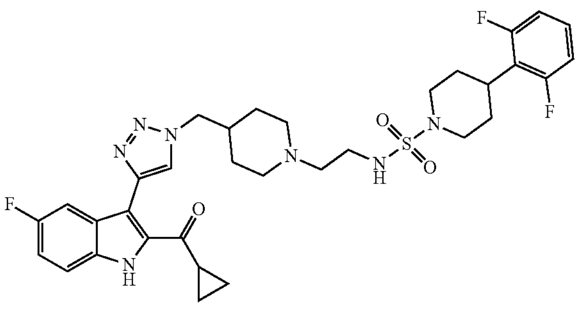 [SMILES: O=C(c1[nH]c2ccc(F)cc2c1-c1cn(CC2CCN(CCNS(=O)(=O)N3CCC(c4c(F)cccc4F)CC3)CC2)nn1)C1CC1]

Prepared by general method G using alkyne 99e (60 mg, 0.26 mmol), azide 88a (122 mg, 0.28 mmol), 2M aqueous of sodium ascorbate (462 μL, 0.92 mmol), 15% aqueous of copper(II) sulfate pentahydrate (382 μL, 0.23 mmol) and tetrahydrofuran-tert-butanol (660 μL). The crude product was purified chromatographically on silica gel (eluting gradient dichloromethane-methanol 98:2 to 96:4) to provide the title compound 160 as a pale yellow solid (111 mg, 63% yield). $^1$H NMR (400 MHz, $d_6$-DMSO) δ=12.21 (s, 1H), 8.60 (s, 1H), 7.82 (dd, J=10.1, 2.6 Hz, 1H), 7.70-7.47 (m, 1H), 7.44-7.18 (m, 2H), 7.18-6.84 (m, 2H), 4.38 (d, J=7.0 Hz, 2H), 3.64 (d, J=11.9 Hz, 2H), 3.21-2.97 (m, 3H), 2.97-2.70 (m, 4H), 2.70-2.55 (m, 3H), 2.47-2.31 (m, 1H), 2.17-1.84 (m, 4H), 1.85-1.63 (m, 2H), 1.53 (s, 2H), 1.43-1.19 (m, 3H), 1.10 (p, J=3.6 Hz, 2H), 1.03-0.72 (m, 2H). LC-MS (ESI+) Found: [M+H]$^+$, 670.3.

N-(2-(4-((4-(2-(cyclopropanecarbonyl)-5-fluoro-1H-indol-3-yl)-1H-1,2,3-triazol-1-yl)methyl)piperidin-1-yl)ethyl)-1-(4-(trifluoromethyl)phenyl)methanesulfonamide (161) (Code AB1305)

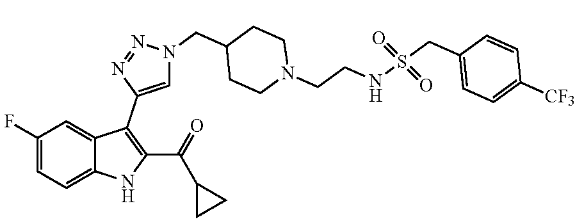 [SMILES: O=C(c1[nH]c2ccc(F)cc2c1-c1cn(CC2CCN(CCNS(=O)(=O)Cc3ccc(C(F)(F)F)cc3)CC2)nn1)C1CC1]

Prepared by general method G using alkyne 99e (60 mg, 0.26 mmol), azide 5r (112 mg, 0.28 mmol), 2M aqueous of sodium ascorbate (462 μL, 0.92 mmol), 15% aqueous of copper(II) sulfate pentahydrate (382 μL, 0.23 mmol) and tetrahydrofuran-tert-butanol (660 μL). The crude product was purified chromatographically on silica gel (eluting gradient dichloromethane-methanol 98:2 to 96:4) to provide the title compound 161 as a white solid (116 mg, 69% yield). $^1$H NMR (400 MHz, $d_6$-DMSO) δ=12.20 (s, 1H), 8.59 (s, 1H), 7.82 (dd, J=10.1, 2.6 Hz, 1H), 7.76-7.59 (m, 4H), 7.55 (dd, J=9.0, 4.6 Hz, 1H), 7.24 (td, J=9.1, 2.6 Hz, 111), 7.04 (t, J=5.6 Hz, 111), 4.52 (s, 2H), 4.37 (d, J=7.0 Hz, 2H), 3.03 (q, J=6.1 Hz, 2H), 2.85 (dt, J=11.7, 3.5 Hz, 2H), 2.61 (ddd, J=7.8, 6.1, 3.8 Hz, 111), 2.34 (t, J=6.7 Hz, 2H), 1.89 (tdd, J=10.9, 7.4, 3.1 Hz, 3H), 1.56-1.44 (m, 2H), 1.36-1.20 (m, 2H), 1.11 (ddt, J=7.3, 4.6, 2.7 Hz, 2H), 1.00 (dt, J=8.1, 3.4 Hz, 2H). LC-MS (ESI+) Found: [M+H]$^+$, 633.2.

N-(2-(4-((4-(5-fluoro-2-(3-methylbutanoyl)-1H-indol-3-yl)-1H-1,2,3-triazol-1-yl)methyl)piperidin-1-yl)ethyl)-1-(4-(trifluoromethyl)phenyl)methanesulfonamide (162) (Code AB1306)

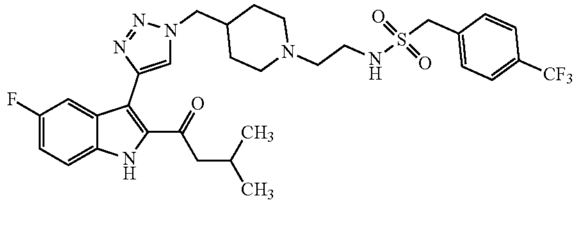 [SMILES: CC(C)CC(=O)c1[nH]c2ccc(F)cc2c1-c1cn(CC2CCN(CCNS(=O)(=O)Cc3ccc(C(F)(F)F)cc3)CC2)nn1]

Prepared by general method G using alkyne 99c (60 mg, 0.25 mmol), azide 5r (105 mg, 0.26 mmol), 2M aqueous of sodium ascorbate (432 μL, 0.86 mmol), 15% aqueous of copper(II) sulfate pentahydrate (358 μL, 0.21 mmol) and tetrahydrofuran-tert-butanol (617 μL). The crude product was purified chromatographically on silica gel (eluting gradient dichloromethane-methanol 98:2 to 96:4) to provide the title compound 162 as a white solid (107 mg, 67% yield). $^1$H NMR (400 MHz, $d_6$-DMSO) δ=12.04 (s, 1H), 8.63 (s, 1H), 7.82-7.72 (m, 3H), 7.61 (d, J=8.0 Hz, 2H), 7.53 (dd, J=9.0, 4.6 Hz, 1H), 7.23 (td, J=9.1, 2.6 Hz, 1H), 7.05 (s, 1H), 4.52 (s, 2H), 4.39 (d, J=7.0 Hz, 2H), 3.04 (d, J=6.3 Hz, 2H), 2.87 (dd, J=9.0, 5.6 Hz, 3H), 2.35 (s, 2H), 2.03-1.84 (m, 3H), 1.59 (tt, J=14.6, 9.7 Hz, 4H), 1.42-1.19 (m, 4H), 0.87 (t, J=7.4 Hz, 3H), 0.85 (m, 1H). LC-MS (ESI+) Found: [M+H]$^+$, 649.3.

N-(2-(4-((4-(2-butyryl-5-fluoro-1H-indol-3-yl)-1H-1,2,3-triazol-1-yl)methyl)piperidin-1-yl)ethyl)-1-(4-(trifluoromethyl)phenyl)methanesulfonamide (163) (Code AB1307)

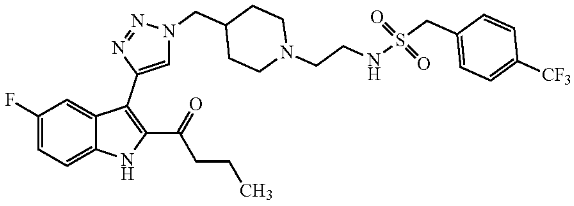 [SMILES: CCCC(=O)c1[nH]c2ccc(F)cc2c1-c1cn(CC2CCN(CCNS(=O)(=O)Cc3ccc(C(F)(F)F)cc3)CC2)nn1]

Prepared by general method G using alkyne 99f (60 mg, 0.26 mmol), azide 5r (111 mg, 0.27 mmol), 2M aqueous of sodium ascorbate (458 μL, 0.92 mmol), 15% aqueous of copper(II) sulfate pentahydrate (380 μL, 0.23 mmol) and tetrahydrofuran-tert-butanol (654 μL). The crude product was purified chromatographically on silica gel (eluting gradient dichloromethane-methanol 98:2 to 96:4) to provide the title compound 163 as a white solid (107 mg, 64% yield). $^1$H NMR (400 MHz, $d_6$-DMSO) δ=12.04 (s, 1H), 8.62 (s, 1H), 7.83-7.70 (m, 3H), 7.61 (d, J=8.0 Hz, 2H), 7.53 (dd, J=9.0, 4.6 Hz, 1H), 7.23 (td, J=9.1, 2.6 Hz, 1H), 7.04 (t, J=5.7 Hz, 1H), 4.52 (s, 2H), 4.39 (d, J=7.0 Hz, 2H), 3.04 (q, J=6.1 Hz, 2H), 2.87 (dd, J=9.4, 5.7 Hz, 2H), 2.77 (d, J=6.9 Hz, 2H), 2.35 (t, J=6.7 Hz, 2H), 2.23-2.04 (m, 1H), 2.04-1.80 (m, 3H), 1.67-1.46 (m, 2H), 1.38-1.20 (m, 3H), 0.85 (d, J=6.7 Hz, 3H). $^{13}$C NMR (101 MHz, $d_6$-DMSO) δ=193.3 ($C_{quat}$), 157.5 (d, J=233.2 Hz, $C_{quat}$), 140.0 ($C_{quat}$), 135.4 ($C_{quat}$), 133.1 ($C_{quat}$), 132.9 ($C_{quat}$), 131.6 ($C_{quat}$), 126.7 (d, J=9.8 Hz, $C_{quat}$), 136.6 (CH), 125.1 (CH), 125.0 (CH), 122.9 ($C_{quat}$), 114.8 (d, J=19.8 Hz, CH), 114.1 (d, J=10.1 Hz, CH), 110.6 (d, J=5.7 Hz, $C_{quat}$), 107.0 (d, J=23.1 Hz, CH), 57.9 ($CH_2$), 56.7 ($CH_2$), 54.5 ($CH_2$), 52.7 ($CH_2$), 48.6 ($CH_2$), 40.2 ($CH_2$), 29.1 ($CH_2$), 24.6 (CH), 22.3 ($CH_3$). LC-MS (ESI+) Found: [M+H]$^+$, 635.2.

N-(2-(4-((4-(2-acetyl-5-fluoro-1H-indol-3-yl)-1H-1,2,3-triazol-1-yl)methyl)piperidin-1-yl)ethyl)-1-(4-(trifluoromethyl)phenyl)methanesulfonamide (164) (Code AB1315)

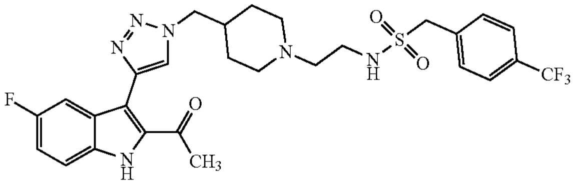 [SMILES: CC(=O)c1[nH]c2ccc(F)cc2c1-c1cn(CC2CCN(CCNS(=O)(=O)Cc3ccc(C(F)(F)F)cc3)CC2)nn1]

Prepared by general method G using alkyne 93 (60 mg, 0.30 mmol), azide 5r (127 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 164 as a pale yellow solid (124 mg, 69% yield). $^1$H NMR (400 MHz, $d_6$-DMSO) δ=12.06 (s, 1H), 8.62 (s, 1H), 7.94-7.70 (m, 3H), 7.61 (d, J=8.0 Hz, 2H), 7.54 (dd, J=9.0, 4.6 Hz, 1H), 7.24 (td, J=9.1, 2.6 Hz, 1H), 7.05 (t, J=5.5 Hz, 1H), 4.52 (s, 2H), 4.38 (d, J=7.0 Hz, 2H), 3.04 (dt, J=10.7, 5.5 Hz, 2H), 2.86 (dt, J=11.5, 3.3 Hz, 2H), 2.50 (s, 3H), 2.35 (t, J=6.7 Hz, 2H), 1.99-1.81 (m, 3H), 1.62-1.49 (m, 2H), 1.42-1.18 (m, 2H). $^{13}$C NMR (101 MHz, $d_6$-DMSO) δ=191.0 ($C_{quat}$), 157.5 (d, J=234.4 Hz, $C_{quat}$), 140.0 ($C_{quat}$), 135.4 ($C_{quat}$), 133.1 ($C_{quat}$), 133.0 ($C_{quat}$), 126.6 (d, J=10.1 Hz, $C_{quat}$), 125.1 (m, $C_{quat}$), 131.6 (CH), 125.1 (CH), 125.0 (CH), 122.9 ($C_{quat}$), 114.8 (d, J=26.5 Hz, CH), 114.1 (d, J=9.6 Hz, CH), 110.7 (d, J=6.3 Hz, $C_{quat}$), 106.8 (d, J=24.3 Hz, CH), 57.9 ($CH_2$), 56.7 ($CH_2$), 54.5 ($CH_2$), 52.7 ($CH_2$), 40.2 ($CH_2$), 36.6 (CH), 29.1 ($CH_2$), 28.7 ($CH_3$). LC-MS (ESI+) Found: $[M+H]^+$, 607.2. N-(2-(4-((4-(2-acetyl-5-fluoro-1H-indol-3-yl)-1H-1,2,3-triazol-1-yl) methyl)piperidin-1-yl)ethyl)-4-(2,6-difluorophenyl)piperidine-1-sulfonamide (165) (Code AB1316)

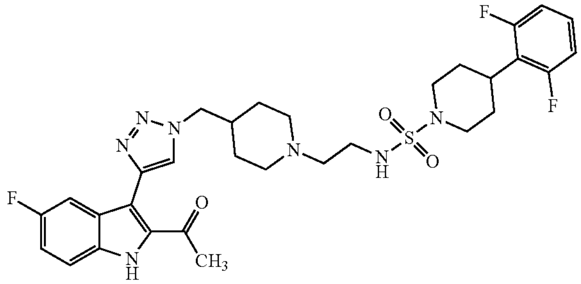 [SMILES: CC(=O)c1[nH]c2ccc(F)cc2c1-c1cn(CC2CCN(CCNS(=O)(=O)N3CCC(c4c(F)cccc4F)CC3)CC2)nn1]

Prepared by general method G using alkyne 93 (60 mg, 0.30 mmol), azide 88a (139 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 165 as a pale yellow solid (119 mg, 62% yield). $^1$H NMR (400 MHz, $d_6$-DMSO) δ=12.05 (s, 1H), 8.62 (s, 1H), 7.78 (dd, J=10.1, 2.6 Hz, 1H), 7.53 (dd, J=9.0, 4.6 Hz, 1H), 7.44-6.71 (m, 5H), 4.38 (d, J=7.1 Hz, 2H), 3.63 (d, J=12.0 Hz, 2H), 3.30 (s, 3H), 3.13-2.98 (m, 2H), 2.86 (d, J=11.1 Hz, 2H), 2.80-2.72 (m, 4H), 2.40 (t, J=7.1 Hz, 211), 2.04-1.85 (m, 4H), 1.85-1.69 (m, 2H), 1.53 (d, J=12.6 Hz, 2H), 1.29 (q, J=13.0 Hz, 211). LC-MS (ESI+) Found: $[M+H]^+$, 644.3.

N-(2-(4-((4-(2-acetyl-5-fluoro-1H-indol-3-yl)-1H-1,2,3-triazol-1-yl)methyl)piperidin-1-yl)ethyl)-4-(cyclopropylmethyl)benzenesulfonamide (166) (Code AB1317)

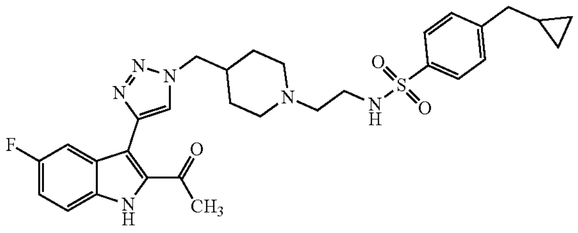 [SMILES: CC(=O)c1[nH]c2ccc(F)cc2c1-c1cn(CC2CCN(CCNS(=O)(=O)c3ccc(CC4CC4)cc3)CC2)nn1]

Prepared by general method G using alkyne 93 (60 mg, 0.30 mmol), azide 5Ao (118 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 166 as a pale yellow solid (122 mg, 71% yield). $^1$H NMR (400 MHz, $d_6$-DMSO) δ=12.06 (s, 1H), 8.60 (s, 1H), 7.85-7.77 (m, 1H), 7.77-7.68 (m, 2H), 7.53 (dd, J=9.0, 4.6 Hz, 1H), 7.48-7.35 (m, 3H), 7.24 (td, J=9.1, 2.6 Hz, 1H), 5.93-5.32 (m, 2H), 4.35 (d, J=7.1 Hz, 2H), 3.50-3.36 (m, 4H), 2.90-2.76 (m, 2H), 2.68 (d, J=11.2 Hz, 3H), 2.31-2.21 (m, 2H), 1.83 (qd, J=9.1, 3.5 Hz, 3H), 1.70-1.60 (m, 3H), 1.53-1.43 (m, 2H), 1.30-1.18 (m, 2H). LC-MS (ESI+) Found: $[M+H]^+$, 579.3.

(S)—N-(2-(3-((4-(2-acetyl-5-fluoro-1H-indol-3-yl)-1H-1,2,3-triazol-1-yl)methyl)pyrrolidin-1-yl)ethyl)-4-isobutylbenzenesulfonamide (167) (Code AB1318)

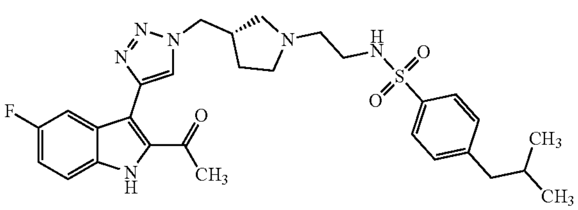 [SMILES: CC(=O)c1[nH]c2ccc(F)cc2c1-c1cn(C[C@H]2CCN(CCNS(=O)(=O)c3ccc(CC(C)C)cc3)C2)nn1]

Prepared by general method G using alkyne 93 (60 mg, 0.30 mmol), azide 5Be (114 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 167 as a pale yellow solid (125 mg, 74% yield). $^1$H NMR (400 MHz, $d_6$-DMSO) δ=12.08 (s, 1H), 8.64 (s, 1H), 7.87-7.65 (m, 3H), 7.55 (dd, J=9.0, 4.6 Hz, 1H), 7.52-7.45 (m, 1H), 7.41-7.30 (m, 2H), 7.24 (td, J=9.1, 2.6

Hz, 1H), 4.51-4.36 (m, 2H), 2.93-2.77 (m, 2H), 2.77-2.56 (m, 2H), 2.49 (s, 3H), 2.47 (d, J=7.3 Hz, 2H), 2.42-2.32 (m, 4H), 2.29 (dd, J=9.2, 5.4 Hz, 1H), 1.82 (dq, J=13.5, 6.4 Hz, 2H), 1.56-1.38 (m, 1H), 0.81 (d, J=6.6 Hz, 6H). $^{13}C$ NMR (101 MHz, $d_6$-DMSO) δ=191.0 ($C_{quat}$), 157.5 (d, J=234.8 Hz, $C_{quat}$), 146.0 ($C_{quat}$), 140.0 ($C_{quat}$), 138.1 ($C_{quat}$), 133.0 ($C_{quat}$), 126.6 (d, J=9.6 Hz, $C_{quat}$), 129.5 (CH), 126.4 (CH), 124.7 (CH), 119.6 ($C_{quat}$), 114.8 (d, J=27.7 Hz, CH), 114.2 (d, J=11.8 Hz, CH), 110.8 (d, J=5.7 Hz, $C_{quat}$), 106.8 (d, J=25.3 Hz, CH), 56.8 ($CH_2$), 54.2 ($CH_2$), 53.4 ($CH_2$), 52.8 ($CH_2$), 44.1 ($CH_2$), 41.5 ($CH_2$), 37.7 (CH), 27.5 ($CH_2$), 29.5 (CH), 28.7 ($CH_3$), 21.9 ($CH_3$). LC-MS (ESI+) Found: $[M+H]^+$, 567.3.

(R)—N-(2-(3-((4-(2-acetyl-5-fluoro-1H-indol-3-yl)-1H-1,2,3-triazol-1-yl)methyl)pyrrolidin-1-yl)ethyl)-4-isobutylbenzenesulfonamide (168) (Code AB1319)

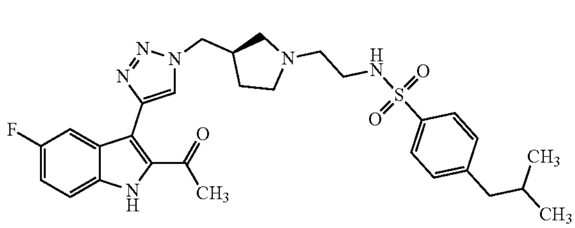 [SMILES: CC(=O)c1[nH]c2ccc(F)cc2c1-c1cn(C[C@@H]2CCN(CCNS(=O)(=O)c3ccc(CC(C)C)cc3)C2)nn1]

Prepared by general method G using alkyne 93 (60 mg, 0.30 mmol), azide 5Bd (114 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 168 as a pale yellow solid (114 mg, 67% yield). $^1H$ NMR (400 MHz, $d_6$-DMSO) δ=12.07 (s, 1H), 8.64 (s, 1H), 7.77 (dd, J=10.1, 2.6 Hz, 1H), 7.73-7.67 (m, 2H), 7.54 (dd, J=9.0, 4.7 Hz, 1H), 7.48 (dt, J=8.4, 4.0 Hz, 1H), 7.35-7.28 (m, 2H), 7.24 (td, J=9.1, 2.6 Hz, 1H), 4.51-4.31 (m, 2H), 2.96-2.76 (m, 2H), 2.76-2.60 (m, 2H), 2.49 (s, 3H), 2.47 (d, J=7.2 Hz, 2H), 2.44-2.29 (m, 4H), 2.29 (td, J=10.1, 6.8 Hz, 1H), 1.88-1.76 (m, 2H), 1.58-1.37 (m, 1H), 0.81 (d, J=6.6 Hz, 6H). $^{13}C$ NMR (101 MHz, $d_6$-DMSO) δ=191.0 ($C_{quat}$), 157.6 (d, J=233.7 Hz, $C_{quat}$), 146.0 ($C_{quat}$), 134.0 ($C_{quat}$), 138.1 ($C_{quat}$), 129.5 (CH), 126.6 (d, J=10.6 Hz, $C_{quat}$), 126.4 (CH), 124.7 (CH), 123.7 ($C_{quat}$), 114.8 (d, J=26.4 Hz, CH), 114.2 (d, J=10.6 Hz, CH), 111.8 (d, J=5.6 Hz, $C_{quat}$), 108.9 ($C_{quat}$), 106.8 (d, J=23.7 Hz, CH), 56.9 ($CH_2$), 54.3 ($CH_2$), 53.4 ($CH_2$), 52.8 ($CH_2$), 44.1 ($CH_2$), 41.6 ($CH_2$), 37.7 (CH), 29.5 (CH), 28.7 ($CH_3$), 27.5 ($CH_2$), 21.9 ($CH_3$). LC-MS (ESI+) Found: $[M+H]^+$, 567.3.

N-(2-(4-(4-(2-acetyl-5-fluoro-1H-indol-3-yl)-1H-1,2,3-triazol-1-yl)piperidin-1-yl)ethyl)-4-isobutylbenzenesulfonamide (169) (Code AB1321)

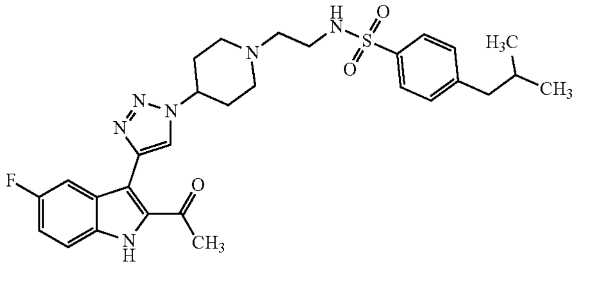 [SMILES: CC(=O)c1[nH]c2ccc(F)cc2c1-c1cn(C2CCN(CCNS(=O)(=O)c3ccc(CC(C)C)cc3)CC2)nn1]

Prepared by general method G using alkyne 93 (60 mg, 0.30 mmol), azide 5Bg (114 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 169 as a pale yellow solid (109 mg, 64% yield). $^1H$ NMR (400 MHz, $d_6$-DMSO) δ 12.05 (s, 1H), 8.65 (s, 1H), 7.90-7.69 (m, 3H), 7.60-7.51 (m, 1H), 7.47 (t, J=5.8 Hz, 1H), 7.43-7.32 (m, 2H), 7.23 (td, J=9.1, 2.6 Hz, 1H), 4.63-4.49 (m, 1H), 2.90 (q, J=6.4 Hz, 2H), 2.82 (d, J=11.1 Hz, 2H), 2.53-2.52 (m, 2H), 2.46 (s, 3H), 2.35 (t, J=6.9 Hz, 2H), 2.25-1.98 (m, 6H), 1.86 (hept, J=6.8 Hz, 1H), 0.85 (d, J=6.6 Hz, 6H). LC-MS (ESI+) Found: $[M+H]^+$, 567.3.

N-(2-(4-((4-(2-acetyl-5-fluoro-1H-indol-3-yl)-1H-1,2,3-triazol-1-yl)methyl)piperidin-1-yl)ethyl)-4-(2-fluoropyridin-3-yl)piperidine-1-sulfonamide (170) (Code AB1322)

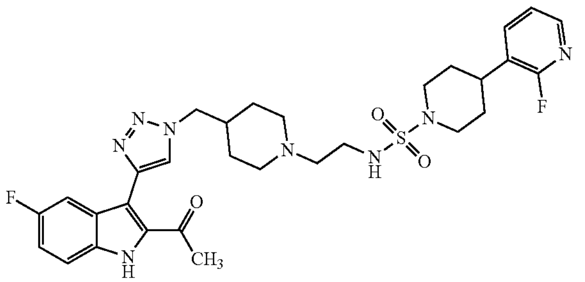 [SMILES: CC(=O)c1[nH]c2ccc(F)cc2c1-c1cn(CC2CCN(CCNS(=O)(=O)N3CCC(c4cccnc4F)CC3)CC2)nn1]

Prepared by general method G using alkyne 93 (60 mg, 0.30 mmol), azide 88b (133 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 170 as a pale yellow solid (118 mg, 63% yield). $^1H$ NMR (400 MHz, $d_6$-DMSO) δ=12.05 (s, 1H), 8.62 (s, 1H), 8.08 (dt, J=4.9, 1.6 Hz, 1H), 7.88 (ddd, J=9.9, 7.5, 1.9 Hz, 1H), 7.78 (dd, J=10.1, 2.6 Hz, 1H), 7.53 (dd, J=9.0, 4.6 Hz, 1H), 7.31 (ddd, J=7.0, 4.8, 1.8 Hz, 1H), 7.24 (td, J=9.1, 2.6 Hz, 1H), 7.18-7.02 (m, 1H), 4.38 (d, J=7.0 Hz, 2H), 3.71-3.54 (m, 2H), 3.01 (q, J=6.7 Hz, 2H), 2.85 (tt, J=7.9, 4.2 Hz, 3H), 2.77 (td, J=12.2, 2.4 Hz, 2H), 2.50 (s, 3H), 2.40 (t, J=7.0 Hz, 2H), 2.05-1.76 (m, 5H), 1.69 (qd, J=12.4, 3.8 Hz, 2H), 1.62-1.50 (m, 2H), 1.31-1.22 (m, 2H). LC-MS (ESI+) Found: $[M+H]^+$, 627.3.

N-(2-(4-((4-(2-acetyl-5-fluoro-1H-indol-3-yl)-1H-1,2,3-triazol-1-yl)methyl)piperidin-1-yl)ethyl)-2'-fluoro-6'-hydroxy-[1,1'-biphenyl]-4-sulfonamide (171) (Code AB1381)

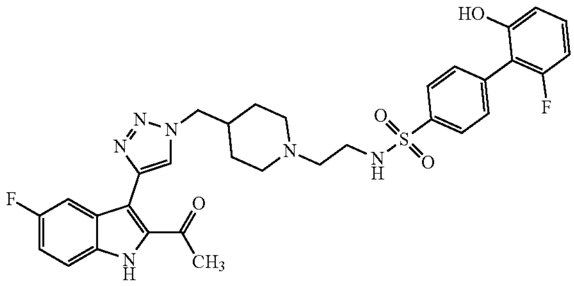

Prepared by general method G using alkyne 93 (60 mg, 0.30 mmol), azide 5Ap (136 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 171 as a pale yellow solid (117 mg, 62% yield). $^1$H NMR (400 MHz, $d_6$-DMSO)=12.06 (s, 1H), 10.11 (s, 1H), 8.60 (s, 1H), 7.92-7.75 (m, 3H), 7.66-7.46 (m, 4H), 7.27-7.16 (m, 2H), 6.82 (d, J=8.2 Hz, 1H), 6.73 (ddd, J=9.5, 8.2, 1.0 Hz, 1H), 4.35 (d, J=7.1 Hz, 2H), 2.91 (t, J=6.9 Hz, 2H), 2.74 (dt, J=11.7, 3.4 Hz, 2H), 2.32 (t, J=6.9 Hz, 2H), 2.01-1.78 (m, 3H), 1.58-1.41 (m, 2H), 1.40-1.13 (m, 4H), 0.90-0.79 (m, 1H). LC-MS (ESI+) Found: $[M+H]^+$, 635.2.

N-(2-(4-((4-(2-acetyl-5-fluoro-1H-indol-3-yl)-1H-1,2,3-triazol-1-yl)methyl)piperidin-1-yl)ethyl)-2'-fluoro-[1,1'-biphenyl]-4-sulfonamide (172) (Code AB1390)

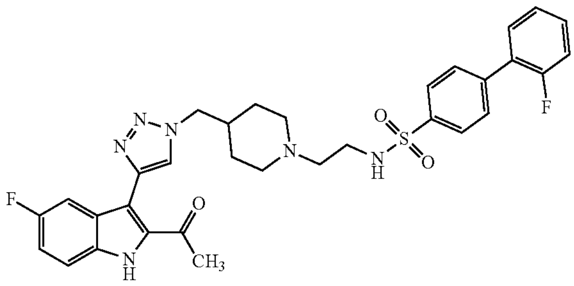 [SMILES: CC(=O)c1[nH]c2ccc(F)cc2c1-c1cn(CC2CCN(CCNS(=O)(=O)c3ccc(-c4ccccc4F)cc3)CC2)nn1]

Prepared by general method G using alkyne 93 (60 mg, 0.30 mmol), azide 5Aq (131 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 172 as a pale yellow solid (124 mg, 67% yield). $^1$H NMR (400 MHz, $d_6$-DMSO) δ=12.06 (s, 1H), 8.60 (s, 1H), 8.02-7.87 (m, 2H), 7.84-7.72 (m, 3H), 7.66-7.51 (m, 3H), 7.51-7.43 (m, 1H), 7.38-7.29 (m, 2H), 7.23 (td, J=9.1, 2.6 Hz, 1H), 4.35 (d, J=7.0 Hz, 2H), 2.90 (t, J=6.7 Hz, 2H), 2.72 (dt, J=11.9, 3.4 Hz, 2H), 2.47 (s, 3H), 2.32 (q, J=6.6 Hz, 2H), 1.85 (t, J=11.2 Hz, 3H), 1.46 (dd, J=13.2, 3.5 Hz, 2H), 1.22 (qd, J=11.5, 3.4 Hz, 2H). LC-MS (ESI+) Found: $[M+H]^+$, 619.2.

N-(2-(4-((4-(2-acetyl-5-fluoro-1H-indol-3-yl)-1H-1,2,3-triazol-1-yl)methyl)piperidin-1-yl)ethyl)-2'-cyano-6'-(trifluoromethyl)-[1,1'-biphenyl]-4-sulfonamide (173) (Code AB1393)

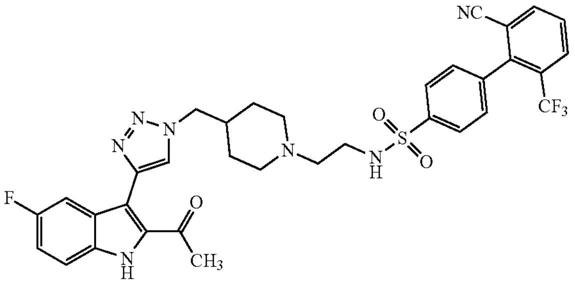 [SMILES: CC(=O)c1[nH]c2ccc(F)cc2c1-c1cn(CC2CCN(CCNS(=O)(=O)c3ccc(-c4c(C#N)cccc4C(F)(F)F)cc3)CC2)nn1]

Prepared by general method G using alkyne 93 (60 mg, 0.30 mmol), azide 5Ar (154 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 173 as a white solid (141 mg, 68% yield). $^1$H NMR (400 MHz, $d_6$-DMSO) δ=12.05 (s, 1H), 8.60 (s, 1H), 8.27 (dd, J=7.9, 1.2 Hz, 1H), 8.19 (dd, J=8.3, 1.2 Hz, 1H), 8.01-7.90 (m, 2H), 7.86 (t, J=8.0 Hz, 1H), 7.77 (dd, J=10.1, 2.6 Hz, 1H), 7.62 (d, J=8.2 Hz, 3H), 7.53 (dd, J=9.0, 4.6 Hz, 1H), 7.23 (td, J=9.1, 2.6 Hz, 1H), 4.35 (d, J=7.0 Hz, 2H), 2.94 (d, J=6.9 Hz, 2H), 2.77-2.66 (m, 2H), 2.50 (s, 3H), 2.25 (t, J=6.9 Hz, 2H), 1.84 (tt, J=11.5, 5.1 Hz, 3H), 1.47 (d, J=12.6 Hz, 2H), 1.26-1.18 (m, 2H). LC-MS (ESI+) Found: $[M+H]^+$, 694.2.

N-(2-(4-((4-(2-acetyl-5-fluoro-1H-indol-3-yl)-1H-1,2,3-triazol-1-yl)methyl)piperidin-1-yl)ethyl)-2'-(trifluoromethyl)-[1,1'-biphenyl]-4-sulfonamide (174) (Code AB1394)

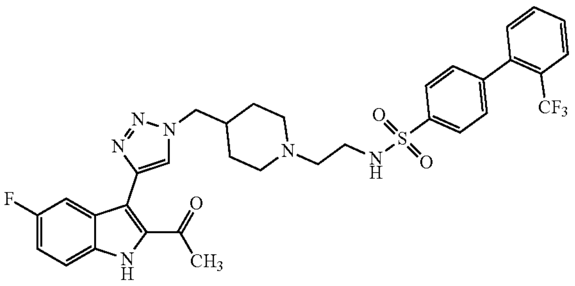

Prepared by general method G using alkyne 93 (60 mg, 0.30 mmol), azide 5As (146 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 174 as a white solid (136 mg, 68% yield). $^1H$ NMR (400 MHz, $d_6$-DMSO) δ=12.06 (s, 1H), 8.61 (s, 1H), 7.88 (d, J=6.6 Hz, 2H), 7.84 (dd, J=7.9, 1.3 Hz, 1H), 7.79 (dd, J=10.1, 2.6 Hz, 1H), 7.74 (td, J=7.6, 1.4 Hz, 1H), 7.69-7.59 (m, 2H), 7.57-7.50 (m, 3H), 7.49-7.39 (m, 1H), 7.23 (td, J=9.1, 2.6 Hz, 1H), 4.36 (d, J=7.1 Hz, 2H), 2.93 (t, J=6.9 Hz, 2H), 2.72 (dd, J=9.5, 5.0 Hz, 2H), 2.50 (s, 3H), 2.29 (t, J=6.9 Hz, 2H), 1.96-1.77 (m, 3H), 1.53-1.38 (m, 2H), 1.38-1.18 (m, 2H). LC-MS (ESI+) Found: $[M+H]^+$, 669.2.

N-(2-(4-((4-(2-acetyl-5-fluoro-1H-indol-3-yl)-1H-1,2,3-triazol-1-yl)methyl)piperidin-1-yl)ethyl)-2'-fluoro-6'-methoxy-[1,1'-biphenyl]-4-sulfonamide (175) (AB1401)

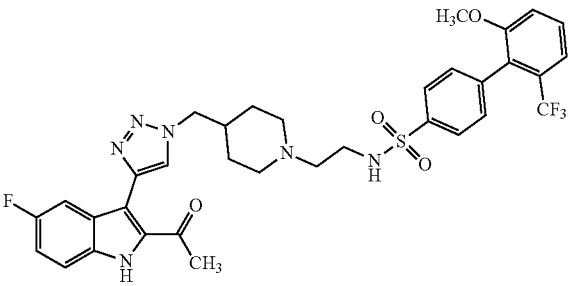

Prepared by general method G using alkyne 93 (60 mg, 0.30 mmol), azide 5At (140 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 175 as a pale yellow solid (138 mg, 72% yield). H NMR (400 MHz, $d_6$-DMSO) δ=12.06 (s, 1H), 8.60 (s, 1H), 7.85 (d, J=8.2 Hz, 2H), 7.78 (dd, J=10.1, 2.6 Hz, 1H), 7.54 (dd, J=10.4, 6.2 Hz, 4H), 7.41 (td, J=8.4, 6.8 Hz, 1H), 7.23 (td, J=9.1, 2.6 Hz, 1H), 6.98 (d, J=8.4 Hz, 1H), 6.92 (t, J=8.9 Hz, 1H), 4.35 (d, J=7.0 Hz, 2H), 3.74 (s, 3H), 2.92 (t, J=6.7 Hz, 2H), 2.73 (d, J=10.9 Hz, 2H), 2.47 (s, 3H), 2.31 (q, J=6.3 Hz, 2H), 1.85 (t, J=11.1 Hz, 3H), 1.56-1.41 (m, 2H), 1.23 (qd, J=11.5, 3.5 Hz, 2H). LC-MS (ESI+) Found: $[M+H]^+$, 649.2.

isobutyl 5-fluoro-3-(1-((1-(2-((2'-fluoro-6'-hydroxy-[1,1'-biphenyl])-4-sulfonamido)ethyl)piperidin-4-yl)methyl)-1H-1,2,3-triazol-4-yl)-1H-indole-2-carboxylate (176) (Code AB1402)

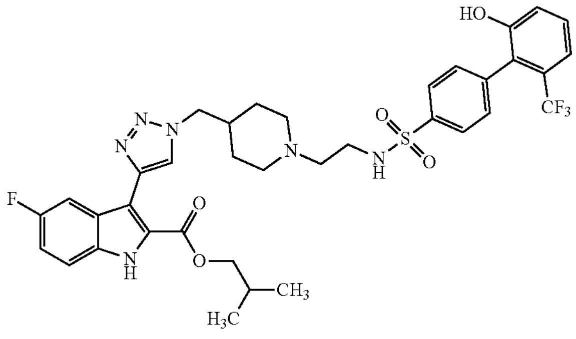 [SMILES: CC(C)COC(=O)c1[nH]c2ccc(F)cc2c1-c1cn(CC2CCN(CCNS(=O)(=O)c3ccc(-c4c(O)cccc4C(F)(F)F)cc3)CC2)nn1]

Prepared by general method G using alkyne 14f (60 mg, 0.23 mmol), azide 5Ap (105 mg, 0.24 mmol), 2M aqueous of sodium ascorbate (405 μL, 0.81 mmol), 15% aqueous of copper(II) sulfate pentahydrate (337 μL, 0.20 mmol) and tetrahydrofuran-tert-butanol (580 μL). The crude product was purified chromatographically on silica gel (eluting gradient dichloromethane-methanol 98:2 to 96:4) to provide the title compound 176 as a pale yellow solid (107 mg, 67% yield). $^1H$ NMR (400 MHz, $d_6$-DMSO) δ=12.01 (s, 1H), 10.09 (s, 1H), 8.54 (s, 1H), 8.03 (dd, J=10.3, 2.6 Hz, 1H), 7.91-7.79 (m, 2H), 7.62-7.51 (m, 4H), 7.42-7.10 (m, 2H), 6.82 (d, J=8.2 Hz, 1H), 6.73 (ddd, J=9.5, 8.2, 1.0 Hz, 1H), 4.34 (d, J=7.0 Hz, 2H), 4.11 (d, J=6.7 Hz, 2H), 2.91 (t, J=6.8 Hz, 2H), 2.73 (dt, J=11.6, 3.6 Hz, 2H), 2.31 (t, J=6.9 Hz, 2H), 2.10-1.93 (m, 1H), 1.84 (qd, J=10.6, 4.9 Hz, 3H), 1.54-1.38 (m, 2H), 1.23 (qd, J=11.7, 3.5 Hz, 2H), 0.94 (d, J=6.7 Hz, 6H). LC-MS (ESI+) Found: $[M+H]^+$, 693.3.

(S)—N-(2-(3-((4-(2-acetyl-5-fluoro-1H-indol-3-yl)-1H-1,2,3-triazol-1-yl)methyl)piperidin-1-yl)ethyl)-4-isobutylbenzenesulfonamide (177) (Code AB1403)

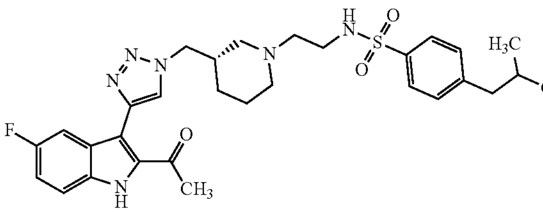

Prepared by general method G using alkyne 93 (60 mg, 0.30 mmol), azide 5Bf (119 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 177 as a pale yellow solid (112 mg, 65% yield). $^1H$ NMR (400 MHz, $d_6$-DMSO) δ=12.07 (s, 1H), 8.60 (s, 1H), 7.78 (dd, J=10.1, 2.6 Hz, 1H), 7.69-7.57 (m, 2H), 7.54 (dd, J=9.0, 4.6 Hz, 1H), 7.39 (t, J=5.7 Hz, 1H), 7.29 (dd, J=9.1, 2.5 Hz, 2H), 7.23 (dd, J=9.1, 2.6 Hz, 1H), 4.37 (d, J=7.2 Hz, 2H), 2.81 (q, J=6.5 Hz, 2H), 2.45 (s, 2H), 2.22 (t, J=7.0 Hz, 2H), 2.12 (s, 2H), 1.95 (m, 1H), 1.88-1.75 (m, 2H), 1.65-1.47 (m, 2H), 1.46-1.18 (m, 2H), 1.14 (s, 3H), 1.09-0.94 (m, 1H), 0.80 (d, J=6.6 Hz, 6H). LC-MS (ESI+) Found: $[M+H]^+$, 581.3.

N-(2-(3-((4-(2-acetyl-5-fluoro-1H-indol-3-yl)-1H-1,2,3-triazol-1-yl)methyl)azetidin-1-yl)ethyl)-4-isobutylbenzenesulfonamide (178) (Code AB1404)

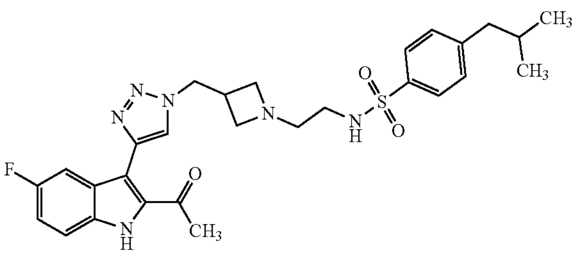 [SMILES: CC(=O)c1[nH]c2ccc(F)cc2c1-c1cn(CC2CN(CCNS(=O)(=O)c3ccc(CC(C)C)cc3)C2)nn1]

Prepared by general method G using alkyne 93 (60 mg, 0.30 mmol), azide 5Bc (110 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 178 as a pale yellow solid (121 mg, 73% yield). $^1$H NMR (400 MHz, $d_6$-DMSO) δ=12.07 (s, 1H), 8.61 (s, 1H), 7.78 (dd, J=10.1, 2.6 Hz, 1H), 7.73-7.66 (m, 2H), 7.54 (dd, J=9.0, 4.6 Hz, 1H), 7.43 (d, J=6.0 Hz, 1H), 7.40-7.31 (m, 2H), 7.24 (td, J=9.1, 2.6 Hz, 1H), 4.71-4.55 (m, 2H), 3.25-3.10 (m, 2H), 3.02-2.81 (m, 3H), 2.66 (q, J=6.0 Hz, 2H), 2.48 (d, J=1.4 Hz, 2H), 2.35 (t, J=6.8 Hz, 2H), 1.83 (hept, J=6.8 Hz, 1H), 1.14 (s, 3H), 0.83 (d, J=6.6 Hz, 6H). LC-MS (ESI+) Found: $[M+H]^+$, 553.2.

N-(2-(4-((4-(5-fluoro-2-(hydroxymethyl)-1H-indol-3-yl)-1H-1,2,3-triazol-1-yl)methyl)piperidin-1-yl)ethyl)-4-isobutylbenzenesulfonamide (179) (Code AB1405)

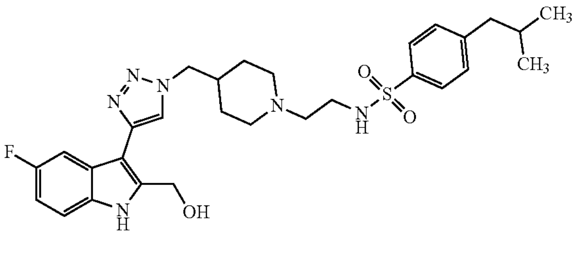 [SMILES: CC(C)Cc1ccc(S(=O)(=O)NCCN2CCC(Cn3cc(-c4c(CO)[nH]c5ccc(F)cc45)nn3)CC2)cc1]

Prepared by general method G using alkyne 103 (60 mg, 0.32 mmol), azide 5h (126 mg, 0.33 mmol), 2M aqueous of sodium ascorbate (555 μL, 1.11 mmol), 15% aqueous of copper(II) sulfate pentahydrate (460 μL, 0.28 mmol) and tetrahydrofuran-tert-butanol (793 μL). The crude product was purified chromatographically on silica gel (eluting gradient dichloromethane-methanol 98:2 to 96:4) to provide the title compound 179 as a yellow solid (113 mg, 63% yield). LC-MS (ESI+) Found: $[M+H]^+$, 569.3.

2'-fluoro-N-(2-(4-((4-(5-fluoro-2-(hydroxymethyl)-1H-indol-3-yl)-1H-1,2,3-triazol-1-yl)methyl)piperidin-1-yl)ethyl)-6'-hydroxy-[1,1'-biphenyl]-4-sulfonamide (180) (Code AB1406)

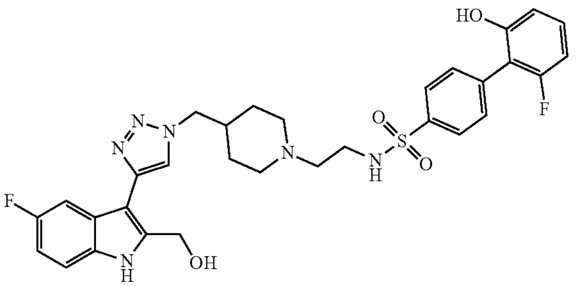 [SMILES: O=S(=O)(NCCN1CCC(Cn2cc(-c3c(CO)[nH]c4ccc(F)cc34)nn2)CC1)c1ccc(-c2c(O)cccc2F)cc1]

Prepared by general method G using alkyne 103 (60 mg, 0.32 mmol), azide 5Ap (144 mg, 0.33 mmol), 2M aqueous of sodium ascorbate (555 μL, 1.11 mmol), 15% aqueous of copper(II) sulfate pentahydrate (460 μL, 0.28 mmol) and tetrahydrofuran-tert-butanol (793 μL). The crude product was purified chromatographically on silica gel (eluting gradient dichloromethane-methanol 98:2 to 95:5) to provide the title compound 180 as a yellow solid (119 mg, 60% yield). LC-MS (ESI+) Found: $[M+H]^+$, 623.2.

2'-fluoro-N-(2-(4-((4-(5-fluoro-2-propionyl-1H-indol-3-yl)-1H-1,2,3-triazol-1-yl)methyl)piperidin-1-yl)ethyl)-6'-hydroxy-[1,1'-biphenyl]-4-sulfonamide (181) (Code AB1415)

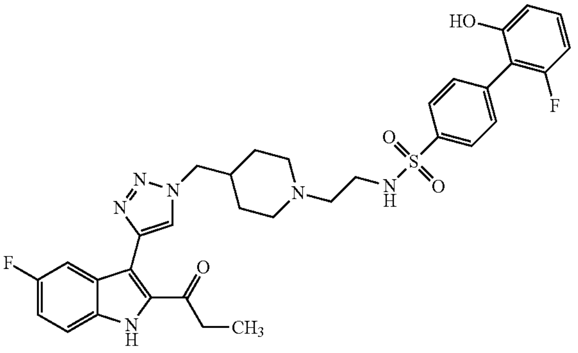 [SMILES: CCC(=O)c1[nH]c2ccc(F)cc2c1-c1cn(CC2CCN(CCNS(=O)(=O)c3ccc(-c4c(O)cccc4F)cc3)CC2)nn1]

Prepared by general method G using alkyne 99a (60 mg, 0.28 mmol), azide 5Ap (127 mg, 0.29 mmol), 2M aqueous of sodium ascorbate (488 μL, 0.98 mmol), 15% aqueous of copper(II) sulfate pentahydrate (404 μL, 0.24 mmol) and tetrahydrofuran-tert-butanol (700 μL). The crude product was purified chromatographically on silica gel (eluting gradient dichloromethane-methanol 98:2 to 96:4) to provide the title compound 181 as a pale yellow solid (124 mg, 69% yield). $^1$H NMR (400 MHz, $d_6$-DMSO) δ=12.04 (s, 1H), 10.08 (s, 1H), 8.63 (s, 1H), 7.90-7.76 (m, 3H), 7.65-7.48 (m, 4H), 7.30-7.18 (m, 2H), 6.81 (dd, J=8.2, 1.1 Hz, 1H), 6.73 (ddd, J=9.5, 8.3, 1.0 Hz, 1H), 4.36 (d, J=7.0 Hz, 2H), 2.96-2.85 (m, 4H), 2.74 (d, J=10.9 Hz, 2H), 2.38-2.26 (m, 2H), 1.98-1.79 (m, 3H), 1.47 (d, J=12.0 Hz, 2H), 1.28-1.20 (m, 2H), 1.05 (t, J=7.2 Hz, 3H). LC-MS (ESI+) Found: $[M+H]^+$, 649.2.

N-(2-(4-((4-(5-fluoro-2-propionyl-1H-indol-3-yl)-1H-1,2,3-triazol-1-yl)methyl)piperidin-1-yl)ethyl)-2',6'-dimethoxy-[1,1'-biphenyl]-4-sulfonamide (182) (Code AB1416)

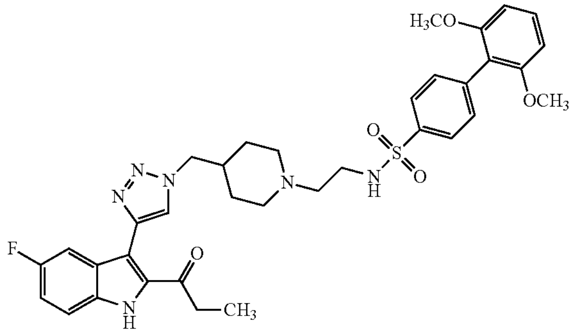 [SMILES: CCC(=O)c1[nH]c2ccc(F)cc2c1-c1cn(CC2CCN(CCNS(=O)(=O)c3ccc(-c4c(OC)cccc4OC)cc3)CC2)nn1]

Prepared by general method G using alkyne 99a (60 mg, 0.28 mmol), azide 5Ai (135 mg, 0.29 mmol), 2M aqueous of sodium ascorbate (488 μL, 0.98 mmol), 15% aqueous of copper(II) sulfate pentahydrate (404 μL, 0.24 mmol) and tetrahydrofuran-tert-butanol (700 μL). The crude product was purified chromatographically on silica gel (eluting gradient dichloromethane-methanol 98:2 to 96:4) to provide the title compound 182 as a pale yellow solid (120 mg, 64% yield). $^1$H NMR (400 MHz, $d_6$-DMSO) δ=12.04 (s, 1H), 8.64 (s, 1H), 7.82 (dd, J=10.1, 2.6 Hz, 1H), 7.79-7.73 (m, 2H), 7.54 (dd, J=9.0, 4.7 Hz, 1H), 7.49 (s, 1H), 7.45-7.39 (m, 2H), 7.32 (t, J=8.4 Hz, 1H), 7.23 (td, J=9.1, 2.6 Hz, 1H), 6.74 (d, J=8.4 Hz, 2H), 4.36 (d, J=7.1 Hz, 2H), 3.66 (s, 6H), 2.93 (q, J=7.1 Hz, 4H), 2.80-2.66 (m, 2H), 2.37-2.27 (m, 2H), 1.96-1.79 (m, 3H), 1.48 (d, J=12.2 Hz, 2H), 1.29-1.21 (m, 2H), 1.06 (t, J=7.2 Hz, 3H). LC-MS (ESI+) Found: $[M+H]^+$, 675.3.

N-(2-(4-((4-(5-fluoro-2-propionyl-1H-indol-3-yl)-1H-1,2,3-triazol-1-yl)methyl)piperidin-1-yl)ethyl)-1-(4-(trifluoromethyl)phenyl)methanesulfonamide (183) (Code AB1417)

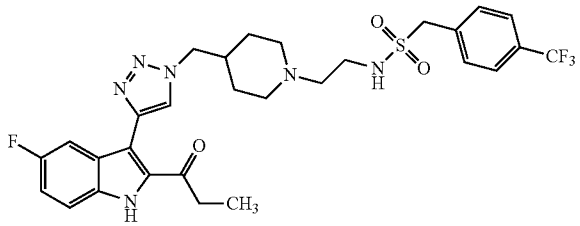 [SMILES: CCC(=O)c1[nH]c2ccc(F)cc2c1-c1cn(CC2CCN(CCNS(=O)(=O)Cc3ccc(C(F)(F)F)cc3)CC2)nn1]

Prepared by general method G using alkyne 99a (60 mg, 0.28 mmol), azide 5r (119 mg, 0.29 mmol), 2M aqueous of sodium ascorbate (488 μL, 0.98 mmol), 15% aqueous of copper(II) sulfate pentahydrate (404 μL, 0.24 mmol) and tetrahydrofuran-tert-butanol (700 μL). The crude product was purified chromatographically on silica gel (eluting gradient dichloromethane-methanol 98:2 to 96:4) to provide the title compound 183 as a white solid (109 mg, 63% yield). $^1$H NMR (400 MHz, $d_6$-DMSO) δ=12.05 (s, 1H), 8.65 (s, 1H), 7.81 (dd, J=10.1, 2.6 Hz, 1H), 7.74 (d, J=8.0 Hz, 2H), 7.61 (d, J=8.1 Hz, 2H), 7.54 (dd, J=9.0, 4.6 Hz, 1H), 7.23 (td, J=9.1, 2.6 Hz, 1H), 7.04 (t, J=5.5 Hz, 1H), 4.52 (s, 2H), 4.39 (d, J=7.0 Hz, 2H), 3.04 (q, J=6.1 Hz, 2H), 2.93 (q, J=7.2 Hz, 2H), 2.86 (dt, J=11.6, 3.4 Hz, 2H), 2.35 (t, J=6.7 Hz, 2H), 2.04-1.84 (m, 3H), 1.59-1.51 (m, 2H), 1.29 (tt, J=11.5, 5.8 Hz, 2H), 1.06 (t, J=7.2 Hz, 3H). LC-MS (ESI+) Found: $[M+H]^+$, 621.2.

N-(2-(4-((4-(2-acetyl-5-fluoro-1H-indol-3-yl)-1H-1,2,3-triazol-1-yl)methyl)piperidin-1-yl)ethyl)-2'-hydroxy-[1,1'-biphenyl]-4-sulfonamide (184) (Code AB1450)

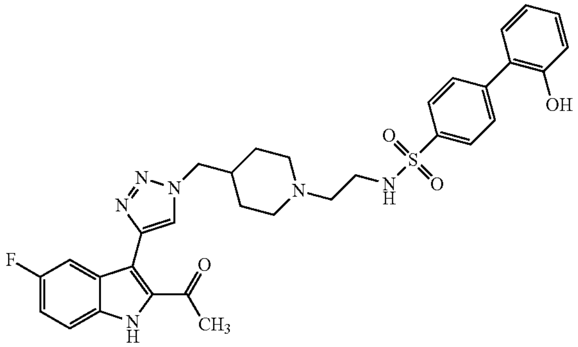 [SMILES: CC(=O)c1[nH]c2ccc(F)cc2c1-c1cn(CC2CCN(CCNS(=O)(=O)c3ccc(-c4ccccc4O)cc3)CC2)nn1]

Prepared by general method G using alkyne 93 (60 mg, 0.30 mmol), azide 5Au (130 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 184 as a white solid (122 mg, 66% yield). $^1$H NMR (400 MHz, $d_6$-DMSO) δ=12.05 (s, 1H), 9.75 (s, 1H), 8.60 (s, 1H), 7.85-7.71 (m, 5H), 7.53 (dd, J=9.0, 4.6 Hz, 1H), 7.50 (s, 1H), 7.30 (dd, J=7.6, 1.7 Hz, 1H), 7.27-7.16 (m, 2H), 6.97 (dd, J=8.1, 1.2 Hz, 1H), 6.89 (td, J=7.4, 1.2 Hz, 1H), 4.35 (d, J=7.0 Hz, 2H), 2.89 (t, J=6.9 Hz, 2H), 2.74 (dd, J=9.4, 5.5 Hz, 2H), 2.48 (s, 1H), 2.32 (t, J=6.8 Hz, 2H), 1.86 (t, J=11.3 Hz, 3H), 1.53-1.38 (m, 2H), 1.22 (dq, J=11.0, 5.3 Hz, 2H), 1.14 (s, 2H). LC-MS (ESI+) Found: $[M+H]^+$, 617.2.

N-(2-(4-((4-(2-acetyl-5-fluoro-1H-indol-3-yl)-1H-1,2,3-triazol-1-yl)methyl)piperidin-1-yl)ethyl)-2'-fluoro-6'-(trifluoromethyl)-[1,1'-biphenyl]-4-sulfonamide (185) (Code AB1451)

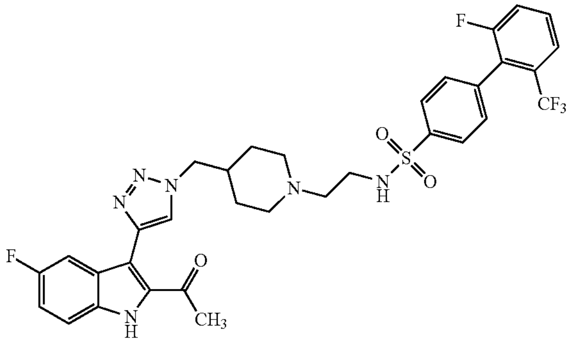 [SMILES: CC(=O)c1[nH]c2ccc(F)cc2c1-c1cn(CC2CCN(CCNS(=O)(=O)c3ccc(-c4c(F)cccc4C(F)(F)F)cc3)CC2)nn1]

Prepared by general method G using alkyne 93 (60 mg, 0.30 mmol), azide 5Av (152 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 185 as a white solid (133 mg, 65% yield). $^1$H NMR (400 MHz, $d_6$-DMSO) δ=12.05 (s, 1H), 8.60 (s, 1H), 7.93-7.88 (m, 2H), 7.78 (dd, J=10.2, 2.6 Hz, 1H), 7.74-7.64 (m, 3H), 7.63 (s, 1H), 7.58-7.51 (m, 3H), 7.23 (td, J=9.1, 2.6 Hz, 1H), 4.35 (d, J=7.0 Hz, 2H), 2.94 (t, J=6.9 Hz, 2H), 2.70 (dt, J=10.9, 3.7 Hz, 2H), 2.48 (s, 3H), 2.26 (t, J=6.8 Hz, 2H), 1.97-1.77 (m, 3H), 1.53-1.42 (m, 2H), 1.34-1.21 (m, 2H). LC-MS (ESI+) Found: $[M+H]^+$, 687.2.

N-(2-(4-((4-(2-acetyl-5-fluoro-1H-indol-3-yl)-1H-1,2,3-triazol-1-yl)methyl)piperidin-1-yl)ethyl)-2'-cyano-6'-methyl-[1,1'-biphenyl]-4-sulfonamide (186) (Code AB1452)

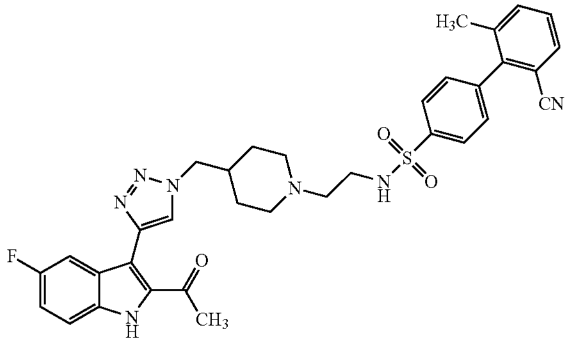 [SMILES: CC(=O)c1[nH]c2ccc(F)cc2c1-c1cn(CC2CCN(CCNS(=O)(=O)c3ccc(-c4c(C)cccc4C#N)cc3)CC2)nn1]

Prepared by general method G using alkyne 93 (60 mg, 0.30 mmol), azide 5Aw (137 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 186 as a white solid (139 mg, 73% yield). $^1$H NMR (400 MHz, $d_6$-DMSO) δ=12.05 (s, 1H), 8.60 (s, 1H), 8.03-7.85 (m, 2H), 7.85-7.72 (m, 2H), 7.69-7.44 (m, 6H), 7.24 (td, J=9.1, 2.6 Hz, 1H), 4.44-4.26 (m, 2H), 3.05-2.87 (m, 2H), 2.82-2.64 (m, 2H), 2.49 (s, 3H), 2.37-2.23 (m, 2H), 2.11 (d, J=5.0 Hz, 3H), 1.83 (t, J=11.1 Hz, 3H), 1.47 (d, J=12.4 Hz, 2H), 1.24 (d, J=6.8 Hz, 2H). LC-MS (ESI+) Found: $[M+H]^+$, 640.2.

N-(2-(4-((4-(2-acetyl-5-fluoro-1H-indol-3-yl)-1H-1,2,3-triazol-1-yl)methyl)piperidin-1-yl)ethyl)-2'-chloro-4'-fluoro-[1,1'-biphenyl]-4-sulfonamide (187) (Code AB1453)

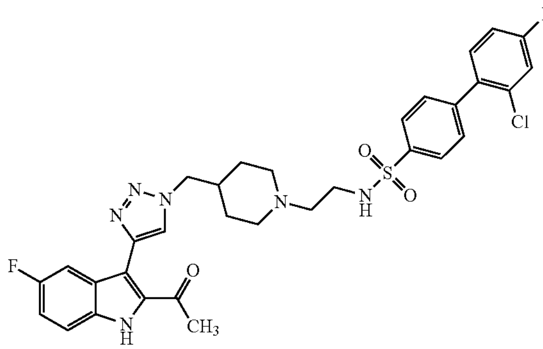

Prepared by general method G using alkyne 93 (60 mg, 0.30 mmol), azide 5Ax (142 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 187 as a white solid (135 mg, 69% yield). $^1$H NMR (400 MHz, $d_6$-DMSO) δ=12.05 (s, 1H), 8.60 (s, 1H), 7.99-7.85 (m, 2H), 7.79 (dd, J=10.1, 2.6 Hz, 1H), 7.66-7.59 (m, 2H), 7.59-7.44 (m, 4H), 7.32 (td, J=8.4, 2.6 Hz, 1H), 7.23 (td, J=9.1, 2.7 Hz, 1H), 4.35 (d, J=7.0 Hz, 2H), 2.92 (t, J=6.8 Hz, 2H), 2.82-2.62 (m, 2H), 2.50 (s, 3H), 2.30 (t, J=6.9 Hz, 2H), 1.84 (dt, J=16.3, 6.0 Hz, 3H), 1.53-1.37 (m, 3H), 1.23 (td, J=12.1, 3.6 Hz, 2H). LC-MS (ESI+) Found: $[M+H]^+$, 653.2.

N-(2-(4-((4-(2-acetyl-5-fluoro-1H-indol-3-yl)-1H-1,2,3-triazol-1-yl)methyl)piperidin-1-yl)ethyl)-2-fluoro-2',6'-dimethoxy-[1,1'-biphenyl]-4-sulfonamide (188) (Code AB1454)

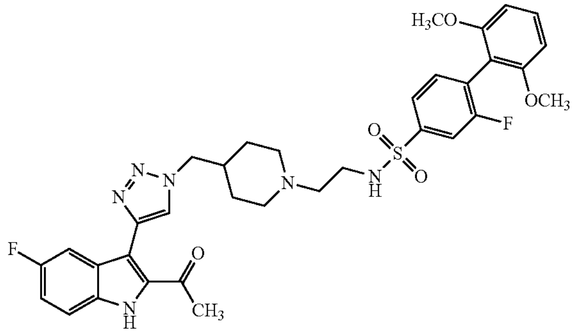 [SMILES: COc1cccc(OC)c1-c1ccc(S(=O)(=O)NCCN2CCC(Cn3cc(-c4c(C(C)=O)[nH]c5ccc(F)cc45)nn3)CC2)cc1F]

Prepared by general method G using alkyne 93 (60 mg, 0.30 mmol), azide 5Ay (150 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 188 as a pale yellow solid (136 mg, 67% yield). $^{1}H$ NMR (400 MHz, $d_6$-DMSO) δ=12.05 (s, 1H), 8.60 (s, 1H), 7.79 (dd, J=10.1, 2.6 Hz, 1H), 7.68 (s, 1H), 7.63 (ddd, J=9.2, 4.8, 1.8 Hz, 2H), 7.54 (dd, J=9.0, 4.6 Hz, 1H), 7.46 (dd, J=8.2, 6.8 Hz, 1H), 7.37 (t, J=8.4 Hz, 1H), 7.23 (td, J=9.1, 2.6 Hz, 1H), 6.75 (d, J=8.5 Hz, 2H), 4.35 (d, J=7.1 Hz, 2H), 3.67 (s, 6H), 2.97 (t, J=6.7 Hz, 2H), 2.74 (dt, J=11.6, 3.6 Hz, 2H), 2.50 (s, 3H), 2.31 (t, J=6.7 Hz, 2H), 1.87 (tt, J=11.6, 3.6 Hz, 3H), 1.62-1.44 (m, 2H), 1.27 (td, J=12.1, 3.6 Hz, 2H). LC-MS (ESI+) Found: $[M+H]^+$, 679.2.

N-(2-(4-((4-(2-acetyl-5-fluoro-1H-indol-3-yl)-1H-1,2,3-triazol-1-yl)methyl)piperidin-1-yl)ethyl)-2',6'-dimethoxy-2-methyl-[1,1'-biphenyl]-4-sulfonamide (189) (Code AB1455)

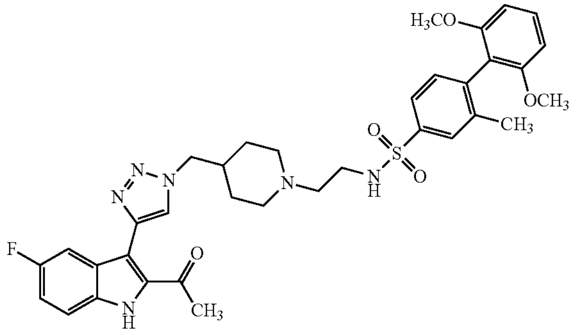 [SMILES: COc1cccc(OC)c1-c1ccc(S(=O)(=O)NCCN2CCC(Cn3cc(-c4c(C(C)=O)[nH]c5ccc(F)cc45)nn3)CC2)cc1C]

Prepared by general method G using alkyne 93 (60 mg, 0.30 mmol), azide 5Az (148 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 189 as a pale yellow solid (130 mg, 65% yield). $^{1}H$ NMR (400 MHz, $d_6$-DMSO) δ=12.06 (s, 1H), 8.61 (s, 1H), 7.79 (dd, J=10.2, 2.6 Hz, 1H), 7.67 (d, J=2.1 Hz, 1H), 7.59 (dd, J=7.9, 2.1 Hz, 1H), 7.54 (dd, J=9.0, 4.6 Hz, 1H), 7.41 (s, 1H), 7.32 (d, J=8.4 Hz, 1H), 7.27-7.17 (m, 2H), 6.73 (d, J=8.5 Hz, 2H), 4.36 (d, J=7.1 Hz, 2H), 3.66 (s, 6H) 2.92 (t, J=7.0 Hz, 2H), 2.80-2.68 (m, 2H), 2.30 (t, J=6.9 Hz, 2H), 2.02 (s, 3H), 1.95-1.80 (m, 3H), 1.54-1.43 (m, 2H), 1.27 (td, J=11.8, 3.2 Hz, 2H), 1.27-1.14 (m, 3H). $^{13}C$ NMR (101 MHz, $d_6$-DMSO) δ=191.0 ($C_{quat}$), 157.5 (d, J=235.1 Hz, $C_{quat}$), 156.8 ($C_{quat}$), 140.0 ($C_{quat}$), 139.1 ($C_{quat}$), 138.9 ($C_{quat}$), 138.1 ($C_{quat}$), 133.1 ($C_{quat}$), 133.0 ($C_{quat}$), 131.5 (CH), 129.7 (CH), 127.1 (CH), 126.6 (d, J=10.6 Hz, $C_{quat}$), 125.0 (CH), 123.4 (CH), 116.4 ($C_{quat}$), 114.8 (d, J=27.4 Hz, CH), 114.2 (d, J=9.3 Hz, CH), 110.7 (d, J=5.7 Hz, $C_{quat}$), 106.8 (d, J=24.0 Hz, CH), 104.2 (CH), 57.0 ($CH_2$), 55.6 ($CH_3$), 54.5 ($CH_2$), 52.5 ($CH_2$), 40.3 ($CH_2$), 37.7 (CH), 27.5 ($CH_2$), 29.6 (CH), 28.7 ($CH_3$), 29.1 ($CH_2$), 19.4 ($CH_3$). LC-MS (ESI+) Found: $[M+H]^+$, 675.3.

N-(2-(4-((4-(2-acetyl-5-fluoro-1H-indol-3-yl)-1H-1,2,3-triazol-1-yl)methyl)piperidin-1-yl)ethyl)-2-chloro-2',6'-dimethoxy-[1,1'-biphenyl]-4-sulfonamide (190) (Code AB1456)

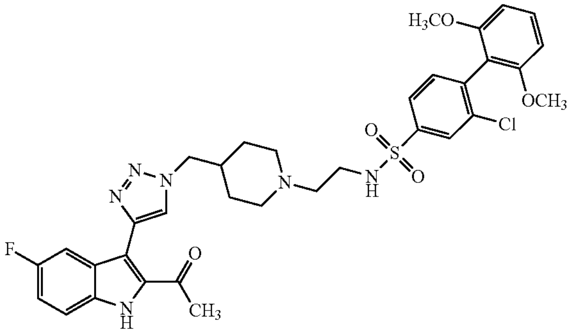 [SMILES: COc1cccc(OC)c1-c1ccc(S(=O)(=O)NCCN2CCC(Cn3cc(-c4c(C(C)=O)[nH]c5ccc(F)cc45)nn3)CC2)cc1Cl]

Prepared by general method G using alkyne 93 (60 mg, 0.30 mmol), azide 5Ba (155 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 VL). The crude product was purified chromatographically on silica gel (eluting gradient dichloromethane-methanol 98:2 to 96:4) to provide the title compound 190 as a pale yellow solid (142 mg, 69% yield). $^{1}H$ NMR (400 MHz, $d_6$-DMSO) δ=12.06 (s, 1H), 8.61 (s, 1H), 7.87 (d, J=1.8 Hz, 1H), 7.79 (dd, J=10.1, 2.6 Hz, 1H), 7.74 (dd, J=8.0, 1.9 Hz, 2H), 7.54 (dd, J=9.0, 4.6 Hz, 1H), 7.43 (d, J=8.0 Hz, 1H), 7.37 (t, J=8.4 Hz, 1H), 7.24 (td, J=9.1, 2.7 Hz, 1H), 6.75 (d, J=8.4 Hz, 2H), 4.36 (d, J=7.1 Hz, 2H), 3.65 (s, 6H), 2.97 (t, J=6.8 Hz, 2H), 2.74 (d, J=9.6 Hz, 2H), 2.50 (s, 3H), 2.30 (d, J=6.9 Hz, 2H), 1.95-1.79 (m, 3H), 1.49 (d, J=12.4 Hz, 2H), 1.27 (tt, J=13.1, 6.6 Hz, 2H). LC-MS (ESI+) Found: $[M+H]^+$, 695.2.

N-(2-(4-((4-(2-acetyl-5-fluoro-1H-indol-3-yl)-1H-1,2,3-triazol-1-yl)methyl)piperidin-1-yl)ethyl)-2,2'-difluoro-6'-hydroxy-[1,1'-biphenyl]-4-sulfonamide (191) (Code AB1457)

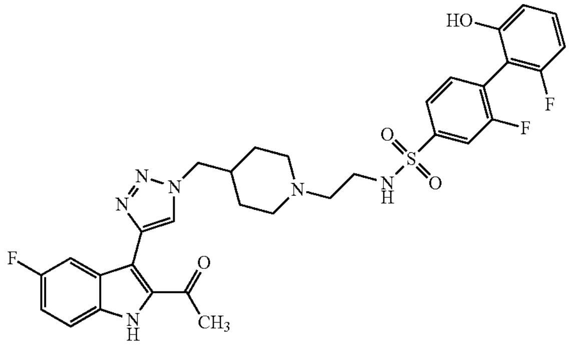 [SMILES: CC(=O)c1[nH]c2ccc(F)cc2c1-c1cn(CC2CCN(CCNS(=O)(=O)c3ccc(-c4c(O)cccc4F)c(F)c3)CC2)nn1]

Prepared by general method G using alkyne 93 (60 mg, 0.30 mmol), azide 5Bb (141 mg, 0.31 mmol), 2M aqueous of sodium ascorbate (522 μL, 1.04 mmol), 15% aqueous of copper(II) sulfate pentahydrate (432 μL, 0.26 mmol) and tetrahydrofuran-tert-butanol (745 μL). The crude product was purified chromatographically on silica gel (eluting gradient dichloromethane-methanol 98:2 to 96:4) to provide the title compound 191 as a white solid (132 mg, 68% yield). $^1H$ NMR (400 MHz, $d_6$-DMSO) δ=12.05 (s, 1H), 10.22 (s, 1H), 8.60 (s, 1H), 7.84-7.65 (m, 3H), 7.61 (dd, J=8.3, 6.8 Hz, 1H), 7.53 (dd, J=9.0, 4.6 Hz, 1H), 7.33-7.19 (m, 2H), 6.82 (d, J=8.3 Hz, 1H), 6.75 (t, J=8.8 Hz, 1H), 4.35 (d, J=7.1 Hz, 2H), 2.95 (t, J=6.8 Hz, 2H), 2.75 (d, J=11.4 Hz, 2H), 2.30 (d, J=6.8 Hz, 3H), 1.93-1.71 (m, 3H), 1.48 (d, J=12.6 Hz, 2H), 1.31-1.17 (m, 4H), 0.93-0.78 (m, 1H). LC-MS (ESI+) Found: $[M+H]^+$, 653.2.

III. References

1. Kufareva, I. et al. Discovery of Holoenzyme-Disrupting Chemicals as Substrate-Selective CK2 Inhibitors. *Sci. Rep.* 9, 15893 (2019).
2. Iyobe, A. et al. Studies on New Platelet Aggregation Inhibitors 1. Synthesis of 7-Nitro-3, 4-dihydroquinoline-2(1H)-one Derivatives. *Chem. Pharm. Bull.* 49, 822-829 (2001).
3. Loudet, A. et al. Non-covalent delivery of proteins into mammalian cells. *Org. Biomol.* Chem. 24 (2008).
4. Tasch, B. O. A.; Merkul, E.; MGller, T. J. J. One-Pot Synthesis of Diazine-Bridged Bisindoles and Concise Synthesis of the Marine Alkaloid Hyrtinadine A. *Eur. J. Org. Chem.* 24, 4532-4535 (2011).
5. McNulty, J.; Keskar, K. A Tandem “On-Palladium” Heck-Jeffery Amination Route Toward the Synthesis of Functionalized Indole-2-carboxylates. *Eur. J. Org. Chem.* 34, 6902-6908 (2011).
6. De Fusco, C. et al. A fragment-based approach leading to the discovery of a novel binding site and the selective CK2 inhibitor CAM4066. *Bioorg. Med. Chem.* 25, 3471-3482 (2017).

Example B—Biology

I. Material and Methods

Protein expression and purification. Human recombinant CK2α subunit was expressed in *E. coli* and purified to homogeneity as previously described.[1] Expression and purification of chicken recombinant MBP (maltose-binding protein)-CK2β were performed as described previously.[2-4] Proteins were quantified by a Bradford assay, and the quality of the purification was asserted by SDS-PAGE analysis.

Radiometric kinase assays. All kinase assays were performed as previously described[5] at −4° C. in a final volume of 18 μL, containing 2 μL of compounds according to the invention diluted in Tris-HCl-glycerol, 0.05% Tween, 3 μL of CK2α (36 ng) and a mixture of 1 mM peptide substrate, 10 mM $MgCl_2$ and 1 μCi [$\gamma^{32}P$]-ATP. Final concentration of ATP was 10 μM if not stated otherwise. Assays were performed under linear kinetic conditions for 5 min at room temperature before termination by the addition of 60 μL of 4% TCA. $^{32}P$ incorporation in peptide substrate was determined by spotting the supernatant onto phospho-cellulose paper disks (Whatman P81, 4 $cm^2$). The disks were washed three times in cold 0.5% phosphoric acid, 5 minutes on a rocking platform per wash then dried and their radioactivity was measured. Percentage inhibition was calculated relative to a DMSO control and $IC_{50}$ or $K_i$ values were calculated using test GraphPad Prism 8.

The peptide substrates employed for different assays were a canonical CK2 peptide substrate Seq. ID No. 1: RRREDEESDDEE, phosphorylated equally by CK2α subunit and CK2 holoenzyme (CK2β-independent peptide substrate), and Seq. ID No. 2: MSG-DEMIFDPTMSKKKKKKKKP exclusively phosphorylated by CK2 holoenzyme (CK2β-dependent peptide substrate).[6]

GST-SIX1 phosphorylation assay was performed following the CK2 radiometric kinase assay. CK2α (200 nM) was incubated with increasing concentrations of CK2β in the absence or presence of AB668 followed by the addition of GST-SIX1 (3.7 μg), 10 mM $MgCl_2$ and 1 μCi [$\gamma^{32}P$]-ATP. Final concentration of ATP was 100 μM. Samples were analyzed by SDS PAGE and subjected to autoradiography. Phosphoproteins were quantified by densitometry scanning.

Kinase selectivity profiling. Kinase selectivity of compound AB668 was assessed using a panel of 69 recombinant protein kinases. The assays were performed by Eurofins Discovery (Cerep, France) at 10 μM of ATP in the presence of 2 μM inhibitor. Inhibition, expressed as the percent of activity, was calculated from the residual activity measured in the presence of 2 μM inhibitor.

Live cell tracking. Cells grown on 96-well flat-bottomed plates (Corning Falcon) were tracked using an Essen IncuCyte Zoom live-cell microscopy instrument, an automated live cell imager with high-throughput capabilities and built-in data analysis. Experiments were conducted at 37° C. and 5% $CO_2$. The software incorporated into the IncuCyte Zoom was used to analyze the images.

Cell death. Cells plated at equal density (786-O, $2\times10^4$ cells/well), (786-O $VHL^+$, $2.0\times10^4$ cells/well), (A549, $1.0\times10^4$ cells/well), (HEK293, $0.8\times10^4$ cells/well), (MDA-MB231, $1.0\times10^4$ cells/well), (MCF10A, $2.0\times10^4$ cells/well), (RPTEC, $0.7\times10^4$ cells/well) were treated with the indicated inhibitors in cell culture medium containing 0.5 μg/ml Propidium iodide (Sigma-Aldrich). Images of PI-stained red fluorescent cells were captured every 3 h for the duration of the experiment and cell death was automatically quantified from images using an Essen IncuCyte Zoom software.

CK2 inhibition in cells. Cells were plated into 6-well plates at $3\times10^5$ cells/well. The following day, the culture medium was replaced with fresh medium containing the inhibitors at various concentrations or DMSO (0.5%) as reference. After incubation for the corresponding time, the medium was removed, cells were washed with cold PBS and frozen at −80° C. Cell extracts were prepared, normalized for protein concentration and assayed for CK2 activity.

Immunoblotting. Cells were lysed in RIPA buffer (10 mM Tris-HCl, pH 7.4, 150 mM NaCl, 1% Triton X-100, 0.1% SDS, 0.5% DOC and 1 mM EDTA) containing both protease- and phosphatase-inhibitor cocktails (Sigma-Aldrich; P8340, P2850, P5726). Cell homogenates were quantified using BCA protein Assay kit (Thermo Scientific). SDS-PAGE was performed using precast 4-12% gradient gel (Bio-Rad) and submitted to electrophoresis in NuPAGE buffer (150 V for 75 min). Separated proteins at 35 μg/lane were transferred to PVDF membranes (100 V for 60 min). Blotted membranes were blocked during 1 h at room temperature with saturation buffer (1% BSA in Tris Buffer Saline 10 mM, Tween 0.1% (TBST)), and then incubated with primary antibody diluted in saturation buffer, for 2 h or overnight. After 3 washes with TBST, secondary antibodies were added for 1 h followed by 3 more washes with TBST. Luminata Forte Western HRP substrate (Millipore) was added and membranes were read with Fusion Fx7 (PerkinElmer). Anti-GAPDH was used as loading control and images were analyzed and band intensities were quantified using ImageJ software. Primary antibodies were GAPDH antibody from Ambion, Aktl, mTOR, p38, p53, PARP, phospho-p38 MAPK, phospho-p53 (Ser15), phospho-mTOR (Ser2448), phospho-Stat3 (Ser727), Stat3 antibodies from Cell Signaling, survivin antibody from Novus Biological, phospho-Aktl (Ser129) antibody from Abgent and phospho-p21(Thr145) antibody from Abcam. Secondary antibodies were peroxidase conjugated affinity pure Goat anti-rabbit IgG (#111035003) and peroxidase conjugated affinity pure Goat anti-mouse IgG (#115035003) from Jackson ImmunoResearch.

In vivo orthotopic tumor xenograft models. All animal studies were approved by the institutional guidelines and those formulated by the European Community for the Use of Experimental Animals. Six-week-old BALB/c Female nude mice (Charles River Laboratories) with a mean body weight of 18-20 g were used to establish orthotopic xenograft tumor models. The mice were housed and fed under specific pathogen-free conditions. To produce tumors, renal cancer cells 786-O-luc ($VHL^-$) were harvested from subconfluent cultures by a brief exposure to 0.25% trypsin-EDTA. Trypsinization was stopped with medium containing 10% FBS, and the cells were washed once in serum-free medium and resuspended in 500 μl PBS. Renal orthotopic implantation was carried out by injection of $3\times10^6$ 786-O luc cells into the right kidney of athymic nude mice. Mice were weighed once a week to monitor their health and tumor growth was measured by imaging luminescence of 786-O-luc cells (IVIS).

Fresh tissue sectioning. A Vibratome VT1200 (Leica Microsystems) was used to cut thin (300 m) slices from fresh tissue. Samples were soaked in ice-cold sterile balanced salt solution (HBSS), orientated, mounted, and immobilized using cyanoacrylate glue. Slicing speed was optimized according to tissue density and type; in general, slower slicing speed was used on the softer tissues and vice versa (0.08-0.12 mm/s neoplastic tissue; 0.01-0.08 mm/s normal tissue). Vibration amplitude was set at 2.95-3.0 mm.

Organotypic tissue cultures. Tissue slices were cultured on organotypic inserts for up to 96 hours (one slice per insert; Millipore). Organotypic inserts are Teflon membranes with 0.4 m pores that allow preservation of 3D tissue structure in culture. Tissue culture was performed at 37° C. in a 5% $CO_2$ humidified incubator using 1 ml of DMEM media supplemented with 20% inactivated FBS (GIBCO), 100 U/ml penicillin (Invitrogen) and place in a rotor agitator to allow gas and fluids exchanges with the medium. The tissue slices were incubated with the compounds of the invention at the indicated concentrations and after 72 hours, they were stained with the Live & Dead kit (Life technologies) as recommended and nuclei were labeled with Hoechst 33342. Images were taken with an Apotome equipped Zeiss Axioimager microscope and dead cells were quantified using ImageJ as previously described (Roelants 20187; 20208).

Statistical analysis. Experimental data are shown as mean t standard error mean (SEM). Statistical analyses were performed using one-way or two-way analysis of variance (ANOVA) with multiple comparisons test (GraphPad Prism 8). A p-value of less than 0.05 was considered statistically significant. (**P<0.0001, *P<0.001, **P<0.01, *P<0.05, ns>0.05 against the DMSO control).

II. Results

In Vitro data relative to IC50 values and % of inhibition of CK2 activity with 0.05 μM, 0.10 μM, or 1 μM of different compounds according to the invention are detailed in the following tables 1 and 2.

TABLE 1

| Compound | IC50 (μM) |
|---|---|
| AB150 | 48.5 |
| AB152 | 35.0 |
| AB153 | 15.1 |
| AB201 | 10.1 |
| AB202 | 12.1 |
| AB401 | 0.98 |
| AB460 | 2.51 |
| AB433 | 8.10 |
| AB504 | 1.80 |
| AB505 | 3.76 |
| AB503 | 9.85 |
| AB529 | 0.70 |
| AB550 | 2.24 |
| AB526 | 0.30 |
| AB543 | 0.93 |
| AB536 | 0.80 |
| AB551 | 1.78 |
| AB579 | 0.43 |
| AB582 | 1.25 |
| AB577 | 2.30 |
| AB578 | 9.20 |
| AB499 | 0.67 |
| AB498 | 0.83 |
| AB600 | 0.35 |
| AB601 | 1.40 |
| AB556 | 0.17 |
| AB557 | 0.56 |
| AB598 | 0.51 |
| AB599 | 3.20 |
| AB603 | 0.15 |
| AB668 | 0.041 |
| AB597 | 1.60 |
| AB614 | 3.24 |
| AB912 | 0.30 |
| AB913 | 0.080 |
| AB914 | 0.071 |
| AB917 | 0.60 |
| AB918 | 0.40 |
| AB929 | 0.058 |
| AB931 | 0.10 |
| AB932 | 0.075 |
| AB933 | 0.062 |
| AB934 | 0.052 |
| AB935 | 0.049 |
| AB936 | 0.55 |
| AB937 | 0.80 |
| AB1030 | 0.054 |
| AB1031 | 0.15 |
| AB1032 | 0.20 |
| AB1070 | 0.20 |
| AB1071 | 0.065 |
| AB1072 | 0.10 |
| AB1073 | 0.018 |
| AB1074 | 0.069 |
| AB1075 | 0.079 |
| AB1076 | 0.046 |
| AB1130 | 0.049 |
| AB1133 | 0.026 |
| AB1135 | 0.048 |
| AB1145 | 0.13 |
| AB1206 | 0.016 |
| AB1208 | 0.045 |
| AB1209 | 0.070 |
| AB1210 | 0.085 |
| AB1231 | 0.46 |
| AB1235 | 0.09 |
| AB1281 | 0.61 |
| AB1285 | 0.93 |
| AB1286 | 0.43 |
| AB1287 | 0.049 |
| AB1288 | 0.078 |
| AB1289 | 0.44 |
| AB1303 | 0.033 |
| AB1304 | 0.50 |
| AB1305 | 0.48 |
| AB1306 | 0.45 |
| AB1316 | 0.28 |
| AB1317 | 0.31 |

TABLE 1-continued

| Compound | IC50 (μM) |
|---|---|
| AB1318 | 0.30 |
| AB1381 | 0.017 |
| AB1394 | 0.023 |
| AB1401 | 0.12 |
| AB1402 | 0.045 |
| AB1415 | 0.050 |
| AB1416 | 0.10 |
| AB1417 | 0.12 |
| AB1450 | 0.049 |
| AB1451 | 0.045 |
| AB1454 | 0.011 |
| AB1455 | 0.0051 |

TABLE 2

| Compound | Inhibition of the kinase activity @ 1 μM (%) (Unless otherwise specified) |
|---|---|
| AB668 | 98 |
| AB651 | 5 |
| AB652 | 4 |
| AB663 | 11 |
| AB664 | 15 |
| AB669 | 32 |
| AB670 | 14 |
| AB671 | 18 |
| AB680 | 11 |
| AB681 | 18 |
| AB689 | 6 |
| AB690 | 31 |
| AB691 | 3 |
| AB692 | 5 |
| AB697 | 16 |
| AB703 | 8 |
| AB704 | 21 |
| AB717 | 2 |
| AB718 | 5 |
| AB713 | 5 |
| AB753 | 18 |
| AB731 | 5 |
| AB739 | 7 |
| AB758 | 17 |
| AB760 | 15 |
| AB746 | 15 |
| AB743 | 9 |
| AB756 | 19 |
| AB755 | 56 |
| AB930 | 45 |
| AB938 | 5 |
| AB939 | 4 |
| AB1131 | 2 (@ 0.10 μM) |
| AB1132 | 4 (@ 0.10 μM) |
| AB1134 | 5 (@ 0.10 μM) |
| AB1205 | 59 (@ 0.05 μM) |
| AB1207 | 61 (@ 0.05 μM) |
| AB1232 | 16 (@ 0.05 μM) |
| AB1233 | 17 (@ 0.05 μM) |
| AB1282 | 15 (@ 0.10 μM) |
| AB1283 | 20 (@ 0.10 μM) |
| AB1284 | 15 (@ 0.10 μM) |
| AB1301 | 3 (@ 0.10 μM) |
| AB1302 | 10 (@ 0.10 μM) |
| AB1307 | 12 (@ 0.10 μM) |
| AB1315 | 27 (@ 0.10 μM) |
| AB1319 | 33 (@ 0.10 μM) |
| AB1321 | 4 (@ 0.10 μM) |
| AB1322 | 10 (@ 0.10 μM) |
| AB1390 | 36 (@ 0.10 μM) |
| AB1393 | 31 (@ 0.10 μM) |
| AB1403 | 9 (@ 0.10 μM) |

TABLE 2-continued

| Compound | Inhibition of the kinase activity @ 1 μM (%) (Unless otherwise specified) |
|---|---|
| AB1404 | 20 (@ 0.10 μM) |
| AB1405 | 11 (@ 0.10 μM) |
| AB1406 | 29 (@ 0.10 μM) |
| AB1452 | 36 (@ 0.10 μM) |
| AB1453 | 40 (@ 0.10 μM) |

The results of FIG. 1 show that compounds according to the invention potently and selectively inhibit CK2 activity in vitro.

More particularly, the inventors have shown that the compounds are non-ATP competitive inhibitors targeting the CK2 holoenzyme, thereby preventing specifically the phosphorylation of CK2β-dependent protein substrates (FIG. 1).

The results of FIGS. 2, 3, and 4 show that compounds according to the invention target and rapidly induce death in different human cancer cell lines.

More particularly, the inventors have shown that the compounds promote cell death of lung, renal, breast, and skin cancer cell lines, while non-affecting the survival of the corresponding normal cells (FIGS. 2, 3, and 4).

In conclusion, the data show that compounds of formula (I) according to the invention are highly specific CK2 inhibitors, which strongly and rapidly induce cancer cell death whereas having low toxicity on normal cell lines, demonstrating thereby a therapeutic potential in cancer diseases.

III. References

1. Hériché, J. K. et al. Regulation of protein phosphatase 2A by direct interaction with casein kinase 2alpha. *Science.* 276, 952-955 (1997).
2. Chantalat, L. et al. Crystal structure of the human protein kinase CK2 regulatory subunit reveals its zinc finger-mediated dimerization. *EMBO J.* 18, 2930-2940 (1999).
3. Leroy, D. et al. Dissecting subdomains involved in multiple functions of the CK2beta subunit. *Mol. Cell. Biochem.* 191, 43-50 (1999).
4. Chantalat, L. et al. Crystallization and preliminary x-ray diffraction analysis of the regulatory subunit of human protein kinase CK2. *Acta Crystallogr. D Biol. Crystallogr.* 55, 895-897 (1999).
5. Prudent, R. et al. Identification of polyoxometalates as nanomolar noncompetitive inhibitors of protein kinase CK2. *Chem. Biol.* 15, 683-692 (2008).
6. Poletto, G. et al. The regulatory beta subunit of protein kinase CK2 contributes to the recognition of the substrate consensus sequence. A study with an eIF2 beta-derived peptide. *Biochemistry* 47, 8317-8325 (2008).
7. Roelants, C. et al. Combined inhibition of PI3K and Src kinases demonstrates synergistic therapeutic efficacy in clear-cell renal carcinoma. *Oncotarget,* 10, 2236-2236 (2018).
8. Roelants, C. et al. Ex-Vivo Treatment of Tumor Tissue Slices as a Predictive Preclinical Method to Evaluate Targeted Therapies for Patients with Renal Carcinoma. *Cancers,* 12, 232 (2020).

The invention claimed is:

1. A compound of formula (I'):

(I')

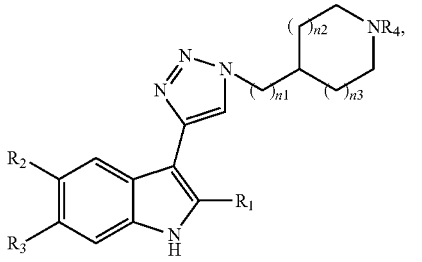

wherein:

$R_1$ is a radical selected in the group consisting of hydrogen, $(C_1-C_6)$alkyl optionally substituted by hydroxy, $(C_1-C_6)$alkyloxy, $NH_2$, —$N(CH_3)_2$, or a heterocycloalkyl, $(C_1-C_6)$alkyloxy, —$CO_2R_5$, —$CONHR_5$, —$COR_8$, or —$CH_2$—O—$R_5$, wherein $R_5$ is a radical selected in the group consisting of hydrogen, $(C_1-C_6)$alkyl optionally substituted by hydroxy, amino group, cycloalkyl, or a heterocycloalkyl, $(C_2-C_6)$alkenyl, and 3-10 membered ring selected in the group consisting of heterocycloalkyl, cycloalkyl, aryl, and heteroaryl, said 3-10 membered ring being optionally substituted by $(C_1-C_6)$alkyl, and heteroaryl optionally substituted by $(C_1-C_6)$alkyl optionally substituted by cycloalkyl;

$R_2$ is hydrogen, halogen, or $(C_1-C_6)$alkyl optionally substituted by at least one fluorine;

$R_3$ is hydrogen or halogen; and $R_4$ is a radical selected in the group consisting of —$CH_2$—$CH_2$—NH—$SO_2$—$R_6$ or a —$CH_2$—$CH_2$—NH—$SO_2$—$CH_2$—$R_6$, wherein $R_6$ is 3-10 membered ring optionally substituted by at least one radical selected in the group consisting of halogen, hydroxy, $(C_1-C_6)$alkyl optionally substituted by at least one fluorine, cycloalkyl or aryl, $(C_1-C_6)$alkyloxy optionally substituted by at least one fluorine, 3-10 membered ring optionally substituted by at least one radical selected in the group consisting of halogen, heterocycloalkyl, $CH_2$-heterocycloalkyl, cyano, $(C_1-C_6)$alkyl optionally substituted by at least one $(C_1-C_6)$alkyloxy or one halogen, $(C_1-C_6)$alkyloxy optionally substituted by at least one halogen, —$N(CH_3)_2$ group, and hydroxy, and —O-3-10 membered ring, X—$R_7$ group in which:

X represents —$CH_2$—, —CO—, —NH—CO—NH—, or —$SO_2$—, and $R_7$ represents a 3-10 membered ring optionally substituted by at least one radical selected in the group consisting of halogen, $(C_1-C_6)$alkyl optionally substituted by at least one fluorine, $(C_1-C_6)$alkyloxy, and 3-10 membered ring, —O-3-10 membered ring, —$CH_2$-3-10 membered ring, or —O—$CH_2$-3-10 membered ring, said rings are optionally substituted by at least one radical selected in the group consisting of $(C_1$-$C_6)$alkyl optionally substituted by at least one $(C_1$-$C_6)$alkyloxy or one halogen,
$(C_1$-$C_6)$alkyloxy,
halogen,
—$COR_8$ with $R_8$ being a hydrogen or a $(C_1$-$C_6)$ alkyl, and
aryl;

n1 is 0 or 1; and n2 and n3 are independently 0, 1, or 2;

and the stereoisomers, the tautomers, the hydrates, and the pharmaceutical salts thereof.

2. The compound according to claim 1, represented by formula (I):

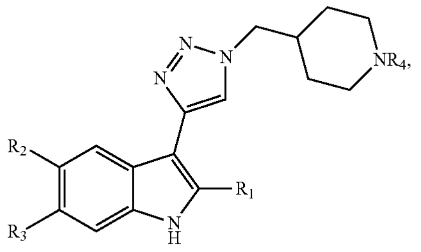

(I)

wherein:

$R_1$ is a radical selected in the group consisting of
hydrogen,
—$CO_2R_5$, a-$CONHR_5$, a —$COR_5$, or a —$CH_2$—O—$R_5$ group with $R_5$ being a radical selected in the group consisting of
hydrogen,
$(C_1$-$C_6)$alkyl optionally substituted by a hydroxy, an amino group, or a cycloalkyl, and
3-10 membered heterocycloalkyl optionally substituted by a $(C_1$-$C_6)$alkyl,
and
heteroaryl optionally substituted a $(C_1$-$C_6)$alkyl optionally substituted by a cycloalkyl;

$R_2$ is a hydrogen, a halogen, or a $(C_1$-$C_6)$alkyl optionally substituted by at least one fluorine;

$R_3$ is a hydrogen or a halogen; and $R_4$ is a radical selected in the group consisting of
—$CH_2$—$CH_2$—NH—$SO_2$—$R_6$ group with $R_6$ being a 3-10 membered ring optionally substituted by a radical selected in the group consisting of
halogen,
$(C_1$-$C_6)$alkyl optionally substituted by at least one fluorine, a cycloalkyl or an aryl,
$(C_1$-$C_6)$alkyloxy optionally substituted by at least one fluorine,
3-10 membered ring, and
—O-3-10 membered ring,
X—$R_7$ group in which:
X represents —$CH_2$—, —CO—, —NH—CO—NH—, or —$SO_2$—, and
$R_7$ represents a 3-10 membered ring optionally substituted by at least one radical selected in the group consisting of
halogen,
$(C_1$-$C_6)$alkyl optionally substituted by at least one fluorine,
$(C_1$-$C_6)$alkyloxy, and
3-10 membered ring, a —O-3-10 membered ring, a —$CH_2$-3-10 membered ring, or a —O—$CH_2$-3-10 membered ring, said rings are optionally substituted by at least one radical selected in the group consisting of
$(C_1$-$C_6)$alkyl optionally substituted by at least one $(C_1$-$C_6)$alkyloxy or one halogen,
$(C_1$-$C_6)$alkyloxy,
halogen,
—$COR_8$ with $R_8$ being a hydrogen or a $(C_1$-$C_6)$ alkyl, and
aryl;

and the stereoisomers, the tautomers, the hydrates, and the pharmaceutical salts thereof.

3. The compound according to claim 1, wherein $R_1$ is a radical selected in the group consisting of
hydrogen,
$(C_1$-$C_6)$alkyl optionally substituted by a hydroxy, and
—$CO_2R_5$, a —$COR_8$, or a-$CONHR_5$ group with $R_5$ being a radical selected in the group consisting of
hydrogen,
$(C_1$-$C_6)$alkyl optionally substituted by a hydroxy or an amino group, and
3-10 membered ring selected from the group consisting of cycloalkyl, heterocycloalkyl, and heteroaryl.

4. The compound according to claim 1, wherein $R_1$ is a —$CO_2R_5$ or —$COR_8$, with $R_5$ being a $(C_1$-$C_6)$alkyl.

5. The compound according to claim 1, wherein $R_2$ is halogen.

6. The compound according to claim 1, wherein $R_3$ is hydrogen.

7. The compound according to claim 1, wherein $R_4$ is a —$CH_2$—$CH_2$—NH—$SO_2$—$R_6$ group with $R_6$ being a phenyl or a naphthalenyl optionally substituted by a radical selected in the group consisting of halogen and $(C_1$-$C_6)$alkyl optionally substituted by at least one fluorine.

8. The compound according to claim 1, wherein $R_4$ is a radical selected in the group consisting of a —$CH_2$—$CH_2$—NH—$SO_2$—$R_6$ group with $R_6$ being a phenyl substituted by a $(C_1$-$C_6)$alkyl.

9. The compound according to claim 1, wherein $R_4$ is a X—$R_7$ group in which:
X represents —$CH_2$—, —CO—, or —$SO_2$—, and
$R_7$ represents a phenyl, a dihydrobenzofuran or a piperazinyl optionally substituted by at least one radical selected in the group consisting of
halogen, preferably a chlorine,
$(C_1$-$C_6)$alkyl optionally substituted by at least one fluorine, preferably an isopropyl, a tert-butyl, or a trifluoromethyl,
$(C_1$-$C_6)$alkyloxy, and
a radical selected in the group consisting of phenyl, indolyl, dihydrobenzofuranyl, dihydrobenzofuranoxy, phenoxy, and benzyl, said radicals are optionally substituted by at least one radical selected in the group consisting of
$(C_1$-$C_6)$alkyl optionally substituted by at least one $(C_1$-$C_6)$alkyloxy or a halogen,
$(C_1$-$C_6)$alkyloxy, and
—$COR_8$ with $R_8$ being $(C_1$-$C_6)$alkyl.

10. The compound according to claim 1, wherein $R_4$ is a X—$R_7$ group in which:
X represents —$CH_2$— or —CO—, and
$R_7$ represents a phenyl disubstituted:
in meta position by a radical selected in the group consisting of
halogen,
$(C_1$-$C_6)$alkyl optionally substituted by at least one fluorine, and phenyl optionally substituted by ($C_1$-$C_6$)alkyl optionally substituted by at least one fluorine, and in para position by a radical selected in the group consisting of ($C_1$-$C_6$)alkyloxy, and phenyl, indolyl, dihydrobenzofuranyl, dihydrobenzofuranoxy, phenoxy, and benzyl, said radicals are optionally substituted by at least one radical selected in the group consisting of ($C_1$-$C_6$)alkyl optionally substituted by at least one ($C_1$-$C_6$)alkyloxy, ($C_1$-$C_6$)alkyloxy, and —$COR_8$ with $R_8$ being ($C_1$-$C_6$)alkyl.

11. The compound according to claim 1, wherein $R_1$ is

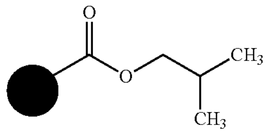

or —$COCH_3$.

12. The compound according to claim 1, wherein $R_4$ is —$CH_2$—$CH_2$—NH—$SO_2$—$R_6$ and $R_6$ is

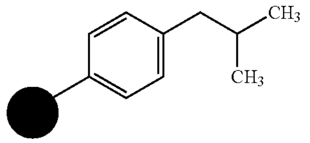

or

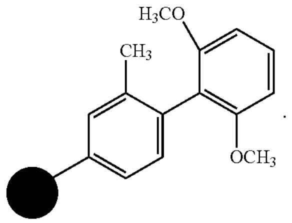

13. The compound according to claim 1, wherein $R_2$ is fluorine.

14. The compound according to claim 1, wherein $R_4$ is a —$CH_2$—$CH_2$—NH—$SO_2$—$R_6$ group with $R_6$ being a phenyl or a naphthalenyl optionally substituted by a radical selected from the group consisting of fluorine, methyl, trifluoromethyl, ethyl, and isopropyl.

15. The compound according to claim 1, wherein $R_4$ is a radical selected in the group consisting of

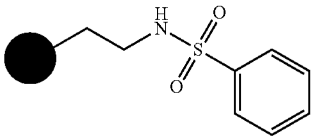

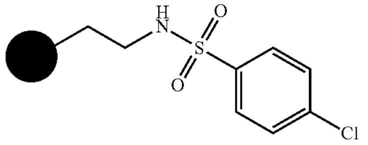

-continued

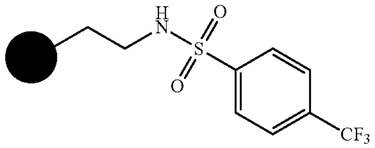

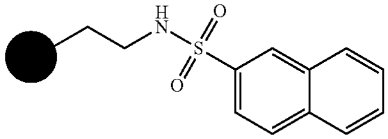

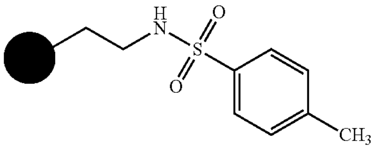

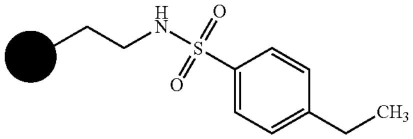

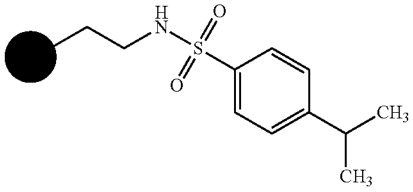

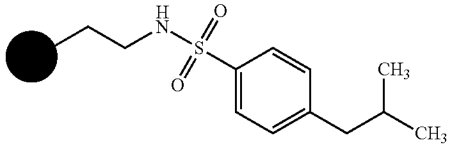

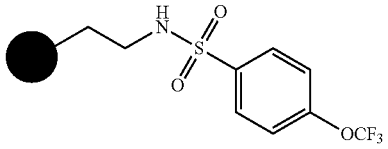

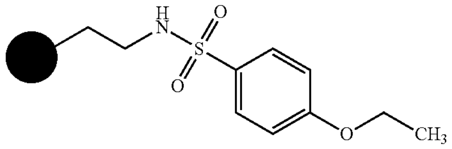

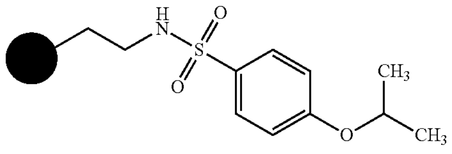

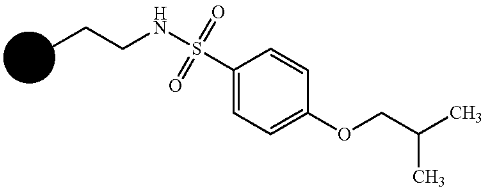

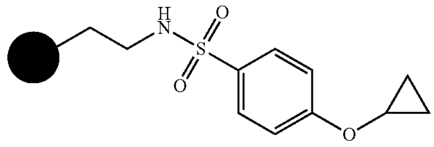

-continued
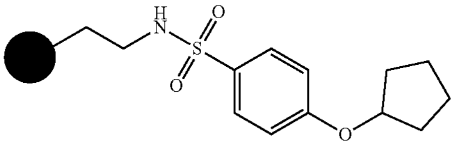
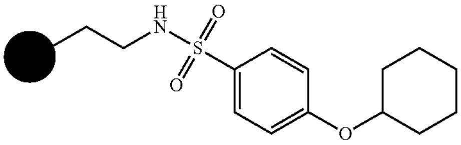
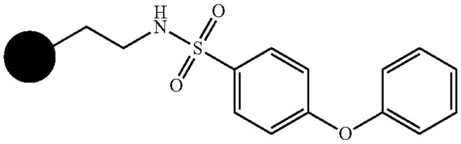
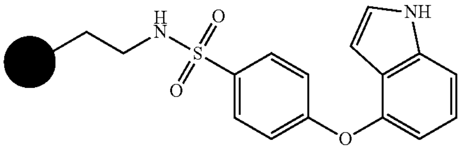
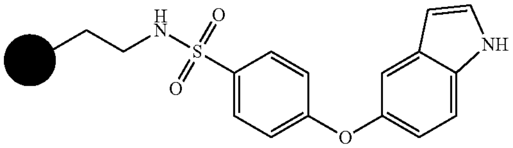
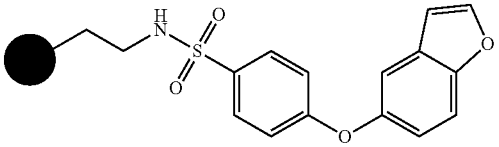
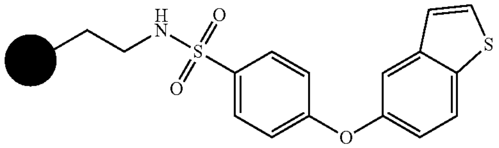
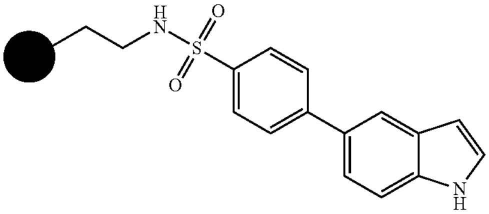
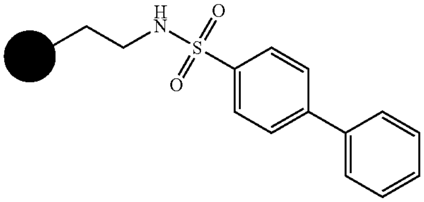
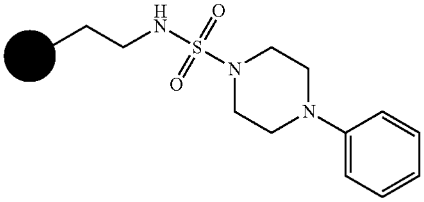
-continued
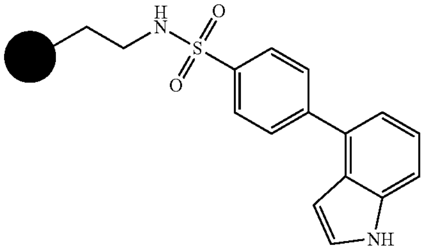
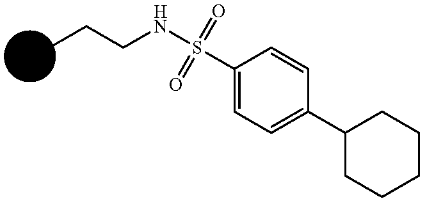
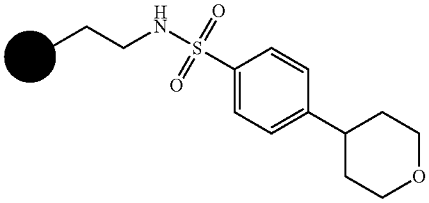
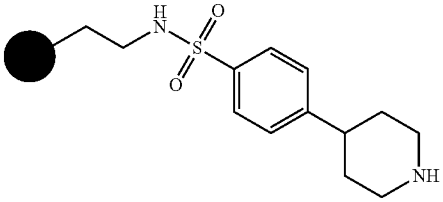
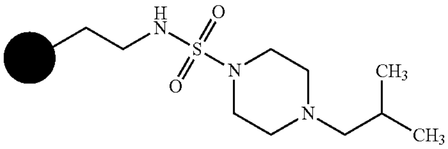
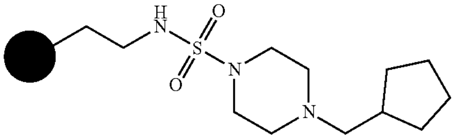
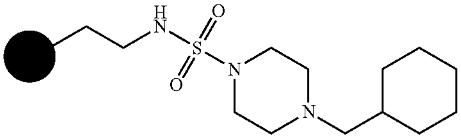
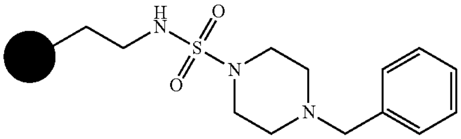
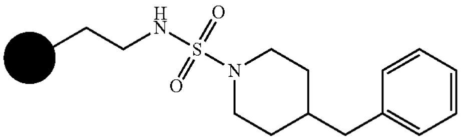

-continued
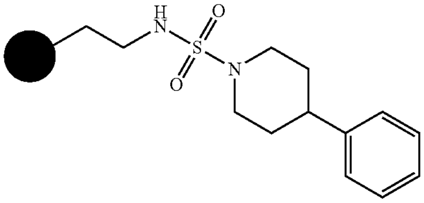
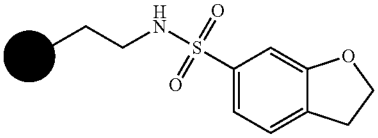
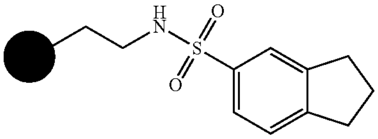
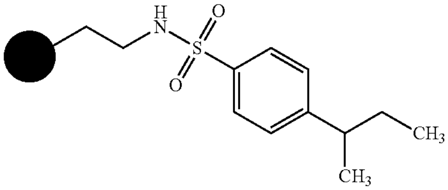
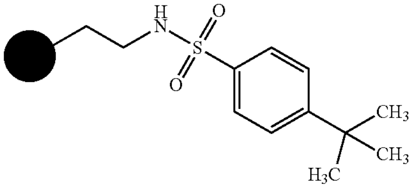
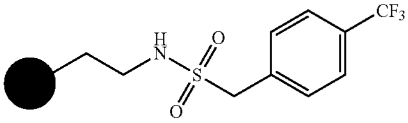
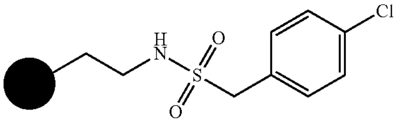
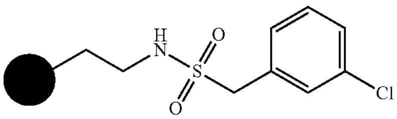
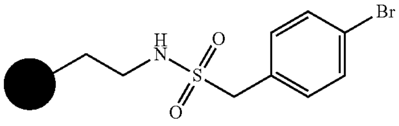
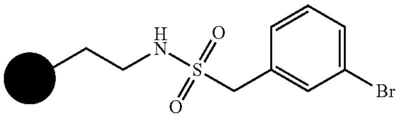
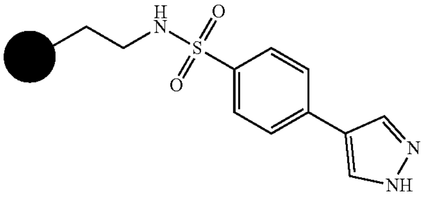
-continued
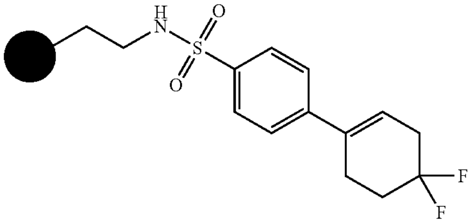
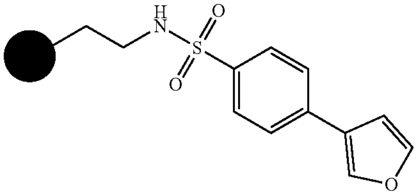
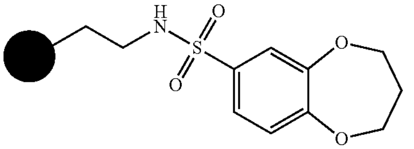
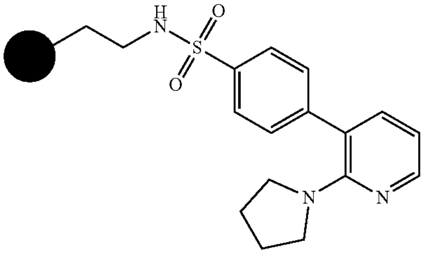
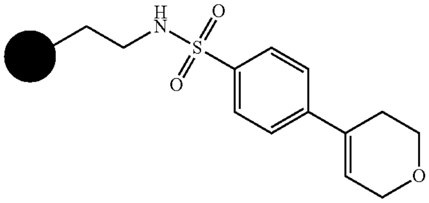
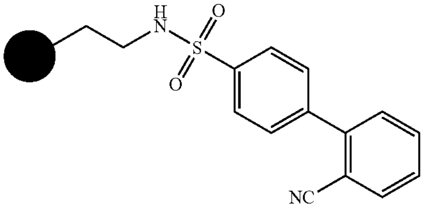
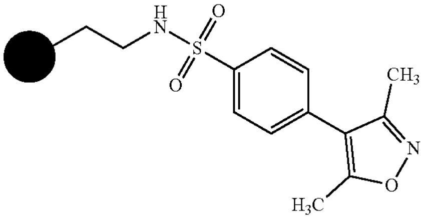
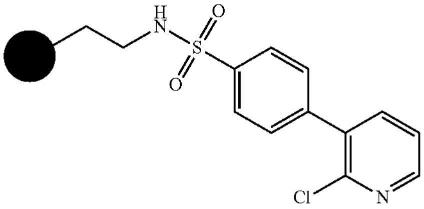

-continued
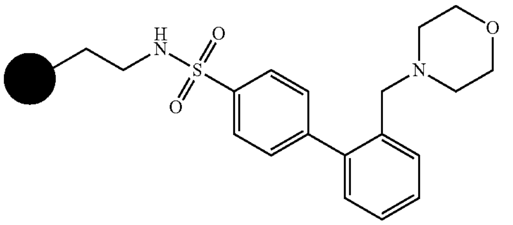
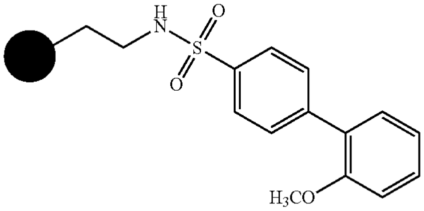
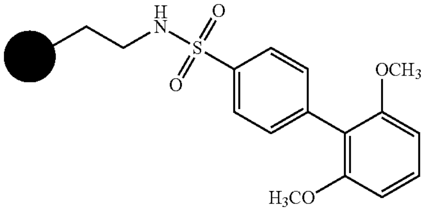
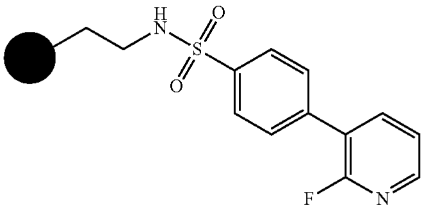
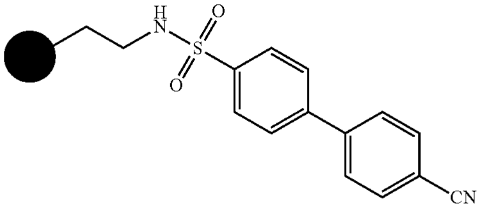
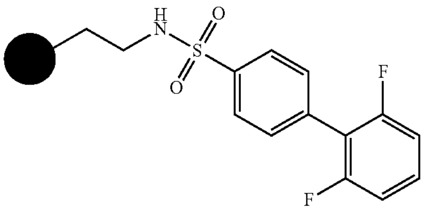
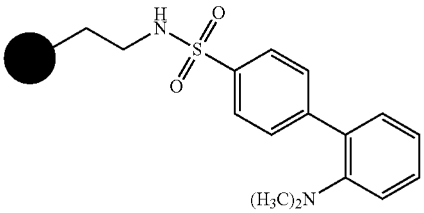
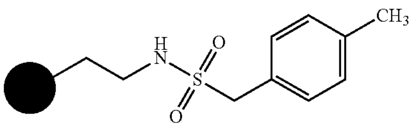
-continued
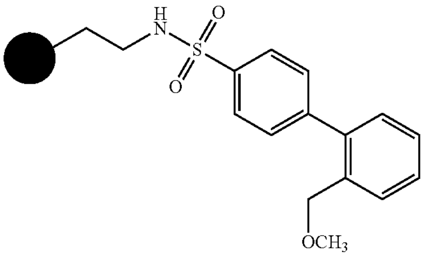
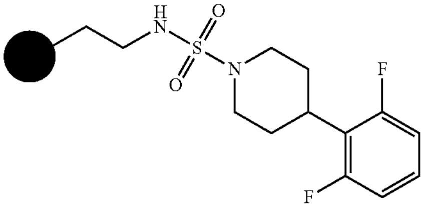
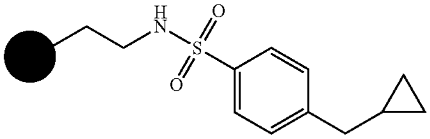
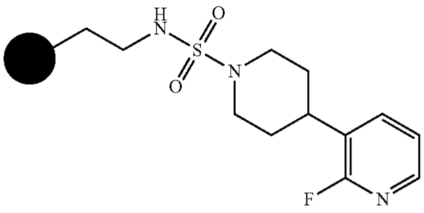
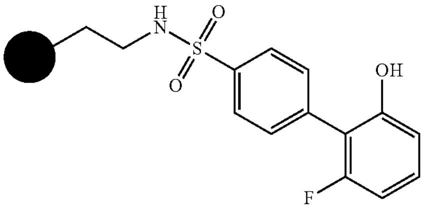
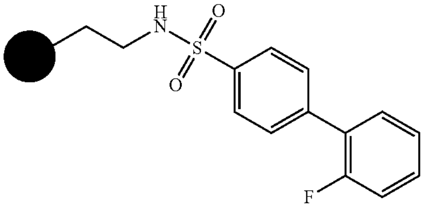
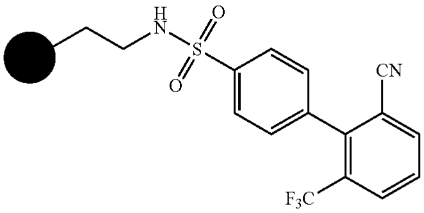
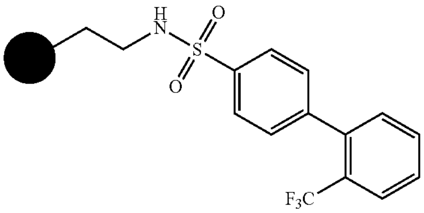

-continued
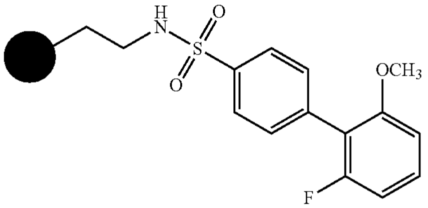
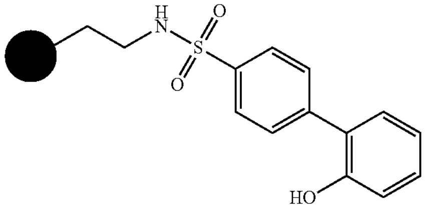
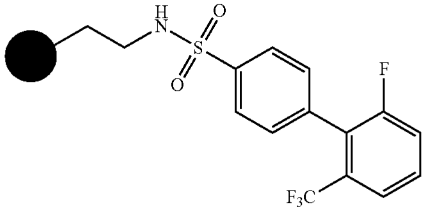
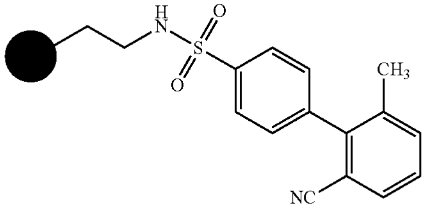
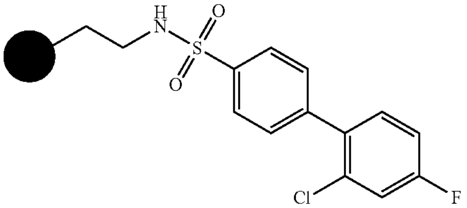
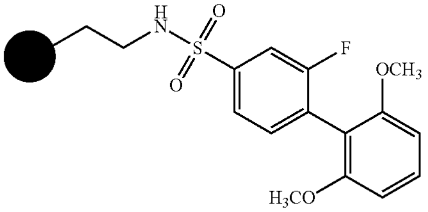
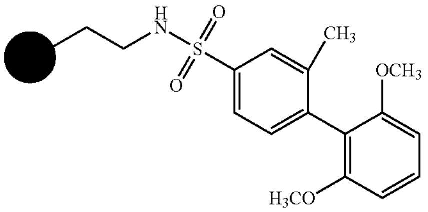
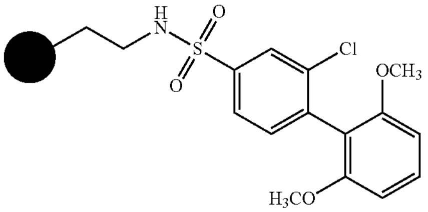
-continued
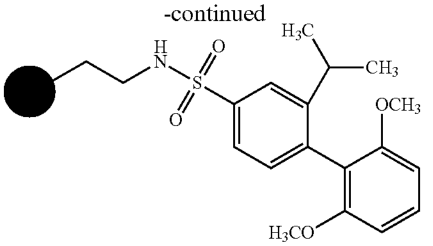
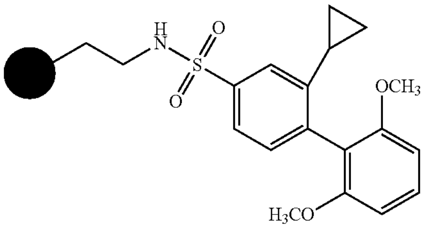
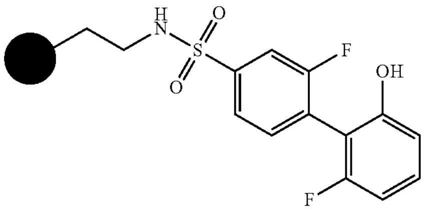
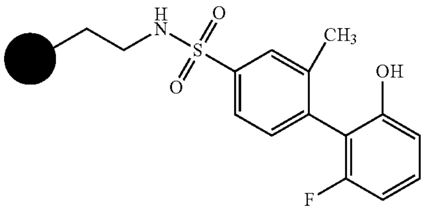
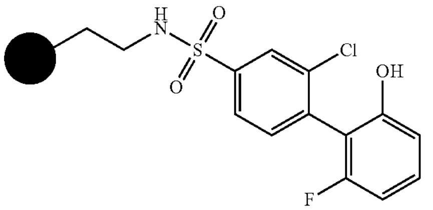
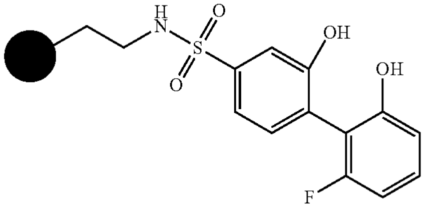
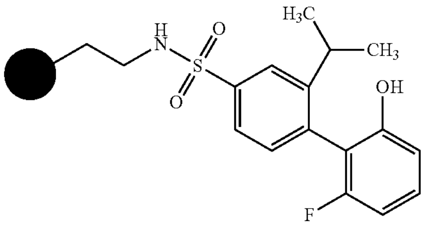
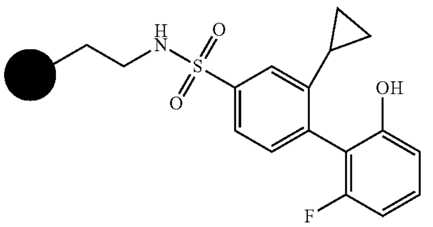

-continued
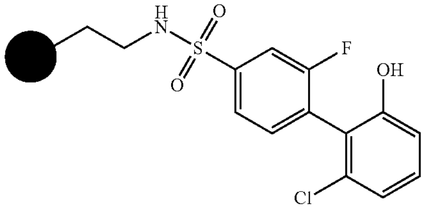
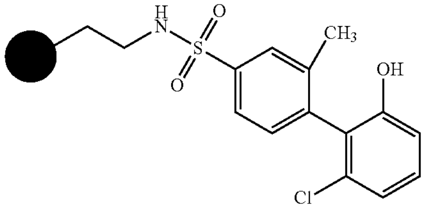
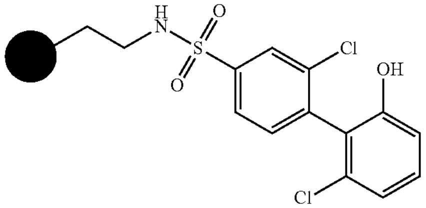
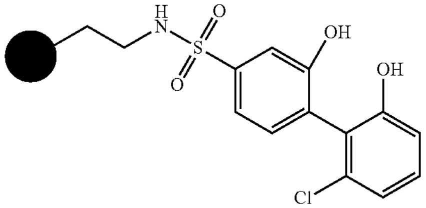
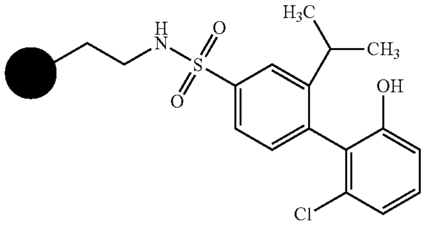
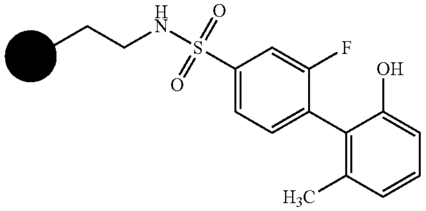
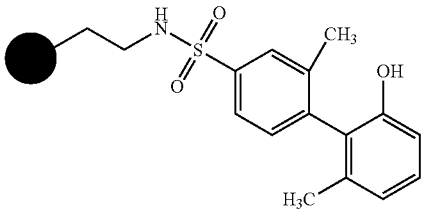
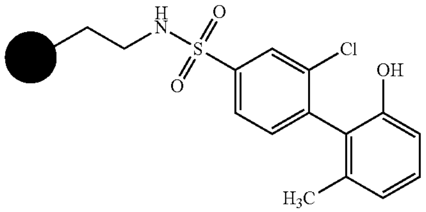
-continued
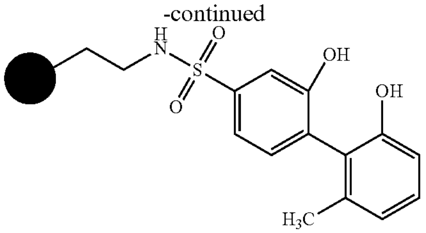
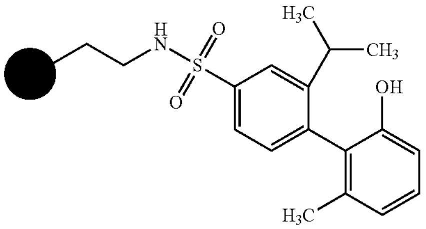
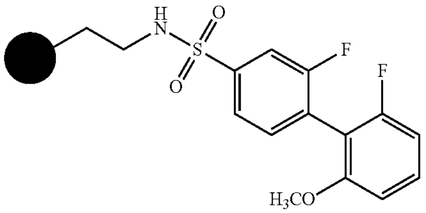
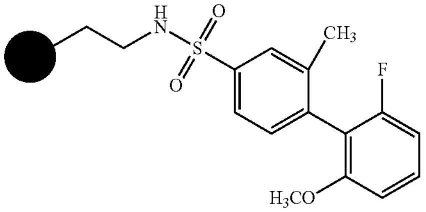
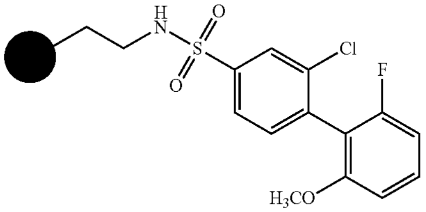
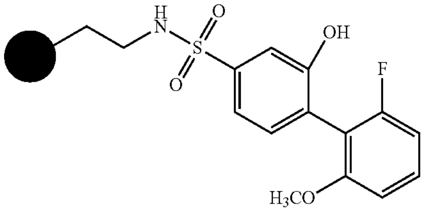
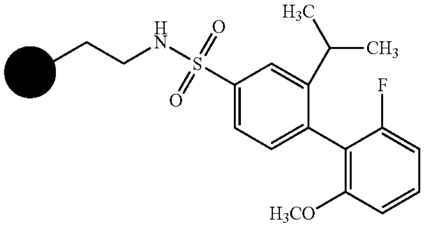
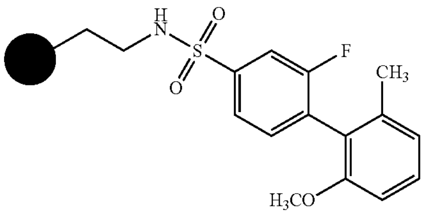

-continued
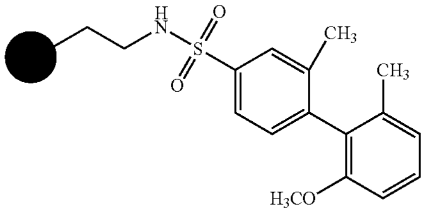
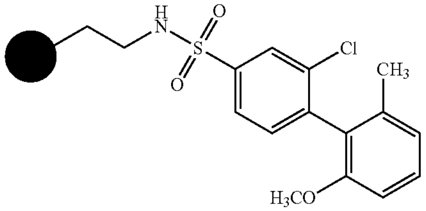
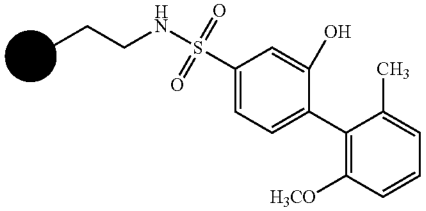
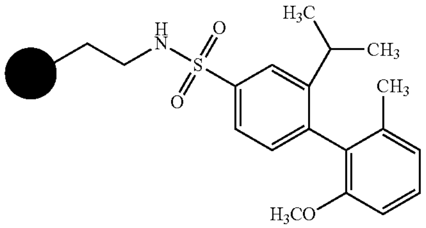
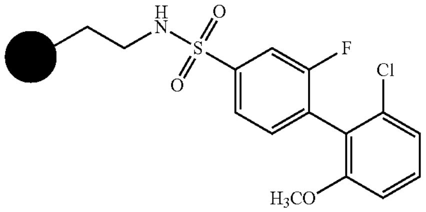
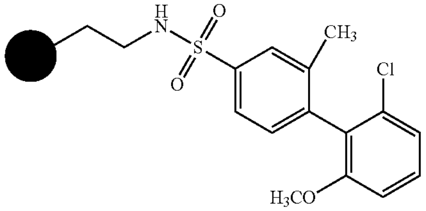
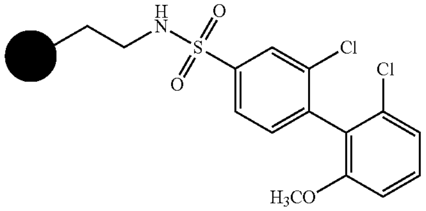
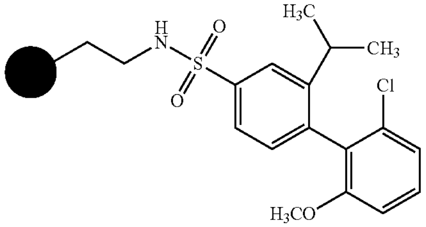
-continued
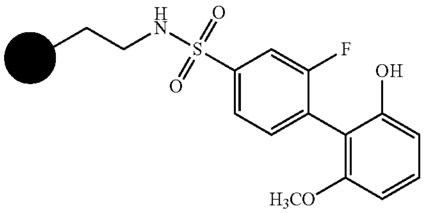
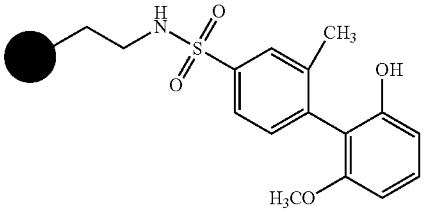
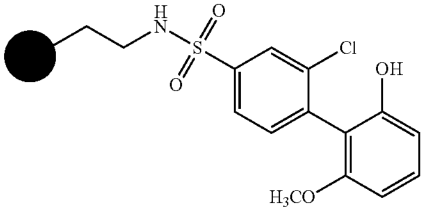
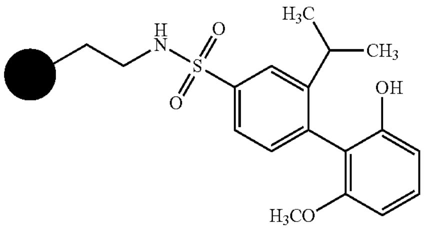
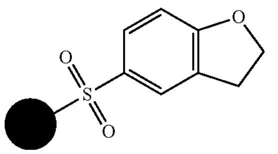
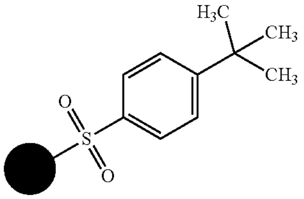
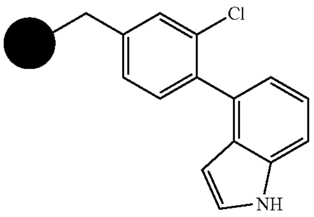
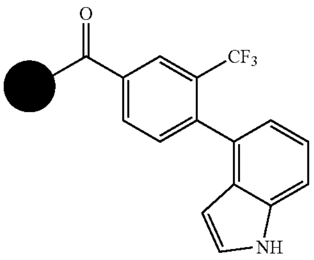

-continued
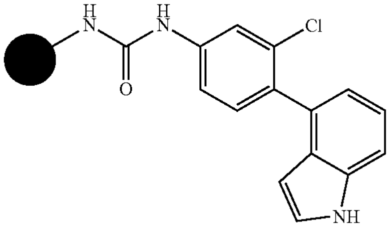
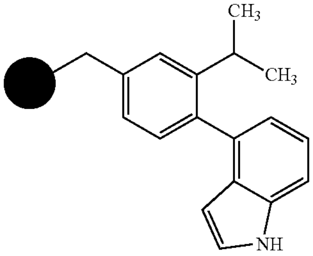
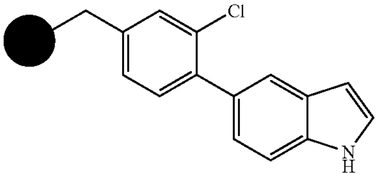
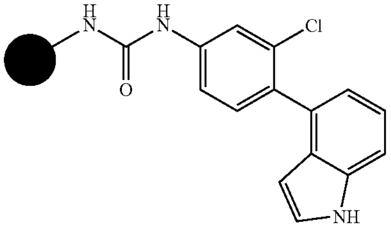
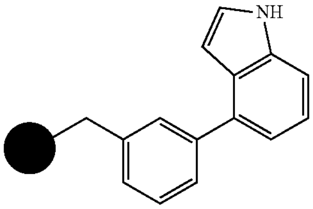
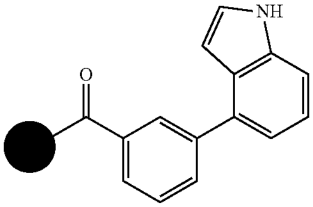
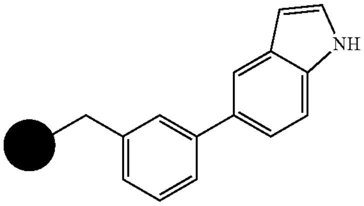
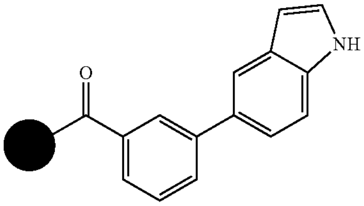
-continued
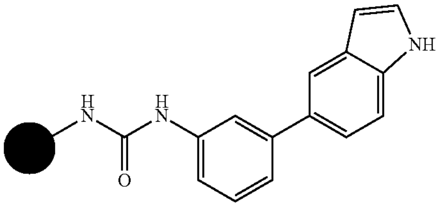
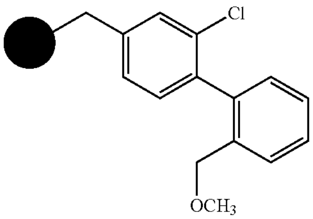
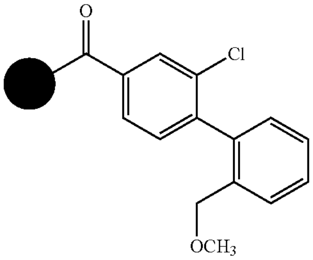
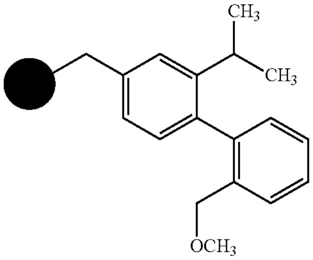
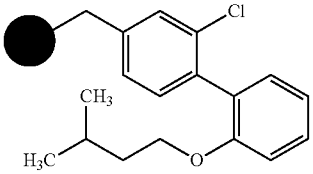
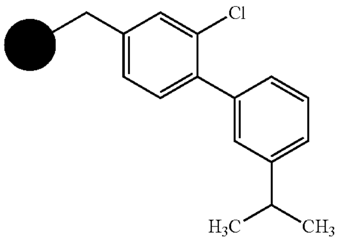
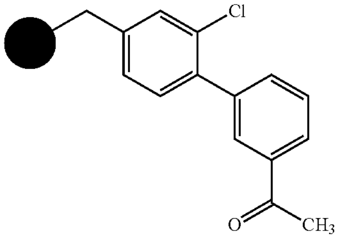

-continued
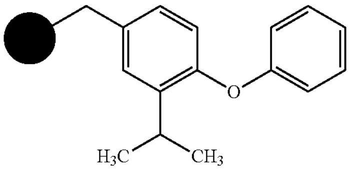
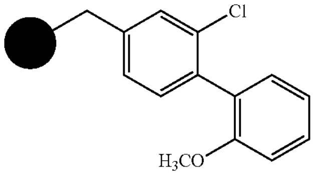
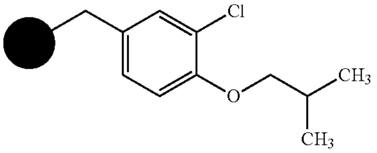
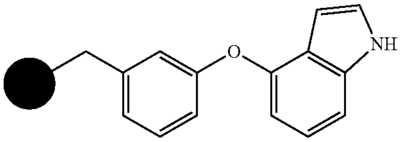
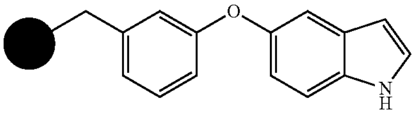
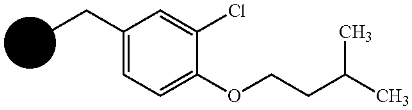
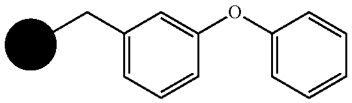
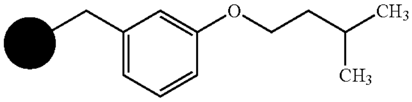
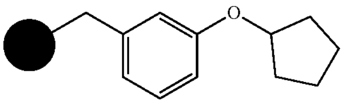
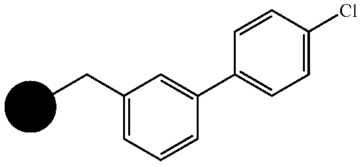
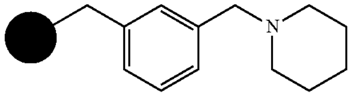
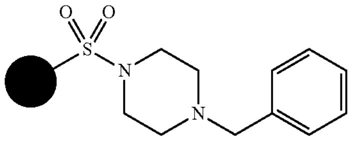
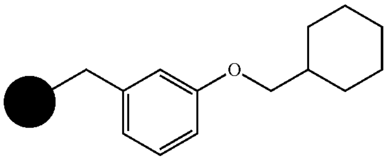
-continued
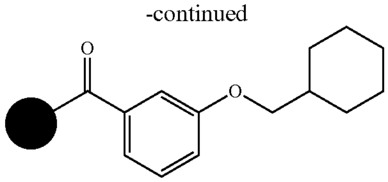
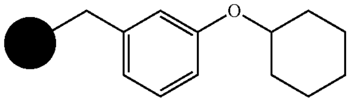
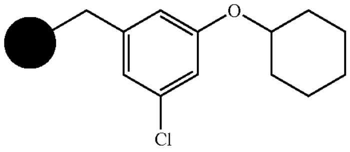
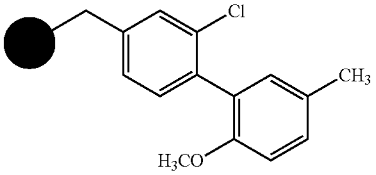
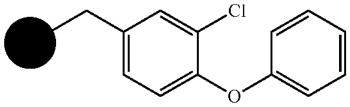
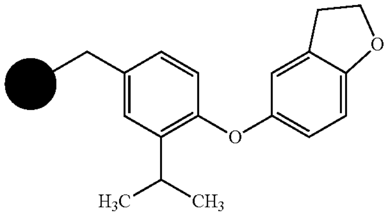
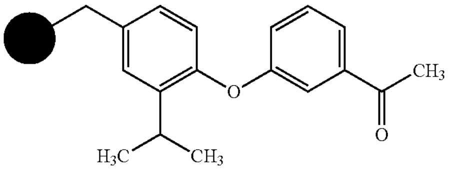
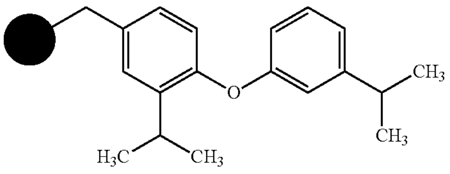
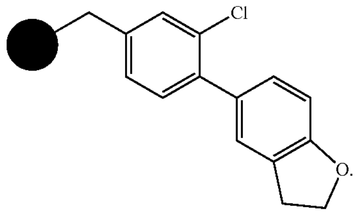
16. The compound according to claim 1, wherein said compound is selected in the group consisting of
AB150: N-(2-(4-((4-(1H-indol-3-yl)-1H-1,2,3-triazol-1-yl)methyl)piperidin-1-yl)ethyl)benzenesulfonamide;
AB152: N-(2-(4-((4-(1H-indol-3-yl)-1H-1,2,3-triazol-1-yl)methyl)piperidin-1-yl)ethyl)-4-chlorobenzenesulfonamide;
AB153: 4-chloro-N-(2-(4-((4-(5-fluoro-1H-indol-3-yl)-1H-1,2,3-triazol-1-yl)methyl)piperidin-1-yl)ethyl)benzenesulfonamide;

AB201: 5-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB202: 6-chloro-3-(1-((1-(2-((4-chlorophenyl)sulfonamido)ethyl)piperidin-4-yl)methyl)-1H-1,2,3-triazol-4-yl)-1H-indole-2-carboxylic acid;

AB401: ethyl 3-(1-((1-(2-((4-chlorophenyl)sulfonamido)ethyl)piperidin-4-yl)methyl)-1H-1,2,3-triazol-4-yl)-5-fluoro-1H-indole-2-carboxylate;

AB460: ethyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB433: ethyl 6-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB504: ethyl 5-fluoro-3-(1-((1-(2-((4-methylphenyl)sulfonamido)ethyl)piperidin-4-yl)methyl)-1H-1,2,3-triazol-4-yl)-1H-indole-2-carboxylate;

AB505: ethyl 5-chloro-3-(1-((1-(2-((4-methylphenyl)sulfonamido)ethyl)piperidin-4-yl)methyl)-1H-1,2,3-triazol-4-yl)-1H-indole-2-carboxylate;

AB503: ethyl 6-chloro-3-(1-((1-(2-((4-methylphenyl)sulfonamido)ethyl)piperidin-4-yl)methyl)-1H-1,2,3-triazol-4-yl)-1H-indole-2-carboxylate;

AB529: ethyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB550: ethyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB526: ethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB543: ethyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB536: ethyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB551: ethyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB579: ethyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB582 ethyl 5-chloro-3-(1-((1-(2-((4-isopropylphenyl)sulfonamido)ethyl)piperidin-4-yl)methyl)-1H-1,2,3-triazol-4-yl)-1H-indole-2-carboxylate;

AB577: isopropyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB578: isopropyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB498: isobutyl 3-(1-((1-(2-((4-chlorophenyl)sulfonamido)ethyl)piperidin-4-yl)methyl)-1H-1,2,3-triazol-4-yl)-5-fluoro-1H-indole-2-carboxylate;

AB499: isobutyl 5-chloro-3-(1-((1-(2-((4-chlorophenyl)sulfonamido)ethyl)piperidin-4-yl)methyl)-1H-1,2,3-triazol-4-yl)-1H-indole-2-carboxylate;

AB600: isobutyl 5-fluoro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB601: isobutyl 5-chloro-3-(1-((1-(2-((4-(trifluoromethyl)phenyl)sulfonamido)ethyl)piperidin-4-yl)methyl)-1H-1,2,3-triazol-4-yl)-1H-indole-2-carboxylate;

AB556: isobutyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB557: isobutyl 5-chloro-3-(1-((1-(2-((4-ethylphenyl)sulfonamido)ethyl)piperidin-4-yl)methyl)-1H-1,2,3-triazol-4-yl)-1H-indole-2-carboxylate;

AB598: isobutyl 5-fluoro-3-(1-((1-(2-(naphthalene-2-sulfonamido)ethyl)piperidin-4-yl)methyl)-1H-1,2,3-triazol-4-yl)-1H-indole-2-carboxylate;

AB599: isobutyl 5-chloro-3-(1-((1-(2-(naphthalene-2-sulfonamido)ethyl)piperidin-4-yl)methyl)-1H-1,2,3-triazol-4-yl)-1H-indole-2-carboxylate;

AB603: isobutyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB668: isobutyl 5-fluoro-3-(1-((1-(2-((4-isobutylphenyl)sulfonamido)ethyl)piperidin-4-yl)methyl)-1H-1,2,3-triazol-4-yl)-1H-indole-2-carboxylate;

AB651: 3-(1-((1-(2-((4-ethylphenyl)sulfonamido)ethyl)piperidin-4-yl)methyl)-1H-1,2,3-triazol-4-yl)-5-fluoro-N-isobutyl-1H-indole-2-carboxamide;

AB652: 5-fluoro-N-isobutyl-3-(1-((1-(2-((4-isopropylphenyl)sulfonamido)ethyl)piperidin-4-yl)methyl)-1H-1,2,3-triazol-4-yl)-1H-indole-2-carboxamide;

AB663: isopentyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB664: isopentyl 5-fluoro-3-(1-((1-(2-((4-isopropylphenyl)sulfonamido)ethyl)piperidin-4-yl)methyl)-1H-1,2,3-triazol-4-yl)-1H-indole-2-carboxylate;

AB669: isopentyl 5-fluoro-3-(1-((1-(2-((4-isobutylphenyl)sulfonamido)ethyl)piperidin-4-yl)methyl)-1H-1,2,3-triazol-4-yl)-1H-indole-2-carboxylate;

AB670: 3-(1-((1-(2-((4-ethylphenyl)sulfonamido)ethyl)piperidin-4-yl)methyl)-1H-1,2,3-triazol-4-yl)-5-fluoro-N-isopentyl-1H-indole-2-carboxamide;

AB671: 5-fluoro-N-isopentyl-3-(1-((1-(2-((4-isopropylphenyl)sulfonamido)ethyl)piperidin-4-yl)methyl)-1H-1,2,3-triazol-4-yl)-1H-indole-2-carboxamide;

AB597: 2-hydroxyethyl 3-(1-((1-(2-((4-ethylphenyl)sulfonamido)ethyl)piperidin-4 yl)methyl)-1H-1,2,3-triazol-4-yl)-5-fluoro-1H-indole-2-carboxylate;

AB614: 2-aminoethyl 3-(1-((1-(2-((4-ethylphenyl)sulfonamido)ethyl)piperidin-4-yl)methyl)-1H-1,2,3-triazol-4-yl)-5-fluoro-1H-indole-2-carboxylate;

AB680: isobutyl 3-(1-((1-((2-chloro-2'-(methoxymethyl)-[1,1'-biphenyl]-4-yl)methyl)piperidin-4-yl)methyl)-1H-1,2,3-triazol-4-yl)-5-fluoro-1H-indole-2-carboxylate;

AB681: isobutyl 3-(1-((1-(2-chloro-2'-(methoxymethyl)-[1,1'-biphenyl]-4-carbonyl)piperidin-4-yl)methyl)-1H-1,2,3-triazol-4-yl)-5-fluoro-1H-indole-2-carboxylate;

AB689: isobutyl 3-(1-((1-((2-chloro-2'-methoxy-[1,1'-biphenyl]-4-yl)methyl)piperidin-4-yl)methyl)-1H-1,2,3-triazol-4-yl)-5-fluoro-1H-indole-2-carboxylate;

AB690: isobutyl 3-(1-((1-(3-chloro-4-(1H-indol-4-yl)benzyl)piperidin-4-yl)methyl)-1H-1,2,3-triazol-4-yl)-5-fluoro-1H-indole-2-carboxylate;

AB691: isobutyl 3-(1-((1-(3-chloro-4-phenoxybenzyl)piperidin-4-yl)methyl)-1H-1,2,3-triazol-4-yl)-5-fluoro-1H-indole-2-carboxylate;

AB692: isobutyl 3-(1-((1-((2-chloro-2'-methoxy-5'-methyl-[1,1'-biphenyl]-4-yl)methyl)piperidin-4-yl)methyl)-1H-1,2,3-triazol-4-yl)-5-fluoro-1H-indole-2-carboxylate;

AB697: isobutyl 5-fluoro-3-(1-((1-(3-isopropyl-4-phenoxybenzyl)piperidin-4-yl)methyl)-1H-1,2,3-triazol-4-yl)-1H-indole-2-carboxylate;

AB703: isobutyl 3-(1-((1-(4-(1H-indol-4-yl)-3-isopropylbenzyl)piperidin-4-yl)methyl)-1H-1,2,3-triazol-4-yl)-5-fluoro-1H-indole-2-carboxylate;

AB704: isobutyl 5-fluoro-3-(1-((1-((2-isopropyl-2'-(methoxymethyl)-[1,1'-biphenyl]-4-yl)methyl)piperidin-4-yl)methyl)-1H-1,2,3-triazol-4-yl)-1H-indole-2-carboxylate;

AB717: isobutyl 3-(1-((1-(4-((2,3-dihydrobenzofuran-5-yl)oxy)-3-isopropylbenzyl)piperidin-4-yl)methyl)-1H-1,2,3-triazol-4-yl)-5-fluoro-1H-indole-2-carboxylate;

AB718: isobutyl 3-(1-((1-(4-(3-acetylphenoxy)-3-isopropylbenzyl)piperidin-4-yl)methyl)-1H-1,2,3-triazol-4-yl)-5-fluoro-1H-indole-2-carboxylate;

AB713: isobutyl 5-fluoro-3-(1-((1-(3-isopropyl-4-(3-isopropylphenoxy)benzyl)piperidin-4-yl)methyl)-1H-1,2,3-triazol-4-yl)-1H-indole-2-carboxylate;

AB753: isobutyl 3-(1-((1-(3-chloro-4-(1H-indol-5-yl)benzyl)piperidin-4-yl)methyl)-1H-1,2,3-triazol-4-yl)-5-fluoro-1H-indole-2-carboxylate;

AB731: isobutyl 3-(1-((1-(3-chloro-4-(2,3-dihydrobenzofuran-5-yl)benzyl)piperidin-4-yl)methyl)-1H-1,2,3-triazol-4-yl)-5-fluoro-1H-indole-2-carboxylate;

AB739: isobutyl 3-(1-((1-((3'-acetyl-2-chloro-[1,1'-biphenyl]-4-yl)methyl)piperidin-4-yl)methyl)-1H-1,2,3-triazol-4-yl)-5-fluoro-1H-indole-2-carboxylate;

AB758: isobutyl 3-(1-((1-((2-chloro-3'-isopropyl-[1,1'-biphenyl]-4-yl)methyl)piperidin-4-yl)methyl)-1H-1,2,3-triazol-4-yl)-5-fluoro-1H-indole-2-carboxylate;

AB760: isobutyl 3-(1-((1-(3-chloro-4-isobutoxybenzyl)piperidin-4-yl)methyl)-1H-1,2,3-triazol-4-yl)-5-fluoro-1H-indole-2-carboxylate;

AB746: isobutyl 3-(1-((1-(3-chloro-4-(isopentyloxy)benzyl)piperidin-4-yl)methyl)-1H-1,2,3-triazol-4-yl)-5-fluoro-1H-indole-2-carboxylate;

AB743: isobutyl 3-(1-((1-(2-chloro-2'-(isopentyloxy)-[1,1'-biphenyl]-4-carbonyl)piperidin-4-yl)methyl)-1H-1,2,3-triazol-4-yl)-5-fluoro-1H-indole-2-carboxylate;

AB756: isobutyl 3-(1-((1-(4-(1H-indol-4-yl)-3-(trifluoromethyl)benzoyl)piperidin-4-yl)methyl)-1H-1,2,3-triazol-4-yl)-5-fluoro-1H-indole-2-carboxylate;

AB755: isobutyl 3-(1-((1-((4-benzylpiperazin-1-yl)sulfonyl)piperidin-4-yl)methyl)-1H-1,2,3-triazol-4-yl)-5-fluoro-1H-indole-2-carboxylate;

AB912: isobutyl 5-fluoro-3-(1-((1-(2-((4-(trifluoromethoxy)phenyl)sulfonamido)ethyl) piperidin-4-yl)methyl)-1H-1,2,3-triazol-4-yl)-1H-indole-2-carboxylate;

AB913: isobutyl 3-(1-((1-(2-([1,1'-biphenyl]-4-sulfonamido)ethyl)piperidin-4-yl)methyl)-1H-1,2,3-triazol-4-yl)-5-fluoro-1H-indole-2-carboxylate;

AB914: isobutyl 3-(1-((1-(2-((4-cyclohexylphenyl)sulfonamido)ethyl)piperidin-4-yl)methyl)-1H-1,2,3-triazol-4-yl)-5-fluoro-1H-indole-2-carboxylate;

AB917: isobutyl 5-fluoro-3-(1-((1-(2-((4-isopropoxyphenyl)sulfonamido)ethyl)piperidin-4-yl)methyl)-1H-1,2,3-triazol-4-yl)-1H-indole-2-carboxylate;

AB918: isobutyl 3-(1-((1-(2-((4-benzylpiperidine)-1-sulfonamido)ethyl)piperidin-4-yl)methyl)-1H-1,2,3-triazol-4-yl)-5-fluoro-1H-indole-2-carboxylate;

AB929: isobutyl 5-fluoro-3-(1-((1-(2-((4-phenylpiperidine)-1-sulfonamido) ethyl)piperidin-4-yl)methyl)-1H-1,2,3-triazol-4-yl)-1H-indole-2-carboxylate;

AB930: isobutyl 3-(1-((1-(2-((2,3-dihydrobenzofuran)-5-sulfonamido)ethyl)piperidin-4-yl)methyl)-1H-1,2,3-triazol-4-yl)-5-fluoro-1H-indole-2-carboxylate;

AB931: isobutyl 3-(1-((1-(2-((4-(sec-butyl)phenyl)sulfonamido)ethyl)piperidin-4-yl)methyl)-1H-1,2,3-triazol-4-yl)-5-fluoro-1H-indole-2-carboxylate;

AB932: isobutyl 3-(1-((1-(2-((2,3-dihydro-1H-indene)-5-sulfonamido)ethyl)piperidin-4-yl)methyl)-1H-1,2,3-triazol-4-yl)-5-fluoro-1H-indole-2-carboxylate;

AB933: isobutyl 5-fluoro-3-(1-((1-(2-((4-phenoxyphenyl)sulfonamido)ethyl)piperidin-4-yl)methyl)-1H-1,2,3-triazol-4-yl)-1H-indole-2-carboxylate AB934: isobutyl 3-(1-((1-(2-((4-(tert-butyl)phenyl)sulfonamido)ethyl)piperidin-4-yl)methyl)-1H-1,2,3-triazol-4-yl)-5-fluoro-1H-indole-2-carboxylate;

AB935: isobutyl 5-fluoro-3-(1-((1-(2-(((4-(trifluoromethyl)phenyl)methyl) sulfonamido)ethyl) piperidin-4-yl)methyl)-1H-1,2,3-triazol-4-yl)-1H-indole-2-carboxylate;

AB936: isobutyl 3-(1-((1-(2-(((4-chlorophenyl)methyl) sulfonamido)ethyl)piperidin-4-yl)methyl)-1H-1,2,3-triazol-4-yl)-5-fluoro-1H-indole-2-carboxylate;

AB937: isobutyl 3-(1-((1-(2-(((3-chlorophenyl)methyl) sulfonamido)ethyl)piperidin-4-yl)methyl)-1H-1,2,3-triazol-4-yl)-5-fluoro-1H-indole-2-carboxylate;

AB938: isobutyl 3-(1-((1-((4-(tert-butyl)phenyl)sulfonyl) piperidin-4-yl)methyl)-1H-1,2,3-triazol-4-yl)-5-fluoro-1H-indole-2-carboxylate;

AB939: isobutyl 3-(1-((1-((2,3-dihydrobenzofuran-6-yl) sulfonyl)piperidin-4-yl)methyl)-1H-1,2,3-triazol-4-yl)-5-fluoro-1H-indole-2-carboxylate;

AB1030: isobutyl 3-(1-((1-(2-(((4-bromophenyl)methyl) sulfonamido)ethyl)piperidin-4-yl)methyl)-1H-1,2,3-triazol-4-yl)-5-fluoro-1H-indole-2-carboxylate;

AB1031: isobutyl 3-(1-((1-(2-(((3-bromophenyl)methyl) sulfonamido)ethyl)piperidin-4-yl)methyl)-1H-1,2,3-triazol-4-yl)-5-fluoro-1H-indole-2-carboxylate;

AB1032: isobutyl 3-(1-((1-(2-((4-(1H-pyrazol-4-yl)phenyl)sulfonamido)ethyl)piperidin-4-yl)methyl)-1H-1,2,3-triazol-4-yl)-5-fluoro-1H-indole-2-carboxylate;

AB1070: isobutyl 3-(1-((1-(2-((4',4'-difluoro-2',3',4',5'-tetrahydro-[1,1'-biphenyl])-4-sulfonamido)ethyl)piperidin-4-yl)methyl)-1H-1,2,3-triazol-4-yl)-5-fluoro-1H-indole-2-carboxylate;

AB1071: isobutyl 5-fluoro-3-(1-((1-(2-((4-(furan-3-yl) phenyl)sulfonamido)ethyl)piperidin-4-yl)methyl)-1H-1,2,3-triazol-4-yl)-1H-indole-2-carboxylate;

AB1072: isobutyl 3-(1-((1-(2-((3,4-dihydro-2H-benzo[b][1,4]dioxepine)-7-sulfonamido)ethyl)piperidin-4-yl)methyl)-1H-1,2,3-triazol-4-yl)-5-fluoro-1H-indole-2-carboxylate;

AB1073: isobutyl 5-fluoro-3-(1-((1-(2-((4-(2-(pyrrolidin-1-yl)pyridin-3-yl)phenyl) sulfonamido)ethyl)piperidin-4-yl)methyl)-1H-1,2,3-triazol-4-yl)-1H-indole-2-carboxylate;

AB1074: isobutyl 3-(1-((1-(2-((4-(3,6-dihydro-2H-pyran-4-yl)phenyl) sulfonamido)ethyl)piperidin-4-yl)methyl)-1H-1,2,3-triazol-4-yl)-5-fluoro-1H-indole-2-carboxylate;

AB1075: isobutyl 5-fluoro-3-(1-((1-(2-((2'-(morpholinomethyl)-[1,1'-biphenyl])-4-sulfonamido)ethyl)piperidin-4-yl)methyl)-1H-1,2,3-triazol-4-yl)-1H-indole-2-carboxylate;

AB1076: isobutyl 3-(1-((1-(2-((2'-cyano-[1,1'-biphenyl])-4-sulfonamido)ethyl)piperidin-4-yl)methyl)-1H-1,2,3-triazol-4-yl)-5-fluoro-1H-indole-2-carboxylate;
AB1130: isobutyl 3-(1-((1-(2-((4-(3,5-dimethylisoxazol-4-yl)phenyl)sulfonamido) ethyl)piperidin-4-yl) methyl)-1H-1,2,3-triazol-4-yl)-5-fluoro-1H-indole-2-carboxylate;
AB1133: isobutyl 3-(1-((1-(2-((4-(2-chloropyridin-3-yl) phenyl)sulfonamido)ethyl)piperidin-4-yl)methyl)-1H-1,2,3-triazol-4-yl)-5-fluoro-1H-indole-2-carboxylate;
AB1134: isobutyl 3-(1-((1-(2-((4'-cyano-[1,1'-biphenyl])-4-sulfonamido)ethyl)piperidin-4-yl)methyl)-1H-1,2,3-triazol-4-yl)-5-fluoro-1H-indole-2-carboxylate;
AB1205: isobutyl 5-fluoro-3-(1-((1-(2-((2'-methoxy-[1,1'-biphenyl])-4-sulfonamido)ethyl) piperidin-4-yl) methyl)-1H-1,2,3-triazol-4-yl)-1H-indole-2-carboxylate;
AB1206: isobutyl 3-(1-((1-(2-((2',6'-dimethoxy-[1,1'-biphenyl])-4-sulfonamido)ethyl) piperidin-4-yl)methyl)-1H-1,2,3-triazol-4-yl)-5-fluoro-1H-indole-2-carboxylate;
AB1207: isobutyl 5-fluoro-3-(1-((1-(2-((4-(2-fluoropyridin-3-yl)phenyl)sulfonamido) ethyl)piperidin-4-yl) methyl)-1H-1,2,3-triazol-4-yl)-1H-indole-2-carboxylate;
AB1208: isobutyl 3-(1-((1-(2-((2',6'-difluoro-[1,1'-biphenyl])-4-sulfonamido)ethyl)piperidin-4-yl)methyl)-1H-1,2,3-triazol-4-yl)-5-fluoro-1H-indole-2-carboxylate;
AB1209: isobutyl 3-(1-((1-(2-((2'-(dimethylamino)-[1,1'-biphenyl])-4-sulfonamido) ethyl)piperidin-4-yl) methyl)-1H-1,2,3-triazol-4-yl)-5-fluoro-1H-indole-2-carboxylate;
AB1210: isobutyl 5-fluoro-3-(1-((1-(2-((p-tolylmethyl) sulfonamido)ethyl)piperidin-4-yl)methyl)-1H-1,2,3-triazol-4-yl)-1H-indole-2-carboxylate;
AB1303: isobutyl 5-fluoro-3-(1-((1-(2-((2'-(methoxymethyl)-[1,1'-biphenyl])-4-sulfonamido)ethyl)piperidin-4-yl)methyl)-1H-1,2,3-triazol-4-yl)-1H-indole-2-carboxylate;
AB1131: N-(2-(4-((4-(5-fluoro-2-(pyrrolidine-1-carbonyl)-1H-indol-3-yl)-1H-1,2,3-triazol-1-yl)methyl)piperidin-1-yl)ethyl)-4-isobutylbenzenesulfonamide;
AB1132: N-(2-(4-((4-(5-fluoro-2-(morpholine-4-carbonyl)-1H-indol-3-yl)-1H-1,2,3-triazol-1-yl)methyl)piperidin-1-yl)ethyl)-4-isobutylbenzenesulfonamide;
AB1135: N-(2-(4-((4-(2-acetyl-5-fluoro-1H-indol-3-yl)-1H-1,2,3-triazol-1-yl)methyl) piperidin-1-yl)ethyl)-4-isobutylbenzenesulfonamide;
AB1145: N-(2-(4-((4-(5-fluoro-2-pentanoyl-1H-indol-3-yl)-1H-1,2,3-triazol-1-yl)methyl) piperidin-1-yl) ethyl)-4-isobutylbenzenesulfonamide;
AB1231: N-(2-(4-((4-(2-(cyclopropanecarbonyl)-5-fluoro-1H-indol-3-yl)-1H-1,2,3-triazol-1-yl)methyl)piperidin-1-yl)ethyl)-4-isobutylbenzenesulfonamide;
AB1232: 4-(2-chloropyridin-3-yl)-N-(2-(4-((4-(2-(cyclopropanecarbonyl)-5-fluoro-1H-indol-3-yl)-1H-1,2,3-triazol-1-yl)methyl)piperidin-1-yl)ethyl)benzenesulfonamide;
AB1233: N-(2-(4-((4-(2-butyryl-5-fluoro-1H-indol-3-yl)-1H-1,2,3-triazol-1-yl)methyl) piperidin-1-yl)ethyl)-4-(2-chloropyridin-3-yl)benzenesulfonamide;
AB1235: N-(2-(4-((4-(5-fluoro-2-formyl-1H-indol-3-yl)-1H-1,2,3-triazol-1-yl)methyl) piperidin-1-yl)ethyl)-4-isobutylbenzenesulfonamide;
AB1281: N-(2-(4-((4-(5-fluoro-2-isobutyryl-1H-indol-3-yl)-1H-1,2,3-triazol-1-yl)methyl) piperidin-1-yl) ethyl)-4-isobutylbenzenesulfonamide;
AB1282: 4-(2-chloropyridin-3-yl)-N-(2-(4-((4-(5-fluoro-2-isobutyryl-1H-indol-3-yl)-1H-1,2,3-triazol-1-yl) methyl)piperidin-1-yl)ethyl)benzenesulfonamide;
AB1283: N-(2-(4-((4-(5-fluoro-2-(3-methylbutanoyl)-1H-indol-3-yl)-1H-1,2,3-triazol-1-yl)methyl)piperidin-1-yl)ethyl)-4-isobutylbenzenesulfonamide;
AB1284: 4-(2-chloropyridin-3-yl)-N-(2-(4-((4-(5-fluoro-2-(3-methylbutanoyl)-1H-indol-3-yl)-1H-1,2,3-triazol-1-yl)methyl)piperidin-1-yl)ethyl)benzenesulfonamide;
AB1285: N-(2-(4-((4-(2-(cyclopropanecarbonyl)-5-fluoro-1H-indol-3-yl)-1H-1,2,3-triazol-1-yl)methyl)piperidin-1-yl)ethyl)-4-(3,5-dimethylisoxazol-4-yl)benzenesulfonamide;
AB1286: N-(2-(4-((4-(2-acetyl-5-fluoro-1H-indol-3-yl)-1H-1,2,3-triazol-1-yl)methyl) piperidin-1-yl)ethyl)-4-(3,5-dimethylisoxazol-4-yl)benzenesulfonamide;
AB1287: N-(2-(4-((4-(2-acetyl-5-fluoro-1H-indol-3-yl)-1H-1,2,3-triazol-1-yl)methyl) piperidin-1-yl)ethyl)-2',6'-dimethoxy-[1,1'-biphenyl]-4-sulfonamide;
AB1288: N-(2-(4-((4-(2-acetyl-5-fluoro-1H-indol-3-yl)-1H-1,2,3-triazol-1-yl)methyl)piperidin-1-yl)ethyl)-2',6'-difluoro-[1,1'-biphenyl]-4-sulfonamide;
AB1289: N-(2-(4-((4-(2-acetyl-5-fluoro-1H-indol-3-yl)-1H-1,2,3-triazol-1-yl)methyl) piperidin-1-yl)ethyl)-4-(2-fluoropyridin-3-yl)benzenesulfonamide;
AB1301: N-(2-(4-((4-(5-fluoro-2-nicotinoyl-1H-indol-3-yl)-1H-1,2,3-triazol-1-yl)methyl) piperidin-1-yl) ethyl)-4-isobutylbenzenesulfonamide;
AB1302: N-(2-(4-((4-(5-fluoro-2-(2-methylbutanoyl)-1H-indol-3-yl)-1H-1,2,3-triazol-1-yl)methyl)piperidin-1-yl)ethyl)-4-isobutylbenzenesulfonamide;
AB1304: N-(2-(4-((4-(2-(cyclopropanecarbonyl)-5-fluoro-1H-indol-3-yl)-1H-1,2,3-triazol-1-yl)methyl)piperidin-1-yl)ethyl)-4-(2,6-difluorophenyl)piperidine-1-sulfonamide;
AB1305: N-(2-(4-((4-(2-(cyclopropanecarbonyl)-5-fluoro-1H-indol-3-yl)-1H-1,2,3-triazol-1-yl)methyl)piperidin-1-yl)ethyl)-1-(4-(trifluoromethyl)phenyl)methanesulfonamide;
AB1306: N-(2-(4-((4-(5-fluoro-2-(3-methylbutanoyl)-1H-indol-3-yl)-1H-1,2,3-triazol-1-yl)methyl)piperidin-1-yl)ethyl)-1-(4-(trifluoromethyl)phenyl)methanesulfonamide;
AB1307: N-(2-(4-((4-(2-butyryl-5-fluoro-1H-indol-3-yl)-1H-1,2,3-triazol-1-yl)methyl) piperidin-1-yl)ethyl)-1-(4-(trifluoromethyl)phenyl)methanesulfonamide;
AB1315: N-(2-(4-((4-(2-acetyl-5-fluoro-1H-indol-3-yl)-1H-1,2,3-triazol-1-yl)methyl) piperidin-1-yl)ethyl)-1-(4-(trifluoromethyl)phenyl)methanesulfonamide;
AB1316: N-(2-(4-((4-(2-acetyl-5-fluoro-1H-indol-3-yl)-1H-1,2,3-triazol-1-yl)methyl) piperidin-1-yl)ethyl)-4-(2,6-difluorophenyl)piperidine-1-sulfonamide
AB1317: N-(2-(4-((4-(2-acetyl-5-fluoro-1H-indol-3-yl)-1H-1,2,3-triazol-1-yl)methyl) piperidin-1-yl)ethyl)-4-(cyclopropylmethyl)benzenesulfonamide;
AB1318: (S)—N-(2-(3-((4-(2-acetyl-5-fluoro-1H-indol-3-yl)-1H-1,2,3-triazol-1-yl)methyl) pyrrolidin-1-yl) ethyl)-4-isobutylbenzenesulfonamide;
AB1319: (R)—N-(2-(3-((4-(2-acetyl-5-fluoro-1H-indol-3-yl)-1H-1,2,3-triazol-1-yl)methyl) pyrrolidin-1-yl) ethyl)-4-isobutylbenzenesulfonamide;
AB1321: N-(2-(4-(4-(2-acetyl-5-fluoro-1H-indol-3-yl)-1H-1,2,3-triazol-1-yl)piperidin-1-yl)ethyl)-4-isobutylbenzenesulfonamide;
AB1322: N-(2-(4-((4-(2-acetyl-5-fluoro-1H-indol-3-yl)-1H-1,2,3-triazol-1-yl)methyl) piperidin-1-yl)ethyl)-4-(2-fluoropyridin-3-yl)piperidine-1-sulfonamide;

AB1381: N-(2-(4-((4-(2-acetyl-5-fluoro-1H-indol-3-yl)-1H-1,2,3-triazol-1-yl)methyl) piperidin-1-yl)ethyl)-2'-fluoro-6'-hydroxy-[1,1'-biphenyl]-4-sulfonamide;

AB1390: N-(2-(4-((4-(2-acetyl-5-fluoro-1H-indol-3-yl)-1H-1,2,3-triazol-1-yl)methyl) piperidin-1-yl)ethyl)-2'-fluoro-[1,1'-biphenyl]-4-sulfonamide;

AB1393: N-(2-(4-((4-(2-acetyl-5-fluoro-1H-indol-3-yl)-1H-1,2,3-triazol-1-yl)methyl) piperidin-1-yl)ethyl)-2'-cyano-6'-(trifluoromethyl)-[1,1'-biphenyl]-4-sulfonamide;

AB1394: N-(2-(4-((4-(2-acetyl-5-fluoro-1H-indol-3-yl)-1H-1,2,3-triazol-1-yl)methyl) piperidin-1-yl)ethyl)-2'-(trifluoromethyl)-[1,1'-biphenyl]-4-sulfonamide;

AB1401: N-(2-(4-((4-(2-acetyl-5-fluoro-1H-indol-3-yl)-1H-1,2,3-triazol-1-yl)methyl) piperidin-1-yl)ethyl)-2'-fluoro-6'-methoxy-[1,1'-biphenyl]-4-sulfonamide;

AB1402: isobutyl 5-fluoro-3-(1-((1-(2-((2'-fluoro-6'-hydroxy-[1,1'-biphenyl])-4-sulfonamido)ethyl)piperidin-4-yl)methyl)-1H-1,2,3-triazol-4-yl)-1H-indole-2-carboxylate;

AB1403: (S)—N-(2-(3-((4-(2-acetyl-5-fluoro-1H-indol-3-yl)-1H-1,2,3-triazol-1-yl)methyl) piperidin-1-yl) ethyl)-4-isobutylbenzenesulfonamide;

AB1404: N-(2-(3-((4-(2-acetyl-5-fluoro-1H-indol-3-yl)-1H-1,2,3-triazol-1-yl)methyl) azetidin-1-yl)ethyl)-4-isobutylbenzenesulfonamide;

AB1405: N-(2-(4-((4-(5-fluoro-2-(hydroxymethyl)-1H-indol-3-yl)-1H-1,2,3-triazol-1-yl)methyl)piperidin-1-yl)ethyl)-4-isobutylbenzenesulfonamide;

AB1406: 2'-fluoro-N-(2-(4-((4-(5-fluoro-2-(hydroxymethyl)-1H-indol-3-yl)-1H-1,2,3-triazol-1-yl)methyl)piperidin-1-yl)ethyl)-6'-hydroxy-[1,1'-biphenyl]-4-sulfonamide;

AB1415: 2'-fluoro-N-(2-(4-((4-(5-fluoro-2-propionyl-1H-indol-3-yl)-1H-1,2,3-triazol-1-yl)methyl)piperidin-1-yl)ethyl)-6'-hydroxy-[1,1'-biphenyl]-4-sulfonamide;

AB1416: N-(2-(4-((4-(5-fluoro-2-propionyl-1H-indol-3-yl)-1H-1,2,3-triazol-1-yl)methyl) piperidin-1-yl) ethyl)-2',6'-dimethoxy-[1,1'-biphenyl]-4-sulfonamide;

AB1417: N-(2-(4-((4-(5-fluoro-2-propionyl-1H-indol-3-yl)-1H-1,2,3-triazol-1-yl)methyl) piperidin-1-yl) ethyl)-1-(4-(trifluoromethyl)phenyl)methanesulfonamide;

AB1450: N-(2-(4-((4-(2-acetyl-5-fluoro-1H-indol-3-yl)-1H-1,2,3-triazol-1-yl)methyl) piperidin-1-yl)ethyl)-2'-hydroxy-[1,1'-biphenyl]-4-sulfonamide;

AB1451: N-(2-(4-((4-(2-acetyl-5-fluoro-1H-indol-3-yl)-1H-1,2,3-triazol-1-yl)methyl) piperidin-1-yl)ethyl)-2'-fluoro-6'-(trifluoromethyl)-[1,1'-biphenyl]-4-sulfonamide;

AB1452: N-(2-(4-((4-(2-acetyl-5-fluoro-1H-indol-3-yl)-1H-1,2,3-triazol-1-yl)methyl) piperidin-1-yl)ethyl)-2'-cyano-6'-methyl-[1,1'-biphenyl]-4-sulfonamide;

AB1453: N-(2-(4-((4-(2-acetyl-5-fluoro-1H-indol-3-yl)-1H-1,2,3-triazol-1-yl)methyl) piperidin-1-yl)ethyl)-2'-chloro-4'-fluoro-[1,1'-biphenyl]-4-sulfonamide;

AB1454: N-(2-(4-((4-(2-acetyl-5-fluoro-1H-indol-3-yl)-1H-1,2,3-triazol-1-yl)methyl) piperidin-1-yl)ethyl)-2-fluoro-2',6'-dimethoxy-[1,1'-biphenyl]-4-sulfonamide;

AB1455: N-(2-(4-((4-(2-acetyl-5-fluoro-1H-indol-3-yl)-1H-1,2,3-triazol-1-yl)methyl) piperidin-1-yl)ethyl)-2',6'-dimethoxy-2-methyl-[1,1'-biphenyl]-4-sulfonamide;

AB1456: N-(2-(4-((4-(2-acetyl-5-fluoro-1H-indol-3-yl)-1H-1,2,3-triazol-1-yl)methyl) piperidin-1-yl)ethyl)-2-chloro-2',6'-dimethoxy-[1,1'-biphenyl]-4-sulfonamide; and AB1457: N-(2-(4-((4-(2-acetyl-5-fluoro-1H-indol-3-yl)-1H-1,2,3-triazol-1-yl)methyl) piperidin-1-yl)ethyl)-2,2'-difluoro-6'-hydroxy-[1,1'-biphenyl]-4-sulfonamide.

17. A pharmaceutical composition comprising the compound of claim 1, and an acceptable pharmaceutical excipient.

18. A method of preventing or treating a cancer in a subject in need thereof, comprising administering to the subject a therapeutically effective amount of the compound of claim 1.

19. The method of claim 18, wherein the cancer is chemoresistant.

20. The method of claim 18, wherein the cancer is selected from the group consisting of multiple myeloma, lymphoma, cholangiocarcinoma, brain cancer, breast cancer, colon cancer, kidney cancer, leukemia, liver cancer, lung cancer, ovarian cancer, glioblastoma multiforme, melanoma, skin cancer, and pancreas cancer.

21. The method of claim 18, further comprising administering to the subject an additional antitumor drug.

* * * * *

SEQUENCE LISTING

```
<160> NUMBER OF SEQ ID NOS: 2

<210> SEQ ID NO 1
<211> LENGTH: 12
<212> TYPE: PRT
<213> ORGANISM: artificial
<220> FEATURE:
<223> OTHER INFORMATION: CK2 peptide substrate

<400> SEQUENCE: 1

Arg Arg Arg Glu Asp Glu Glu Ser Asp Asp Glu Glu
1               5                   10


<210> SEQ ID NO 2
<211> LENGTH: 22
<212> TYPE: PRT
<213> ORGANISM: artificial
<220> FEATURE:
<223> OTHER INFORMATION: CK2 peptide substrate

<400> SEQUENCE: 2

Met Ser Gly Asp Glu Met Ile Phe Asp Pro Thr Met Ser Lys Lys Lys
1               5                   10                  15

Lys Lys Lys Lys Lys Pro
            20
```